US010562964B2

(12) United States Patent
Paszty

(10) Patent No.: US 10,562,964 B2
(45) **Date of Patent: *Feb. 18, 2020**

(54) METHODS FOR ISOLATING ANTIBODIES THAT BIND SCLEROSTIN

(71) Applicant: AMGEN INC., Thousand Oaks, CA (US)

(72) Inventor: Christopher J. Paszty, Ventura, CA (US)

(73) Assignee: AMGEN INC., Thousand Oaks, CA (US)

(*) Notice: Subject to any disclaimer, the term of this patent is extended or adjusted under 35 U.S.C. 154(b) by 475 days.

This patent is subject to a terminal disclaimer.

(21) Appl. No.: 15/043,925

(22) Filed: Feb. 15, 2016

(65) Prior Publication Data

US 2016/0168241 A1 Jun. 16, 2016

Related U.S. Application Data

(62) Division of application No. 13/691,344, filed on Nov. 30, 2012, now Pat. No. 9,296,812, which is a division of application No. 12/950,094, filed on Nov. 19, 2010, now Pat. No. 8,383,801, which is a division of application No. 12/276,889, filed on Nov. 24, 2008, now Pat. No. 7,872,106, which is a division of application No. 11/411,003, filed on Apr. 25, 2006, now Pat. No. 7,592,429.

(60) Provisional application No. 60/792,645, filed on Apr. 17, 2006, provisional application No. 60/782,244, filed on Mar. 13, 2006, provisional application No. 60/776,847, filed on Feb. 24, 2006, provisional application No. 60/677,583, filed on May 3, 2005.

(51) Int. Cl.

| | |
|---|---|
| ***C07K 16/22*** | (2006.01) |
| ***C07K 14/76*** | (2006.01) |
| ***A61K 39/395*** | (2006.01) |
| ***A61K 45/06*** | (2006.01) |
| ***C07K 16/18*** | (2006.01) |
| ***C07K 14/79*** | (2006.01) |
| ***A61K 47/60*** | (2017.01) |
| *A61K 39/00* | (2006.01) |

(52) U.S. Cl.

CPC .......... *C07K 16/22* (2013.01); *A61K 39/3955* (2013.01); *A61K 45/06* (2013.01); *A61K 47/60* (2017.08); *C07K 14/76* (2013.01); *C07K 14/79* (2013.01); *C07K 16/18* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 4,331,647 | A | 5/1982 | Goldenberg |
| 4,376,110 | A | 3/1983 | David et al. |
| 4,411,993 | A | 10/1983 | Gillis |
| 4,427,115 | A | 1/1984 | Laipply |
| 4,543,439 | A | 9/1985 | Frackelton, Jr. et al. |
| RE32,011 | E | 10/1985 | Zimmerman et al. |
| 4,837,440 | A | 6/1989 | Burtscher et al. |
| 4,902,614 | A | 2/1990 | Wakabayashi et al. |
| 5,070,108 | A | 12/1991 | Margolis |
| 5,145,684 | A | 9/1992 | Liversidge et al. |
| 5,223,409 | A | 6/1993 | Ladner et al. |
| 5,399,363 | A | 3/1995 | Liversidge et al. |
| 5,453,492 | A | 9/1995 | Butzow et al. |
| 5,466,468 | A | 11/1995 | Schneider et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,571,714 | A | 11/1996 | Dasch et al. |
| 5,627,052 | A | 5/1997 | Schrader |
| 5,641,515 | A | 6/1997 | Ramtoola |
| 5,698,426 | A | 12/1997 | Huse |
| 5,738,868 | A | 4/1998 | Shinkarenko |
| 5,780,263 | A | 7/1998 | Hastings et al. |
| 5,795,587 | A | 8/1998 | Gao et al. |
| 5,795,965 | A | 8/1998 | Tsuchiya et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,877,397 | A | 3/1999 | Lonberg et al. |
| 6,054,561 | A | 4/2000 | Ring |
| 6,057,421 | A | 5/2000 | Muller et al. |

(Continued)

FOREIGN PATENT DOCUMENTS

| | | |
|---|---|---|
| JP | 4-141095 B2 | 8/2008 |
| WO | WO-1991/013152 A1 | 9/1991 |

(Continued)

OTHER PUBLICATIONS

A diagram of a relevant part of the human genome (D64), citation in Appeal, European Patent No. 1133558, dated Apr. 15, 2010.
Alberts et al. (Eds.), Molecular Biology of the Cell, Third Edition, Chapter 23, p. 1212 (1994).
Albertsen et al., A physical map and candidate genes in the BRCA1 region on chromosome 17q12-21. *Nat. Genet.*, 7:472-9 (1994).
Alting-Mees et al., Monoclonal antibody expression libraries: A rapid alternative to hybridomas. *Strat Molec. Biol.*, 3:1-9 (1990).
Alves et al., Sclerosteosis: A marker of Dutch ancestry? *Rev. Bras. Genet.*, 4:825-34 (1982).

(Continued)

*Primary Examiner* — Sharon X Wen

(74) *Attorney, Agent, or Firm* — Marshall, Gerstein & Borun LLP

(57) ABSTRACT

Compositions and methods relating to epitopes of sclerostin protein, and sclerostin binding agents, such as antibodies capable of binding to sclerostin, are provided.

12 Claims, 25 Drawing Sheets

Specification includes a Sequence Listing.

(56) References Cited

U.S. PATENT DOCUMENTS

| | | | | |
|---|---|---|---|---|
| 6,117,911 | A | 9/2000 | Grainger et al. | |
| 6,133,426 | A | 10/2000 | Gonzalez et al. | |
| 6,180,370 | B1 | 1/2001 | Queen et al. | |
| 6,207,153 | B1 | 3/2001 | Dan et al. | |
| 6,395,511 | B1 | 5/2002 | Brunkow et al. | |
| 6,489,445 | B1 | 12/2002 | Brunkow et al. | |
| 6,495,736 | B1 | 12/2002 | Brunkow et al. | |
| 6,703,199 | B1 | 3/2004 | Koide | |
| 6,803,453 | B1 | 10/2004 | Brunkow et al. | |
| 6,806,055 | B2 | 10/2004 | Berman et al. | |
| 6,815,201 | B2 | 11/2004 | Pinter | |
| 6,818,748 | B2 | 11/2004 | Fulton et al. | |
| 7,192,583 | B2 | 3/2007 | Brunkow et al. | |
| 7,226,902 | B2 | 6/2007 | Winkler et al. | |
| 7,381,409 | B2 | 6/2008 | Winkler et al. | |
| 7,572,899 | B2 | 8/2009 | Brunkow et al. | |
| 7,578,999 | B2 | 8/2009 | Winkler et al. | |
| 7,592,429 | B2 * | 9/2009 | Paszty .................... | C07K 16/22 530/388.24 |
| 7,642,238 | B2 | 1/2010 | Shaughnessy | |
| 7,758,858 | B2 | 7/2010 | Brunkow et al. | |
| 7,868,134 | B2 | 1/2011 | Winkler et al. | |
| 7,872,106 | B2 | 1/2011 | Paszty et al. | |
| 8,178,099 | B2 | 5/2012 | Ellies | |
| 9,296,812 | B2 * | 3/2016 | Paszty .................... | C07K 16/22 |
| 2003/0165410 | A1 | 9/2003 | Taylor | |
| 2003/0166247 | A1 | 9/2003 | Brunkow et al. | |
| 2003/0186915 | A1 | 10/2003 | Pan et al. | |
| 2003/0229041 | A1 | 12/2003 | Sutherland et al. | |
| 2004/0009535 | A1 | 1/2004 | Brunkow et al. | |
| 2004/0023356 | A1 | 2/2004 | Krumlauf et al. | |
| 2004/0058321 | A1 | 3/2004 | Brunkow et al. | |
| 2004/0141875 | A1 | 7/2004 | Doshi | |
| 2004/0146888 | A1 | 7/2004 | Paszty et al. | |
| 2004/0158045 | A1 | 8/2004 | Brunkow et al. | |
| 2005/0014650 | A1 | 1/2005 | Seitz et al. | |
| 2005/0085418 | A1 | 4/2005 | Winkler et al. | |
| 2005/0106683 | A1 | 5/2005 | Winkler et al. | |
| 2005/0238646 | A1 | 10/2005 | Ledbetter et al. | |
| 2006/0233801 | A1 | 10/2006 | Brunkow et al. | |
| 2007/0072797 | A1 | 3/2007 | Robinson et al. | |
| 2007/0110747 | A1 | 5/2007 | Paszty et al. | |
| 2007/0292444 | A1 | 12/2007 | Krumlauf et al. | |
| 2008/0182788 | A1 | 7/2008 | Brunkow et al. | |
| 2008/0234219 | A1 | 9/2008 | Brunkow et al. | |
| 2009/0074763 | A1 | 3/2009 | Padhi et al. | |
| 2009/0117118 | A1 | 5/2009 | Winkler et al. | |
| 2009/0304713 | A1 | 12/2009 | Paszty et al. | |
| 2010/0015665 | A1 | 1/2010 | Latham et al. | |
| 2010/0036091 | A1 | 2/2010 | Robinson et al. | |
| 2010/0151524 | A1 | 6/2010 | Winkler et al. | |
| 2011/0044978 | A1 | 2/2011 | Ke | |
| 2011/0097342 | A1 | 4/2011 | Paszty et al. | |
| 2011/0150866 | A1 | 6/2011 | Brunkow et al. | |

FOREIGN PATENT DOCUMENTS

| | | | |
|---|---|---|---|
| WO | WO-1992/001047 | A1 | 1/1992 |
| WO | WO-1992/002551 | A1 | 2/1992 |
| WO | WO-1992/006693 | A1 | 4/1992 |
| WO | WO-1995/030003 | A2 | 11/1995 |
| WO | WO-1996/004375 | A1 | 2/1996 |
| WO | WO-1998/021335 | A1 | 5/1998 |
| WO | WO-1999/003996 | A1 | 1/1999 |
| WO | WO-1999/006554 | A2 | 2/1999 |
| WO | WO-1999/015556 | A1 | 4/1999 |
| WO | WO-2000/032773 | A1 | 6/2000 |
| WO | WO-2000/044777 | A1 | 8/2000 |
| WO | WO-2000/075317 | A2 | 12/2000 |
| WO | WO-2001/064885 | A1 | 9/2001 |
| WO | WO-2001/092308 | A2 | 12/2001 |
| WO | WO-2001/098491 | A2 | 12/2001 |
| WO | WO-2002/024888 | A2 | 3/2002 |
| WO | WO-2002/030463 | A2 | 4/2002 |
| WO | WO-2003/050513 | A2 | 6/2003 |
| WO | WO-2003/087763 | A2 | 10/2003 |
| WO | WO-2003/106657 | A2 | 12/2003 |
| WO | WO-2004/082608 | A2 | 9/2004 |
| WO | WO-2004/094477 | A1 | 11/2004 |
| WO | WO-2004/098491 | A2 | 11/2004 |
| WO | WO-2005/003158 | A2 | 1/2005 |
| WO | WO-2005/014650 | A2 | 2/2005 |
| WO | WO-2005/115356 | A2 | 12/2005 |
| WO | WO-2006/015373 | A2 | 2/2006 |
| WO | WO-2006/065746 | A2 | 6/2006 |
| WO | WO-2006/102070 | A2 | 9/2006 |
| WO | WO-2006/119062 | A2 | 11/2006 |
| WO | WO-2006/119107 | A2 | 11/2006 |
| WO | WO-2007/080129 | A1 | 7/2007 |
| WO | WO-2008/061013 | A2 | 5/2008 |
| WO | WO-2008/092894 | A1 | 8/2008 |
| WO | WO-2008/115732 | A2 | 9/2008 |
| WO | WO-2008/133722 | A2 | 11/2008 |
| WO | WO-2009/039175 | A2 | 3/2009 |
| WO | WO-2009/047356 | A1 | 4/2009 |
| WO | WO-2009/056634 | A2 | 5/2009 |
| WO | WO-2009/079471 | A1 | 6/2009 |
| WO | WO-2009/131553 | A2 | 10/2009 |
| WO | WO-2009/149189 | A2 | 12/2009 |
| WO | WO-2010/100179 | A2 | 9/2010 |
| WO | WO-2010/100200 | A2 | 9/2010 |
| WO | WO-2010/115932 | A1 | 10/2010 |
| WO | WO-2010/130830 | A2 | 11/2010 |
| WO | WO-2012/028683 | A1 | 3/2012 |
| WO | WO-2012/058393 | A2 | 5/2012 |

OTHER PUBLICATIONS

Andersson et al., Molecular genetics and pathophysiology of 17β-hydroxysteriod dehydrogenase 3 deficiency. *J. Clin. Endrocrinol. Metab.*, 81(1): 130-6 (1996).

Angal et al., A single amino acid substitution abolishes the heterogeneity of chimeric mouse/human (IgG4) antibody. *Mol. Immunol.*, 30(1):105-8 (1993).

Annex regarding the purported relevance of gene/peptides mentioned by Professor Arnett.

Anonymous, Amgen presents denosumab and sclerostin antibody data at American Society for Bone and Mineral Research Annual Meeting. Amgen Media Press Release. <www.amgen.com/media/media_pr_detail.jsp?releaseID-907028> (2006).

Anonymous, UCB on track. UCB News <http://hugin.info/133973/R/1176122/233395.pdf> (2007).

Arnett et al., Effect of pH on bone resorption by rat osteoclasts in vitro. *Endocrinol.*, 119(1): 119-124 (1986).

Attana Application Example, cited in Opposition against European Patent No. 1721979 by Opponent: Novartis AG, dated Jun. 15, 2011.

Avsian-Kretchmer et al., Comparative genomic analysis of the eight-membered ring cystine knot-containing bone morphogenetic protein antagonists. *Molec. Endocrinol.*, 18(1):1-12 (2004).

Babcook et al., A novel strategy for generating monoclonal antibodies from single, isolated lymphocytes producing antibodies of defined specificities, *Proc. Natl. Acad. Sci. USA*, 93:7843-8 (1996).

Baines et al., Purification of immunoglobulin G (IgG). *Meth. Molec. Biol.*, 10:79-104 (1992).

Balemans et al., Extracellular regulation of BMP signaling in vertebrates: A cocktail of modulators. *Dev. Biol.*, 250:231-50 (2002).

Balemans et al., Increased bone density in sclerosteosis is due to the deficiency of a novel secreted protein (SOST). *Hum. Mol. Genet.*, 10:537-43 (2001).

Balemans et al., Localization of the gene for sclerosteosis to the van Buchem disease-gene region on chromosome 17q12-q21. *Am. J. Hum. Genet.*, 64:1661-9 (1999).

Balint et al., Antibody engineering by parsimonious mutagenesis. *Gene*, 137(1):109-18 (1993).

Bateman et al., Granulins: The structure and function of an emerging family of growth factors. *J. Endocrinol.*, 158: 145-51 (1998).

Baxevanis (Ed.) et al., Bioinformatics: A practical guide to the analysis of genes and proteins, John Wiley & Sons, Inc. p. 234 (1998).

(56) References Cited

OTHER PUBLICATIONS

Beighton et al., Heterzygous manifestations in the heritable disorders of the skeleton. *Pediatr. Radiol.*, 27: 397-401 (1997).
Beighton et al., The clinical features of sclerosteosis. *Clin. Genet.*, 25:175-81 (1984).
Beighton et al., The syndromic status of sclerosteosis and van Buchem disease. *Ann. Intern. Med.*, 84:393-7 (1976).
Bellows et al., Parathyroid hormone reversibly suppresses the differentiation of osteoprogenitor cells in functional osteoblasts. *Endocrinol.*, 127(6): 3111-6 (1990).
Bendayan, Possibilities of false immunocytochemical results generated by the use of monoclonal antibodies: The example of the anti-proinsulin antibody. *J. Histochem. Cytochem.*, 43(9):881-6 (1995).
Bendig, Humanization of rodent monoclonal antibodies by CDR grafting. *Methods*, 8:83-93 (1995).
Bergfeld et al., Release of ATP from human erythrocytes in response to a brief period of hypoxia and hypercapnia. *Cardiovascular Res.*, 26: 40-7 (1992).
Berman et al., The Protein Data Bank. *Acta. Cryst.*, 58(1):899-907 (2002).
Bird et al., Single-Chain Antigen-Binding Proteins. *Science*, 242:423-6 (1988).
Birren et al., EMBL Sequence Database Accession No. AC003098. 2, Nov. 14, 1997.
Bishop (Ed.), Guide to Human Genome Computing, Second Edition, Academic Press, Chapter 1: Introduction to human genome computer via the world wide web, pp. 1-14 (2003).
Black et al., A somatic cell hybrid map of the long arm of human chromosome 17, containing the familial breast cancer ILocus (BRCAI). *Am. J. Genet.*, 52:702-10 (1993).
Blum et al., Study plan for German students in the summer of 1998, University Bioinformatik lecture announcement (1998).
Boden et al., Glucocorticoid-induced differentiation of fetal rat calvarial osteoblasts is mediated by bone morphogenetic protein-6. *Endocrinology*, 138(7):2820-8 (1997).
Boerner et al., Production of antigen-specific human monoclonal antibodies from in vitro-primed human splenocytes. *J. Immunol.*, 147:86-95 (1991).
Bonaldo et al., EMBL Sequence Database Accession No. AI113131, Sep. 4, 1998.
Bonaldo et al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bork et al., Go hunting in sequence databases by watch out for the traps. *Trends Genet*. 12: 425-7 (1996).
Bost et al., Antibodies against a peptide sequence within the HIV envelope protein crossreacts with human interleukin-2. *Immunol. Invest.*, 17(6&7):577-86 (1988).
Bostrom et al., Ligand and signaling components of the transforming growth factor β family. *J. Orth. Res.*, 13:357-67 (1995).
Bottcher et al., NCBI Sequence Database Accession No. NM_004329, Aug. 2, 2009.
Bouffard et al., A physical map of human chromosome 7: An integrated YAC contig map with average STS spacing of 79 kb. *Genome Res.*, 7: 673-92 (1997).
Bowie et al., A method to identify protein sequences that fold into a known three-dimensional structure. *Science*, 253:164-70 (1991).
Bowie et al., Deciphering the message in protein sequences: Tolerance to amino acid substitutions. *Science*, 247(4948):1306-10 (1990).
Bradley et al., Modifying the mouse: Design and desire. *Bio/Technology*, 10:534-9 (1992).
Brandao-Burch et al., Acidosis inhibits bone formation by osteoblasts in vitro by preventing mineralization. *Calcif. Tissue Int.*, 77: 167-74 (2005).
Brenner et al., Population statistics of protein structures: Lessons from structural classifications. *Curr. Op. Struct. Biol.*, 7(3):369-76 (1997).
Brown, Hybridization Analysis of DNA Blots, *Current Protocols in Protein Science*, 13:A.4H.1-A.4H.9 (1990).
Brown, Hybridization Analysis of DNA Blots, *Current Protocols in Protein Science*, 2.10.1-2.10.16 (2000).
Bruggemann et al., Production of human antibody repertoires in transgenic mice. *Curr. Opin. Biotechnol.*, 8:455-8 (1997).
Brunkow et al., Bone dysplasia sclerosteosis results from loss of the SOST gene product, a novel cysteine knot-containing protein. *Am. J. Hum. Genet.*, 68:577-89 (2001).
Burton et al., Human antibodies from combinatorial libraries. *Adv. Immunol.*, 57:191-280 (1994).
Butcher et al., Increased salt concentration reversibly destabilizes p53 quaternary structure and sequence-specific DNA binding. *Biochem. J.*, 298: 513-6 (1994).
Byrne et al., CD4+CD45RBHi T cell transfer induced colitis in mice is accompanied by osteopenia which is treatable with recombinant human osteoprotegerin. *Gut*, 54:78-86 (2005).
Campbell et al., Totipotency or multipotentiality of cultured cells: Applications and progress. *Theriogenology*, 47:63-72 (1997).
Caverzasio et al., Characteristics and regulation of Pi transport in osteogenic cells for bone metabolism. *Kindey Int.*, 49: 975-80 (1996).
Chan et al., A new paradigm in the treatment of osteoporosis: Wnt pathway proteins and their antagonists. *Curr. Opin. Invest. Drugs.*, 8:293-8 (2007).
Chandran et al., Recent trends in drug delivery systems: Liposomal drug delivery system—Preparation and characterisation. *Indian J. Exp. Biol.*, 35(8):801-9 (1997).
Charlier et al., A pore mutation in a novel KQT-like potassium channel gene in an idiopathic epilepsy family. *Nat. Genet.*, 18:53-5 (1998).
Chenu et al., Glutamate receptors are expressed by bone cells and are involved in bone resorption. *Bone*, 22(4): 295-9 (1998).
Chou et al., Empirical predication of protein conformation. *Ann. Rev. Biochem.*, 47:251-76 (1979).
Chou et al., Prediction of the secondary structure of proteins from their amino acid sequence. *Adv. Enzymol. Relat. Areas Mol. Biol.*, 47:145-8 (1978).
Clark, Antibody humanization: A case of the 'Emperor's New Clothes'?. *Immunology Today*, 21(8):397-402 (2000).
Cogan et al., NCBI Sequence Database Accession No. NM_033346, Jul. 19, 2005.
Collins, Identifying human disease genes by positional cloning. *The Harvey Lectures*, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec.Res. Inst.*,55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Couvreur et al., Polyalkylcyanoacrylates as colloidal drug carriers. *Crit. Rev. Ther. Drug Carrier Syst.*, 5(1):1-20 (1988).
Craig et al., Sclerostin binds and regulates the activity of cysteine rich protein 61. *Biochem. Biophys. Res. Commun.*, 293(1): 36-40 (2010).
Craig et al., Sclerostin-erbB-3 interactions: Modulation of erbB-3 activity by sclerostin. *Biochem. Biophys. Res. Commun.*, 402: 421-4 (2010).
Crameri et al., DNA shuffling of a family of genes from diverse species accelerates directed evolution. *Nature*, 391:288-91 (1998).
Dall'Acqua et al., Antibody humanization by framework shuffling. *Methods*, 36(1):43-60 (2005).
Davies, et al., Affinity improvement of single antibody VH domains: Residues in all three hypervariable regions affect antigen binding. *Immunotechnology*, 2(3): 169-79 (1996).

(56) References Cited

OTHER PUBLICATIONS

De Jong et al., Evolution of the α-crystallin/small heat-shock protein family. *Mol. Biol. Evol.*, 10(1): 103-26 (1993).
Dean et al., Matrix vesicles produced by osteoblast-like cells in culture become significantly enriched in proteoglycan-degrading metalloproteinases after addition of β-glycerophosphate and ascorbic acid. *Calcif. Tissue*, 54: 399-408 (1994).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Alistair J. Henry, citation in Appeal, European Patent No. 1133558, dated Apr. 2, 2010.
Declaration of Dr. Martyn Robinson, submitted in Opposition to European Patent No. 1133558.
Declaration of Dr. Mary E. Brunkow, submitted in Opposition to European Patent No. 1133558.
Declaration of Prof. Edgar Wingender filed in connection with that Opposition regarding European Patent EP 1133558 B1, dated Mar. 10, 2011.
Declaration of Professor Teresa Attwood, citation in Appeal, European Patent No. 1133558, dated Apr. 13, 2010.
Declaration of Tim Arnett, citation in Appeal, European Patent No. 1133558, dated Apr. 2, 2010.
Delmas et al., The use of biochemical markers of bone turnover in osteoporosis. *Osteoporosis International.*, Suppl. 6:S2-17 (2000).
Ducy et al., 5-HT and bone biology. *Curr. Opin. Pharmacol.*, 11: 34-8 (2011).
Ducy et al., Genetic control of cell differentiation in the skeleton. *Curr. Opin. Cell Biol.*, 10: 614-9 (1998).
Durham et al., Alterations in insulin-like growth factor (IGF)-dependent Igf-binding protein-4 proteolysis in transformed osteoblastic cells. *Endocrinology*, 136(4):1374-80 (1995).
Ebara et al., Mechanism for the action of bone morphogenetic proteins and regulation of their activity. *Spine*, 27(165):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference C193, dated Sep. 28, 2009.
Epstein et al., Endocrine function in sclerosteosis. *S. Afr. Med. J.*, 55:1105-10 (1979).
European Patent Office Communication, Opposition to European Patent No. 1133558, dated Nov. 4, 2008.
European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], cited Jun. 15, 2011.
Expert Opinion from Dr. Catalina Lopez-Correa, submitted in Opposition to European Patent No. 1133558, dated Mar. 6, 2009.
Expert opinion of Professor Dr.-Ing Ulrich Vollrath, citation in Appeal of European Patent No. 1133558, dated Apr. 12, 2005.
Extract from Sigma Aldrich catalogue, cited in Opposition against European Patent No. 1721979 by Opponent: Laudens, dated Jun. 15, 2011.
Eyre et al., Characterization of aromatase and 17β-hydroxysteroid dehydrogenase expression in rat osteoblastic cells. *J. Bone Miner. Res.*, 13(6): 996-1004 (1998).
Foster et al., Establishment of interference in osteoblasts by an osteopetrosis-inducing Avian Leukosis virus. *Virology*, 205: 376-8 (1994).
Fouser et al., Feedback regulation of collagen gene expression: A Trojan horse approach. *Proc. Natl. Acad. Sci. USA*, 88: 10158-62 (1991).
Frost et al., On the rat model of human osteopenias and osteoporoses. *Bone and Mineral*, 18:227-36 (1992).
Fujiwara et al., GenBank Sequence Database Accession No. D79813, Feb. 9, 1996.
Gardner et al., Bone mineral density in sclerosteosis; Affected individuals and gene carriers. *J. Clin. Endocrinol. Metab.*, 90(12): 6392-5 (2005).
Gavarini et al., Opposite effects of PSD-95 and MPP3 PDZ proteins on serotonin 5-hydroxytryptamine2C receptor desensitization and membrane stability. *Molec. Biol.*, 17: 4619-31 (2006).
Gazzerro et al., Bone morphogenetic proteins induce the expression of noggin which limits their activity in cultured rat osteoblasts. *J. Clin. Invest.*, 102(12):2106-14 (1998).
Gazzerro et al., Potential drug targets within bone morphogenetic protein signaling pathways. *Curr. Opin. Pharmacol.*, 7: 325-3 (2007).
Geissler et la., Male pseudohermaphroditism caused by mutations of testicular 17β-hydroxysteroid hehydrogenase 3. *Nat. Genetics*, 7: 34-9 (1994).
Gencic et al., Conservative amino acid substitution in the myelin proteolipid protein of Jimpymsd mice. *J. Neurosci.*, 10(1):117-24 (1990).
Geysen et al., Cognitive features of continuous antigenic determinants. *J. Molec. Recog.*, 1(1):32-41 (1988).
Gitelman et al., Vgr-1/BMP-6 induces osteoblastic differentiation of pluripotential mesenchymal cells. *Cell Growth & Differentiation*, 6:827-36 (1995).
Glasky et al., Stability of specific immunoglobulin secretion by EBV-transformed lymphoblastoid cells and human-murine heterohybridomas. *Hybridoma*, 8:377-89 (1989).
Gowen et al., Actions of recombinant human γ-interferon and tumor necrosis factor α on the proliferation and osteoblastic characteristics of human trabecular bone cells in vitro. *Arthritis Rheumatism*, 31(12): 1500-7 (1988).
Graner et al., Splice variants of the *Drosophila* PS2 integrins differentially interact with RGD-containing fragments of the extracellular proteins tiggrin, Ten-m and D-laminin α2. *J. Biol. Chem.*, 1273(29): 18235-41 (1998).
Green et al., Antigen-specific human monoclonal antibodies from mice engineered with human Ig heavy and light chain YACs. *Nat. Genet.*, 7:13 (1994).
Green et al., Cytosolic pH regulation in osteoblasts. *J. Gen. Physiol.*, 95: 121-45 (1990).
Greene et al., Screening Recombinant DNA Libraries. *Current Protocols in Molecular Biology*, Ch. 6(1) (1990).
Gribskov et al., Profile analysis. *Meth. Enzym.*, 183:146-59 (1990).
Gribskov et al., Profile analysis: Detection of distantly related proteins. *Proc. Nat. Acad. Sci. USA*, 84(13):4355-8 (1987).
Groeneveld et al., Bone morphogenetic proteins in human bone regeneration. *Eur. J. Endocrinol.*, 142:9-21 (2000).
Gronthos et al., Integrin expression and function on human osteoblast-like cells. *J. Bone Miner. Res.*, 12(8): 1189-97 (1997).
Groppe et al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et al., Crystal structure of the human TβR2 ectodomain-TGF-β3 complex. *Nat. Struc. Biol.*, 9(3):203-8 (2002).
Hay et al., ATCC Cell Line and Hybridomas, American Type Culture Collection, 8th Ed., pp. 149, 258, 428 (1994).

(56) References Cited

OTHER PUBLICATIONS

He et al., High-throughput dynamic light scattering method for measuring viscosity of concentrated protein solutions. *Anal. Biochem.*, 399(1): 141-3 (2010).
Heinecke et al., Receptor oligomerization and beyond: A case study in bone morphogenetic proteins, *BMC Biol.*, 7: 59 (2009).
Hill et al., Multiple extracellular signals promote osteoblast survival and apoptosis. *Endocrinology*, 138(9):3849-58 (1997).
Hillier et al., EMBL Sequence Database Accession No. AA393939, May 19, 1997.
Hillier et al., GenBank Sequence Database Accession No. AA393768, Apr. 24, 1997.
Hillier et al., Generation and analysis of 280,000 human expressed sequence tags. *Genome Res.*, 6: 807-28 (1996).
Hilliker et al., Truncation of the amino terminus of PTH alters its anabolic activity on bone in vivo. *Bone*, 19(5): 469-77 (1996).
Hock et al., Perspective: Osteoblast apoptosis and bone turnover. *J. Bone Miner. Res.*, 16(6):975-84 (2001).
Hoffman et al., BMP Signaling Pathways in Cartilage and Bone Formation, Critical Review in Eukaryotic Gene Expression, 11(1-3):23-45 (2001).
Hoggard et al., Localization of leptin receptor mRNA splice variants in murine peripheral tissues by RT-PCR and in situ hybridization. *Biochem. Biophys. Res. Commun.*, 232: 383-7 (1997).
Hollinger et al., Engineered antibody fragments and the rise of single domains. *Nat. Biotech.*, 23(9):1126-36 (2005).
Holm et al., Protein folds and families: Sequence and structure alignments. *Nucl. Acid Res.*, 27(1):244-7 (1999).
Holt, et al., Domain antibodies: proteins for therapy. *Trends Biotechnol.*, 21(11):484-90 (2003).
Hoogenboom et al., By-passing immunisation: Human antibodies from synthetic repertoires of germline VH gene segmens rearranged in vitro. *J. Molec. Biol.*, 227:381-8 (1992).
Hoogewerf et al., Glycosaminoglycans mediate cell surface oligomerization of chemokines. *Biochemistry*, 36: 13570-8 (1997).
Horton et al., Arg-Gly-Asp (RGD) peptides and the anti-vitronectin receptor antibody 23C6 inhibit dentine resorption and cell spreading by osteoclats. *Exp. Cell Res.*, 195: 368-75 (1991).
Hsu et al., The Xenopus dorsalizing factor gremlin indentified a novel family of secreted proteins that antagonize BMP activities. *Molecular Cell*, 1:673-83 (1998).
Hufner et al., Evidence for an osteoblast-activating factor in a patient with peripheral T-cell lymphoma and osteosclerosis. *Klin. Wochenscher.*, 67: 402-7 (1989).
Hulley et al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et al., Generation of a large combinatorial library of the immunoglobulin repertoire in phage lambda. *Science*, 246:1275-81 (1989).
Hwang et al., Use of human germline genes in a CDR homoloy-based approach to antibody humanization. *Methods*, 36(1):35-42 (2005).
Ide et al., GenBank Sequence Database Accession No. BAA19765, Feb. 7, 1999.
Ide et al., GenBank Sequence Datacase Accession No. D89675, Feb. 7, 1999.
Iemura et al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et al., Evolutionary trace analysis of TGF-B and related growth factors: Implications for stie-directed mutagenesis. *Protein Engineering*, 13(12):839-47 (2000).
Jakobovits et al., Production of antigen-specific human antibodies from mice engineered with human heavy and light chain YACsa. *Ann. N.Y. Acad. Sci.*, 764:525-35 (1995).
Jee et al., Overview: Animal models of osteopenia and osteoporosis. *J. Musculoskel. Neuron. Interact.*, 1:193-207 (2001).
Jilka et al., Increased bone formation by prevention of osteoblast apoptosis with parathyroid hormone. *J. Clin. Invest.*, 104:439-46 (1999).
Jilka et al., Osteoblast programmed cell death (apoptosis): Modulation by growth factors and cytokines. *J. Bone Miner. Res.*, 13(5): 793-802 (1998).
Jones, Progress in protein structure predication. *Curr. Opin. Struct. Biol.*, 7(3):377-387 (1997).
Kabat et al., *Sequences of Proteins of Immunological Interest*, U.S. Department of Health and Human Services, NIH, USA (1987) (Table of Contents).
Kalu, The ovariectomized rat model of postmenopausal bone loss. *Bone and Mineral*, 15:175-92 (1991).
Kang et al., Linkage of recognition and replication functions by assembling combinatorial antibody Fab libraries along phage surfaces. *Proc. Natl. Acad. Sci. USA*, 88:4363-6 (1991).
Katagiri et al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et al., Signal transduction by bone morphogenetic proteins. *Cytokine and Growth Factor Reviews*, 9(1):49-61 (1998).
Keller et al., Molecular recognition of BMP-2 and BMP receptor IA. *Nat. Struct. Mol. Biol.*, 11(5):481-488 (2004).
Khalil, TGF-β: From latent to active. *Microbes and Infection*, 1(15):1255-63 (1999).
Khosla et al., Concise review for primary-care physicians. Treatment pptions for osteoporosis. *Mayo Clin. Proc.*, 70:978-82 (1995).
Kirsch et al., BMP-2 antagonists emerge from alterations in the low-affinity binding epitope for receptor BMPR-II, *EMBO J.* 19(13): 3314-24 (2000).
Kohler et al., Continuous cultures of fused cells secreting antibody of predefined specificity. *Nature*, 256:495 (1975).
Koli et al., Latency, activation, and binding proteins of TGF-. *Microscopy Res. Tech.*, 52:354-62 (2001).
Koreth et al., Microsatellites and PCR genomic analysis. *J. Pathology*, 178:239-48 (1996).
Kramer et al., the gapped duplex DNA approach to oligonucleotide-directed mutation construction. *Nucleic Acids Res.*, 12:9441 (1984).
Krause et al., Distinct modes of inhibition by sclerostin on bone morphogenetic protein and Wnt signaling pathways. *J. Biol. Chem.* ,285(53): 41614-26 (2010).
Kunkel et al., Rapid and efficient site-specific mutagenesis without phenoypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).
Kurahashi et al., Regions of genomic instability on 22q11 and 11q23 as the etiology for the recurrent constitutional t (11;22). *Hum. Molec. Genet.*, 9: 1665-70 (2000).
Kusu et al., Sclerostin is a novel secreted osteoclast-dervied bone morphogenetic protein antagonist with unique ligand specificity. *J. Biol. Chem.*, 278:24113-7 (2003).
Labat et al., Retroviral expression in mononuclear blood cells isolated from a patient with osteopetrosis (Albers-Schonberg disease). *J. Bone Miner. Res.*, 5(5): 425-35 (1989).
Labat, A new approach to the study of the origin of genetic disease: Retroviral etiology of osteopetrosis. *Biomed. Pharmacother.*, 45: 23-7 (1991).
Lasic, Novel applications of liposomes. *Trends Biotechnol.*, 16(7):307-21 (1998).
Leppert et al., Benign familial neonatal epilepsy with mutations in two potassium channel genes. *Curr. Opin. Neurol.*, 12: 143-7 (1999).
Hirschhorn, Letter to the Editor: Dominance and Homozygosity in Man. *Am. J. Med. Genetics*, 18: 541 (1984).
Lewiecki et al., Sclerostin monoclonal antibody therapy with AMG 785: A potential treatment for osteoporosis. *Exp. Opin. Biol. Ther.*, 11(1): 117-27 (2011).
Li et al., Sclerostin binds to LRP5/6 and antagonizes canonical Wnt signaling. *J. Biol. Chem.*, 280: 19883-7 (2005).

(56) References Cited

OTHER PUBLICATIONS

Li et al., Treatment with an anti-sclerostin antibody directly stimulates bone formation in a dose-dependent manner in ovariectomized rats with established osteopenia. *J. Bone Min. Res.*, 22(Suppl. S1): S65 (2007).
Lian et al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Lierop et al., Van Buchem disease: Clinical, biochemical and densitometric features of patients and disease carriers. *J. Bone Miner. Res.* Accepted Article (2012).
Liu et al., GenBank Sequence Database Accession No. U25110, Feb. 2, 1996.
Liu et al., Human type II receptor for bone morphogenic proteins (BMPs): Extension of the two-kinase receptor model to the BMPs. *Molec. Cell. Biol.*, 15(7):3479-86 (1995).
Lonberg et al., Antigen-specific human antibodies from mice comprising four distinct genetic modifications. *Nature*, 368:856 (1994).
Loots et al., Genomic deletion of a long-range bone enhancer misregulates sclerostin in Van Buchem disease. *Genome Res.*, 15: 928-35 (2005).
Low et al., Mimicking somatic hypermutation: Affinity maturation of antibodies displayed on bacteriophage using a bacterial mutator strain. *J. Mol. Biol.*, 250:350-68 (1996).
Lowik et al., Wnt signaling is involved in the inhibitory action of sclerostin on BMP-stimulated bone formation. *J. Musculoskeleton Neuronal Interact.* 6: 357 (2006).
Luckman et al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).
Luckman et al., Nitrogen-containing bisphosphonates inhibit the mevalonate pathway and prevent post-translational prenylation of GTP-binding proteins, including Ras. *J. Bone Miner. Res.*, 13(4): 581-9 (1998).
Malone et al., Bone anabolism achieved by reducing sclerostin bioavailability with an anti-sclerostin antibody. 37th International Sun Valley Workshop on Skeletal Tissue Biology. Aug. 5-8, 2007.
Mango et al., Carboxy-terminal truncation activates glp-1 protein to specify vulval fates in *Caenorhabditis elegans*. *Lett. Nature*, 352: 811-15 (1991).
Margalit et al., Comparative analysis of structurally defined herparin binding sequences reveals a distinct spatial distribution of basic residues. *J. Biol. Chem.*, 268 (26): 19228-31 (1993).
Margalit, Liposome-mediated drug targeting in topical and regional therapies. *Crit. Rev. Ther. Drug Carrier Syst.*, 12(2-3):233-61 (1995).
Marks et al., By-passing immunization: Building high affinity human antibodies by chain shuffling. Bio/Technology, 10:779-83 (1992).
Matthews et al., Adenovirus protein-protein interactions: Hexon and protein VI. *J. Gen. Virol.*, 75: 3365-74 (1994).
Mayer et al., Differentiation of osteogenetic cells: Systems and regulators, *Z. Orthop.*, 130: 276-84 (1992)—Abstract Only.
McClung et al., Inhibition of sclerostin with AMG 785 in postmenopausal women with low bone mineral density: Phase 2 trial results—Abstract presented at the 2012 meeting of the American Society for Bone and Mineral Reasearch (2012).
Memorandum C, Munich Diplomatic Conference, Sep. 1 to Oct. 6, 1973.
Minabe-Saegusa et al., Genbank Sequence Database Accession No. AB011030, Jun. 23, 1998.
Miyazono et al., Divergence and convergence of TGF-β/BMP signaling. *J. Cell. Physiol.*, 187:265-76 (2001).
Miyazono et al., TGF-β signaling by Smad proteins. *Adv. Immunology*, 75:115-57 (2000).
Morais et al., In vitro biomineralization by osteoblast-like cells I. Retardation of tissue mineralization by metal salts. *Biomaterials*, 19: 13-21 (1998).
Mori et al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Mosekilde et al., Assessing bone quality—Animcal models in preclinincal osteoporosis research. *Bone*, 17 (4): 343S-52S (1995).
Moult, The current state of the art in protein structure predicion. *Curr. Opin. Biotech.*, 7(4):422-7 (1996).
Mullins et al., Perspectives series: Molecular medicine in genetically engineered animals; Transgenesis in the rat and larger mammals. *J. Clin. Invest.*, 97(7):1557-60 (1996).
Muntoni et al., A mutation in the dystrophin gene selectively affecting dystrophin expression in the heart. *J. Clin. Invest.*,96: 693-9 (1995).
Nagaraja et al., X chromosome map at 75-kb STS resolution, revealing extremes of recombination and GC content. *Genome Res.* 7: 210-22 (1997).
Nakase et al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et al., The crystal structure of the BMP-2: BMPR-1A complex and the generation of BMP-2 antagonists. *J. Bone Joint Surg.*, 83-A:S1-7-S1-14 (2001).
Nicolas et al., An age-related decrease in the concentration of insulin-like growth factor binding protein-5 in human cortical bone. *Calcif. Tissue Int.*, 57:206-12 (1995).
Nifuji et al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et al., Separation of univalent fragments from the bivalent rabbit antidody molecule by reduction of disulfide bonds. *Arch. Biochem. Biophys.*, 89:230-44 (1960).
Niu et al., Sclerostin inhibition leads to increased periosteal and endocortical bone formation as well as decreased cortical porosity in aged ovariectomized rats. *J. Bone Min. Res.*, 22(Suppl. S1) S65 (2007).
Nordsletten et al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition to European Patent No. 1 133 558, dated May 29, 2007.
Nygren et al., Scaffolds for engineering novel binding sites in proteins. *Curr. Opin. Struct. Biol.*, 7:463-9 (1997).
Oelgeschlager et al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et al., Sclerostin monoclonal antibody treatment increases bone strength in aged osteopenic ovariectomozed rats. J. Bone Min. Res., 21(1): S44 PRES1161 (2006). Abstract.
Oreffo et al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Orriss et al., Purinergic signaling and bone remodeling. *Curr. Opin. Pharmacol.*, 10:322-30 (2010).
Utting et al., Hypoxia stimulates osteoclast formation from human peripheral blood. *Cell Biochem. Funct.*, 28:374-80 (2010). Orriss et al., Osteoblast cultures. *Methods Molec. Med.*, (2010b).
Oshima et al., TGF-β receptor type II deficiency results in defects of yolk Sac hematopoiesis and vasculogenesis. *Dev. Biol.*, 179:297-302 (1996).

(56) References Cited

OTHER PUBLICATIONS

Padhi et al., Anti-sclerostin antibody increases markers of bone formation in healthy postmenopausal women. *J. Bone Min. Res.*, 22: S37 (2007).
Padhi et al., OC35—Effects of anti-sclerostin monoclonal antibody in healthy postmenopausal women. *Osteoporosis Int.*, 19: Suppl. 1: S19 (2008).
Padlan et al., Structure of an antibody-antigen complex; Crystal structure of the HyHEL-10 Feb-lysozyme complex. *Proc. Natl. Acad. Sci. USA*, 86:5938-42 (1989).
Palokangas et al., Endocytic pathway from the basal plasma membrane to the ruffled border membrane in bone-resorbing osteoclasts. *J. Cell Sci.*, 110: 1767-80 (1997).
Pandey et al., Nucleotide sequence database: A gold mine for biologists. *TIBS.* 24: 276-80 (1999).
Papapoulos et al., Targeting sclerostin as potential treatment of osteoporosis. *Ann. Rheum. Dis.*, 70(Suppl. 1): I119-22 (2011).
Patel et al., Current and potential future drug treatments for osteoporosis. *Ann. Rheumatic Dis.*, 55: 700-14 (1996).
Patten et al., Applications of DNA shuffling to pharmaceuticals and vaccines. *Curr. Opin. Biotechnol.*, 8:724-33 (1997).
Pearson et al., Effective protein sequence comparison. Chapter 15, pp. 227-258 (1996).
Piao et al., The proximal promotor region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et al., The head inducer Cerberus is a multifunctional antagonist of nodal, BMP and Wnt signals. *Nature*, 397: 707-10 (1999).
Piek et al., Specificity, diversity, and regulation of TGF-β superfamily signaling. *FASEB J.*, 13:2105-24 (1999).
Pietromonaco et al., Protein kinase C-⊖ phosphorylation of moesin in the actin-binding sequence. *J. Biol. Chem.*, 273:7594-603 (1998).
Pignatti et al., Tracking disease genes by reverse genetics. *J. Psychiar. Res.*, 26(4):287-98 (1992).
Pittenger et al., Multilineage potential of adult human mesenchymal stem cells. *Science,* 284:143-7 (1999).
Pluckthun et al., Expression of functional anitbody Fv and Fab fragments in *Escherichia coli. Meth. Enzymol.*, 178:497-515 (1989).
Pockwinse et al., Expression of cell growth and bone specific genes at single cell resolution during development of bone tissue-like organization in primary osteoblast cultures. *J. Cell. Biol.*, 49:310-23 (1992).
Poole et al., Sclerostin is a delayed secreted product of osteocytes that inhibit bone formation. *FESEB J.* 19: 1842-4 (2005).
Porter, The hydrolysis of rabbit γ-globulin and antibodies with crystalline papain. *Biochem. J.*, 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Quintanar-Guerrero et al., Preparation techniques and mechanisms of formation of biodegradable nanoparticles from preformed polymers. *Drug Dev. Ind. Pharm.*, 24(12):1113-28 (1998).
Rachner et al., Osteoporosis: Now and the future. *Lancet*, 377(9773): 1276-87 (2011).
Rawadi et al., BMP-2 controls alkaline phosphatase expression and osteoblast mineralization by a Wnt autocrine loop. *J. Bone Min. Res.* 18: 1842-53 (2003).
Reb, Antikorpergegen Sclerostin, *Medical Tribune*, 39:12 (2007).
Reddi et al., The *Escherichia coli* chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
RnD Systems catalogue excerpt, cited in Opposition against European Patent No. 1721979 by Opponent: Novartis AG dated Jun. 15, 2011.
Roberts et al., Essential functional interactions of SAFA, a *Saccharomyces cerevisiae* complex of Spt, Ada, and Gcn5 proteins, with the Snf/Swi and Srb/Mediator complexes. *Genetics*, 147: 451-65 (1997).
Robinson et al., The sclerostin antibody project. *Hum. Antibodies*, 16: 36 (2007).
Roitt et la., Roitt's Essential Immunology, 9th Edition, pp. 90-91 (1997).
Rosenzweig et al., Cloning and characterization of a human type II receptor for bone morphogenetic proteins. *Proc. Natl. Acad. Sci, USA*, 92:7632-7636 (1995).
Rosenzweig et al., GenBank Sequence Database Accession No. CAA88759, Oct. 7, 2008.
Rosenzweig et al., GenBank Sequence Database Accession No. Z48923, Oct. 7, 2008.
Rudikoff, et al., Single amino acid substitution altering antigen-binding specificity. *Proc. Natl. Acad. Sci. USA*, 79:1979-83 (1982).
Ruppert et al., Human bone morphogenetic protein 2 contains a heparin-binding site which modifies its biological activity. *Eur. J. Biochem.*, 237: 295-302 (1996).
Sada et al., Adsorption equilibirum in immuno-affinity chromatography with polyclonal and monoclonal antibodies. *Biotechnol. Bioengin.*, 28 (1986). Abstract.
Sali et al., Comparative protein modeling by satisfaction of spatial restraints. *J. Mol. Biol.*, 234(3):779-815 (1993).
Sambrook et al., Synthetic Oligonucleotide Probes, *Molecular Cloning—A Laboratory Manual*, Ch.11:11.1-11.19 and 11.58-11.61 (1989).
Sanger et al., DNA sequencing with chain-terminating inhibitors. *Proc. Natl. Acad. Sci. USA*, 74:5463-7 (1997).
Sastry et al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et al., The attractions of proteins for small molecules and ions. *Ann. N.Y. Acad. Sci.*, 51:660-72 (1949).
Scheufler et al., Crystal structure of human bone morphogenetic protein-2 at 2.7 A resolution. *J. Mol. Biol.*, 287(1):101-15 (1999).
Schlebusch et al., Production of a single-chain fragment of the murine anti-idiotypic antibody ACA125 as phage-displayed and soluble antibody by recombinant phage antibody technique. *Hybridoma*, 16:47-52 (1997).
Schlunegger et al., Refined crystal structure of human transforming growth factor β2 at 1.95 A Resolution*J. Mol. Biol.*, 231(2):445-458 (1993).
Schmidt et al., Retrovirus-induced osteopetrosis in mice: Effects of viral infection on osteogenic differentiation in skeletoblast cell cultures. *Am. J. Pathol.*, 129(3): 503-10 (1987).
Schmitt et al., Bone morphogenetic proteins: An update on basic biology and clinical relevance. *J. Orth. Res.*, 17:269-78 (1999).
Schwappacher et al., NCBI Sequence Database Accession No. NM_001204, Aug. 16, 2009.
Scully et al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.
Serra et al., Expression of a truncated, kinase-defective TGF-β type II receoptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc.* Biol., 20:1425-9 (2000).
Silverman et al., Sclerostin, *J. Osteoporosis*, 2010: 1-3 (2010).
Sippl et al., Threading thrills and threats. *Structure*, 4(1):15-19 (1996).
Siris, Clinical Review: Paget's disease of bone. *J. Bone Miner. Res.*, 13(7): 1061-5 (1998).
Sivakumar et al., New insights into extracellular matrix assembly and reorganization from dynamic imaging of extracellular matrix proteins in living osteoblasts. *J. Cell. Sci.*, 119(7):1350-60 (2006).

(56) References Cited

OTHER PUBLICATIONS

Skiple Skjerpen et al., Binding of FGF-1 variants to protein kinase CK2 correlates with mitogenicity. *EMBO J.* 21(15): 4058-69 (2002).
Slater et al., Involvement of platelets in stimulating osteogenic activity. *J. Orthopaedic Res.*, 13: 655-63 (1995).
Smith et al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et al., A range of clinical phenotypes associated with mutations in CRX, a photoreceptor transcription-factor gene. *Am. J. Hum. Genet.*, 63: 1307-15 (1998).
Staehling-Hampton et al., A 52-kb delection in the SOST-MEOX1 intergenic region on 17q12-q21 is associated with van Buchem disease in the Dutch population. *Am. J. Med. Gen.* 110: 144-52 (2002).
Stanley et al., DAN is a secreted glycopeotein related to *Xenopus cerberus. Mech. Dev.*, 77: 173-84 (1998).
Statement of Grounds of Appeal to Decision of Opposition against European Patent No. 1133558, dated Sep. 28, 2009.
Stenmark et al., Distinct structural elements of rab5 define its functional specificity. *EMBO J.*, 13(3): 575-83 (1994).
Strachan et al., Human Molecular Genetics, 2nd Edition, Figure 15.4 (1999).
Sudo et al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Sutherland et al., Sclerostin romotes the apoptosis of human osteoblastic cells: A novel regulation of bone formation. *Bone*, 35:828-35 (2004).
Suzawa et al., Extracellular matrix-associated bone morphogenetic proteins are essential for differentiation of murine osteoblastic cells in vitro. *Endocrinology*, 140:2125-33 (1999).
Sverdlov et al., Perpetually mobile footprints of ancient infections in human genome. *FEBS Lett.*, 428: 1-6 (1998).
Sylatron label, cited in Opposition against European Patent No. 1721979 by Opponent: Novartis AG, dated Jun. 15, 2011.
Takakura, Drug delivery systems in gene therapy. *Nippon Rinsho*, 56(3):691-5 (1998) (Abstract Only).
Takeda et al., GenBank Sequence Database Accession No. AAB33865, May 27, 1995.
Takeda et al., GenBank Sequence Database Accession No. D38082, dated Dec. 27, 2006.
Takeda et al., GenBank Sequence Database Accession No. S75359, May 27, 1995.
Takeda et al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et al., Human immunoglobulin transgenes undergo rearrangement, somatic mutation and class switching in mice that lack endogenous IgM. *Int. Immun.*, 6:579 (1994).
The Merck Manual—Second Home Edition, Ch. 61:1-3 (2005).
Thompson et al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et al., Prediction of progress at last. *Nature*, 354:105-6 (1991).
Tjaderhane et al., A high sucrose diet decreases the mechanical strength of bones in growing rats. J. *Nutr.*, 128: 1807-10 (1998).
Tuncay et al., Oxygen tension regulates osteoblast function. *Am. J. Orthod. Dentofac. Orthop.*, 105: 457-63 (1994).
Uitterlinden et al., Relation of alleles of the collagen type Iα1 gene to bone density and the risk of osteoporotic fractures in postmenopausal women. *New Engl. J. Med.*, 338: 1016-21 (1998).
Valero et al., Quaternary structure of casein kinase 2. *J. Biol. Chem.*, 27(14): 8345-52 (1995).
Van Bezooijen et al., Sclerostin is an osteocyte-expressed negative regulator of bone formation, but not a classical BMP antagonist. *J. Exp. Med.*, 199: 805-14 (2004).
Van Bezooijen et al., SOST/sclerostin, an osteocyte-derived negative regulator of bone formation, *Cytokine Growth Factor Rev.*, 16: 319-27 (2005).
Van Bezooijen et al., Wnt but not BMP signaling is involved in the inhibitory action of sclerostin on BMP-stimulated bone formation. *J. Bone. Miner. Res.* 22:19-28 (2007).
Van Hul et al., Van Buchem Disease (hyperostosis corticalis generalisata) maps to chromosome 17q12-a21. *Am. J. Hum. Genet.*, 2:391-9 (1998).
Vanier et al., Recent advances in elucidating Niemann-Pick C disease. *Brain Pathol.* 8: 163-74 (1998).
Veverka et al., Characterization of the structural features and interactions of sclerostin. *J. Biol. Chem.*, 284(16): 10890-900 (2009).
Viter et al., Analysis of antigenic structure of potato virus M Ukrainian strains. *Biopolimery I Kletka, Naukova Dumka, Kiev K*, UK, 16: 312-9 (2000).
Von Bubnoff et al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang et al., IFP 35 forms complexes with B-ATF, a member of the AP1 family of transcription factors. *Biochem. Biophys. Res. Commun.*, 229: 316-22 (1996).
Wang, Bone morphogenetic proteins (BMPs): Therapeutic potential in healing bony defects. *TIBTECH*, 11:379-83 (1993).
Warmington et al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).
Warmington et al., Sclerostin monoclonal antibody treatment of osteoporotic rats completely reverses one year of overiectomy-induced systemic bone loss, *J. Bone Min. Res.*, 20:S22 (2005).
Winkler et al., Noggin and sclerostin bone morphogenetic protein antagonists form a mutually inhibitory complex. *J. Biol. Chem.*, 279(35): 36296-8 (2004).
Winkler et al., Osteocyte control of bone formation via sclerostin, a novel BMP antagonist. *EMBO J.* 22: 6267-76 (2003).
Winkler et al., Sclerostin inhibition of Wnt-3a-induced C3H10T1/2 cell differentiation is indirect and mediated by bone morphogenetic proteins. *J. Biol. Chem.* 280: 2498-502 (2005).
Winter et al., Making antibodies by phase display technology. *Annu. Rev. Immunol.*, 12:433-55 (1994).
Wolff et al., Monoclonal antibody homodimers: Enhanced antitumor activity in nude mice. *Cancer Res.*, 53:2560-5 (1993).
Written submission—Observation by a Third Party According to Art.115 EPC, Opposition to European Patent No. 1133558, dated Nov. 25, 2008.
Written submission of Eli Lilly & Company to European Patent Office, Opposition to European Patent No. 1133558, dated May 29, 2007.
Written Submission of Eli Lilly & Company, Opposition to European Patent No. 1133558, dated Mar. 9, 2009.
Written submission of UCB S.A., Proprietor's Preliminary Response to the Opponent's submission of Mar. 9, 2009, Opposition to European Patent No. 1133558, dated Mar. 20, 2009.
Written submission of UCB S.A., Proprietor's Response to Opposition against European Patent No. 1133558, dated Mar. 14, 2008.
Yanagita et al., USAG-1: A bone morphogenetic protein antagonist abundantly expressed in the kidney. *Biochem. Biophys. Res. Comm.* 316: 490-550 (2004).
Yang et al., CDR walking mutagenesis for the affinity maturation of a potent human Anti-HIV-1 antibody into the picomolar range. *J. Mol. Biol.*, 254:392-403 (1995).

(56) References Cited

OTHER PUBLICATIONS

Yates et al., Inhibition of bone resorption by inorganic phosphate in mediated by both reduced osteoclast formation and decreased activity of mature osteoclasts. *J. Bone Miner. Res.*, 6(5): 476-8 (1990).
Yerges et al., NCBI Sequence Database Accession No. NM_001203, Jul. 12, 2009.
Yerges et al., NCBI Sequence Database Accession No. NP_001194, Jul. 12, 2009.
Yoshida et al., Osteoinduction capability of recombinant human bone morphogenetic protein-2 in intramuscular and subcutaneous sites: An experimental study. *J. Cranio-Maxillofac. Surg.*, 26: 112-5 (1998).
Zambaux et al., Influence of experimental parameters on the characteristics of poly(lactic acid) nanoparticles prepared by a double emulsion method. *J. Controlled Rel.*, 50(1-3):31-40 (1998).
Zhang et al., Humanization of an anti-human TNF-β antibody by variable region resurfacing with the aid of molecular modeling. *Molec. Immunol.*, 42(12):1445-51 (2005).
Zimmerman et al., The spemann organizer signal noggin binds and inactives bone morphogenetic protein 4. *Cell*, 86(4):599-606 (1996).
Zur Muhlen et al., Solid lipid nanoparticles (SLN) for controlled drug delivery—Drug release and release mechanism. *Eur. J. Pharm. Biopharm.*, 45(2):149-55 (1998).
Opposition Statement of May 20, 2007 filed by Opponent 2 (Eli Lilly) against European Patent No. 1133558.
Strachan et al. (Eds.), Diagram from text book entitled Human Molecular Genetics, 2nd Edition (1999).
Declaration of Dr. Raymond Dalgleish dated Dec. 8, 2011, citation in Appeal, European Patent No. 1133558.
Morrison et al., ATP is a potent stimulator of the activiation and formation of rodent osteoclasts. *J. Physiol.*, 511.2: 495-500 (1998).
Zlotogora et al., Dominance and homozygosity, *Am. J. Med. Genet.*, 68: 412-6 (1997).
Bos et al., ras ongogenes in human cancer: A review, *Cancer Res.*, 49: 4682-9 (1989).
Diagram of the candidate interval, citation by Propriator in Opposition against European Patent No. 1721979 on Feb. 20, 2012.
Strachan et al. (Eds.), Human Molecular Genetics, 1st Edition, p. 420 (1996).
Spranger, International classification of osteochondrodysplasias, *Eur. J. Pediatr.*, 151: 407-15 (1992).
UCB and Amgen announce positive phase 2 results of CDP7851/AMG785 in patients with post menopausal osteoporosis (PMO), dated Apr. 21, 2011—Citation in Opposition against European Patent No. 1721979.
Bigger versions of Figures from Declaration of Professor Teresa Attwood, citation in Appeal, European Patent No. 1133558, dated Apr. 13, 2010.
Summons to attend oral proceedings in Opposition against European Patent No. 1721979, dated Nov. 12, 2012.
Written submission in response to summons to oral proceedings in Opposition against European Patent No. 1721979, Opponent: Norvartis AG, dated Feb. 25, 2013.
Written submission in response to summons to oral proceedings in Opposition against European Patent No. 1721979, Opponent: Eli Lilly Company, dated Feb. 25, 2013.
Proprietor's Written submission in preparation for oral proceedings in Opposition against European Patent No. 1721979, Proprietor: UCB Pharma S.A., dated Feb. 25, 2013.
Observations of Opponent: Laudens in response to summons to oral proceedings in Opposition against European Patent No. 1721979, dated Feb. 25, 2013.
Annex EW6 to Declaration filed in connection with the European Patent EP 1133558 Opposition, Expert opinion of Prof. Dr. Edgar Wingender, dated Sep. 24, 2009.
Abbas et al. (Eds.), Cellular and Molecular Immunology, Third Edition, Section II, p. 54 (1997).
Wollenberger et al. (Eds.), Analytische Biochemie, Chapter 3, pp. 47-49 (2003).
Submission in response to oral proceedings in Opposition against European Patent No. 1721979, Opponent: Eli Lilly, dated Apr. 24, 2013.
Minutes of the oral proceedings before the opposition division for Opposition against European Patent No. 1721979, dated May 10, 2013.
Opposition Decision for Opposition against European Patent No. 1721979, dated Aug. 2, 2013.
Latham, The biochemical and cellular characterization of sclerostin, The causative gene for sclerostenosis. *Calcified Tissue International*, 70(4):244 (2002).

* cited by examiner

A.

```
  1 AQVLTQTPAS VSAAVGGTVT INCQSSQSVY DNNWLAWFQQ KPGQPPKLLI
 51 YDASDLASGV PSRFSGSGSG TQFTLTISGV QCADAATYYC QGAYNDVIYA
101 FGGGTEVVVK RTDAAPTVSI FPPSSEQLTS GGASVVCFLN NFYPKDINVK
151 WKIDGSERQN GVLNSWTDQD SKDSTYSMSS TLTLTKDEYE RHNSYTCEAT
201 HKTSTSPIVK SFNRNEC
```

B.

```
  1 QSLEESGGRL VTPGTPLTLT CTASGFSLSS YWMNWVRQAP GEGLEWIGTI
 51 DSGGRTDYAS WAKGRFTISR TSTTMDLKMT SLTTGDTARY FCARNWNLWG
101 QGTLVTVSSA STKGPSVYPL APGSAAQTNS MVTLGCLVKG YFPEPVTVTW
151 NSGSLSSGVH TFPAVLQSDL YTLSSSVTVP SSTWPSETVT CNVAHPASST
201 KVDKKIVPRD CGCKPCICTV PEVSSVFIFP PKPKDVLTIT LTPKVTCVVV
251 DISKDDPEVQ FSWFVDDVEV HTAQTQPREE QFNSTFRSVS ELPIMHQDWL
301 NGKEFKCRVN SAAFPAPIEK TISKTKGRPK APQVYTIPPP KEQMAKDKVS
351 LTCMITDFFP EDITVEWQWN GQPAENYKNT QPIMNTNGSY FVYSKLNVQK
401 SNWEAGNTFT CSVLHEGLHN HHTEKSLSHS PGK
```

```
  1 QIVLTQSPTI VSASPGEKVT LICSASSSVS FVDWFQQKPG TSPKRWIYRT
 51 SNLGFGVPAR FSGGGSGTSH SLTISRMEAE DAATYYCQQR STYPPTFGAG
101 TKLELKRADA APTVSIFPPS SEQLTSGGAS VVCFLNNFYP KDINVKWKID
151 GSERQNGVLN SWTDQDSKDS TYSMSSTLTL TKDEYERHNS YTCEATHKTS
201 TSPIVKSFNR NEC
```

B.

```
  1 QVTLKESGPG ILQPSQTLSL TCSFSGFSLS TSGMGVGWIR HPSGKNLEWL
 51 AHIWWDDVKR YNPVLKSRLT ISKDTSNSQV FLKIANVDTA DTATYYCARI
101 EDFDYDEEYY AMDYWGQGTS VIVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFVYS KLNVQKSNWE AGNTFTCSVL HEGLHNHHTE KSLSHSPGK
```

```
  1 DIVLTQSPAS LTVSLGLRAT ISCKASQSVD YDGDSYMNWY QQKPGQPPKL
 51 LIYAASNLES GIPARFSGNG SGTDFTLNIH PVEEEDAVTY YCQQSNEDPW
101 TFGGGTKLEI KRADAAPTVS IFPPSSEQLT SGGASVVCFL NNFYPKDINV
151 KWKIDGSERQ NGVLNSWTDQ DSKDSTYSMS STLTLTKDEY ERHNSYTCEA
201 THKTSTSPIV KSFNRNEC
```

B.

```
  1 EVQLQQSGPE LVKPGTSVKM SCKASGYTFT DCYMNWVKQS HGKSLEWIGD
 51 INPFNGGTTY NQKFKGKATL TVDKSSSTAY MQLNSLTSDD SAVYYCARSH
101 YYFDGRVPWD AMDYWGQGTS VTVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFIYS KLNVQKSNWE AGNTFTCSVL HEGLHNHHTE KSLSHSPGK
```

```
  1 DVQMIQSPSS LSASLGDIVT MTCQASQGTS INLNWFQQKP GKAPKLLIYG
 51 SSNLEDGVPS RFSGSRYGTD FTLTISSLED EDLATYFCLQ HSYLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

B.

```
  1 EVQLQQSGPE LVTPGASVKI SCKASGYTFT DHYMSWVKQS HGKSLEWIGD
 51 INPYSGETTY NQKFKGTATL TVDKSSSIAY MEIRGLTSED SAVYYCARDD
101 YDASPFAYWG QGTLVTVSAA KTTPPSVYPL APGSAAQTNS MVTLGCLVKG
151 YFPEPVTVTW NSGSLSSGVH TFPAVLQSDL YTLSSSVTVP SSTWPSETVT
201 CNVAHPASST KVDKKIVPRD CGCKPCICTV PEVSSVFIFP PKPKDVLTIT
251 LTPKVTCVVV DISKDDPEVQ FSWFVDDVEV HTAQTQPREE QFNSTFRSVS
301 ELPIMHQDWL NGKEFKCRVN SPAFPAPIEK TISKTKGRPK APQVYTIPPP
351 KEQMAKDKVS LTCMITDFFP EDITVEWQWN GQPAENYKNT QPIMDTDGSY
401 FIYSKLNVQK SNWEAGNTFT CSVLHEGLHN HHTEKSLSHS PGK
```

Figure 4

* = statistically significantly different from Vehicle

Error bars = Mean +/- standard deviation

```
1   QGWQAFKNDA TEIIPELGEY PEPPPELENN KTMNRAENGG RPPHHPFETK

51  DVSEYSCREL HFTRYVTDGP CRSAKPVTEL VCSGQCGPAR LLPNAIGRGK
          C1              C2             C3   C4
101 WWRPSGPDFR CIPDRYRAQR VQLLCPGGEA PRARKVRLVA SCKCKRLTRF
               C5             C6                C7 C8
151 HNQSELKDFG TEAARPQKGR KPRPRARSAK ANQAELENAY
```

```
1   CAGGGGTGGC AGGCGTTCAA GAATGATGCC ACGGAAATCA TCCCCGAGCT
51  CGGAGAGTAC CCCGAGCCTC CACCGGAGCT GGAGAACAAC AAGACCATGA
101 ACCGGGCGGA GAACGGAGGG CGGCCTCCCC ACCACCCCTT TGAGACCAAA
151 GACGTGTCCG AGTACAGCTG CCGCGAGCTG CACTTCACCC GCTACGTGAC
201 CGATGGGCCG TGCCGCAGCG CCAAGCCGGT CACCGAGCTG GTGTGCTCCG
251 GCCAGTGCGG CCCGGCGCGC CTGCTGCCCA ACGCCATCGG CCGCGGCAAG
301 TGGTGGCGAC CTAGTGGGCC CGACTTCCGC TGCATCCCCG ACCGCTACCG
351 CGCGCAGCGC GTGCAGCTGC TGTGTCCCGG TGGTGAGGCG CCGCGCGCGC
401 GCAAGGTGCG CCTGGTGGCC TCGTGCAAGT GCAAGCGCCT CACCCGCTTC
451 CACAACCAGT CGGAGCTCAA GGACTTCGGG ACCGAGGCCG CTCGGCCGCA
501 GAAGGGCCGG AAGCCGCGGC CCCGCGCCCG GAGCGCCAAA GCCAACCAGG
551 CCGAGCTGGA GAACGCCTAC
```

Figure 8

| Peptides | Seq.pos. | Obs. Mass | Sequence |
|---|---|---|---|
| T19.2 | 65-72 | 2146.34 | 1. YVTDGP CR (910) C2 |
| | 121-132 | (2145.8) | 2. VQLLCPGGEA PR (1239) C6 |
| T20 | | 9620.8 (MALDI); 9638.41 (ESI-MS) | |
| | 51-90 | (4419.1) | 1. DVSEYSCREL HFTRYVTDGP CRSAKPVTEL VCSGQCGPAR |
| | 104-149 | (5226.2) | 2. PSGPDFR CIPDRYRAQR VQLLCPGGEA PRARKVRLVA SCKCKRLT R |
| T20.6 | | 7105.7 (MALDI); 7122.0 (ESI-MS) | |
| | 51-64 | 3944.5 | 1. DVSEYSCREL HFTR (1740.9) C1 |
| | 101-117 | | 2. WWRPSGPPFR CIPDRYR (2206.6) C5 |
| | 73-90 | 3177.0 | 3. SAKPVTELVC SGQCGPAR (1802.2) C3,C4 |
| | 138-149 | | 4. LVASCKCKRL TR (1378.5) C7,C8 |
| T21-22 | | 10,147 (MALDI); 10170.3 (ESI-MS) | |
| | 51-90 | (4419.1) | 1. DVSEYSCREL HFTRYVTDGP CRSAKPVTEL VCSGQCGPAR |
| | 101-149 | (5754.8) | 2. WWRPSGPDFR CIPDRYRAQR VQLLCPGGEA PRARKVRLVA SCKCKRLTR |

Figure 11

| Peptides | Seq.pos. | Obs.Mass | Sequence |
|---|---|---|---|
| AspN14.6 | 34-47 | 1245.5 | ENGGRPPHHPF |
| | 12-25 | 1585.4 | EIIPELGFYP EPPP |
| | 158-184 | 2964.5 | DFGTEAARPQ KGRKPRPRAR SAKANQA |
| AspN18.6 | 9-50 | | DATEIIPELG EYPEPPPELE NNKTMNRAEN GGRPPHHPFE TK (Glycopeptide) |
| AspN22.7-23.5 | 51-154 | 11,740 | DVSEYSCREL HFTRYVTDGP CRSAKPVTEL VCSGQCGPAR LLPNAIGRGK WWRPSGPDFR CIPDRYRAQR VQLLCPGGEA PRARKVRLVA SCKCKRLTRF HNQS |

Figure 12

```
  1 QGWQAFKNDA TEIIPELGEY PEPPPELENN KTMNRAENGG RPPHHPFETK
                       |------Loop 1------|
                       C1           C2    C3 C4
 51 DVSEYSCREL HFTRYVTDGP CRSAKPVTEL VCSGQCGPAR LLPNAIGRGK
                          |---Loop 2---|
                         C5
101 WWRPSGPDFR CIPDRYRAQR VQLLCPGGEA PRARKVRLVA SCKCKRLTRF
    |---Loop 2---|            |---Loop 3---|
                                              C7 C8
                                             C6
151 HNQSELKDFG TEAARPQKGR KPRPRARSAK ANQAELENAY
```

*A. Loop 2 epitope for Mab-A and Mab-B*

C4GPARLLPNAIGRGKWWRPSGPDFRC5

*B. T20.6 epitope for Mab-C and Mab-D*

DVSEYSC1RELHFTR SAKPVTELVC3SGQC4GPAR

WWRPSGPDFRC5IPDRYR LVASC7KC8KRLTR

T20.6

*"T20.6 derivative 1 (cystine-knot + 4 arms)" epitope for Mab-D*
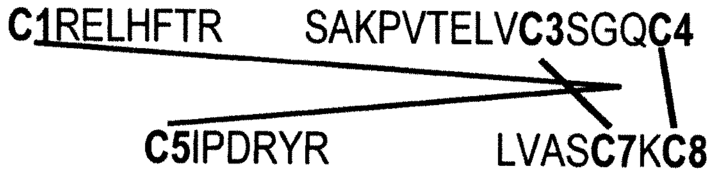
"T20.6 derivative 1 (cystine-knot + 4 arms)"
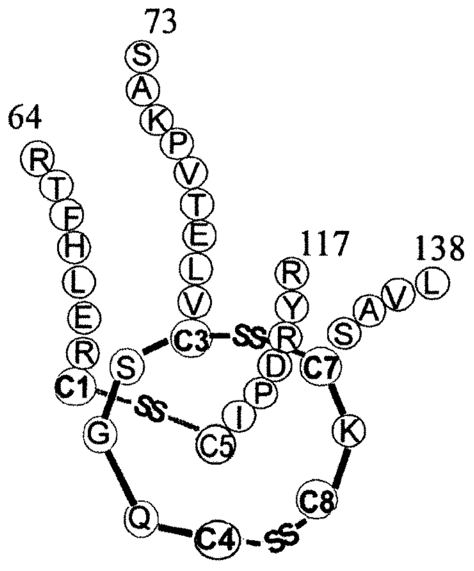
Figure 21

* = statistically significantly different from Mouse Scl group.

Error bars = Mean +/- SEM

* = statistically significantly different from Human Scl group.

Error bars = Mean +/- SEM

SEQUENCE LISTING

<160> NUMBER OF SEQ ID NOS: 396

<210> SEQ ID NO 1
<211> LENGTH: 190
<212> TYPE: PRT
<213> ORGANISM: Homo sapiens

<400> SEQUENCE: 1

```
Gln Gly Trp Gln Ala Phe Lys Asn Asp Ala Thr Glu Ile Ile Pro Glu
1               5                   10                  15

Leu Gly Glu Tyr Pro Glu Pro Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190
```

<210> SEQ ID NO 2
<211> LENGTH: 14
<212> TYPE: PRT
<213> ORGANISM: Homo sapiens

<400> SEQUENCE: 2

```
Asp Val Ser Glu Tyr Ser Cys Arg Glu Leu His Phe Thr Arg
1               5                   10
```

<210> SEQ ID NO 3
<211> LENGTH: 16
<212> TYPE: PRT
<213> ORGANISM: Homo sapiens

<400> SEQUENCE: 3

```
Ser Ala Lys Pro Val Thr Glu Leu Val Cys Ser Gly Gln Cys Gly Pro
1               5                   10                  15
```

<210> SEQ ID NO 4
<211> LENGTH: 16
<212> TYPE: PRT
<213> ORGANISM: Homo sapiens

<400> SEQUENCE: 4

```
Trp Trp Arg Pro Ser Gly Pro Asp Phe Arg Cys Ile Pro Asp Arg Tyr
1               5                   10                  15
```

<210> SEQ ID NO 5
<211> LENGTH: 12
<212> TYPE: PRT
<213> ORGANISM: Homo sapiens

<400> SEQUENCE: 5

```
Leu Val Ala Ser Cys Lys Cys Lys Arg Leu Thr Arg
1               5                   10
```

<210> SEQ ID NO 6
<211> LENGTH: 26
<212> TYPE: PRT
<213> ORGANISM: Homo sapiens

<400> SEQUENCE: 6

```
Cys Gly Pro Ala Arg Leu Leu Pro Asn Ala Ile Gly Arg Gly Lys Trp
1               5                   10                  15

Trp Arg Pro Ser Gly Pro Asp Phe Arg Cys
            20                  25
```

<210> SEQ ID NO 7
<211> LENGTH: 214
<212> TYPE: PRT
<213> ORGANISM: Mus musculus

<400> SEQUENCE: 7

```
Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Leu Ala Thr Tyr Phe Cys Leu Gln His Ser Tyr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 8
<211> LENGTH: 645
<212> TYPE: DNA

<213> ORGANISM: Mus musculus

<400> SEQUENCE: 8

```
gatgtccaga tgattcagtc tccatcctcc ctgtctgcat ctttgggaga catagtcacc     60

atgacttgcc aggcaagtca gggcactagc attaatttaa actggtttca gcaaaaacca    120

gggaaggctc ctaagctcct gatctatggt tcaagcaact tggaagatgg ggtcccatca    180

aggttcagtg gcagtagata tgggacagat ttcactctca ccatcagcag cctggaggat    240

gaagatctgg caacttattt ctgtctacaa catagttatc tcccgtacac gttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 9
<211> LENGTH: 236
<212> TYPE: PRT
<213> ORGANISM: Mus musculus

<400> SEQUENCE: 9

```
Met Asn Thr Arg Ala Pro Ala Glu Phe Leu Gly Phe Leu Leu Leu Trp
1               5                   10                  15

Phe Leu Gly Ala Arg Cys Asp Val Gln Met Ile Gln Ser Pro Ser Ser
            20                  25                  30

Leu Ser Ala Ser Leu Gly Asp Ile Val Thr Met Thr Cys Gln Ala Ser
        35                  40                  45

Gln Gly Thr Ser Ile Asn Leu Asn Trp Phe Gln Gln Lys Pro Gly Lys
    50                  55                  60

Ala Pro Lys Leu Leu Ile Tyr Gly Ser Ser Asn Leu Glu Asp Gly Val
65                  70                  75                  80

Pro Ser Arg Phe Ser Gly Ser Arg Tyr Gly Thr Asp Phe Thr Leu Thr
                85                  90                  95

Ile Ser Ser Leu Glu Asp Glu Asp Leu Ala Thr Tyr Phe Cys Leu Gln
            100                 105                 110

His Ser Tyr Leu Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235
```

<210> SEQ ID NO 10
<211> LENGTH: 711
<212> TYPE: DNA
<213> ORGANISM: Mus musculus

<400> SEQUENCE: 10
atgaacacga gggcccctgc tgagttcctt gggttcctgt tgctctggtt tttaggtgcc 60
agatgtgatg tccagatgat tcagtctcca tcctccctgt ctgcatcttt gggagacata 120
gtcaccatga cttgccaggc aagtcagggc actagcatta atttaaactg gtttcagcaa 180
aaaccaggga aggctcctaa gctcctgatc tatggttcaa gcaacttgga agatggggtc 240
ccatcaaggt tcagtggcag tagatatggg acagatttca ctctcaccat cagcagcctg 300
gaggatgaag atctggcaac ttatttctgt ctacaacata gttatctccc gtacacgttc 360 ggaggggga ccaagctgga aataaaacgg gctgatgctg caccaactgt atccatcttc 420
ccaccatcca gtgagcagtt aacatctgga ggtgcctcag tcgtgtgctt cttgaacaac 480
ttctacccca aagacatcaa tgtcaagtgg aagattgatg gcagtgaacg acaaaatggc 540
gtcctgaaca gttggactga tcaggacagc aaagacagca cctacagcat gagcagcacc 600
ctcacgttga ccaaggacga gtatgaacga cataacagct atacctgtga ggccactcac 660
aagacatcaa cttcacccat tgtcaagagc ttcaacagga atgagtgtta g 711

<210> SEQ ID NO 11
<211> LENGTH: 443
<212> TYPE: PRT
<213> ORGANISM: Mus musculus

<400> SEQUENCE: 11

Glu Val Gln Leu Gln Gln Ser Gly Pro Glu Leu Val Thr Pro Gly Ala
1 5 10 15

Ser Val Lys Ile Ser Cys Lys Ala Ser Gly Tyr Thr Phe Thr Asp His
20 25 30

Tyr Met Ser Trp Val Lys Gln Ser His Gly Lys Ser Leu Glu Trp Ile
35 40 45

Gly Asp Ile Asn Pro Tyr Ser Gly Glu Thr Thr Tyr Asn Gln Lys Phe
50 55 60

Lys Gly Thr Ala Thr Leu Thr Val Asp Lys Ser Ser Ser Ile Ala Tyr
65 70 75 80

Met Glu Ile Arg Gly Leu Thr Ser Glu Asp Ser Ala Val Tyr Tyr Cys
85 90 95

Ala Arg Asp Asp Tyr Asp Ala Ser Pro Phe Ala Tyr Trp Gly Gln Gly
100 105 110

Thr Leu Val Thr Val Ser Ala Ala Lys Thr Thr Pro Pro Ser Val Tyr
115 120 125

Pro Leu Ala Pro Gly Ser Ala Ala Gln Thr Asn Ser Met Val Thr Leu
130 135 140

Gly Cys Leu Val Lys Gly Tyr Phe Pro Glu Pro Val Thr Val Thr Trp
145 150 155 160

Asn Ser Gly Ser Leu Ser Ser Gly Val His Thr Phe Pro Ala Val Leu
165 170 175

Gln Ser Asp Leu Tyr Thr Leu Ser Ser Ser Val Thr Val Pro Ser Ser
180 185 190

Thr Trp Pro Ser Glu Thr Val Thr Cys Asn Val Ala His Pro Ala Ser
195 200 205

-continued

```
Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Pro Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 12
<211> LENGTH: 1332
<212> TYPE: DNA
<213> ORGANISM: Mus musculus

<400> SEQUENCE: 12

```
gaggtccagc tgcaacagtc tggacctgaa ctggtgacgc ctggggcttc agtgaagata     60

tcttgtaagg cttctggata cacattcact gaccactaca tgagctgggt gaagcagagt    120

catggaaaaa gccttgagtg gattggagat attaatccct attctggtga aactacctac    180

aaccagaagt tcaagggcac ggccacattg actgtagaca agtcttccag tatagcctac    240

atggagatcc gcggcctgac atctgaggac tctgcagtct attactgtgc aagagatgat    300

tacgacgcct ctccgtttgc ttactggggc caagggactc tggtcactgt ctctgcagcc    360

aaaacgacac ccccatctgt ctatccactg gcccctggat ctgctgccca aactaactcc    420

atggtgaccc tgggatgcct ggtcaagggc tatttccctg agccagtgac agtgacctgg    480

aactctggat ccctgtccag cggtgtgcac accttcccag ctgtcctgca gtctgacctc    540

tacactctga gcagctcagt gactgtcccc tccagcacct ggcccagcga gaccgtcacc    600

tgcaacgttg cccacccggc cagcagcacc aaggtggaca agaaaattgt gcccagggat    660

tgtggttgta agccttgcat atgtacagtc ccagaagtat catctgtctt catcttcccc    720

ccaaagccca aggatgtgct caccattact ctgactccta aggtcacgtg tgttgtggta    780
```

```
gacatcagca aggatgatcc cgaggtccag ttcagctggt ttgtagatga tgtggaggtg    840

cacacagctc agacgcaacc ccgggaggag cagttcaaca gcactttccg ctcagtcagt    900

gaacttccca tcatgcacca ggactggctc aatggcaagg agttcaaatg cagggtcaac    960

agtccagctt tccctgcccc catcgagaaa accatctcca aaaccaaagg cagaccgaag   1020

gctccacagg tgtacaccat tccacctccc aaggagcaga tggccaagga taaagtcagt   1080

ctgacctgca tgataacaga cttcttccct gaagacatta ctgtggagtg gcagtggaat   1140

gggcagccag cggagaacta caagaacact cagcccatca tggacacaga tggctcttac   1200

ttcatctaca gcaagctcaa tgtgcagaag agcaactggg aggcaggaaa tactttcacc   1260

tgctctgtgt tacatgaggg cctgcacaac caccatactg agaagagcct ctcccactct   1320

cctggtaaat ga                                                        1332


<210> SEQ ID NO 13
<211> LENGTH: 462
<212> TYPE: PRT
<213> ORGANISM: Mus musculus

<400> SEQUENCE: 13

Met Arg Cys Arg Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Thr
            20                  25                  30

Pro Gly Ala Ser Val Lys Ile Ser Cys Lys Ala Ser Gly Tyr Thr Phe
        35                  40                  45

Thr Asp His Tyr Met Ser Trp Val Lys Gln Ser His Gly Lys Ser Leu
    50                  55                  60

Glu Trp Ile Gly Asp Ile Asn Pro Tyr Ser Gly Glu Thr Thr Tyr Asn
65                  70                  75                  80

Gln Lys Phe Lys Gly Thr Ala Thr Leu Thr Val Asp Lys Ser Ser Ser
                85                  90                  95

Ile Ala Tyr Met Glu Ile Arg Gly Leu Thr Ser Glu Asp Ser Ala Val
            100                 105                 110

Tyr Tyr Cys Ala Arg Asp Asp Tyr Asp Ala Ser Pro Phe Ala Tyr Trp
        115                 120                 125

Gly Gln Gly Thr Leu Val Thr Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270
```

```
Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Pro Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Ile Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460


<210> SEQ ID NO 14
<211> LENGTH: 1389
<212> TYPE: DNA
<213> ORGANISM: Mus musculus

<400> SEQUENCE: 14

atgagatgca ggtggatctt tctctttctc ctgtcaggaa ctgcaggtgt cctctctgag     60

gtccagctgc aacagtctgg acctgaactg gtgacgcctg ggcttcagt gaagatatct    120

tgtaaggctt ctggatacac attcactgac cactacatga gctgggtgaa gcagagtcat    180

ggaaaaagcc ttgagtggat tggagatatt aatccctatt ctggtgaaac tacctacaac    240

cagaagttca agggcacggc cacattgact gtagacaagt cttccagtat agcctacatg    300

gagatccgcg gcctgacatc tgaggactct gcagtctatt actgtgcaag agatgattac    360

gacgcctctc cgtttgctta ctggggccaa gggactctgg tcactgtctc tgcagccaaa    420

acgacacccc catctgtcta tccactggcc cctggatctg ctgcccaaac taactccatg    480

gtgaccctgg gatgcctggt caagggctat ttccctgagc cagtgacagt gacctggaac    540

tctggatccc tgtccagcgg tgtgcacacc ttcccagctg tcctgcagtc tgacctctac    600

actctgagca gctcagtgac tgtcccctcc agcacctggc ccagcgagac cgtcacctgc    660

aacgttgccc acccggccag cagcaccaag gtggacaaga aaattgtgcc cagggattgt    720

ggttgtaagc cttgcatatg tacagtccca gaagtatcat ctgtcttcat cttcccccca    780

aagcccaagg atgtgctcac cattactctg actcctaagg tcacgtgtgt tgtggtagac    840

atcagcaagg atgatcccga ggtccagttc agctggtttg tagatgatgt ggaggtgcac    900

acagctcaga cgcaaccccg ggaggagcag ttcaacagca ctttccgctc agtcagtgaa    960

cttcccatca tgcaccagga ctggctcaat ggcaaggagt tcaaatgcag ggtcaacagt   1020

ccagctttcc ctgcccccat cgagaaaacc atctccaaaa ccaaaggcag accgaaggct   1080
```

```
ccacaggtgt acaccattcc acctcccaag gagcagatgg ccaaggataa agtcagtctg   1140

acctgcatga taacagactt cttccctgaa gacattactg tggagtggca gtggaatggg   1200

cagccagcgg agaactacaa gaacactcag cccatcatgg acacagatgg ctcttacttc   1260

atctacagca agctcaatgt gcagaagagc aactgggagg caggaaatac tttcacctgc   1320

tctgtgttac atgagggcct gcacaaccac catactgaga agagcctctc ccactctcct   1380

ggtaaatga                                                           1389
```

<210> SEQ ID NO 15
<211> LENGTH: 218
<212> TYPE: PRT
<213> ORGANISM: Mus musculus

<400> SEQUENCE: 15

```
Asp Ile Val Leu Thr Gln Ser Pro Ala Ser Leu Thr Val Ser Leu Gly
1               5                   10                  15

Leu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Asn Gly Ser Gly Thr Asp Phe Thr Leu Asn Ile His
65                  70                  75                  80

Pro Val Glu Glu Glu Asp Ala Val Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 16
<211> LENGTH: 657
<212> TYPE: DNA
<213> ORGANISM: Mus musculus

<400> SEQUENCE: 16

```
gacattgtgc tgacccaatc tccagcttct ttgactgtgt ctctaggcct gagggccacc     60

atctcctgca aggccagcca aagtgttgat tatgatggtg atagttatat gaactggtac    120

cagcagaaac caggacagcc acccaaactc ctcatctatg ctgcatccaa tctagaatct    180

gggatcccag ccaggtttag tggcaatggg tctgggacag acttcaccct caacatccat    240
```

```
cctgtggagg aggaggatgc tgtaacctat tactgtcaac aaagtaatga ggatccgtgg    300

acgttcggtg gaggcaccaa gctggaaatc aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgttag       657
```

<210> SEQ ID NO 17
<211> LENGTH: 238
<212> TYPE: PRT
<213> ORGANISM: Mus musculus

<400> SEQUENCE: 17

```
Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Leu Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Asn Gly Ser Gly Thr Asp Phe Thr
                85                  90                  95

Leu Asn Ile His Pro Val Glu Glu Glu Asp Ala Val Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 18
<211> LENGTH: 717
<212> TYPE: DNA
<213> ORGANISM: Mus musculus

<400> SEQUENCE: 18

```
atggagacag acacaatcct gctatgggtg ctgctgctct gggttccagg ctccactggt     60

gacattgtgc tgacccaatc tccagcttct ttgactgtgt ctctaggcct gagggccacc    120
```

-continued

```
atctcctgca aggccagcca aagtgttgat tatgatggtg atagttatat gaactggtac    180

cagcagaaac caggacagcc acccaaactc ctcatctatg ctgcatccaa tctagaatct    240

gggatcccag ccaggtttag tggcaatggg tctgggacag acttcaccct caacatccat    300

cctgtggagg aggaggatgc tgtaacctat tactgtcaac aaagtaatga ggatccgtgg    360

acgttcggtg gaggcaccaa gctggaaatc aaacgggctg atgctgcacc aactgtatcc    420

atcttcccac catccagtga gcagttaaca tctggaggtg cctcagtcgt gtgcttcttg    480

aacaacttct accccaaaga catcaatgtc aagtggaaga ttgatggcag tgaacgacaa    540

aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttag       717


<210> SEQ ID NO 19
<211> LENGTH: 449
<212> TYPE: PRT
<213> ORGANISM: Mus musculus

<400> SEQUENCE: 19

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Cys
            20                  25                  30

Tyr Met Asn Trp Val Lys Gln Ser His Gly Lys Ser Leu Glu Trp Ile
        35                  40                  45

Gly Asp Ile Asn Pro Phe Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Ser His Tyr Tyr Phe Asp Gly Arg Val Pro Trp Asp Ala Met
            100                 105                 110

Asp Tyr Trp Gly Gln Gly Thr Ser Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270
```

```
Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys


<210> SEQ ID NO 20
<211> LENGTH: 1350
<212> TYPE: DNA
<213> ORGANISM: Mus musculus

<400> SEQUENCE: 20

gaggtccagc tgcaacaatc tggacctgag ctggtgaagc ctgggacttc agtgaagatg      60

tcctgtaagg cttctggata cacattcact gactgctaca tgaactgggt gaagcagagc     120

catgggaaga gccttgaatg gattggagat attaatcctt tcaacggtgg tactacctac     180

aaccagaagt tcaagggcaa ggccacattg actgtagaca aatcctccag cacagcctac     240

atgcagctca acagcctgac atctgacgac tctgcagtct attactgtgc aagatcccat     300

tattacttcg atggtagagt cccttgggat gctatggact actggggtca aggaacctca     360

gtcaccgtct cctcagccaa aacgacaccc ccatctgtct atccactggc ccctggatct     420

gctgcccaaa ctaactccat ggtgaccctg ggatgcctgg tcaagggcta tttccctgag     480

ccagtgacag tgacctggaa ctctggatcc ctgtccagcg gtgtgcacac cttcccagct     540

gtcctgcagt ctgacctcta cactctgagc agctcagtga ctgtcccctc cagcacctgg     600

cccagcgaga ccgtcacctg caacgttgcc cacccggcca gcagcaccaa ggtggacaag     660

aaaattgtgc ccagggattg tggttgtaag ccttgcatat gtacagtccc agaagtatca     720

tctgtcttca tcttcccccc aaagcccaag gatgtgctca ccattactct gactcctaag     780

gtcacgtgtg ttgtggtaga catcagcaag gatgatcccg aggtccagtt cagctggttt     840

gtagatgatg tggaggtgca cacagctcag acgcaacccc gggaggagca gttcaacagc     900

actttccgct cagtcagtga acttcccatc atgcaccagg actggctcaa tggcaaggag     960

ttcaaatgca gggtcaacag tgcagctttc cctgccccca tcgagaaaac catctccaaa    1020

accaaaggca gaccgaaggc tccacaggtg tacaccattc cacctcccaa ggagcagatg    1080
```

-continued

```
gccaaggata aagtcagtct gacctgcatg ataacagact tcttccctga agacattact   1140

gtggagtggc agtggaatgg gcagccagcg gagaactaca agaacactca gcccatcatg   1200

gacacagatg gctcttactt catctacagc aagctcaatg tgcagaagag caactgggag   1260

gcaggaaata ctttcacctg ctctgtgtta catgagggcc tgcacaacca ccatactgag   1320

aagagcctct cccactctcc tggtaaatga                                    1350


<210> SEQ ID NO 21
<211> LENGTH: 468
<212> TYPE: PRT
<213> ORGANISM: Mus musculus

<400> SEQUENCE: 21

Met Gly Trp Asn Trp Ile Phe Leu Phe Leu Leu Ser Gly Thr Ala Gly
1               5                   10                  15

Val Tyr Ser Glu Val Gln Leu Gln Gln Ser Gly Pro Glu Leu Val Lys
            20                  25                  30

Pro Gly Thr Ser Val Lys Met Ser Cys Lys Ala Ser Gly Tyr Thr Phe
        35                  40                  45

Thr Asp Cys Tyr Met Asn Trp Val Lys Gln Ser His Gly Lys Ser Leu
    50                  55                  60

Glu Trp Ile Gly Asp Ile Asn Pro Phe Asn Gly Gly Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Asp Asp Ser Ala Val
            100                 105                 110

Tyr Tyr Cys Ala Arg Ser His Tyr Tyr Phe Asp Gly Arg Val Pro Trp
        115                 120                 125

Asp Ala Met Asp Tyr Trp Gly Gln Gly Thr Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
```

-continued

```
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465


<210> SEQ ID NO 22
<211> LENGTH: 1407
<212> TYPE: DNA
<213> ORGANISM: Mus musculus

<400> SEQUENCE: 22

atgggatgga actggatctt tctcttcctc ttgtcaggaa ctgcaggtgt ctactctgag     60

gtccagctgc aacaatctgg acctgagctg gtgaagcctg ggacttcagt gaagatgtcc    120

tgtaaggctt ctggatacac attcactgac tgctacatga actgggtgaa gcagagccat    180

gggaagagcc ttgaatggat tggagatatt aatcctttca acggtggtac tacctacaac    240

cagaagttca agggcaaggc cacattgact gtagacaaat cctccagcac agcctacatg    300

cagctcaaca gcctgacatc tgacgactct gcagtctatt actgtgcaag atcccattat    360

tacttcgatg gtagagtccc ttgggatgct atggactact ggggtcaagg aacctcagtc    420

accgtctcct cagccaaaac gacaccccca tctgtctatc cactggcccc tggatctgct    480

gcccaaacta actccatggt gaccctggga tgcctggtca agggctattt ccctgagcca    540

gtgacagtga cctggaactc tggatccctg tccagcggtg tgcacacctt cccagctgtc    600

ctgcagtctg acctctacac tctgagcagc tcagtgactg tcccctccag cacctggccc    660

agcgagaccg tcacctgcaa cgttgcccac ccggccagca gcaccaaggt ggacaagaaa    720

attgtgccca gggattgtgg ttgtaagcct tgcatatgta cagtcccaga agtatcatct    780

gtcttcatct tccccccaaa gcccaaggat gtgctcacca ttactctgac tcctaaggtc    840

acgtgtgttg tggtagacat cagcaaggat gatcccgagg tccagttcag ctggtttgta    900

gatgatgtgg aggtgcacac agctcagacg caaccccggg aggagcagtt caacagcact    960

ttccgctcag tcagtgaact tcccatcatg caccaggact ggctcaatgg caaggagttc   1020

aaatgcaggg tcaacagtgc agctttccct gcccccatcg agaaaaccat ctccaaaacc   1080

aaaggcagac cgaaggctcc acaggtgtac accattccac ctcccaagga gcagatggcc   1140

aaggataaag tcagtctgac ctgcatgata acagacttct tccctgaaga cattactgtg   1200

gagtggcagt ggaatgggca gccagcggag aactacaaga acactcagcc catcatggac   1260
```

acagatggct cttacttcat ctacagcaag ctcaatgtgc agaagagcaa ctgggaggca 1320
ggaaatactt tcacctgctc tgtgttacat gagggcctgc acaaccacca tactgagaag 1380
agcctctccc actctcctgg taaatga 1407

<210> SEQ ID NO 23
<211> LENGTH: 217
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 23

Ala Gln Val Leu Thr Gln Thr Pro Ala Ser Val Ser Ala Ala Val Gly
1 5 10 15

Gly Thr Val Thr Ile Asn Cys Gln Ser Ser Gln Ser Val Tyr Asp Asn
20 25 30

Asn Trp Leu Ala Trp Phe Gln Gln Lys Pro Gly Gln Pro Pro Lys Leu
35 40 45

Leu Ile Tyr Asp Ala Ser Asp Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Ala Asp Ala Ala Thr Tyr Tyr Cys Gln Gly Ala Tyr Asn Asp
85 90 95

Val Ile Tyr Ala Phe Gly Gly Gly Thr Glu Val Val Val Lys Arg Thr
100 105 110

Asp Ala Ala Pro Thr Val Ser Ile Phe Pro Pro Ser Ser Glu Gln Leu
115 120 125

Thr Ser Gly Gly Ala Ser Val Val Cys Phe Leu Asn Asn Phe Tyr Pro
130 135 140

Lys Asp Ile Asn Val Lys Trp Lys Ile Asp Gly Ser Glu Arg Gln Asn
145 150 155 160

Gly Val Leu Asn Ser Trp Thr Asp Gln Asp Ser Lys Asp Ser Thr Tyr
165 170 175

Ser Met Ser Ser Thr Leu Thr Leu Thr Lys Asp Glu Tyr Glu Arg His
180 185 190

Asn Ser Tyr Thr Cys Glu Ala Thr His Lys Thr Ser Thr Ser Pro Ile
195 200 205

Val Lys Ser Phe Asn Arg Asn Glu Cys
210 215

<210> SEQ ID NO 24
<211> LENGTH: 654
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Rabbit-mouse chimera

<400> SEQUENCE: 24
gcgcaagtgc tgacccagac tccagcctcc gtgtctgcag ctgtgggagg cacagtcacc 60
atcaattgcc agtccagtca gagtgtttat gataacaact ggttagcctg gtttcagcag 120
aaaccagggc agcctcccaa gctcctgatt tatgatgcat ccgatctggc atctggggtc 180

```
ccatcgcggt tcagtggcag tggatctggg acacagttca ctctcaccat cagcggcgtg    240

cagtgtgccg atgctgccac ttactactgt caaggcgctt ataatgatgt tatttatgct    300

ttcggcggag ggaccgaggt ggtggtcaaa cgtacggatg ctgcaccaac tgtatccatc    360

ttcccaccat ccagtgagca gttaacatct ggaggtgcct cagtcgtgtg cttcttgaac    420

aacttctacc ccaaagacat caatgtcaag tggaagattg atggcagtga acgacaaaat    480

ggcgtcctga acagttggac tgatcaggac agcaaagaca gcacctacag catgagcagc    540

accctcacgt tgaccaagga cgagtatgaa cgacataaca gctatacctg tgaggccact    600

cacaagacat caacttcacc cattgtcaag agcttcaaca ggaatgagtg ttag          654
```

<210> SEQ ID NO 25
<211> LENGTH: 239
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 25

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
            20                  25                  30

Val Ser Ala Ala Val Gly Gly Thr Val Thr Ile Asn Cys Gln Ser Ser
        35                  40                  45

Gln Ser Val Tyr Asp Asn Asn Trp Leu Ala Trp Phe Gln Gln Lys Pro
    50                  55                  60

Gly Gln Pro Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Ala Asp Ala Ala Thr Tyr Tyr Cys
            100                 105                 110

Gln Gly Ala Tyr Asn Asp Val Ile Tyr Ala Phe Gly Gly Gly Thr Glu
        115                 120                 125

Val Val Val Lys Arg Thr Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 26
<211> LENGTH: 720
<212> TYPE: DNA

<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: Rabbit-mouse chimera

<400> SEQUENCE: 26
atggacacga gggcccccac tcagctgctg gggctcctgc tgctctggct cccaggtgcc 60
acatttgcgc aagtgctgac ccagactcca gcctccgtgt ctgcagctgt gggaggcaca 120
gtcaccatca attgccagtc cagtcagagt gtttatgata acaactggtt agcctggttt 180
cagcagaaac cagggcagcc tcccaagctc ctgatttatg atgcatccga tctggcatct 240
ggggtcccat cgcggttcag tggcagtgga tctgggacac agttcactct caccatcagc 300
ggcgtgcagt gtgccgatgc tgccacttac tactgtcaag gcgcttataa tgatgttatt 360
tatgctttcg gcggagggac cgaggtggtg gtcaaacgta cggatgctgc accaactgta 420
tccatcttcc caccatccag tgagcagtta acatctggag gtgcctcagt cgtgtgcttc 480
ttgaacaact tctaccccaa agacatcaat gtcaagtgga agattgatgg cagtgaacga 540
caaaatggcg tcctgaacag ttggactgat caggacagca aagacagcac ctacagcatg 600
agcagcaccc tcacgttgac caaggacgag tatgaacgac ataacagcta tacctgtgag 660
gccactcaca agacatcaac ttcacccatt gtcaagagct tcaacaggaa tgagtgttag 720

<210> SEQ ID NO 27
<211> LENGTH: 433
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody

<400> SEQUENCE: 27

Gln Ser Leu Glu Glu Ser Gly Gly Arg Leu Val Thr Pro Gly Thr Pro
1 5 10 15

Leu Thr Leu Thr Cys Thr Ala Ser Gly Phe Ser Leu Ser Ser Tyr Trp
20 25 30

Met Asn Trp Val Arg Gln Ala Pro Gly Glu Gly Leu Glu Trp Ile Gly
35 40 45

Thr Ile Asp Ser Gly Gly Arg Thr Asp Tyr Ala Ser Trp Ala Lys Gly
50 55 60

Arg Phe Thr Ile Ser Arg Thr Ser Thr Thr Met Asp Leu Lys Met Thr
65 70 75 80

Ser Leu Thr Thr Gly Asp Thr Ala Arg Tyr Phe Cys Ala Arg Asn Trp
85 90 95

Asn Leu Trp Gly Gln Gly Thr Leu Val Thr Val Ser Ser Ala Ser Thr
100 105 110

Lys Gly Pro Ser Val Tyr Pro Leu Ala Pro Gly Ser Ala Ala Gln Thr
115 120 125

Asn Ser Met Val Thr Leu Gly Cys Leu Val Lys Gly Tyr Phe Pro Glu
130 135 140

Pro Val Thr Val Thr Trp Asn Ser Gly Ser Leu Ser Ser Gly Val His
145 150 155 160

Thr Phe Pro Ala Val Leu Gln Ser Asp Leu Tyr Thr Leu Ser Ser Ser
165 170 175

-continued

```
Val Thr Val Pro Ser Ser Thr Trp Pro Ser Glu Thr Val Thr Cys Asn
            180                 185                 190

Val Ala His Pro Ala Ser Ser Thr Lys Val Asp Lys Lys Ile Val Pro
        195                 200                 205

Arg Asp Cys Gly Cys Lys Pro Cys Ile Cys Thr Val Pro Glu Val Ser
    210                 215                 220

Ser Val Phe Ile Phe Pro Pro Lys Pro Lys Asp Val Leu Thr Ile Thr
225                 230                 235                 240

Leu Thr Pro Lys Val Thr Cys Val Val Val Asp Ile Ser Lys Asp Asp
                245                 250                 255

Pro Glu Val Gln Phe Ser Trp Phe Val Asp Asp Val Glu Val His Thr
            260                 265                 270

Ala Gln Thr Gln Pro Arg Glu Glu Gln Phe Asn Ser Thr Phe Arg Ser
        275                 280                 285

Val Ser Glu Leu Pro Ile Met His Gln Asp Trp Leu Asn Gly Lys Glu
    290                 295                 300

Phe Lys Cys Arg Val Asn Ser Ala Ala Phe Pro Ala Pro Ile Glu Lys
305                 310                 315                 320

Thr Ile Ser Lys Thr Lys Gly Arg Pro Lys Ala Pro Gln Val Tyr Thr
                325                 330                 335

Ile Pro Pro Pro Lys Glu Gln Met Ala Lys Asp Lys Val Ser Leu Thr
            340                 345                 350

Cys Met Ile Thr Asp Phe Phe Pro Glu Asp Ile Thr Val Glu Trp Gln
        355                 360                 365

Trp Asn Gly Gln Pro Ala Glu Asn Tyr Lys Asn Thr Gln Pro Ile Met
    370                 375                 380

Asn Thr Asn Gly Ser Tyr Phe Val Tyr Ser Lys Leu Asn Val Gln Lys
385                 390                 395                 400

Ser Asn Trp Glu Ala Gly Asn Thr Phe Thr Cys Ser Val Leu His Glu
                405                 410                 415

Gly Leu His Asn His His Thr Glu Lys Ser Leu Ser His Ser Pro Gly
            420                 425                 430

Lys
```

<210> SEQ ID NO 28
<211> LENGTH: 1302
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody

<400> SEQUENCE: 28

```
cagtcgctgg aggagtccgg gggtcgcctg gtcacgcctg ggacacccct gacactcacc      60

tgcacagcct ctggattctc cctcagtagt tattggatga actgggtccg ccaggctcca     120

ggggaggggc tggaatggat cggaaccatt gattctggtg gtaggacgga ctacgcgagc     180

tgggcaaaag gccgattcac catctccaga acctcgacta cgatggatct gaaaatgacc     240

agtctgacga ccggggacac ggcccgttat ttctgtgcca gaaattggaa cttgtggggc     300

caaggcaccc tcgtcaccgt ctcgagcgct tctacaaagg gcccatctgt ctatccactg     360

gcccctggat ctgctgccca aactaactcc atggtgaccc tgggatgcct ggtcaagggc     420

tatttccctg agccagtgac agtgacctgg aactctggat ccctgtccag cggtgtgcac     480
```

```
accttcccag ctgtcctgca gtctgacctc tacactctga gcagctcagt gactgtcccc    540

tccagcacct ggcccagcga gaccgtcacc tgcaacgttg cccacccggc cagcagcacc    600

aaggtggaca agaaaattgt gcccagggat tgtggttgta agccttgcat atgtacagtc    660

ccagaagtat catctgtctt catcttcccc ccaaagccca aggatgtgct caccattact    720

ctgactccta aggtcacgtg tgttgtggta gacatcagca aggatgatcc cgaggtccag    780

ttcagctggt ttgtagatga tgtggaggtg cacacagctc agacgcaacc ccgggaggag    840

cagttcaaca gcactttccg ctcagtcagt gaacttccca tcatgcacca ggactggctc    900

aatggcaagg agttcaaatg cagggtcaac agtgcagctt tccctgcccc catcgagaaa    960

accatctcca aaaccaaagg cagaccgaag gctccacagg tgtacaccat tccacctccc   1020

aaggagcaga tggccaagga taaagtcagt ctgacctgca tgataacaga cttcttccct   1080

gaagacatta ctgtggagtg gcagtggaat gggcagccag cggagaacta caagaacact   1140

cagcccatca tggacacaga tggctcttac ttcgtctaca gcaagctcaa tgtgcagaag   1200

agcaactggg aggcaggaaa tactttcacc tgctctgtgt tacatgaggg cctgcacaac   1260

caccatactg agaagagcct ctcccactct cctggtaaat ga                       1302
```

<210> SEQ ID NO 29
<211> LENGTH: 452
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody

<400> SEQUENCE: 29

```
Met Glu Thr Gly Leu Arg Trp Leu Leu Leu Val Ala Val Leu Lys Gly
1               5                   10                  15

Val His Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Trp Met Asn Trp Val Arg Gln Ala Pro Gly Glu Gly Leu Glu
    50                  55                  60

Trp Ile Gly Thr Ile Asp Ser Gly Gly Arg Thr Asp Tyr Ala Ser Trp
65                  70                  75                  80

Ala Lys Gly Arg Phe Thr Ile Ser Arg Thr Ser Thr Thr Met Asp Leu
                85                  90                  95

Lys Met Thr Ser Leu Thr Thr Gly Asp Thr Ala Arg Tyr Phe Cys Ala
            100                 105                 110

Arg Asn Trp Asn Leu Trp Gly Gln Gly Thr Leu Val Thr Val Ser Ser
        115                 120                 125

Ala Ser Thr Lys Gly Pro Ser Val Tyr Pro Leu Ala Pro Gly Ser Ala
    130                 135                 140

Ala Gln Thr Asn Ser Met Val Thr Leu Gly Cys Leu Val Lys Gly Tyr
145                 150                 155                 160

Phe Pro Glu Pro Val Thr Val Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Pro Ser Ser Thr Trp Pro Ser Glu Thr Val
        195                 200                 205
```

```
Thr Cys Asn Val Ala His Pro Ala Ser Ser Thr Lys Val Asp Lys Lys
    210                 215                 220

Ile Val Pro Arg Asp Cys Gly Cys Lys Pro Cys Ile Cys Thr Val Pro
225                 230                 235                 240

Glu Val Ser Ser Val Phe Ile Phe Pro Pro Lys Pro Lys Asp Val Leu
                245                 250                 255

Thr Ile Thr Leu Thr Pro Lys Val Thr Cys Val Val Val Asp Ile Ser
            260                 265                 270

Lys Asp Asp Pro Glu Val Gln Phe Ser Trp Phe Val Asp Asp Val Glu
        275                 280                 285

Val His Thr Ala Gln Thr Gln Pro Arg Glu Glu Gln Phe Asn Ser Thr
    290                 295                 300

Phe Arg Ser Val Ser Glu Leu Pro Ile Met His Gln Asp Trp Leu Asn
305                 310                 315                 320

Gly Lys Glu Phe Lys Cys Arg Val Asn Ser Ala Ala Phe Pro Ala Pro
                325                 330                 335

Ile Glu Lys Thr Ile Ser Lys Thr Lys Gly Arg Pro Lys Ala Pro Gln
            340                 345                 350

Val Tyr Thr Ile Pro Pro Pro Lys Glu Gln Met Ala Lys Asp Lys Val
        355                 360                 365

Ser Leu Thr Cys Met Ile Thr Asp Phe Phe Pro Glu Asp Ile Thr Val
    370                 375                 380

Glu Trp Gln Trp Asn Gly Gln Pro Ala Glu Asn Tyr Lys Asn Thr Gln
385                 390                 395                 400

Pro Ile Met Asn Thr Asn Gly Ser Tyr Phe Val Tyr Ser Lys Leu Asn
                405                 410                 415

Val Gln Lys Ser Asn Trp Glu Ala Gly Asn Thr Phe Thr Cys Ser Val
            420                 425                 430

Leu His Glu Gly Leu His Asn His His Thr Glu Lys Ser Leu Ser His
        435                 440                 445

Ser Pro Gly Lys
    450
```

<210> SEQ ID NO 30
<211> LENGTH: 1359
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody

<400> SEQUENCE: 30

```
atggagactg ggctgcgctg gcttctcctg gtcgctgtgc tcaaaggtgt ccactgtcag      60

tcgctggagg agtccggggg tcgcctggtc acgcctggga cacccctgac actcacctgc     120

acagcctctg gattctccct cagtagttat tggatgaact gggtccgcca ggctccaggg     180

gaggggctgg aatggatcgg aaccattgat tctggtggta ggacggacta cgcgagctgg     240

gcaaaaggcc gattcaccat ctccagaacc tcgactacga tggatctgaa aatgaccagt     300

ctgacgaccg gggacacggc ccgttatttc tgtgccagaa attggaactt gtggggccaa     360

ggcaccctcg tcaccgtctc gagcgcttct acaaagggcc catctgtcta tccactggcc     420

cctggatctg ctgcccaaac taactccatg gtgaccctgg gatgcctggt caagggctat     480

ttccctgagc cagtgacagt gacctggaac tctggatccc tgtccagcgg tgtgcacacc     540
```

-continued

```
ttcccagctg tcctgcagtc tgacctctac actctgagca gctcagtgac tgtcccctcc    600

agcacctggc ccagcgagac cgtcacctgc aacgttgccc acccggccag cagcaccaag    660

gtggacaaga aaattgtgcc cagggattgt ggttgtaagc cttgcatatg tacagtccca    720

gaagtatcat ctgtcttcat cttcccccca aagcccaagg atgtgctcac cattactctg    780

actcctaagg tcacgtgtgt tgtggtagac atcagcaagg atgatcccga ggtccagttc    840

agctggtttg tagatgatgt ggaggtgcac acagctcaga cgcaaccccg ggaggagcag    900

ttcaacagca ctttccgctc agtcagtgaa cttcccatca tgcaccagga ctggctcaat    960

ggcaaggagt tcaaatgcag ggtcaacagt gcagctttcc ctgcccccat cgagaaaacc   1020

atctccaaaa ccaaaggcag accgaaggct ccacaggtgt acaccattcc acctcccaag   1080

gagcagatgg ccaaggataa agtcagtctg acctgcatga taacagactt cttccctgaa   1140

gacattactg tggagtggca gtggaatggg cagccagcgg agaactacaa gaacactcag   1200

cccatcatgg acacagatgg ctcttacttc gtctacagca agctcaatgt gcagaagagc   1260

aactgggagg caggaaatac tttcacctgc tctgtgttac atgagggcct gcacaaccac   1320

catactgaga agagcctctc ccactctcct ggtaaatga                          1359
```

<210> SEQ ID NO 31
<211> LENGTH: 213
<212> TYPE: PRT
<213> ORGANISM: Mus musculus

<400> SEQUENCE: 31

```
Gln Ile Val Leu Thr Gln Ser Pro Thr Ile Val Ser Ala Ser Pro Gly
1               5                   10                  15

Glu Lys Val Thr Leu Ile Cys Ser Ala Ser Ser Ser Val Ser Phe Val
            20                  25                  30

Asp Trp Phe Gln Gln Lys Pro Gly Thr Ser Pro Lys Arg Trp Ile Tyr
        35                  40                  45

Arg Thr Ser Asn Leu Gly Phe Gly Val Pro Ala Arg Phe Ser Gly Gly
    50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Arg Ser Thr Tyr Pro Pro Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 32
<211> LENGTH: 642
<212> TYPE: DNA
<213> ORGANISM: Mus musculus

<400> SEQUENCE: 32
caaattgttc tcacccagtc tccaacaatc gtgtctgcat ctccagggga gaaggtcacc 60
ctaatctgca gtgccagttc aagtgtaagt ttcgtggact ggttccagca gaagccaggc 120
acttctccca aacgctggat ttacagaaca tccaacctgg gttttggagt ccctgctcgc 180
ttcagtggcg gtggatctgg gacctctcac tctctcacaa tcagccgaat ggaggctgaa 240
gatgctgcca cttattactg ccagcaaagg agtacttacc cacccacgtt cggtgctggg 300
accaagctgg aactgaaacg ggctgatgct gcaccaactg tatccatctt cccaccatcc 360
agtgagcagt taacatctgg aggtgcctca gtcgtgtgct tcttgaacaa cttctacccc 420
aaagacatca atgtcaagtg gaagattgat ggcagtgaac gacaaaatgg cgtcctgaac 480
agttggactg atcaggacag caaagacagc acctacagca tgagcagcac cctcacgttg 540
accaaggacg agtatgaacg acataacagc tatacctgtg aggccactca caagacatca 600
acttcaccca ttgtcaagag cttcaacagg aatgagtgtt ag 642

<210> SEQ ID NO 33
<211> LENGTH: 235
<212> TYPE: PRT
<213> ORGANISM: Mus musculus

<400> SEQUENCE: 33

Met His Phe Gln Val Gln Ile Phe Ser Phe Leu Leu Ile Ser Ala Ser
1 5 10 15

Val Ile Val Ser Arg Gly Gln Ile Val Leu Thr Gln Ser Pro Thr Ile
20 25 30

Val Ser Ala Ser Pro Gly Glu Lys Val Thr Leu Ile Cys Ser Ala Ser
35 40 45

Ser Ser Val Ser Phe Val Asp Trp Phe Gln Gln Lys Pro Gly Thr Ser
50 55 60

Pro Lys Arg Trp Ile Tyr Arg Thr Ser Asn Leu Gly Phe Gly Val Pro
65 70 75 80

Ala Arg Phe Ser Gly Gly Gly Ser Gly Thr Ser His Ser Leu Thr Ile
85 90 95

Ser Arg Met Glu Ala Glu Asp Ala Ala Thr Tyr Tyr Cys Gln Gln Arg
100 105 110

Ser Thr Tyr Pro Pro Thr Phe Gly Ala Gly Thr Lys Leu Glu Leu Lys
115 120 125

Arg Ala Asp Ala Ala Pro Thr Val Ser Ile Phe Pro Pro Ser Ser Glu
130 135 140

Gln Leu Thr Ser Gly Gly Ala Ser Val Val Cys Phe Leu Asn Asn Phe
145 150 155 160

Tyr Pro Lys Asp Ile Asn Val Lys Trp Lys Ile Asp Gly Ser Glu Arg
165 170 175

Gln Asn Gly Val Leu Asn Ser Trp Thr Asp Gln Asp Ser Lys Asp Ser
180 185 190

Thr Tyr Ser Met Ser Ser Thr Leu Thr Leu Thr Lys Asp Glu Tyr Glu
195 200 205

Arg His Asn Ser Tyr Thr Cys Glu Ala Thr His Lys Thr Ser Thr Ser
210 215 220

Pro Ile Val Lys Ser Phe Asn Arg Asn Glu Cys
225 230 235

<210> SEQ ID NO 34
<211> LENGTH: 708
<212> TYPE: DNA
<213> ORGANISM: Mus musculus

<400> SEQUENCE: 34
atgcattttc aagtgcagat tttcagcttc ctgctaatca gtgcctcagt catagtgtcc 60
agagggcaaa ttgttctcac ccagtctcca acaatcgtgt ctgcatctcc aggggagaag 120
gtcaccctaa tctgcagtgc cagttcaagt gtaagtttcg tggactggtt ccagcagaag 180
ccaggcactt ctcccaaacg ctggatttac agaacatcca acctgggttt tggagtccct 240
gctcgcttca gtggcggtgg atctgggacc tctcactctc tcacaatcag ccgaatggag 300
gctgaagatg ctgccactta ttactgccag caaaggagta cttacccacc cacgttcggt 360
gctgggacca agctggaact gaaacgggct gatgctgcac caactgtatc catcttccca 420
ccatccagtg agcagttaac atctggaggt gcctcagtcg tgtgcttctt gaacaacttc 480
taccccaaag acatcaatgt caagtggaag attgatggca gtgaacgaca aaatggcgtc 540
ctgaacagtt ggactgatca ggacagcaaa gacagcacct acagcatgag cagcaccctc 600
acgttgacca aggacgagta tgaacgacat aacagctata cctgtgaggc cactcacaag 660
acatcaactt cacccattgt caagagcttc aacaggaatg agtgttag 708

<210> SEQ ID NO 35
<211> LENGTH: 449
<212> TYPE: PRT
<213> ORGANISM: Mus musculus

<400> SEQUENCE: 35

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Ser
20 25 30

Gly Met Gly Val Gly Trp Ile Arg His Pro Ser Gly Lys Asn Leu Glu
35 40 45

Trp Leu Ala His Ile Trp Trp Asp Asp Val Lys Arg Tyr Asn Pro Val
50 55 60

Leu Lys Ser Arg Leu Thr Ile Ser Lys Asp Thr Ser Asn Ser Gln Val
65 70 75 80

Phe Leu Lys Ile Ala Asn Val Asp Thr Ala Asp Thr Ala Thr Tyr Tyr
85 90 95

Cys Ala Arg Ile Glu Asp Phe Asp Tyr Asp Glu Glu Tyr Tyr Ala Met
100 105 110

Asp Tyr Trp Gly Gln Gly Thr Ser Val Ile Val Ser Ser Ala Lys Thr
115 120 125

Thr Pro Pro Ser Val Tyr Pro Leu Ala Pro Gly Ser Ala Ala Gln Thr
130 135 140

Asn Ser Met Val Thr Leu Gly Cys Leu Val Lys Gly Tyr Phe Pro Glu
145 150 155 160

Pro Val Thr Val Thr Trp Asn Ser Gly Ser Leu Ser Ser Gly Val His
165 170 175

Thr Phe Pro Ala Val Leu Gln Ser Asp Leu Tyr Thr Leu Ser Ser Ser
180 185 190

Val Thr Val Pro Ser Ser Thr Trp Pro Ser Glu Thr Val Thr Cys Asn
195 200 205

Val Ala His Pro Ala Ser Ser Thr Lys Val Asp Lys Lys Ile Val Pro
210 215 220

Arg Asp Cys Gly Cys Lys Pro Cys Ile Cys Thr Val Pro Glu Val Ser
225 230 235 240

Ser Val Phe Ile Phe Pro Pro Lys Pro Lys Asp Val Leu Thr Ile Thr
245 250 255

Leu Thr Pro Lys Val Thr Cys Val Val Val Asp Ile Ser Lys Asp Asp
260 265 270

Pro Glu Val Gln Phe Ser Trp Phe Val Asp Asp Val Glu Val His Thr
275 280 285

Ala Gln Thr Gln Pro Arg Glu Glu Gln Phe Asn Ser Thr Phe Arg Ser
290 295 300

Val Ser Glu Leu Pro Ile Met His Gln Asp Trp Leu Asn Gly Lys Glu
305 310 315 320

Phe Lys Cys Arg Val Asn Ser Ala Ala Phe Pro Ala Pro Ile Glu Lys
325 330 335

Thr Ile Ser Lys Thr Lys Gly Arg Pro Lys Ala Pro Gln Val Tyr Thr
340 345 350

Ile Pro Pro Pro Lys Glu Gln Met Ala Lys Asp Lys Val Ser Leu Thr
355 360 365

Cys Met Ile Thr Asp Phe Phe Pro Glu Asp Ile Thr Val Glu Trp Gln
370 375 380

Trp Asn Gly Gln Pro Ala Glu Asn Tyr Lys Asn Thr Gln Pro Ile Met
385 390 395 400

Asp Thr Asp Gly Ser Tyr Phe Val Tyr Ser Lys Leu Asn Val Gln Lys
405 410 415

Ser Asn Trp Glu Ala Gly Asn Thr Phe Thr Cys Ser Val Leu His Glu
420 425 430

Gly Leu His Asn His His Thr Glu Lys Ser Leu Ser His Ser Pro Gly
435 440 445

Lys

<210> SEQ ID NO 36
<211> LENGTH: 1350
<212> TYPE: DNA
<213> ORGANISM: Mus musculus

<400> SEQUENCE: 36
caggttactc tgaaagagtc tggccctggg atattgcagc cctcccagac cctcagtctg 60
acttgttctt tctctgggtt ttcactgagc acttctggta tgggtgtagg ctggattcgt 120
cacccatcag ggaagaatct ggagtggctg gcacacattt ggtgggatga tgtcaagcgc 180
tataacccag tcctgaagag ccgactgact atctccaagg atacctccaa cagccaggta 240
ttcctcaaga tcgccaatgt ggacactgca gatactgcca catactactg tgctcgaata 300
gaggactttg attacgacga ggagtattat gctatggact actggggtca aggaacctca 360
gtcatcgtct cctcagccaa aacgacaccc ccatctgtct atccactggc ccctggatct 420
gctgcccaaa ctaactccat ggtgaccctg ggatgcctgg tcaagggcta tttccctgag 480
ccagtgacag tgacctggaa ctctggatcc ctgtccagcg gtgtgcacac cttcccagct 540
gtcctgcagt ctgacctcta cactctgagc agctcagtga ctgtcccctc cagcacctgg 600

-continued

```
cccagcgaga ccgtcacctg caacgttgcc cacccggcca gcagcaccaa ggtggacaag    660

aaaattgtgc ccagggattg tggttgtaag ccttgcatat gtacagtccc agaagtatca    720

tctgtcttca tcttcccccc aaagcccaag gatgtgctca ccattactct gactcctaag    780

gtcacgtgtg ttgtggtaga catcagcaag gatgatcccg aggtccagtt cagctggttt    840

gtagatgatg tggaggtgca cacagctcag acgcaacccc gggaggagca gttcaacagc    900

actttccgct cagtcagtga acttcccatc atgcaccagg actggctcaa tggcaaggag    960

ttcaaatgca gggtcaacag tgcagctttc cctgccccca tcgagaaaac catctccaaa   1020

accaaaggca gaccgaaggc tccacaggtg tacaccattc cacctcccaa ggagcagatg   1080

gccaaggata aagtcagtct gacctgcatg ataacagact tcttccctga agacattact   1140

gtggagtggc agtggaatgg gcagccagcg gagaactaca agaacactca gcccatcatg   1200

gacacagatg gctcttactt cgtctacagc aagctcaatg tgcagaagag caactgggag   1260

gcaggaaata ctttcacctg ctctgtgtta catgagggcc tgcacaacca ccatactgag   1320

aagagcctct cccactctcc tggtaaatga                                    1350


<210> SEQ ID NO 37
<211> LENGTH: 468
<212> TYPE: PRT
<213> ORGANISM: Mus musculus

<400> SEQUENCE: 37

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg His Pro Ser Gly Lys
    50                  55                  60

Asn Leu Glu Trp Leu Ala His Ile Trp Trp Asp Asp Val Lys Arg Tyr
65                  70                  75                  80

Asn Pro Val Leu Lys Ser Arg Leu Thr Ile Ser Lys Asp Thr Ser Asn
                85                  90                  95

Ser Gln Val Phe Leu Lys Ile Ala Asn Val Asp Thr Ala Asp Thr Ala
            100                 105                 110

Thr Tyr Tyr Cys Ala Arg Ile Glu Asp Phe Asp Tyr Asp Glu Glu Tyr
        115                 120                 125

Tyr Ala Met Asp Tyr Trp Gly Gln Gly Thr Ser Val Ile Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240
```

```
Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465


<210> SEQ ID NO 38
<211> LENGTH: 1407
<212> TYPE: DNA
<213> ORGANISM: Mus musculus

<400> SEQUENCE: 38

atgggcaggc ttacttcttc attcctgcta ctgattgtcc ctgcatatgt cctgtcccag     60

gttactctga aagagtctgg ccctgggata ttgcagccct cccagaccct cagtctgact    120

tgttctttct ctgggttttc actgagcact tctggtatgg gtgtaggctg gattcgtcac    180

ccatcaggga agaatctgga gtggctggca cacatttggt gggatgatgt caagcgctat    240

aacccagtcc tgaagagccg actgactatc tccaaggata cctccaacag ccaggtattc    300

ctcaagatcg ccaatgtgga cactgcagat actgccacat actactgtgc tcgaatagag    360

gactttgatt acgacgagga gtattatgct atggactact ggggtcaagg aacctcagtc    420

atcgtctcct cagccaaaac gacaccccca tctgtctatc cactggcccc tggatctgct    480

gcccaaacta actccatggt gaccctggga tgcctggtca agggctattt ccctgagcca    540

gtgacagtga cctggaactc tggatccctg tccagcggtg tgcacacctt cccagctgtc    600

ctgcagtctg acctctacac tctgagcagc tcagtgactg tcccctccag cacctggccc    660

agcgagaccg tcacctgcaa cgttgcccac ccggccagca gcaccaaggt ggacaagaaa    720

attgtgccca gggattgtgg ttgtaagcct tgcatatgta cagtcccaga agtatcatct    780
```

```
gtcttcatct tcccccccaaa gcccaaggat gtgctcacca ttactctgac tcctaaggtc    840

acgtgtgttg tggtagacat cagcaaggat gatcccgagg tccagttcag ctggtttgta    900

gatgatgtgg aggtgcacac agctcagacg caaccccggg aggagcagtt caacagcact    960

ttccgctcag tcagtgaact tcccatcatg caccaggact ggctcaatgg caaggagttc   1020

aaatgcaggg tcaacagtgc agctttccct gcccccatcg agaaaaccat ctccaaaacc   1080

aaaggcagac cgaaggctcc acaggtgtac accattccac ctcccaagga gcagatggcc   1140

aaggataaag tcagtctgac ctgcatgata acagacttct tccctgaaga cattactgtg   1200

gagtggcagt ggaatgggca gccagcggag aactacaaga acactcagcc catcatggac   1260

acagatggct cttacttcgt ctacagcaag ctcaatgtgc agaagagcaa ctgggaggca   1320

ggaaatactt tcacctgctc tgtgttacat gagggcctgc acaaccacca tactgagaag   1380

agcctctccc actctcctgg taaatga                                        1407


<210> SEQ ID NO 39
<211> LENGTH: 5
<212> TYPE: PRT
<213> ORGANISM: Mus musculus

<400> SEQUENCE: 39

Asp His Tyr Met Ser
1               5


<210> SEQ ID NO 40
<211> LENGTH: 17
<212> TYPE: PRT
<213> ORGANISM: Mus musculus

<400> SEQUENCE: 40

Asp Ile Asn Pro Tyr Ser Gly Glu Thr Thr Tyr Asn Gln Lys Phe Lys
1               5                   10                  15

Gly


<210> SEQ ID NO 41
<211> LENGTH: 10
<212> TYPE: PRT
<213> ORGANISM: Mus musculus

<400> SEQUENCE: 41

Asp Asp Tyr Asp Ala Ser Pro Phe Ala Tyr
1               5                   10


<210> SEQ ID NO 42
<211> LENGTH: 11
<212> TYPE: PRT
<213> ORGANISM: Mus musculus

<400> SEQUENCE: 42

Gln Ala Ser Gln Gly Thr Ser Ile Asn Leu Asn
1               5                   10


<210> SEQ ID NO 43
<211> LENGTH: 7
<212> TYPE: PRT
<213> ORGANISM: Mus musculus

<400> SEQUENCE: 43

Gly Ser Ser Asn Leu Glu Asp
1               5
```

<210> SEQ ID NO 44
<211> LENGTH: 9
<212> TYPE: PRT
<213> ORGANISM: Mus musculus

<400> SEQUENCE: 44

Leu Gln His Ser Tyr Leu Pro Tyr Thr
1               5

<210> SEQ ID NO 45
<211> LENGTH: 5
<212> TYPE: PRT
<213> ORGANISM: Mus musculus

<400> SEQUENCE: 45

Asp Cys Tyr Met Asn
1               5

<210> SEQ ID NO 46
<211> LENGTH: 17
<212> TYPE: PRT
<213> ORGANISM: Mus musculus

<400> SEQUENCE: 46

Asp Ile Asn Pro Phe Asn Gly Gly Thr Thr Tyr Asn Gln Lys Phe Lys
1               5                   10                  15

Gly

<210> SEQ ID NO 47
<211> LENGTH: 16
<212> TYPE: PRT
<213> ORGANISM: Mus musculus

<400> SEQUENCE: 47

Ser His Tyr Tyr Phe Asp Gly Arg Val Pro Trp Asp Ala Met Asp Tyr
1               5                   10                  15

<210> SEQ ID NO 48
<211> LENGTH: 15
<212> TYPE: PRT
<213> ORGANISM: Mus musculus

<400> SEQUENCE: 48

Lys Ala Ser Gln Ser Val Asp Tyr Asp Gly Asp Ser Tyr Met Asn
1               5                   10                  15

<210> SEQ ID NO 49
<211> LENGTH: 7
<212> TYPE: PRT
<213> ORGANISM: Mus musculus

<400> SEQUENCE: 49

Ala Ala Ser Asn Leu Glu Ser
1               5

<210> SEQ ID NO 50
<211> LENGTH: 9
<212> TYPE: PRT
<213> ORGANISM: Mus musculus

<400> SEQUENCE: 50

Gln Gln Ser Asn Glu Asp Pro Trp Thr
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 51

Ser Tyr Trp Met Asn
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 52

Thr Ile Asp Ser Gly Gly Arg Thr Asp Tyr Ala Ser Trp Ala Lys Gly
1               5                   10                  15

<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 53

Asn Trp Asn Leu
1

<210> SEQ ID NO 54
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 54

Gln Ser Ser Gln Ser Val Tyr Asp Asn Asn Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 55

Asp Ala Ser Asp Leu Ala Ser
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rabbit-mouse chimera

<400> SEQUENCE: 56

Gln Gly Ala Tyr Asn Asp Val Ile Tyr Ala
1 5 10

<210> SEQ ID NO 57
<211> LENGTH: 7
<212> TYPE: PRT
<213> ORGANISM: Mus musculus

<400> SEQUENCE: 57

Thr Ser Gly Met Gly Val Gly
1 5

<210> SEQ ID NO 58
<211> LENGTH: 16
<212> TYPE: PRT
<213> ORGANISM: Mus musculus

<400> SEQUENCE: 58

His Ile Trp Trp Asp Asp Val Lys Arg Tyr Asn Pro Val Leu Lys Ser
1 5 10 15

<210> SEQ ID NO 59
<211> LENGTH: 14
<212> TYPE: PRT
<213> ORGANISM: Mus musculus

<400> SEQUENCE: 59

Glu Asp Phe Asp Tyr Asp Glu Glu Tyr Tyr Ala Met Asp Tyr
1 5 10

<210> SEQ ID NO 60
<211> LENGTH: 10
<212> TYPE: PRT
<213> ORGANISM: Mus musculus

<400> SEQUENCE: 60

Ser Ala Ser Ser Ser Val Ser Phe Val Asp
1 5 10

<210> SEQ ID NO 61
<211> LENGTH: 7
<212> TYPE: PRT
<213> ORGANISM: Mus musculus

<400> SEQUENCE: 61

Arg Thr Ser Asn Leu Gly Phe
1 5

<210> SEQ ID NO 62
<211> LENGTH: 9
<212> TYPE: PRT
<213> ORGANISM: Mus musculus

<400> SEQUENCE: 62

```
Gln Gln Arg Ser Thr Tyr Pro Pro Thr
1               5

<210> SEQ ID NO 63
<211> LENGTH: 20
<212> TYPE: PRT
<213> ORGANISM: Homo sapiens

<400> SEQUENCE: 63

Cys Gly Pro Ala Arg Leu Leu Pro Asn Ala Ile Gly Arg Gly Lys Trp
1               5                   10                  15

Trp Arg Pro Ser
            20

<210> SEQ ID NO 64
<211> LENGTH: 20
<212> TYPE: PRT
<213> ORGANISM: Homo sapiens

<400> SEQUENCE: 64

Gly Pro Ala Arg Leu Leu Pro Asn Ala Ile Gly Arg Gly Lys Trp Trp
1               5                   10                  15

Arg Pro Ser Gly
            20

<210> SEQ ID NO 65
<211> LENGTH: 20
<212> TYPE: PRT
<213> ORGANISM: Homo sapiens

<400> SEQUENCE: 65

Pro Ala Arg Leu Leu Pro Asn Ala Ile Gly Arg Gly Lys Trp Trp Arg
1               5                   10                  15

Pro Ser Gly Pro
            20

<210> SEQ ID NO 66
<211> LENGTH: 20
<212> TYPE: PRT
<213> ORGANISM: Homo sapiens

<400> SEQUENCE: 66

Ala Arg Leu Leu Pro Asn Ala Ile Gly Arg Gly Lys Trp Trp Arg Pro
1               5                   10                  15

Ser Gly Pro Asp
            20

<210> SEQ ID NO 67
<211> LENGTH: 20
<212> TYPE: PRT
<213> ORGANISM: Homo sapiens

<400> SEQUENCE: 67

Arg Leu Leu Pro Asn Ala Ile Gly Arg Gly Lys Trp Trp Arg Pro Ser
1               5                   10                  15

Gly Pro Asp Phe
            20

<210> SEQ ID NO 68
<211> LENGTH: 20
<212> TYPE: PRT
<213> ORGANISM: Homo sapiens
```

<400> SEQUENCE: 68

Leu Leu Pro Asn Ala Ile Gly Arg Gly Lys Trp Trp Arg Pro Ser Gly
1               5                   10                  15

Pro Asp Phe Arg
            20

<210> SEQ ID NO 69
<211> LENGTH: 20
<212> TYPE: PRT
<213> ORGANISM: Homo sapiens

<400> SEQUENCE: 69

Leu Pro Asn Ala Ile Gly Arg Gly Lys Trp Trp Arg Pro Ser Gly Pro
1               5                   10                  15

Asp Phe Arg Cys
            20

<210> SEQ ID NO 70
<211> LENGTH: 14
<212> TYPE: PRT
<213> ORGANISM: Homo sapiens

<400> SEQUENCE: 70

Ser Ala Lys Pro Val Thr Glu Leu Val Cys Ser Gly Gln Cys
1               5                   10

<210> SEQ ID NO 71
<211> LENGTH: 7
<212> TYPE: PRT
<213> ORGANISM: Homo sapiens

<400> SEQUENCE: 71

Leu Val Ala Ser Cys Lys Cys
1               5

<210> SEQ ID NO 72
<211> LENGTH: 8
<212> TYPE: PRT
<213> ORGANISM: Homo sapiens

<400> SEQUENCE: 72

Cys Arg Glu Leu His Phe Thr Arg
1               5

<210> SEQ ID NO 73
<211> LENGTH: 7
<212> TYPE: PRT
<213> ORGANISM: Homo sapiens

<400> SEQUENCE: 73

Cys Ile Pro Asp Arg Tyr Arg
1               5

<210> SEQ ID NO 74
<211> LENGTH: 399
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 74
atggacacga gggcccccac tcagctgctg gggctcctgc tgctctggct cccaggtgcc 60
acatttgctc aagttctgac ccagagtcca agcagtctct ccgccagcgt aggcgatcgt 120
gtgactatta cctgtcaatc tagtcagagc gtgtatgata acaattggct ggcgtggtac 180
cagcaaaaac cgggcaaagc ccccgaagctg ctcatctatg acgcgtccga tctggctagc 240
ggtgtgccaa gccgtttcag tggcagtggc agcggtactg actttaccct cacaatttcg 300
tctctccagc cggaagattt cgccacttac tattgtcaag gtgcttacaa cgatgtgatt 360
tatgccttcg gtcagggcac taaagtagaa atcaaacgt 399

<210> SEQ ID NO 75
<211> LENGTH: 133
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 75

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Ser Pro Ser Ser
20 25 30

Leu Ser Ala Ser Val Gly Asp Arg Val Thr Ile Thr Cys Gln Ser Ser
35 40 45

Gln Ser Val Tyr Asp Asn Asn Trp Leu Ala Trp Tyr Gln Gln Lys Pro
50 55 60

Gly Lys Ala Pro Lys Leu Leu Ile Tyr Asp Ala Ser Asp Leu Ala Ser
65 70 75 80

Gly Val Pro Ser Arg Phe Ser Gly Ser Gly Ser Gly Thr Asp Phe Thr
85 90 95

Leu Thr Ile Ser Ser Leu Gln Pro Glu Asp Phe Ala Thr Tyr Tyr Cys
100 105 110

Gln Gly Ala Tyr Asn Asp Val Ile Tyr Ala Phe Gly Gln Gly Thr Lys
115 120 125

Val Glu Ile Lys Arg
130

<210> SEQ ID NO 76
<211> LENGTH: 393
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 76
atggagactg ggctgcgctg gcttctcctg gtcgctgtgc tcaaaggtgt ccactgtgag 60
gtgcagctgt tggagtctgg aggcgggctt gtccagcctg gagggagcct gcgtctctct 120
tgtgcagcaa gcggcttcag cttatcctct tactggatga attgggtgcg gcaggcacct 180
gggaagggcc tggagtgggt gggcaccatt gattccggag gccgtacaga ctacgcgtct 240
tgggcaaagg gccgtttcac catttcccgc gacaactcca aaaataccat gtacctccag 300
atgaactctc tccgcgcaga ggacacagca cgttattact gtgcacgcaa ctggaatctg 360
tggggtcaag gtactcttgt aacagtctcg agc 393

<210> SEQ ID NO 77
<211> LENGTH: 131
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 77

Met Glu Thr Gly Leu Arg Trp Leu Leu Leu Val Ala Val Leu Lys Gly
1 5 10 15

Val His Cys Glu Val Gln Leu Leu Glu Ser Gly Gly Gly Leu Val Gln
20 25 30

Pro Gly Gly Ser Leu Arg Leu Ser Cys Ala Ala Ser Gly Phe Ser Leu
35 40 45

Ser Ser Tyr Trp Met Asn Trp Val Arg Gln Ala Pro Gly Lys Gly Leu
50 55 60

Glu Trp Val Gly Thr Ile Asp Ser Gly Gly Arg Thr Asp Tyr Ala Ser
65 70 75 80

Trp Ala Lys Gly Arg Phe Thr Ile Ser Arg Asp Asn Ser Lys Asn Thr
85 90 95

Met Tyr Leu Gln Met Asn Ser Leu Arg Ala Glu Asp Thr Ala Arg Tyr
100 105 110

Tyr Cys Ala Arg Asn Trp Asn Leu Trp Gly Gln Gly Thr Leu Val Thr
115 120 125

Val Ser Ser
130

<210> SEQ ID NO 78
<211> LENGTH: 11
<212> TYPE: PRT
<213> ORGANISM: Mus musculus

<400> SEQUENCE: 78

Arg Ala Ser Gln Asp Ile Ser Asn Tyr Leu Asn
1 5 10

<210> SEQ ID NO 79
<211> LENGTH: 7
<212> TYPE: PRT
<213> ORGANISM: Mus musculus

<400> SEQUENCE: 79

Tyr Thr Ser Arg Leu Leu Ser
1 5

<210> SEQ ID NO 80
<211> LENGTH: 9
<212> TYPE: PRT
<213> ORGANISM: Mus musculus

<400> SEQUENCE: 80

Gln Gln Gly Asp Thr Leu Pro Tyr Thr
1 5

<210> SEQ ID NO 81
<211> LENGTH: 11

<212> TYPE: PRT
<213> ORGANISM: Mus musculus

<400> SEQUENCE: 81

Arg Ala Ser Gln Asp Ile Ser Asn Tyr Leu Asn
1               5                   10

<210> SEQ ID NO 82
<211> LENGTH: 24
<212> TYPE: PRT
<213> ORGANISM: Rattus norvegicus

<400> SEQUENCE: 82

Gln Gly Trp Gln Ala Phe Lys Asn Asp Ala Thr Glu Ile Ile Pro Gly
1               5                   10                  15

Leu Arg Glu Tyr Pro Glu Pro Pro
            20

<210> SEQ ID NO 83
<211> LENGTH: 20
<212> TYPE: PRT
<213> ORGANISM: Rattus norvegicus

<400> SEQUENCE: 83

Thr Glu Ile Ile Pro Gly Leu Arg Glu Tyr Pro Glu Pro Pro Gln Glu
1               5                   10                  15

Leu Glu Asn Asn
            20

<210> SEQ ID NO 84
<211> LENGTH: 20
<212> TYPE: PRT
<213> ORGANISM: Rattus norvegicus

<400> SEQUENCE: 84

Pro Glu Pro Pro Gln Glu Leu Glu Asn Asn Gln Thr Met Asn Arg Ala
1               5                   10                  15

Glu Asn Gly Gly
            20

<210> SEQ ID NO 85
<211> LENGTH: 20
<212> TYPE: PRT
<213> ORGANISM: Rattus norvegicus

<400> SEQUENCE: 85

Glu Asn Gly Gly Arg Pro Pro His His Pro Tyr Asp Thr Lys Asp Val
1               5                   10                  15

Ser Glu Tyr Ser
            20

<210> SEQ ID NO 86
<211> LENGTH: 14
<212> TYPE: PRT
<213> ORGANISM: Rattus norvegicus

<400> SEQUENCE: 86

Cys Arg Glu Leu His Tyr Thr Arg Phe Val Thr Asp Gly Pro
1               5                   10

<210> SEQ ID NO 87
<211> LENGTH: 25
<212> TYPE: PRT

<213> ORGANISM: Rattus norvegicus

<400> SEQUENCE: 87

Cys Arg Glu Leu His Tyr Thr Arg Phe Val Thr Asp Gly Pro Ser Arg
1               5                   10                  15

Ser Ala Lys Pro Val Thr Glu Leu Val
            20                  25

<210> SEQ ID NO 88
<211> LENGTH: 23
<212> TYPE: PRT
<213> ORGANISM: Rattus norvegicus

<400> SEQUENCE: 88

Cys Arg Ser Ala Lys Pro Val Thr Glu Leu Val Ser Ser Gly Gln Ser
1               5                   10                  15

Gly Pro Arg Ala Arg Leu Leu
            20

<210> SEQ ID NO 89
<211> LENGTH: 25
<212> TYPE: PRT
<213> ORGANISM: Rattus norvegicus

<400> SEQUENCE: 89

Cys Gly Pro Ala Arg Leu Leu Pro Asn Ala Ile Gly Arg Val Lys Trp
1               5                   10                  15

Trp Arg Pro Asn Gly Pro Asp Phe Arg
            20                  25

<210> SEQ ID NO 90
<211> LENGTH: 20
<212> TYPE: PRT
<213> ORGANISM: Rattus norvegicus

<400> SEQUENCE: 90

Arg Ala Gln Arg Val Gln Leu Leu Cys Pro Gly Gly Ala Ala Pro Arg
1               5                   10                  15

Ser Arg Lys Val
            20

<210> SEQ ID NO 91
<211> LENGTH: 16
<212> TYPE: PRT
<213> ORGANISM: Rattus norvegicus

<400> SEQUENCE: 91

Pro Gly Gly Ala Ala Pro Arg Ser Arg Lys Val Arg Leu Val Ala Ser
1               5                   10                  15

<210> SEQ ID NO 92
<211> LENGTH: 23
<212> TYPE: PRT
<213> ORGANISM: Rattus norvegicus

<400> SEQUENCE: 92

Lys Arg Leu Thr Arg Phe His Asn Gln Ser Glu Leu Lys Asp Phe Gly
1               5                   10                  15

Pro Glu Thr Ala Arg Pro Gln
            20

<210> SEQ ID NO 93

<211> LENGTH: 16
<212> TYPE: PRT
<213> ORGANISM: Rattus norvegicus

<400> SEQUENCE: 93

Ile Pro Asp Arg Tyr Ala Gln Arg Val Gln Leu Leu Ser Pro Gly Gly
1 5 10 15

<210> SEQ ID NO 94
<211> LENGTH: 24
<212> TYPE: PRT
<213> ORGANISM: Rattus norvegicus

<400> SEQUENCE: 94

Ser Glu Leu Lys Asp Phe Gly Pro Glu Thr Ala Arg Pro Gln Lys Gly
1 5 10 15

Arg Lys Pro Arg Pro Arg Ala Arg
20

<210> SEQ ID NO 95
<211> LENGTH: 23
<212> TYPE: PRT
<213> ORGANISM: Rattus norvegicus

<400> SEQUENCE: 95

Lys Gly Arg Lys Pro Arg Pro Arg Ala Arg Gly Ala Lys Ala Asn Gln
1 5 10 15

Ala Glu Leu Glu Asn Ala Tyr
20

<210> SEQ ID NO 96
<211> LENGTH: 18
<212> TYPE: PRT
<213> ORGANISM: Rattus norvegicus

<400> SEQUENCE: 96

Pro Asn Ala Ile Gly Arg Val Lys Trp Trp Arg Pro Asn Gly Pro Asp
1 5 10 15

Phe Arg

<210> SEQ ID NO 97
<211> LENGTH: 22
<212> TYPE: PRT
<213> ORGANISM: Rattus norvegicus

<400> SEQUENCE: 97

Lys Trp Trp Arg Pro Asn Gly Pro Asp Phe Arg Cys Ile Pro Asp Arg
1 5 10 15

Tyr Arg Ala Gln Arg Val
20

<210> SEQ ID NO 98
<211> LENGTH: 213
<212> TYPE: PRT
<213> ORGANISM: Rattus norvegicus

<400> SEQUENCE: 98

Met Gln Leu Ser Leu Ala Pro Cys Leu Ala Cys Leu Leu Val His Ala
1 5 10 15

Ala Phe Val Ala Val Glu Ser Gln Gly Trp Gln Ala Phe Lys Asn Asp
20 25 30

Ala Thr Glu Ile Ile Pro Gly Leu Arg Glu Tyr Pro Glu Pro Pro Gln

-continued

```
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210


<210> SEQ ID NO 99
<211> LENGTH: 7
<212> TYPE: PRT
<213> ORGANISM: Mus musculus

<400> SEQUENCE: 99

Tyr Thr Ser Arg Leu His Ser
1               5


<210> SEQ ID NO 100
<211> LENGTH: 9
<212> TYPE: PRT
<213> ORGANISM: Mus musculus

<400> SEQUENCE: 100

Gln Gln Gly Asp Thr Leu Pro Tyr Thr
1               5


<210> SEQ ID NO 101
<211> LENGTH: 11
<212> TYPE: PRT
<213> ORGANISM: Mus musculus

<400> SEQUENCE: 101

Arg Ala Ser Gln Val Ile Thr Asn Tyr Leu Tyr
1               5                   10


<210> SEQ ID NO 102
<211> LENGTH: 7
<212> TYPE: PRT
<213> ORGANISM: Mus musculus

<400> SEQUENCE: 102

Tyr Thr Ser Arg Leu His Ser
1               5
```

<210> SEQ ID NO 103
<211> LENGTH: 9
<212> TYPE: PRT
<213> ORGANISM: Mus musculus

<400> SEQUENCE: 103

Gln Gln Gly Asp Thr Leu Pro Tyr Thr
1               5

<210> SEQ ID NO 104
<211> LENGTH: 11
<212> TYPE: PRT
<213> ORGANISM: Mus musculus

<400> SEQUENCE: 104

Arg Ala Ser Gln Asp Ile Ser Asn Tyr Leu Asn
1               5                   10

<210> SEQ ID NO 105
<211> LENGTH: 7
<212> TYPE: PRT
<213> ORGANISM: Mus musculus

<400> SEQUENCE: 105

Tyr Thr Ser Arg Leu Leu Ser
1               5

<210> SEQ ID NO 106
<211> LENGTH: 9
<212> TYPE: PRT
<213> ORGANISM: Mus musculus

<400> SEQUENCE: 106

Gln Gln Gly Asp Thr Leu Pro Tyr Thr
1               5

<210> SEQ ID NO 107
<211> LENGTH: 11
<212> TYPE: PRT
<213> ORGANISM: Mus musculus

<400> SEQUENCE: 107

Arg Ala Ser Gln Asp Ile Ser Asn Tyr Leu Asn
1               5                   10

<210> SEQ ID NO 108
<211> LENGTH: 7
<212> TYPE: PRT
<213> ORGANISM: Mus musculus

<400> SEQUENCE: 108

Tyr Thr Ser Arg Leu Phe Ser
1               5

<210> SEQ ID NO 109
<211> LENGTH: 9
<212> TYPE: PRT
<213> ORGANISM: Mus musculus

<400> SEQUENCE: 109

Gln Gln Gly Asp Thr Leu Pro Tyr Thr
1               5

<210> SEQ ID NO 110

<211> LENGTH: 11
<212> TYPE: PRT
<213> ORGANISM: Mus musculus

<400> SEQUENCE: 110

Arg Ala Ser Gln Asp Ile Ser Asn Tyr Leu Asn
1 5 10

<210> SEQ ID NO 111
<211> LENGTH: 7
<212> TYPE: PRT
<213> ORGANISM: Mus musculus

<400> SEQUENCE: 111

Tyr Thr Ser Arg Leu Leu Ser
1 5

<210> SEQ ID NO 112
<211> LENGTH: 9
<212> TYPE: PRT
<213> ORGANISM: Mus musculus

<400> SEQUENCE: 112

Gln Gln Gly Asp Thr Leu Pro Tyr Thr
1 5

<210> SEQ ID NO 113
<211> LENGTH: 11
<212> TYPE: PRT
<213> ORGANISM: Mus musculus

<400> SEQUENCE: 113

Arg Ala Ser Gln Asp Ile Ser Asn Tyr Leu Asn
1 5 10

<210> SEQ ID NO 114
<211> LENGTH: 7
<212> TYPE: PRT
<213> ORGANISM: Mus musculus

<400> SEQUENCE: 114

Tyr Thr Ser Thr Leu Gln Ser
1 5

<210> SEQ ID NO 115
<211> LENGTH: 9
<212> TYPE: PRT
<213> ORGANISM: Mus musculus

<400> SEQUENCE: 115

Gln Gln Gly Asp Thr Leu Pro Tyr Thr
1 5

<210> SEQ ID NO 116
<211> LENGTH: 12
<212> TYPE: PRT
<213> ORGANISM: Mus musculus

<400> SEQUENCE: 116

Ser Val Ser Ser Ser Ile Ser Ser Ser Asn Leu His
1 5 10

<210> SEQ ID NO 117
<211> LENGTH: 213
<212> TYPE: PRT

<213> ORGANISM: Mus musculus

<400> SEQUENCE: 117

```
Gln Ile Val Leu Ser Gln Ser Pro Ala Ile Leu Ser Thr Ser Pro Gly
1               5                   10                  15

Glu Lys Val Thr Met Thr Cys Arg Ala Ser Ser Ser Val Tyr Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 118
<211> LENGTH: 642
<212> TYPE: DNA
<213> ORGANISM: Mus musculus

<400> SEQUENCE: 118

```
caaattgttc tctcccagtc tccagcaatc ctgtctacat ctccagggga gaaggtcaca      60

atgacttgca gggccagctc aagtgtatat tacatgcact ggtaccagca gaagccagga     120

tcctccccca aaccctggat ttatgccaca tccaacctgg cttctggagt ccctgttcgc     180

ttcagtggca gtgggtctgg gacctcttac tctctcacaa tcaccagagt ggaggctgaa     240

gatgctgcca cttattactg ccagcagtgg agtagtgacc cactcacgtt cggtgctggg     300

accaagctgg agctgaaacg ggctgatgct gcaccaactg tatccatctt cccaccatcc     360

agtgagcagt taacatctgg aggtgcctca gtcgtgtgct tcttgaacaa cttctacccc     420

aaagacatca atgtcaagtg gaagattgat ggcagtgaac gacaaaatgg cgtcctgaac     480

agttggactg atcaggacag caaagacagc acctacagca tgagcagcac cctcacgttg     540

accaaggacg agtatgaacg acataacagc tatacctgtg aggccactca caagacatca     600

acttcaccca ttgtcaagag cttcaacagg aatgagtgtt ag                        642
```

<210> SEQ ID NO 119
<211> LENGTH: 235

<212> TYPE: PRT
<213> ORGANISM: Mus musculus

<400> SEQUENCE: 119

Met Asp Phe Gln Val Gln Ile Phe Ser Phe Leu Leu Ile Ser Ala Ser
1 5 10 15

Val Ile Met Ser Arg Gly Gln Ile Val Leu Ser Gln Ser Pro Ala Ile
20 25 30

Leu Ser Thr Ser Pro Gly Glu Lys Val Thr Met Thr Cys Arg Ala Ser
35 40 45

Ser Ser Val Tyr Tyr Met His Trp Tyr Gln Gln Lys Pro Gly Ser Ser
50 55 60

Pro Lys Pro Trp Ile Tyr Ala Thr Ser Asn Leu Ala Ser Gly Val Pro
65 70 75 80

Val Arg Phe Ser Gly Ser Gly Ser Gly Thr Ser Tyr Ser Leu Thr Ile
85 90 95

Thr Arg Val Glu Ala Glu Asp Ala Ala Thr Tyr Tyr Cys Gln Gln Trp
100 105 110

Ser Ser Asp Pro Leu Thr Phe Gly Ala Gly Thr Lys Leu Glu Leu Lys
115 120 125

Arg Ala Asp Ala Ala Pro Thr Val Ser Ile Phe Pro Pro Ser Ser Glu
130 135 140

Gln Leu Thr Ser Gly Gly Ala Ser Val Val Cys Phe Leu Asn Asn Phe
145 150 155 160

Tyr Pro Lys Asp Ile Asn Val Lys Trp Lys Ile Asp Gly Ser Glu Arg
165 170 175

Gln Asn Gly Val Leu Asn Ser Trp Thr Asp Gln Asp Ser Lys Asp Ser
180 185 190

Thr Tyr Ser Met Ser Ser Thr Leu Thr Leu Thr Lys Asp Glu Tyr Glu
195 200 205

Arg His Asn Ser Tyr Thr Cys Glu Ala Thr His Lys Thr Ser Thr Ser
210 215 220

Pro Ile Val Lys Ser Phe Asn Arg Asn Glu Cys
225 230 235

<210> SEQ ID NO 120
<211> LENGTH: 708
<212> TYPE: DNA
<213> ORGANISM: Mus musculus

<400> SEQUENCE: 120
atggattttc aagtgcagat tttcagcttc ctgctaatca gtgcttcagt cattatgtcc 60
aggggacaaa ttgttctctc ccagtctcca gcaatcctgt ctacatctcc aggggagaag 120
gtcacaatga cttgcagggc cagctcaagt gtatattaca tgcactggta ccagcagaag 180
ccaggatcct cccccaaacc ctggatttat gccacatcca acctggcttc tggagtccct 240
gttcgcttca gtggcagtgg gtctgggacc tcttactctc tcacaatcac cagagtggag 300
gctgaagatg ctgccactta ttactgccag cagtggagta gtgacccact cacgttcggt 360
gctgggacca agctggagct gaaacgggct gatgctgcac caactgtatc catcttccca 420
ccatccagtg agcagttaac atctggaggt gcctcagtcg tgtgcttctt gaacaacttc 480
taccccaaag acatcaatgt caagtggaag attgatggca gtgaacgaca aaatggcgtc 540
ctgaacagtt ggactgatca ggacagcaaa gacagcacct acagcatgag cagcaccctc 600
acgttgacca aggacgagta tgaacgacat aacagctata cctgtgaggc cactcacaag 660
acatcaactt cacccattgt caagagcttc aacaggaatg agtgttag 708

<210> SEQ ID NO 121
<211> LENGTH: 445
<212> TYPE: PRT
<213> ORGANISM: Mus musculus

<400> SEQUENCE: 121

```
Glu Val Gln Val Gln Gln Ser Gly Pro Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Arg Leu Asp Pro Glu Asp Gly Glu Ser Asp Tyr Ala Pro Lys Phe
    50                  55                  60

Gln Asp Lys Ala Ile Met Thr Ala Asp Thr Ser Ser Asn Thr Ala Tyr
65                  70                  75                  80

Leu Gln Leu Arg Ser Leu Thr Ser Glu Asp Thr Ala Ile Tyr Tyr Cys
                85                  90                  95

Glu Arg Glu Asp Tyr Asp Gly Thr Tyr Thr Phe Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365
```

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 122
<211> LENGTH: 1338
<212> TYPE: DNA
<213> ORGANISM: Mus musculus

<400> SEQUENCE: 122
gaggttcagg tgcagcagtc tgggccagaa cttgtgaagc caggggcctc agtcaagttg 60
tcctgcacag cttctggctt caacattaaa gactacttta tacactgggt gaagcagagg 120
cctgaacagg gcctggagtg gattggaagg cttgatcctg aggatggtga aagtgattat 180
gccccgaagt tccaggacaa ggccattatg acagcagaca catcatccaa cacagcctat 240
cttcagctca gaagcctgac atctgaggac actgccatct attattgtga gagagaggac 300
tacgatggta cctacacctt ttttccttac tggggccaag ggactctggt cactgtctct 360
gcagccaaaa cgacaccccc atctgtctat ccactggccc ctggatctgc tgcccaaact 420
aactccatgg tgaccctggg atgcctggtc aagggctatt tccctgagcc agtgacagtg 480
acctggaact ctggatccct gtccagcggt gtgcacacct tcccagctgt cctgcagtct 540
gacctctaca ctctgagcag ctcagtgact gtcccctcca gcacctggcc cagcgagacc 600
gtcacctgca acgttgccca cccggccagc agcaccaagg tggacaagaa aattgtgccc 660
agggattgtg gttgtaagcc ttgcatatgt acagtcccag aagtatcatc tgtcttcatc 720
ttccccccaa agcccaagga tgtgctcacc attactctga ctcctaaggt cacgtgtgtt 780
gtggtagaca tcagcaagga tgatcccgag gtccagttca gctggtttgt agatgatgtg 840
gaggtgcaca cagctcagac gcaaccccgg gaggagcagt tcaacagcac tttccgctca 900
gtcagtgaac ttcccatcat gcaccaggac tggctcaatg gcaaggagtt caaatgcagg 960
gtcaacagtg cagctttccc tgcccccatc gagaaaacca tctccaaaac caaaggcaga 1020
ccgaaggctc cacaggtgta caccattcca cctcccaagg agcagatggc caaggataaa 1080
gtcagtctga cctgcatgat aacagacttc ttccctgaag acattactgt ggagtggcag 1140
tggaatgggc agccagcgga gaactacaag aacactcagc ccatcatgga cacagatggc 1200
tcttacttca tctacagcaa gctcaatgtg cagaagagca actgggaggc aggaaatact 1260
ttcacctgct ctgtgttaca tgagggcctg cacaaccacc atactgagaa gagcctctcc 1320
cactctcctg gtaaatga 1338

<210> SEQ ID NO 123
<211> LENGTH: 464
<212> TYPE: PRT
<213> ORGANISM: Mus musculus

<400> SEQUENCE: 123

Met Lys Cys Ser Trp Val Ile Phe Phe Leu Met Ala Val Val Thr Gly

-continued

```
1               5                   10                  15

Val Asn Ser Glu Val Gln Val Gln Gln Ser Gly Pro Glu Leu Val Lys
            20                  25                  30

Pro Gly Ala Ser Val Lys Leu Ser Cys Thr Ala Ser Gly Phe Asn Ile
        35                  40                  45

Lys Asp Tyr Phe Ile His Trp Val Lys Gln Arg Pro Glu Gln Gly Leu
    50                  55                  60

Glu Trp Ile Gly Arg Leu Asp Pro Glu Asp Gly Glu Ser Asp Tyr Ala
65                  70                  75                  80

Pro Lys Phe Gln Asp Lys Ala Ile Met Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Glu Arg Glu Asp Tyr Asp Gly Thr Tyr Thr Phe Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430
```

```
Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 124
<211> LENGTH: 1395
<212> TYPE: DNA
<213> ORGANISM: Mus musculus

<400> SEQUENCE: 124

atgaaatgca gctgggtcat cttcttcctg atggcagtgg ttacaggggt caattcagag      60

gttcaggtgc agcagtctgg gccagaactt gtgaagccag gggcctcagt caagttgtcc     120

tgcacagctt ctggcttcaa cattaaagac tactttatac actgggtgaa gcagaggcct     180

gaacagggcc tggagtggat tggaaggctt gatcctgagg atggtgaaag tgattatgcc     240

ccgaagttcc aggacaaggc cattatgaca gcagacacat catccaacac agcctatctt     300

cagctcagaa gcctgacatc tgaggacact gccatctatt attgtgagag agaggactac     360

gatggtacct acaccttttt tccttactgg ggccaaggga ctctggtcac tgtctctgca     420

gccaaaacga cacccccatc tgtctatcca ctggcccctg gatctgctgc ccaaactaac     480

tccatggtga ccctgggatg cctggtcaag ggctatttcc ctgagccagt gacagtgacc     540

tggaactctg gatccctgtc cagcggtgtg cacaccttcc cagctgtcct gcagtctgac     600

ctctacactc tgagcagctc agtgactgtc ccctccagca cctggcccag cgagaccgtc     660

acctgcaacg ttgcccaccc ggccagcagc accaaggtgg acaagaaaat tgtgcccagg     720

gattgtggtt gtaagccttg catatgtaca gtcccagaag tatcatctgt cttcatcttc     780

cccccaaagc ccaaggatgt gctcaccatt actctgactc ctaaggtcac gtgtgttgtg     840

gtagacatca gcaaggatga tcccgaggtc cagttcagct ggtttgtaga tgatgtggag     900

gtgcacacag ctcagacgca accccgggag gagcagttca acagcacttt ccgctcagtc     960

agtgaacttc ccatcatgca ccaggactgg ctcaatggca aggagttcaa atgcagggtc    1020

aacagtgcag ctttccctgc ccccatcgag aaaaccatct ccaaaaccaa aggcagaccg    1080

aaggctccac aggtgtacac cattccacct cccaaggagc agatggccaa ggataaagtc    1140

agtctgacct gcatgataac agacttcttc cctgaagaca ttactgtgga gtggcagtgg    1200

aatgggcagc cagcggagaa ctacaagaac actcagccca tcatggacac agatggctct    1260

tacttcatct acagcaagct caatgtgcag aagagcaact gggaggcagg aaatactttc    1320

acctgctctg tgttacatga gggcctgcac aaccaccata ctgagaagag cctctcccac    1380

tctcctggta aatga                                                     1395


<210> SEQ ID NO 125
<211> LENGTH: 215
<212> TYPE: PRT
<213> ORGANISM: Mus musculus

<400> SEQUENCE: 125

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Thr Ile Ser Ser Asn
            20                  25                  30

His Leu His Trp Phe Gln Gln Lys Ser Asp Thr Ser Pro Lys Pro Trp
        35                  40                  45
```

```
Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Arg Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215


<210> SEQ ID NO 126
<211> LENGTH: 648
<212> TYPE: DNA
<213> ORGANISM: Mus musculus

<400> SEQUENCE: 126

gaaattgtgc tcacccagtc tccagcactc atggctgcat ctccggggga gaaggtcacc      60

atcacctgca gtgtcagttc aactataagt tccaaccact tgcactggtt ccagcagaag     120

tcagacacct cccccaaacc ctggatttat ggcacatcca acctggcttc tggagtccct     180

gttcgcttca gtggcagtgg atctgggacc tcttattctc tcacaatcag cagcatggag     240

gctgaggatg ctgccactta ttactgtcaa cagtggagta gttacccact cacgttcggc     300

gctgggacca agctggagct gagacgggct gatgctgcac caactgtatc catcttccca     360

ccatccagtg agcagttaac atctggaggt gcctcagtcg tgtgcttctt gaacaacttc     420

taccccaaag acatcaatgt caagtggaag attgatggca gtgaacgaca aaatggcgtc     480

ctgaacagtt ggactgatca ggacagcaaa gacagcacct acagcatgag cagcaccctc     540

acgttgacca aggacgagta tgaacgacat aacagctata cctgtgaggc cactcacaag     600

acatcaactt cacccattgt caagagcttc aacaggaatg agtgttag                  648


<210> SEQ ID NO 127
<211> LENGTH: 237
<212> TYPE: PRT
<213> ORGANISM: Mus musculus

<400> SEQUENCE: 127

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
```

```
        35                  40                  45

Ser Thr Ile Ser Ser Asn His Leu His Trp Phe Gln Gln Lys Ser Asp
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Arg Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

<210> SEQ ID NO 128
<211> LENGTH: 714
<212> TYPE: DNA
<213> ORGANISM: Mus musculus

<400> SEQUENCE: 128

```
atggattttc atgtgcagat tttcagcttc atgctaatca gtgtcacagt cattttgtcc      60

agtggagaaa ttgtgctcac ccagtctcca gcactcatgg ctgcatctcc gggggagaag     120

gtcaccatca cctgcagtgt cagttcaact ataagttcca accacttgca ctggttccag     180

cagaagtcag acacctcccc caaaccctgg atttatggca catccaacct ggcttctgga     240

gtccctgttc gcttcagtgg cagtggatct gggacctctt attctctcac aatcagcagc     300

atggaggctg aggatgctgc cacttattac tgtcaacagt ggagtagtta cccactcacg     360

ttcggcgctg ggaccaagct ggagctgaga cgggctgatg ctgcaccaac tgtatccatc     420

ttcccaccat ccagtgagca gttaacatct ggaggtgcct cagtcgtgtg cttcttgaac     480

aacttctacc ccaaagacat caatgtcaag tggaagattg atggcagtga acgacaaaat     540

ggcgtcctga acagttggac tgatcaggac agcaaagaca gcacctacag catgagcagc     600

accctcacgt tgaccaagga cgagtatgaa cgacataaca gctatacctg tgaggccact     660

cacaagacat caacttcacc cattgtcaag agcttcaaca ggaatgagtg ttag           714
```

<210> SEQ ID NO 129
<211> LENGTH: 449
<212> TYPE: PRT
<213> ORGANISM: Mus musculus

<400> SEQUENCE: 129

```
Glu Val Gln Leu Gln Gln Ser Gly Ala Glu Leu Val Arg Pro Gly Ala
```

-continued

```
1               5                   10                  15

Leu Val Lys Leu Ser Cys Thr Ala Ser Asp Phe Asn Ile Lys Asp Phe
            20                  25                  30

Tyr Leu His Trp Met Arg Gln Arg Pro Glu Gln Gly Leu Asp Trp Ile
        35                  40                  45

Gly Arg Ile Asp Pro Glu Asn Gly Asp Thr Leu Tyr Asp Pro Lys Phe
    50                  55                  60

Gln Asp Lys Ala Thr Leu Thr Thr Asp Thr Ser Ser Asn Thr Ala Tyr
65                  70                  75                  80

Leu Gln Leu Ser Gly Leu Thr Ser Glu Thr Thr Ala Val Tyr Tyr Cys
                85                  90                  95

Ser Arg Glu Ala Asp Tyr Phe His Asp Gly Thr Ser Tyr Trp Tyr Phe
            100                 105                 110

Asp Val Trp Gly Ala Gly Thr Thr Ile Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430
```

-continued

Gly Leu His Asn His His Thr Glu Lys Ser Leu Ser His Ser Pro Gly
435 440 445

Lys

<210> SEQ ID NO 130
<211> LENGTH: 1350
<212> TYPE: DNA
<213> ORGANISM: Mus musculus

<400> SEQUENCE: 130
gaggttcagc tgcagcagtc tggggctgaa cttgtgaggc caggggcctt agtcaagttg 60
tcctgcacag cttctgactt caacattaaa gacttctatc tacactggat gaggcagcgg 120
cctgaacagg gcctggactg gattggaagg attgatcctg agaatggtga tactttatat 180
gacccgaagt tccaggacaa ggccactctt acaacagaca catcctccaa cacagcctac 240
ctgcagctca gcggcctgac atctgagacc actgccgtct attactgttc tagagaggcg 300
gattatttcc acgatggtac ctcctactgg tacttcgatg tctggggcgc agggaccaca 360
atcaccgtct cctcagccaa aacgacaccc ccatctgtct atccactggc ccctggatct 420
gctgcccaaa ctaactccat ggtgaccctg ggatgcctgg tcaagggcta tttccctgag 480
ccagtgacag tgacctggaa ctctggatcc ctgtccagcg gtgtgcacac cttcccagct 540
gtcctgcagt ctgacctcta cactctgagc agctcagtga ctgtcccctc cagcacctgg 600
cccagcgaga ccgtcacctg caacgttgcc cacccggcca gcagcaccaa ggtggacaag 660
aaaattgtgc ccagggattg tggttgtaag ccttgcatat gtacagtccc agaagtatca 720
tctgtcttca tcttcccccc aaagcccaag gatgtgctca ccattactct gactcctaag 780
gtcacgtgtg ttgtggtaga catcagcaag gatgatcccg aggtccagtt cagctggttt 840
gtagatgatg tggaggtgca cacagctcag acgcaacccc gggaggagca gttcaacagc 900
actttccgct cagtcagtga acttcccatc atgcaccagg actggctcaa tggcaaggag 960
ttcaaatgca gggtcaacag tgcagctttc cctgccccca tcgagaaaac catctccaaa 1020
accaaaggca gaccgaaggc tccacaggtg tacaccattc cacctcccaa ggagcagatg 1080
gccaaggata aagtcagtct gacctgcatg ataacagact tcttccctga agacattact 1140
gtggagtggc agtggaatgg gcagccagcg gagaactaca agaacactca gcccatcatg 1200
gacacagatg gctcttactt catctacagc aagctcaatg tgcagaagag caactgggag 1260
gcaggaaata ctttcacctg ctctgtgtta catgagggcc tgcacaacca ccatactgag 1320
aagagcctct cccactctcc tggtaaatga 1350

<210> SEQ ID NO 131
<211> LENGTH: 468
<212> TYPE: PRT
<213> ORGANISM: Mus musculus

<400> SEQUENCE: 131

Met Lys Cys Ser Trp Val Ile Phe Phe Leu Met Ala Val Val Thr Gly
1 5 10 15

Val Asn Ser Glu Val Gln Leu Gln Gln Ser Gly Ala Glu Leu Val Arg
20 25 30

Pro Gly Ala Leu Val Lys Leu Ser Cys Thr Ala Ser Asp Phe Asn Ile
35 40 45

Lys Asp Phe Tyr Leu His Trp Met Arg Gln Arg Pro Glu Gln Gly Leu
50 55 60

```
Asp Trp Ile Gly Arg Ile Asp Pro Glu Asn Gly Asp Thr Leu Tyr Asp
65                  70                  75                  80

Pro Lys Phe Gln Asp Lys Ala Thr Leu Thr Thr Asp Thr Ser Ser Asn
                85                  90                  95

Thr Ala Tyr Leu Gln Leu Ser Gly Leu Thr Ser Glu Thr Thr Ala Val
            100                 105                 110

Tyr Tyr Cys Ser Arg Glu Ala Asp Tyr Phe His Asp Gly Thr Ser Tyr
        115                 120                 125

Trp Tyr Phe Asp Val Trp Gly Ala Gly Thr Thr Ile Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465
```

<210> SEQ ID NO 132
<211> LENGTH: 1407
<212> TYPE: DNA
<213> ORGANISM: Mus musculus

<400> SEQUENCE: 132

```
atgaaatgca gctgggtcat cttcttcctg atggcagtgg ttacaggggt caattcagag     60
gttcagctgc agcagtctgg ggctgaactt gtgaggccag gggccttagt caagttgtcc    120
tgcacagctt ctgacttcaa cattaaagac ttctatctac actggatgag gcagcggcct    180
gaacagggcc tggactggat tggaaggatt gatcctgaga atggtgatac tttatatgac    240
ccgaagttcc aggacaaggc cactcttaca acagacacat cctccaacac agcctacctg    300
cagctcagcg gcctgacatc tgagaccact gccgtctatt actgttctag agaggcggat    360
tatttccacg atggtacctc ctactggtac ttcgatgtct ggggcgcagg gaccacaatc    420
accgtctcct cagccaaaac gacaccccca tctgtctatc cactggcccc tggatctgct    480
gcccaaacta actccatggt gaccctggga tgcctggtca agggctattt ccctgagcca    540
gtgacagtga cctggaactc tggatccctg tccagcggtg tgcacacctt cccagctgtc    600
ctgcagtctg acctctacac tctgagcagc tcagtgactg tcccctccag cacctggccc    660
agcgagaccg tcacctgcaa cgttgcccac ccggccagca gcaccaaggt ggacaagaaa    720
attgtgccca gggattgtgg ttgtaagcct tgcatatgta cagtcccaga agtatcatct    780
gtcttcatct tccccccaaa gcccaaggat gtgctcacca ttactctgac tcctaaggtc    840
acgtgtgttg tggtagacat cagcaaggat gatcccgagg tccagttcag ctggtttgta    900
gatgatgtgg aggtgcacac agctcagacg caaccccggg aggagcagtt caacagcact    960
ttccgctcag tcagtgaact tcccatcatg caccaggact ggctcaatgg caaggagttc   1020
aaatgcaggg tcaacagtgc agctttccct gcccccatcg agaaaaccat ctccaaaacc   1080
aaaggcagac cgaaggctcc acaggtgtac accattccac ctcccaagga gcagatggcc   1140
aaggataaag tcagtctgac ctgcatgata acagacttct tccctgaaga cattactgtg   1200
gagtggcagt ggaatgggca gccagcggag aactacaaga acactcagcc catcatggac   1260
acagatggct cttacttcat ctacagcaag ctcaatgtgc agaagagcaa ctgggaggca   1320
ggaaatactt tcacctgctc tgtgttacat gagggcctgc acaaccacca tactgagaag   1380
agcctctccc actctcctgg taaatga                                       1407
```

<210> SEQ ID NO 133
<211> LENGTH: 214
<212> TYPE: PRT
<213> ORGANISM: Mus musculus

<400> SEQUENCE: 133

```
Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80
```

```
Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 134
<211> LENGTH: 645
<212> TYPE: DNA
<213> ORGANISM: Mus musculus

<400> SEQUENCE: 134

```
gatatccaga tgacacagat tacatcctcc ctgtctgcct ctctgggaga cagggtctcc      60

atcagttgca gggcaagtca agacattagc aattatttaa actggtatca gcagaaacca     120

gatggaactt ttaaactcct tatcttctac acatcaagat tactctcagg agtcccatca     180

aggttcagtg gcagtgggtc tggaacagat tattctctca ccatttacaa cctggagcaa     240

gaagattttg ccacttactt ttgccaacag ggagatacgc ttccgtacac tttcggaggg     300

gggaccaagc tggaaataaa acgggctgat gctgcaccaa ctgtatccat cttcccacca     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gttag                     645
```

<210> SEQ ID NO 135
<211> LENGTH: 234
<212> TYPE: PRT
<213> ORGANISM: Mus musculus

<400> SEQUENCE: 135

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80
```

```
Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 136
<211> LENGTH: 705
<212> TYPE: DNA
<213> ORGANISM: Mus musculus

<400> SEQUENCE: 136

```
atgatgtcct ctgctcagtt ccttggtctc ctgttgctct gttttcaagg taccagatgt      60

gatatccaga tgacacagat tacatcctcc ctgtctgcct ctctgggaga cagggtctcc     120

atcagttgca gggcaagtca agacattagc aattatttaa actggtatca gcagaaacca     180

gatggaactt ttaaactcct tatcttctac acatcaagat tactctcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaagc tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttag                     705
```

<210> SEQ ID NO 137
<211> LENGTH: 447
<212> TYPE: PRT
<213> ORGANISM: Mus musculus

<400> SEQUENCE: 137

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45
```

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 138
<211> LENGTH: 1344

<212> TYPE: DNA
<213> ORGANISM: Mus musculus

<400> SEQUENCE: 138
gaggtccaac tgcaacagtc tggacctgaa ctaatgaagc ctggggcttc agtgaagatg 60
tcctgcaagg cttctggata tacattcact gactacaaca tgcactgggt gaagcagaac 120
caaggaaaga ccctagagtg gataggagaa attaatccta acagtggtgg tgctggctac 180
aaccagaagt tcaagggcaa ggccacattg actgtagaca agtcctccac cacagcctac 240
atggagctcc gcagcctgac atctgaggac tctgcagtct attactgtgc aagattgggc 300
tacgatgata tctacgacga ctggtacttc gatgtctggg gcgcagggac cacggtcacc 360
gtctcctcag ccaaaacgac acccccatct gtctatccac tggcccctgg atctgctgcc 420
caaactaact ccatggtgac cctgggatgc ctggtcaagg gctatttccc tgagccagtg 480
acagtgacct ggaactctgg atccctgtcc agcggtgtgc acaccttccc agctgtcctg 540
cagtctgacc tctacactct gagcagctca gtgactgtcc cctccagcac ctggcccagc 600
gagaccgtca cctgcaacgt tgcccacccg gccagcagca ccaaggtgga caagaaaatt 660
gtgcccaggg attgtggttg taagccttgc atatgtacag tcccagaagt atcatctgtc 720
ttcatcttcc ccccaaagcc caaggatgtg ctcaccatta ctctgactcc taaggtcacg 780
tgtgttgtgg tagacatcag caaggatgat cccgaggtcc agttcagctg gtttgtagat 840
gatgtggagg tgcacacagc tcagacgcaa ccccgggagg agcagttcaa cagcactttc 900
cgctcagtca gtgaacttcc catcatgcac caggactggc tcaatggcaa ggagttcaaa 960
tgcagggtca acagtgcagc tttccctgcc cccatcgaga aaaccatctc caaaaccaaa 1020
ggcagaccga aggctccaca ggtgtacacc attccacctc ccaaggagca gatggccaag 1080
gataaagtca gtctgacctg catgataaca gacttcttcc ctgaagacat tactgtggag 1140
tggcagtgga atgggcagcc agcggagaac tacaagaaca ctcagcccat catggacaca 1200
gatggctctt acttcatcta cagcaagctc aatgtgcaga agagcaactg ggaggcagga 1260
aatactttca cctgctctgt gttacatgag ggcctgcaca accaccatac tgagaagagc 1320
ctctcccact ctcctggtaa atga 1344

<210> SEQ ID NO 139
<211> LENGTH: 466
<212> TYPE: PRT
<213> ORGANISM: Mus musculus

<400> SEQUENCE: 139

Met Gly Trp Ser Trp Thr Phe Leu Phe Leu Leu Ser Gly Thr Ala Gly
1 5 10 15

Val Leu Ser Glu Val Gln Leu Gln Gln Ser Gly Pro Glu Leu Met Lys
20 25 30

Pro Gly Ala Ser Val Lys Met Ser Cys Lys Ala Ser Gly Tyr Thr Phe
35 40 45

Thr Asp Tyr Asn Met His Trp Val Lys Gln Asn Gln Gly Lys Thr Leu
50 55 60

Glu Trp Ile Gly Glu Ile Asn Pro Asn Ser Gly Gly Ala Gly Tyr Asn
65 70 75 80

Gln Lys Phe Lys Gly Lys Ala Thr Leu Thr Val Asp Lys Ser Ser Thr
85 90 95

Thr Ala Tyr Met Glu Leu Arg Ser Leu Thr Ser Glu Asp Ser Ala Val
100 105 110

```
Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 140
<211> LENGTH: 1401
<212> TYPE: DNA
<213> ORGANISM: Mus musculus

<400> SEQUENCE: 140

```
atgggatgga gctggacctt tctcttcctc ctgtcaggaa ctgcaggtgt cctctctgag     60
```

gtccaactgc aacagtctgg acctgaacta atgaagcctg gggcttcagt gaagatgtcc 120
tgcaaggctt ctggatatac attcactgac tacaacatgc actgggtgaa gcagaaccaa 180
ggaaagaccc tagagtggat aggagaaatt aatcctaaca gtggtggtgc tggctacaac 240
cagaagttca agggcaaggc cacattgact gtagacaagt cctccaccac agcctacatg 300
gagctccgca gcctgacatc tgaggactct gcagtctatt actgtgcaag attgggctac 360
gatgatatct acgacgactg gtacttcgat gtctggggcg cagggaccac ggtcaccgtc 420
tcctcagcca aaacgacacc cccatctgtc tatccactgg cccctggatc tgctgcccaa 480
actaactcca tggtgaccct gggatgcctg gtcaagggct atttccctga gccagtgaca 540
gtgacctgga actctggatc cctgtccagc ggtgtgcaca ccttcccagc tgtcctgcag 600
tctgacctct acactctgag cagctcagtg actgtcccct ccagcacctg gcccagcgag 660
accgtcacct gcaacgttgc ccacccggcc agcagcacca aggtggacaa gaaaattgtg 720
cccagggatt gtggttgtaa gccttgcata tgtacagtcc cagaagtatc atctgtcttc 780
atcttccccc caaagcccaa ggatgtgctc accattactc tgactcctaa ggtcacgtgt 840
gttgtggtag acatcagcaa ggatgatccc gaggtccagt tcagctggtt tgtagatgat 900
gtggaggtgc acacagctca gacgcaaccc cgggaggagc agttcaacag cactttccgc 960
tcagtcagtg aacttcccat catgcaccag gactggctca atggcaagga gttcaaatgc 1020
agggtcaaca gtgcagcttt ccctgccccc atcgagaaaa ccatctccaa aaccaaaggc 1080
agaccgaagg ctccacaggt gtacaccatt ccacctccca aggagcagat ggccaaggat 1140
aaagtcagtc tgacctgcat gataacagac ttcttccctg aagacattac tgtggagtgg 1200
cagtggaatg ggcagccagc ggagaactac aagaacactc agcccatcat ggacacagat 1260
ggctcttact tcatctacag caagctcaat gtgcagaaga gcaactggga ggcaggaaat 1320
actttcacct gctctgtgtt acatgagggc ctgcacaacc accatactga gaagagcctc 1380
tcccactctc ctggtaaatg a 1401

<210> SEQ ID NO 141
<211> LENGTH: 214
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 642
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 142

```
gacatccaga tgacccagtc tccatcctcc ctctccgcat ccgtaggcga ccgcgtaacc     60

ataacatgta gagcatctca agatatttcc aactatttga attggtacca acaaaaaccc    120

ggcaaagcac ctaaactcct catttactat acatcaagac tcctctccgg cgttccatca    180

cgattctcag gctccggctc cggcacagat ttcacactca ctatttcctc cctccaacca    240

gaagattttg caacctatta ctgtcaacaa ggcgatacac tcccatacac attcggcggc    300

ggcacaaaag ttgaaattaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 143
<211> LENGTH: 236
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 143

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45
```

```
Gln Asp Ile Ser Asn Tyr Leu Asn Trp Tyr Gln Gln Lys Pro Gly Lys
    50                  55                  60

Ala Pro Lys Leu Leu Ile Tyr Tyr Thr Ser Arg Leu Leu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Gly Asp Thr Leu Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 144
<211> LENGTH: 708
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 144

```
atggacatga gggtccccgc tcagctcctg gggctcctgc tactctggct ccgaggtgcc     60

agatgtgaca tccagatgac ccagtctcca tcctccctct ccgcatccgt aggcgaccgc    120

gtaaccataa catgtagagc atctcaagat atttccaact atttgaattg gtaccaacaa    180

aaacccggca aagcacctaa actcctcatt tactatacat caagactcct ctccggcgtt    240

ccatcacgat tctcaggctc cggctccggc acagatttca cactcactat ttcctccctc    300

caaccagaag attttgcaac ctattactgt caacaaggcg atacactccc atacacattc    360

ggcggcggca caaaagttga aattaaacgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgt                708
```

<210> SEQ ID NO 145
<211> LENGTH: 449
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 145

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Asn Tyr Lys Thr Thr Pro Pro Met Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 146
<211> LENGTH: 1347
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 146
gaggtgcagc tggtgcagag cggcgccgag gtaaaaaaac caggagcaag cgttaaagtt 60
tcttgtaaag caagcggata tacatttaca gattacaaca tgcattgggt aagacaagcg 120
ccaggacaag gattggaatg gatgggcgaa attaacccta atagtggagg agcaggctac 180
aatcaaaaat tcaaagggag agttacaatg acaacagaca caagcacttc aacagcatat 240
atggaactgc gatcacttag aagcgacgat acagctgtat actattgcgc acgacttggg 300
tatgatgata tatatgatga ctggtatttc gatgtttggg gccagggaac aacagttacc 360
gtctctagtg cctccaccaa gggcccatcg gtcttccccc tggcgccctg ctccaggagc 420
acctccgaga gcacagcggc cctgggctgc ctggtcaagg actacttccc cgaaccggtg 480
acggtgtcgt ggaactcagg cgctctgacc agcggcgtgc acaccttccc agctgtccta 540
cagtcctcag gactctactc cctcagcagc gtggtgaccg tgccctccag caacttcggc 600
acccagacct acacctgcaa cgtagatcac aagcccagca acaccaaggt ggacaagaca 660
gttgagcgca aatgttgtgt cgagtgccca ccgtgcccag caccacctgt ggcaggaccg 720
tcagtcttcc tcttcccccc aaaacccaag gacaccctca tgatctcccg gacccctgag 780
gtcacgtgcg tggtggtgga cgtgagccac gaagaccccg aggtccagtt caactggtac 840
gtggacggcg tggaggtgca taatgccaag acaaagccac gggaggagca gttcaacagc 900
acgttccgtg tggtcagcgt cctcaccgtt gtgcaccagg actggctgaa cggcaaggag 960
tacaagtgca aggtctccaa caaaggcctc ccagccccca tcgagaaaac catctccaaa 1020
accaaagggc agccccgaga accacaggtg tacaccctgc ccccatcccg ggaggagatg 1080
accaagaacc aggtcagcct gacctgcctg gtcaaaggct tctaccccag cgacatcgcc 1140
gtggagtggg agagcaatgg gcagccggag aacaactaca agaccacacc tcccatgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaa 1347

<210> SEQ ID NO 147
<211> LENGTH: 468
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 147

Met Asp Trp Thr Trp Arg Ile Leu Phe Leu Val Ala Ala Ala Thr Gly
1 5 10 15

Ala His Ser Glu Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Asp Tyr Asn Met His Trp Val Arg Gln Ala Pro Gly Gln Gly Leu
50 55 60

Glu Trp Met Gly Glu Ile Asn Pro Asn Ser Gly Gly Ala Gly Tyr Asn
65 70 75 80

Gln Lys Phe Lys Gly Arg Val Thr Met Thr Thr Asp Thr Ser Thr Ser
85 90 95

Thr Ala Tyr Met Glu Leu Arg Ser Leu Arg Ser Asp Asp Thr Ala Val
100 105 110

Tyr Tyr Cys Ala Arg Leu Gly Tyr Asp Asp Ile Tyr Asp Asp Trp Tyr
115 120 125

Phe Asp Val Trp Gly Gln Gly Thr Thr Val Thr Val Ser Ser Ala Ser
130 135 140

Thr Lys Gly Pro Ser Val Phe Pro Leu Ala Pro Cys Ser Arg Ser Thr
145 150 155 160

Ser Glu Ser Thr Ala Ala Leu Gly Cys Leu Val Lys Asp Tyr Phe Pro
165 170 175

Glu Pro Val Thr Val Ser Trp Asn Ser Gly Ala Leu Thr Ser Gly Val
180 185 190

His Thr Phe Pro Ala Val Leu Gln Ser Ser Gly Leu Tyr Ser Leu Ser
195 200 205

Ser Val Val Thr Val Pro Ser Ser Asn Phe Gly Thr Gln Thr Tyr Thr
210 215 220

Cys Asn Val Asp His Lys Pro Ser Asn Thr Lys Val Asp Lys Thr Val
225 230 235 240

Glu Arg Lys Cys Cys Val Glu Cys Pro Pro Cys Pro Ala Pro Pro Val
245 250 255

Ala Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

His Glu Asp Pro Glu Val Gln Phe Asn Trp Tyr Val Asp Gly Val Glu
290 295 300

Val His Asn Ala Lys Thr Lys Pro Arg Glu Glu Gln Phe Asn Ser Thr
305 310 315 320

Phe Arg Val Val Ser Val Leu Thr Val Val His Gln Asp Trp Leu Asn
325 330 335

Gly Lys Glu Tyr Lys Cys Lys Val Ser Asn Lys Gly Leu Pro Ala Pro
340 345 350

Ile Glu Lys Thr Ile Ser Lys Thr Lys Gly Gln Pro Arg Glu Pro Gln
355 360 365

Val Tyr Thr Leu Pro Pro Ser Arg Glu Glu Met Thr Lys Asn Gln Val
370 375 380

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 148
<211> LENGTH: 1404
<212> TYPE: DNA
<213> ORGANISM: Mus musculus

<400> SEQUENCE: 148

```
atggactgga cctggaggat cctcttcttg gtggcagcag ccacaggagc ccactccgag     60

gtgcagctgg tgcagagcgg cgccgaggta aaaaaaccag gagcaagcgt taaagtttct    120

tgtaaagcaa gcggatatac atttacagat tacaacatgc attgggtaag acaagcgcca    180

ggacaaggat tggaatggat gggcgaaatt aaccctaata gtggaggagc aggctacaat    240

caaaaattca aagggagagt tacaatgaca acagacacaa gcacttcaac agcatatatg    300

gaactgcgat cacttagaag cgacgataca gctgtatact attgcgcacg acttgggtat    360

gatgatatat atgatgactg gtatttcgat gtttggggcc agggaacaac agttaccgtc    420

tctagtgcct ccaccaaggg cccatcggtc ttccccctgg cgccctgctc caggagcacc    480

tccgagagca cagcggccct gggctgcctg gtcaaggact acttccccga accggtgacg    540

gtgtcgtgga actcaggcgc tctgaccagc ggcgtgcaca ccttcccagc tgtcctacag    600

tcctcaggac tctactccct cagcagcgtg gtgaccgtgc cctccagcaa cttcggcacc    660

cagacctaca cctgcaacgt agatcacaag cccagcaaca ccaaggtgga caagacagtt    720

gagcgcaaat gttgtgtcga gtgcccaccg tgcccagcac cacctgtggc aggaccgtca    780

gtcttcctct tccccccaaa acccaaggac accctcatga tctcccggac ccctgaggtc    840

acgtgcgtgg tggtggacgt gagccacgaa gaccccgagg tccagttcaa ctggtacgtg    900

gacggcgtgg aggtgcataa tgccaagaca aagccacggg aggagcagtt caacagcacg    960

ttccgtgtgg tcagcgtcct caccgttgtg caccaggact ggctgaacgg caaggagtac   1020

aagtgcaagg tctccaacaa aggcctccca gcccccatcg agaaaaccat ctccaaaacc   1080

aaagggcagc cccgagaacc acaggtgtac accctgcccc catcccggga ggagatgacc   1140

aagaaccagg tcagcctgac ctgcctggtc aaaggcttct accccagcga catcgccgtg   1200

gagtgggaga gcaatgggca gccggagaac aactacaaga ccacacctcc catgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaa                                          1404
```

<210> SEQ ID NO 149
<211> LENGTH: 214
<212> TYPE: PRT

<213> ORGANISM: Mus musculus

<400> SEQUENCE: 149

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Asn Tyr
20 25 30

Leu Asn Trp Phe Gln Gln Lys Pro Asp Gly Thr Leu Lys Leu Leu Ile
35 40 45

Phe Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asp Thr Leu Pro Tyr
85 90 95

Thr Phe Gly Gly Gly Thr Lys Leu Glu Ile Arg Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 150
<211> LENGTH: 645
<212> TYPE: DNA
<213> ORGANISM: Mus musculus

<400> SEQUENCE: 150
gatatccaga tgacacagac tacatcctcc ctgtctgcct ctctgggaga cagagtcacc 60
atcagttgca gggcaagtca ggacattagc aattatttaa actggtttca gcagaaacca 120
gatggaactc ttaaactcct gatcttctac acatcaagat tacactcagg agttccatca 180
aggttcagtg gcagtgggtc tggaacagat tattctctca ccattagcaa cctggagcaa 240
gaagatattg ccacttactt ttgccaacag ggtgatacgc ttccgtacac gttcgggggg 300
gggaccaagc tggaaataag acgggctgat gctgcaccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gttag 645

<210> SEQ ID NO 151
<211> LENGTH: 234

<212> TYPE: PRT
<213> ORGANISM: Mus musculus

<400> SEQUENCE: 151

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Phe Gln Gln Lys Pro Asp Gly Thr Leu
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Arg Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 152
<211> LENGTH: 705
<212> TYPE: DNA
<213> ORGANISM: Mus musculus

<400> SEQUENCE: 152

```
atgatgtcct ctgctcagtt ccttggtctc ctgttgctct gttttcaagg taccagatgt     60

gatatccaga tgacacagac tacatcctcc ctgtctgcct ctctgggaga cagagtcacc    120

atcagttgca gggcaagtca ggacattagc aattatttaa actggtttca gcagaaacca    180

gatggaactc ttaaactcct gatcttctac acatcaagat tacactcagg agttccatca    240

aggttcagtg gcagtgggtc tggaacagat tattctctca ccattagcaa cctggagcaa    300

gaagatattg ccacttactt ttgccaacag ggtgatacgc ttccgtacac gttcgggggg    360

gggaccaagc tggaaataag acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660
```

tcaacttcac ccattgtcaa gagcttcaac aggaatgagt gttag 705

<210> SEQ ID NO 153
<211> LENGTH: 447
<212> TYPE: PRT
<213> ORGANISM: Mus musculus

<400> SEQUENCE: 153

Glu Val Gln Leu Gln Gln Ser Gly Pro Glu Leu Met Lys Pro Gly Ala
1 5 10 15

Ser Val Lys Met Ser Cys Lys Ala Ser Gly Tyr Thr Phe Thr Asp Tyr
20 25 30

Asn Met His Trp Val Lys Gln Asn Gln Gly Lys Ser Leu Glu Trp Ile
35 40 45

Gly Glu Ile Asn Pro Asn Ser Gly Gly Ser Gly Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Arg Leu Val Tyr Asp Gly Ser Tyr Glu Asp Trp Tyr Phe Asp Val
100 105 110

Trp Gly Ala Gly Thr Thr Val Thr Val Ser Ser Ala Lys Thr Thr Pro
115 120 125

Pro Ser Val Tyr Pro Leu Ala Pro Gly Ser Ala Ala Gln Thr Asn Ser
130 135 140

Met Val Thr Leu Gly Cys Leu Val Lys Gly Tyr Phe Pro Glu Pro Val
145 150 155 160

Thr Val Thr Trp Asn Ser Gly Ser Leu Ser Ser Gly Val His Thr Phe
165 170 175

Pro Ala Val Leu Gln Ser Asp Leu Tyr Thr Leu Ser Ser Ser Val Thr
180 185 190

Val Pro Ser Ser Thr Trp Pro Ser Glu Thr Val Thr Cys Asn Val Ala
195 200 205

His Pro Ala Ser Ser Thr Lys Val Asp Lys Lys Ile Val Pro Arg Asp
210 215 220

Cys Gly Cys Lys Pro Cys Ile Cys Thr Val Pro Glu Val Ser Ser Val
225 230 235 240

Phe Ile Phe Pro Pro Lys Pro Lys Asp Val Leu Thr Ile Thr Leu Thr
245 250 255

Pro Lys Val Thr Cys Val Val Val Asp Ile Ser Lys Asp Asp Pro Glu
260 265 270

Val Gln Phe Ser Trp Phe Val Asp Asp Val Glu Val His Thr Ala Gln
275 280 285

Thr Gln Pro Arg Glu Glu Gln Phe Asn Ser Thr Phe Arg Ser Val Ser
290 295 300

Glu Leu Pro Ile Met His Gln Asp Trp Leu Asn Gly Lys Glu Phe Lys
305 310 315 320

Cys Arg Val Asn Ser Ala Ala Phe Pro Ala Pro Ile Glu Lys Thr Ile
325 330 335

Ser Lys Thr Lys Gly Arg Pro Lys Ala Pro Gln Val Tyr Thr Ile Pro
340 345 350

Pro Pro Lys Glu Gln Met Ala Lys Asp Lys Val Ser Leu Thr Cys Met
355 360 365

```
Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445


<210> SEQ ID NO 154
<211> LENGTH: 1344
<212> TYPE: DNA
<213> ORGANISM: Mus musculus

<400> SEQUENCE: 154

gaggtccagc tgcaacagtc tggacctgaa ctaatgaagc ctggggcttc agtgaagatg     60

tcctgcaagg cttctggata cacattcact gactacaaca tgcactgggt gaaacagaac    120

caaggaaaga gcctagagtg gataggagaa attaatccta acagtggtgg tagtggctac    180

aaccaaaagt tcaaaggcaa ggccacattg actgtagaca agtcttccag cacagcctac    240

atggagctcc gcagcctgac atctgaggac tctgcagtct attactgtgc aagattggtc    300

tacgatggca gctacgagga ctggtacttc gatgtctggg gcgcagggac cacggtcacc    360

gtctcctcag ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900

cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                          1344


<210> SEQ ID NO 155
<211> LENGTH: 466
<212> TYPE: PRT
<213> ORGANISM: Mus musculus

<400> SEQUENCE: 155

Met Gly Trp Ser Trp Thr Phe Leu Phe Leu Leu Ser Gly Thr Ala Gly
```

-continued

```
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Ser Leu
    50                  55                  60

Glu Trp Ile Gly Glu Ile Asn Pro Asn Ser Gly Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Val Tyr Asp Gly Ser Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430
```

Lys Ser Asn Trp Glu Ala Gly Asn Thr Phe Thr Cys Ser Val Leu His
435 440 445

Glu Gly Leu His Asn His His Thr Glu Lys Ser Leu Ser His Ser Pro
450 455 460

Gly Lys
465

<210> SEQ ID NO 156
<211> LENGTH: 1401
<212> TYPE: DNA
<213> ORGANISM: Mus musculus

<400> SEQUENCE: 156
atgggatgga gctggacctt tctcttcctc ctgtcaggaa ctgcaggtgt cctctctgag 60
gtccagctgc aacagtctgg acctgaacta atgaagcctg gggcttcagt gaagatgtcc 120
tgcaaggctt ctggatacac attcactgac tacaacatgc actgggtgaa acagaaccaa 180
ggaaagagcc tagagtggat aggagaaatt aatcctaaca gtggtggtag tggctacaac 240
caaaagttca aaggcaaggc cacattgact gtagacaagt cttccagcac agcctacatg 300
gagctccgca gcctgacatc tgaggactct gcagtctatt actgtgcaag attggtctac 360
gatggcagct acgaggactg gtacttcgat gtctggggcg cagggaccac ggtcaccgtc 420
tcctcagcca aaacgacacc cccatctgtc tatccactgg cccctggatc tgctgcccaa 480
actaactcca tggtgaccct gggatgcctg gtcaagggct atttccctga gccagtgaca 540
gtgacctgga actctggatc cctgtccagc ggtgtgcaca ccttcccagc tgtcctgcag 600
tctgacctct acactctgag cagctcagtg actgtcccct ccagcacctg gcccagcgag 660
accgtcacct gcaacgttgc ccacccggcc agcagcacca aggtggacaa gaaaattgtg 720
cccagggatt gtggttgtaa gccttgcata tgtacagtcc cagaagtatc atctgtcttc 780
atcttccccc caaagcccaa ggatgtgctc accattactc tgactcctaa ggtcacgtgt 840
gttgtggtag acatcagcaa ggatgatccc gaggtccagt tcagctggtt tgtagatgat 900
gtggaggtgc acacagctca gacgcaaccc cgggaggagc agttcaacag cactttccgc 960
tcagtcagtg aacttcccat catgcaccag gactggctca atggcaagga gttcaaatgc 1020
agggtcaaca gtgcagcttt ccctgccccc atcgagaaaa ccatctccaa aaccaaaggc 1080
agaccgaagg ctccacaggt gtacaccatt ccacctccca aggagcagat ggccaaggat 1140
aaagtcagtc tgacctgcat gataacagac ttcttccctg aagacattac tgtggagtgg 1200
cagtggaatg ggcagccagc ggagaactac aagaacactc agcccatcat ggacacagat 1260
ggctcttact tcatctacag caagctcaat gtgcagaaga gcaactggga ggcaggaaat 1320
actttcacct gctctgtgtt acatgagggc ctgcacaacc accatactga gaagagcctc 1380
tcccactctc ctggtaaatg a 1401

<210> SEQ ID NO 157
<211> LENGTH: 214
<212> TYPE: PRT
<213> ORGANISM: Mus musculus

<400> SEQUENCE: 157

Asp Ile Gln Met Thr Gln Thr Thr Ser Ser Leu Ser Ala Ser Leu Gly
1 5 10 15

Asp Arg Val Thr Ile Cys Cys Arg Ala Ser Gln Val Ile Thr Asn Tyr
20 25 30

```
Leu Tyr Trp Tyr Gln Gln Lys Pro Asp Gly Thr Phe Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 158
<211> LENGTH: 642
<212> TYPE: DNA
<213> ORGANISM: Mus musculus

<400> SEQUENCE: 158

```
gatatccaga tgacacagac tacatcctcc ctgtctgcct ctctgggaga cagagtcacc      60

atctgttgca gggcaagtca ggtcattacc aattatttat actggtatca gcagaaacca     120

gatggaactt ttaaactcct gatctactac acatcaagat tacactcagg agtcccatca     180

aggttcagtg gcagtgggtc tggaacagat tattctctca ccattagcaa cctggaacag     240

gaagatattg ccacttactt ttgccaacag ggtgatacgc ttccgtacac gttcggaggg     300

gggaccaagc tggaaataaa acgggctgat gctgcaccaa ctgtatccat cttcccacca     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gt                        642
```

<210> SEQ ID NO 159
<211> LENGTH: 234
<212> TYPE: PRT
<213> ORGANISM: Mus musculus

<400> SEQUENCE: 159

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
```

```
            20                  25                  30

Ala Ser Leu Gly Asp Arg Val Thr Ile Cys Cys Arg Ala Ser Gln Val
        35                  40                  45

Ile Thr Asn Tyr Leu Tyr Trp Tyr Gln Gln Lys Pro Asp Gly Thr Phe
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 160
<211> LENGTH: 702
<212> TYPE: DNA
<213> ORGANISM: Mus musculus

<400> SEQUENCE: 160

```
atgatgtcct ctgctcagtt ccttggtctc ctgttgctct gttttcaagg taccagatgt      60

gatatccaga tgacacagac tacatcctcc ctgtctgcct ctctgggaga cagagtcacc     120

atctgttgca gggcaagtca ggtcattacc aattatttat actggtatca gcagaaacca     180

gatggaactt ttaaactcct gatctactac acatcaagat tacactcagg agtcccatca     240

aggttcagtg gcagtgggtc tggaacagat tattctctca ccattagcaa cctggaacag     300

gaagatattg ccacttactt ttgccaacag ggtgatacgc ttccgtacac gttcggaggg     360

gggaccaagc tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gt                        702
```

<210> SEQ ID NO 161
<211> LENGTH: 447
<212> TYPE: PRT
<213> ORGANISM: Mus musculus

<400> SEQUENCE: 161

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Met Lys Gln Asn Gln Gly Lys Ser Leu Glu Trp Ile
        35                  40                  45

Gly Glu Ile Asn Pro Asn Ser Gly Gly Ala Gly Tyr Asn Gln Gln Phe
    50                  55                  60

Lys Gly Lys Ala Thr Leu Thr Val Asp Lys Ser Ser Arg Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Val Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
420 425 430

His Asn His His Thr Glu Lys Ser Leu Ser His Ser Pro Gly Lys
435 440 445

<210> SEQ ID NO 162
<211> LENGTH: 1341
<212> TYPE: DNA
<213> ORGANISM: Mus musculus

<400> SEQUENCE: 162
gaggtccagc tgcaacagtc tggacctgaa ctaatgaagc ctggggcttc agtgaagatg 60
tcctgcaagg cttctggata cacattcact gactacaaca tgcactggat gaagcagaac 120
caaggaaaga gcctagaatg gataggagaa attaatccta acagtggtgg tgctggctac 180
aaccagcagt tcaaaggcaa ggccacattg actgtagaca agtcctccag gacagcctac 240
atggagctcc gcagcctgac atctgaggac tctgcagtct attactgtgc aagattgggc 300
tacgttggta attacgagga ctggtacttc gatgtctggg gcgcagggac cacggtcacc 360
gtctcctcag ccaaaacgac acccccatct gtctatccac tggcccctgg atctgctgcc 420
caaactaact ccatggtgac cctgggatgc ctggtcaagg gctatttccc tgagccagtg 480
acagtgacct ggaactctgg atccctgtcc agcggtgtgc acaccttccc agctgtcctg 540
cagtctgacc tctacactct gagcagctca gtgactgtcc cctccagcac ctggcccagc 600
gagaccgtca cctgcaacgt tgcccacccg gccagcagca ccaaggtgga caagaaaatt 660
gtgcccaggg attgtggttg taagccttgc atatgtacag tcccagaagt atcatctgtc 720
ttcatcttcc ccccaaagcc caaggatgtg ctcaccatta ctctgactcc taaggtcacg 780
tgtgttgtgg tagacatcag caaggatgat cccgaggtcc agttcagctg gtttgtagat 840
gatgtggagg tgcacacagc tcagacgcaa ccccgggagg agcagttcaa cagcactttc 900
cgctcagtca gtgaacttcc catcatgcac caggactggc tcaatggcaa ggagttcaaa 960
tgcagggtca acagtgcagc tttccctgcc cccatcgaga aaaccatctc caaaaccaaa 1020
ggcagaccga aggctccaca ggtgtacacc attccacctc ccaaggagca gatggccaag 1080
gataaagtca gtctgacctg catgataaca gacttcttcc ctgaagacat tactgtggag 1140
tggcagtgga atgggcagcc agcggagaac tacaagaaca ctcagcccat catggacaca 1200
gatggctctt acttcatcta cagcaagctc aatgtgcaga agagcaactg ggaggcagga 1260
aatactttca cctgctctgt gttacatgag ggcctgcaca accaccatac tgagaagagc 1320
ctctcccact ctcctggtaa a 1341

<210> SEQ ID NO 163
<211> LENGTH: 466
<212> TYPE: PRT
<213> ORGANISM: Mus musculus

<400> SEQUENCE: 163

Met Gly Trp Ser Trp Thr Phe Leu Phe Leu Leu Ser Gly Thr Ala Gly
1 5 10 15

Val Leu Ser Glu Val Gln Leu Gln Gln Ser Gly Pro Glu Leu Met Lys
20 25 30

Pro Gly Ala Ser Val Lys Met Ser Cys Lys Ala Ser Gly Tyr Thr Phe
35 40 45

Thr Asp Tyr Asn Met His Trp Met Lys Gln Asn Gln Gly Lys Ser Leu

```
    50                  55                  60

Glu Trp Ile Gly Glu Ile Asn Pro Asn Ser Gly Gly Ala Gly Tyr Asn
65                  70                  75                  80

Gln Gln Phe Lys Gly Lys Ala Thr Leu Thr Val Asp Lys Ser Ser Arg
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Val Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 164
<211> LENGTH: 1398
<212> TYPE: DNA
<213> ORGANISM: Mus musculus

<400> SEQUENCE: 164
atgggatgga gctggacctt tctcttcctc ctgtcaggaa ctgcaggtgt cctctctgag 60
gtccagctgc aacagtctgg acctgaacta atgaagcctg gggcttcagt gaagatgtcc 120
tgcaaggctt ctggatacac attcactgac tacaacatgc actggatgaa gcagaaccaa 180
ggaaagagcc tagaatggat aggagaaatt aatcctaaca gtggtggtgc tggctacaac 240
cagcagttca aaggcaaggc cacattgact gtagacaagt cctccaggac agcctacatg 300
gagctccgca gcctgacatc tgaggactct gcagtctatt actgtgcaag attgggctac 360
gttggtaatt acgaggactg gtacttcgat gtctggggcg cagggaccac ggtcaccgtc 420
tcctcagcca aaacgacacc cccatctgtc tatccactgg cccctggatc tgctgcccaa 480
actaactcca tggtgaccct gggatgcctg gtcaagggct atttccctga gccagtgaca 540
gtgacctgga actctggatc cctgtccagc ggtgtgcaca ccttcccagc tgtcctgcag 600
tctgacctct acactctgag cagctcagtg actgtcccct ccagcacctg gcccagcgag 660
accgtcacct gcaacgttgc ccacccggcc agcagcacca aggtggacaa gaaaattgtg 720
cccagggatt gtggttgtaa gccttgcata tgtacagtcc cagaagtatc atctgtcttc 780
atcttccccc caaagcccaa ggatgtgctc accattactc tgactcctaa ggtcacgtgt 840
gttgtggtag acatcagcaa ggatgatccc gaggtccagt tcagctggtt tgtagatgat 900
gtggaggtgc acacagctca gacgcaaccc cgggaggagc agttcaacag cactttccgc 960
tcagtcagtg aacttcccat catgcaccag gactggctca atggcaagga gttcaaatgc 1020
agggtcaaca gtgcagcttt ccctgccccc atcgagaaaa ccatctccaa aaccaaaggc 1080
agaccgaagg ctccacaggt gtacaccatt ccacctccca aggagcagat ggccaaggat 1140
aaagtcagtc tgacctgcat gataacagac ttcttccctg aagacattac tgtggagtgg 1200
cagtggaatg ggcagccagc ggagaactac aagaacactc agcccatcat ggacacagat 1260
ggctcttact tcatctacag caagctcaat gtgcagaaga gcaactggga ggcaggaaat 1320
actttcacct gctctgtgtt acatgagggc ctgcacaacc accatactga gaagagcctc 1380
tcccactctc ctggtaaa 1398

<210> SEQ ID NO 165
<211> LENGTH: 214
<212> TYPE: PRT
<213> ORGANISM: Mus musculus

<400> SEQUENCE: 165

Asp Ile Gln Met Thr Gln Thr Thr Ser Ser Leu Ser Ala Ser Leu Gly
1 5 10 15

Asp Arg Val Ser Ile Ser Cys Arg Ala Ser Gln Asp Ile Ser Asn Tyr
20 25 30

Leu Asn Trp Tyr Gln Gln Lys Pro Asp Gly Thr Phe Lys Leu Leu Ile
35 40 45

Phe Tyr Thr Ser Arg Leu Leu Ser Gly Val Pro Ser Arg Phe Ser Gly
50 55 60

Ser Gly Ser Gly Thr Asp Tyr Ser Leu Thr Ile Tyr Asn Leu Glu Gln
65 70 75 80

Glu Asp Phe Ala Thr Tyr Phe Cys Gln Gln Gly Asp Thr Leu Pro Tyr
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 166
<211> LENGTH: 645
<212> TYPE: DNA
<213> ORGANISM: Mus musculus

<400> SEQUENCE: 166
gatatccaga tgacacagac tacatcctcc ctgtctgcct ctctgggaga cagggtctcc 60
atcagttgca gggcaagtca agacattagc aattatttaa actggtatca gcagaaacca 120
gatggaactt ttaaactcct tatcttctac acatcaagat tactctcagg agtcccatca 180
aggttcagtg gcagtgggtc tggaacagat tattctctca ccatttacaa cctggagcaa 240
gaagattttg ccacttactt ttgccaacag ggagatacgc ttccgtacac tttcggaggg 300
gggaccaaac tggaaataaa acgggctgat gctgcaccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gttag 645

<210> SEQ ID NO 167
<211> LENGTH: 234
<212> TYPE: PRT
<213> ORGANISM: Mus musculus

<400> SEQUENCE: 167

Met Met Ser Ser Ala Gln Phe Leu Gly Leu Leu Leu Leu Cys Phe Gln
1 5 10 15

Gly Thr Arg Cys Asp Ile Gln Met Thr Gln Thr Thr Ser Ser Leu Ser
20 25 30

Ala Ser Leu Gly Asp Arg Val Ser Ile Ser Cys Arg Ala Ser Gln Asp
35 40 45

Ile Ser Asn Tyr Leu Asn Trp Tyr Gln Gln Lys Pro Asp Gly Thr Phe
50 55 60

Lys Leu Leu Ile Phe Tyr Thr Ser Arg Leu Leu Ser Gly Val Pro Ser

```
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 168
<211> LENGTH: 705
<212> TYPE: DNA
<213> ORGANISM: Mus musculus

<400> SEQUENCE: 168

atgatgtcct ctgctcagtt ccttggtctc ctgttgctct gttttcaagg taccagatgt      60

gatatccaga tgacacagac tacatcctcc ctgtctgcct ctctgggaga cagggtctcc     120

atcagttgca gggcaagtca agacattagc aattatttaa actggtatca gcagaaacca     180

gatggaactt ttaaactcct tatcttctac acatcaagat tactctcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaaac tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttag                     705


<210> SEQ ID NO 169
<211> LENGTH: 447
<212> TYPE: PRT
<213> ORGANISM: Mus musculus

<400> SEQUENCE: 169

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Asp Trp Ile
```

```
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445
```

<210> SEQ ID NO 170

<211> LENGTH: 1344
<212> TYPE: DNA
<213> ORGANISM: Mus musculus

<400> SEQUENCE: 170
gaggtccaac tgcaacagtc tggacctgaa ctaatgaagc ctggggcttc agtgaagatg 60
tcctgcaagg cttctggata tacattcact gactacaaca tgcactgggt gaagcagaac 120
caaggaaaga ccctagactg gataggagaa attaatccta acagtggtgg tgctggctac 180
aaccagaagt tcaagggcaa ggccacattg actgtagaca agtcctccac cacagcctac 240
atggagctcc gcagcctgac atctgaggac tctgcagtct attactgtgc aagattgggc 300
tacgatgata tctacgacga ctggtacttc gatgtctggg gcgcagggac cacggtcacc 360
gtctcctcag ccaaaacgac acccccatct gtctatccac tggcccctgg atctgctgcc 420
caaactaact ccatggtgac cctgggatgc ctggtcaagg gctatttccc tgagccagtg 480
acagtgacct ggaactctgg atccctgtcc agcggtgtgc acaccttccc agctgtcctg 540
cagtctgacc tctacactct gagcagctca gtgactgtcc cctccagcac ctggcccagc 600
gagaccgtca cctgcaacgt tgcccacccg gccagcagca ccaaggtgga caagaaaatt 660
gtgcccaggg attgtggttg taagccttgc atatgtacag tcccagaagt atcatctgtc 720
ttcatcttcc ccccaaagcc caaggatgtg ctcaccatta ctctgactcc taaggtcacg 780
tgtgttgtgg tagacatcag caaggatgat cccgaggtcc agttcagctg gtttgtagat 840
gatgtggagg tgcacacagc tcagacgcaa ccccgggagg agcagttcaa cagcactttc 900
cgctcagtca gtgaacttcc catcatgcac caggactggc tcaatggcaa ggagttcaaa 960
tgcagggtca acagtgcagc tttccctgcc cccatcgaga aaaccatctc caaaaccaaa 1020
ggcagaccga aggctccaca ggtgtacacc attccacctc ccaaggagca gatggccaag 1080
gataaagtca gtctgacctg catgataaca gacttcttcc ctgaagacat tactgtggag 1140
tggcagtgga atgggcagcc agcggagaac tacaagaaca ctcagcccat catggacaca 1200
gatggctctt acttcatcta cagcaagctc aatgtgcaga agagcaactg ggaggcagga 1260
aatactttca cctgctctgt gttacatgag ggcctgcaca accaccatac tgagaagagc 1320
ctctcccact ctcctggtaa atga 1344

<210> SEQ ID NO 171
<211> LENGTH: 466
<212> TYPE: PRT
<213> ORGANISM: Mus musculus

<400> SEQUENCE: 171

Met Gly Trp Ser Trp Thr Phe Leu Phe Leu Leu Ser Gly Thr Ala Gly
1 5 10 15

Val Leu Ser Glu Val Gln Leu Gln Gln Ser Gly Pro Glu Leu Met Lys
20 25 30

Pro Gly Ala Ser Val Lys Met Ser Cys Lys Ala Ser Gly Tyr Thr Phe
35 40 45

Thr Asp Tyr Asn Met His Trp Val Lys Gln Asn Gln Gly Lys Thr Leu
50 55 60

Asp Trp Ile Gly Glu Ile Asn Pro Asn Ser Gly Gly Ala Gly Tyr Asn
65 70 75 80

Gln Lys Phe Lys Gly Lys Ala Thr Leu Thr Val Asp Lys Ser Ser Thr
85 90 95

Thr Ala Tyr Met Glu Leu Arg Ser Leu Thr Ser Glu Asp Ser Ala Val

```
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 172
<211> LENGTH: 1401
<212> TYPE: DNA
<213> ORGANISM: Mus musculus

<400> SEQUENCE: 172

```
atgggatgga gctggacctt tctcttcctc ctgtcaggaa ctgcaggtgt cctctctgag     60

gtccaactgc aacagtctgg acctgaacta atgaagcctg gggcttcagt gaagatgtcc    120

tgcaaggctt ctggatatac attcactgac tacaacatgc actgggtgaa gcagaaccaa    180

ggaaagaccc tagactggat aggagaaatt aatcctaaca gtggtggtgc tggctacaac    240

cagaagttca agggcaaggc cacattgact gtagacaagt cctccaccac agcctacatg    300

gagctccgca gcctgacatc tgaggactct gcagtctatt actgtgcaag attgggctac    360

gatgatatct acgacgactg gtacttcgat gtctggggcg cagggaccac ggtcaccgtc    420

tcctcagcca aaacgacacc cccatctgtc tatccactgg cccctggatc tgctgcccaa    480

actaactcca tggtgaccct gggatgcctg gtcaagggct atttccctga gccagtgaca    540

gtgacctgga actctggatc cctgtccagc ggtgtgcaca ccttcccagc tgtcctgcag    600

tctgacctct acactctgag cagctcagtg actgtcccct ccagcacctg gcccagcgag    660

accgtcacct gcaacgttgc ccacccggcc agcagcacca aggtggacaa gaaaattgtg    720

cccagggatt gtggttgtaa gccttgcata tgtacagtcc cagaagtatc atctgtcttc    780

atcttccccc caaagcccaa ggatgtgctc accattactc tgactcctaa ggtcacgtgt    840

gttgtggtag acatcagcaa ggatgatccc gaggtccagt tcagctggtt tgtagatgat    900

gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacagat   1260

ggctcttact tcatctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                             1401
```

<210> SEQ ID NO 173
<211> LENGTH: 214
<212> TYPE: PRT
<213> ORGANISM: Mus musculus

<400> SEQUENCE: 173

```
Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Phe Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125
```

```
Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 174
<211> LENGTH: 642
<212> TYPE: DNA
<213> ORGANISM: Mus musculus

<400> SEQUENCE: 174

gatatccaga tgacacagat tacatcctcc ctgtctgcct ctctgggaga cagggtctcc      60

atcagttgca gggcaagtca agacattagc aattatttaa attggtatca gcagaaacca     120

gatggaactt ttaaactcct tatcttctac acatcaagat tattttcagg agtcccatca     180

aggttcagtg gcagtgggtc tggaacagat tattctctca ccatttacaa cctggagcaa     240

gaagattttg ccacttactt ttgccaacag ggagatacgc ttccgtacac tttcggaggg     300

gggaccaagg tggaaataaa acgggctgat gctgcaccaa ctgtatccat cttcccacca     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gt                        642


<210> SEQ ID NO 175
<211> LENGTH: 234
<212> TYPE: PRT
<213> ORGANISM: Mus musculus

<400> SEQUENCE: 175

Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Phe Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Val Glu Ile Lys Arg
```

```
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 176
<211> LENGTH: 702
<212> TYPE: DNA
<213> ORGANISM: Mus musculus

<400> SEQUENCE: 176

atgatgtcct ctgctcagtt ccttggtctc ctgttgctct gttttcaagg taccagatgt      60

gatatccaga tgacacagat tacatcctcc ctgtctgcct ctctgggaga cagggtctcc     120

atcagttgca gggcaagtca agacattagc aattatttaa attggtatca gcagaaacca     180

gatggaactt ttaaactcct tatcttctac acatcaagat tattttcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaagg tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gt                        702


<210> SEQ ID NO 177
<211> LENGTH: 450
<212> TYPE: PRT
<213> ORGANISM: Mus musculus

<400> SEQUENCE: 177

Glu Val Gln Leu Gln Gln Ser Gly Pro Glu Leu Met Lys Pro Gly Thr
1               5                   10                  15

Ser Val Lys Met Ser Cys Lys Ala Ser Gly Tyr Thr Phe Thr Asp Tyr
            20                  25                  30

Asn Met His Trp Val Lys Gln Thr Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
```

-continued

```
                85                  90                  95

Ala Lys Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Ala
        115                 120                 125

Pro Ser Val Tyr Pro Leu Ala Pro Val Cys Gly Asp Thr Thr Gly Ser
    130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Asp Val His Thr Phe
                165                 170                 175

Pro Ala Leu Leu Gln Ser Gly Leu Tyr Thr Leu Ser Ser Ser Val Thr
            180                 185                 190

Val Thr Thr Trp Pro Ser Gln Thr Ile Thr Cys Asn Val Ala His Pro
        195                 200                 205

Ala Ser Ser Thr Lys Val Asp Lys Lys Ile Glu Pro Arg Gly Ser Pro
    210                 215                 220

Thr His Lys Pro Cys Pro Pro Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Met Val Thr Cys Val Val Val Asp Val Ser Glu Asp
            260                 265                 270

Asp Pro Asp Val His Val Ser Trp Phe Val Asn Asn Val Glu Val His
        275                 280                 285

Thr Ala Gln Thr Gln Thr His Arg Glu Asp Tyr Asn Ser Thr Ile Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Ala Leu Pro Ala Pro Ile Glu
                325                 330                 335

Arg Thr Ile Ser Lys Pro Lys Gly Pro Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Ile Thr Asp Phe Met Pro Glu Asp Ile Tyr Val Glu Trp
    370                 375                 380

Thr Asn Asn Gly Gln Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 178
<211> LENGTH: 1350
<212> TYPE: DNA
<213> ORGANISM: Mus musculus

<400> SEQUENCE: 178

-continued

```
gaggtccaac tgcaacagtc tggacctgaa ctaatgaagc ctgggacttc agtgaagatg      60
tcctgcaagg cttctggata tacattcact gactacaaca tgcactgggt gaagcagacc     120
caaggaaaga ccctagagtg gataggagaa attaatccta acagtggtgg tgctggctac     180
aaccagaagt tcaagggcaa ggccacattg actgtagaca agtcctccac cacagcctac     240
atggagctcc gcagcctgac atctgaggac tctgcagtct attactgtgc aaaattgggc     300
tacgatgata tctacgacga ctggtatttc gatgtctggg gcgcagggac cacggtcacc     360
gtctcctcag ccaaaacaac agccccatcg gtctatccac tggcccctgt gtgtggagat     420
acaactggct cctcggtgac tctaggatgc ctggtcaagg gttatttccc tgagccagtg     480
accttgacct ggaactctgg atccctgtcc agtgatgtgc acaccttccc agctctcctg     540
cagtctggcc tctacaccct cagcagctca gtgactgtaa ccacctggcc cagccagacc     600
atcacctgca atgtggccca cccggcaagc agcaccaaag tggacaagaa aattgagccc     660
agagggtccc caacacataa accctgtcct ccatgcccag ctcctaacct cttgggtgga     720
ccatccgtct tcatcttccc tccaaagatc aaggatgtac tcatgatctc cctgagcccc     780
atggtcacgt gtgtggtggt ggatgtgagc gaggatgacc cagatgtcca tgtcagctgg     840
ttcgtgaaca acgtggaagt acacacagct cagacacaaa cccatagaga ggattacaac     900
agtactatcc gggtggtcag tgccctcccc atccagcacc aggactggat gagtggcaag     960
gagttcaaat gcaaggtcaa caacaaagcc ctcccagcgc ccatcgagag aaccatctca    1020
aaacccaaag ggccagtaag agctccacag gtatatgtct tgcctccacc agaagaagag    1080
atgactaaga aacaggtcac tctgacctgc atgatcacag acttcatgcc tgaagacatt    1140
tacgtggagt ggaccaacaa cgggcaaaca gagctaaact acaagaacac tgaaccagtc    1200
ctggactctg atggttctta cttcatgtac agcaagctga gagtggaaaa gaagaactgg    1260
gtggaaagaa atagctactc ctgttcagtg gtccacgagg gtctgcacaa tcaccacacg    1320
actaagagct tctcccggac tccgggtaaa                                     1350
```

<210> SEQ ID NO 179
<211> LENGTH: 469
<212> TYPE: PRT
<213> ORGANISM: Mus musculus

<400> SEQUENCE: 179

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Thr Ser Val Lys Met Ser Cys Lys Ala Ser Gly Tyr Thr Phe
        35                  40                  45

Thr Asp Tyr Asn Met His Trp Val Lys Gln Thr Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Lys Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
```

```
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Asp Val
            180                 185                 190

His Thr Phe Pro Ala Leu Leu Gln Ser Gly Leu Tyr Thr Leu Ser Ser
        195                 200                 205

Ser Val Thr Val Thr Thr Trp Pro Ser Gln Thr Ile Thr Cys Asn Val
    210                 215                 220

Ala His Pro Ala Ser Ser Thr Lys Val Asp Lys Lys Ile Glu Pro Arg
225                 230                 235                 240

Gly Ser Pro Thr His Lys Pro Cys Pro Pro Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Met Val Thr Cys Val Val Val Asp Val
        275                 280                 285

Ser Glu Asp Asp Pro Asp Val His Val Ser Trp Phe Val Asn Asn Val
    290                 295                 300

Glu Val His Thr Ala Gln Thr Gln Thr His Arg Glu Asp Tyr Asn Ser
305                 310                 315                 320

Thr Ile Arg Val Val Ser Ala Leu Pro Ile Gln His Gln Asp Trp Met
                325                 330                 335

Ser Gly Lys Glu Phe Lys Cys Lys Val Asn Asn Lys Ala Leu Pro Ala
            340                 345                 350

Pro Ile Glu Arg Thr Ile Ser Lys Pro Lys Gly Pro Val Arg Ala Pro
        355                 360                 365

Gln Val Tyr Val Leu Pro Pro Pro Glu Glu Glu Met Thr Lys Lys Gln
    370                 375                 380

Val Thr Leu Thr Cys Met Ile Thr Asp Phe Met Pro Glu Asp Ile Tyr
385                 390                 395                 400

Val Glu Trp Thr Asn Asn Gly Gln Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465


<210> SEQ ID NO 180
<211> LENGTH: 1407
<212> TYPE: DNA
<213> ORGANISM: Mus musculus

<400> SEQUENCE: 180

atgggatgga gctggacctt tctcttcctc ctgtcaggaa ctgcaggtgt cctctctgag      60

gtccaactgc aacagtctgg acctgaacta atgaagcctg ggacttcagt gaagatgtcc     120

tgcaaggctt ctggatatac attcactgac tacaacatgc actgggtgaa gcagacccaa     180
```

```
ggaaagaccc tagagtggat aggagaaatt aatcctaaca gtggtggtgc tggctacaac    240

cagaagttca agggcaaggc cacattgact gtagacaagt cctccaccac agcctacatg    300

gagctccgca gcctgacatc tgaggactct gcagtctatt actgtgcaaa attgggctac    360

gatgatatct acgacgactg gtatttcgat gtctggggcg cagggaccac ggtcaccgtc    420

tcctcagcca aaacaacagc cccatcggtc tatccactgg cccctgtgtg tggagataca    480

actggctcct cggtgactct aggatgcctg gtcaagggtt atttccctga gccagtgacc    540

ttgacctgga actctggatc cctgtccagt gatgtgcaca ccttcccagc tctcctgcag    600

tctggcctct acaccctcag cagctcagtg actgtaacca cctggcccag ccagaccatc    660

acctgcaatg tggcccaccc ggcaagcagc accaaagtgg acaagaaaat tgagcccaga    720

gggtccccaa cacataaacc ctgtcctcca tgcccagctc ctaacctctt gggtggacca    780

tccgtcttca tcttccctcc aaagatcaag gatgtactca tgatctccct gagccccatg    840

gtcacgtgtg tggtggtgga tgtgagcgag gatgacccag atgtccatgt cagctggttc    900

gtgaacaacg tggaagtaca cacagctcag acacaaaccc atagagagga ttacaacagt    960

actatccggg tggtcagtgc cctccccatc cagcaccagg actggatgag tggcaaggag   1020

ttcaaatgca aggtcaacaa caaagccctc ccagcgccca tcgagagaac catctcaaaa   1080

cccaaagggc cagtaagagc tccacaggta tatgtcttgc ctccaccaga agaagagatg   1140

actaagaaac aggtcactct gacctgcatg atcacagact tcatgcctga agacatttac   1200

gtggagtgga ccaacaacgg gcaaacagag ctaaactaca agaacactga accagtcctg   1260

gactctgatg gttcttactt catgtacagc aagctgagag tggaaaagaa gaactgggtg   1320

gaaagaaata gctactcctg ttcagtggtc cacgagggtc tgcacaatca ccacacgact   1380

aagagcttct cccggactcc gggtaaa                                       1407
```

<210> SEQ ID NO 181
<211> LENGTH: 214
<212> TYPE: PRT
<213> ORGANISM: Mus musculus

<400> SEQUENCE: 181

```
Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Leu Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

```
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 182
<211> LENGTH: 645
<212> TYPE: DNA
<213> ORGANISM: Mus musculus

<400> SEQUENCE: 182

gatatccaga tgacacagac tacatcctcc ctgtctgcct ctctgggaga cagggtctcc      60

atcagttgca gggcaagtca agacattagc aattatttaa actggtatca gcagaaacca     120

gatggaactt ttaaactcct tatcttctac acatcaagat tactctcagg agtcccatca     180

aggttcagtg gcagtgggtc tggaacagat tattctctca ccatttacaa cctggagcaa     240

gaagattttg ccacttactt ttgccaacag ggagatacgc ttccgtacac tttcggaggg     300

gggaccaaac tggaaataaa acgggctgat gctgcaccaa ctgtatccat cttcccacta     360

tccagtgagc agttaacatc tggaggtgcc tcagtcgtgt gcttcttgaa caacttctac     420

cccaaagaca tcaatgtcaa gtggaagatt gatggcagtg aacgacaaaa tggcgtcctg     480

aacagttgga ctgatcagga cagcaaagac agcacctaca gcatgagcag caccctcacg     540

ttgaccaagg acgagtatga acgacataac agctatacct gtgaggccac tcacaagaca     600

tcaacttcac ccattgtcaa gagcttcaac aggaatgagt gttag                    645


<210> SEQ ID NO 183
<211> LENGTH: 234
<212> TYPE: PRT
<213> ORGANISM: Mus musculus

<400> SEQUENCE: 183

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Leu Ser Ser Glu Gln
    130                 135                 140

Leu Thr Ser Gly Gly Ala Ser Val Val Cys Phe Leu Asn Asn Phe Tyr
```

```
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 184
<211> LENGTH: 705
<212> TYPE: DNA
<213> ORGANISM: Mus musculus

<400> SEQUENCE: 184

```
atgatgtcct ctgctcagtt ccttggtctc ctgttgctct gttttcaagg taccagatgt      60

gatatccaga tgacacagac tacatcctcc ctgtctgcct ctctgggaga cagggtctcc     120

atcagttgca gggcaagtca agacattagc aattatttaa actggtatca gcagaaacca     180

gatggaactt ttaaactcct tatcttctac acatcaagat tactctcagg agtcccatca     240

aggttcagtg gcagtgggtc tggaacagat tattctctca ccatttacaa cctggagcaa     300

gaagattttg ccacttactt ttgccaacag ggagatacgc ttccgtacac tttcggaggg     360

gggaccaaac tggaaataaa acgggctgat gctgcaccaa ctgtatccat cttcccacta     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttag                     705
```

<210> SEQ ID NO 185
<211> LENGTH: 447
<212> TYPE: PRT
<213> ORGANISM: Mus musculus

<400> SEQUENCE: 185

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
```

```
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445
```

<210> SEQ ID NO 186
<211> LENGTH: 1344
<212> TYPE: DNA
<213> ORGANISM: Mus musculus

<400> SEQUENCE: 186

```
gaggtccaac tgcaacagtc tggacctgaa ctaatgaagc ctggggcttc agtgaagatg     60

tcctgcaagg cttctggata tacattcact gactacaaca tgcactgggt gaagcagaac    120

caaggaaaga ccctagaatg gataggagaa attaatccta acagtggtgg tgctggctac    180

aaccagaagt tcaagggcaa ggccacattg actgtagaca agtcctccac cacagcctac    240

atggagctcc gcagcctgac atctgaggac tctgcagtct attactgtgc aagattgggc    300
```

```
tacgatgata tctacgacga ctggtacttc gatgtctggg gcgcagggac cacggtcacc    360

gtctcctcag ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900

cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                          1344
```

<210> SEQ ID NO 187
<211> LENGTH: 466
<212> TYPE: PRT
<213> ORGANISM: Mus musculus

<400> SEQUENCE: 187

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
```

```
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465


<210> SEQ ID NO 188
<211> LENGTH: 1401
<212> TYPE: DNA
<213> ORGANISM: Mus musculus

<400> SEQUENCE: 188

atgggatgga gctggacctt tctcttcctc ctgtcaggaa ctgcaggtgt cctctctgag      60

gtccaactgc aacagtctgg acctgaacta atgaagcctg gggcttcagt gaagatgtcc     120

tgcaaggctt ctggatatac attcactgac tacaacatgc actgggtgaa gcagaaccaa     180

ggaaagaccc tagaatggat aggagaaatt aatcctaaca gtggtggtgc tggctacaac     240

cagaagttca agggcaaggc cacattgact gtagacaagt cctccaccac agcctacatg     300

gagctccgca gcctgacatc tgaggactct gcagtctatt actgtgcaag attgggctac     360

gatgatatct acgacgactg gtacttcgat gtctggggcg cagggaccac ggtcaccgtc     420

tcctcagcca aaacgacacc cccatctgtc tatccactgg cccctggatc tgctgcccaa     480
```

```
actaactcca tggtgaccct gggatgcctg gtcaagggct atttccctga gccagtgaca    540

gtgacctgga actctggatc cctgtccagc ggtgtgcaca ccttcccagc tgtcctgcag    600

tctgacctct acactctgag cagctcagtg actgtcccct ccagcacctg gcccagcgag    660

accgtcacct gcaacgttgc ccacccggcc agcagcacca aggtggacaa gaaaattgtg    720

cccagggatt gtggttgtaa gccttgcata tgtacagtcc cagaagtatc atctgtcttc    780

atcttccccc caaagcccaa ggatgtgctc accattactc tgactcctaa ggtcacgtgt    840

gttgtggtag acatcagcaa ggatgatccc gaggtccagt tcagctggtt tgtagatgat    900

gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacagat   1260

ggctcttact tcatctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                              1401
```

```
<210> SEQ ID NO 189
<211> LENGTH: 213
<212> TYPE: PRT
<213> ORGANISM: Mus musculus

<400> SEQUENCE: 189

Gln Ile Val Leu Ser Gln Ser Pro Ala Phe Leu Ser Val Ser Pro Gly
1               5                   10                  15

Asp Lys Val Thr Met Thr Cys Arg Ala Ser Ser Ser Ile Ser Tyr Ile
            20                  25                  30

His Trp Phe Gln Gln Lys Pro Gly Ser Ser Pro Arg Ser Trp Ile Tyr
        35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205
```

```
Asn Arg Asn Glu Cys
    210


<210> SEQ ID NO 190
<211> LENGTH: 642
<212> TYPE: DNA
<213> ORGANISM: Mus musculus

<400> SEQUENCE: 190

caaattgttc tctcccagtc tccagcattc ctgtctgtat ctccagggga taaggtcaca      60

atgacttgca gggccagctc aagtataagt tacatacact ggtttcagca gaagccagga     120

tcctccccca gatcctggat ttatgccaca tccaacctgg cttctggagt ccctggtcgc     180

ttcagtggca gtgggtctgg gacctcttac tctctcacaa tcagcagagt ggaggctgag     240

gatgctgcca cttattactg ccagcagtgg agtagtgacc cactcacgtt cggtgctggg     300

accaagctgg agctgaaacg ggctgatgct gcaccaactg tatccatctt cccaccatcc     360

agtgagcagt taacatctgg aggtgcctca gtcgtgtgct tcttgaacaa cttctacccc     420

aaagacatca atgtcaagtg gaagattgat ggcagtgaac gacaaaatgg cgtcctgaac     480

agttggactg atcaggacag caaagacagc acctacagca tgagcagcac cctcacgttg     540

accaaggacg agtatgaacg acataacagc tatacctgtg aggccactca caagacatca     600

acttcaccca ttgtcaagag cttcaacagg aatgagtgtt ag                        642


<210> SEQ ID NO 191
<211> LENGTH: 235
<212> TYPE: PRT
<213> ORGANISM: Mus musculus

<400> SEQUENCE: 191

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Phe
            20                  25                  30

Leu Ser Val Ser Pro Gly Asp Lys Val Thr Met Thr Cys Arg Ala Ser
        35                  40                  45

Ser Ser Ile Ser Tyr Ile His Trp Phe Gln Gln Lys Pro Gly Ser Ser
    50                  55                  60

Pro Arg Ser Trp Ile Tyr Ala Thr Ser Asn Leu Ala Ser Gly Val Pro
65                  70                  75                  80

Gly Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asp Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
```

```
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 192
<211> LENGTH: 708
<212> TYPE: DNA
<213> ORGANISM: Mus musculus

<400> SEQUENCE: 192

atggattttc aagtgcagat tttcagcttc ctgctaatca gtgcttcagt cataatgtcc      60

agaggacaaa ttgttctctc ccagtctcca gcattcctgt ctgtatctcc aggggataag     120

gtcacaatga cttgcagggc cagctcaagt ataagttaca tacactggtt tcagcagaag     180

ccaggatcct cccccagatc ctggatttat gccacatcca acctggcttc tggagtccct     240

ggtcgcttca gtggcagtgg gtctgggacc tcttactctc tcacaatcag cagagtggag     300

gctgaggatg ctgccactta ttactgccag cagtggagta gtgacccact cacgttcggt     360

gctgggacca agctggagct gaaacgggct gatgctgcac caactgtatc catcttccca     420

ccatccagtg agcagttaac atctggaggt gcctcagtcg tgtgcttctt gaacaacttc     480

taccccaaag acatcaatgt caagtggaag attgatggca gtgaacgaca aaatggcgtc     540

ctgaacagtt ggactgatca ggacagcaaa gacagcacct acagcatgag cagcaccctc     600

acgttgacca aggacgagta tgaacgacat aacagctata cctgtgaggc cactcacaag     660

acatcaactt cacccattgt caagagcttc aacaggaatg agtgttag                  708


<210> SEQ ID NO 193
<211> LENGTH: 445
<212> TYPE: PRT
<213> ORGANISM: Mus musculus

<400> SEQUENCE: 193

Glu Val Gln Leu Gln Gln Ser Gly Ala Asp Leu Val Gln Pro Gly Ala
1               5                   10                  15

Ser Val Lys Val Ser Cys Thr Ala Ser Gly Phe Asp Ile Lys Asp Tyr
            20                  25                  30

Tyr Ile His Trp Met Lys Gln Arg Pro Asp Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Ala Thr Phe Thr Thr Asp Thr Ser Ser Asn Thr Ala Tyr
65                  70                  75                  80

Leu Gln Leu Arg Gly Leu Thr Ser Glu Asp Thr Ala Ile Tyr Tyr Cys
                85                  90                  95

Gly Arg Glu Asp Tyr Asp Gly Thr Tyr Thr Trp Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
```

```
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 194
<211> LENGTH: 1338
<212> TYPE: DNA
<213> ORGANISM: Mus musculus

<400> SEQUENCE: 194

gaagttcagc tgcaacagtc tggggcagac cttgtgcagc caggggcctc agtcaaggtg      60

tcctgcacag cttctggctt cgacattaag gactactata tacactggat gaaacagagg     120

cctgaccagg gcctggagtg gattggaagg gttgatcctg acaatggtga gactgaattt     180

gccccgaagt tcccgggcaa ggccactttt acaacagaca catcctccaa cacagcctac     240

ctacaactca gaggcctgac atctgaggac actgccatct attactgtgg gagagaagac     300

tacgatggta cctacacctg gtttccttat tggggccaag ggactctggt cactgtctct     360

gcagccaaaa cgacaccccc atctgtctat ccactggccc ctggatctgc tgcccaaact     420

aactccatgg tgaccctggg atgcctggtc aagggctatt tccctgagcc agtgacagtg     480

acctggaact ctggatccct gtccagcggt gtgcacacct tcccagctgt cctgcagtct     540
```

-continued

```
gacctctaca ctctgagcag ctcagtgact gtcccctcca gcacctggcc cagcgagacc    600

gtcacctgca acgttgccca cccggccagc agcaccaagg tggacaagaa aattgtgccc    660

agggattgtg gttgtaagcc ttgcatatgt acagtcccag aagtatcatc tgtcttcatc    720

ttccccccaa agcccaagga tgtgctcacc attactctga ctcctaaggt cacgtgtgtt    780

gtggtagaca tcagcaagga tgatcccgag gtccagttca gctggtttgt agatgatgtg    840

gaggtgcaca cagctcagac gcaaccccgg gaggagcagt tcaacagcac tttccgctca    900

gtcagtgaac ttcccatcat gcaccaggac tggctcaatg gcaaggagtt caaatgcagg    960

gtcaacagtg cagctttccc tgcccccatc gagaaaacca tctccaaaac caaaggcaga   1020

ccgaaggctc cacaggtgta caccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200

tcttacttca tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaatga                                                 1338
```

<210> SEQ ID NO 195
<211> LENGTH: 464
<212> TYPE: PRT
<213> ORGANISM: Mus musculus

<400> SEQUENCE: 195

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Asp Leu Val Gln
            20                  25                  30

Pro Gly Ala Ser Val Lys Val Ser Cys Thr Ala Ser Gly Phe Asp Ile
        35                  40                  45

Lys Asp Tyr Tyr Ile His Trp Met Lys Gln Arg Pro Asp Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Ala Thr Phe Thr Thr Asp Thr Ser Ser Asn
                85                  90                  95

Thr Ala Tyr Leu Gln Leu Arg Gly Leu Thr Ser Glu Asp Thr Ala Ile
            100                 105                 110

Tyr Tyr Cys Gly Arg Glu Asp Tyr Asp Gly Thr Tyr Thr Trp Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
```

225 230 235 240

Asp Cys Gly Cys Lys Pro Cys Ile Cys Thr Val Pro Glu Val Ser Ser
245 250 255

Val Phe Ile Phe Pro Pro Lys Pro Lys Asp Val Leu Thr Ile Thr Leu
260 265 270

Thr Pro Lys Val Thr Cys Val Val Val Asp Ile Ser Lys Asp Asp Pro
275 280 285

Glu Val Gln Phe Ser Trp Phe Val Asp Asp Val Glu Val His Thr Ala
290 295 300

Gln Thr Gln Pro Arg Glu Glu Gln Phe Asn Ser Thr Phe Arg Ser Val
305 310 315 320

Ser Glu Leu Pro Ile Met His Gln Asp Trp Leu Asn Gly Lys Glu Phe
325 330 335

Lys Cys Arg Val Asn Ser Ala Ala Phe Pro Ala Pro Ile Glu Lys Thr
340 345 350

Ile Ser Lys Thr Lys Gly Arg Pro Lys Ala Pro Gln Val Tyr Thr Ile
355 360 365

Pro Pro Pro Lys Glu Gln Met Ala Lys Asp Lys Val Ser Leu Thr Cys
370 375 380

Met Ile Thr Asp Phe Phe Pro Glu Asp Ile Thr Val Glu Trp Gln Trp
385 390 395 400

Asn Gly Gln Pro Ala Glu Asn Tyr Lys Asn Thr Gln Pro Ile Met Asp
405 410 415

Thr Asp Gly Ser Tyr Phe Ile Tyr Ser Lys Leu Asn Val Gln Lys Ser
420 425 430

Asn Trp Glu Ala Gly Asn Thr Phe Thr Cys Ser Val Leu His Glu Gly
435 440 445

Leu His Asn His His Thr Glu Lys Ser Leu Ser His Ser Pro Gly Lys
450 455 460

<210> SEQ ID NO 196
<211> LENGTH: 1395
<212> TYPE: DNA
<213> ORGANISM: Mus musculus

<400> SEQUENCE: 196
atgaaatgca gctgggtcat cttcttcctg atggcagtgg ttacaggggt caattcagaa 60
gttcagctgc aacagtctgg ggcagacctt gtgcagccag gggcctcagt caaggtgtcc 120
tgcacagctt ctggcttcga cattaaggac tactatatac actggatgaa acagaggcct 180
gaccagggcc tggagtggat tggaagggtt gatcctgaca atggtgagac tgaatttgcc 240
ccgaagttcc cgggcaaggc cacttttaca acagacacat cctccaacac agcctaccta 300
caactcagag gcctgacatc tgaggacact gccatctatt actgtgggag agaagactac 360
gatggtacct acacctggtt tccttattgg ggccaaggga ctctggtcac tgtctctgca 420
gccaaaacga cacccccatc tgtctatcca ctggcccctg gatctgctgc ccaaactaac 480
tccatggtga ccctgggatg cctggtcaag ggctatttcc ctgagccagt gacagtgacc 540
tggaactctg gatccctgtc cagcggtgtg cacaccttcc cagctgtcct gcagtctgac 600
ctctacactc tgagcagctc agtgactgtc ccctccagca cctggcccag cgagaccgtc 660
acctgcaacg ttgcccaccc ggccagcagc accaaggtgg acaagaaaat tgtgcccagg 720
gattgtggtt gtaagccttg catatgtaca gtcccagaag tatcatctgt cttcatcttc 780
cccccaaagc ccaaggatgt gctcaccatt actctgactc ctaaggtcac gtgtgttgtg 840

```
gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcatct acagcaagct caatgtgcag aagagcaact gggaggcagg aaatactttc   1320

acctgctctg tgttacatga gggcctgcac aaccaccata ctgagaagag cctctcccac   1380

tctcctggta aatga                                                    1395
```

<210> SEQ ID NO 197
<211> LENGTH: 214
<212> TYPE: PRT
<213> ORGANISM: Mus musculus

<400> SEQUENCE: 197

```
Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Thr Leu Gln Ser Gly Val Pro Ser Arg Phe Ser Gly
    50                  55                  60

Ser Gly Ser Gly Thr Asn Tyr Ser Leu Thr Ile Thr Asn Leu Glu Gln
65                  70                  75                  80

Asp Asp Ala Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 198
<211> LENGTH: 645
<212> TYPE: DNA
<213> ORGANISM: Mus musculus

<400> SEQUENCE: 198

```
gatctccaga tgacacagac tacttcctcc ctgtctgcct ctctgggaga cagagtcacc     60

atcagttgca gggcaagtca ggacattagc aattatttaa actggtatca gcagaaacca    120

gatggaactg ttaagctcct gatcttctac acatcaacat tacagtcagg agtcccatcg    180

aggttcagtg gcagtgggtc tggaacaaat tattctctca ccattaccaa cctggagcaa    240

gatgatgctg ccacttactt ttgccaacag ggtgatacgc ttccgtacac gttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gttag                    645
```

<210> SEQ ID NO 199
<211> LENGTH: 234
<212> TYPE: PRT
<213> ORGANISM: Mus musculus

<400> SEQUENCE: 199

```
Met Met Ser Ser Ala Gln Phe Leu Gly Leu Leu Leu Leu Cys Phe Gln
1               5                   10                  15

Gly Ser Arg Cys Asp Leu Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Phe Tyr Thr Ser Thr Leu Gln Ser Gly Val Pro Ser
65                  70                  75                  80

Arg Phe Ser Gly Ser Gly Ser Gly Thr Asn Tyr Ser Leu Thr Ile Thr
                85                  90                  95

Asn Leu Glu Gln Asp Asp Ala Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 200
<211> LENGTH: 705
<212> TYPE: DNA

<213> ORGANISM: Mus musculus

<400> SEQUENCE: 200
atgatgtcct ctgctcagtt ccttggtctc ctgttgctct gttttcaagg ttccagatgt 60
gatctccaga tgacacagac tacttcctcc ctgtctgcct ctctgggaga cagagtcacc 120
atcagttgca gggcaagtca ggacattagc aattatttaa actggtatca gcagaaacca 180
gatggaactg ttaagctcct gatcttctac acatcaacat tacagtcagg agtcccatcg 240
aggttcagtg gcagtgggtc tggaacaaat tattctctca ccattaccaa cctggagcaa 300
gatgatgctg ccacttactt ttgccaacag ggtgatacgc ttccgtacac gttcggaggg 360
gggaccaagc tggaaataaa acgggctgat gctgcaccaa ctgtatccat cttcccacca 420
tccagtgagc agttaacatc tggaggtgcc tcagtcgtgt gcttcttgaa caacttctac 480
cccaaagaca tcaatgtcaa gtggaagatt gatggcagtg aacgacaaaa tggcgtcctg 540
aacagttgga ctgatcagga cagcaaagac agcacctaca gcatgagcag caccctcacg 600
ttgaccaagg acgagtatga acgacataac agctatacct gtgaggccac tcacaagaca 660
tcaacttcac ccattgtcaa gagcttcaac aggaatgagt gttag 705

<210> SEQ ID NO 201
<211> LENGTH: 447
<212> TYPE: PRT
<213> ORGANISM: Mus musculus

<400> SEQUENCE: 201

Glu Val Gln Leu Gln Gln Ser Gly Pro Glu Leu Met Lys Pro Gly Ala
1 5 10 15

Ser Val Lys Met Ser Cys Lys Ala Ser Gly Tyr Thr Phe Thr Asp Tyr
20 25 30

Asn Met His Trp Met Lys Gln Asn Gln Gly Lys Ser Leu Glu Trp Ile
35 40 45

Gly Glu Ile Asn Pro Asn Ser Gly Gly Ser Gly Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Arg Leu Gly Tyr Tyr Gly Asn Tyr Glu Asp Trp Tyr Phe Asp Val
100 105 110

Trp Gly Ala Gly Thr Thr Val Thr Val Ser Ser Ala Lys Thr Thr Pro
115 120 125

Pro Ser Val Tyr Pro Leu Ala Pro Gly Ser Ala Ala Gln Thr Asn Ser
130 135 140

Met Val Thr Leu Gly Cys Leu Val Lys Gly Tyr Phe Pro Glu Pro Val
145 150 155 160

Thr Val Thr Trp Asn Ser Gly Ser Leu Ser Ser Gly Val His Thr Phe
165 170 175

Pro Ala Val Leu Gln Ser Asp Leu Tyr Thr Leu Ser Ser Ser Val Thr
180 185 190

Val Pro Ser Ser Thr Trp Pro Ser Glu Thr Val Thr Cys Asn Val Ala
195 200 205

His Pro Ala Ser Ser Thr Lys Val Asp Lys Lys Ile Val Pro Arg Asp
210 215 220

Cys Gly Cys Lys Pro Cys Ile Cys Thr Val Pro Glu Val Ser Ser Val

```
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445
```

<210> SEQ ID NO 202
<211> LENGTH: 1344
<212> TYPE: DNA
<213> ORGANISM: Mus musculus

<400> SEQUENCE: 202

```
gaggtccagt tgcaacagtc tggacctgaa ctaatgaagc ctggggcttc agtgaagatg     60

tcctgcaagg cttctggata cacattcact gactacaaca tgcactggat gaagcagaac    120

caaggaaaga gcctagagtg gataggagag attaatccta acagtggtgg ttctggttac    180

aaccagaagt tcaaaggcaa ggccacattg actgtagaca agtcctccag cacagcctac    240

atggagctcc gcagcctgac atctgaggac tctgcagtct attactgtgc aagattgggc    300

tactatggta actacgagga ctggtatttc gatgtctggg gcgcagggac cacggtcacc    360

gtctcctctg ccaaaacgac acccccatct gtctatccac tggcccctgg atctgctgcc    420

caaactaact ccatggtgac cctgggatgc ctggtcaagg gctatttccc tgagccagtg    480

acagtgacct ggaactctgg atccctgtcc agcggtgtgc acaccttccc agctgtcctg    540

cagtctgacc tctacactct gagcagctca gtgactgtcc cctccagcac ctggcccagc    600

gagaccgtca cctgcaacgt tgcccacccg gccagcagca ccaaggtgga caagaaaatt    660

gtgcccaggg attgtggttg taagccttgc atatgtacag tcccagaagt atcatctgtc    720

ttcatcttcc ccccaaagcc caaggatgtg ctcaccatta ctctgactcc taaggtcacg    780

tgtgttgtgg tagacatcag caaggatgat cccgaggtcc agttcagctg gtttgtagat    840

gatgtggagg tgcacacagc tcagacgcaa ccccgggagg agcagttcaa cagcactttc    900
```

```
cgctcagtca gtgaacttcc catcatgcac caggactggc tcaatggcaa ggagttcaaa    960

tgcagggtca acagtgcagc tttccctgcc cccatcgaga aaaccatctc caaaaccaaa   1020

ggcagaccga aggctccaca ggtgtacacc attccacctc ccaaggagca gatggccaag   1080

gataaagtca gtctgacctg catgataaca gacttcttcc ctgaagacat tactgtggag   1140

tggcagtgga atgggcagcc agcggagaac tacaagaaca ctcagcccat catggacaca   1200

gatggctctt acttcatcta cagcaagctc aatgtgcaga agagcaactg ggaggcagga   1260

aatactttca cctgctctgt gttacatgag ggcctgcaca accaccatac tgagaagagc   1320

ctctcccact ctcctggtaa atga                                          1344
```

```
<210> SEQ ID NO 203
<211> LENGTH: 466
<212> TYPE: PRT
<213> ORGANISM: Mus musculus

<400> SEQUENCE: 203

Met Gly Trp Ser Trp Thr Phe Leu Phe Leu Leu Ser Gly Thr Ser Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Met Lys Gln Asn Gln Gly Lys Ser Leu
    50                  55                  60

Glu Trp Ile Gly Glu Ile Asn Pro Asn Ser Gly Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Tyr Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
```

```
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465


<210> SEQ ID NO 204
<211> LENGTH: 1401
<212> TYPE: DNA
<213> ORGANISM: Mus musculus

<400> SEQUENCE: 204

atgggatgga gctggacctt tctcttcctc ctgtcaggaa cttcgggtgt cctctctgag      60

gtccagttgc aacagtctgg acctgaacta atgaagcctg gggcttcagt gaagatgtcc     120

tgcaaggctt ctggatacac attcactgac tacaacatgc actggatgaa gcagaaccaa     180

ggaaagagcc tagagtggat aggagagatt aatcctaaca gtggtggttc tggttacaac     240

cagaagttca aaggcaaggc cacattgact gtagacaagt cctccagcac agcctacatg     300

gagctccgca gcctgacatc tgaggactct gcagtctatt actgtgcaag attgggctac     360

tatggtaact acgaggactg gtatttcgat gtctggggcg cagggaccac ggtcaccgtc     420

tcctctgcca aaacgacacc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900

gtggaggtgc acacagctca gacgcaaccc cgggaggagc agttcaacag cactttccgc     960

tcagtcagtg aacttcccat catgcaccag gactggctca atggcaagga gttcaaatgc    1020

agggtcaaca gtgcagcttt ccctgccccc atcgagaaaa ccatctccaa aaccaaaggc    1080
```

-continued agaccgaagg ctccacaggt gtacaccatt ccacctccca aggagcagat ggccaaggat 1140
aaagtcagtc tgacctgcat gataacagac ttcttccctg aagacattac tgtggagtgg 1200
cagtggaatg ggcagccagc ggagaactac aagaacactc agcccatcat ggacacagat 1260
ggctcttact tcatctacag caagctcaat gtgcagaaga gcaactggga ggcaggaaat 1320
actttcacct gctctgtgtt acatgagggc ctgcacaacc accatactga gaagagcctc 1380
tcccactctc ctggtaaatg a 1401

<210> SEQ ID NO 205
<211> LENGTH: 215
<212> TYPE: PRT
<213> ORGANISM: Mus musculus

<400> SEQUENCE: 205

Gln Ile Val Leu Thr Gln Ser Pro Ala Ile Met Ser Ala Ser Pro Gly
1 5 10 15

Glu Lys Val Thr Met Thr Cys Arg Ala Ser Ser Ser Val Thr Ser Ser
20 25 30

Tyr Leu Asn Trp Tyr Gln Gln Lys Pro Gly Ser Ser Pro Lys Leu Trp
35 40 45

Ile Tyr Ser Thr Ser Asn Leu Ala Ser Gly Val Pro Ala Arg Phe Ser
50 55 60

Gly Ser Gly Ser Gly Thr Ser Tyr Ser Leu Thr Ile Ser Ser Val Glu
65 70 75 80

Ala Glu Asp Ala Ala Thr Tyr Tyr Cys Gln Gln Tyr Asp Phe Phe Pro
85 90 95

Ser Thr Phe Gly Gly Gly Thr Lys Leu Glu Ile Lys Arg Ala Asp Ala
100 105 110

Ala Pro Thr Val Ser Ile Phe Pro Pro Ser Ser Glu Gln Leu Thr Ser
115 120 125

Gly Gly Ala Ser Val Val Cys Phe Leu Asn Asn Phe Tyr Pro Lys Asp
130 135 140

Ile Asn Val Lys Trp Lys Ile Asp Gly Ser Glu Arg Gln Asn Gly Val
145 150 155 160

Leu Asn Ser Trp Thr Asp Gln Asp Ser Lys Asp Ser Thr Tyr Ser Met
165 170 175

Ser Ser Thr Leu Thr Leu Thr Lys Asp Glu Tyr Glu Arg His Asn Ser
180 185 190

Tyr Thr Cys Glu Ala Thr His Lys Thr Ser Thr Ser Pro Ile Val Lys
195 200 205

Ser Phe Asn Arg Asn Glu Cys
210 215

<210> SEQ ID NO 206
<211> LENGTH: 645
<212> TYPE: DNA
<213> ORGANISM: Mus musculus

<400> SEQUENCE: 206
cagattgttc tcacccagtc tccagcaatc atgtctgcat ctccagggga gaaggtcacc 60
atgacctgca gggccagctc aagtgtaact tccagttact tgaactggta ccagcagaag 120
ccaggatctt cccccaaact ctggatttat agcacatcca acctggcttc aggagtccca 180
gctcgcttca gtggcagtgg gtctgggacc tcttactctc tcacaatcag cagtgtggag 240
gctgaggatg ctgccactta ttactgccag cagtatgatt ttttcccatc gacgttcggt 300

```
ggaggcacca agctggaaat caagcgggct gatgctgcac caactgtatc catcttccca    360

ccatccagtg agcagttaac atctggaggt gcctcagtcg tgtgcttctt gaacaacttc    420

taccccaaag acatcaatgt caagtggaag attgatggca gtgaacgaca aaatggcgtc    480

ctgaacagtt ggactgatca ggacagcaaa gacagcacct acagcatgag cagcaccctc    540

acgttgacca aggacgagta tgaacgacat aacagctata cctgtgaggc cactcacaag    600

acatcaactt cacccatcgt caagagcttc aacaggaatg agtgt                    645
```

<210> SEQ ID NO 207
<211> LENGTH: 237
<212> TYPE: PRT
<213> ORGANISM: Mus musculus

<400> SEQUENCE: 207

```
Met Asp Ser Gln Val Gln Ile Phe Ser Phe Leu Leu Ile Ser Ala Leu
1               5                   10                  15

Val Lys Met Ser Arg Gly Gln Ile Val Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Thr Ser Ser Tyr Leu Asn Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Asp Phe Phe Pro Ser Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

<210> SEQ ID NO 208
<211> LENGTH: 711
<212> TYPE: DNA
<213> ORGANISM: Mus musculus

<400> SEQUENCE: 208

```
atggattctc aagtgcagat tttcagcttc cttctaatca gtgccttagt caaaatgtcc     60

agaggacaga ttgttctcac ccagtctcca gcaatcatgt ctgcatctcc aggggagaag    120

gtcaccatga cctgcagggc cagctcaagt gtaacttcca gttacttgaa ctggtaccag    180
```

```
cagaagccag gatcttcccc caaactctgg atttatagca catccaacct ggcttcagga    240

gtcccagctc gcttcagtgg cagtgggtct gggacctctt actctctcac aatcagcagt    300

gtggaggctg aggatgctgc cacttattac tgccagcagt atgatttttt cccatcgacg    360

ttcggtggag gcaccaagct ggaaatcaag cgggctgatg ctgcaccaac tgtatccatc    420

ttcccaccat ccagtgagca gttaacatct ggaggtgcct cagtcgtgtg cttcttgaac    480

aacttctacc ccaaagacat caatgtcaag tggaagattg atggcagtga acgacaaaat    540

ggcgtcctga acagttggac tgatcaggac agcaaagaca gcacctacag catgagcagc    600

accctcacgt tgaccaagga cgagtatgaa cgacataaca gctatacctg tgaggccact    660

cacaagacat caacttcacc catcgtcaag agcttcaaca ggaatgagtg t             711


<210> SEQ ID NO 209
<211> LENGTH: 445
<212> TYPE: PRT
<213> ORGANISM: Mus musculus

<400> SEQUENCE: 209

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Glu Ser Leu Glu Trp Ile
        35                  40                  45

Gly Asp Ile Asn Pro Tyr Asn Asp Asp Thr Thr Tyr Asn His Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
```

-continued

```
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 210
<211> LENGTH: 1335
<212> TYPE: DNA
<213> ORGANISM: Mus musculus

<400> SEQUENCE: 210

gaggtccagc tgcaacaatc tggacctgag ctggtgaagc ctggggcttc agtgaagatg      60

tcctgtaagg cttctggata cacattcact gactactaca tgaactgggt gaagcagagc     120

catggagaga gccttgagtg gattggagat attaatcctt acaacgatga tactacctac     180

aaccacaagt tcaagggcaa ggccacattg actgtagaca aatcctccaa cacagcctac     240

atgcagctca acagcctgac atctgaggac tctgcagtct attactgtgc aagagagacg     300

gccgttatta ctacgaatgc tatggactac tggggtcaag gaacctcagt caccgtctcc     360

tcagccaaaa cgacaccccc atctgtctat ccactggccc ctggatctgc tgcccaaact     420

aactccatgg tgaccctggg atgcctggtc aagggctatt tccctgagcc agtgacagtg     480

acctggaact ctggatccct gtccagcggt gtgcacacct tcccagctgt cctgcagtct     540

gacctctaca ctctgagcag ctcagtgact gtcccctcca gcacctggcc cagcgagacc     600

gtcacctgca acgttgccca cccggccagc agcaccaagg tggacaagaa aattgtgccc     660

agggattgtg gttgtaagcc ttgcatatgt acagtcccag aagtatcatc tgtcttcatc     720

ttccccccaa agcccaagga tgtgctcacc attactctga ctcctaaggt cacgtgtgtt     780

gtggtagaca tcagcaagga tgatcccgag gtccagttca gctggtttgt agatgatgtg     840

gaggtgcaca cagctcagac gcaaccccgg gaggagcagt tcaacagcac tttccgctca     900

gtcagtgaac ttcccatcat gcaccaggac tggctcaatg gcaaggagtt caaatgcagg     960

gtcaacagtg cagctttccc tgcccccatc gagaaaacca tctccaaaac caaaggcaga    1020

ccgaaggctc cacaggtgta caccattcca cctcccaagg agcagatggc caaggataaa    1080

gtcagtctga cctgcatgat aacagacttc ttccctgaag acattactgt ggagtggcag    1140

tggaatgggc agccagcgga gaactacaag aacactcagc ccatcatgga cacagatggc    1200
```

tcttacttca tctacagcaa gctcaatgtg cagaagagca actgggaggc aggaaatact 1260
ttcacctgct ctgtgttaca tgagggcctg cacaaccacc atactgagaa gagcctctcc 1320
cactctcctg gtaaa 1335

<210> SEQ ID NO 211
<211> LENGTH: 464
<212> TYPE: PRT
<213> ORGANISM: Mus musculus

<400> SEQUENCE: 211

Met Gly Trp Asn Trp Ile Phe Leu Phe Leu Leu Ser Gly Thr Ala Gly
1 5 10 15

Val Tyr Ser Glu Val Gln Leu Gln Gln Ser Gly Pro Glu Leu Val Lys
20 25 30

Pro Gly Ala Ser Val Lys Met Ser Cys Lys Ala Ser Gly Tyr Thr Phe
35 40 45

Thr Asp Tyr Tyr Met Asn Trp Val Lys Gln Ser His Gly Glu Ser Leu
50 55 60

Glu Trp Ile Gly Asp Ile Asn Pro Tyr Asn Asp Asp Thr Thr Tyr Asn
65 70 75 80

His Lys Phe Lys Gly Lys Ala Thr Leu Thr Val Asp Lys Ser Ser Asn
85 90 95

Thr Ala Tyr Met Gln Leu Asn Ser Leu Thr Ser Glu Asp Ser Ala Val
100 105 110

Tyr Tyr Cys Ala Arg Glu Thr Ala Val Ile Thr Thr Asn Ala Met Asp
115 120 125

Tyr Trp Gly Gln Gly Thr Ser Val Thr Val Ser Ser Ala Lys Thr Thr
130 135 140

Pro Pro Ser Val Tyr Pro Leu Ala Pro Gly Ser Ala Ala Gln Thr Asn
145 150 155 160

Ser Met Val Thr Leu Gly Cys Leu Val Lys Gly Tyr Phe Pro Glu Pro
165 170 175

Val Thr Val Thr Trp Asn Ser Gly Ser Leu Ser Ser Gly Val His Thr
180 185 190

Phe Pro Ala Val Leu Gln Ser Asp Leu Tyr Thr Leu Ser Ser Ser Val
195 200 205

Thr Val Pro Ser Ser Thr Trp Pro Ser Glu Thr Val Thr Cys Asn Val
210 215 220

Ala His Pro Ala Ser Ser Thr Lys Val Asp Lys Lys Ile Val Pro Arg
225 230 235 240

Asp Cys Gly Cys Lys Pro Cys Ile Cys Thr Val Pro Glu Val Ser Ser
245 250 255

Val Phe Ile Phe Pro Pro Lys Pro Lys Asp Val Leu Thr Ile Thr Leu
260 265 270

Thr Pro Lys Val Thr Cys Val Val Val Asp Ile Ser Lys Asp Asp Pro
275 280 285

Glu Val Gln Phe Ser Trp Phe Val Asp Asp Val Glu Val His Thr Ala
290 295 300

Gln Thr Gln Pro Arg Glu Glu Gln Phe Asn Ser Thr Phe Arg Ser Val
305 310 315 320

Ser Glu Leu Pro Ile Met His Gln Asp Trp Leu Asn Gly Lys Glu Phe
325 330 335

Lys Cys Arg Val Asn Ser Ala Ala Phe Pro Ala Pro Ile Glu Lys Thr

```
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 212
<211> LENGTH: 1392
<212> TYPE: DNA
<213> ORGANISM: Mus musculus

<400> SEQUENCE: 212

atgggatgga actggatctt tctcttcctc ttgtcaggaa ctgcaggtgt ctactctgag     60

gtccagctgc aacaatctgg acctgagctg gtgaagcctg gggcttcagt gaagatgtcc    120

tgtaaggctt ctggatacac attcactgac tactacatga actgggtgaa gcagagccat    180

ggagagagcc ttgagtggat tggagatatt aatccttaca acgatgatac tacctacaac    240

cacaagttca agggcaaggc cacattgact gtagacaaat cctccaacac agcctacatg    300

cagctcaaca gcctgacatc tgaggactct gcagtctatt actgtgcaag agagacggcc    360

gttattacta cgaatgctat ggactactgg ggtcaaggaa cctcagtcac cgtctcctca    420

gccaaaacga cacccccatc tgtctatcca ctggcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcatct acagcaagct caatgtgcag aagagcaact gggaggcagg aaatactttc   1320

acctgctctg tgttacatga gggcctgcac aaccaccata ctgagaagag cctctcccac   1380

tctcctggta aa                                                        1392
```

<210> SEQ ID NO 213
<211> LENGTH: 215
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 213

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 214
<211> LENGTH: 645
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 214
gacatccagc tgacccagag ccccagcttc ctttccgcat ccgttggtga ccgagtaaca     60
atcacatgcc gcgcctcatc ttcagttaca tcttcttatc ttaattggta tcaacaaaaa    120
ccaggaaaag cacctaaact tcttatatac tctacatcta atctcgcatc aggagttccc    180
tctcgatttt caggatctgg atcaggcaca gaatttacac ttactatatc atcactccaa    240
ccagaagact tcgccactta ttactgccaa caatacgatt tttttccaag cacattcgga    300
ggaggtacaa aagtagaaat caagcgtacg gtggctgcac catctgtctt catcttcccg    360

```
ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 215
<211> LENGTH: 237
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 215

```
Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Val Thr Ser Ser Tyr Leu Asn Trp Tyr Gln Gln Lys Pro Gly
    50                  55                  60

Lys Ala Pro Lys Leu Leu Ile Tyr Ser Thr Ser Asn Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Tyr Asp Phe Phe Pro Ser Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 216
<211> LENGTH: 711
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 216
atggacatga gggtccccgc tcagctcctg gggctcctgc tactctggct cccaggtgcc 60
agatgtgaca tccagctgac ccagagcccc agcttccttt ccgcatccgt tggtgaccga 120
gtaacaatca catgccgcgc ctcatcttca gttacatctt cttatcttaa ttggtatcaa 180
caaaaaccag gaaaagcacc taaacttctt atatactcta catctaatct cgcatcagga 240
gttccctctc gattttcagg atctggatca ggcacagaat ttacacttac tatatcatca 300
ctccaaccag aagacttcgc cacttattac tgccaacaat acgatttttt tccaagcaca 360
ttcggaggag gtacaaaagt agaaatcaag cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg t 711

<210> SEQ ID NO 217
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 217

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met Asn Trp Val Arg Gln Ala Pro Gly Gln Arg Leu Glu Trp Met
35 40 45

Gly Asp Ile Asn Pro Tyr Asn Asp Asp Thr Thr Tyr Asn His Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Glu Thr Ala Val Ile Thr Thr Asn Ala Met Asp Tyr Trp Gly
100 105 110

Gln Gly Thr Thr Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

```
Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 218
<211> LENGTH: 1341
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 218

```
gaggtgcagc tggtgcagag cggcgccgag gtcaagaaac ctggagcaag cgtaaaggtt     60

agttgcaaag catctggata cacatttacc gactactaca tgaattgggt acgacaagcc    120

cctggacaaa gacttgaatg gatgggagac attaaccctt ataacgacga cactacatac    180

aatcataaat ttaaaggaag agttacaatt acaagagata catccgcatc aaccgcctat    240

atggaacttt cctcattgag atctgaagac actgctgttt attactgtgc aagagaaact    300

gccgttatta ctactaacgc tatggattac tggggtcaag gaaccactgt taccgtctct    360

agtgcctcca ccaagggccc atcggtcttc cccctggcgc cctgctccag gagcacctcc    420

gagagcacag cggccctggg ctgcctggtc aaggactact tccccgaacc ggtgacggtg    480

tcgtggaact caggcgctct gaccagcggc gtgcacacct tcccagctgt cctacagtcc    540

tcaggactct actccctcag cagcgtggtg accgtgccct ccagcaactt cggcacccag    600

acctacacct gcaacgtaga tcacaagccc agcaacacca aggtggacaa gacagttgag    660
```

```
cgcaaatgtt gtgtcgagtg cccaccgtgc ccagcaccac ctgtggcagg accgtcagtc    720

ttcctcttcc ccccaaaacc caaggacacc ctcatgatct cccggacccc tgaggtcacg    780

tgcgtggtgg tggacgtgag ccacgaagac cccgaggtcc agttcaactg gtacgtggac    840

ggcgtggagg tgcataatgc caagacaaag ccacgggagg agcagttcaa cagcacgttc    900

cgtgtggtca gcgtcctcac cgttgtgcac caggactggc tgaacggcaa ggagtacaag    960

tgcaaggtct ccaacaaagg cctcccagcc cccatcgaga aaaccatctc caaaaccaaa   1020

gggcagcccc gagaaccaca ggtgtacacc ctgcccccat cccgggagga gatgaccaag   1080

aaccaggtca gcctgacctg cctggtcaaa ggcttctacc ccagcgacat cgccgtggag   1140

tgggagagca atgggcagcc ggagaacaac tacaagacca cacctcccat gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341


<210> SEQ ID NO 219
<211> LENGTH: 466
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 219

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Met Asn Trp Val Arg Gln Ala Pro Gly Gln Arg Leu
    50                  55                  60

Glu Trp Met Gly Asp Ile Asn Pro Tyr Asn Asp Asp Thr Thr Tyr Asn
65                  70                  75                  80

His Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220
```

Val Asp His Lys Pro Ser Asn Thr Lys Val Asp Lys Thr Val Glu Arg
225 230 235 240

Lys Cys Cys Val Glu Cys Pro Pro Cys Pro Ala Pro Pro Val Ala Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Gln Phe Asn Trp Tyr Val Asp Gly Val Glu Val His
290 295 300

Asn Ala Lys Thr Lys Pro Arg Glu Glu Gln Phe Asn Ser Thr Phe Arg
305 310 315 320

Val Val Ser Val Leu Thr Val Val His Gln Asp Trp Leu Asn Gly Lys
325 330 335

Glu Tyr Lys Cys Lys Val Ser Asn Lys Gly Leu Pro Ala Pro Ile Glu
340 345 350

Lys Thr Ile Ser Lys Thr Lys Gly Gln Pro Arg Glu Pro Gln Val Tyr
355 360 365

Thr Leu Pro Pro Ser Arg Glu Glu Met Thr Lys Asn Gln Val Ser Leu
370 375 380

Thr Cys Leu Val Lys Gly Phe Tyr Pro Ser Asp Ile Ala Val Glu Trp
385 390 395 400

Glu Ser Asn Gly Gln Pro Glu Asn Asn Tyr Lys Thr Thr Pro Pro Met
405 410 415

Leu Asp Ser Asp Gly Ser Phe Phe Leu Tyr Ser Lys Leu Thr Val Asp
420 425 430

Lys Ser Arg Trp Gln Gln Gly Asn Val Phe Ser Cys Ser Val Met His
435 440 445

Glu Ala Leu His Asn His Tyr Thr Gln Lys Ser Leu Ser Leu Ser Pro
450 455 460

Gly Lys
465

<210> SEQ ID NO 220
<211> LENGTH: 1398
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 220
atggactgga cctggaggat cctcttcttg gtggcagcag ccacaggagc ccactccgag 60
gtgcagctgg tgcagagcgg cgccgaggtc aagaaacctg gagcaagcgt aaaggttagt 120
tgcaaagcat ctggatacac atttaccgac tactacatga attgggtacg acaagcccct 180
ggacaaagac ttgaatggat gggagacatt aacccttata acgacgacac tacatacaat 240
cataaattta aaggaagagt tacaattaca agagatacat ccgcatcaac cgcctatatg 300
gaactttcct cattgagatc tgaagacact gctgtttatt actgtgcaag agaaactgcc 360
gttattacta ctaacgctat ggattactgg ggtcaaggaa ccactgttac cgtctctagt 420
gcctccacca agggcccatc ggtcttcccc ctggcgccct gctccaggag cacctccgag 480
agcacagcgg ccctgggctg cctggtcaag gactacttcc ccgaaccggt gacggtgtcg 540

```
tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080

cagccccgag aaccacaggt gtacaccctg cccccatccc gggaggagat gaccaagaac   1140

caggtcagcc tgacctgcct ggtcaaaggc ttctacccca gcgacatcgc cgtggagtgg   1200

gagagcaatg ggcagccgga gaacaactac aagaccacac ctcccatgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaa                                                 1398
```

```
<210> SEQ ID NO 221
<211> LENGTH: 215
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 222
<211> LENGTH: 645
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 222
gacatccaga tgacccagtc tccatcctcc ctctcagcat ccgtaggcga tagagttaca 60
ataacatgca gcgtatcatc aactatatca tcaaatcatc ttcattggtt ccaacagaaa 120
cccggcaaag cacctaaatc acttatatac ggcacatcaa atctcgcatc aggcgttcct 180
tcaagatttt caggctctgg ctcaggcacc gactttactc ttacaatatc ctccctccaa 240
cccgaagact tcgcaaccta ttactgtcaa caatggtcct catatccact cacatttggc 300
ggcggcacaa aagtagaaat taaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 223
<211> LENGTH: 237
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 223

Met Asp Met Arg Val Pro Ala Gln Leu Leu Gly Leu Leu Leu Leu Trp
1 5 10 15

Leu Arg Gly Ala Arg Cys Asp Ile Gln Met Thr Gln Ser Pro Ser Ser
20 25 30

Leu Ser Ala Ser Val Gly Asp Arg Val Thr Ile Thr Cys Ser Val Ser
35 40 45

Ser Thr Ile Ser Ser Asn His Leu His Trp Phe Gln Gln Lys Pro Gly
50 55 60

Lys Ala Pro Lys Ser Leu Ile Tyr Gly Thr Ser Asn Leu Ala Ser Gly
65 70 75 80

Val Pro Ser Arg Phe Ser Gly Ser Gly Ser Gly Thr Asp Phe Thr Leu
85 90 95

Thr Ile Ser Ser Leu Gln Pro Glu Asp Phe Ala Thr Tyr Tyr Cys Gln
100 105 110

Gln Trp Ser Ser Tyr Pro Leu Thr Phe Gly Gly Gly Thr Lys Val Glu
115 120 125

```
Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 224
<211> LENGTH: 711
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 224

atggacatga gggtccccgc tcagctcctg gggctcctgc tactctggct ccgaggtgcc     60

agatgtgaca tccagatgac ccagtctcca tcctccctct cagcatccgt aggcgataga    120

gttacaataa catgcagcgt atcatcaact atatcatcaa atcatcttca ttggttccaa    180

cagaaacccg gcaaagcacc taaatcactt atatacggca catcaaatct cgcatcaggc    240

gttccttcaa gattttcagg ctctggctca ggcaccgact ttactcttac aatatcctcc    300

ctccaacccg aagacttcgc aacctattac tgtcaacaat ggtcctcata tccactcaca    360

tttggcggcg gcacaaaagt agaaattaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg t             711


<210> SEQ ID NO 225
<211> LENGTH: 451
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 225

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45
```

```
Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 226
<211> LENGTH: 1353
<212> TYPE: DNA
<213> ORGANISM: Artificial Sequence
<220> FEATURE:
<223> OTHER INFORMATION: Synthetic Polynucleotide

<400> SEQUENCE: 226

```
gaggtgcagc tggtgcagtc tggggctgag gtgaagaagc ctggggcctc agtgaaggtc     60

tcctgcaagg cttctgactt caacattaaa gacttctatc tacactgggt gcgacaggcc    120

cctggacaag ggcttgagtg gattggaagg attgatcctg agaatggtga tactttatat    180

gacccgaagt tccaggacaa ggtcaccatg accacagaca cgtccaccag cacagcctac    240

atggagctga ggagcctgag atctgacgac acggccgtgt attactgtgc gagagaggcg    300

gattatttcc acgatggtac ctcctactgg tacttcgatg tctggggccg tggcaccctg    360

gtcaccgtct ctagtgcctc caccaagggc ccatcggtct tccccctggc gccctgctcc    420

aggagcacct ccgagagcac agcggccctg ggctgcctgg tcaaggacta cttccccgaa    480

ccggtgacgg tgtcgtggaa ctcaggcgct ctgaccagcg gcgtgcacac cttcccagct    540

gtcctacagt cctcaggact ctactccctc agcagcgtgg tgaccgtgcc ctccagcaac    600

ttcggcaccc agacctacac ctgcaacgta gatcacaagc ccagcaacac caaggtggac    660

aagacagttg agcgcaaatg ttgtgtcgag tgcccaccgt gcccagcacc acctgtggca    720

ggaccgtcag tcttcctctt ccccccaaaa cccaaggaca ccctcatgat ctcccggacc    780

cctgaggtca cgtgcgtggt ggtggacgtg agccacgaag accccgaggt ccagttcaac    840

tggtacgtgg acggcgtgga ggtgcataat gccaagacaa agccacggga ggagcagttc    900

aacagcacgt tccgtgtggt cagcgtcctc accgttgtgc accaggactg gctgaacggc    960

aaggagtaca agtgcaaggt ctccaacaaa ggcctcccag cccccatcga gaaaaccatc   1020

tccaaaacca aagggcagcc ccgagaacca caggtgtaca ccctgccccc atcccgggag   1080

gagatgacca agaaccaggt cagcctgacc tgcctggtca aaggcttcta ccccagcgac   1140

atcgccgtgg agtgggagag caatgggcag ccggagaaca actacaagac cacacctccc   1200

atgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

<210> SEQ ID NO 227
<211> LENGTH: 470
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 227

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Asp Phe Asn Ile
        35                  40                  45

Lys Asp Phe Tyr Leu His Trp Val Arg Gln Ala Pro Gly Gln Gly Leu
```

-continued

```
    50                  55                  60

Glu Trp Ile Gly Arg Ile Asp Pro Glu Asn Gly Asp Thr Leu Tyr Asp
65                  70                  75                  80

Pro Lys Phe Gln Asp Lys Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ala Asp Tyr Phe His Asp Gly Thr Ser Tyr
        115                 120                 125

Trp Tyr Phe Asp Val Trp Gly Arg Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 228
<211> LENGTH: 1410
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 228
atggactgga cctggaggat cctcttcttg gtggcagcag ccacaggagc ccactccgag 60
gtgcagctgg tgcagtctgg ggctgaggtg aagaagcctg gggcctcagt gaaggtctcc 120
tgcaaggctt ctgacttcaa cattaaagac ttctatctac actgggtgcg acaggcccct 180
ggacaagggc ttgagtggat tggaaggatt gatcctgaga atggtgatac tttatatgac 240
ccgaagttcc aggacaaggt caccatgacc acagacacgt ccaccagcac agcctacatg 300
gagctgagga gcctgagatc tgacgacacg gccgtgtatt actgtgcgag agaggcggat 360
tatttccacg atggtacctc ctactggtac ttcgatgtct ggggccgtgg caccctggtc 420
accgtctcta gtgcctccac caagggccca tcggtcttcc ccctggcgcc ctgctccagg 480
agcacctccg agagcacagc ggccctgggc tgcctggtca aggactactt ccccgaaccg 540
gtgacggtgt cgtggaactc aggcgctctg accagcggcg tgcacacctt cccagctgtc 600
ctacagtcct caggactcta ctccctcagc agcgtggtga ccgtgccctc cagcaacttc 660
ggcacccaga cctacacctg caacgtagat cacaagccca gcaacaccaa ggtggacaag 720
acagttgagc gcaaatgttg tgtcgagtgc ccaccgtgcc cagcaccacc tgtggcagga 780
ccgtcagtct tcctcttccc cccaaaaccc aaggacaccc tcatgatctc ccggacccct 840
gaggtcacgt gcgtggtggt ggacgtgagc cacgaagacc ccgaggtcca gttcaactgg 900
tacgtggacg gcgtggaggt gcataatgcc aagacaaagc cacgggagga gcagttcaac 960
agcacgttcc gtgtggtcag cgtcctcacc gttgtgcacc aggactggct gaacggcaag 1020
gagtacaagt gcaaggtctc caacaaaggc ctcccagccc ccatcgagaa aaccatctcc 1080
aaaaccaaag ggcagccccg agaaccacag gtgtacaccc tgcccccatc ccgggaggag 1140
atgaccaaga accaggtcag cctgacctgc ctggtcaaag gcttctaccc cagcgacatc 1200
gccgtggagt gggagagcaa tgggcagccg gagaacaact acaagaccac acctcccatg 1260
ctggactccg acggctcctt cttcctctac agcaagctca ccgtggacaa gagcaggtgg 1320
cagcagggga acgtcttctc atgctccgtg atgcatgagg ctctgcacaa ccactacacg 1380
cagaagagcc tctccctgtc tccgggtaaa 1410

<210> SEQ ID NO 229
<211> LENGTH: 213
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 229

Asp Ile Gln Leu Thr Gln Ser Pro Ser Phe Leu Ser Ala Ser Val Gly
1 5 10 15

Asp Arg Val Thr Ile Thr Cys Arg Ala Ser Ser Ser Ile Ser Tyr Ile

```
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 230
<211> LENGTH: 639
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 230

```
gacatccagt tgacccagtc tccatccttc ctgtctgcat ctgtaggaga cagagtcacc     60

atcacttgca gggccagctc aagtataagt tacatacact ggtatcagca aaaaccaggg    120

aaagccccta agctcctgat ctatgccaca tccaacctgg cttctggggt cccatcaagg    180

ttcagcggca gtggatctgg gacagaattc actctcacaa tcagcagcct gcagcctgaa    240

gattttgcaa cttattactg tcagcagtgg agtagtgacc cactcacgtt cggcggaggg    300

accaaggtgg agatcaaacg tacggtggct gcaccatctg tcttcatctt cccgccatct    360

gatgagcagt tgaaatctgg aactgcctct gttgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaagtc tacgcctgcg aagtcaccca tcagggcctg    600

agctcgcccg tcacaaagag cttcaacagg ggagagtgt                           639
```

<210> SEQ ID NO 231
<211> LENGTH: 235
<212> TYPE: PRT
<213> ORGANISM: Artificial Sequence
<220> FEATURE:

<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 231

Met Asp Met Arg Val Pro Ala Gln Leu Leu Gly Leu Leu Leu Leu Trp
1 5 10 15

Leu Pro Gly Ala Arg Cys Asp Ile Gln Leu Thr Gln Ser Pro Ser Phe
20 25 30

Leu Ser Ala Ser Val Gly Asp Arg Val Thr Ile Thr Cys Arg Ala Ser
35 40 45

Ser Ser Ile Ser Tyr Ile His Trp Tyr Gln Gln Lys Pro Gly Lys Ala
50 55 60

Pro Lys Leu Leu Ile Tyr Ala Thr Ser Asn Leu Ala Ser Gly Val Pro
65 70 75 80

Ser Arg Phe Ser Gly Ser Gly Ser Gly Thr Glu Phe Thr Leu Thr Ile
85 90 95

Ser Ser Leu Gln Pro Glu Asp Phe Ala Thr Tyr Tyr Cys Gln Gln Trp
100 105 110

Ser Ser Asp Pro Leu Thr Phe Gly Gly Gly Thr Lys Val Glu Ile Lys
115 120 125

Arg Thr Val Ala Ala Pro Ser Val Phe Ile Phe Pro Pro Ser Asp Glu
130 135 140

Gln Leu Lys Ser Gly Thr Ala Ser Val Val Cys Leu Leu Asn Asn Phe
145 150 155 160

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Ser Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys
225 230 235

<210> SEQ ID NO 232
<211> LENGTH: 705
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 232
atggacatga gggtccccgc tcagctcctg gggctcctgc tgctctggct cccaggtgcc 60
agatgtgaca tccagttgac ccagtctcca tccttcctgt ctgcatctgt aggagacaga 120
gtcaccatca cttgcagggc cagctcaagt ataagttaca tacactggta tcagcaaaaa 180
ccagggaaag cccctaagct cctgatctat gccacatcca acctggcttc tggggtccca 240
tcaaggttca gcggcagtgg atctgggaca gaattcactc tcacaatcag cagcctgcag 300
cctgaagatt ttgcaactta ttactgtcag cagtggagta gtgacccact cacgttcggc 360
ggagggacca aggtggagat caaacgtacg gtggctgcac catctgtctt catcttcccg 420

-continued

```
ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705


<210> SEQ ID NO 233
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 233

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300
```

```
Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 234
<211> LENGTH: 1341
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 234

```
gaggtgcagc tggtgcagtc tggggctgag gtgaagaagc ctggggcctc agtgaaggtc     60
tcctgcaagg cttctggatt cgacattaag gactactata tacactgggt gcgacaggcc    120
cctggacaag ggcttgagtg gatcggaagg gttgatcctg acaatggtga gactgaattt    180
gccccgaagt tcccgggcaa ggtcaccatg accacagaca cgtccatcag cacagcctac    240
atggagctga gcaggctgag atctgacgac acggccgtgt attactgtgc gagagaagac    300
tacgatggta cctacacctg gtttccttat tggggccaag ggactctggt caccgtctct    360
agtgcctcca ccaagggccc atcggtcttc cccctggcgc cctgctccag gagcacctcc    420
gagagcacag cggccctggg ctgcctggtc aaggactact tccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttgtgcac caggactggc tgaacggcaa ggagtacaag    960
tgcaaggtct ccaacaaagg cctcccagcc cccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
```

```
tgggagagca atgggcagcc ggagaacaac tacaagacca cacctcccat gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341


<210> SEQ ID NO 235
<211> LENGTH: 466
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 235

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asp Ile
        35                  40                  45

Lys Asp Tyr Tyr Ile His Trp Val Arg Gln Ala Pro Gly Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Val Thr Met Thr Thr Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Glu Asp Tyr Asp Gly Thr Tyr Thr Trp Phe Pro
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
```

-continued

```
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 236
<211> LENGTH: 1398
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 236

```
atggactgga cctggaggat cctcttcttg gtggcagcag ccacaggagc ccactccgag     60

gtgcagctgg tgcagtctgg ggctgaggtg aagaagcctg gggcctcagt gaaggtctcc    120

tgcaaggctt ctggattcga cattaaggac tactatatac actgggtgcg acaggcccct    180

ggacaagggc ttgagtggat cggaagggtt gatcctgaca atggtgagac tgaatttgcc    240

ccgaagttcc cgggcaaggt caccatgacc acagacacgt ccatcagcac agcctacatg    300

gagctgagca ggctgagatc tgacgacacg gccgtgtatt actgtgcgag agaagactac    360

gatggtacct acacctggtt tccttattgg ggccaaggga ctctggtcac cgtctctagt    420

gcctccacca agggcccatc ggtcttcccc ctggcgccct gctccaggag cacctccgag    480

agcacagcgg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020
```

aaggtctcca acaaaggcct cccagccccc atcgagaaaa ccatctccaa aaccaaaggg 1080
cagccccgag aaccacaggt gtacaccctg cccccatccc gggaggagat gaccaagaac 1140
caggtcagcc tgacctgcct ggtcaaaggc ttctacccca gcgacatcgc cgtggagtgg 1200
gagagcaatg ggcagccgga gaacaactac aagaccacac ctcccatgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaa 1398

<210> SEQ ID NO 237
<211> LENGTH: 7
<212> TYPE: PRT
<213> ORGANISM: Mus musculus

<400> SEQUENCE: 237

Gly Thr Ser Asn Leu Ala Ser
1 5

<210> SEQ ID NO 238
<211> LENGTH: 8
<212> TYPE: PRT
<213> ORGANISM: Mus musculus

<400> SEQUENCE: 238

Gln Gln Trp Thr Thr Thr Tyr Thr
1 5

<210> SEQ ID NO 239
<211> LENGTH: 11
<212> TYPE: PRT
<213> ORGANISM: Mus musculus

<400> SEQUENCE: 239

Arg Ala Ser Gln Asp Ile Ser Ser Tyr Leu Asn
1 5 10

<210> SEQ ID NO 240
<211> LENGTH: 7
<212> TYPE: PRT
<213> ORGANISM: Mus musculus

<400> SEQUENCE: 240

Ser Thr Ser Arg Leu Asn Ser
1 5

<210> SEQ ID NO 241
<211> LENGTH: 8
<212> TYPE: PRT
<213> ORGANISM: Mus musculus

<400> SEQUENCE: 241

Gln Gln Asp Ile Lys His Pro Thr
1 5

<210> SEQ ID NO 242
<211> LENGTH: 11
<212> TYPE: PRT
<213> ORGANISM: Mus musculus

<400> SEQUENCE: 242

Lys Ala Ser Gln Asp Val Phe Thr Ala Val Ala
1 5 10

<210> SEQ ID NO 243
<211> LENGTH: 7
<212> TYPE: PRT
<213> ORGANISM: Mus musculus

<400> SEQUENCE: 243

Trp Ala Ser Thr Arg His Thr
1               5

<210> SEQ ID NO 244
<211> LENGTH: 9
<212> TYPE: PRT
<213> ORGANISM: Mus musculus

<400> SEQUENCE: 244

Gln Gln Tyr Ser Ser Tyr Pro Leu Thr
1               5

<210> SEQ ID NO 245
<211> LENGTH: 5
<212> TYPE: PRT
<213> ORGANISM: Mus musculus

<400> SEQUENCE: 245

Asp Tyr Asn Met His
1               5

<210> SEQ ID NO 246
<211> LENGTH: 17
<212> TYPE: PRT
<213> ORGANISM: Mus musculus

<400> SEQUENCE: 246

Glu Ile Asn Pro Asn Ser Gly Gly Ala Gly Tyr Asn Gln Lys Phe Lys
1               5                   10                  15

Gly

<210> SEQ ID NO 247
<211> LENGTH: 14
<212> TYPE: PRT
<213> ORGANISM: Mus musculus

<400> SEQUENCE: 247

Leu Gly Tyr Asp Asp Ile Tyr Asp Asp Trp Tyr Phe Asp Val
1               5                   10

<210> SEQ ID NO 248
<211> LENGTH: 5
<212> TYPE: PRT
<213> ORGANISM: Mus musculus

<400> SEQUENCE: 248

Asp Tyr Asn Met His
1               5

<210> SEQ ID NO 249
<211> LENGTH: 17
<212> TYPE: PRT
<213> ORGANISM: Mus musculus

<400> SEQUENCE: 249

Glu Ile Asn Pro Asn Ser Gly Gly Ser Gly Tyr Asn Gln Lys Phe Lys
1               5                   10                  15

Gly

<210> SEQ ID NO 250
<211> LENGTH: 14
<212> TYPE: PRT
<213> ORGANISM: Mus musculus

<400> SEQUENCE: 250

Leu Val Tyr Asp Gly Ser Tyr Glu Asp Trp Tyr Phe Asp Val
1               5                   10

<210> SEQ ID NO 251
<211> LENGTH: 5
<212> TYPE: PRT
<213> ORGANISM: Mus musculus

<400> SEQUENCE: 251

Asp Tyr Asn Met His
1               5

<210> SEQ ID NO 252
<211> LENGTH: 17
<212> TYPE: PRT
<213> ORGANISM: Mus musculus

<400> SEQUENCE: 252

Glu Ile Asn Pro Asn Ser Gly Gly Ala Gly Tyr Asn Gln Gln Phe Lys
1               5                   10                  15

Gly

<210> SEQ ID NO 253
<211> LENGTH: 14
<212> TYPE: PRT
<213> ORGANISM: Mus musculus

<400> SEQUENCE: 253

Leu Gly Tyr Val Gly Asn Tyr Glu Asp Trp Tyr Phe Asp Val
1               5                   10

<210> SEQ ID NO 254
<211> LENGTH: 5
<212> TYPE: PRT
<213> ORGANISM: Mus musculus

<400> SEQUENCE: 254

Asp Tyr Asn Met His
1               5

<210> SEQ ID NO 255
<211> LENGTH: 17
<212> TYPE: PRT
<213> ORGANISM: Mus musculus

<400> SEQUENCE: 255

Glu Ile Asn Pro Asn Ser Gly Gly Ala Gly Tyr Asn Gln Lys Phe Lys
1               5                   10                  15

Gly

<210> SEQ ID NO 256
<211> LENGTH: 14
<212> TYPE: PRT
<213> ORGANISM: Mus musculus

<400> SEQUENCE: 256

Leu Gly Tyr Asp Asp Ile Tyr Asp Asp Trp Tyr Phe Asp Val
1 5 10

<210> SEQ ID NO 257
<211> LENGTH: 5
<212> TYPE: PRT
<213> ORGANISM: Mus musculus

<400> SEQUENCE: 257

Asp Tyr Asn Met His
1 5

<210> SEQ ID NO 258
<211> LENGTH: 17
<212> TYPE: PRT
<213> ORGANISM: Mus musculus

<400> SEQUENCE: 258

Glu Ile Asn Pro Asn Ser Gly Gly Ala Gly Tyr Asn Gln Lys Phe Lys
1 5 10 15

Gly

<210> SEQ ID NO 259
<211> LENGTH: 14
<212> TYPE: PRT
<213> ORGANISM: Mus musculus

<400> SEQUENCE: 259

Leu Gly Tyr Asp Asp Ile Tyr Asp Asp Trp Tyr Phe Asp Val
1 5 10

<210> SEQ ID NO 260
<211> LENGTH: 5
<212> TYPE: PRT
<213> ORGANISM: Mus musculus

<400> SEQUENCE: 260

Asp Tyr Asn Met His
1 5

<210> SEQ ID NO 261
<211> LENGTH: 17
<212> TYPE: PRT
<213> ORGANISM: Mus musculus

<400> SEQUENCE: 261

Glu Ile Asn Pro Asn Ser Gly Gly Ala Gly Tyr Asn Gln Lys Phe Lys
1 5 10 15

Gly

<210> SEQ ID NO 262
<211> LENGTH: 14
<212> TYPE: PRT
<213> ORGANISM: Mus musculus

<400> SEQUENCE: 262

Leu Gly Tyr Asp Asp Ile Tyr Asp Asp Trp Tyr Phe Asp Val
1 5 10

<210> SEQ ID NO 263
<211> LENGTH: 5
<212> TYPE: PRT

<213> ORGANISM: Mus musculus

<400> SEQUENCE: 263

Asp Tyr Asn Met His
1 5

<210> SEQ ID NO 264
<211> LENGTH: 17
<212> TYPE: PRT
<213> ORGANISM: Mus musculus

<400> SEQUENCE: 264

Glu Ile Asn Pro Asn Ser Gly Gly Ser Gly Tyr Asn Gln Lys Phe Lys
1 5 10 15

Gly

<210> SEQ ID NO 265
<211> LENGTH: 14
<212> TYPE: PRT
<213> ORGANISM: Mus musculus

<400> SEQUENCE: 265

Leu Gly Tyr Tyr Gly Asn Tyr Glu Asp Trp Tyr Phe Asp Val
1 5 10

<210> SEQ ID NO 266
<211> LENGTH: 5
<212> TYPE: PRT
<213> ORGANISM: Mus musculus

<400> SEQUENCE: 266

Asp Tyr Tyr Ile His
1 5

<210> SEQ ID NO 267
<211> LENGTH: 17
<212> TYPE: PRT
<213> ORGANISM: Mus musculus

<400> SEQUENCE: 267

Arg Ile Asp Pro Asp Asn Gly Glu Ser Thr Tyr Val Pro Lys Phe Gln
1 5 10 15

Gly

<210> SEQ ID NO 268
<211> LENGTH: 13
<212> TYPE: PRT
<213> ORGANISM: Mus musculus

<400> SEQUENCE: 268

Glu Gly Leu Asp Tyr Gly Asp Tyr Tyr Ala Val Asp Tyr
1 5 10

<210> SEQ ID NO 269
<211> LENGTH: 5
<212> TYPE: PRT
<213> ORGANISM: Mus musculus

<400> SEQUENCE: 269

Asp Tyr Ile Met His
1 5

<210> SEQ ID NO 270

<211> LENGTH: 17
<212> TYPE: PRT
<213> ORGANISM: Mus musculus

<400> SEQUENCE: 270

Tyr Ile Asn Pro Tyr Asn Asp Asp Thr Glu Tyr Asn Glu Lys Phe Lys
1 5 10 15

Gly

<210> SEQ ID NO 271
<211> LENGTH: 11
<212> TYPE: PRT
<213> ORGANISM: Mus musculus

<400> SEQUENCE: 271

Ser Ile Tyr Tyr Tyr Asp Ala Pro Phe Ala Tyr
1 5 10

<210> SEQ ID NO 272
<211> LENGTH: 5
<212> TYPE: PRT
<213> ORGANISM: Mus musculus

<400> SEQUENCE: 272

Asp Tyr Tyr Met His
1 5

<210> SEQ ID NO 273
<211> LENGTH: 17
<212> TYPE: PRT
<213> ORGANISM: Mus musculus

<400> SEQUENCE: 273

Arg Ile Asp Pro Glu Asn Gly Asp Ile Ile Tyr Asp Pro Lys Phe Gln
1 5 10 15

Gly

<210> SEQ ID NO 274
<211> LENGTH: 10
<212> TYPE: PRT
<213> ORGANISM: Mus musculus

<400> SEQUENCE: 274

Asp Ala Gly Asp Pro Ala Trp Phe Thr Tyr
1 5 10

<210> SEQ ID NO 275
<211> LENGTH: 10
<212> TYPE: PRT
<213> ORGANISM: Mus musculus

<400> SEQUENCE: 275

Arg Ala Ser Ser Ser Val Tyr Tyr Met His
1 5 10

<210> SEQ ID NO 276
<211> LENGTH: 7
<212> TYPE: PRT
<213> ORGANISM: Mus musculus

<400> SEQUENCE: 276

Ala Thr Ser Asn Leu Ala Ser
1 5

<210> SEQ ID NO 277
<211> LENGTH: 9
<212> TYPE: PRT
<213> ORGANISM: Mus musculus

<400> SEQUENCE: 277

Gln Gln Trp Ser Ser Asp Pro Leu Thr
1 5

<210> SEQ ID NO 278
<211> LENGTH: 12
<212> TYPE: PRT
<213> ORGANISM: Mus musculus

<400> SEQUENCE: 278

Ser Val Ser Ser Thr Ile Ser Ser Asn His Leu His
1 5 10

<210> SEQ ID NO 279
<211> LENGTH: 7
<212> TYPE: PRT
<213> ORGANISM: Mus musculus

<400> SEQUENCE: 279

Gly Thr Ser Asn Leu Ala Ser
1 5

<210> SEQ ID NO 280
<211> LENGTH: 9
<212> TYPE: PRT
<213> ORGANISM: Mus musculus

<400> SEQUENCE: 280

Gln Gln Trp Ser Ser Tyr Pro Leu Thr
1 5

<210> SEQ ID NO 281
<211> LENGTH: 10
<212> TYPE: PRT
<213> ORGANISM: Mus musculus

<400> SEQUENCE: 281

Arg Ala Ser Ser Ser Ile Ser Tyr Ile His
1 5 10

<210> SEQ ID NO 282
<211> LENGTH: 7
<212> TYPE: PRT
<213> ORGANISM: Mus musculus

<400> SEQUENCE: 282

Ala Thr Ser Asn Leu Ala Ser
1 5

<210> SEQ ID NO 283
<211> LENGTH: 9
<212> TYPE: PRT
<213> ORGANISM: Mus musculus

<400> SEQUENCE: 283

Gln Gln Trp Ser Ser Asp Pro Leu Thr
1 5

<210> SEQ ID NO 284

-continued

<211> LENGTH: 12
<212> TYPE: PRT
<213> ORGANISM: Mus musculus

<400> SEQUENCE: 284

Arg Ala Ser Ser Ser Val Thr Ser Ser Tyr Leu Asn
1 5 10

<210> SEQ ID NO 285
<211> LENGTH: 7
<212> TYPE: PRT
<213> ORGANISM: Mus musculus

<400> SEQUENCE: 285

Ser Thr Ser Asn Leu Ala Ser
1 5

<210> SEQ ID NO 286
<211> LENGTH: 9
<212> TYPE: PRT
<213> ORGANISM: Mus musculus

<400> SEQUENCE: 286

Gln Gln Tyr Asp Phe Phe Pro Ser Thr
1 5

<210> SEQ ID NO 287
<211> LENGTH: 5
<212> TYPE: PRT
<213> ORGANISM: Mus musculus

<400> SEQUENCE: 287

Asp Tyr Phe Ile His
1 5

<210> SEQ ID NO 288
<211> LENGTH: 17
<212> TYPE: PRT
<213> ORGANISM: Mus musculus

<400> SEQUENCE: 288

Arg Leu Asp Pro Glu Asp Gly Glu Ser Asp Tyr Ala Pro Lys Phe Gln
1 5 10 15

Asp

<210> SEQ ID NO 289
<211> LENGTH: 12
<212> TYPE: PRT
<213> ORGANISM: Mus musculus

<400> SEQUENCE: 289

Glu Asp Tyr Asp Gly Thr Tyr Thr Phe Phe Pro Tyr
1 5 10

<210> SEQ ID NO 290
<211> LENGTH: 5
<212> TYPE: PRT
<213> ORGANISM: Mus musculus

<400> SEQUENCE: 290

Asp Phe Tyr Leu His
1 5

<210> SEQ ID NO 291

<211> LENGTH: 17
<212> TYPE: PRT
<213> ORGANISM: Mus musculus

<400> SEQUENCE: 291

Arg Ile Asp Pro Glu Asn Gly Asp Thr Leu Tyr Asp Pro Lys Phe Gln
1 5 10 15

Asp

<210> SEQ ID NO 292
<211> LENGTH: 16
<212> TYPE: PRT
<213> ORGANISM: Mus musculus

<400> SEQUENCE: 292

Glu Ala Asp Tyr Phe His Asp Gly Thr Ser Tyr Trp Tyr Phe Asp Val
1 5 10 15

<210> SEQ ID NO 293
<211> LENGTH: 5
<212> TYPE: PRT
<213> ORGANISM: Mus musculus

<400> SEQUENCE: 293

Asp Tyr Tyr Ile His
1 5

<210> SEQ ID NO 294
<211> LENGTH: 17
<212> TYPE: PRT
<213> ORGANISM: Mus musculus

<400> SEQUENCE: 294

Arg Val Asp Pro Asp Asn Gly Glu Thr Glu Phe Ala Pro Lys Phe Pro
1 5 10 15

Gly

<210> SEQ ID NO 295
<211> LENGTH: 12
<212> TYPE: PRT
<213> ORGANISM: Mus musculus

<400> SEQUENCE: 295

Glu Asp Tyr Asp Gly Thr Tyr Thr Trp Phe Pro Tyr
1 5 10

<210> SEQ ID NO 296
<211> LENGTH: 5
<212> TYPE: PRT
<213> ORGANISM: Mus musculus

<400> SEQUENCE: 296

Asp Tyr Tyr Met Asn
1 5

<210> SEQ ID NO 297
<211> LENGTH: 17
<212> TYPE: PRT
<213> ORGANISM: Mus musculus

<400> SEQUENCE: 297

Asp Ile Asn Pro Tyr Asn Asp Asp Thr Thr Tyr Asn His Lys Phe Lys
1 5 10 15

Gly

<210> SEQ ID NO 298
<211> LENGTH: 11
<212> TYPE: PRT
<213> ORGANISM: Mus musculus

<400> SEQUENCE: 298

Glu Thr Ala Val Ile Thr Thr Asn Ala Met Asp
1               5                   10

<210> SEQ ID NO 299
<211> LENGTH: 130
<212> TYPE: PRT
<213> ORGANISM: Mus musculus

<400> SEQUENCE: 299

Met Asp Phe Gln Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Ser Gln Gln Lys Ser Gly
    50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Thr Thr Thr Tyr Thr Phe Gly Ser Gly Thr Lys Leu Glu Leu
        115                 120                 125

Lys Arg
    130

<210> SEQ ID NO 300
<211> LENGTH: 390
<212> TYPE: DNA
<213> ORGANISM: Mus musculus

<400> SEQUENCE: 300
atggattttc aggtgcagat tttcagcttc atgctaatca gtgtcacagt catattgtcc      60
agtggagaaa ttgtgctcac ccagtctcca gcactcatgg ctgcatctcc aggggagaag     120
gtcaccatca cctgcagtgt cagctcgagt ataagttcca gcaacttaca ctggtcccag     180
cagaagtcag gaacctcccc caaactctgg atttatggca catccaacct tgcttctgga     240
gtccctgttc gcttcagtgg cagtggatct gggacctctt attctctcac aatcagcagc     300
atggaggctg aagatgctgc cacttattac tgtcaacagt ggactactac gtatacgttc     360
ggatcgggga ccaagctgga gctgaaacgt                                      390

<210> SEQ ID NO 301
<211> LENGTH: 141
<212> TYPE: PRT
<213> ORGANISM: Mus musculus

<400> SEQUENCE: 301

Met Gly Trp Asn Trp Ile Ile Phe Phe Leu Met Ala Val Val Thr Gly

```
1               5                   10                  15

Val Asn Ser Glu Val Gln Leu Arg Gln Ser Gly Ala Asp Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Arg Ile Asp Pro Asp Asn Gly Glu Ser Thr Tyr Val
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Gly Arg Glu Gly Leu Asp Tyr Gly Asp Tyr Tyr Ala Val
        115                 120                 125

Asp Tyr Trp Gly Gln Gly Thr Ser Val Thr Val Ser Ser
    130                 135                 140
```

<210> SEQ ID NO 302
<211> LENGTH: 423
<212> TYPE: DNA
<213> ORGANISM: Mus musculus

<400> SEQUENCE: 302

```
atgggatgga actggatcat cttcttcctg atggcagtgg ttacaggggt caattcagag     60

gtgcagttgc ggcagtctgg ggcagacctt gtgaagccag gggcctcagt caagttgtcc    120

tgcacagctt ctggcttcaa cattaaagac tactatatac actgggtgaa gcagaggcct    180

gaacagggcc tggagtggat tggaaggatt gatcctgata atggtgaaag tacatatgtc    240

ccgaagttcc agggcaaggc cactataaca gcagacacat catccaacac agcctaccta    300

caactcagaa gcctgacatc tgaggacact gccatctatt attgtgggag agaggggctc    360

gactatggtg actactatgc tgtggactac tggggtcaag gaacctcggt cacagtctcg    420

agc                                                                  423
```

<210> SEQ ID NO 303
<211> LENGTH: 130
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 303

```
Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Ser Val Ser
        35                  40                  45

Ser Ser Ile Ser Ser Ser Asn Leu His Trp Tyr Gln Gln Lys Pro Gly
    50                  55                  60

Lys Ala Pro Lys Leu Leu Ile Tyr Gly Thr Ser Asn Leu Ala Ser Gly
65                  70                  75                  80

Val Pro Ser Arg Phe Ser Gly Ser Gly Ser Gly Thr Glu Phe Thr Leu
```

```
                85                  90                  95

Thr Ile Ser Ser Leu Gln Pro Glu Asp Phe Ala Thr Tyr Tyr Cys Gln
            100                 105                 110

Gln Trp Thr Thr Thr Tyr Thr Phe Gly Gln Gly Thr Lys Leu Glu Ile
        115                 120                 125

Lys Arg
    130


<210> SEQ ID NO 304
<211> LENGTH: 390
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 304

atggatatgc gcgtgccggc gcagctgctg ggcctgctgc tgctgtggct gccgggcgcg      60

cgctgcgata ttcagctgac ccagagcccg agctttctga gcgcgagcgt gggcgatcgc     120

gtgaccatta cctgcagcgt gagcagcagc attagcagca gcaacctgca ttggtatcag     180

cagaaaccgg gcaaagcgcc gaaactgctg atttatggca ccagcaacct ggcgagcggc     240

gtgccgagcc gctttagcgg cagcggcagc ggcaccgaat ttaccctgac cattagcagc     300

ctgcagccgg aagattttgc gacctattat tgccagcagt ggaccaccac ctataccttt     360

ggccagggca ccaaactgga aattaaacgt                                      390


<210> SEQ ID NO 305
<211> LENGTH: 141
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 305

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Ile His Trp Val Arg Gln Ala Pro Gly Gln Gly Leu
    50                  55                  60

Glu Trp Met Gly Arg Ile Asp Pro Asp Asn Gly Glu Ser Thr Tyr Val
65                  70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Gly Leu Asp Tyr Gly Asp Tyr Tyr Ala Val
        115                 120                 125

Asp Tyr Trp Gly Gln Gly Thr Leu Val Thr Val Ser Ser
    130                 135                 140
```

<210> SEQ ID NO 306
<211> LENGTH: 423
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 306
atggattgga cctggagcat tctgtttctg gtggcggcgc cgaccggcgc gcatagcgaa 60
gtgcagctgg tgcagagcgg cgcggaagtg aaaaaaccgg gcgcgagcgt gaaagtgagc 120
tgcaaagcga gcggctttaa cattaaagat tattatattc attgggtgcg ccaggcgccg 180
ggccagggcc tggaatggat gggccgcatt gatccggata acggcgaaag cacctatgtg 240
ccgaaatttc agggccgcgt gaccatgacc accgatacca gcaccagcac cgcgtatatg 300
gaactgcgca gcctgcgcag cgatgatacc gcggtgtatt attgcgcgcg cgaaggcctg 360
gattatggcg attattatgc ggtggattat tggggccagg gcaccctggt gaccgtctcg 420
agc 423

<210> SEQ ID NO 307
<211> LENGTH: 127
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 307

Met Met Ser Ser Ala Gln Phe Leu Gly Leu Leu Leu Leu Cys Phe Gln
1 5 10 15

Gly Thr Arg Cys Asp Ile Gln Met Thr Gln Thr Thr Ser Ser Leu Ser
20 25 30

Ala Ser Leu Gly Asp Arg Val Asn Ile Ser Cys Arg Ala Ser Gln Asp
35 40 45

Ile Ser Ser Tyr Leu Asn Trp Tyr Gln Gln Lys Pro Asp Gly Thr Val
50 55 60

Lys Leu Leu Ile Tyr Ser Thr Ser Arg Leu Asn Ser Gly Val Pro Ser
65 70 75 80

Arg Phe Ser Gly Ser Gly Ser Gly Thr Asp Tyr Ser Leu Thr Ile Ser
85 90 95

Asn Leu Ala Gln Glu Asp Ile Ala Thr Tyr Phe Cys Gln Gln Asp Ile
100 105 110

Lys His Pro Thr Phe Gly Gly Gly Thr Lys Leu Glu Leu Lys Arg
115 120 125

<210> SEQ ID NO 308
<211> LENGTH: 381
<212> TYPE: DNA
<213> ORGANISM: Mus musculus

<400> SEQUENCE: 308
atgatgtcct ctgctcagtt ccttggtctc ctgttgctct gttttcaagg taccagatgt 60
gatatccaga tgacacagac tacatcctcc ctgtctgcct ctctgggaga cagagtcaac 120
atcagctgca gggcaagtca ggacattagc agttatttaa actggtatca gcagaaacca 180
gatggaactg ttaaactcct gatctactcc acatcaagat taaactcagg agtcccatca 240
aggttcagtg gcagtgggtc tgggacagat tattctctca ctattagcaa cctggcacaa 300
gaagatattg ccacttactt ttgccaacag gatattaagc atccgacgtt cggtggaggc 360
accaagttgg agctgaaacg t 381

<210> SEQ ID NO 309
<211> LENGTH: 139
<212> TYPE: PRT
<213> ORGANISM: Mus musculus

<400> SEQUENCE: 309

Met Glu Trp Ile Trp Ile Phe Leu Phe Leu Leu Ser Gly Thr Ala Gly
1 5 10 15

Val His Ser Glu Val Gln Leu Gln Gln Ser Gly Pro Glu Leu Val Lys
20 25 30

Pro Gly Ala Ser Val Lys Met Ser Cys Lys Ala Ser Gly Phe Thr Phe
35 40 45

Thr Asp Tyr Ile Met His Trp Val Lys Gln Lys Pro Gly Gln Gly Leu
50 55 60

Glu Trp Ile Gly Tyr Ile Asn Pro Tyr Asn Asp Asp Thr Glu Tyr Asn
65 70 75 80

Glu Lys Phe Lys Gly Lys Ala Thr Leu Thr Ser Asp Lys Ser Ser Ser
85 90 95

Thr Ala Tyr Met Asp Leu Ser Ser Leu Thr Ser Glu Gly Ser Ala Val
100 105 110

Tyr Tyr Cys Ala Arg Ser Ile Tyr Tyr Tyr Asp Ala Pro Phe Ala Tyr
115 120 125

Trp Gly Gln Gly Thr Leu Val Thr Val Ser Ser
130 135

<210> SEQ ID NO 310
<211> LENGTH: 417
<212> TYPE: DNA
<213> ORGANISM: Mus musculus

<400> SEQUENCE: 310
atggaatgga tctggatatt tctcttcctc ctgtcaggaa ctgcaggtgt ccactctgag 60
gtccagctgc agcagtctgg acctgagctg gtaaagcctg gggcttcagt gaagatgtcc 120
tgcaaggctt ctgggttcac attcactgac tacattatgc actgggtgaa gcagaagcct 180
gggcagggcc ttgagtggat tggatatatt aatccttaca atgatgatac tgaatacaat 240
gagaagttca aaggcaaggc cacactgact tcagacaaat cctccagcac agcctacatg 300
gatctcagca gtctgacctc tgagggctct gcggtctatt actgtgcaag atcgatttat 360
tactacgatg ccccgtttgc ttactggggc caagggactc tggtcacagt ctcgagc 417

<210> SEQ ID NO 311
<211> LENGTH: 127
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 311

Met Met Ser Ser Ala Gln Phe Leu Gly Leu Leu Leu Leu Cys Phe Gln

-continued

```
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Ser Tyr Leu Asn Trp Tyr Gln Gln Lys Pro Gly Lys Ala Pro
    50                  55                  60

Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Asp Ile
            100                 105                 110

Lys His Pro Thr Phe Gly Gln Gly Thr Lys Val Glu Ile Lys Arg
        115                 120                 125
```

<210> SEQ ID NO 312
<211> LENGTH: 381
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 312

```
atgatgtcct ctgctcagtt ccttggtctc ctgttgctct gttttcaagg taccagatgt      60

gatatccaga tgacccagtc tccatcctcc ctgtctgcat ctgtaggtga ccgtgtcacc     120

atcacttgcc gcgcaagtca ggatattagc agctatttaa attggtatca gcagaaacca     180

gggaaagccc ctaagctcct gatctattct acttcccgtt tgaatagtgg ggtcccatca     240

cgcttcagtg gcagtggctc tgggacagat ttcactctca ccatcagcag tctgcaacct     300

gaagattttg caacttacta ctgtcaacag gatattaaac accctacgtt cggtcaaggc     360

accaaggtgg agatcaaacg t                                               381
```

<210> SEQ ID NO 313
<211> LENGTH: 139
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 313

```
Met Glu Trp Ile Trp Ile Phe Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
```

```
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135


<210> SEQ ID NO 314
<211> LENGTH: 107
<212> TYPE: PRT
<213> ORGANISM: Mus musculus

<400> SEQUENCE: 314

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg
            100                 105


<210> SEQ ID NO 315
<211> LENGTH: 128
<212> TYPE: PRT
<213> ORGANISM: Mus musculus

<400> SEQUENCE: 315

Met Lys Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Thr Ile Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys Arg
        115                 120                 125


<210> SEQ ID NO 316
<211> LENGTH: 381
<212> TYPE: DNA
<213> ORGANISM: Mus musculus

<400> SEQUENCE: 316
```

atgaagtcac agacccaggt ctttgtatac atgttgctgt ggttgtctgg tgttgaagga 60
gacattgtga tgacccagtc tcacaaattc atgtccacgt cagtaggaga cagggtcacc 120
atcacctgca aggccagtca ggatgtcttt actgctgtag cctggtatca acagaaacca 180
ggacaatctc ctaaactact gatttactgg gcatccaccc ggcacactgg agtccctgat 240
cgcttcacag gcagtggatc tgggacagat ttcactctca ccattagcaa tgtgcagtct 300
gaagacttgg cagattattt ctgtcaacaa tatagcagct atcctctcac gttcggtgct 360
gggaccaagt tggagctgaa a 381

<210> SEQ ID NO 317
<211> LENGTH: 138
<212> TYPE: PRT
<213> ORGANISM: Mus musculus

<400> SEQUENCE: 317

Met Gly Trp Asn Trp Ile Ile Phe Phe Leu Met Ala Val Val Thr Gly
1 5 10 15

Val Asn Ser Glu Val Gln Leu Gln Gln Ser Gly Ala Glu Leu Val Arg
20 25 30

Pro Gly Ala Leu Val Lys Leu Ser Cys Lys Ala Ser Gly Phe Asn Ile
35 40 45

Lys Asp Tyr Tyr Met His Trp Val Lys Gln Arg Pro Glu Gln Gly Leu
50 55 60

Glu Trp Ile Gly Arg Ile Asp Pro Glu Asn Gly Asp Ile Ile Tyr Asp
65 70 75 80

Pro Lys Phe Gln Gly Lys Ala Ser Ile Thr Thr Asp Thr Ser Ser Asn
85 90 95

Thr Ala Tyr Leu Gln Leu Ser Ser Leu Thr Ser Glu Asp Thr Ala Val
100 105 110

Tyr Tyr Cys Ala Tyr Asp Ala Gly Asp Pro Ala Trp Phe Thr Tyr Trp
115 120 125

Gly Gln Gly Thr Leu Val Thr Val Ser Ser
130 135

<210> SEQ ID NO 318
<211> LENGTH: 411
<212> TYPE: DNA
<213> ORGANISM: Mus musculus

<400> SEQUENCE: 318
atgggatgga actggatcat cttcttcctg atggcagtgg ttacaggggt caattcagag 60
gttcagctgc agcagtctgg ggctgagctt gtgaggccag gggccttagt caagttgtcc 120
tgcaaagctt ctggcttcaa tattaaagac tactatatgc actgggtgaa gcagaggcct 180
gaacagggcc tggagtggat tggaaggatt gatcctgaga atggtgatat tatatatgac 240
ccgaagttcc agggcaaggc cagtataaca acagacacat cctccaacac agcctacctg 300
cagctcagca gcctgacgtc tgaggacact gccgtctatt actgtgctta cgatgctggt 360 gacccccgcct ggtttactta ctggggccaa gggactctgg tcaccgtctc g 411

<210> SEQ ID NO 319
<211> LENGTH: 130
<212> TYPE: PRT
<213> ORGANISM: Mus musculus

<400> SEQUENCE: 319

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Phe Thr Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Ser Tyr Pro Leu Thr Phe Gly Gly Gly Thr Lys Val Glu Ile
        115                 120                 125

Lys Arg
    130
```

<210> SEQ ID NO 320
<211> LENGTH: 390
<212> TYPE: DNA
<213> ORGANISM: Mus musculus

<400> SEQUENCE: 320

```
atggatatgc gcgtgccggc gcagctgctg ggcctgctgc tgctgtggct gcgcggcgcg     60

cgctgcgata tccagatgac ccagagcccg agcagcctga gcgcgagcgt gggcgatcgc    120

gtgaccatta cctgcaaagc gagccaggat gtgtttaccg cggtggcgtg gtatcagcag    180

aaaccgggca aagcgccgaa actgctgatt tattgggcga gcacccgcca taccggcgtg    240

ccgagtcgct ttagcggcag cggcagcggc accgatttta ccctgaccat tagcagcctg    300

cagccggaag attttgcgac ctattattgc cagcagtata gcagctatcc gctgaccttt    360

ggcggcggca ccaaagtgga aattaaacgt                                     390
```

<210> SEQ ID NO 321
<211> LENGTH: 138
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 321

```
Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Met His Trp Val Arg Gln Ala Pro Gly Gln Gly Leu
    50                  55                  60

Glu Trp Ile Gly Arg Ile Asp Pro Glu Asn Gly Asp Ile Ile Tyr Asp
65                  70                  75                  80

Pro Lys Phe Gln Gly Arg Val Thr Met Thr Thr Asp Thr Ser Thr Ser
```

```
                85                  90                  95

Thr Ala Tyr Met Glu Leu Arg Ser Leu Arg Ser Asp Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135
```

<210> SEQ ID NO 322
<211> LENGTH: 414
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 322

```
atggattgga cctggagcat tctgtttctg gtggcggcgc cgaccggcgc gcatagcgaa     60

gtgcagctgg tgcagagcgg cgcggaagtg aaaaaaccgg gcgcgagcgt gaaagtgagc    120

tgcaaagcga gcggctttaa cattaaagat tattatatgc attgggtgcg ccaggcgccg    180

ggccagggcc tggaatggat cggccgcatt gatccggaaa acggcgatat tatttatgat    240

ccgaaatttc agggccgcgt gaccatgacc accgatacca gcaccagcac cgcgtatatg    300

gaactgcgca gcctgcgcag cgatgatacc gcggtgtatt attgcgcgta tgatgcgggc    360

gatccggcgt ggtttaccta ttggggccag ggcaccctgg tgaccgtctc gagc          414
```

<210> SEQ ID NO 323
<211> LENGTH: 106
<212> TYPE: PRT
<213> ORGANISM: Mus musculus

<400> SEQUENCE: 323

```
Thr Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

<210> SEQ ID NO 324
<211> LENGTH: 320
<212> TYPE: PRT
<213> ORGANISM: Mus musculus

<400> SEQUENCE: 324

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
```

```
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320


<210> SEQ ID NO 325
<211> LENGTH: 106
<212> TYPE: PRT
<213> ORGANISM: Homo sapiens

<400> SEQUENCE: 325

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80
```

```
His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 326
<211> LENGTH: 327
<212> TYPE: PRT
<213> ORGANISM: Homo sapiens

<400> SEQUENCE: 326

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 327
```

<211> LENGTH: 120
<212> TYPE: PRT
<213> ORGANISM: Mus musculus

<400> SEQUENCE: 327

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120

<210> SEQ ID NO 328
<211> LENGTH: 120
<212> TYPE: PRT
<213> ORGANISM: Mus musculus

<400> SEQUENCE: 328

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120

<210> SEQ ID NO 329
<211> LENGTH: 120
<212> TYPE: PRT
<213> ORGANISM: Mus musculus

<400> SEQUENCE: 329

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

```
Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120
```

<210> SEQ ID NO 330
<211> LENGTH: 226
<212> TYPE: PRT
<213> ORGANISM: Mus musculus

<400> SEQUENCE: 330

```
Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225
```

<210> SEQ ID NO 331
<211> LENGTH: 447
<212> TYPE: PRT
<213> ORGANISM: Mus musculus

<400> SEQUENCE: 331

```
Glu Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
```

435 440 445

<210> SEQ ID NO 332
<211> LENGTH: 107
<212> TYPE: PRT
<213> ORGANISM: Mus musculus

<400> SEQUENCE: 332

Asp Ile Gln Met Thr Gln Ile Thr Ser Ser Leu Ser Ala Ser Leu Gly
1 5 10 15

Asp Arg Val Ser Ile Ser Cys Arg Ala Ser Gln Asp Ile Ser Asn Tyr
20 25 30

Leu Asn Trp Tyr Gln Gln Lys Pro Asp Gly Thr Phe Lys Leu Leu Ile
35 40 45

Phe Tyr Thr Ser Arg Leu Leu Ser Gly Val Pro Ser Arg Phe Ser Gly
50 55 60

Ser Gly Ser Gly Thr Asp Tyr Ser Leu Thr Ile Tyr Asn Leu Glu Gln
65 70 75 80

Glu Asp Phe Ala Thr Tyr Phe Cys Gln Gln Gly Asp Thr Leu Pro Tyr
85 90 95

Thr Phe Gly Gly Gly Thr Lys Leu Glu Ile Lys
100 105

<210> SEQ ID NO 333
<211> LENGTH: 324
<212> TYPE: PRT
<213> ORGANISM: Mus musculus

<400> SEQUENCE: 333

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Pro Ser Ser Thr Trp Pro Ser Glu Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Gln Pro Arg Glu Glu Gln Phe Asn Ser Thr
165 170 175

Phe Arg Ser Val Ser Glu Leu Pro Ile Met His Gln Asp Trp Leu Asn
180 185 190

Gly Lys Glu Phe Lys Cys Arg Val Asn Ser Ala Ala Phe Pro Ala Pro
195 200 205

Ile Glu Lys Thr Ile Ser Lys Thr Lys Gly Arg Pro Lys Ala Pro Gln

-continued

```
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Ile Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 334
<211> LENGTH: 213
<212> TYPE: PRT
<213> ORGANISM: Mus musculus

<400> SEQUENCE: 334

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg Thr Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 335
<211> LENGTH: 444
<212> TYPE: PRT
<213> ORGANISM: Mus musculus

<400> SEQUENCE: 335
```

```
Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415
```

```
Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 336
<211> LENGTH: 108
<212> TYPE: PRT
<213> ORGANISM: Mus musculus

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105


<210> SEQ ID NO 337
<211> LENGTH: 324
<212> TYPE: DNA
<213> ORGANISM: Mus musculus

<400> SEQUENCE: 337

gatatccaga tgacccagag cccgagcagc ctgagcgcga gcgtgggcga tcgcgtgacc      60

attacctgca aagcgagcca ggatgtgttt accgcggtgg cgtggtatca gcagaaaccg     120

ggcaaagcgc cgaaactgct gatttattgg gcgagcaccc gccataccgg cgtgccgagt     180

cgctttagcg gcagcggcag cggcaccgat tttaccctga ccattagcag cctgcagccg     240

gaagattttg cgacctatta ttgccagcag tatagcagct atccgctgac ctttggcggc     300

ggcaccaaag tggaaattaa acgt                                            324


<210> SEQ ID NO 338
<211> LENGTH: 119
<212> TYPE: PRT
<213> ORGANISM: Mus musculus

<400> SEQUENCE: 338

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

-continued

```
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115
```

<210> SEQ ID NO 339
<211> LENGTH: 357
<212> TYPE: DNA
<213> ORGANISM: Mus musculus

<400> SEQUENCE: 339

```
gaagtgcagc tggtgcagag cggcgcggaa gtgaaaaaac cgggcgcgag cgtgaaagtg      60

agctgcaaag cgagcggctt taacattaaa gattattata tgcattgggt gcgccaggcg     120

ccgggccagg gcctggaatg gatcggccgc attgatccgg aaaacggcga tattatttat     180

gatccgaaat ttcagggccg cgtgaccatg accaccgata ccagcaccag caccgcgtat     240

atggaactgc gcagcctgcg cagcgatgat accgcggtgt attattgcgc gtatgatgcg     300

ggcgatccgg cgtggtttac ctattggggc cagggcaccc tggtgaccgt ctcgagc        357
```

<210> SEQ ID NO 340
<211> LENGTH: 1395
<212> TYPE: DNA
<213> ORGANISM: Mus musculus

<400> SEQUENCE: 340

```
atggactgga cctggaggat cctcttcttg gtggcagcag ccacaggagc ccactccgag      60

gtgcagctgg tgcagtctgg ggctgaggtg aagaagcctg ggtcctcggt gaaggtctcc     120

tgcaaggctt ctggttttac cttcaccgac tatattatgc actgggtgcg tcaggcccct     180

ggtcaagggc ttgagtggat gggctatatc aacccttata atgatgacac cgaatacaac     240

gagaagttca agggccgtgt cacgattacc gcggacaaat ccacgagcac agcctacatg     300

gagctgagca gcctgcgctc tgaggacacg gccgtgtatt actgtgcgcg ttcgatttat     360

tactacgatg ccccgtttgc ttactggggc caagggactc tggtcaccgt ctctagtgcc     420

tccaccaagg gcccatcggt cttccccctg gcgccctgct ccaggagcac ctccgagagc     480

acagcggccc tgggctgcct ggtcaaggac tacttccccg aaccggtgac ggtgtcgtgg     540

aactcaggcg ctctgaccag cggcgtgcac accttcccag ctgtcctaca gtcctcagga     600

ctctactccc tcagcagcgt ggtgaccgtg ccctccagca acttcggcac ccagacctac     660

acctgcaacg tagatcacaa gcccagcaac accaaggtgg acaagacagt tgagcgcaaa     720

tgttgtgtcg agtgcccacc gtgcccagca ccacctgtgg caggaccgtc agtcttcctc     780

ttccccccaa aacccaagga caccctcatg atctcccgga cccctgaggt cacgtgcgtg     840

gtggtggacg tgagccacga agaccccgag gtccagttca actggtacgt ggacggcgtg     900

gaggtgcata atgccaagac aaagccacgg gaggagcagt tcaacagcac gttccgtgtg     960

gtcagcgtcc tcaccgttgt gcaccaggac tggctgaacg gcaaggagta caagtgcaag    1020

gtctccaaca aaggcctccc agcccccatc gagaaaacca tctccaaaac caaagggcag    1080

ccccgagaac cacaggtgta caccctgccc ccatcccggg aggagatgac caagaaccag    1140

gtcagcctga cctgcctggt caaaggcttc taccccagcg acatcgccgt ggagtgggag    1200

agcaatgggc agccggagaa caactacaag accacacctc ccatgctgga ctccgacggc    1260

tccttcttcc tctacagcaa gctcaccgtg gacaagagca ggtggcagca ggggaacgtc    1320
```

ttctcatgct ccgtgatgca tgaggctctg cacaaccact acacgcagaa gagcctctcc 1380
ctgtctccgg gtaaa 1395

<210> SEQ ID NO 341
<211> LENGTH: 213
<212> TYPE: PRT
<213> ORGANISM: Mus musculus

<400> SEQUENCE: 341

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Tyr
20 25 30

Leu Asn Trp Tyr Gln Gln Lys Pro Gly Lys Ala Pro Lys Leu Leu Ile
35 40 45

Tyr Ser Thr Ser Arg Leu Asn Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Asp Ile Lys His Pro Thr
85 90 95

Phe Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 342
<211> LENGTH: 639
<212> TYPE: DNA
<213> ORGANISM: Mus musculus

<400> SEQUENCE: 342
gacatccaga tgacccagtc tccatcctcc ctgtctgcat ctgtaggtga ccgtgtcacc 60
atcacttgcc gcgcaagtca ggatattagc agctatttaa attggtatca gcagaaacca 120
gggaaagccc ctaagctcct gatctattct acttcccgtt tgaatagtgg ggtcccatca 180
cgcttcagtg gcagtggctc tgggacagat ttcactctca ccatcagcag tctgcaacct 240
gaagattttg caacttacta ctgtcaacag gatattaaac accctacgtt cggtcaaggc 300
accaaggtgg agatcaaacg tacggtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 343
<211> LENGTH: 235
<212> TYPE: PRT
<213> ORGANISM: Mus musculus

<400> SEQUENCE: 343

Met Asp Met Arg Val Pro Ala Gln Leu Leu Gly Leu Leu Leu Leu Trp
1 5 10 15

Leu Arg Gly Ala Arg Cys Asp Ile Gln Met Thr Gln Ser Pro Ser Ser
20 25 30

Leu Ser Ala Ser Val Gly Asp Arg Val Thr Ile Thr Cys Arg Ala Ser
35 40 45

Gln Asp Ile Ser Ser Tyr Leu Asn Trp Tyr Gln Gln Lys Pro Gly Lys
50 55 60

Ala Pro Lys Leu Leu Ile Tyr Ser Thr Ser Arg Leu Asn Ser Gly Val
65 70 75 80

Pro Ser Arg Phe Ser Gly Ser Gly Ser Gly Thr Asp Phe Thr Leu Thr
85 90 95

Ile Ser Ser Leu Gln Pro Glu Asp Phe Ala Thr Tyr Tyr Cys Gln Gln
100 105 110

Asp Ile Lys His Pro Thr Phe Gly Gln Gly Thr Lys Val Glu Ile Lys
115 120 125

Arg Thr Val Ala Ala Pro Ser Val Phe Ile Phe Pro Pro Ser Asp Glu
130 135 140

Gln Leu Lys Ser Gly Thr Ala Ser Val Val Cys Leu Leu Asn Asn Phe
145 150 155 160

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Ser Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys
225 230 235

<210> SEQ ID NO 344
<211> LENGTH: 705
<212> TYPE: DNA
<213> ORGANISM: Mus musculus

<400> SEQUENCE: 344
atggacatga gggtgcccgc tcagctcctg gggctcctgc tgctgtggct gagaggtgcc 60
agatgtgaca tccagatgac ccagtctcca tcctccctgt ctgcatctgt aggtgaccgt 120
gtcaccatca cttgccgcgc aagtcaggat attagcagct atttaaattg gtatcagcag 180
aaaccaggga aagcccctaa gctcctgatc tattctactt cccgtttgaa tagtggggtc 240
ccatcacgct tcagtggcag tggctctggg acagatttca ctctcaccat cagcagtctg 300
caacctgaag attttgcaac ttactactgt caacaggata ttaaacaccc tacgttcggt 360
caaggcacca aggtggagat caaacgtacg gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgt 705

<210> SEQ ID NO 345
<211> LENGTH: 446
<212> TYPE: PRT
<213> ORGANISM: Mus musculus

<400> SEQUENCE: 345

Glu Val Gln Leu Val Gln Ser Gly Ala Glu Val Lys Lys Pro Gly Ser
1 5 10 15

Ser Val Lys Val Ser Cys Lys Ala Ser Gly Phe Thr Phe Thr Asp Tyr
20 25 30

Ile Met His Trp Val Arg Gln Ala Pro Gly Gln Gly Leu Glu Trp Met
35 40 45

Gly Tyr Ile Asn Pro Tyr Asn Asp Asp Thr Glu Tyr Asn Glu Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Ile Tyr Tyr Tyr Asp Ala Pro Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Asn Phe Gly Thr Gln Thr Tyr Thr Cys Asn Val Asp His Lys
195 200 205

Pro Ser Asn Thr Lys Val Asp Lys Thr Val Glu Arg Lys Cys Cys Val
210 215 220

Glu Cys Pro Pro Cys Pro Ala Pro Pro Val Ala Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Gln Phe Asn Trp Tyr Val Asp Gly Val Glu Val His Asn Ala Lys Thr
275 280 285

Lys Pro Arg Glu Glu Gln Phe Asn Ser Thr Phe Arg Val Val Ser Val
290 295 300

Leu Thr Val Val His Gln Asp Trp Leu Asn Gly Lys Glu Tyr Lys Cys
305 310 315 320

```
Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 346
<211> LENGTH: 1338
<212> TYPE: DNA
<213> ORGANISM: Mus musculus

<400> SEQUENCE: 346

gaggtgcagc tggtgcagtc tggggctgag gtgaagaagc ctgggtcctc ggtgaaggtc     60

tcctgcaagg cttctggttt taccttcacc gactatatta tgcactgggt gcgtcaggcc    120

cctggtcaag ggcttgagtg gatgggctat atcaaccctt ataatgatga caccgaatac    180

aacgagaagt tcaagggccg tgtcacgatt accgcggaca aatccacgag cacagcctac    240

atggagctga gcagcctgcg ctctgaggac acggccgtgt attactgtgc gcgttcgatt    300

tattactacg atgccccgtt tgcttactgg ggccaaggga ctctggtcac cgtctctagt    360

gcctccacca agggcccatc ggtcttcccc ctggcgccct gctccaggag cacctccgag    420

agcacagcgg ccctgggctg cctggtcaag gactacttcc ccgaaccggt gacggtgtcg    480

tggaactcag gcgctctgac cagcggcgtg cacaccttcc cagctgtcct acagtcctca    540

ggactctact ccctcagcag cgtggtgacc gtgccctcca gcaacttcgg cacccagacc    600

tacacctgca acgtagatca caagcccagc aacaccaagg tggacaagac agttgagcgc    660

aaatgttgtg tcgagtgccc accgtgccca gcaccacctg tggcaggacc gtcagtcttc    720

ctcttccccc caaaacccaa ggacaccctc atgatctccc ggacccctga ggtcacgtgc    780

gtggtggtgg acgtgagcca cgaagacccc gaggtccagt tcaactggta cgtggacggc    840

gtggaggtgc ataatgccaa gacaaagcca cgggaggagc agttcaacag cacgttccgt    900

gtggtcagcg tcctcaccgt tgtgcaccag gactggctga acggcaagga gtacaagtgc    960

aaggtctcca acaaaggcct cccagccccc atcgagaaaa ccatctccaa aaccaaaggg   1020

cagccccgag aaccacaggt gtacaccctg cccccatccc gggaggagat gaccaagaac   1080

caggtcagcc tgacctgcct ggtcaaaggc ttctacccca gcgacatcgc cgtggagtgg   1140

gagagcaatg ggcagccgga gaacaactac aagaccacac ctcccatgct ggactccgac   1200

ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 347
<211> LENGTH: 465
<212> TYPE: PRT
<213> ORGANISM: Mus musculus

<400> SEQUENCE: 347

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380
```

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 348
<211> LENGTH: 1395
<212> TYPE: DNA
<213> ORGANISM: Mus musculus

<400> SEQUENCE: 348

atggactgga cctggaggat cctcttcttg gtggcagcag ccacaggagc ccactccgag      60

gtgcagctgg tgcagtctgg ggctgaggtg aagaagcctg ggtcctcggt gaaggtctcc     120

tgcaaggctt ctggttttac cttcaccgac tatattatgc actgggtgcg tcaggcccct     180

ggtcaagggc ttgagtggat gggctatatc aacccttata atgatgacac cgaatacaac     240

gagaagttca agggccgtgt cacgattacc gcggacaaat ccacgagcac agcctacatg     300

gagctgagca gcctgcgctc tgaggacacg gccgtgtatt actgtgcgcg ttcgatttat     360

tactacgatg ccccgtttgc ttactggggc caagggactc tggtcaccgt ctctagtgcc     420

tccaccaagg gcccatcggt cttccccctg gcgccctgct ccaggagcac ctccgagagc     480

acagcggccc tgggctgcct ggtcaaggac tacttccccg aaccggtgac ggtgtcgtgg     540

aactcaggcg ctctgaccag cggcgtgcac accttcccag ctgtcctaca gtcctcagga     600

ctctactccc tcagcagcgt ggtgaccgtg ccctccagca acttcggcac ccagacctac     660

acctgcaacg tagatcacaa gcccagcaac accaaggtgg acaagacagt tgagcgcaaa     720

tgttgtgtcg agtgcccacc gtgcccagca ccacctgtgg caggaccgtc agtcttcctc     780

ttccccccaa aacccaagga caccctcatg atctcccgga cccctgaggt cacgtgcgtg     840

gtggtggacg tgagccacga agaccccgag gtccagttca actggtacgt ggacggcgtg     900

gaggtgcata atgccaagac aaagccacgg gaggagcagt tcaacagcac gttccgtgtg     960

gtcagcgtcc tcaccgttgt gcaccaggac tggctgaacg gcaaggagta caagtgcaag    1020

gtctccaaca aaggcctccc agcccccatc gagaaaacca tctccaaaac caaagggcag    1080

ccccgagaac cacaggtgta caccctgccc ccatcccggg aggagatgac caagaaccag    1140

gtcagcctga cctgcctggt caaaggcttc taccccagcg acatcgccgt ggagtgggag    1200

agcaatgggc agccggagaa caactacaag accacacctc ccatgctgga ctccgacggc    1260

tccttcttcc tctacagcaa gctcaccgtg gacaagagca ggtggcagca ggggaacgtc    1320

ttctcatgct ccgtgatgca tgaggctctg cacaaccact acacgcagaa gagcctctcc    1380

ctgtctccgg gtaaa                                                     1395


<210> SEQ ID NO 349
<211> LENGTH: 417
<212> TYPE: DNA
```

<213> ORGANISM: Mus musculus

<400> SEQUENCE: 349
atggaatgga tctggatatt tctcttcctc ctgtcaggaa ctgcaggtgt ccactctgag 60
gtgcagctgg tgcagtctgg ggctgaggtg aagaagcctg ggtcctcggt gaaggtctcc 120
tgcaaggctt ctggttttac cttcaccgac tatattatgc actgggtgcg tcaggcccct 180
ggtcaagggc ttgagtggat gggctatatc aacccttata atgatgacac cgaatacaac 240
gagaagttca agggccgtgt cacgattacc gcggacaaat ccacgagcac agcctacatg 300
gagctgagca gcctgcgctc tgaggacacg gccgtgtatt actgtgcgcg ttcgatttat 360
tactacgatg ccccgtttgc ttactggggc caagggactc tggtcacagt ctcgagc 417

<210> SEQ ID NO 350
<211> LENGTH: 218
<212> TYPE: PRT
<213> ORGANISM: Mus musculus

<400> SEQUENCE: 350

Asp Ile Val Leu Thr Gln Ser Pro Ala Ser Leu Ala Val Ser Leu Gly
1 5 10 15

Gln Arg Ala Thr Ile Ala Cys Lys Ala Ser Gln Ser Val Asp Tyr Asp
20 25 30

Gly Thr Ser Tyr Met Asn Trp Tyr Gln Gln Lys Pro Gly Gln Pro Pro
35 40 45

Lys Leu Leu Ile Tyr Ala Ala Ser Asn Leu Glu Ser Glu Ile Pro Ala
50 55 60

Arg Phe Ser Gly Thr Gly Ser Gly Thr Asp Phe Thr Leu Asn Ile His
65 70 75 80

Pro Val Glu Glu Glu Asp Ile Thr Thr Tyr Tyr Cys Gln Gln Ser Asn
85 90 95

Glu Asp Pro Phe Thr Phe Gly Gly Gly Thr Lys Leu Glu Ile Lys Arg
100 105 110

Ala Asp Ala Ala Pro Thr Val Ser Ile Phe Pro Pro Ser Ser Glu Gln
115 120 125

Leu Thr Ser Gly Gly Ala Ser Val Val Cys Phe Leu Asn Asn Phe Tyr
130 135 140

Pro Lys Asp Ile Asn Val Lys Trp Lys Ile Asp Gly Ser Glu Arg Gln
145 150 155 160

Asn Gly Val Leu Asn Ser Trp Thr Asp Gln Asp Ser Lys Asp Ser Thr
165 170 175

Tyr Ser Met Ser Ser Thr Leu Thr Leu Thr Lys Asp Glu Tyr Glu Arg
180 185 190

His Asn Ser Tyr Thr Cys Glu Ala Thr His Lys Thr Ser Thr Ser Pro
195 200 205

Ile Val Lys Ser Phe Asn Arg Asn Glu Cys
210 215

<210> SEQ ID NO 351
<211> LENGTH: 15
<212> TYPE: PRT
<213> ORGANISM: Mus musculus

<400> SEQUENCE: 351

Lys Ala Ser Gln Ser Val Asp Tyr Asp Gly Thr Ser Tyr Met Asn
1 5 10 15

<210> SEQ ID NO 352
<211> LENGTH: 7
<212> TYPE: PRT
<213> ORGANISM: Mus musculus

<400> SEQUENCE: 352

Ala Ala Ser Asn Leu Glu Ser
1 5

<210> SEQ ID NO 353
<211> LENGTH: 9
<212> TYPE: PRT
<213> ORGANISM: Mus musculus

<400> SEQUENCE: 353

Gln Gln Ser Asn Glu Asp Pro Phe Thr
1 5

<210> SEQ ID NO 354
<211> LENGTH: 657
<212> TYPE: DNA
<213> ORGANISM: Mus musculus

<400> SEQUENCE: 354
gacattgtgt tgacccagtc tccagcttct ttggctgtgt ctctagggca gagggccacc 60
atcgcctgca aggccagcca aagtgttgat tatgatggta ctagttatat gaattggtac 120
caacagaaac caggacagcc acccaaactc ctcatctatg ctgcatccaa tctagaatct 180
gagatcccag ccaggtttag tggcactggg tctgggacag acttcaccct caacatccat 240
cctgtggagg aggaggatat cacaacctat tactgtcagc aaagtaatga ggatccgttc 300
acgttcggag gggggaccaa gttggaaata aaacgggctg atgctgcacc aactgtatcc 360
atcttcccac catccagtga gcagttaaca tctggaggtg cctcagtcgt gtgcttcttg 420
aacaacttct accccaaaga catcaatgtc aagtggaaga ttgatggcag tgaacgacaa 480
aatggcgtcc tgaacagttg gactgatcag gacagcaaag acagcaccta cagcatgagc 540
agcaccctca cgttgaccaa ggacgagtat gaacgacata acagctatac ctgtgaggcc 600
actcacaaga catcaacttc acccattgtc aagagcttca acaggaatga gtgttag 657

<210> SEQ ID NO 355
<211> LENGTH: 238
<212> TYPE: PRT
<213> ORGANISM: Mus musculus

<400> SEQUENCE: 355

Met Glu Thr Asp Thr Ile Leu Leu Trp Val Leu Leu Leu Trp Val Pro
1 5 10 15

Gly Ser Thr Gly Asp Ile Val Leu Thr Gln Ser Pro Ala Ser Leu Ala
20 25 30

Val Ser Leu Gly Gln Arg Ala Thr Ile Ala Cys Lys Ala Ser Gln Ser
35 40 45

Val Asp Tyr Asp Gly Thr Ser Tyr Met Asn Trp Tyr Gln Gln Lys Pro
50 55 60

Gly Gln Pro Pro Lys Leu Leu Ile Tyr Ala Ala Ser Asn Leu Glu Ser
65 70 75 80

Glu Ile Pro Ala Arg Phe Ser Gly Thr Gly Ser Gly Thr Asp Phe Thr
85 90 95

Leu Asn Ile His Pro Val Glu Glu Glu Asp Ile Thr Thr Tyr Tyr Cys

```
            100                 105                 110

Gln Gln Ser Asn Glu Asp Pro Phe Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 356
<211> LENGTH: 717
<212> TYPE: DNA
<213> ORGANISM: Mus musculus

<400> SEQUENCE: 356

atggagacag acacaatcct gctatgggtg ctgctgctct gggttccagg ctccactggt     60

gacattgtgt tgacccagtc tccagcttct ttggctgtgt ctctagggca gagggccacc    120

atcgcctgca aggccagcca aagtgttgat tatgatggta ctagttatat gaattggtac    180

caacagaaac caggacagcc acccaaactc ctcatctatg ctgcatccaa tctagaatct    240

gagatcccag ccaggtttag tggcactggg tctgggacag acttcaccct caacatccat    300

cctgtggagg aggaggatat cacaacctat tactgtcagc aaagtaatga ggatccgttc    360

acgttcggag gggggaccaa gttggaaata aaacgggctg atgctgcacc aactgtatcc    420

atcttcccac catccagtga gcagttaaca tctggaggtg cctcagtcgt gtgcttcttg    480

aacaacttct accccaaaga catcaatgtc aagtggaaga ttgatggcag tgaacgacaa    540

aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttag       717


<210> SEQ ID NO 357
<211> LENGTH: 442
<212> TYPE: PRT
<213> ORGANISM: Mus musculus

<400> SEQUENCE: 357

Gln Val Gln Leu Gln Gln Pro Gly Thr Glu Leu Val Arg Pro Gly Thr
1               5                   10                  15

Ser Val Lys Leu Ser Cys Lys Ala Ser Gly Tyr Ile Phe Thr Thr Tyr
            20                  25                  30

Trp Met Asn Trp Val Lys Gln Arg Pro Gly Gln Gly Leu Glu Trp Ile
        35                  40                  45

Gly Met Ile His Pro Ser Ala Ser Glu Ile Arg Leu Asp Gln Lys Phe
    50                  55                  60

Lys Asp Lys Ala Thr Leu Thr Leu Asp Lys Ser Ser Ser Thr Ala Tyr
```

65 70 75 80

Met His Leu Ser Gly Pro Thr Ser Val Asp Ser Ala Val Tyr Tyr Cys
85 90 95

Ala Arg Ser Gly Glu Trp Gly Ser Met Asp Tyr Trp Gly Gln Gly Thr
100 105 110

Ser Val Thr Val Ser Ser Ala Lys Thr Thr Pro Pro Ser Val Tyr Pro
115 120 125

Leu Ala Pro Gly Ser Ala Ala Gln Thr Asn Ser Met Val Thr Leu Gly
130 135 140

Cys Leu Val Lys Gly Tyr Phe Pro Glu Pro Val Thr Val Thr Trp Asn
145 150 155 160

Ser Gly Ser Leu Ser Ser Gly Val His Thr Phe Pro Ala Val Leu Gln
165 170 175

Ser Asp Leu Tyr Thr Leu Ser Ser Ser Val Thr Val Pro Ser Ser Thr
180 185 190

Trp Pro Ser Glu Thr Val Thr Cys Asn Val Ala His Pro Ala Ser Ser
195 200 205

Thr Lys Val Asp Lys Lys Ile Val Pro Arg Asp Cys Gly Cys Lys Pro
210 215 220

Cys Ile Cys Thr Val Pro Glu Val Ser Ser Val Phe Ile Phe Pro Pro
225 230 235 240

Lys Pro Lys Asp Val Leu Thr Ile Thr Leu Thr Pro Lys Val Thr Cys
245 250 255

Val Val Val Asp Ile Ser Lys Asp Asp Pro Glu Val Gln Phe Ser Trp
260 265 270

Phe Val Asp Asp Val Glu Val His Thr Ala Gln Thr Gln Pro Arg Glu
275 280 285

Glu Gln Phe Asn Ser Thr Phe Arg Ser Val Ser Glu Leu Pro Ile Met
290 295 300

His Gln Asp Trp Leu Asn Gly Lys Glu Phe Lys Cys Arg Val Asn Ser
305 310 315 320

Ala Ala Phe Pro Ala Pro Ile Glu Lys Thr Ile Ser Lys Thr Lys Gly
325 330 335

Arg Pro Lys Ala Pro Gln Val Tyr Thr Ile Pro Pro Pro Lys Glu Gln
340 345 350

Met Ala Lys Asp Lys Val Ser Leu Thr Cys Met Ile Thr Asp Phe Phe
355 360 365

Pro Glu Asp Ile Thr Val Glu Trp Gln Trp Asn Gly Gln Pro Ala Glu
370 375 380

Asn Tyr Lys Asn Thr Gln Pro Ile Met Asp Thr Asp Gly Ser Tyr Phe
385 390 395 400

Ile Tyr Ser Lys Leu Asn Val Gln Lys Ser Asn Trp Glu Ala Gly Asn
405 410 415

Thr Phe Thr Cys Ser Val Leu His Glu Gly Leu His Asn His His Thr
420 425 430

Glu Lys Ser Leu Ser His Ser Pro Gly Lys
435 440

<210> SEQ ID NO 358
<211> LENGTH: 5
<212> TYPE: PRT
<213> ORGANISM: Mus musculus

<400> SEQUENCE: 358

Thr Tyr Trp Met Asn
1               5

<210> SEQ ID NO 359
<211> LENGTH: 17
<212> TYPE: PRT
<213> ORGANISM: Mus musculus

<400> SEQUENCE: 359

Met Ile His Pro Ser Ala Ser Glu Ile Arg Leu Asp Gln Lys Phe Lys
1               5                   10                  15

Asp

<210> SEQ ID NO 360
<211> LENGTH: 9
<212> TYPE: PRT
<213> ORGANISM: Mus musculus

<400> SEQUENCE: 360

Ser Gly Glu Trp Gly Ser Met Asp Tyr
1               5

<210> SEQ ID NO 361
<211> LENGTH: 1329
<212> TYPE: DNA
<213> ORGANISM: Mus musculus

<400> SEQUENCE: 361
caggtccaac tacagcagcc tgggactgag ctggtgaggc ctggaacttc agtgaagttg 60
tcctgtaagg cttctggcta catcttcacc acctactgga tgaactgggt gaaacagagg 120
cctggacaag gccttgagtg gattggcatg attcatcctt ccgcaagtga aattaggttg 180
gatcagaaat tcaaggacaa ggccacattg actcttgaca aatcctccag cacagcctat 240
atgcacctca gcggcccgac atctgtggat tctgcggtct attactgtgc aagatcaggg 300
gaatgggggt ctatggacta ctggggtcaa ggaacctcag tcaccgtctc ctcagccaaa 360
acgacacccc catctgtcta tccactggcc cctggatctg ctgcccaaac taactccatg 420
gtgaccctgg gatgcctggt caagggctat ttccctgagc cagtgacagt gacctggaac 480
tctggatccc tgtccagcgg tgtgcacacc ttcccagctg tcctgcagtc tgacctctac 540
actctgagca gctcagtgac tgtcccctcc agcacctggc ccagcgagac cgtcacctgc 600
aacgttgccc acccggccag cagcaccaag gtggacaaga aaattgtgcc cagggattgt 660
ggttgtaagc cttgcatatg tacagtccca gaagtatcat ctgtcttcat cttcccccca 720
aagcccaagg atgtgctcac cattactctg actcctaagg tcacgtgtgt tgtggtagac 780
atcagcaagg atgatcccga ggtccagttc agctggtttg tagatgatgt ggaggtgcac 840
acagctcaga cgcaaccccg ggaggagcag ttcaacagca ctttccgctc agtcagtgaa 900
cttcccatca tgcaccagga ctggctcaat ggcaaggagt tcaaatgcag ggtcaacagt 960
gcagctttcc ctgcccccat cgagaaaacc atctccaaaa ccaaaggcag accgaaggct 1020
ccacaggtgt acaccattcc acctcccaag gagcagatgg ccaaggataa agtcagtctg 1080
acctgcatga taacagactt cttccctgaa gacattactg tggagtggca gtggaatggg 1140
cagccagcgg agaactacaa gaacactcag cccatcatgg acacagatgg ctcttacttc 1200
atctacagca agctcaatgt gcagaagagc aactgggagg caggaaatac tttcacctgc 1260
tctgtgttac atgagggcct gcacaaccac catactgaga agagcctctc ccactctcct 1320
ggtaaatga 1329

<210> SEQ ID NO 362
<211> LENGTH: 461
<212> TYPE: PRT
<213> ORGANISM: Mus musculus

<400> SEQUENCE: 362

Met Gly Trp Ser Ser Ile Ile Leu Phe Leu Val Ala Thr Ala Thr Gly
1 5 10 15

Val His Ser Gln Val Gln Leu Gln Gln Pro Gly Thr Glu Leu Val Arg
20 25 30

Pro Gly Thr Ser Val Lys Leu Ser Cys Lys Ala Ser Gly Tyr Ile Phe
35 40 45

Thr Thr Tyr Trp Met Asn Trp Val Lys Gln Arg Pro Gly Gln Gly Leu
50 55 60

Glu Trp Ile Gly Met Ile His Pro Ser Ala Ser Glu Ile Arg Leu Asp
65 70 75 80

Gln Lys Phe Lys Asp Lys Ala Thr Leu Thr Leu Asp Lys Ser Ser Ser
85 90 95

Thr Ala Tyr Met His Leu Ser Gly Pro Thr Ser Val Asp Ser Ala Val
100 105 110

Tyr Tyr Cys Ala Arg Ser Gly Glu Trp Gly Ser Met Asp Tyr Trp Gly
115 120 125

Gln Gly Thr Ser Val Thr Val Ser Ser Ala Lys Thr Thr Pro Pro Ser
130 135 140

Val Tyr Pro Leu Ala Pro Gly Ser Ala Ala Gln Thr Asn Ser Met Val
145 150 155 160

Thr Leu Gly Cys Leu Val Lys Gly Tyr Phe Pro Glu Pro Val Thr Val
165 170 175

Thr Trp Asn Ser Gly Ser Leu Ser Ser Gly Val His Thr Phe Pro Ala
180 185 190

Val Leu Gln Ser Asp Leu Tyr Thr Leu Ser Ser Ser Val Thr Val Pro
195 200 205

Ser Ser Thr Trp Pro Ser Glu Thr Val Thr Cys Asn Val Ala His Pro
210 215 220

Ala Ser Ser Thr Lys Val Asp Lys Lys Ile Val Pro Arg Asp Cys Gly
225 230 235 240

Cys Lys Pro Cys Ile Cys Thr Val Pro Glu Val Ser Ser Val Phe Ile
245 250 255

Phe Pro Pro Lys Pro Lys Asp Val Leu Thr Ile Thr Leu Thr Pro Lys
260 265 270

Val Thr Cys Val Val Val Asp Ile Ser Lys Asp Asp Pro Glu Val Gln
275 280 285

Phe Ser Trp Phe Val Asp Asp Val Glu Val His Thr Ala Gln Thr Gln
290 295 300

Pro Arg Glu Glu Gln Phe Asn Ser Thr Phe Arg Ser Val Ser Glu Leu
305 310 315 320

Pro Ile Met His Gln Asp Trp Leu Asn Gly Lys Glu Phe Lys Cys Arg
325 330 335

Val Asn Ser Ala Ala Phe Pro Ala Pro Ile Glu Lys Thr Ile Ser Lys
340 345 350

Thr Lys Gly Arg Pro Lys Ala Pro Gln Val Tyr Thr Ile Pro Pro Pro
355 360 365

-continued

```
Lys Glu Gln Met Ala Lys Asp Lys Val Ser Leu Thr Cys Met Ile Thr
    370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Ile Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460


<210> SEQ ID NO 363
<211> LENGTH: 1386
<212> TYPE: DNA
<213> ORGANISM: Mus musculus

<400> SEQUENCE: 363

atgggatgga gctctatcat cctcttcttg gtagcaacag ctacaggtgt ccactcccag      60

gtccaactac agcagcctgg gactgagctg gtgaggcctg gaacttcagt gaagttgtcc     120

tgtaaggctt ctggctacat cttcaccacc tactggatga actgggtgaa acagaggcct     180

ggacaaggcc ttgagtggat tggcatgatt catccttccg caagtgaaat taggttggat     240

cagaaattca aggacaaggc cacattgact cttgacaaat cctccagcac agcctatatg     300

cacctcagcg gcccgacatc tgtggattct gcggtctatt actgtgcaag atcaggggaa     360

tgggggtcta tggactactg gggtcaagga acctcagtca ccgtctcctc agccaaaacg     420

acacccccat ctgtctatcc actggcccct ggatctgctg cccaaactaa ctccatggtg     480

accctgggat gcctggtcaa gggctatttc cctgagccag tgacagtgac ctggaactct     540

ggatccctgt ccagcggtgt gcacaccttc ccagctgtcc tgcagtctga cctctacact     600

ctgagcagct cagtgactgt cccctccagc acctggccca gcgagaccgt cacctgcaac     660

gttgcccacc cggccagcag caccaaggtg gacaagaaaa ttgtgcccag ggattgtggt     720

tgtaagcctt gcatatgtac agtcccagaa gtatcatctg tcttcatctt ccccccaaag     780

cccaaggatg tgctcaccat tactctgact cctaaggtca cgtgtgttgt ggtagacatc     840

agcaaggatg atcccgaggt ccagttcagc tggtttgtag atgatgtgga ggtgcacaca     900

gctcagacgc aaccccggga ggagcagttc aacagcactt tccgctcagt cagtgaactt     960

cccatcatgc accaggactg gctcaatggc aaggagttca aatgcagggt caacagtgca    1020

gctttccctg cccccatcga gaaaaccatc tccaaaacca aaggcagacc gaaggctcca    1080

caggtgtaca ccattccacc tcccaaggag cagatggcca aggataaagt cagtctgacc    1140

tgcatgataa cagacttctt ccctgaagac attactgtgg agtggcagtg gaatgggcag    1200

ccagcggaga actacaagaa cactcagccc atcatggaca cagatggctc ttacttcatc    1260

tacagcaagc tcaatgtgca gaagagcaac tgggaggcag gaaatacttt cacctgctct    1320

gtgttacatg agggcctgca caaccaccat actgagaaga gcctctccca ctctcctggt    1380

aaatga                                                               1386


<210> SEQ ID NO 364
<211> LENGTH: 106
<212> TYPE: PRT
<213> ORGANISM: Mus musculus
```

<400> SEQUENCE: 364

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Tyr
20 25 30

Leu Asn Trp Tyr Gln Gln Lys Pro Gly Lys Ala Pro Lys Leu Leu Ile
35 40 45

Tyr Ser Thr Ser Arg Leu Asn Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Asp Ile Lys His Pro Thr
85 90 95

Phe Gly Gln Gly Thr Lys Val Glu Ile Lys
100 105

<210> SEQ ID NO 365
<211> LENGTH: 318
<212> TYPE: DNA
<213> ORGANISM: Mus musculus

<400> SEQUENCE: 365
gacatccaga tgacccagtc tccatcctcc ctgtctgcat ctgtaggtga ccgtgtcacc 60
atcacttgcc gcgcaagtca ggatattagc agctatttaa attggtatca gcagaaacca 120
gggaaagccc ctaagctcct gatctattct acttcccgtt tgaatagtgg ggtcccatca 180
cgcttcagtg gcagtggctc tgggacagat ttcactctca ccatcagcag tctgcaacct 240
gaagattttg caacttacta ctgtcaacag gatattaaac accctacgtt cggtcaaggc 300
accaaggtgg agatcaaa 318

<210> SEQ ID NO 366
<211> LENGTH: 120
<212> TYPE: PRT
<213> ORGANISM: Mus musculus

<400> SEQUENCE: 366

Glu Val Gln Leu Val Gln Ser Gly Ala Glu Val Lys Lys Pro Gly Ser
1 5 10 15

Ser Val Lys Val Ser Cys Lys Ala Ser Gly Phe Thr Phe Thr Asp Tyr
20 25 30

Ile Met His Trp Val Arg Gln Ala Pro Gly Gln Gly Leu Glu Trp Met
35 40 45

Gly Tyr Ile Asn Pro Tyr Asn Asp Asp Thr Glu Tyr Asn Glu Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Ile Tyr Tyr Tyr Asp Ala Pro Phe Ala Tyr Trp Gly Gln
100 105 110

Gly Thr Leu Val Thr Val Ser Ser
115 120

<210> SEQ ID NO 367
<211> LENGTH: 360

<212> TYPE: DNA
<213> ORGANISM: Mus musculus

<400> SEQUENCE: 367
gaggtgcagc tggtgcagtc tggggctgag gtgaagaagc ctgggtcctc ggtgaaggtc 60
tcctgcaagg cttctggttt taccttcacc gactatatta tgcactgggt gcgtcaggcc 120
cctggtcaag ggcttgagtg gatgggctat atcaaccctt ataatgatga caccgaatac 180
aacgagaagt tcaagggccg tgtcacgatt accgcggaca aatccacgag cacagcctac 240
atggagctga gcagcctgcg ctctgaggac acggccgtgt attactgtgc gcgttcgatt 300
tattactacg atgccccgtt tgcttactgg ggccaaggga ctctggtcac cgtctctagt 360

<210> SEQ ID NO 368
<211> LENGTH: 108
<212> TYPE: PRT
<213> ORGANISM: Mus musculus

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105

<210> SEQ ID NO 369
<211> LENGTH: 324
<212> TYPE: DNA
<213> ORGANISM: Mus musculus

<400> SEQUENCE: 369
gatatccaga tgacccagag cccgagcagc ctgagcgcga gcgtgggcga tcgcgtgacc 60
attacctgca aagcgagcca ggatgtgttt accgcggtgg cgtggtatca gcagaaaccg 120
ggcaaagcgc cgaaactgct gatttattgg gcgagcaccc gccataccgg cgtgccgagt 180
cgctttagcg gcagcggcag cggcaccgat tttaccctga ccattagcag cctgcagccg 240
gaagattttg cgacctatta ttgccagcag tatagcagct atccgctgac ctttggcggc 300
ggcaccaaag tggaaattaa acgt 324

<210> SEQ ID NO 370
<211> LENGTH: 119
<212> TYPE: PRT
<213> ORGANISM: Mus musculus

<400> SEQUENCE: 370

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

```
Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115
```

<210> SEQ ID NO 371
<211> LENGTH: 357
<212> TYPE: DNA
<213> ORGANISM: Mus musculus

<400> SEQUENCE: 371

```
gaagtgcagc tggtgcagag cggcgcggaa gtgaaaaaac cgggcgcgag cgtgaaagtg      60

agctgcaaag cgagcggctt taacattaaa gattattata tgcattgggt gcgccaggcg     120

ccgggccagg gcctggaatg gatcggccgc attgatccgg aaaacggcga tattatttat     180

gatccgaaat ttcagggccg cgtgaccatg accaccgata ccagcaccag caccgcgtat     240

atggaactgc gcagcctgcg cagcgatgat accgcggtgt attattgcgc gtatgatgcg     300

ggcgatccgg cgtggtttac ctattggggc cagggcaccc tggtgaccgt ctcgagc        357
```

<210> SEQ ID NO 372
<211> LENGTH: 108
<212> TYPE: PRT
<213> ORGANISM: Mus musculus

<400> SEQUENCE: 372

```
Asp Ile Gln Leu Thr Gln Ser Pro Ser Phe Leu Ser Ala Ser Val Gly
1               5                   10                  15

Asp Arg Val Thr Ile Thr Cys Ser Val Ser Ser Ser Ile Ser Ser Ser
            20                  25                  30

Asn Leu His Trp Tyr Gln Gln Lys Pro Gly Lys Ala Pro Lys Leu Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Trp Thr Thr Thr Tyr
                85                  90                  95

Thr Phe Gly Gln Gly Thr Lys Leu Glu Ile Lys Arg
            100                 105
```

<210> SEQ ID NO 373
<211> LENGTH: 324
<212> TYPE: DNA
<213> ORGANISM: Mus musculus

<400> SEQUENCE: 373

```
gatattcagc tgacccagag cccgagcttt ctgagcgcga gcgtgggcga tcgcgtgacc      60

attacctgca gcgtgagcag cagcattagc agcagcaacc tgcattggta tcagcagaaa     120
```

```
ccgggcaaag cgccgaaact gctgatttat ggcaccagca acctggcgag cggcgtgccg    180

agccgcttta gcggcagcgg cagcggcacc gaatttaccc tgaccattag cagcctgcag    240

ccggaagatt ttgcgaccta ttattgccag cagtggacca ccacctatac ctttggccag    300

ggcaccaaac tggaaattaa acgt                                           324
```

<210> SEQ ID NO 374
<211> LENGTH: 122
<212> TYPE: PRT
<213> ORGANISM: Mus musculus

<400> SEQUENCE: 374

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Asp Asn Gly Glu Ser Thr Tyr Val Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Leu Asp Tyr Gly Asp Tyr Tyr Ala Val Asp Tyr Trp
            100                 105                 110

Gly Gln Gly Thr Leu Val Thr Val Ser Ser
        115                 120
```

<210> SEQ ID NO 375
<211> LENGTH: 366
<212> TYPE: DNA
<213> ORGANISM: Mus musculus

<400> SEQUENCE: 375

```
gaagtgcagc tggtgcagag cggcgcggaa gtgaaaaaac cgggcgcgag cgtgaaagtg     60

agctgcaaag cgagcggctt taacattaaa gattattata ttcattgggt gcgccaggcg    120

ccgggccagg gcctggaatg gatgggccgc attgatccgg ataacggcga aagcacctat    180

gtgccgaaat ttcagggccg cgtgaccatg accaccgata ccagcaccag caccgcgtat    240

atggaactgc gcagcctgcg cagcgatgat accgcggtgt attattgcgc gcgcgaaggc    300

ctggattatg gcgattatta tgcggtggat tattggggcc agggcaccct ggtgaccgtc    360

tcgagc                                                               366
```

<210> SEQ ID NO 376
<211> LENGTH: 107
<212> TYPE: PRT
<213> ORGANISM: Mus musculus

<400> SEQUENCE: 376

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105


<210> SEQ ID NO 377
<211> LENGTH: 321
<212> TYPE: DNA
<213> ORGANISM: Mus musculus

<400> SEQUENCE: 377

gacatccaga tgacccagtc tccatcctcc ctctccgcat ccgtaggcga ccgcgtaacc      60

ataacatgta gagcatctca agatatttcc aactatttga attggtacca acaaaaaccc     120

ggcaaagcac ctaaactcct catttactat acatcaagac tcctctccgg cgttccatca     180

cgattctcag gctccggctc cggcacagat ttcacactca ctatttcctc cctccaacca     240

gaagattttg caacctatta ctgtcaacaa ggcgatacac tcccatacac attcggcggc     300

ggcacaaaag ttgaaattaa a                                               321


<210> SEQ ID NO 378
<211> LENGTH: 123
<212> TYPE: PRT
<213> ORGANISM: Mus musculus

<400> SEQUENCE: 378

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120


<210> SEQ ID NO 379
<211> LENGTH: 369
<212> TYPE: DNA
<213> ORGANISM: Mus musculus

<400> SEQUENCE: 379

gaggtgcagc tggtgcagag cggcgccgag gtaaaaaaac caggagcaag cgttaaagtt      60

tcttgtaaag caagcggata tacatttaca gattacaaca tgcattgggt aagacaagcg     120

ccaggacaag gattggaatg gatgggcgaa attaacccta atagtggagg agcaggctac     180
```

aatcaaaaat tcaaagggag agttacaatg acaacagaca caagcacttc aacagcatat 240
atggaactgc gatcacttag aagcgacgat acagctgtat actattgcgc acgacttggg 300
tatgatgata tatatgatga ctggtatttc gatgtttggg gccagggaac aacagttacc 360
gtctctagt 369

<210> SEQ ID NO 380
<211> LENGTH: 108
<212> TYPE: PRT
<213> ORGANISM: Mus musculus

<400> SEQUENCE: 380

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys
            100                 105

<210> SEQ ID NO 381
<211> LENGTH: 324
<212> TYPE: DNA
<213> ORGANISM: Mus musculus

<400> SEQUENCE: 381
gacatccagc tgacccagag ccccagcttc ctttccgcat ccgttggtga ccgagtaaca 60
atcacatgcc gcgcctcatc ttcagttaca tcttcttatc ttaattggta tcaacaaaaa 120
ccaggaaaag cacctaaact tcttatatac tctacatcta atctcgcatc aggagttccc 180
tctcgatttt caggatctgg atcaggcaca gaatttacac ttactatatc atcactccaa 240
ccagaagact tcgccactta ttactgccaa caatacgatt tttttccaag cacattcgga 300
ggaggtacaa aagtagaaat caag 324

<210> SEQ ID NO 382
<211> LENGTH: 121
<212> TYPE: PRT
<213> ORGANISM: Mus musculus

<400> SEQUENCE: 382

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser
        115                 120


<210> SEQ ID NO 383
<211> LENGTH: 363
<212> TYPE: DNA
<213> ORGANISM: Mus musculus

<400> SEQUENCE: 383

gaggtgcagc tggtgcagag cggcgccgag gtcaagaaac ctggagcaag cgtaaaggtt      60

agttgcaaag catctggata cacatttacc gactactaca tgaattgggt acgacaagcc     120

cctggacaaa gacttgaatg gatgggagac attaaccctt ataacgacga cactacatac     180

aatcataaat ttaaaggaag agttacaatt acaagagata catccgcatc aaccgcctat     240

atggaacttt cctcattgag atctgaagac actgctgttt attactgtgc aagagaaact     300

gccgttatta ctactaacgc tatggattac tggggtcaag gaaccactgt taccgtctct     360

agt                                                                   363


<210> SEQ ID NO 384
<211> LENGTH: 108
<212> TYPE: PRT
<213> ORGANISM: Mus musculus

<400> SEQUENCE: 384

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys
            100                 105


<210> SEQ ID NO 385
<211> LENGTH: 324
<212> TYPE: DNA
<213> ORGANISM: Mus musculus

<400> SEQUENCE: 385

gacatccaga tgacccagtc tccatcctcc ctctcagcat ccgtaggcga tagagttaca      60

ataacatgca gcgtatcatc aactatatca tcaaatcatc ttcattggtt ccaacagaaa     120

cccggcaaag cacctaaatc acttatatac ggcacatcaa atctcgcatc aggcgttcct     180

tcaagatttt caggctctgg ctcaggcacc gactttactc ttacaatatc ctccctccaa     240

cccgaagact tcgcaaccta ttactgtcaa caatggtcct catatccact cacatttggc     300
```

ggcggcacaa aagtagaaat taaa 324

<210> SEQ ID NO 386
<211> LENGTH: 125
<212> TYPE: PRT
<213> ORGANISM: Mus musculus

<400> SEQUENCE: 386

Glu Val Gln Leu Val Gln Ser Gly Ala Glu Val Lys Lys Pro Gly Ala
1 5 10 15

Ser Val Lys Val Ser Cys Lys Ala Ser Asp Phe Asn Ile Lys Asp Phe
20 25 30

Tyr Leu His Trp Val Arg Gln Ala Pro Gly Gln Gly Leu Glu Trp Ile
35 40 45

Gly Arg Ile Asp Pro Glu Asn Gly Asp Thr Leu Tyr Asp Pro Lys Phe
50 55 60

Gln Asp Lys Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Glu Ala Asp Tyr Phe His Asp Gly Thr Ser Tyr Trp Tyr Phe
100 105 110

Asp Val Trp Gly Arg Gly Thr Leu Val Thr Val Ser Ser
115 120 125

<210> SEQ ID NO 387
<211> LENGTH: 375
<212> TYPE: DNA
<213> ORGANISM: Mus musculus

<400> SEQUENCE: 387
gaggtgcagc tggtgcagtc tggggctgag gtgaagaagc ctggggcctc agtgaaggtc 60
tcctgcaagg cttctgactt caacattaaa gacttctatc tacactgggt gcgacaggcc 120
cctggacaag ggcttgagtg gattggaagg attgatcctg agaatggtga tactttatat 180
gacccgaagt tccaggacaa ggtcaccatg accacagaca cgtccaccag cacagcctac 240
atggagctga ggagcctgag atctgacgac acggccgtgt attactgtgc gagagaggcg 300
gattatttcc acgatggtac ctcctactgg tacttcgatg tctggggccg tggcaccctg 360
gtcaccgtct ctagt 375

<210> SEQ ID NO 388
<211> LENGTH: 106
<212> TYPE: PRT
<213> ORGANISM: Mus musculus

<400> SEQUENCE: 388

Asp Ile Gln Leu Thr Gln Ser Pro Ser Phe Leu Ser Ala Ser Val Gly
1 5 10 15

Asp Arg Val Thr Ile Thr Cys Arg Ala Ser Ser Ser Ile Ser Tyr Ile
20 25 30

His Trp Tyr Gln Gln Lys Pro Gly Lys Ala Pro Lys Leu Leu Ile Tyr
35 40 45

Ala Thr Ser Asn Leu Ala Ser Gly Val Pro Ser Arg Phe Ser Gly Ser
50 55 60

Gly Ser Gly Thr Glu Phe Thr Leu Thr Ile Ser Ser Leu Gln Pro Glu
65 70 75 80

```
Asp Phe Ala Thr Tyr Tyr Cys Gln Gln Trp Ser Ser Asp Pro Leu Thr
                85                  90                  95

Phe Gly Gly Gly Thr Lys Val Glu Ile Lys
            100                 105


<210> SEQ ID NO 389
<211> LENGTH: 318
<212> TYPE: DNA
<213> ORGANISM: Mus musculus

<400> SEQUENCE: 389

gacatccagt tgacccagtc tccatccttc ctgtctgcat ctgtaggaga cagagtcacc     60

atcacttgca gggccagctc aagtataagt tacatacact ggtatcagca aaaaccaggg    120

aaagccccta agctcctgat ctatgccaca tccaacctgg cttctggggt cccatcaagg    180

ttcagcggca gtggatctgg gacagaattc actctcacaa tcagcagcct gcagcctgaa    240

gattttgcaa cttattactg tcagcagtgg agtagtgacc cactcacgtt cggcggaggg    300

accaaggtgg agatcaaa                                                  318


<210> SEQ ID NO 390
<211> LENGTH: 121
<212> TYPE: PRT
<213> ORGANISM: Mus musculus

<400> SEQUENCE: 390

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser
        115                 120


<210> SEQ ID NO 391
<211> LENGTH: 363
<212> TYPE: DNA
<213> ORGANISM: Mus musculus

<400> SEQUENCE: 391

gaggtgcagc tggtgcagtc tggggctgag gtgaagaagc ctggggcctc agtgaaggtc     60

tcctgcaagg cttctggatt cgacattaag gactactata tacactgggt gcgacaggcc    120

cctggacaag ggcttgagtg gatcggaagg gttgatcctg acaatggtga gactgaattt    180

gccccgaagt tcccgggcaa ggtcaccatg accacagaca cgtccatcag cacagcctac    240

atggagctga gcaggctgag atctgacgac acggccgtgt attactgtgc gagagaagac    300

tacgatggta cctacacctg gtttccttat tggggccaag ggactctggt caccgtctct    360

agt                                                                  363
```

<210> SEQ ID NO 392
<211> LENGTH: 448
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 392

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Met Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 393
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 393

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met Asn Trp Val Arg Gln Ala Pro Gly Gln Arg Leu Glu Trp Met
35 40 45

Gly Asp Ile Asn Pro Tyr Asn Asp Asp Thr Thr Tyr Asn His Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Glu Thr Ala Val Ile Thr Thr Asn Ala Met Asp Tyr Trp Gly
100 105 110

Gln Gly Thr Thr Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Cys Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 394
<211> LENGTH: 450
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 394

Glu Val Gln Leu Val Gln Ser Gly Ala Glu Val Lys Lys Pro Gly Ala
1 5 10 15

Ser Val Lys Val Ser Cys Lys Ala Ser Asp Phe Asn Ile Lys Asp Phe
20 25 30

Tyr Leu His Trp Val Arg Gln Ala Pro Gly Gln Gly Leu Glu Trp Ile
35 40 45

Gly Arg Ile Asp Pro Glu Asn Gly Asp Thr Leu Tyr Asp Pro Lys Phe
50 55 60

Gln Asp Lys Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Glu Ala Asp Tyr Phe His Asp Gly Thr Ser Tyr Trp Tyr Phe
100 105 110

Asp Val Trp Gly Arg Gly Thr Leu Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 395
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45
```

```
Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 396
<211> LENGTH: 445

-continued

<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 396

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

-continued

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```

METHODS FOR ISOLATING ANTIBODIES THAT BIND SCLEROSTIN

The present application is a divisional of U.S. patent application Ser. No. 14/691,344, filed Nov. 30, 2012, which is a divisional of U.S. patent application Ser. No. 12/950,094, filed Nov. 19, 2010 (now U.S. Pat. No. 8,383,801), which is a divisional of U.S. patent application Ser. No. 12/276,889 (now U.S. Pat. No. 7,872,106), filed Nov. 24, 2008, which is a divisional of U.S. patent application Ser. No. 11/411,003 (now U.S. Pat. No. 7,592,429), filed Apr. 25, 2006, which claims the benefit of priority from U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005, under 35 U.S.C. § 119. The foregoing patent applications are incorporated herein by reference in their entirety.

TECHNICAL FIELD

The present invention relates generally to epitopes of sclerostin protein, including human sclerostin protein, and binding agents (such as antibodies) capable of binding to sclerostin or fragments thereof.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "40000E_SeqListing.txt," 507,622 bytes, created Feb. 12, 2016.

BACKGROUND OF THE INVENTION

Two or three distinct phases of changes to bone mass occur over the life of an individual (see Riggs, West J. Med. 154:63-77 (1991)). The first phase occurs in both men and women and proceeds to attainment of a peak bone mass. This first phase is achieved through linear growth of the endochondral growth plates and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss and occurs in both men and women. In women, a third phase of bone loss also occurs, most likely due to postmenopausal estrogen deficiencies. During this phase alone, women may lose an additional bone mass from the cortical bone and from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long-term benefit and whether estrogen has any effect on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, *Mayo Clin. Proc.* 70:978982, 1995).

Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (see Khosla and Riggs, supra).

Sclerostin, the product of the SOST gene, is absent in sclerosteosis, a skeletal disease characterized by bone overgrowth and strong dense bones (Brunkow et al., Am. J. Hum. Genet., 68:577-589, 2001; Balemans et al., Hum. Mol. Genet., 10:537-543, 2001). The amino acid sequence of human sclerostin is reported by Brunkow et al. ibid and is disclosed herein as SEQ ID NO:1.

BRIEF SUMMARY OF THE INVENTION

Disclosed herein are compositions and methods that can be used to increase at least one of bone formation, bone mineral density, bone mineral content, bone mass, bone quality and bone strength, and that therefore may be used to treat a wide variety of conditions in which an increase in at least one of bone formation, bone mineral density, bone mineral content, bone mass, bone quality and bone strength is desirable. The present invention also offers other related advantages described herein.

The invention relates to regions (epitopes) of human sclerostin recognized by the binding agents disclosed herein, methods of using these epitopes, and methods of making such epitopes.

The invention also relates to epitopes specific to the region of sclerostin identified as Loop 2, and binding agents which specifically bind to that region.

The invention also relates to epitopes specific to the cystine-knot region of sclerostin, and binding agents such as antibodies specifically binding to that region.

The invention relates to binding agents, such as antibodies, that specifically bind to sclerostin. The binding agents can be characterized by their ability to cross-block the binding of at least one antibody disclosed herein to sclerostin and/or to be cross-blocked from binding sclerostin by at least one antibody disclosed herein. The antibodies and other binding agents can also be characterized by their binding pattern to human sclerostin peptides in a "human sclerostin peptide epitope competition binding assay" as disclosed herein.

The invention relates to binding agents, such as antibodies, that can increase at least one of bone formation, bone mineral density, bone mineral content, bone mass, bone quality and bone strength in a mammal.

The invention relates to binding agents, such as antibodies, that can block the inhibitory effect of sclerostin in a cell based mineralization assay.

The invention further relates to polypeptide constructs comprising two, three, or four polypeptide fragments linked by at least one disulfide bond, representing a core region of the cystine-knot of sclerostin, and antibodies capable of specifically binding thereto.

The invention relates to methods of obtaining epitopes suitable for use as immunogens for generating, in mammals, binding agents, such as antibodies capable of binding specifically to sclerostin; in certain embodiments the binding agents generated are capable of neutralizing sclerostin activity in vivo.

The invention relates to a composition for eliciting an antibody specific for sclerostin when the composition is administered to an animal, the composition comprising a polypeptide having the amino acid sequence of SEQ ID NO:6, SEQ ID NO:63, SEQ ID NO:64, SEQ ID NO:65, SEQ ID NO:66, SEQ ID NO:67, SEQ ID NO:68, or SEQ ID NO:69.

The invention also relates to a composition for eliciting an antibody specific for sclerostin when the composition is administered to an animal, the composition comprising at least one polypeptide consisting essentially of the amino acid sequence of SEQ ID NO:2, SEQ ID NO:3, SEQ ID NO:4 or SEQ ID NO:5; the composition may comprise at least two or at least three of the amino acid sequences of SEQ ID NO:2, SEQ ID NO:3, SEQ ID NO:4 and SEQ ID NO:5, and the composition may comprise all four of the amino acid sequences of SEQ ID NO:2, SEQ ID NO:3, SEQ ID NO:4 and SEQ ID NO:5.

The invention further relates to a composition for eliciting an antibody specific for sclerostin when the composition is administered to an animal, the composition comprising a polypeptide having the amino acid sequences of SEQ ID NO:2, SEQ ID NO:3, SEQ ID NO:4 and SEQ ID NO:5, wherein SEQ ID NO:2 and 4 are joined by a disulfide bond at amino acid positions 57 and 111 with reference to SEQ ID NO:1, and SEQ ID NO:3 and 5 are joined by at least one of (a) a disulfide bond at amino acid positions 82 and 142 with reference to SEQ ID NO:1, and (b) a disulfide bond at amino acid positions 86 and 144 with reference to SEQ ID NO:1; the polypeptide may retain the tertiary structure of the corresponding polypeptide region of human sclerostin of SEQ ID NO:1.

The invention also relates to polypeptide T20.6 consisting essentially of a multiply truncated human sclerostin protein of SEQ ID NO:1, wherein amino acids 1-50, 65-72, 91-100, 118-137, and 150-190 of SEQ ID NO:1 are absent from the polypeptide; this polypeptide may be obtained by tryptic digestion of human sclerostin, and the protein may be isolated by HPLC fractionation.

The invention further relates to immunogenic portion T20.6 of human sclerostin comprising amino acids 51-64, 73-90, 101-117, and 138-149 of SEQ ID NO:1, wherein the immunogenic portion comprises at least one of:

(a) a disulfide bond between amino acids 57 and 111;
(b) a disulfide bond between amino acids 82 and 142; and
(c) a disulfide bond between amino acids 86 and 144;

the immunogenic portion may have at least two of these disulfide bonds; and the immunogenic portion may have all three disulfide bonds.

The invention further relates to an immunogenic portion T20.6 derivative of human sclerostin comprising amino acids 57-64, 73-86, 111-117, and 138-144 of SEQ ID NO:1, wherein the immunogenic portion comprises at least one of:

(a) a disulfide bond between amino acids 57 and 111;
(b) a disulfide bond between amino acids 82 and 142; and
(c) a disulfide bond between amino acids 86 and 144;

the immunogenic portion may have at least two of these disulfide bonds; and the immunogenic portion may have all three disulfide bonds.

The invention yet further relates to a polypeptide consisting essentially of a human sclerostin protein of SEQ ID NO:1 truncated at the C-terminal and N-terminal ends, wherein amino acids 1-85 and 112-190 of SEQ ID NO:1 are absent from the polypeptide.

The invention also relates to an immunogenic portion of human sclerostin, comprising amino acids 86-111 of SEQ ID NO:1; the immunogenic portion may consist essentially of contiguous amino acids CGPARLLPNAIGRGKWWRPSGPDFRC (SEQ ID NO:6).

The invention further relates to an immunogenic portion of rat sclerostin, comprising amino acids 92-109 of SEQ ID NO:98; the immunogenic portion may consist essentially of contiguous amino acids PNAIGRVKWWRPNGPDFR (SEQ ID NO:96).

The invention still further relates to an immunogenic portion of rat sclerostin, comprising amino acids 99-120 of SEQ ID NO:98; the immunogenic portion may consist essentially of contiguous amino acids KWWRPNGPDFRCIPDRYRAQRV (SEQ ID NO:97).

The invention relates to a method of producing an immunogenic portion of human sclerostin, comprising the steps of:

(a) treating human sclerostin to achieve complete tryptic digestion;
(b) collecting the tryptic digest sample having average molecular weight of 7,122.0 Daltons (theoretical mass 7121.5 Daltons) or retention time of about 20.6 minutes as determined by elution from a reverse-phase HPLC column with linear gradient from 0.05% trifluoroacetic acid to 90% acetonitrile in 0.05% TFA at a flow rate of 0.2 ml/min; and
(c) purifying the immunogenic portion.

The invention relates to a method of generating an antibody capable of specifically binding to sclerostin, comprising:

(a) immunizing an animal with a composition comprising a polypeptide of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97;
(b) collecting sera from the animal; and
(c) isolating from the sera an antibody capable of specifically binding to sclerostin.

The invention also relates to a method of generating an antibody capable of specifically binding to sclerostin, the method comprising:

(a) immunizing an animal with a composition comprising polypeptide T20.6 or a derivative of T20.6;

(b) collecting sera from the animal; and (c) isolating from the sera an antibody capable of specifically binding to sclerostin.

The invention further relates to a method of detecting an anti-sclerostin antibody in a biological sample, comprising the steps of (a) contacting the biological sample with a polypeptide consisting essentially of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97 under conditions allowing a complex to form between the antibody and the polypeptide; and (b) detecting the presence or absence of the complex, wherein the presence of the complex indicates that the biological sample contains an anti-sclerostin antibody.

The invention also relates to a method of detecting an anti-sclerostin antibody in a biological sample, comprising the steps of (a) contacting the biological sample with polypeptide T20.6 or a derivative of T20.6 under conditions allowing a complex to form between the antibody and the polypeptide; and (b) detecting the presence or absence of the complex, wherein the presence of the complex indicates that the biological sample contains an anti-sclerostin antibody.

The invention further relates to a sclerostin binding agent, such as an antibody, that cross-blocks the binding of at least one of antibodies Ab-A, Ab-B, Ab-C, or Ab-D to a sclerostin protein. The sclerostin binding agent may also be cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an antibody, that is cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an isolated antibody, that cross-blocks the binding of at least one of antibodies 1-24 (Ab-1 to Ab-24) to a sclerostin protein. The sclerostin binding agent may also be cross-blocked from binding to sclerostin by at least one of antibodies 1-24 (Ab-1 to Ab-24). The isolated antibody, or an antigen-binding fragment thereof, may be a polyclonal antibody, a monoclonal antibody, a humanized antibody, a human antibody, or a chimeric antibody.

The invention further relates to a sclerostin binding agent, such as an isolated antibody, that is cross-blocked from binding to sclerostin by at least one of antibodies 1-24 (Ab-1 to Ab-24); the isolated antibody, or an antigen-binding fragment thereof, may be a polyclonal antibody, a monoclonal antibody, a humanized antibody, a human antibody, or a chimeric antibody.

The invention further relates to a binding agent, such as an isolated antibody that exhibits a similar binding pattern to human sclerostin peptides in a "human sclerostin peptide epitope competition binding assay" as that exhibited by at least one of the antibodies Ab-A, Ab-B, Ab-C or Ab-D; the isolated antibody, or an antigen-binding fragment thereof, may be a polyclonal antibody, a monoclonal antibody, a humanized antibody, a human antibody, or a chimeric antibody.

The invention still further relates to a method for treating a bone disorder associated with at least one of low bone formation, low bone mineral density, low bone mineral content, low bone mass, low bone quality and low bone strength in a mammalian subject which comprises providing to a subject in need of such treatment an amount of an anti-sclerostin binding agent sufficient to increase at least one of bone formation, bone mineral density, bone mineral content, bone mass, bone quality and bone strength wherein the anti-sclerostin binding agent comprises an antibody, or sclerostin-binding fragment thereof.

The invention also relates to an isolated sclerostin polypeptide or fragments thereof, wherein the polypeptide contains 6 conserved cysteine residues and the fragments thereof comprise from 7 to 14 amino acids of SEQ ID NO:2; 8 to 17 amino acids of SEQ ID NO:3; 8 to 18 residues of SEQ ID NO:4; and 6 to 12 residues of SEQ ID NO:5, and the polypeptide or fragments thereof are stabilized by disulfide bonds between SEQ ID NO:2 and 4, and between SEQ ID NO:3 and 5; the polypeptide or fragments may comprise 10-14 amino acids of SEQ ID NO:2; 14 to 17 amino acids of SEQ ID NO:3; 13 to 18 amino acids of SEQ ID NO:4; and 8 to 12 residues of SEQ ID NO:5; and the polypeptide or fragments may comprise SEQ ID NO:2, SEQ ID NO:3, SEQ ID NO:4, and SEQ ID NO:5.

Provided herein are antibodies that specifically bind to human sclerostin. The antibodies are characterized by their ability to cross-block the binding of at least one antibody disclosed herein to human sclerostin and/or to be cross-blocked from binding human sclerostin by at least one antibody disclosed herein.

Also provided is an isolated antibody, or an antigen-binding fragment thereof, that can increase at least one of bone formation, bone mineral density, bone mineral content, bone mass, bone quality and bone strength in a mammal.

Also provided in an isolated antibody, or an antigen-binding fragment thereof, that can block the inhibitory effect of sclerostin in a cell based mineralization assay.

Also provided is a binding agent, such as an antibody, that specifically binds to human sclerostin and has at least one CDR sequence selected from SEQ ID NOs: 39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof, wherein the antibody or antigen-binding fragment thereof neutralizes sclerostin.

Also provided is a binding agent, such as an antibody, that specifically binds to human sclerostin and has at least one CDR sequence selected from SEQ ID NOs:39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof.

Also provided are regions of human sclerostin which are important for the in vivo activity of the protein.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 1 depicts the amino acid sequences of the mature form (signal peptides cleaved off) of the light chain (FIG. 1A) (SEQ ID NO:23) and heavy chain (FIG. 1B) (SEQ ID NO:27) for the anti-human sclerostin and anti-mouse sclerostin antibody Ab-A.

FIG. 2 depicts the amino acid sequences of the mature form (signal peptides cleaved off) of the light chain (FIG. 2A) (SEQ ID NO:31) and heavy chain (FIG. 2B) (SEQ ID NO:35) for the anti-human sclerostin and anti-mouse sclerostin antibody Ab-B.

FIG. 3 depicts the amino acid sequences of the mature form (signal peptides cleaved off) of the light chain (FIG. 3A) (SEQ ID NO:15) and heavy chain (FIG. 3B) (SEQ ID NO:19) for the anti-human sclerostin and anti-mouse sclerostin antibody Ab-C.

FIG. 4 depicts the amino acid sequences of the mature form (signal peptides cleaved off) of the light chain (FIG. 4A) (SEQ ID NO:7) and heavy chain (FIG. 4B) (SEQ ID NO:11) for the anti-human sclerostin and anti-mouse sclerostin antibody Ab-D.

FIG. 8 depicts the amino acid sequence of the mature form (signal peptide cleaved off) of human sclerostin (SEQ ID NO:1). Also depicted is the nucleotide sequence of the human sclerostin coding region that encodes the mature form of human sclerostin. The eight cysteines are numbered C1 through C8. The cystine-knot is formed by three disulfide bonds (C1-05; C3-C7; C4-C8). C2 and C6 also form a disulfide bond, however this disulfide is not part of the cystine-knot.

FIG. 11 depicts sequence and mass information for the isolated human sclerostin disulfide linked peptides generated by trypsin digestion. Seq. pos.=sequence position. Obs.=observed. Observed mass was determined by ESI-LC-MS analysis.

FIG. 12 depicts sequence and mass information for the isolated human sclerostin peptides generated by AspN digestion. The AspN22.7-23.5 peptide contains the 4 disulfide bonds. Seq. pos.=sequence position. Obs.=observed. Observed mass was determined by ESI-LC-MS analysis.

FIG. 19A shows sequence of the Loop 2 epitope for binding of Ab-A and Ab-B to human sclerostin (SEQ ID NO:6). FIG. 19B shows sequence, disulfide bonding and schematic of the T20.6 epitope for binding of Ab-C and Ab-D to human sclerostin (SEQ ID NO:2-5).

FIG. 20A shows digestion of the human sclerostin Ab-D complex. FIG. 20B shows digestion of human sclerostin alone. The T19.2, T20, T20.6 and T21-22 peptide peaks are indicated.

FIG. 21 shows the sequence, disulfide bonding and schematic of the "T20.6 derivative 1 (cystine-knot+4 arms)" epitope for binding of Ab-D to human sclerostin. (SEQ ID NO:70-73).

DETAILED DESCRIPTION

Figure 5:
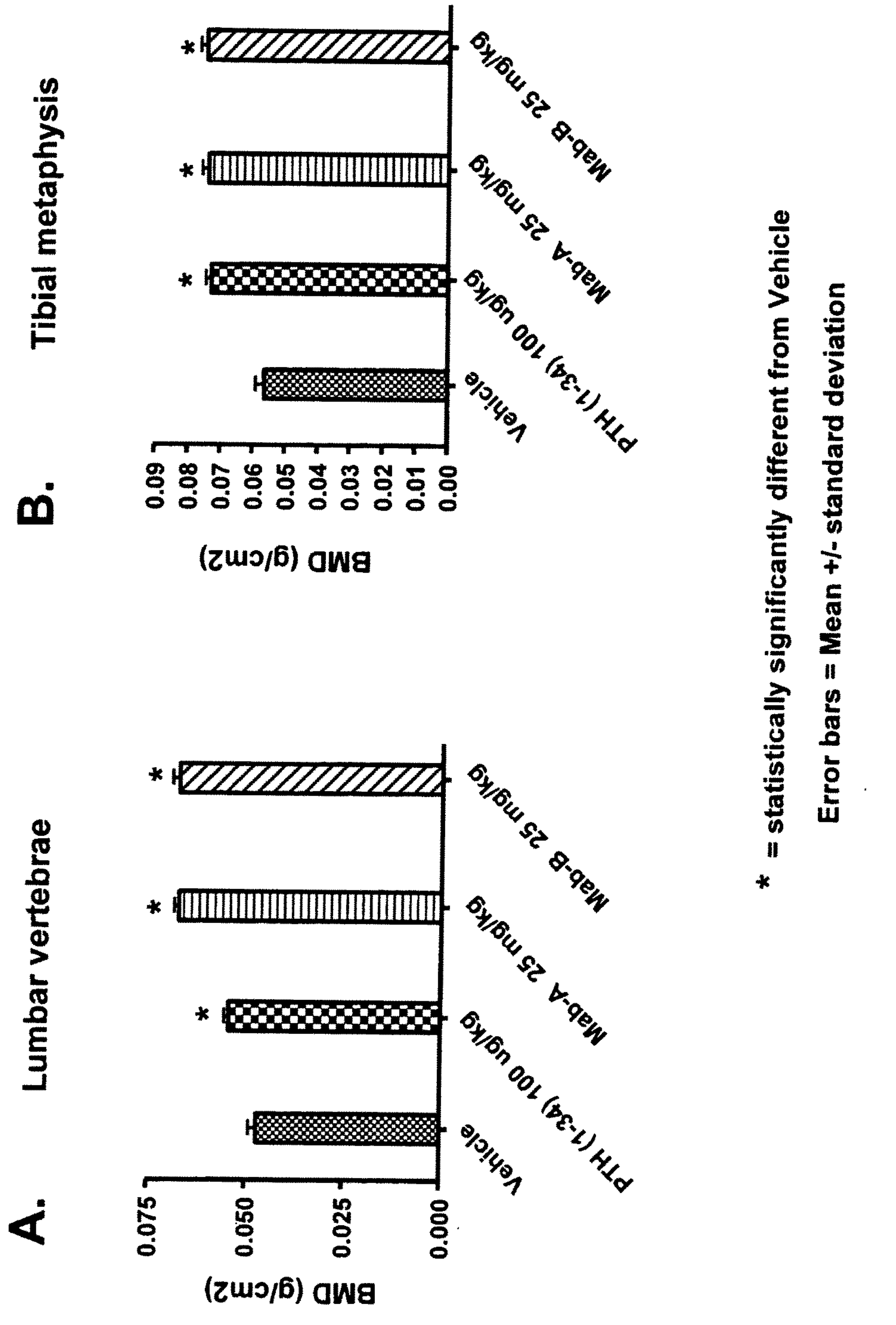
FIG. 5 depicts bone mineral density in mice measured at two skeletal sites (lumbar vertebrae and tibial metaphysis) after 3 weeks of treatment with vehicle, PTH (1-34), Ab-A or Ab-B.

The present invention relates to regions of the human sclerostin protein that contain epitopes recognized by antibodies that also bind to full-length sclerostin, and methods of making and using these epitopes. The invention also provides binding agents (such as antibodies) that specifically bind to sclerostin or portions of sclerostin, and methods for using such binding agents. The binding agents are useful to block or impair binding of human sclerostin to one or more ligand.

Recombinant human sclerostin/SOST is commercially available from R&D Systems (Minneapolis, Minn., USA; 2006 cat#1406-ST-025). Additionally, recombinant mouse sclerostin/SOST is commercially available from R&D Systems (Minneapolis, Minn., USA; 2006 cat#1589-ST-025). Research grade sclerostin binding monoclonal antibodies are commercially available from R&D Systems (Minneapolis, Minn., USA; mouse monoclonal: 2006 cat# MAB1406; rat monoclonal: 2006 cat# MAB1589). U.S. Pat. Nos. 6,395,511 and 6,803,453, and U.S. Patent Publications 20040009535 and 20050106683 refer to anti-sclerostin antibodies generally.

As used herein, the term human sclerostin is intended to include the protein of SEQ ID NO:1 and allelic variants thereof. Sclerostin can be purified from 293T host cells that have been transfected by a gene encoding sclerostin by elution of filtered supernatant of host cell culture fluid using a Heparin HP column, using a salt gradient. The preparation and further purification using cation exchange chromatography are described in Examples 1 and 2.

Binding agents of the invention are preferably antibodies, as defined herein. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003). pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human sclerostin, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding human sclerostin with an affinity at least equal to $1\times10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_v$). If desired, the chains may be covalently coupled either directly, for example via a disulfide bond between the two variable domains, or through a linker, for example a peptide linker, to form a single chain Fv ($scF_v$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, binding agents comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain preferred embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative, that do not destroy the sclerostin binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to sclerostin, or to increase or decrease the affinity of the antibodies to sclerostin described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See e.g., Nygren and Uhlen, 1997, Current Opinion in Structural Biology, 7, 463-469).

In preferred embodiments, it will be appreciated that the binding agents of the invention include the humanized antibodies described herein. Humanized antibodies such as those described herein can be produced using techniques known to those skilled in the art (Mang, W., et al., *Molecular Immunology.* 42(12):1445-1451, 2005; Hwang W. et al., *Methods.* 36(1):35-42, 2005; Dall'Acqua W F, et al., *Methods* 36(1):43-60, 2005; and Clark, M., Immunology Today. 21(8):397-402, 2000).

Additionally, one skilled in the art will recognize that suitable binding agents include portions of these antibodies, such as one or more of CDR-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to sclerostin and/or neutralizes sclerostin. The non-CDR portion of the binding agent may be a non-protein molecule in which the binding agent exhibits a similar binding pattern to human sclerostin peptides in a "human sclerostin peptide epitope competition binding assay" as that exhibited by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin. The non-CDR portion of the binding agent may be composed of amino acids, wherein the binding agent is a recombinant binding protein or a synthetic peptide, and the recombinant binding protein cross-blocks the binding of an antibody disclosed herein to sclerostin and/or neutralizes sclerostin. The non-CDR portion of the binding agent may be composed of amino acids, wherein the binding agent is a recombinant binding protein, and the recombinant binding protein exhibits a similar binding pattern to human sclerostin peptides in the human sclerostin peptide epitope competition binding assay (described hereinbelow) as that exhibited by at least one of the antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®. Each of the above-mentioned CDRs will be typically located in a variable region framework at positions 31-35 (CDR-H1), 50-65 (CDR-H2) and 95-102 (CDR-H3) of the heavy chain and positions 24-34 (CDR-L1), 50-56 (CDR-L2) and 89-97 (CDR-L3) of the light chain according to the Kabat numbering system (Kabat et al., 1987 in Sequences of Proteins of Immunological Interest, U.S. Department of Health and Human Services, NIH, USA).

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 Methods Enzymol. 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual,* 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J. Mol. Biol.,* 254, 392-403, 1995), chain shuffling (Marks et al., *Bio/Technology,* 10, 779-783, 1992), use of mutation strains of *E. coli.* (Low et al., *J. Mol. Biol.,* 250, 350-368, 1996), DNA shuffling (Patten et al., *Curr. Opin. Biotechnol.,* 8, 724-733, 1997), phage display (Thompson et al., *J. Mol. Biol.,* 256, 7-88, 1996) and sexual PCR (Crameri, et al., *Nature,* 391, 288-291, 1998). All of these methods of affinity maturation are discussed by Vaughan et al. (*Nature Biotechnology,* 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., *Nature* 256:495, 1975; Coligan et al. (eds.), *Current Protocols in Immunology,* 1:2.5.12.6.7 (John Wiley & Sons 1991); U.S. Patent Nos. RE 32,011, 4,902,614, 4,543,439, and 4,411,993*; Monoclonal Antibodies, Hybridomas: A New Dimension in Biological Analyses*, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al., "Production of monoclonal antibodies against proteins expressed in *E. coli*," in DNA Cloning 2: *Expression Systems, 2nd Edition*, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human sclerostin of SEQ ID NO:1, or a fragment thereof, according to methods known in the art and described herein. The presence of specific antibody production may be monitored after the initial injection and/or after a booster injection by obtaining a serum sample and detecting the presence of an antibody that binds to human sclerostin or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human sclerostin, using any one of a variety of immunoassays known in the art and described herein. The hybridomas are cloned (e.g., by limited dilution cloning or by soft agar plaque isolation) and positive clones that produce an antibody specific to sclerostin are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, and a TGF-beta binding protein, or fragment or variant thereof.

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N. Y. Acad. Sci.* 764:525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for sclerostin. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to sclerostin can be identified by immunodetection methods as provided herein, for example, an ELISA, and then isolated by standard cloning techniques. The stability of the lymphoblastoid cell line producing an anti-sclerostin antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with human sclerostin, followed by fusion of primed B cells with a heterohybrid fusion partner. See, e.g., Boerner et al., 1991 *J. Immunol.* 147:86-95.

In certain embodiments, a B cell that is producing an anti-human sclerostin antibody is selected and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. B cells from an immunized animal may be isolated from the spleen, lymph node, or peripheral blood sample by selecting a cell that is producing an antibody that specifically binds to sclerostin. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human sclerostin. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J. Molec. Biol.* 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZap™(L) vectors (Stratagene, La Jolla, Calif.). Briefly, mRNA is isolated from a B cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli.*

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents specifically bind to sclerostin. As with all binding agents and binding assays, one of skill in this art recognizes that the various moieties to which a binding agent should not detectably bind in order to be therapeutically effective and suitable would be exhaustive and impractical to list. Therefore, for a binding agent disclosed herein, the term "specifically binds" refers to the ability of a binding agent to bind to sclerostin, preferably human sclerostin, with greater affinity than it binds to an unrelated control protein. Preferably the control protein is hen egg white lysozyme. Preferably the binding agents bind to sclerostin with an affinity that is at least, 50, 100, 250, 500, 1000, or 10,000 times greater than the affinity for a control protein. A binding agent may have a binding affinity for human sclerostin of less than or equal to $1\times10^{-7}$M, less than or equal to $1\times10^{-8}$M, less than or equal to $1\times10^{-9}$M, less than or equal to $1\times10^{-1o}$ M, less than or equal to $1\times10^{-11}$M, or less than or equal to $1\times10^{-12}$M.

Affinity may be determined by an affinity ELISA assay. In certain embodiments, affinity may be determined by a BIAcore assay. In certain embodiments, affinity may be determined by a kinetic method. In certain embodiments, affinity may be determined by an equilibrium/solution method. Such methods are described in further detail herein or known in the art.

Sclerostin binding agents of the present invention preferably modulate sclerostin function in the cell-based assay described herein and/or the in vivo assay described herein and/or bind to one or more of the epitopes described herein and/or cross-block the binding of one of the antibodies described in this application and/or are cross-blocked from binding sclerostin by one of the antibodies described in this application. Accordingly such binding agents can be identified using the assays described herein.

In certain embodiments, binding agents are generated by first identifying antibodies that bind to one more of the epitopes provided herein and/or neutralize in the cell-based and/or in vivo assays described herein and/or cross-block the antibodies described in this application and/or are cross-blocked from binding sclerostin by one of the antibodies described in this application. The CDR regions from these antibodies are then used to insert into appropriate biocompatible frameworks to generate sclerostin binding agents. The non-CDR portion of the binding agent may be composed of amino acids, or may be a non-protein molecule. The assays described herein allow the characterization of binding agents. Preferably the binding agents of the present invention are antibodies as defined herein.

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

Antibodies referred to as Ab-A, Ab-B, Ab-C, Ab-D and Ab-1 are described below. "HC" refers to the heavy chain and "LC" refers to the light chain. For some antibodies below, the CDRs are underlined and the constant (C) regions are shown in bold italics.

Ab-D

Figure 18:
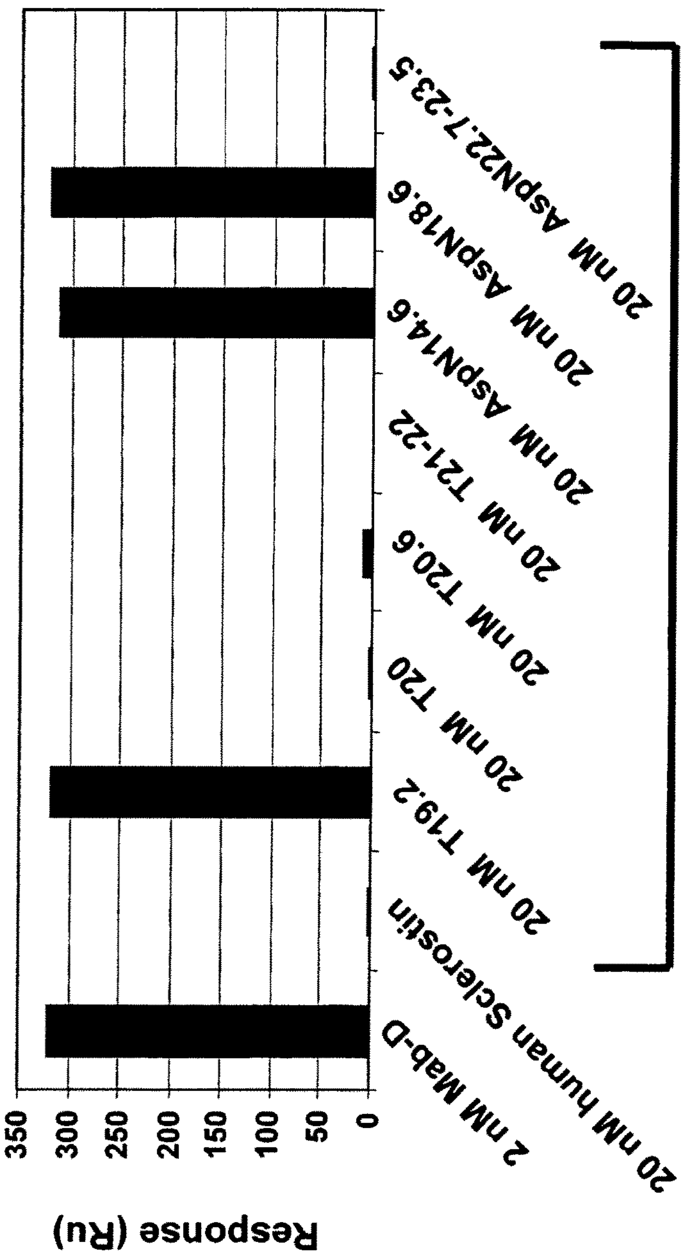
FIG. 18 shows the resonance unit (Ru) signal from Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-D. Human sclerostin peptides used were T19.2, T20, T20.6, T21-22, AspN14.6, AspN18.6 and AspN22.7-23.5.

Antibody D (also referred to herein as Ab-D and Mab-D) is a mouse antibody which exhibits high affinity binding to sclerostin. The BIAcore binding pattern of Ab-D is shown in FIG. 18.

The amino acid sequence of the mature form (signal peptide removed) of Ab-D light chain:

(SEQ ID NO: 7)

1 DVQMIQSPSS LSASLGDIVT MTCQASQGTS INLNWFQQKP GKAPKLLIYG

51 SSNLEDGVPS RFSGSRYGTD FTLTISSLED EDLATYFCLQHSYLPYTFGG

101 GTKLEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of Ab-D LC is as follows:

(SEQ ID NO: 8)

1 GATGTCCAGA TGATTCAGTC TCCATCCTCC CTGTCTGCAT CTTTGGGAGA

51 CATAGTCACC ATGACTTGCC AGGCAAGTCA GGGCACTAGC ATTAATTTAA

101 ACTGGTTTCA GCAAAAACCA GGGAAGGCTC CTAAGCTCCT GATCTATGGT

151 TCAAGCAACT TGGAAGATGG GGTCCCATCA AGGTTCAGTG GCAGTAGATA

201 TGGGACAGAT TTCACTCTCA CCATCAGCAG CCTGGAGGAT GAAGATCTGG

251 CAACTTATTT CTGTCTACAA CATAGTTATC TCCCGTACAC GTTCGGAGGG

301 GGGACCAAGC TGGAAATAAA ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG

The amino acid sequence of Ab-D LC including signal peptide is as follows:

(SEQ ID NO: 9)

1 MNTRAPAEFL GFLLLWFLGA RCDVQMIQSP SSLSASLGDI VTMTCQASQG

51 TSINLNWFQQ KPGKAPKLLI YGSSNLEDGV PSRFSGSRYG TDFTLTISSL

101 EDEDLATYFC LQHSYLPYTF GGGTKLEIKR ADAAPTVSIF PPSSEQLTSG

151 GASVVCFLNN FYPKDINVKW KIDGSERQNG VLNSWTDQDS KDSTYSMSST

201 LTLTKDEYER HNSYTCEATH KTSTSPIVKS FNRNEC

Nucleic acid sequence of Ab-D LC including signal peptide encoding sequence:

(SEQ ID NO: 10)

1 ATGAACACGA GGGCCCCTGC TGAGTTCCTT GGGTTCCTGT TGCTCTGGTT

51 TTTAGGTGCC AGATGTGATG TCCAGATGAT TCAGTCTCCA TCCTCCCTGT

101 CTGCATCTTT GGGAGACATA GTCACCATGA CTTGCCAGGC AAGTCAGGGC

151 ACTAGCATTA ATTTAAACTG GTTTCAGCAA AAACCAGGGA AGGCTCCTAA

201 GCTCCTGATC TATGGTTCAA GCAACTTGGA AGATGGGGTC CCATCAAGGT

251 TCAGTGGCAG TAGATATGGG ACAGATTTCA CTCTCACCAT CAGCAGCCTG

301 GAGGATGAAG ATCTGGCAAC TTATTTCTGT CTACAACATA GTTATCTCCC

351 GTACACGTTC GGAGGGGGGA CCAAGCTGGA AATAAAACGG GCTGATGCTG

401 CACCAACTGT ATCCATCTTC CCACCATCCA GTGAGCAGTT AACATCTGGA

451 GGTGCCTCAG TCGTGTGCTT CTTGAACAAC TTCTACCCCA AAGACATCAA

501 TGTCAAGTGG AAGATTGATG GCAGTGAACG ACAAAATGGC GTCCTGAACA

551 GTTGGACTGA TCAGGACAGC AAAGACAGCA CCTACAGCAT GAGCAGCACC

601 CTCACGTTGA CCAAGGACGA GTATGAACGA CATAACAGCT ATACCTGTGA

651 GGCCACTCAC AAGACATCAA CTTCACCCAT TGTCAAGAGC TTCAACAGGA

701 ATGAGTGTTA G

The amino acid sequence of the mature form (signal peptide removed) of Ab-D HC heavy chain is as follows:

(SEQ ID NO: 11)

1 EVQLQQSGPE LVTPGASVKI SCKASGYTFT DHYMSWVKQS HGKSLEWIGD

51 INPYSGETTY NQKFKGTATL TVDKSSSIAY MEIRGLTSED SAVYYCARDD

101 YDASPFAYWG QGTLVTVSA*A KTTPPSVYPL APGSAAQTNS MVTLGCLVKG*

*151 YFPEPVTVTW NSGSLSSGVH TFPAVLQSDL YTLSSSVTVP SSTWPSETVT*

*201 CNVAHPASST KVDKKIVPRD CGCKPCICTV PEVSSVFIFP PKPKDVLTIT*

*251 LTPKVTCVVV DISKDDPEVQ FSWFVDDVEV HTAQTQPREE QFNSTFRSVS*

*301 ELPIMHQDWL NGKEFKCRVN SPAFPAPIEK TISKTKGRPK APQVYTIPPP*

*351 KEQMAKDKVS LTCMITDFFP EDITVEWQWN GQPAENYKNT QPIMDTDGSY*

*401 FIYSKLNVQK SNWEAGNTFT CSVLHEGLHN HHTEKSLSHS PGK*

The nucleic acid sequence encoding the mature form (signal peptide removed) of Ab-D HC is:

(SEQ ID NO: 12)

1 GAGGTCCAGC TGCAACAGTC TGGACCTGAA CTGGTGACGC CTGGGGCTTC

51 AGTGAAGATA TCTTGTAAGG CTTCTGGATA CACATTCACT GACCACTACA

101 TGAGCTGGGT GAAGCAGAGT CATGGAAAAA GCCTTGAGTG GATTGGAGAT

151 ATTAATCCCT ATTCTGGTGA AACTACCTAC AACCAGAAGT TCAAGGGCAC

201 GGCCACATTG ACTGTAGACA AGTCTTCCAG TATAGCCTAC ATGGAGATCC

251 GCGGCCTGAC ATCTGAGGAC TCTGCAGTCT ATTACTGTGC AAGAGATGAT

301 TACGACGCCT CTCCGTTTGC TTACTGGGGC CAAGGGACTC TGGTCACTGT

351 CTCTGCAGCC AAAACGACAC CCCCATCTGT CTATCCACTG GCCCCTGGAT

-continued

401 CTGCTGCCCA AACTAACTCC ATGGTGACCC TGGGATGCCT GGTCAAGGGC

451 TATTTCCCTG AGCCAGTGAC AGTGACCTGG AACTCTGGAT CCCTGTCCAG

501 CGGTGTGCAC ACCTTCCCAG CTGTCCTGCA GTCTGACCTC TACACTCTGA

551 GCAGCTCAGT GACTGTCCCC TCCAGCACCT GGCCCAGCGA GACCGTCACC

601 TGCAACGTTG CCCACCCGGC CAGCAGCACC AAGGTGGACA AGAAAATTGT

651 GCCCAGGGAT TGTGGTTGTA AGCCTTGCAT ATGTACAGTC CCAGAAGTAT

701 CATCTGTCTT CATCTTCCCC CCAAAGCCCA AGGATGTGCT CACCATTACT

751 CTGACTCCTA AGGTCACGTG TGTTGTGGTA GACATCAGCA AGGATGATCC

801 CGAGGTCCAG TTCAGCTGGT TTGTAGATGA TGTGGAGGTG CACACAGCTC

851 AGACGCAACC CCGGGAGGAG CAGTTCAACA GCACTTTCCG CTCAGTCAGT

901 GAACTTCCCA TCATGCACCA GGACTGGCTC AATGGCAAGG AGTTCAAATG

951 CAGGGTCAAC AGTCCAGCTT TCCCTGCCCC CATCGAGAAA ACCATCTCCA

1001 AAACCAAAGG CAGACCGAAG GCTCCACAGG TGTACACCAT TCCACCTCCC

1051 AAGGAGCAGA TGGCCAAGGA TAAAGTCAGT CTGACCTGCA TGATAACAGA

1101 CTTCTTCCCT GAAGACATTA CTGTGGAGTG GCAGTGGAAT GGGCAGCCAG

1151 CGGAGAACTA CAAGAACACT CAGCCCATCA TGGACACAGA TGGCTCTTAC

1201 TTCATCTACA GCAAGCTCAA TGTGCAGAAG AGCAACTGGG AGGCAGGAAA

1251 TACTTTCACC TGCTCTGTGT TACATGAGGG CCTGCACAAC CACCATACTG

1301 AGAAGAGCCT CTCCCACTCT CCTGGTAAAT GA

The amino acid sequence of Ab-D HC including signal peptide is:

(SEQ ID NO: 13)

1 MRCRWIFLFL LSGTAGVLSE VQLQQSGPEL VTPGASVKIS CKASGYTFTD

51 HYMSWVKQSH GKSLEWIGDI NPYSGETTYN QKFKGTATLT VDKSSSIAYM

101 EIRGLTSEDS AVYYCARDDY DASPFAYWGQ GTLVTVSAAK TTPPSVYPLA

151 PGSAAQTNSM VTLGCLVKGY FPEPVTVTWN SGSLSSGVHT FPAVLQSDLY

201 TLSSSVTVPS STWPSETVTC NVAHPASSTK VDKKIVPRDC GCKPCICTVP

251 EVSSVFIFPP KPKDVLTITL TPKVTCVVVD ISKDDPEVQF SWFVDDVEVH

301 TAQTQPREEQ FNSTFRSVSE LPIMHQDWLN GKEFKCRVNS PAFPAPIEKT

351 ISKTKGRPKA PQVYTIPPPK EQMAKDKVSL TCMITDFFPE DITVEWQWNG

401 QPAENYKNTQ PIMDTDGSYF IYSKLNVQKS NWEAGNTFTC SVLHEGLHNH

451 HTEKSLSHSP GK

The nucleic acid sequence of Ab-D HC including signal peptide encoding sequence is:

(SEQ ID NO: 14)

1 ATGAGATGCA GGTGGATCTT TCTCTTTCTC CTGTCAGGAA CTGCAGGTGT

51 CCTCTCTGAG GTCCAGCTGC AACAGTCTGG ACCTGAACTG GTGACGCCTG

101 GGGCTTCAGT GAAGATATCT TGTAAGGCTT CTGGATACAC ATTCACTGAC

151 CACTACATGA GCTGGGTGAA GCAGAGTCAT GGAAAAAGCC TTGAGTGGAT

201 TGGAGATATT AATCCCTATT CTGGTGAAAC TACCTACAAC CAGAAGTTCA

-continued

```
251 AGGGCACGGC CACATTGACT GTAGACAAGT CTTCCAGTAT AGCCTACATG
301 GAGATCCGCG GCCTGACATC TGAGGACTCT GCAGTCTATT ACTGTGCAAG
351 AGATGATTAC GACGCCTCTC CGTTTGCTTA CTGGGGCCAA GGGACTCTGG
401 TCACTGTCTC TGCAGCCAAA ACGACACCCC CATCTGTCTA TCCACTGGCC
451 CCTGGATCTG CTGCCCAAAC TAACTCCATG GTGACCCTGG GATGCCTGGT
501 CAAGGGCTAT TTCCCTGAGC CAGTGACAGT GACCTGGAAC TCTGGATCCC
551 TGTCCAGCGG TGTGCACACC TTCCCAGCTG TCCTGCAGTC TGACCTCTAC
601 ACTCTGAGCA GCTCAGTGAC TGTCCCCTCC AGCACCTGGC CCAGCGAGAC
651 CGTCACCTGC AACGTTGCCC ACCCGGCCAG CAGCACCAAG GTGGACAAGA
701 AAATTGTGCC CAGGGATTGT GGTTGTAAGC CTTGCATATG TACAGTCCCA
751 GAAGTATCAT CTGTCTTCAT CTTCCCCCCA AAGCCCAAGG ATGTGCTCAC
801 CATTACTCTG ACTCCTAAGG TCACGTGTGT TGTGGTAGAC ATCAGCAAGG
851 ATGATCCCGA GGTCCAGTTC AGCTGGTTTG TAGATGATGT GGAGGTGCAC
901 ACAGCTCAGA CGCAACCCCG GGAGGAGCAG TTCAACAGCA CTTTCCGCTC
951 AGTCAGTGAA CTTCCCATCA TGCACCAGGA CTGGCTCAAT GGCAAGGAGT
1001 TCAAATGCAG GGTCAACAGT CCAGCTTTCC CTGCCCCCAT CGAGAAAACC
1051 ATCTCCAAAA CCAAAGGCAG ACCGAAGGCT CCACAGGTGT ACACCATTCC
1101 ACCTCCCAAG GAGCAGATGG CCAAGGATAA AGTCAGTCTG ACCTGCATGA
1151 TAACAGACTT CTTCCCTGAA GACATTACTG TGGAGTGGCA GTGGAATGGG
1201 CAGCCAGCGG AGAACTACAA GAACACTCAG CCCATCATGG ACACAGATGG
1251 CTCTTACTTC ATCTACAGCA AGCTCAATGT GCAGAAGAGC AACTGGGAGG
1301 CAGGAAATAC TTTCACCTGC TCTGTGTTAC ATGAGGGCCT GCACAACCAC
1351 CATACTGAGA AGAGCCTCTC CCACTCTCCT GGTAAATGA
```

The CDR (complementarity determining region) sequences in the variable region of the heavy chain of Ab-D are as follows:

CDR-H1: DHYMS (SEQ ID NO: 39)

CDR-H2: DINPYSGETTYNQKFKG (SEQ ID NO: 40)

CDR-H3: DDYDASPFAY (SEQ ID NO: 41)

The light chain variable region CDR sequences of Ab-D are:

CDR-L1: QASQGTSINLN (SEQ ID NO: 42)

CDR-L2: GSSNLED (SEQ ID NO: 43)

CDR-L3: LQHSYLPYT (SEQ ID NO: 44)

Ab-C

Figure 17:
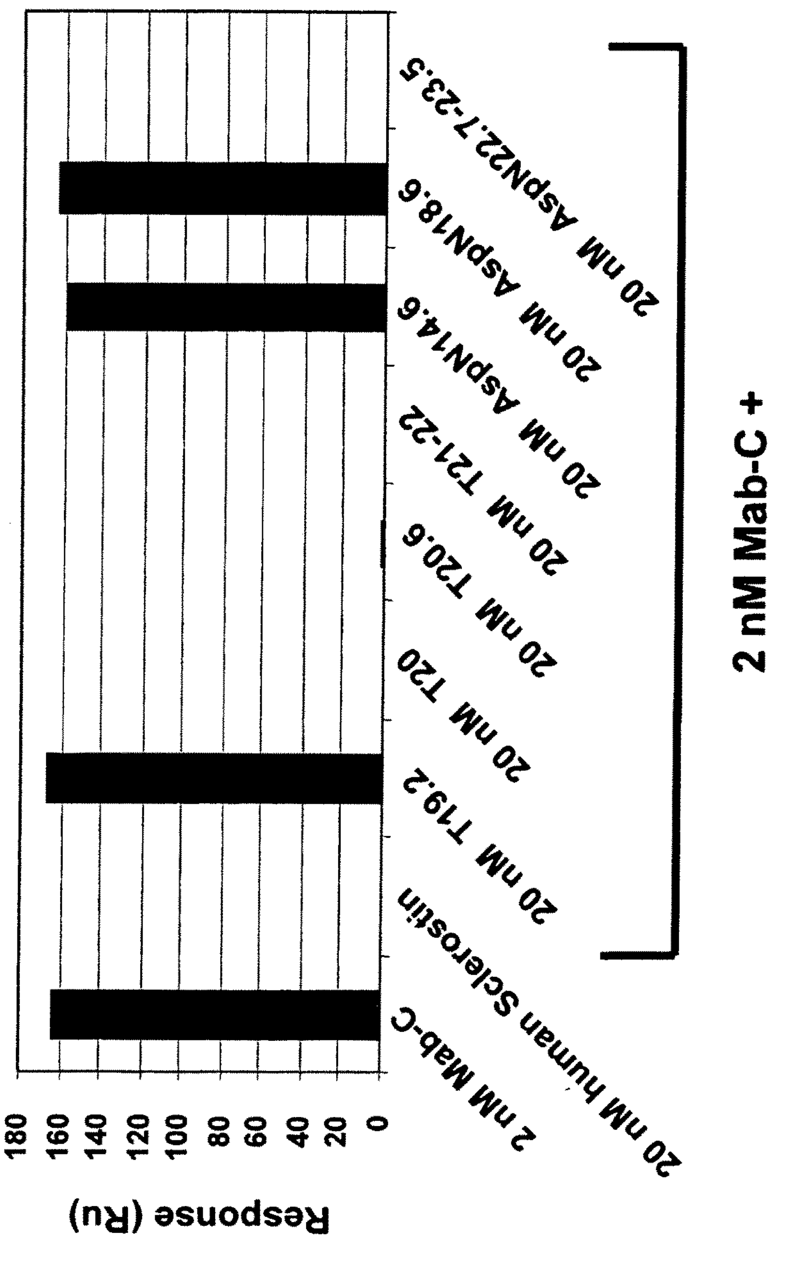
FIG. 17 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-C. Human sclerostin peptides used were T19.2, T20, T20.6, T21-22, AspN14.6, AspN18.6 and AspN22.7-23.5.

Antibody C (also referred to herein as Ab-C and Mab-C) is a mouse antibody which exhibits high affinity binding to sclerostin. The BIAcore binding pattern of Ab-C is shown in FIG. 17. The amino acid sequence of the mature form (signal peptide removed) of Ab-C Light Chain is as follows:

(SEQ ID NO: 15)

```
1 DIVLTQSPAS LTVSLGLRAT ISCKASQSVD YDGDSYMNWY QQKPGQPPKL
51 LIYAASNLES GIPARFSGNG SGTDFTLNIH PVEEEDAVTY YCQQSNEDPW
101 TFGGGTKLEI KRADAAPTVS IFPPSSEQLT SGGASVVCFL NNFYPKDINV
151 KWKIDGSERQ NGVLNSWTDQ DSKDSTYSMS STLTLTKDEY ERHNSYTCEA
201 THKTSTSPIV KSFNRNEC
```

The nucleic acid sequence encoding the mature form (signal peptide removed) of Ab-C LC is:

```
                                         (SEQ ID NO: 16)
  1 GACATTGTGC TGACCCAATC TCCAGCTTCT TTGACTGTGT CTCTAGGCCT

 51 GAGGGCCACC ATCTCCTGCA AGGCCAGCCA AAGTGTTGAT TATGATGGTG

101 ATAGTTATAT GAACTGGTAC CAGCAGAAAC CAGGACAGCC ACCCAAACTC

151 CTCATCTATG CTGCATCCAA TCTAGAATCT GGGATCCCAG CCAGGTTTAG

201 TGGCAATGGG TCTGGGACAG ACTTCACCCT CAACATCCAT CCTGTGGAGG

251 AGGAGGATGC TGTAACCTAT TACTGTCAAC AAAGTAATGA GGATCCGTGG

301 ACGTTCGGTG GAGGCACCAA GCTGGAAATC AAACGGGCTG ATGCTGCACC

351 AACTGTATCC ATCTTCCCAC CATCCAGTGA GCAGTTAACA TCTGGAGGTG

401 CCTCAGTCGT GTGCTTCTTG AACAACTTCT ACCCCAAAGA CATCAATGTC

451 AAGTGGAAGA TTGATGGCAG TGAACGACAA AATGGCGTCC TGAACAGTTG

501 GACTGATCAG GACAGCAAAG ACAGCACCTA CAGCATGAGC AGCACCCTCA

551 CGTTGACCAA GGACGAGTAT GAACGACATA ACAGCTATAC CTGTGAGGCC

601 ACTCACAAGA CATCAACTTC ACCCATTGTC AAGAGCTTCA ACAGGAATGA

651 GTGTTAG
```

The amino acid sequence of Ab-C LC including signal peptide is:

```
                                         (SEQ ID NO: 17)
  1 METDTILLWV LLLWVPGSTG DIVLTQSPAS LTVSLGLRAT ISCKASQSVD

 51 YDGDSYMNWY QQKPGQPPKL LIYAASNLES GIPARFSGNG SGTDFTLNIH

101 PVEEEDAVTY YCQQSNEDPW TFGGGTKLEI KRADAAPTVS IFPPSSEQLT

151 SGGASVVCFL NNFYPKDINV KWKIDGSERQ NGVLNSWTDQ DSKDSTYSMS

201 STLTLTKDEY ERHNSYTCEA THKTSTSPIV KSFNRNEC
```

The nucleic acid sequence of Ab-C LC including signal peptide encoding sequence is:

```
                                         (SEQ ID NO: 18)
  1 ATGGAGACAG ACACAATCCT GCTATGGGTG CTGCTGCTCT GGGTTCCAGG

 51 CTCCACTGGT GACATTGTGC TGACCCAATC TCCAGCTTCT TTGACTGTGT

101 CTCTAGGCCT GAGGGCCACC ATCTCCTGCA AGGCCAGCCA AAGTGTTGAT

151 TATGATGGTG ATAGTTATAT GAACTGGTAC CAGCAGAAAC CAGGACAGCC

201 ACCCAAACTC CTCATCTATG CTGCATCCAA TCTAGAATCT GGGATCCCAG

251 CCAGGTTTAG TGGCAATGGG TCTGGGACAG ACTTCACCCT CAACATCCAT

301 CCTGTGGAGG AGGAGGATGC TGTAACCTAT TACTGTCAAC AAAGTAATGA

351 GGATCCGTGG ACGTTCGGTG GAGGCACCAA GCTGGAAATC AAACGGGCTG

401 ATGCTGCACC AACTGTATCC ATCTTCCCAC CATCCAGTGA GCAGTTAACA

451 TCTGGAGGTG CCTCAGTCGT GTGCTTCTTG AACAACTTCT ACCCCAAAGA

501 CATCAATGTC AAGTGGAAGA TTGATGGCAG TGAACGACAA AATGGCGTCC

551 TGAACAGTTG GACTGATCAG GACAGCAAAG ACAGCACCTA CAGCATGAGC

601 AGCACCCTCA CGTTGACCAA GGACGAGTAT GAACGACATA ACAGCTATAC
```

-continued

```
651 CTGTGAGGCC ACTCACAAGA CATCAACTTC ACCCATTGTC AAGAGCTTCA

701 ACAGGAATGA GTGTTAG
```

Ab-C Heavy Chain

The amino acid sequence of the mature form (signal peptide removed) of Ab-C HC is:

```
                                               (SEQ ID NO: 19)
  1 EVQLQQSGPE LVKPGTSVKM SCKASGYTFT DCYMNWVKQS HGKSLEWIGD

 51 INPFNGGTTY NQKFKGKATL TVDKSSSTAY MQLNSLTSDD SAVYYCARSH

101 YYFDGRVPWD AMDYWGQGTS VTVSSAKTTP PSVYPLAPGS AAQTNSMVTL

151 GCLVKGYFPE PVTVTWNSGS LSSGVHTFPA VLQSDLYTLS SSVTVPSSTW

201 PSETVTCNVA HPASSTKVDK KIVPRDCGCK PCICTVPEVS SVFIFPPKPK

251 DVLTITLTPK VTCVVVDISK DDPEVQFSWF VDDVEVHTAQ TQPREEQFNS

301 TFRSVSELPI MHQDWLNGKE FKCRVNSAAF PAPIEKTISK TKGRPKAPQV

351 YTIPPPKEQM AKDKVSLTCM ITDFFPEDIT VEWQWNGQPA ENYKNTQPIM

401 DTDGSYFIYS KLNVQKSNWE AGNTFTCSVL HEGLHNHHTE KSLSHSPGK
```

The nucleic acid sequence encoding the mature form (signal peptide removed) of Ab-C HC is as follows:

```
                                                 (SEQ ID NO: 20)
   1 GAGGTCCAGC TGCAACAATC TGGACCTGAG CTGGTGAAGC CTGGGACTTC

  51 AGTGAAGATG TCCTGTAAGG CTTCTGGATA CACATTCACT GACTGCTACA

 101 TGAACTGGGT GAAGCAGAGC CATGGGAAGA GCCTTGAATG GATTGGAGAT

 151 ATTAATCCTT TCAACGGTGG TACTACCTAC AACCAGAAGT TCAAGGGCAA

 201 GGCCACATTG ACTGTAGACA AATCCTCCAG CACAGCCTAC ATGCAGCTCA

 251 ACAGCCTGAC ATCTGACGAC TCTGCAGTCT ATTACTGTGC AAGATCCCAT

 301 TATTACTTCG ATGGTAGAGT CCCTTGGGAT GCTATGGACT ACTGGGGTCA

 351 AGGAACCTCA GTCACCGTCT CCTCAGCCAA AACGACACCC CCATCTGTCT

 401 ATCCACTGGC CCCTGGATCT GCTGCCCAAA CTAACTCCAT GGTGACCCTG

 451 GGATGCCTGG TCAAGGGCTA TTTCCCTGAG CCAGTGACAG TGACCTGGAA

 501 CTCTGGATCC CTGTCCAGCG GTGTGCACAC CTTCCCAGCT GTCCTGCAGT

 551 CTGACCTCTA CACTCTGAGC AGCTCAGTGA CTGTCCCCTC CAGCACCTGG

 601 CCCAGCGAGA CCGTCACCTG CAACGTTGCC CACCCGGCCA GCAGCACCAA

 651 GGTGGACAAG AAAATTGTGC CCAGGGATTG TGGTTGTAAG CCTTGCATAT

 701 GTACAGTCCC AGAAGTATCA TCTGTCTTCA TCTTCCCCCC AAAGCCCAAG

 751 GATGTGCTCA CCATTACTCT GACTCCTAAG GTCACGTGTG TTGTGGTAGA

 801 CATCAGCAAG GATGATCCCG AGGTCCAGTT CAGCTGGTTT GTAGATGATG

 851 TGGAGGTGCA CACAGCTCAG ACGCAACCCC GGGAGGAGCA GTTCAACAGC

 901 ACTTTCCGCT CAGTCAGTGA ACTTCCCATC ATGCACCAGG ACTGGCTCAA

 951 TGGCAAGGAG TTCAAATGCA GGGTCAACAG TGCAGCTTTC CCTGCCCCCA

1001 TCGAGAAAAC CATCTCCAAA ACCAAAGGCA GACCGAAGGC TCCACAGGTG

1051 TACACCATTC CACCTCCCAA GGAGCAGATG GCCAAGGATA AAGTCAGTCT

1101 GACCTGCATG ATAACAGACT TCTTCCCTGA AGACATTACT GTGGAGTGGC
```

-continued

```
1151 AGTGGAATGG GCAGCCAGCG GAGAACTACA AGAACACTCA GCCCATCATG

1201 GACACAGATG GCTCTTACTT CATCTACAGC AAGCTCAATG TGCAGAAGAG

1251 CAACTGGGAG GCAGGAAATA CTTTCACCTG CTCTGTGTTA CATGAGGGCC

1301 TGCACAACCA CCATACTGAG AAGAGCCTCT CCCACTCTCC TGGTAAATGA
```

The amino acid sequence of Ab-C HC including signal peptide is:

```
                                              (SEQ ID NO: 21)
  1 MGWNWIFLFL LSGTAGVYSE VQLQQSGPEL VKPGTSVKMS CKASGYTFTD

 51 CYMNWVKQSH GKSLEWIGDI NPFNGGTTYN QKFKGKATLT VDKSSSTAYM

101 QLNSLTSDDS AVYYCARSHY YFDGRVPWDA MDYWGQGTSV TVSSAKTTPP

151 SVYPLAPGSA AQTNSMVTLG CLVKGYFPEP VTVTWNSGSL SSGVHTFPAV

201 LQSDLYTLSS SVTVPSSTWP SETVTCNVAH PASSTKVDKK IVPRDCGCKP

251 CICTVPEVSS VFIFPPKPKD VLTITLTPKV TCVVVDISKD DPEVQFSWFV

301 DDVEVHTAQT QPREEQFNST FRSVSELPIM HQDWLNGKEF KCRVNSAAFP

351 APIEKTISKT KGRPKAPQVY TIPPPKEQMA KDKVSLTCMI TDFFPEDITV

401 EWQWNGQPAE NYKNTQPIMD TDGSYFIYSK LNVQKSNWEA GNTFTCSVLH

451 EGLHNHHTEK SLSHSPGK
```

The nucleic acid sequence of Ab-C HC including signal peptide encoding sequence is:

```
                                              (SEQ ID NO: 22)
   1 ATGGGATGGA ACTGGATCTT TCTCTTCCTC TTGTCAGGAA CTGCAGGTGT

  51 CTACTCTGAG GTCCAGCTGC AACAATCTGG ACCTGAGCTG GTGAAGCCTG

 101 GGACTTCAGT GAAGATGTCC TGTAAGGCTT CTGGATACAC ATTCACTGAC

 151 TGCTACATGA ACTGGGTGAA GCAGAGCCAT GGGAAGAGCC TTGAATGGAT

 201 TGGAGATATT AATCCTTTCA ACGGTGGTAC TACCTACAAC CAGAAGTTCA

 251 AGGGCAAGGC CACATTGACT GTAGACAAAT CCTCCAGCAC AGCCTACATG

 301 CAGCTCAACA GCCTGACATC TGACGACTCT GCAGTCTATT ACTGTGCAAG

 351 ATCCCATTAT TACTTCGATG GTAGAGTCCC TTGGGATGCT ATGGACTACT

 401 GGGGTCAAGG AACCTCAGTC ACCGTCTCCT CAGCCAAAAC GACACCCCCA

 451 TCTGTCTATC CACTGGCCCC TGGATCTGCT GCCCAAACTA ACTCCATGGT

 501 GACCCTGGGA TGCCTGGTCA AGGGCTATTT CCCTGAGCCA GTGACAGTGA

 551 CCTGGAACTC TGGATCCCTG TCCAGCGGTG TGCACACCTT CCCAGCTGTC

 601 CTGCAGTCTG ACCTCTACAC TCTGAGCAGC TCAGTGACTG TCCCCTCCAG

 651 CACCTGGCCC AGCGAGACCG TCACCTGCAA CGTTGCCCAC CCGGCCAGCA

 701 GCACCAAGGT GGACAAGAAA ATTGTGCCCA GGGATTGTGG TTGTAAGCCT

 751 TGCATATGTA CAGTCCCAGA AGTATCATCT GTCTTCATCT TCCCCCCAAA

 801 GCCCAAGGAT GTGCTCACCA TTACTCTGAC TCCTAAGGTC ACGTGTGTTG

 851 TGGTAGACAT CAGCAAGGAT GATCCCGAGG TCCAGTTCAG CTGGTTTGTA

 901 GATGATGTGG AGGTGCACAC AGCTCAGACG CAACCCCGGG AGGAGCAGTT

 951 CAACAGCACT TTCCGCTCAG TCAGTGAACT TCCCATCATG CACCAGGACT
```

-continued

```
1001 GGCTCAATGG CAAGGAGTTC AAATGCAGGG TCAACAGTGC AGCTTTCCCT
1051 GCCCCCATCG AGAAAACCAT CTCCAAAACC AAAGGCAGAC CGAAGGCTCC
1101 ACAGGTGTAC ACCATTCCAC CTCCCAAGGA GCAGATGGCC AAGGATAAAG
1151 TCAGTCTGAC CTGCATGATA ACAGACTTCT TCCCTGAAGA CATTACTGTG
1201 GAGTGGCAGT GGAATGGGCA GCCAGCGGAG AACTACAAGA ACACTCAGCC
1251 CATCATGGAC ACAGATGGCT CTTACTTCAT CTACAGCAAG CTCAATGTGC
1301 AGAAGAGCAA CTGGGAGGCA GGAAATACTT TCACCTGCTC TGTGTTACAT
1351 GAGGGCCTGC ACAACCACCA TACTGAGAAG AGCCTCTCCC ACTCTCCTGG
1401 TAAATGA
```

The CDR (complementarity determining region) sequences in the variable region of the heavy chain of Ab-C are as follows:

CDR-H1: (SEQ ID NO: 45)
DCYMN

CDR-H2: (SEQ ID NO: 46)
DINPFNGGTTYNQKFKG

CDR-H3: (SEQ ID NO: 47)
SHYYFDGRVPWDAMDY

The light chain variable region CDR sequences of Ab-C are:

CDR-L1: (SEQ ID NO: 48)
KASQSVDYDGDSYMN

CDR-L2: (SEQ ID NO: 49)
AASNLES

CDR-L3: (SEQ ID NO: 50)
QQSNEDPWT

Ab-A

Figure 15:
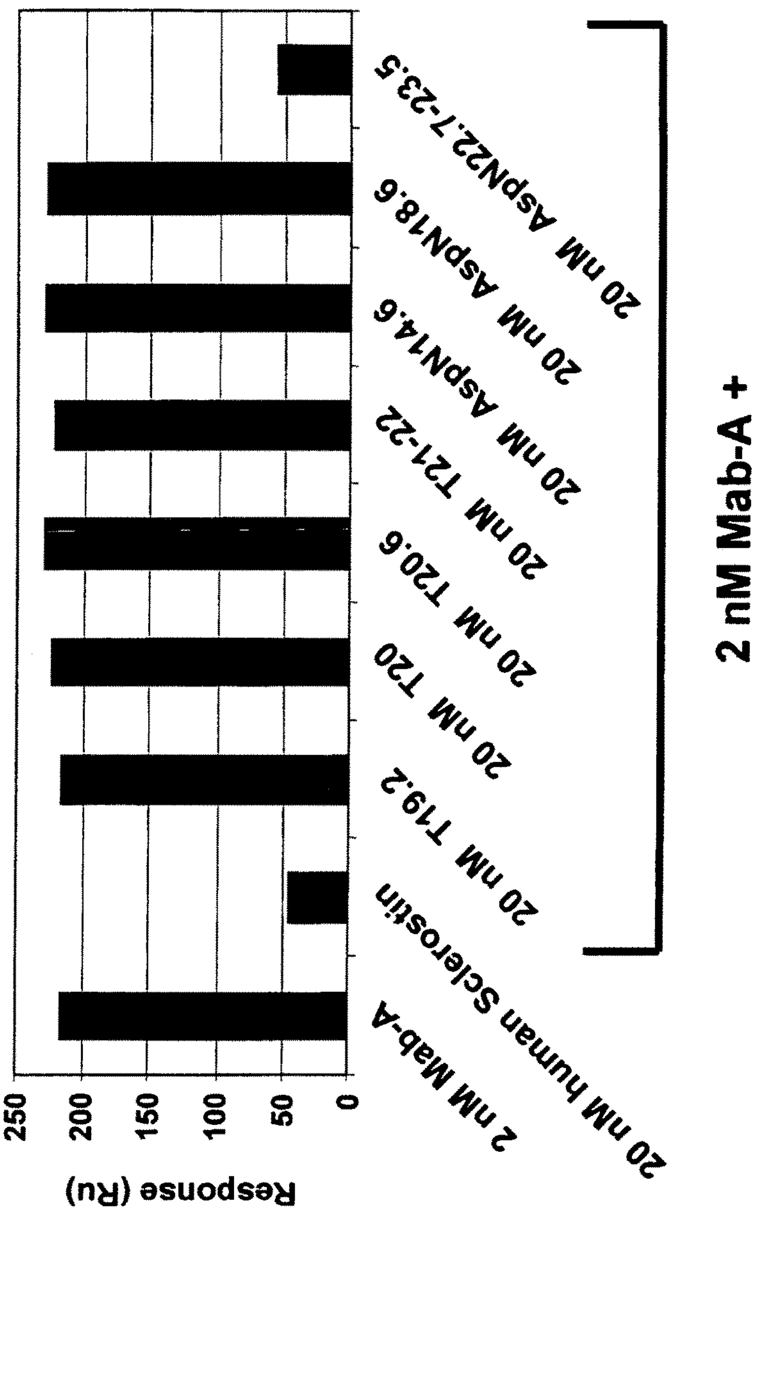
FIG. 15 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-A. Human sclerostin peptides used were T19.2, T20, T20.6, T21-22, AspN14.6, AspN18.6 and AspN22.7-23.5.

Antibody A (also referred to herein as Ab-A and Mab-A) is a rabbit-mouse chimeric antibody which exhibits high affinity binding to sclerostin. The BIAcore binding pattern of Ab-A is shown in FIG. 15.

Ab-A Light Chain

The amino acid sequence of the mature form (signal peptide removed) of Ab-A LC:

(SEQ IS NO: 23)

1 AQVLTQTPAS VSAAVGGTVT INC<u>QSSQSVY DNNWLA</u>WFQQ KPGQPPKLLI

51 Y<u>DASDLAS</u>GV PSRFSGSGSG TQFTLTISGV QCADAATYYC <u>QGAYNDVIYA</u>

101 FGGGTEVVVK *RTDAAPTVSI FPPSSEQLTS GGASVVCFLN NFYPKDINVK*

*151 WKIDGSERQN GVLNSWTDQD SKDSTYSMSS TLTLTKDEYE RHNSYTCEAT*

*201 HKTSTSPIVK SFNRNEC*

The nucleic acid sequence encoding the mature form (signal peptide removed) of Ab-A LC:

(SEQ ID NO: 24)

```
  1 GCGCAAGTGC TGACCCAGAC TCCAGCCTCC GTGTCTGCAG CTGTGGGAGG
 51 CACAGTCACC ATCAATTGCC AGTCCAGTCA GAGTGTTTAT GATAACAACT
101 GGTTAGCCTG GTTTCAGCAG AAACCAGGGC AGCCTCCCAA GCTCCTGATT
151 TATGATGCAT CCGATCTGGC ATCTGGGGTC CCATCGCGGT TCAGTGGCAG
201 TGGATCTGGG ACACAGTTCA CTCTCACCAT CAGCGGCGTG CAGTGTGCCG
251 ATGCTGCCAC TTACTACTGT CAAGGCGCTT ATAATGATGT TATTTATGCT
301 TTCGGCGGAG GGACCGAGGT GGTGGTCAAA CGTACGGATG CTGCACCAAC
351 TGTATCCATC TTCCCACCAT CCAGTGAGCA GTTAACATCT GGAGGTGCCT
401 CAGTCGTGTG CTTCTTGAAC AACTTCTACC CCAAAGACAT CAATGTCAAG
451 TGGAAGATTG ATGGCAGTGA ACGACAAAAT GGCGTCCTGA ACAGTTGGAC
```

-continued

```
501 TGATCAGGAC AGCAAAGACA GCACCTACAG CATGAGCAGC ACCCTCACGT

551 TGACCAAGGA CGAGTATGAA CGACATAACA GCTATACCTG TGAGGCCACT

601 CACAAGACAT CAACTTCACC CATTGTCAAG AGCTTCAACA GGAATGAGTG

651 TTAG
```

The amino acid sequence of Ab-A LC including signal peptide is:

```
                                         (SEQ ID NO: 25)
  1 MDTRAPTQLL GLLLLWLPGA TFAQVLTQTP ASVSAAVGGT VTINCQSSQS

 51 VYDNNWLAWF QQKPGQPPKL LIYDASDLAS GVPSRFSGSG SGTQFTLTIS

101 GVQCADAATY YCQGAYNDVI YAFGGGTEVV VKRTDAAPTV SIFPPSSEQL

151 TSGGASVVCF LNNFYPKDIN VKWKIDGSER QNGVLNSWTD QDSKDSTYSM

201 SSTLTLTKDE YERHNSYTCE ATHKTSTSPI VKSFNRNEC
```

The nucleic acid sequence of Ab-A LC including signal peptide encoding sequence is:

```
                                         (SEQ ID NO: 26)
  1 ATGGACACGA GGGCCCCCAC TCAGCTGCTG GGGCTCCTGC TGCTCTGGCT

 51 CCCAGGTGCC ACATTTGCGC AAGTGCTGAC CCAGACTCCA GCCTCCGTGT

101 CTGCAGCTGT GGGAGGCACA GTCACCATCA ATTGCCAGTC CAGTCAGAGT

151 GTTTATGATA ACAACTGGTT AGCCTGGTTT CAGCAGAAAC CAGGGCAGCC

201 TCCCAAGCTC CTGATTTATG ATGCATCCGA TCTGGCATCT GGGGTCCCAT

251 CGCGGTTCAG TGGCAGTGGA TCTGGGACAC AGTTCACTCT CACCATCAGC

301 GGCGTGCAGT GTGCCGATGC TGCCACTTAC TACTGTCAAG GCGCTTATAA

351 TGATGTTATT TATGCTTTCG GCGGAGGGAC CGAGGTGGTG GTCAAACGTA

401 CGGATGCTGC ACCAACTGTA TCCATCTTCC CACCATCCAG TGAGCAGTTA

451 ACATCTGGAG GTGCCTCAGT CGTGTGCTTC TTGAACAACT TCTACCCCAA

501 AGACATCAAT GTCAAGTGGA AGATTGATGG CAGTGAACGA CAAAATGGCG

551 TCCTGAACAG TTGGACTGAT CAGGACAGCA AAGACAGCAC CTACAGCATG

601 AGCAGCACCC TCACGTTGAC CAAGGACGAG TATGAACGAC ATAACAGCTA

651 TACCTGTGAG GCCACTCACA AGACATCAAC TTCACCCATT GTCAAGAGCT

701 TCAACAGGAA TGAGTGTTAG
```

The amino acid sequence of the mature form (signal peptide removed) of Ab-A HC is:

(SEQ ID NO: 27)

1 QSLEESGGRL VTPGTPLTLT CTASGFSLSS YWMNWVRQAP GEGLEWIGTI

51 DSGGRTDYAS WAKGRFTISR TSTTMDLKMT SLTTGDTARY FCARNWNLWG

101 QGTLVTVSS*A STKGPSVYPL APGSAAQTNS MVTLGCLVKG YFPEPVTVTW*

*151 NSGSLSSGVH TFPAVLQSDL YTLSSSVTVP SSTWPSETVT CNVAHPASST*

*201 KVDKKIVPRD CGCKPCICTV PEVSSVFIFP PKPKDVLTIT LTPKVTCVVV*

*251 DISKDDPEVQ FSWFVDDVEV HTAQTQPREE QFNSTFRSVS ELPIMHQDWL*

*301 NGKEFKCRVN SAAFPAPIEK TISKTKGRPK APQVYTIPPP KEQMAKDKVS*

-continued

*351 LTCMITDFFP EDITVEWQWN GQPAENYKNT QPIMNTNGSY FVYSKLNVQK*

*401 SNWEAGNTFT CSVLHEGLHN HHTEKSLSHS PGK*

The nucleic acid sequence encoding the mature form (signal peptide removed) of Ab-A HC:

(SEQ ID NO: 28)

```
   1 CAGTCGCTGG AGGAGTCCGG GGGTCGCCTG GTCACGCCTG GGACACCCCT
  51 GACACTCACC TGCACAGCCT CTGGATTCTC CCTCAGTAGT TATTGGATGA
 101 ACTGGGTCCG CCAGGCTCCA GGGGAGGGGC TGGAATGGAT CGGAACCATT
 151 GATTCTGGTG GTAGGACGGA CTACGCGAGC TGGGCAAAAG GCCGATTCAC
 201 CATCTCCAGA ACCTCGACTA CGATGGATCT GAAAATGACC AGTCTGACGA
 251 CCGGGGACAC GGCCCGTTAT TTCTGTGCCA GAAATTGGAA CTTGTGGGGC
 301 CAAGGCACCC TCGTCACCGT CTCGAGCGCT TCTACAAAGG GCCCATCTGT
 351 CTATCCACTG GCCCCTGGAT CTGCTGCCCA AACTAACTCC ATGGTGACCC
 401 TGGGATGCCT GGTCAAGGGC TATTTCCCTG AGCCAGTGAC AGTGACCTGG
 451 AACTCTGGAT CCCTGTCCAG CGGTGTGCAC ACCTTCCCAG CTGTCCTGCA
 501 GTCTGACCTC TACACTCTGA GCAGCTCAGT GACTGTCCCC TCCAGCACCT
 551 GGCCCAGCGA GACCGTCACC TGCAACGTTG CCCACCCGGC CAGCAGCACC
 601 AAGGTGGACA AGAAAATTGT GCCCAGGGAT TGTGGTTGTA AGCCTTGCAT
 651 ATGTACAGTC CCAGAAGTAT CATCTGTCTT CATCTTCCCC CCAAAGCCCA
 701 AGGATGTGCT CACCATTACT CTGACTCCTA AGGTCACGTG TGTTGTGGTA
 751 GACATCAGCA AGGATGATCC CGAGGTCCAG TTCAGCTGGT TTGTAGATGA
 801 TGTGGAGGTG CACACAGCTC AGACGCAACC CCGGGAGGAG CAGTTCAACA
 851 GCACTTTCCG CTCAGTCAGT GAACTTCCCA TCATGCACCA GGACTGGCTC
 901 AATGGCAAGG AGTTCAAATG CAGGGTCAAC AGTGCAGCTT TCCCTGCCCC
 951 CATCGAGAAA ACCATCTCCA AAACCAAAGG CAGACCGAAG GCTCCACAGG
1001 TGTACACCAT TCCACCTCCC AAGGAGCAGA TGGCCAAGGA TAAAGTCAGT
1051 CTGACCTGCA TGATAACAGA CTTCTTCCCT GAAGACATTA CTGTGGAGTG
1101 GCAGTGGAAT GGGCAGCCAG CGGAGAACTA CAAGAACACT CAGCCCATCA
1151 TGGACACAGA TGGCTCTTAC TTCGTCTACA GCAAGCTCAA TGTGCAGAAG
1201 AGCAACTGGG AGGCAGGAAA TACTTTCACC TGCTCTGTGT TACATGAGGG
1251 CCTGCACAAC CACCATACTG AGAAGAGCCT CTCCCACTCT CCTGGTAAAT
1301 GA
```

The amino acid sequence of the Ab-A HC including signal peptide is:

(SEQ ID NO: 29)

```
   1 METGLRWLLL VAVLKGVHCQ SLEESGGRLV TPGTPLTLTC TASGFSLSSY
  51 WMNWVRQAPG EGLEWIGTID SGGRTDYASW AKGRFTISRT STTMDLKMTS
 101 LTTGDTARYF CARNWNLWGQ GTLVTVSSAS TKGPSVYPLA PGSAAQTNSM
 151 VTLGCLVKGY FPEPVTVTWN SGSLSSGVHT FPAVLQSDLY TLSSSVTVPS
 201 STWPSETVTC NVAHPASSTK VDKKIVPRDC GCKPCICTVP EVSSVFIFPP
```

-continued

```
251  KPKDVLTITL TPKVTCVVVD ISKDDPEVQF SWFVDDVEVH TAQTQPREEQ

301  FNSTFRSVSE LPIMHQDWLN GKEFKCRVNS AAFPAPIEKT ISKTKGRPKA

351  PQVYTIPPPK EQMAKDKVSL TCMITDFFPE DITVEWQWNG QPAENYKNTQ

401  PIMNTNGSYF VYSKLNVQKS NWEAGNTFTC SVLHEGLHNH HTEKSLSHSP

451  GK
```

The nucleic acid sequence of Ab-A HC including signal peptide encoding sequence:

```
                                                  (SEQ ID NO: 30)
   1 ATGGAGACTG GGCTGCGCTG GCTTCTCCTG GTCGCTGTGC TCAAAGGTGT

  51 CCACTGTCAG TCGCTGGAGG AGTCCGGGGG TCGCCTGGTC ACGCCTGGGA

 101 CACCCCTGAC ACTCACCTGC ACAGCCTCTG GATTCTCCCT CAGTAGTTAT

 151 TGGATGAACT GGGTCCGCCA GGCTCCAGGG GAGGGGCTGG AATGGATCGG

 201 AACCATTGAT TCTGGTGGTA GGACGGACTA CGCGAGCTGG GCAAAAGGCC

 251 GATTCACCAT CTCCAGAACC TCGACTACGA TGGATCTGAA AATGACCAGT

 301 CTGACGACCG GGGACACGGC CCGTTATTTC TGTGCCAGAA ATTGGAACTT

 351 GTGGGGCCAA GGCACCCTCG TCACCGTCTC GAGCGCTTCT ACAAAGGGCC

 401 CATCTGTCTA TCCACTGGCC CCTGGATCTG CTGCCCAAAC TAACTCCATG

 451 GTGACCCTGG GATGCCTGGT CAAGGGCTAT TTCCCTGAGC CAGTGACAGT

 501 GACCTGGAAC TCTGGATCCC TGTCCAGCGG TGTGCACACC TTCCCAGCTG

 551 TCCTGCAGTC TGACCTCTAC ACTCTGAGCA GCTCAGTGAC TGTCCCCTCC

 601 AGCACCTGGC CCAGCGAGAC CGTCACCTGC AACGTTGCCC ACCCGGCCAG

 651 CAGCACCAAG GTGGACAAGA AAATTGTGCC CAGGGATTGT GGTTGTAAGC

 701 CTTGCATATG TACAGTCCCA GAAGTATCAT CTGTCTTCAT CTTCCCCCCA

 751 AAGCCCAAGG ATGTGCTCAC CATTACTCTG ACTCCTAAGG TCACGTGTGT

 801 TGTGGTAGAC ATCAGCAAGG ATGATCCCGA GGTCCAGTTC AGCTGGTTTG

 851 TAGATGATGT GGAGGTGCAC ACAGCTCAGA CGCAACCCCG GGAGGAGCAG

 901 TTCAACAGCA CTTTCCGCTC AGTCAGTGAA CTTCCCATCA TGCACCAGGA

 951 CTGGCTCAAT GGCAAGGAGT TCAAATGCAG GGTCAACAGT GCAGCTTTCC

1001 CTGCCCCCAT CGAGAAAACC ATCTCCAAAA CCAAAGGCAG ACCGAAGGCT

1051 CCACAGGTGT ACACCATTCC ACCTCCCAAG GAGCAGATGG CCAAGGATAA

1101 AGTCAGTCTG ACCTGCATGA TAACAGACTT CTTCCCTGAA GACATTACTG

1151 TGGAGTGGCA GTGGAATGGG CAGCCAGCGG AGAACTACAA GAACACTCAG

1201 CCCATCATGG ACACAGATGG CTCTTACTTC GTCTACAGCA AGCTCAATGT

1251 GCAGAAGAGC AACTGGGAGG CAGGAAATAC TTTCACCTGC TCTGTGTTAC

1301 ATGAGGGCCT GCACAACCAC CATACTGAGA AGAGCCTCTC CCACTCTCCT

1351 GGTAAATGA
```

The CDR (complementarity determining region) sequences in the variable region of the heavy chain of Ab-A are as follows:

```
CDR-H1:
                              (SEQ ID NO: 51)
SYWMN

CDR-H2:
                              (SEQ ID NO: 52)
TIDSGGRTDYASWAKG

CDR-H3:
                              (SEQ ID NO: 53)
NWNL
```

The light chain variable region CDR sequences of Ab-A are:

```
CDR-L1:
                              (SEQ ID NO: 54)
QSSQSVYDNNWLA

CDR-L2:
                              (SEQ ID NO: 55)
DASDLAS

CDR-L3:
                              (SEQ ID NO: 56)
QGAYNDVIYA
```

Ab-A was humanized, and is referred to as Antibody 1 (also referred to herein as Ab-1), having the following sequences:

The nucleic acid sequence of the Ab-1 LC variable region including signal peptide encoding sequence is

```
                                     (SEQ ID NO: 74)
ATGGACACGAGGGCCCCCACTCAGCTGCTGGGGCTCCTGCTGCTCTGGCT

CCCAGGTGCCACATTTGCTCAAGTTCTGACCCAGAGTCCAAGCAGTCTCT

CCGCCAGCGTAGGCGATCGTGTGACTATTACCTGTCAATCTAGTCAGAGC

GTGTATGATAACAATTGGCTGGCGTGGTACCAGCAAAAACCGGGCAAAGC

CCCGAAGCTGCTCATCTATGACGCGTCCGATCTGGCTAGCGGTGTGCCAA

GCCGTTTCAGTGGCAGTGGCAGCGGTACTGACTTTACCCTCACAATTTCG

TCTCTCCAGCCGGAAGATTTCGCCACTTACTATTGTCAAGGTGCTTACAA

CGATGTGATTTATGCCTTCGGTCAGGGCACTAAAGTAGAAATCAAACGT
```

The amino acid sequence of Ab-1 LC variable region including signal peptide is:

(SEQ ID NO: 75)

*MDTRAPTQLLGLLLLWLPGATFA*QVLTQSPSSLSASVGDRVTITCQSSQS

VYDNNWLAWYQQKPGKAPKLLIYDASDLASGVPSRFSGSGSGTDFTL

TISSLQPEDFATYYCQGAYNDVIYAFGQGTKVEIKR

The nucleic acid sequence of Ab-1 HC variable region including signal peptide encoding sequence is:

```
                                     (SEQ ID NO: 76)
ATGGAGACTGGGCTGCGCTGGCTTCTCCTGGTCGCTGTGCTCAAAGGTGT

CCACTGTGAGGTGCAGCTGTTGGAGTCTGGAGGCGGGCTTGTCCAGCCTG

GAGGGAGCCTGCGTCTCTCTTGTGCAGCAAGCGGCTTCAGCTTATCCTCT

TACTGGATGAATTGGGTGCGGCAGGCACCTGGGAAGGGCCTGGAGTGG

GTGGGCACCATTGATTCCGGAGGCCGTACAGACTACGCGTCTTGGGCAA

AGGGCCGTTTCACCATTTCCCGCGACAACTCCAAAAATACCATGTACCT

CCAGATGAACTCTCTCCGCGCAGAGGACACAGCACGTTATTACTGTGC

ACGCAACTGGAATCTGTGGGGTCAAGGTACTCTTGTAACAGTCTCGAGC
```

Amino acid sequence of Ab-1 HC variable region including signal peptide (SEQ IS NO: 77)

*METGLRWLLLVAVLKGVHC*EVQLLESGGGLVQPGGSLRLSCAASGF

SLSSYWMNWVRQAPGKGLEWVGTIDSGGRTDYASWAKGRFTISRDNS

KNTMYLQMNSLRAEDTARYYCARNWNLWGQGTLVTVSS

The CDR (complementarity determining region) sequences in the variable region of the heavy chain of Ab-1 are as follows:

```
                              (SEQ ID NO: 51)
CDR-H1: SYWMN

                              (SEQ ID NO: 52)
CDR-H2: TIDSGGRTDYASWAKG

                              (SEQ ID NO: 53)
CDR-H3: NWNL
```

The light chain variable region CDR sequences of Ab-1 are:

```
                              (SEQ ID NO: 54)
CDR-L1: QSSQSVYDNNWLA

                              (SEQ ID NO: 55)
CDR-L2: DASDLAS

                              (SEQ ID NO: 56)
CDR-L3: QGAYNDVIYA
```

Ab-B

Figure 16:
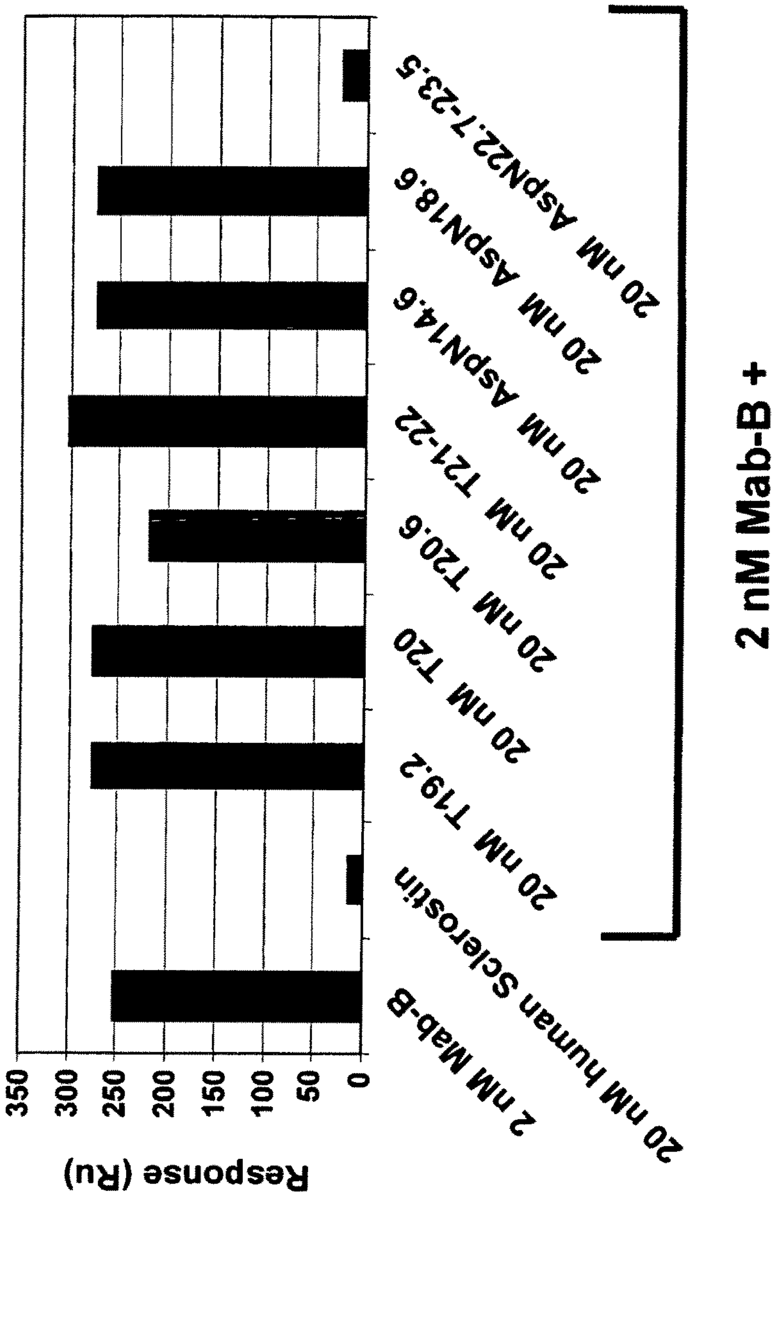
FIG. 16 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-B. Human sclerostin peptides used were T19.2, T20, T20.6, T21-22, AspN14.6, AspN18.6 and AspN22.7-23.5.

Antibody B (also referred to herein as Ab-B and Mab-B) is a mouse antibody which exhibits high affinity binding to sclerostin. The BIAcore binding pattern of Ab-B is shown in FIG. 16.

Ab-B Light Chain

The amino acid sequence of the mature form (signal peptide removed) of the Ab-B LC is:

(SEQ ID NO: 31)

1 QIVLTQSPTI VSASPGEKVT LICSASSSVS FVDWFQQKPG TSPKRWIYRT

51 SNLGFGVPAR FSGGGSGTSH SLTISRMEAE DAATYYCQQR STYPPTFGAG

101 TKLELK*RADA APTVSIFPPS SEQLTSGGAS VVCFLNNFYP KDINVKWKID*

-continued

*151 GSERQNFVLN SWTDQDSKDS TYSMSSTLTL TKDEYERHNS YTCEATHKTS*

*201 TSPIVKSFNR NEC*

The nucleic acid sequence encoding the mature form (signal peptide removed) of Ab-B LC is:

(SEQ ID NO: 32)

```
  1 CAAATTGTTC TCACCCAGTC TCCAACAATC GTGTCTGCAT CTCCAGGGGA
 51 GAAGGTCACC CTAATCTGCA GTGCCAGTTC AAGTGTAAGT TTCGTGGACT
101 GGTTCCAGCA GAAGGCAGGC ACTTCTCCCA AACGCTGGAT TTACAGAACA
151 TCCAACCTGG GTTTTGGAGT CCCTGCTCGC TTCAGTGGCG GTGGATCTGG
201 GACCTCTCAC TCTCTCACAA TCAGCCGAAT GGAGGCTGAA GATGCTGCCA
251 CTTATTACTG CCAGCAAAGG AGTACTTACC CACCCACGTT CGGTGCTGGG
301 ACCAAGCTGG AACTGAAACG GGCTGATGCT GCACCAACTG TATCCATCTT
351 CCCACCATCC AGTGAGCAGT TAACATCTGG AGGTGCCTCA GTCGTGTGCT
401 TCTTGAACAA CTTCTACCCC AAAGACATCA ATGTCAAGTG GAAGATTGAT
451 GGCAGTGAAC GACAAAATGG CGTCCTGAAC AGTTGGACTG ATCAGGACAG
501 CAAAGACAGC ACCTACAGCA TGAGCAGCAC CCTCACGTTG ACCAAGGACG
551 AGTATGAACG ACATAACAGC TATACCTGTG AGGCCACTCA CAAGAGATCA
601 ACTTCACCCA TTGTCAAGAG CTTCAACAGG AATGAGTGTT AG
```

The amino acid sequence of Ab-B LC including signal peptide is:

(SEQ ID NO: 33)

```
  1 MHFQVQIFSF LLISASVIVS RGQIVLTQSP TIVSASPGEK VTLICSASSS
 51 VSFVDWFQQK PGTSPKRWIY RTSNLGFGVP ARFSGGGSGT SHSLTISRME
101 AEDAATYYCQ QRSTYPPTFG AGTKLELKRA DAAPTVSIFP PSSEQLTSGG
151 ASVVCFLNNF YPKDINVKWK IDGSERQNGV LNSWTDQDSK DSTYSMSSTL
201 TLTKDEYERH NSYTCEATHK TSTSPIVKSF NRNEC
```

The nucleic acid sequence of Ab-B LC including signal peptide encoding sequence is:

(SEQ ID NO: 34)

```
  1 ATGCATTTTC AAGTGCAGAT TTTCAGCTTC CTGCTAATCA GTGCCTCAGT
 51 CATAGTGTCC AGAGGGCAAA TTGTTCTCAC CCAGTCTCCA ACAATCGTGT
101 CTGCATCTCC AGGGGAGAAG GTCACCCTAA TCTGCAGTGC CAGTTCAAGT
151 GTAAGTTTCG TGGACTGGTT CCAGCAGAAG CCAGGCACTT CTCCCAAACG
201 CTGGATTTAC AGAACATCCA ACCTGGGTTT TGGAGTCCCT GCTCGCTTCA
251 GTGGCGGTGG ATCTGGGACC TCTCACTCTC TCACAATCAG CCGAATGGAG
301 GCTGAAGATG CTGCCACTTA TTACTGCCAG CAAAGGAGTA CTTACCCACC
351 CACGTTCGGT GCTGGGACCA AGCTGGAACT GAAACGGGCT GATGCTGCAC
401 CAACTGTATC CATCTTCCCA CCATCCAGTG AGCAGTTAAC ATCTGGAGGT
451 GCCTCAGTCG TGTGCTTCTT GAACAACTTC TACCCCAAAG ACATCAATGT
501 CAAGTGGAAG ATTGATGGCA GTGAACGACA AAATGGCGTC CTGAACAGTT
```

-continued

```
551 GGACTGATCA GGACAGCAAA GACAGCACCT ACAGCATGAG CAGCACCCTC

601 ACGTTGACCA AGGACGAGTA TGAACGACAT AACAGCTATA CCTGTGAGGC

651 CACTCACAAG ACATCAACTT CACCCATTGT CAAGAGCTTC AACAGGAATG

701 AGTGTTAG
```

Ab-B Heavy Chain

The amino acid sequence of the mature form (signal peptide removed) of Ab-B HC:

```
                                              (SEQ ID NO: 35)
  1 QVTLKESGPG ILQPSQTLSL TCSFSGFSLS TSGMGVGWIR HPSGKNLEWL

 51 AHIWWDDVKR YNPVLKSRLT ISKDTSNSQV FLKIANVDTA DTATYYCARI

101 EDFDYDEEYY AMDYWGQGTS VIVSSAKTTP PSVYPLAPGS AAQTNSMVTL

151 GCLVKGYFPE PVTVTWNSGS LSSGVHTFPA VLQSDLYTLS SSVTVPSSTW

201 PSETVTCNVA HPASSTKVDK KIVPRDCGCK PCICTVPEVS SVFIFPPKPK

251 DVLTITLTPK VTCVVVDISK DDPEVQFSWF VDDVEVHTAQ TQPREEQFNS

301 TFRSVSELPI MHQDWLNGKE FKCRVNSAAF PAPIEKTISK TKGRPKAPQV

351 YTIPPPKEQM AKDKVSLTCM ITDFFPEDIT VEWQWNGQPA ENYKNTQPIM

401 DTDGSYFVYS KLNVQKSNWE AGNTFTCSVL HEGLHNHHTE KSLSHSPGK
```

The nucleic acid sequence encoding the mature form (signal peptide removed) of Ab-B HC:

```
                                              (SEQ ID NO: 36)
  1 CAGGTTACTC TGAAAGAGTC TGGCCCTGGG ATATTGCAGC CCTCCCAGAC

 51 CCTCAGTCTG ACTTGTTCTT TCTCTGGGTT TTCACTGAGC ACTTCTGGTA

101 TGGGTGTAGG CTGGATTCGT CACCCATCAG GGAAGAATCT GGAGTGGCTG

151 GCACACATTT GGTGGGATGA TGTCAAGCGC TATAACCCAG TCCTGAAGAG

201 CCGACTGACT ATCTCCAAGG ATACCTCCAA CAGCCAGGTA TTCCTCAAGA

251 TCGCCAATGT GGACACTGCA GATACTGCCA CATACTACTG TGCTCGAATA

301 GAGGACTTTG ATTACGACGA GGAGTATTAT GCTATGGACT ACTGGGGTCA

351 AGGAACCTCA GTCATCGTCT CCTCAGCCAA AACGACACCC CCATCTGTCT

401 ATCCACTGGC CCCTGGATCT GCTGCCCAAA CTAACTCCAT GGTGACCCTG

451 GGATGCCTGG TCAAGGGCTA TTTCCCTGAG CCAGTGACAG TGACCTGGAA

501 CTCTGGATCC CTGTCCAGCG GTGTGCACAC CTTCCCAGCT GTCCTGCAGT

551 CTGACCTCTA CACTCTGAGC AGCTCAGTGA CTGTCCCCTC CAGCACCTGG

601 CCCAGCGAGA CCGTCACCTG CAACGTTGCC CACCCGGCCA GCAGCACCAA

651 GGTGGACAAG AAAATTGTGC CCAGGGATTG TGGTTGTAAG CCTTGCATAT

701 GTACAGTCCC AGAAGTATCA TCTGTCTTCA TCTTCCCCCC AAAGCCCAAG

751 GATGTGCTCA CCATTACTCT GACTCCTAAG GTCACGTGTG TTGTGGTAGA

801 CATCAGCAAG GATGATCCCG AGGTCCAGTT CAGCTGGTTT GTAGATGATG

851 TGGAGGTGCA CACAGCTCAG ACGCAACCCC GGGAGGAGCA GTTCAACAGC

901 ACTTTCCGCT CAGTCAGTGA ACTTCCCATC ATGCACCAGG ACTGGCTCAA

951 TGGCAAGGAG TTCAAATGCA GGGTCAACAG TGCAGCTTTC CCTGCCCCCA
```

-continued

```
1001 TCGAGAAAAC CATCTCCAAA ACCAAAGGCA GACCGAAGGC TCCACAGGTG

1051 TACACCATTC CACCTCCCAA GGAGCAGATG GCCAAGGATA AAGTCAGTCT

1101 GACCTGCATG ATAACAGACT TCTTCCCTGA AGACATTACT GTGGAGTGGC

1151 AGTGGAATGG GCAGCCAGCG GAGAACTACA AGAACACTCA GCCCATCATG

1201 GACACAGATG GCTCTTACTT CGTCTACAGC AAGCTCAATG TGCAGAAGAG

1251 CAACTGGGAG GCAGGAAATA CTTTCACCTG CTCTGTGTTA CATGAGGGCC

1301 TGCACAACCA CCATACTGAG AAGAGCCTCT CCCACTCTCC TGGTAAATGA
```

The amino acid sequence of Ab-B HC including signal peptide:

```
                                              (SEQ ID NO: 37)
  1 MGRLTSSFLL LIVPAYVLSQ VTLKESGPGI LQPSQTLSLT CSFSGFSLST

 51 SGMGVGWIRH PSGKNLEWLA HIWWDDVKRY NPVLKSRLTI SKDTSNSQVF

101 LKIANVDTAD TATYYCARIE DFDYDEEYYA MDYWGQGTSV IVSSAKTTPP

151 SVYPLAPGSA AQTNSMVTLG CLVKGYFPEP VTVTWNSGSL SSGVHTFPAV

201 LQSDLYTLSS SVTVPSSTWP SETVTCNVAH PASSTKVDKK IVPRDCGCKP

251 CICTVPEVSS VFIFPPKPKD VLTITLTPKV TCVVVDISKD DPEVQFSWFV

301 DDVEVHTAQT QPREEQFNST FRSVSELPIM HQDWLNGKEF KCRVNSAAFP

351 APIEKTISKT KGRPKAPQVY TIPPPKEQMA KDKVSLTCMI TDFFPEDITV

401 EWQWNGQPAE NYKNTQPIMD TDGSYFVYSK LNVQKSNWEA GNTFTCSVLH

451 EGLHNHHTEK SLSHSPGK
```

The nucleic acid sequence of Ab-B HC including signal peptide encoding sequence:

```
                                              (SEQ ID NO: 38)
  1 ATGGGCAGGC TTACTTCTTC ATTCCTGCTA CTGATTGTCC CTGCATATGT

 51 CCTGTCCCAG GTTACTCTGA AAGAGTCTGG CCCTGGGATA TTGCAGCCCT

101 CCCAGACCCT CAGTCTGACT TGTTCTTTCT CTGGGTTTTC ACTGAGCACT

151 TCTGGTATGG GTGTAGGCTG GATTCGTCAC CCATCAGGGA AGAATCTGGA

201 GTGGCTGGCA CACATTTGGT GGGATGATGT CAAGCGCTAT AACCCAGTCC

251 TGAAGAGCCG ACTGACTATC TCCAAGGATA CCTCCAACAG CCAGGTATTC

301 CTCAAGATCG CCAATGTGGA CACTGCAGAT ACTGCCACAT ACTACTGTGC

351 TCGAATAGAG GACTTTGATT ACGACGAGGA GTATTATGCT ATGGACTACT

401 GGGGTCAAGG AACCTCAGTC ATCGTCTCCT CAGCCAAAAC GACACCCCCA

451 TCTGTCTATC CACTGGCCCC TGGATCTGCT GCCCAAACTA ACTCCATGGT

501 GACCCTGGGA TGCCTGGTCA AGGGCTATTT CCCTGAGCCA GTGACAGTGA

551 CCTGGAACTC TGGATCCCTG TCCAGCGGTG TGCACACCTT CCCAGCTGTC

601 CTGCAGTCTG ACCTCTACAC TCTGAGCAGC TCAGTGACTG TCCCCTCCAG

651 CACCTGGCCC AGCGAGACCG TCACCTGCAA CGTTGCCCAC CCGGCCAGCA

701 GCACCAAGGT GGACAAGAAA ATTGTGCCCA GGGATTGTGG TTGTAAGCCT

751 TGCATATGTA CAGTCCCAGA AGTATCATCT GTCTTCATCT TCCCCCCAAA

801 GCCCAAGGAT GTGCTCACCA TTACTCTGAC TCCTAAGGTC ACGTGTGTTG
```

-continued

```
851  TGGTAGACAT CAGCAAGGAT GATCCCGAGG TCCAGTTCAG CTGGTTTGTA

901  GATGATGTGG AGGTGCACAC AGCTCAGACG CAACCCCGGG AGGAGCAGTT

951  CAACAGCACT TTCCGCTCAG TCAGTGAACT TCCCATCATG CACCAGGACT

1001 GGCTCAATGG CAAGGAGTTC AAATGCAGGG TCAACAGTGC AGCTTTCCCT

1051 GCCCCCATCG AGAAAACCAT CTCCAAAACC AAAGGCAGAC CGAAGGCTCC

1101 ACAGGTGTAC ACCATTCCAC CTCCCAAGGA GCAGATGGCC AAGGATAAAG

1151 TCAGTCTGAC CTGCATGATA ACAGACTTCT TCCCTGAAGA CATTACTGTG

1201 GAGTGGCAGT GGAATGGGCA GCCAGCGGAG AACTACAAGA ACACTCAGCC

1251 CATCATGGAC ACAGATGGCT CTTACTTCGT CTACAGCAAG CTCAATGTGC

1301 AGAAGAGCAA CTGGGAGGCA GGAAATACTT TCACCTGCTC TGTGTTACAT

1351 GAGGGCCTGC ACAACCACCA TACTGAGAAG AGCCTCTCCC ACTCTCCTGG

1401 TAAATGA
```

The CDR (complementarity determining region) sequences in the variable region of the heavy chain of Ab-B are as follows:

```
                                (SEQ ID NO: 57)
CDR-H1: TSGMGVG

                                (SEQ ID NO: 58)
CDR-H2: HIWWDDVKRYNPVLKS

                                (SEQ ID NO: 59)
CDR-H3: EDFDYDEEYYAMDY
```

The light chain variable region CDR sequences of Ab-B are:

```
                                (SEQ ID NO: 60)
CDR-L1: SASSSVSFVD

                                (SEQ ID NO: 61)
CDR-L2: RTSNLGF

                                (SEQ ID NO: 62)
CDR-L3: QQRSTYPPT
```

Antibodies disclosed herein bind to regions of human sclerostin which are important for the in vivo activity of the protein. Binding of an antibody to sclerostin can be correlated with increases in, for example, the bone mineral density achieved by use of the antibody in vivo such as described in Examples 5 and 9 (mice) and Example 12 (monkey). Increases in at least one of bone formation, bone mineral content, bone mass, bone quality and bone strength can also be achieved by use of the antibody in vivo such as described in Examples 5 and 9 (mice) and Example 12 (monkey). Since the binding of an antibody to sclerostin is primarily determined by its CDR sequences, an antibody for practicing the invention may be generated with all or some of the disclosed CDR sequences in an appropriate framework, wherein the antibody retains the ability to bind specifically to sclerostin, and can be expected to achieve increases in, for example, bone mineral density. Such antibodies are useful in the treatment of human or animal conditions that are caused by, associated with, or result in at least one of low bone formation, low bone mineral density, low bone mineral content, low bone mass, low bone quality and low bone strength. Methods of constructing and expressing antibodies and fragments thereof comprising CDR's of the present invention are known to those of skill in the art.

The present invention therefore relates in one embodiment to an isolated antibody, including Ab-A, or an antigen binding fragment thereof, which specifically binds to sclerostin and wherein the variable domain of the heavy chain comprises at least one CDR having the sequences given in SEQ ID NO:51 for CDR-H1, SEQ ID NO:52 for CDR-H2 and SEQ ID NO:53 for CDR-H3. The antibody or antigen binding fragment thereof may comprise a heavy chain variable domain in which the CDRs consist of at least one of the peptides of SEQ ID NO:51 for CDR-H1, SEQ ID NO:52 for CDR-H2 and SEQ ID NO:53 for CDR-H3.

When in antibodies of the invention a light chain is present the light chain may be any suitable complementary chain and may in particular be selected from a light chain wherein the variable domain comprises at least one CDR having the sequences given in SEQ ID NO:54 for CDR-L1, SEQ ID NO:55 for CDR-L2 and SEQ ID NO:56 for CDR-L3. The antibody or antigen binding fragment thereof may comprise a light chain variable domain in which the CDRs consist of at least one of the peptides of SEQ ID NO:54 for CDR-L1, SEQ ID NO:55 for CDR-L2 and SEQ ID NO:56 for CDR-L3.

The present invention further relates to an isolated antibody, including Ab-B, or an antigen binding fragment hereof, which specifically binds to sclerostin and wherein the variable domain of the heavy chain comprises at least one CDR having the sequences given in SEQ ID NO:57 for CDR-H1, SEQ ID NO:58 for CDR-H2 and SEQ ID NO:59 for CDR-H3. The antibody or antigen binding fragment thereof may comprise a heavy chain variable domain in which the CDRs consist of at least one of the peptides of SEQ ID NO:57 for CDR-H1, SEQ ID NO:58 for CDR-H2 and SEQ ID NO:59 for CDR-H3.

When in antibodies of the invention a light chain is present the light chain may be any suitable complementary chain and may in particular be selected from a light chain wherein the variable domain comprises at least one CDR having the sequences given in SEQ ID NO:60 for CDR-L1, SEQ ID NO:61 for CDR-L2 and SEQ ID NO:62 for CDR-L3. The antibody or antigen binding fragment thereof may comprise a light chain variable domain in which the CDRs consist of at least one of the peptides of SEQ ID NO:60 for CDR-L1, SEQ ID NO:61 for CDR-L2 and SEQ ID NO:62 for CDR-L3.

The present invention still further relates to an isolated antibody, including Ab-C, or an antigen binding fragment hereof, which specifically binds to sclerostin and wherein the variable domain of the heavy chain comprises at least one CDR having the sequences given in SEQ ID NO:45 for CDR-H1, SEQ ID NO:46 for CDR-H2 and SEQ ID NO:47 for CDR-H3. The antibody or antigen binding fragment thereof may comprise a heavy chain variable domain in which the CDRs consist of at least one of the peptides of SEQ ID NO:45 for CDR-H1, SEQ ID NO:46 for CDR-H2 and SEQ ID NO:47 for CDR-H3.

When in antibodies of the invention a light chain is present the light chain may be any suitable complementary chain and may in particular be selected from a light chain wherein the variable domain comprises at least one CDR having the sequences given in SEQ ID NO:48 for CDR-L1, SEQ ID NO:49 for CDR-L2 and SEQ ID NO:50 for CDR-L3. The antibody or antigen binding fragment thereof may comprise a light chain variable domain in which the CDRs consist of at least one of the peptides of SEQ ID NO:48 for CDR-L1, SEQ ID NO:49 for CDR-L2 and SEQ ID NO:50 for CDR-L3.

The present invention also relates to an isolated antibody, including Ab-D, or an antigen binding fragment hereof, which specifically binds to sclerostin and wherein the variable domain of the heavy chain comprises at least one CDR having the sequences given in SEQ ID NO:39 for CDR-H1, SEQ ID NO:40 for CDR-H2 and SEQ ID NO:41 for CDR-H3. The antibody or antigen binding fragment thereof may comprise a heavy chain variable domain in which the CDRs consist of at least one of the peptides of SEQ ID NO:39 for CDR-H1, SEQ ID NO:40 for CDR-H2 and SEQ ID NO:41 for CDR-H3.

When in antibodies of the invention a light chain is present the light chain may be any suitable complementary chain and may in particular be selected from a light chain wherein the variable domain comprises at least one CDR having the sequences given in SEQ ID NO:42 for CDR-L1, SEQ ID NO:43 for CDR-L2 and SEQ ID NO:44 for CDR-L3. The antibody or antigen binding fragment thereof may comprise a light chain variable domain in which the CDRs consist of at least one of the peptides of SEQ ID NO:42 for CDR-L1, SEQ ID NO:43 for CDR-L2 and SEQ ID NO:44 for CDR-L3.

Additional anti-sclerostin antibodies are described below. For some of the amino acid sequences the complementarity-determining regions (CDRs) are boxed-shaded and the constant regions are in bold-italics.

Ab-2

The sequences of the Antibody 2 (also referred to as Ab-2) LC and HC are as follows:

Ab-2 Light Chain:

Amino acid sequence of the mature form (signal peptide removed) of the Ab-2 LC:

(SEQ ID NO: 117)

1 QIVLSQSPAI LSTSPGEKVT MTCRASSSVY YMHWYQQKPG SSPKPWIYAT

51 SNLASGVPVR FSGSGSGTSY SLTITRVEAE DAATYYCQQW SSDPLTFGAG

101 TKLELK*RADA APTVSIFPPS SEQLTSGGAS VVCFLNNFYP KDINVKWKID*

*151 GSERQNGVLN SWTDQDSKDS TYSMSSTLTL TKDEYERHNS YTCEATHKTS*

*201 TSPIVKSFNR NEC*

Nucleic acid sequence encoding the mature form (signal peptide removed) of the Ab-2 LC:

(SEQ ID NO: 118)

1 CAAATTGTTC TCTCCCAGTC TCCAGCAATC CTGTCTACAT CTCCAGGGGA

51 GAAGGTCACA ATGACTTGCA GGGCCAGCTC AAGTGTATAT TACATGCACT

101 GGTACCAGCA GAAGCCAGGA TCCTCCCCCA AACCCTGGAT TTATGCCACA

151 TCCAACCTGG CTTCTGGAGT CCCTGTTCGC TTCAGTGGCA GTGGGTCTGG

201 GACCTCTTAC TCTCTCACAA TCACCAGAGT GGAGGCTGAA GATGCTGCCA

251 CTTATTACTG CCAGCAGTGG AGTAGTGACC CACTCACGTT CGGTGCTGGG

301 ACCAAGCTGG AGCTGAAACG GGCTGATGCT GCACCAACTG TATCCATCTT

351 CCCACCATCC AGTGAGCAGT TAACATCTGG AGGTGCCTCA GTCGTGTGCT

401 TCTTGAACAA CTTCTACCCC AAAGACATCA ATGTCAAGTG GAAGATTGAT

451 GGCAGTGAAC GACAAAATGG CGTCCTGAAC AGTTGGACTG ATCAGGACAG

501 CAAAGACAGC ACCTACAGCA TGAGCAGCAC CCTCACGTTG ACCAAGGACG

551 AGTATGAACG ACATAACAGC TATACCTGTG AGGCCACTCA CAAGACATCA

601 ACTTCACCCA TTGTCAAGAG CTTCAACAGG AATGAGTGTT AG

Amino acid sequence of the Ab-2 LC including signal peptide:

```
                                        (SEQ ID NO: 119)
  1 MDFQVQIFSF LLISASVIMS RGQIVLSQSP AILSTSPGEK VTMTCRASSS

 51 VYYMHWYQQK PGSSPKPWIY ATSNLASGVP VRFSGSGSGT SYSLTITRVE

101 AEDAATYYCQ QWSSDPLTFG AGTKLELKRA DAAPTVSIFP PSSEQLTSGG

151 ASVVCFLNNF YPKDINVKWK IDGSERQNGV LNSWTDQDSK DSTYSMSSTL

201 TLTKDEYERH NSYTCEATHK TSTSPIVKSF NRNEC
```

Nucleic acid sequence of the Ab-2 LC including signal peptide encoding sequence:

```
                                        (SEQ ID NO: 120)
  1 ATGGATTTTC AAGTGCAGAT TTTCAGCTTC CTGCTAATCA GTGCTTCAGT

 51 CATTATGTCC AGGGGACAAA TTGTTCTCTC CCAGTCTCCA GCAATCCTGT

101 CTACATCTCC AGGGGAGAAG GTCACAATGA CTTGCAGGGC CAGCTCAAGT

151 GTATATTACA TGCACTGGTA CCAGCAGAAG CCAGGATCCT CCCCCAAACC

201 CTGGATTTAT GCCACATCCA ACCTGGCTTC TGGAGTCCCT GTTCGCTTCA

251 GTGGCAGTGG GTCTGGGACC TCTTACTCTC TCACAATCAC CAGAGTGGAG

301 GCTGAAGATG CTGCCACTTA TTACTGCCAG CAGTGGAGTA GTGACCCACT

351 CACGTTCGGT GCTGGGACCA AGCTGGAGCT GAAACGGGCT GATGCTGCAC

401 CAACTGTATC CATCTTCCCA CCATCCAGTG AGCAGTTAAC ATCTGGAGGT

451 GCCTCAGTCG TGTGCTTCTT GAACAACTTC TACCCCAAAG ACATCAATGT

501 CAAGTGGAAG ATTGATGGCA GTGAACGACA AAATGGCGTC CTGAACAGTT

551 GGACTGATCA GGACAGCAAA GACAGCACCT ACAGCATGAG CAGCACCCTC

601 ACGTTGACCA AGGACGAGTA TGAACGACAT AACAGCTATA CCTGTGAGGC

651 CACTCACAAG ACATCAACTT CACCCATTGT CAAGAGCTTC AACAGGAATG

701 AGTGTTAG
```

Ab-2 Heavy Chain

Amino acid sequence of the mature form (signal peptide removed) of the Ab-2 HC:

```
                                        (SEQ ID NO: 121)
  1 EVQVQQSGPE LVKPGASVKL SCTASGFNIK DYFIHWVKQR PEQGLEWIGR

 51 LDPEDGESDY APKFQDKAIM TADTSSNTAY LQLRSLTSED TAIYYCERED

101 YDGTYTFFPY WGQGTLVTVS AAKTTPPSVY PLAPGSAAQT NSMVTLGCLV

151 KGYFPEPVTV TWNSGSLSSG VHTFPAVLQS DLYTLSSSVT VPSSTWPSET

201 VTCNVAHPAS STKVDKKIVP RDCGCKPCIC TVPEVSSVFI FPPKPKDVLT

251 ITLTPKVTCV VVDISKDDPE VQFSWFVDDV EVHTAQTQPR EEQFNSTFRS

301 VSELPIMHQD WLNGKEFKCR VNSAAFPAPI EKTISKTKGR PKAPQVYTIP

351 PPKEQMAKDK VSLTCMITDF FPEDITVEWQ WNGQPAENYK NTQPIMDTDG

401 SYFIYSKLNV QKSNWEAGNT FTCSVLHEGL HNHHTEKSLS HSPGK
```

Nucleic acid sequence encoding the mature form (signal peptide removed) of the Ab-2 HC:

```
                                        (SEQ ID NO: 122)
   1 GAGGTTCAGG TGCAGCAGTC TGGGCCAGAA CTTGTGAAGC CAGGGGCCTC

  51 AGTCAAGTTG TCCTGCACAG CTTCTGGCTT CAACATTAAA GACTACTTTA

 101 TACACTGGGT GAAGCAGAGG CCTGAACAGG GCCTGGAGTG GATTGGAAGG

 151 CTTGATCCTG AGGATGGTGA AAGTGATTAT GCCCCGAAGT TCCAGGACAA

 201 GGCCATTATG ACAGCAGACA CATCATCCAA CACAGCCTAT CTTCAGCTCA

 251 GAAGCCTGAC ATCTGAGGAC ACTGCCATCT ATTATTGTGA GAGAGAGGAC

 301 TACGATGGTA CCTACACCTT TTTTCCTTAC TGGGGCCAAG GGACTCTGGT

 351 CACTGTCTCT GCAGCCAAAA CGACACCCCC ATCTGTCTAT CCACTGGCCC

 401 CTGGATCTGC TGCCCAAACT AACTCCATGG TGACCCTGGG ATGCCTGGTC

 451 AAGGGCTATT TCCCTGAGCC AGTGACAGTG ACCTGGAACT CTGGATCCCT

 501 GTCCAGCGGT GTGCACACCT TCCCAGCTGT CCTGCAGTCT GACCTCTACA

 551 CTCTGAGCAG CTCAGTGACT GTCCCCTCCA GCACCTGGCC CAGCGAGACC

 601 GTCACCTGCA ACGTTGCCCA CCCGGCCAGC AGCACCAAGG TGGACAAGAA

 651 AATTGTGCCC AGGGATTGTG GTTGTAAGCC TTGCATATGT ACAGTCCCAG

 701 AAGTATCATC TGTCTTCATC TTCCCCCCAA AGCCCAAGGA TGTGCTCACC

 751 ATTACTCTGA CTCCTAAGGT CACGTGTGTT GTGGTAGACA TCAGCAAGGA

 801 TGATCCCGAG GTCCAGTTCA GCTGGTTTGT AGATGATGTG GAGGTGCACA

 851 CAGCTCAGAC GCAACCCCGG GAGGAGCAGT TCAACAGCAC TTTCCGCTCA

 901 GTCAGTGAAC TTCCCATCAT GCACCAGGAC TGGCTCAATG GCAAGGAGTT

 951 CAAATGCAGG GTCAACAGTG CAGCTTTCCC TGCCCCCATC GAGAAAACCA

1001 TCTCCAAAAC CAAAGGCAGA CCGAAGGCTC CACAGGTGTA CACCATTCCA

1051 CCTCCCAAGG AGCAGATGGC CAAGGATAAA GTCAGTCTGA CCTGCATGAT

1101 AACAGACTTC TTCCCTGAAG ACATTACTGT GGAGTGGCAG TGGAATGGGC

1151 AGCCAGCGGA GAACTACAAG AACACTCAGC CCATCATGGA CACAGATGGC

1201 TCTTACTTCA TCTACAGCAA GCTCAATGTG CAGAAGAGCA ACTGGGAGGC

1251 AGGAAATACT TTCACCTGCT CTGTGTTACA TGAGGGCCTG CACAACCACC

1301 ATACTGAGAA GAGCCTCTCC CACTCTCCTG GTAAATGA
```

Amino acid sequence of the Ab-2 HC including signal peptide:

```
                                          (SEQ ID NO: 123)
  1 MKCSWVIFFL MAVVTGVNSE VQVQQSGPEL VKPGASVKLS CTASGFNIKD

 51 YFIHWVKQRP EQGLEWIGRL DPEDGESDYA PKFQDKAIMT ADTSSNTAYL

101 QLRSLTSEDT AIYYCEREDY DGTYTFFPYW GQGTLVTVSA AKTTPPSVYP

151 LAPGSAAQTN SMVTLGCLVK GYFPEPVTVT WNSGSLSSGV HTFPAVLQSD

201 LYTLSSSVTV PSSTWPSETV TCNVAHPASS TKVDKKIVPR DCGCKPCICT

251 VPEVSSVFIF PPKPKDVLTI TLTPKVTCVV VDISKDDPEV QFSWFVDDVE

301 VHTAQTQPRE EQFNSTFRSV SELPIMHQDW LNGKEFKCRV NSAAFPAPIE

351 KTISKTKGRP KAPQVYTIPP PKEQMAKDKV SLTCMITDFF PEDITVEWQW
```

-continued

```
401 NGQPAENYKN TQPIMDTDGS YFIYSKLNVQ KSNWEAGNTF TCSVLHEGLH

451 NHHTEKSLSH SPGK
```

Nucleic acid sequence of the Ab-2 HC including signal peptide encoding sequence:

(SEQ ID NO: 124)

```
   1 ATGAAATGCA GCTGGGTCAT CTTCTTCCTG ATGGCAGTGG TTACAGGGGT

  51 CAATTCAGAG GTTCAGGTGC AGCAGTCTGG GCCAGAACTT GTGAAGCCAG

 101 GGGCCTCAGT CAAGTTGTCC TGCACAGCTT CTGGCTTCAA CATTAAAGAC

 151 TACTTTATAC ACTGGGTGAA GCAGAGGCCT GAACAGGGCC TGGAGTGGAT

 201 TGGAAGGCTT GATCCTGAGG ATGGTGAAAG TGATTATGCC CCGAAGTTCC

 251 AGGACAAGGC CATTATGACA GCAGACACAT CATCCAACAC AGCCTATCTT

 301 CAGCTCAGAA GCCTGACATC TGAGGACACT GCCATCTATT ATTGTGAGAG

 351 AGAGGACTAC GATGGTACCT ACACCTTTTT TCCTTACTGG GGCCAAGGGA

 401 CTCTGGTCAC TGTCTCTGCA GCCAAAACGA CACCCCCATC TGTCTATCCA

 451 CTGGCCCCTG GATCTGCTGC CCAAACTAAC TCCATGGTGA CCCTGGGATG

 501 CCTGGTCAAG GGCTATTTCC CTGAGCCAGT GACAGTGACC TGGAACTCTG

 551 GATCCCTGTC CAGCGGTGTG CACACCTTCC CAGCTGTCCT GCAGTCTGAC

 601 CTCTACACTC TGAGCAGCTC AGTGACTGTC CCCTCCAGCA CCTGGCCCAG

 651 CGAGACCGTC ACCTGCAACG TTGCCCACCC GGCCAGCAGC ACCAAGGTGG

 701 ACAAGAAAAT TGTGCCCAGG GATTGTGGTT GTAAGCCTTG CATATGTACA

 751 GTCCCAGAAG TATCATCTGT CTTCATCTTC CCCCCAAAGC CCAAGGATGT

 801 GCTCACCATT ACTCTGACTC CTAAGGTCAC GTGTGTTGTG GTAGACATCA

 851 GCAAGGATGA TCCCGAGGTC CAGTTCAGCT GGTTTGTAGA TGATGTGGAG

 901 GTGCACACAG CTCAGACGCA ACCCCGGGAG GAGCAGTTCA ACAGCACTTT

 951 CCGCTCAGTC AGTGAACTTC CCATCATGCA CCAGGACTGG CTCAATGGCA

1001 AGGAGTTCAA ATGCAGGGTC AACAGTGCAG CTTTCCCTGC CCCCATCGAG

1051 AAAACCATCT CCAAAACCAA AGGCAGACCG AAGGCTCCAC AGGTGTACAC

1101 CATTCCACCT CCCAAGGAGC AGATGGCCAA GGATAAAGTC AGTCTGACCT

1151 GCATGATAAC AGACTTCTTC CCTGAAGACA TTACTGTGGA GTGGCAGTGG

1201 AATGGGCAGC CAGCGGAGAA CTACAAGAAC ACTCAGCCCA TCATGGACAC

1251 AGATGGCTCT TACTTCATCT ACAGCAAGCT CAATGTGCAG AAGAGCAACT

1301 GGGAGGCAGG AAATACTTTC ACCTGCTCTG TGTTACATGA GGGCCTGCAC

1351 AACCACCATA CTGAGAAGAG CCTCTCCCAC TCTCCTGGTA AATGA
```

Ab-3

The sequences of the Antibody 3 (also referred to herein as Ab-3) LC and HC are as follows:

Ab-3 Light Chain

Amino acid sequence of the mature form (signal peptide removed) of the Ab-3 LC:

(SEQ ID NO: 125)

1 EIVLTQSPAL MAASPGEKVT ITCSVSSTIS SNHLHWFQQK SDTSPKPWIY

51 GTSNLASGVP VRFSGSGSGT SYSLTISSME AEDAATYYCQ QWSSYPLTFG

101 AGTKLELR*RA DAAPTVSIFP PSSEQLTSGG ASVVCFLNNF YPKDINVKWK*

-continued

*151 IDGSERQNGV LNSWTDQDSK DSTYSMSSTL TLTKDEYERH NSYTCEATHK*

*201 TSTSPIVKSF NRNEC*

Nucleic acid sequence encoding the mature form (signal peptide removed) of the Ab-3 LC:

```
                                            (SEQ ID NO: 126)
  1 GAAATTGTGC TCACCCAGTC TCCAGCACTC ATGGCTGCAT CTCCGGGGGA

 51 GAAGGTCACC ATCACCTGCA GTGTCAGTTC AACTATAAGT TCCAACCACT

101 TGCACTGGTT CCAGCAGAAG TCAGACACCT CCCCCAAACC CTGGATTTAT

151 GGCACATCCA ACCTGGCTTC TGGAGTCCCT GTTCGCTTCA GTGGCAGTGG

201 ATCTGGGACC TCTTATTCTC TCACAATCAG CAGCATGGAG GCTGAGGATG

251 CTGCCACTTA TTACTGTCAA CAGTGGAGTA GTTACCCACT CACGTTCGGC

301 GCTGGGACCA AGCTGGAGCT GAGACGGGCT GATGCTGCAC CAACTGTATC

351 CATCTTCCCA CCATCCAGTG AGCAGTTAAC ATCTGGAGGT GCCTCAGTCG

401 TGTGCTTCTT GAACAACTTC TACCCCAAAG ACATCAATGT CAAGTGGAAG

451 ATTGATGGCA GTGAACGACA AAATGGCGTC CTGAACAGTT GGACTGATCA

501 GGACAGCAAA GACAGCACCT ACAGCATGAG CAGCACCCTC ACGTTGACCA

551 AGGACGAGTA TGAACGACAT AACAGCTATA CCTGTGAGGC CACTCACAAG

601 ACATCAACTT CACCCATTGT CAAGAGCTTC AACAGGAATG AGTGTTAG
```

Amino acid sequence of the Ab-3 LC including signal peptide:

```
                                            (SEQ ID NO: 127)
  1 MDFHVQIFSF MLISVTVILS SGEIVLTQSP ALMAASPGEK VTITCSVSST

 51 ISSNHLHWFQ QKSDTSPKPW IYGTSNLASG VPVRFSGSGS GTSYSLTISS

101 MEAEDAATYY CQQWSSYPLT FGAGTKLELR RADAAPTVSI FPPSSEQLTS

151 GGASVVCFLN NFYPKDINVK WKIDGSERQN GVLNSWTDQD SKDSTYSMSS

201 TLTLTKDEYE RHNSYTCEAT HKTSTSPIVK SFNRNEC
```

Nucleic acid sequence of the Ab-3 LC including signal peptide encoding sequence:

```
                                            (SEQ ID NO: 128)
  1 ATGGATTTTC ATGTGCAGAT TTTCAGCTTC ATGCTAATCA GTGTCACAGT

 51 CATTTTGTCC AGTGGAGAAA TTGTGCTCAC CCAGTCTCCA GCACTCATGG

101 CTGCATCTCC GGGGGAGAAG GTCACCATCA CCTGCAGTGT CAGTTCAACT

151 ATAAGTTCCA ACCACTTGCA CTGGTTCCAG CAGAAGTCAG ACACCTCCCC

201 CAAACCCTGG ATTTATGGCA CATCCAACCT GGCTTCTGGA GTCCCTGTTC

251 GCTTCAGTGG CAGTGGATCT GGGACCTCTT ATTCTCTCAC AATCAGCAGC

301 ATGGAGGCTG AGGATGCTGC CACTTATTAC TGTCAACAGT GGAGTAGTTA

351 CCCACTCACG TTCGGCGCTG GGACCAAGCT GGAGCTGAGA CGGGCTGATG

401 CTGCACCAAC TGTATCCATC TTCCCACCAT CCAGTGAGCA GTTAACATCT

451 GGAGGTGCCT CAGTCGTGTG CTTCTTGAAC AACTTCTACC CCAAAGACAT

501 CAATGTCAAG TGGAAGATTG ATGGCAGTGA ACGACAAAAT GGCGTCCTGA
```

-continued

```
551 ACAGTTGGAC TGATCAGGAC AGCAAAGACA GCACCTACAG CATGAGCAGC

601 ACCCTCACGT TGACCAAGGA CGAGTATGAA CGACATAACA GCTATACCTG

651 TGAGGCCACT CACAAGACAT CAACTTCACC CATTGTCAAG AGCTTCAACA

701 GGAATGAGTG TTAG
```

Ab-3 Heavy Chain

Amino acid sequence of the mature form (signal peptide removed) of the Ab-3 HC:

```
                                                  (SEQ ID NO: 129)
  1 EVQLQQSGAE LVRPGALVKL SCTASDFNIK DFYLHWMRQR PEQGLDWIGR

 51 IDPENGDTLY DPKFQDKATL TTDTSSNTAY LQLSGLTSET TAVYYCSREA

101 DYFHDGTSYW YFDVWGAGTT ITVSSAKTTP PSVYPLAPGS AAQTNSMVTL

151 GCLVKGYFPE PVTVTWNSGS LSSGVHTFPA VLQSDLYTLS SSVTVPSSTW

201 PSETVTCNVA HPASSTKVDK KIVPRDCGCK PCICTVPEVS SVFIFPPKPK

251 DVLTITLTPK VTCVVVDISK DDPEVQFSWF VDDVEVHTAQ TQPREEQFNS

301 TFRSVSELPI MHQDWLNGKE FKCRVNSAAF PAPIEKTISK TKGRPKAPQV

351 YTIPPPKEQM AKDKVSLTCM ITDFFPEDIT VEWQWNGQPA ENYKNTQPIM

401 DTDGSYFIYS KLNVQKSNWE AGNTFTCSVL HEGLHNHHTE KSLSHSPGK
```

Nucleic acid sequence encoding the mature form (signal peptide removed) of the Ab-3 HC:

```
                                                  (SEQ ID NO: 130)
  1 GAGGTTCAGC TGCAGCAGTC TGGGGCTGAA CTTGTGAGGC CAGGGGCCTT

 51 AGTCAAGTTG TCCTGCACAG CTTCTGACTT CAACATTAAA GACTTCTATC

101 TACACTGGAT GAGGCAGCGG CCTGAACAGG GCCTGGACTG GATTGGAAGG

151 ATTGATCCTG AGAATGGTGA TACTTTATAT GACCCGAAGT TCCAGGACAA

201 GGCCACTCTT ACAACAGACA CATCCTCCAA CACAGCCTAC CTGCAGCTCA

251 GCGGCCTGAC ATCTGAGACC ACTGCCGTCT ATTACTGTTC TAGAGAGGCG

301 GATTATTTCC ACGATGGTAC CTCCTACTGG TACTTCGATG TCTGGGGCGC

351 AGGGACCACA ATCACCGTCT CCTCAGCCAA AACGACACCC CCATCTGTCT

401 ATCCACTGGC CCCTGGATCT GCTGCCCAAA CTAACTCCAT GGTGACCCTG

451 GGATGCCTGG TCAAGGGCTA TTTCCCTGAG CCAGTGACAG TGACCTGGAA

501 CTCTGGATCC CTGTCCAGCG GTGTGCACAC CTTCCCAGCT GTCCTGCAGT

551 CTGACCTCTA CACTCTGAGC AGCTCAGTGA CTGTCCCCTC CAGCACCTGG

601 CCCAGCGAGA CCGTCACCTG CAACGTTGCC CACCCGGCCA GCAGCACCAA

651 GGTGGACAAG AAAATTGTGC CCAGGGATTG TGGTTGTAAG CCTTGCATAT

701 GTACAGTCCC AGAAGTATCA TCTGTCTTCA TCTTCCCCCC AAAGCCCAAG

751 GATGTGCTCA CCATTACTCT GACTCCTAAG GTCACGTGTG TTGTGGTAGA

801 CATCAGCAAG GATGATCCCG AGGTCCAGTT CAGCTGGTTT GTAGATGATG

851 TGGAGGTGCA CACAGCTCAG ACGCAACCCC GGGAGGAGCA GTTCAACAGC

901 ACTTTCCGCT CAGTCAGTGA ACTTCCCATC ATGCACCAGG ACTGGCTCAA

951 TGGCAAGGAG TTCAAATGCA GGGTCAACAG TGCAGCTTTC CCTGCCCCCA
```

-continued

1001 TCGAGAAAAC CATCTCCAAA ACCAAAGGCA GACCGAAGGC TCCACAGGTG

1051 TACACCATTC CACCTCCCAA GGAGCAGATG GCCAAGGATA AAGTCAGTCT

1101 GACCTGCATG ATAACAGACT TCTTCCCTGA AGACATTACT GTGGAGTGGC

1151 AGTGGAATGG GCAGCCAGCG GAGAACTACA AGAACACTCA GCCCATCATG

1201 GACACAGATG GCTCTTACTT CATCTACAGC AAGCTCAATG TGCAGAAGAG

1251 CAACTGGGAG GCAGGAAATA CTTTCACCTG CTCTGTGTTA CATGAGGGCC

1301 TGCACAACCA CCATACTGAG AAGAGCCTCT CCCACTCTCC TGGTAAATGA

Amino acid sequence of the Ab-3 HC including signal peptide:

(SEQ ID NO: 131)

1 MKCSWVIFFL MAVVTGVNSE VQLQQSGAEL VRPGALVKLS CTASDFNIKD

51 FYLHWMRQRP EQGLDWIGRI DPENGDTLYD PKFQDKATLT TDTSSNTAYL

101 QLSGLTSETT AVYYCSREAD YFHDGTSYWY FDVWGAGTTI TVSSAKTTPP

151 SVYPLAPGSA AQTNSMVTLG CLVKGYFPEP VTVTWNSGSL SSGVHTFPAV

201 LQSDLYTLSS SVTVPSSTWP SETVTCNVAH PASSTKVDKK IVPRDCGCKP

251 CICTVPEVSS VFIFPPKPKD VLTITLTPKV TCVVVDISKD DPEVQFSWFV

301 DDVEVHTAQT QPREEQFNST FRSVSELPIM HQDWLNGKEF KCRVNSAAFP

351 APIEKTISKT KGRPKAPQVY TIPPPKEQMA KDKVSLTCMI TDFFPEDITV

401 EWQWNGQPAE NYKNTQPIMD TDGSYFIYSK LNVQKSNWEA GNTFTCSVLH

451 EGLHNHHTEK SLSHSPGK

Nucleic acid sequence of the Ab-3 HC including signal peptide encoding sequence:

(SEQ ID NO: 132)

1 ATGAAATGCA GCTGGGTCAT CTTCTTCCTG ATGGCAGTGG TTACAGGGGT

51 CAATTCAGAG GTTCAGCTGC AGCAGTCTGG GGCTGAACTT GTGAGGCCAG

101 GGGCCTTAGT CAAGTTGTCC TGCACAGCTT CTGACTTCAA CATTAAAGAC

151 TTCTATCTAC ACTGGATGAG GCAGCGGCCT GAACAGGGCC TGGACTGGAT

201 TGGAAGGATT GATCCTGAGA ATGGTGATAC TTTATATGAC CCGAAGTTCC

251 AGGACAAGGC CACTCTTACA ACAGACACAT CCTCCAACAC AGCCTACCTG

301 CAGCTCAGCG GCCTGACATC TGAGACCACT GCCGTCTATT ACTGTTCTAG

351 AGAGGCGGAT TATTTCCACG ATGGTACCTC CTACTGGTAC TTCGATGTCT

401 GGGGCGCAGG GACCACAATC ACCGTCTCCT CAGCCAAAAC GACACCCCCA

451 TCTGTCTATC CACTGGCCCC TGGATCTGCT GCCCAAACTA ACTCCATGGT

501 GACCCTGGGA TGCCTGGTCA AGGGCTATTT CCCTGAGCCA GTGACAGTGA

551 CCTGGAACTC TGGATCCCTG TCCAGCGGTG TGCACACCTT CCCAGCTGTC

601 CTGCAGTCTG ACCTCTACAC TCTGAGCAGC TCAGTGACTG TCCCCTCCAG

651 CACCTGGCCC AGCGAGACCG TCACCTGCAA CGTTGCCCAC CCGGCCAGCA

701 GCACCAAGGT GGACAAGAAA ATTGTGCCCA GGGATTGTGG TTGTAAGCCT

751 TGCATATGTA CAGTCCCAGA AGTATCATCT GTCTTCATCT TCCCCCCAAA

801 GCCCAAGGAT GTGCTCACCA TTACTCTGAC TCCTAAGGTC ACGTGTGTTG

-continued

```
 851 TGGTAGACAT CAGCAAGGAT GATCCCGAGG TCCAGTTCAG CTGGTTTGTA

 901 GATGATGTGG AGGTGCACAC AGCTCAGACG CAACCCCGGG AGGAGCAGTT

 951 CAACAGCACT TTCCGCTCAG TCAGTGAACT TCCCATCATG CACCAGGACT

1001 GGCTCAATGG CAAGGAGTTC AAATGCAGGG TCAACAGTGC AGCTTTCCCT

1051 GCCCCCATCG AGAAAACCAT CTCCAAAACC AAAGGCAGAC CGAAGGCTCC

1101 ACAGGTGTAC ACCATTCCAC CTCCCAAGGA GCAGATGGCC AAGGATAAAG

1151 TCAGTCTGAC CTGCATGATA ACAGACTTCT TCCCTGAAGA CATTACTGTG

1201 GAGTGGCAGT GGAATGGGCA GCCAGCGGAG AACTACAAGA ACACTCAGCC

1251 CATCATGGAC ACAGATGGCT CTTACTTCAT CTACAGCAAG CTCAATGTGC

1301 AGAAGAGCAA CTGGGAGGCA GGAAATACTT TCACCTGCTC TGTGTTACAT

1351 GAGGGCCTGC ACAACCACCA TACTGAGAAG AGCCTCTCCC ACTCTCCTGG

1401 TAAATGA
```

Ab-4

The sequences of the Antibody 4 (also referred to herein as Ab-4) LC and HC are as follows:

Ab-4 Light Chain:

Amino acid sequence of the mature form (signal peptide removed) of the Ab-4 LC:

(SEQ ID NO: 133)

1 DIQMTQITSS LSASLGDRVS ISCRASQDIS NYLNWYQQKP DGTFKLLIFY

51 TSRLLSGVPS RFSGSGSGTD YSLTIYNLEQ EDFATYFCQQ GDTLPYTFGG

101 GTKLEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-4 LC:

(SEQ ID NO: 134)

```
  1 GATATCCAGA TGACACAGAT TACATCCTCC CTGTCTGCCT CTCTGGGAGA

 51 CAGGGTCTCC ATCAGTTGCA GGGCAAGTCA AGACATTAGC AATTATTTAA

101 ACTGGTATCA GCAGAAACCA GATGGAACTT TTAAACTCCT TATCTTCTAC

151 ACATCAAGAT TACTCTCAGG AGTCCCATCA AGGTTCAGTG GCAGTGGGTC

201 TGGAACAGAT TATTCTCTCA CCATTTACAA CCTGGAGCAA GAAGATTTTG

251 CCACTTACTT TTGCCAACAG GGAGATACGC TTCCGTACAC TTTCGGAGGG

301 GGGACCAAGC TGGAAATAAA ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG
```

Amino acid sequence of the Ab-4 LC including signal peptide:

(SEQ ID NO: 135)

```
  1 MMSSAQFLGL LLLCFQGTRC DIQMTQITSS LSASLGDRVS ISCRASQDIS
 51 NYLNWYQQKP DGTFKLLIFY TSRLLSGVPS RFSGSGSGTD YSLTIYNLEQ
101 EDFATYFCQQ GDTLPYTFGG GTKLEIKRAD AAPTVSIFPP SSEQLTSGGA
151 SVVCFLNNFY PKDINVKWKI DGSERQNGVL NSWTDQDSKD STYSMSSTLT
201 LTKDEYERHN SYTCEATHKT STSPIVKSFN RNEC
```

Nucleic acid sequence of the Ab-4 LC including signal peptide encoding sequence:

(SEQ ID NO: 136)

```
  1 ATGATGTCCT CTGCTCAGTT CCTTGGTCTC CTGTTGCTCT GTTTTCAAGG
 51 TACCAGATGT GATATCCAGA TGACACAGAT TACATCCTCC CTGTCTGCCT
101 CTCTGGGAGA CAGGGTCTCC ATCAGTTGCA GGGCAAGTCA AGACATTAGC
151 AATTATTTAA ACTGGTATCA GCAGAAACCA GATGGAACTT TTAAACTCCT
201 TATCTTCTAC ACATCAAGAT TACTCTCAGG AGTCCCATCA AGGTTCAGTG
251 GCAGTGGGTC TGGAACAGAT TATTCTCTCA CCATTTACAA CCTGGAGCAA
301 GAAGATTTTG CCACTTACTT TTGCCAACAG GGAGATACGC TTCCGTACAC
351 TTTCGGAGGG GGGACCAAGC TGGAAATAAA ACGGGCTGAT GCTGCACCAA
401 CTGTATCCAT CTTCCCACCA TCCAGTGAGC AGTTAACATC TGGAGGTGCC
451 TCAGTCGTGT GCTTCTTGAA CAACTTCTAC CCCAAAGACA TCAATGTCAA
501 GTGGAAGATT GATGGCAGTG AACGACAAAA TGGCGTCCTG AACAGTTGGA
551 CTGATCAGGA CAGCAAAGAC AGCACCTACA GCATGAGCAG CACCCTCACG
601 TTGACCAAGG ACGAGTATGA ACGACATAAC AGCTATACCT GTGAGGCCAC
651 TCACAAGACA TCAACTTCAC CCATTGTCAA GAGCTTCAAC AGGAATGAGT
701 GTTAG
```

Ab-4 Heavy Chain:

Amino acid sequence of the mature form (signal peptide removed) of the Ab-4 HC:

(SEQ ID NO: 137)

```
  1 EVQLQQSGPE LMKPGASVKM SCKASGYTFT DYNMHWVKQN QGKTLEWIGE
 51 INPNSGGAGY NQKFKGKATL TVDKSSTTAY MELRSLTSED SAVYYCARLG
101 YDDIYDDWYF DVWGAGTTVT VSSAKTTPPS VYPLAPGSAA QTNSMVTLGC
151 LVKGYFPEPV TVTWNSGSLS SGVHTFPAVL QSDLYTLSSS VTVPSSTWPS
201 ETVTCNVAHP ASSTKVDKKI VPRDCGCKPC ICTVPEVSSV FIFPPKPKDV
251 LTITLTPKVT CVVVDISKDD PEVQFSWFVD DVEVHTAQTQ PREEQFNSTF
301 RSVSELPIMH QDWLNGKEFK CRVNSAAFPA PIEKTISKTK GRPKAPQVYT
351 IPPPKEQMAK DKVSLTCMIT DFFPEDITVE WQWNGQPAEN YKNTQPIMDT
401 DGSYFIYSKL NVQKSNWEAG NTFTCSVLHE GLHNHHTEKS LSHSPGK
```

Nucleic acid sequence encoding the mature form (signal peptide removed) of the Ab-4 HC:

```
                                            (SEQ ID NO: 138)
   1 GAGGTCCAAC TGCAACAGTC TGGACCTGAA CTAATGAAGC CTGGGGCTTC
  51 AGTGAAGATG TCCTGCAAGG CTTCTGGATA TACATTCACT GACTACAACA
 101 TGCACTGGGT GAAGCAGAAC CAAGGAAAGA CCCTAGAGTG GATAGGAGAA
 151 ATTAATCCTA ACAGTGGTGG TGCTGGCTAC AACCAGAAGT TCAAGGGCAA
 201 GGCCACATTG ACTGTAGACA AGTCCTCCAC CACAGCCTAC ATGGAGCTCC
 251 GCAGCCTGAC ATCTGAGGAC TCTGCAGTCT ATTACTGTGC AAGATTGGGC
 301 TACGATGATA TCTACGACGA CTGGTACTTC GATGTCTGGG GCGCAGGGAC
 351 CACGGTCACC GTCTCCTCAG CCAAAACGAC ACCCCCATCT GTCTATCCAC
 401 TGGCCCCTGG ATCTGCTGCC CAAACTAACT CCATGGTGAC CCTGGGATGC
 451 CTGGTCAAGG GCTATTTCCC TGAGCCAGTG ACAGTGACCT GGAACTCTGG
 501 ATCCCTGTCC AGCGGTGTGC ACACCTTCCC AGCTGTCCTG CAGTCTGACC
 551 TCTACACTCT GAGCAGCTCA GTGACTGTCC CCTCCAGCAC CTGGCCCAGC
 601 GAGACCGTCA CCTGCAACGT TGCCCACCCG GCCAGCAGCA CCAAGGTGGA
 651 CAAGAAAATT GTGCCCAGGG ATTGTGGTTG TAAGCCTTGC ATATGTACAG
 701 TCCCAGAAGT ATCATCTGTC TTCATCTTCC CCCCAAAGCC CAAGGATGTG
 751 CTCACCATTA CTCTGACTCC TAAGGTCACG TGTGTTGTGG TAGACATCAG
 801 CAAGGATGAT CCCGAGGTCC AGTTCAGCTG GTTTGTAGAT GATGTGGAGG
 851 TGCACACAGC TCAGACGCAA CCCCGGGAGG AGCAGTTCAA CAGCACTTTC
 901 CGCTCAGTCA GTGAACTTCC CATCATGCAC CAGGACTGGC TCAATGGCAA
 951 GGAGTTCAAA TGCAGGGTCA ACAGTGCAGC TTTCCCTGCC CCCATCGAGA
1001 AAACCATCTC CAAAACCAAA GGCAGACCGA AGGCTCCACA GGTGTACACC
1051 ATTCCACCTC CCAAGGAGCA GATGGCCAAG GATAAAGTCA GTCTGACCTG
1101 CATGATAACA GACTTCTTCC CTGAAGACAT TACTGTGGAG TGGCAGTGGA
1151 ATGGGCAGCC AGCGGAGAAC TACAAGAACA CTCAGCCCAT CATGGACACA
1201 GATGGCTCTT ACTTCATCTA CAGCAAGCTC AATGTGCAGA AGAGCAACTG
1251 GGAGGCAGGA AATACTTTCA CCTGCTCTGT GTTACATGAG GGCCTGCACA
1301 ACCACCATAC TGAGAAGAGC CTCTCCCACT CTCCTGGTAA ATGA
```

Amino acid sequence of the Ab-4 HC including signal peptide:

```
                                            (SEQ ID NO: 139)
   1 MGWSWTFLFL LSGTAGVLSE VQLQQSGPEL MKPGASVKMS CKASGYTFTD
  51 YNMHWVKQNQ GKTLEWIGEI NPNSGGAGYN QKFKGKATLT VDKSSTTAYM
 101 ELRSLTSEDS AVYYCARLGY DDIYDDWYFD VWGAGTTVTV SSAKTTPPSV
 151 YPLAPGSAAQ TNSMVTLGCL VKGYFPEPVT VTWNSGSLSS GVHTFPAVLQ
 201 SDLYTLSSSV TVPSSTWPSE TVTCNVAHPA SSTKVDKKIV PRDCGCKPCI
 251 CTVPEVSSVF IFPPKPKDVL TITLTPKVTC VVVDISKDDP EVQFSWFVDD
 301 VEVHTAQTQP REEQFNSTFR SVSELPIMHQ DWLNGKEFKC RVNSAAFPAP
 351 IEKTISKTKG RPKAPQVYTI PPPKEQMAKD KVSLTCMITD FFPEDITVEW
```

-continued

```
401 QWNGQPAENY KNTQPIMDTD GSYFIYSKLN VQKSNWEAGN TFTCSVLHEG

451 LHNHHTEKSL SHSPGK
```

Nucleic acid sequence of the Ab-4 HC including signal peptide encoding sequence:

```
                                        (SEQ ID NO: 140)
   1 ATGGGATGGA GCTGGACCTT TCTCTTCCTC CTGTCAGGAA CTGCAGGTGT

  51 CCTCTCTGAG GTCCAACTGC AACAGTCTGG ACCTGAACTA ATGAAGCCTG

 101 GGGCTTCAGT GAAGATGTCC TGCAAGGCTT CTGGATATAC ATTCACTGAC

 151 TACAACATGC ACTGGGTGAA GCAGAACCAA GGAAAGACCC TAGAGTGGAT

 201 AGGAGAAATT AATCCTAACA GTGGTGGTGC TGGCTACAAC CAGAAGTTCA

 251 AGGGCAAGGC CACATTGACT GTAGACAAGT CCTCCACCAC AGCCTACATG

 301 GAGCTCCGCA GCCTGACATC TGAGGACTCT GCAGTCTATT ACTGTGCAAG

 351 ATTGGGCTAC GATGATATCT ACGACGACTG GTACTTCGAT GTCTGGGGCG

 401 CAGGGACCAC GGTCACCGTC TCCTCAGCCA AAACGACACC CCCATCTGTC

 451 TATCCACTGG CCCCTGGATC TGCTGCCCAA ACTAACTCCA TGGTGACCCT

 501 GGGATGCCTG GTCAAGGGCT ATTTCCCTGA GCCAGTGACA GTGACCTGGA

 551 ACTCTGGATC CCTGTCCAGC GGTGTGCACA CCTTCCCAGC TGTCCTGCAG

 601 TCTGACCTCT ACACTCTGAG CAGCTCAGTG ACTGTCCCCT CCAGCACCTG

 651 GCCCAGCGAG ACCGTCACCT GCAACGTTGC CCACCCGGCC AGCAGCACCA

 701 AGGTGGACAA GAAAATTGTG CCCAGGGATT GTGGTTGTAA GCCTTGCATA

 751 TGTACAGTCC CAGAAGTATC ATCTGTCTTC ATCTTCCCCC CAAAGCCCAA

 801 GGATGTGCTC ACCATTACTC TGACTCCTAA GGTCACGTGT GTTGTGGTAG

 851 ACATCAGCAA GGATGATCCC GAGGTCCAGT TCAGCTGGTT TGTAGATGAT

 901 GTGGAGGTGC ACACAGCTCA GACGCAACCC CGGGAGGAGC AGTTCAACAG

 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT

1101 GTACACCATT CCACCTCCCA AGGAGCAGAT GGCCAAGGAT AAAGTCAGTC

1151 TGACCTGCAT GATAACAGAC TTCTTCCCTG AAGACATTAC TGTGGAGTGG

1201 CAGTGGAATG GGCAGCCAGC GGAGAACTAC AAGAACACTC AGCCCATCAT

1251 GGACACAGAT GGCTCTTACT TCATCTACAG CAAGCTCAAT GTGCAGAAGA

1301 GCAACTGGGA GGCAGGAAAT ACTTTCACCT GCTCTGTGTT ACATGAGGGC

1351 CTGCACAACC ACCATACTGA GAAGAGCCTC TCCCACTCTC CTGGTAAATG

1401 A
```

Ab-4 was humanized to generate Ab-5.

Ab-5

The sequences of the Antibody 5 (also referred to herein as Ab-5) LC and HC are as follows:

Ab-5 Light Chain:

Amino acid sequence of the mature form (signal peptide removed) of the Ab-5 LC:

```
                                                    (SEQ ID NO: 141)
 1 DIQMTQSPSS LSASVGDRVT ITCRASQDIS NYLNWYQQKP GKAPKLLIYY

51 TSRLLSGVPS RFSGSGSGTD FTLTISSLQP EDFATYYCQQ GDTLPYTFGG
```

-continued

101 GTKVEIK*RTV AAPSVFIFPP SDEQLKSGTA SVVCLLNNFY PREAKVQWKV*

*151 DNALQSGNSQ ESVTEQDSKD STYSLSSTLT LSKADYEKHK VYACEVTHQG*

*201 LSSPVTKSFN RGEC*

Nucleic acid sequence encoding the mature form (signal peptide removed) of the Ab-5 LC:

(SEQ ID NO: 142)

1 GACATCCAGA TGACCCAGTC TCCATCCTCC CTCTCCGCAT CCGTAGGCGA

51 CCGCGTAACC ATAACATGTA GAGCATCTCA AGATATTTCC AACTATTTGA

101 ATTGGTACCA ACAAAAACCC GGCAAAGCAC CTAAACTCCT CATTTACTAT

151 ACATCAAGAC TCCTCTCCGG CGTTCCATCA CGATTCTCAG GCTCCGGCTC

201 CGGCACAGAT TTCACACTCA CTATTTCCTC CCTCCAACCA GAAGATTTTG

251 CAACCTATTA CTGTCAACAA GGCGATACAC TCCCATACAC ATTCGGCGGC

301 GGCACAAAAG TTGAAATTAA ACGTACGGTG GCTGCACCAT CTGTCTTCAT

351 CTTCCCGCCA TCTGATGAGC AGTTGAAATC TGGAACTGCC TCTGTTGTGT

401 GCCTGCTGAA TAACTTCTAT CCCAGAGAGG CCAAAGTACA GTGGAAGGTG

451 GATAACGCCC TCCAATCGGG TAACTCCCAG GAGAGTGTCA CAGAGCAGGA

501 CAGCAAGGAC AGCACCTACA GCCTCAGCAG CACCCTGACG CTGAGCAAAG

551 CAGACTACGA GAAACACAAA GTCTACGCCT GCGAAGTCAC CCATCAGGGC

601 CTGAGCTCGC CCGTCACAAA GAGCTTCAAC AGGGGAGAGT GT

Amino acid sequence of the Ab-5 LC including signal peptide:

(SEQ ID NO: 143)

1 MDMRVPAQLL GLLLLWLRGA RCDIQMTQSP SSLSASVGDR VTITCRASQD

51 ISNYLNWYQQ KPGKAPKLLI YYTSRLLSGV PSRFSGSGSG TDFTLTISSL

101 QPEDFATYYC QQGDTLPYTF GGGTKVEIKR TVAAPSVFIF PPSDEQLKSG

151 TASVVCLLNN FYPREAKVQW KVDNALQSGN SQESVTEQDS KDSTYSLSST

201 LTLSKADYEK HKVYACEVTH QGLSSPVTKS FNRGEC

Nucleic acid sequence of the Ab-5 LC including signal peptide encoding sequence:

(SEQ ID NO: 144)

1 ATGGACATGA GGGTCCCCGC TCAGCTCCTG GGGCTCCTGC TACTCTGGCT

51 CCGAGGTGCC AGATGTGACA TCCAGATGAC CCAGTCTCCA TCCTCCCTCT

101 CCGCATCCGT AGGCGACCGC GTAACCATAA CATGTAGAGC ATCTCAAGAT

151 ATTTCCAACT ATTTGAATTG GTACCAACAA AAACCCGGCA AAGCACCTAA

201 ACTCCTCATT TACTATACAT CAAGACTCCT CTCCGGCGTT CCATCACGAT

251 TCTCAGGCTC CGGCTCCGGC ACAGATTTCA CACTCACTAT TTCCTCCCTC

301 CAACCAGAAG ATTTTGCAAC CTATTACTGT CAACAAGGCG ATACACTCCC

351 ATACACATTC GGCGGCGGCA CAAAAGTTGA AATTAAACGT ACGGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

-continued

```
501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGT
```

Ab-5 Heavy Chain:

Amino acid sequence of the mature form (signal peptide removed) of the Ab-5 HC:

```
                                                  (SEQ ID NO: 145)
  1 EVQLVQSGAE VKKPGASVKV SCKASGYTFT DYNMHWVRQA PGQGLEWMGE

 51 INPNSGGAGY NQKFKGRVTM TTDTSTSTAY MELRSLRSDD TAVYYCARLG

101 YDDIYDDWYF DVWGQGTTVT VSSASTKGPS VFPLAPCSRS TSESTAALGC

151 LVKDYFPEPV TVSWNSGALT SGVHTFPAVL QSSGLYSLSS VVTVPSSNFG

201 TQTYTCNVDH KPSNTKVDKT VERKCCVECP PCPAPPVAGP SVFLFPPKPK

251 DTLMISRTPE VTCVVVDVSH EDPEVQFNWY VDGVEVHNAK TKPREEQFNS

301 TFRVVSVLTV VHQDWLNGKE YKCKVSNKGL PAPIEKTISK TKGQPREPQV

351 YTLPPSREEM TKNQVSLTCL VKGFYPSDIA VEWESNGQPE NNYKTTPPML

401 DSDGSFFLYS KLTVDKSRWQ QGNVFSCSVM HEALHNHYTQ KSLSLSPGK
```

Amino acid sequence of the mature form (signal peptide removed) of the Ab-5 HC without carboxy-terminal lysine:

```
                                                  (SEQ ID NO: 392)
  1 EVQLVQSGAE VKKPGASVKV SCKASGYTFT DYNMHWVRQA PGQGLEWMGE

 51 INPNSGGAGY NQKFKGRVTM TTDTSTSTAY MELRSLRSDD TAVYYCARLG

101 YDDIYDDWYF DVWGQGTTVT VSSASTKGPS VFPLAPCSRS TSESTAALGC

151 LVKDYFPEPV TVSWNSGALT SGVHTFPAVL QSSGLYSLSS VVTVPSSNFG

201 TQTYTCNVDH KPSNTKVDKT VERKCCVECP PCPAPPVAGP SVFLFPPKPK

251 DTLMISRTPE VTCVVVDVSH EDPEVQFNWY VDGVEVHNAK TKPREEQFNS

301 TFRVVSVLTV VHQDWLNGKE YKCKVSNKGL PAPIEKTISK TKGQPREPQV

351 YTLPPSREEM TKNQVSLTCL VKGFYPSDIA VEWESNGQPE NNYKTTPPML

401 DSDGSFFLYS KLTVDKSRWQ QGNVFSCSVM HEALHNHYTQ KSLSLSPG
```

Nucleic acid sequence encoding the mature form (signal peptide removed) of the Ab-5 HC:

```
                                                  (SEQ ID NO: 146)
  1  GAGGTGCAGC TGGTGCAGAG CGGCGCCGAG GTAAAAAAAC CAGGAGCAAG

 51  CGTTAAAGTT TCTTGTAAAG CAAGCGGATA TACATTTACA GATTACAACA

101  TGCATTGGGT AAGACAAGCG CCAGGACAAG GATTGGAATG GATGGGCGAA

151  ATTAACCCTA ATAGTGGAGG AGCAGGCTAC AATCAAAAAT TCAAAGGGAG

201  AGTTACAATG ACAACAGACA CAAGCACTTC AACAGCATAT ATGGAACTGC

251  GATCACTTAG AAGCGACGAT ACAGCTGTAT ACTATTGCGC ACGACTTGGG

301  TATGATGATA TATATGATGA CTGGTATTTC GATGTTTGGG GCCAGGGAAC
```

-continued

```
 351  AACAGTTACC GTCTCTAGTG CCTCCACCAA GGGCCCATCG GTCTTCCCCC
 401  TGGCGCCCTG CTCCAGGAGC ACCTCCGAGA GCACAGCGGC CCTGGGCTGC
 451  CTGGTCAAGG ACTACTTCCC CGAACCGGTG ACGGTGTCGT GGAACTCAGG
 501  CGCTCTGACC AGCGGCGTGC ACACCTTCCC AGCTGTCCTA CAGTCCTCAG
 551  GACTCTACTC CCTCAGCAGC GTGGTGACCG TGCCCTCCAG CAACTTCGGC
 601  ACCCAGACCT ACACCTGCAA CGTAGATCAC AAGCCCAGCA ACACCAAGGT
 651  GGACAAGACA GTTGAGCGCA AATGTTGTGT CGAGTGCCCA CCGTGCCCAG
 701  CACCACCTGT GGCAGGACCG TCAGTCTTCC TCTTCCCCCC AAAACCCAAG
 751  GACACCCTCA TGATCTCCCG GACCCCTGAG GTCACGTGCG TGGTGGTGGA
 801  CGTGAGCCAC GAAGACCCCG AGGTCCAGTT CAACTGGTAC GTGGACGGCG
 851  TGGAGGTGCA TAATGCCAAG ACAAAGCCAC GGGAGGAGCA GTTCAACAGC
 901  ACGTTCCGTG TGGTCAGCGT CCTCACCGTT GTGCACCAGG ACTGGCTGAA
 951  CGGCAAGGAG TACAAGTGCA AGGTCTCCAA CAAAGGCCTC CCAGCCCCCA
1001  TCGAGAAAAC CATCTCCAAA ACCAAAGGGC AGCCCCGAGA ACCACAGGTG
1051  TACACCCTGC CCCCATCCCG GGAGGAGATG ACCAAGAACC AGGTCAGCCT
1101  GACCTGCCTG GTCAAAGGCT TCTACCCCAG CGACATCGCC GTGGAGTGGG
1151  AGAGCAATGG GCAGCCGGAG AACAACTACA AGACCACACC TCCCATGCTG
1201  GACTCCGACG GCTCCTTCTT CCTCTACAGC AAGCTCACCG TGGACAAGAG
1251  CAGGTGGCAG CAGGGGAACG TCTTCTCATG CTCCGTGATG CATGAGGCTC
1301  TGCACAACCA CTACACGCAG AAGAGCCTCT CCCTGTCTCC GGGTAAA
```

Amino acid sequence of the Ab-5 HC including signal peptide:

```
                                             (SEQ ID NO: 147)
  1 MDWTWRILFL VAAATGAHSE VQLVQSGAEV KKPGASVKVS CKASGYTFTD
 51 YNMHWVRQAP GQGLEWMGEI NPNSGGAGYN QKFKGRVTMT TDTSTSTAYM
101 ELRSLRSDDT AVYYCARLGY DDIYDDWYFD VWGQGTTVTV SSASTKGPSV
151 FPLAPCSRST SESTAALGCL VKDYFPEPVT VSWNSGALTS GVHTFPAVLQ
201 SSGLYSLSSV VTVPSSNFGT QTYTCNVDHK PSNTKVDKTV ERKCCVECPP
251 CPAPPVAGPS VFLFPPKPKD TLMISRTPEV TCVVVDVSHE DPEVQFNWYV
301 DGVEVHNAKT KPREEQFNST FRVVSVLTVV HQDWLNGKEY KCKVSNKGLP
351 APIEKTISKT KGQPREPQVY TLPPSREEMT KNQVSLTCLV KGFYPSDIAV
401 EWESNGQPEN NYKTTPPMLD SDGSFFLYSK LTVDKSRWQQ GNVFSCSVMH
451 EALHNHYTQK SLSLSPGK
```

Nucleic acid sequence of the Ab-5 HC including signal peptide encoding sequence:

```
                                             (SEQ ID NO: 148)
  1  ATGGACTGGA CCTGGAGGAT CCTCTTCTTG GTGGCAGCAG CCACAGGAGC
 51  CCACTCCGAG GTGCAGCTGG TGCAGAGCGG CGCCGAGGTA AAAAAACCAG
101  GAGCAAGCGT TAAAGTTTCT TGTAAAGCAA GCGGATATAC ATTTACAGAT
151  TACAACATGC ATTGGGTAAG ACAAGCGCCA GGACAAGGAT TGGAATGGAT
```

-continued

```
 201 GGGCGAAATT AACCCTAATA GTGGAGGAGC AGGCTACAAT CAAAAATTCA
 251 AAGGGAGAGT TACAATGACA ACAGACACAA GCACTTCAAC AGCATATATG
 301 GAACTGCGAT CACTTAGAAG CGACGATACA GCTGTATACT ATTGCGCACG
 351 ACTTGGGTAT GATGATATAT ATGATGACTG GTATTTCGAT GTTTGGGGCC
 401 AGGGAACAAC AGTTACCGTC TCTAGTGCCT CCACCAAGGG CCCATCGGTC
 451 TTCCCCCTGG CGCCCTGCTC CAGGAGCACC TCCGAGAGCA CAGCGGCCCT
 501 GGGCTGCCTG GTCAAGGACT ACTTCCCCGA ACCGGTGACG GTGTCGTGGA
 551 ACTCAGGCGC TCTGACCAGC GGCGTGCACA CCTTCCCAGC TGTCCTACAG
 601 TCCTCAGGAC TCTACTCCCT CAGCAGCGTG GTGACCGTGC CCTCCAGCAA
 651 CTTCGGCACC CAGACCTACA CCTGCAACGT AGATCACAAG CCCAGCAACA
 701 CCAAGGTGGA CAAGACAGTT GAGCGCAAAT GTTGTGTCGA GTGCCCACCG
 751 TGCCCAGCAC CACCTGTGGC AGGACCGTCA GTCTTCCTCT TCCCCCCAAA
 801 ACCCAAGGAC ACCCTCATGA TCTCCCGGAC CCCTGAGGTC ACGTGCGTGG
 851 TGGTGGACGT GAGCCACGAA GACCCCGAGG TCCAGTTCAA CTGGTACGTG
 901 GACGGCGTGG AGGTGCATAA TGCCAAGACA AAGCCACGGG AGGAGCAGTT
 951 CAACAGCACG TTCCGTGTGG TCAGCGTCCT CACCGTTGTG CACCAGGACT
1001 GGCTGAACGG CAAGGAGTAC AAGTGCAAGG TCTCCAACAA AGGCCTCCCA
1051 GCCCCCATCG AGAAAACCAT CTCCAAAACC AAAGGGCAGC CCCGAGAACC
1101 ACAGGTGTAC ACCCTGCCCC CATCCCGGGA GGAGATGACC AAGAACCAGG
1151 TCAGCCTGAC CTGCCTGGTC AAAGGCTTCT ACCCCAGCGA CATCGCCGTG
1201 GAGTGGGAGA GCAATGGGCA GCCGGAGAAC AACTACAAGA CCACACCTCC
1251 CATGCTGGAC TCCGACGGCT CCTTCTTCCT CTACAGCAAG CTCACCGTGG
1301 ACAAGAGCAG GTGGCAGCAG GGGAACGTCT TCTCATGCTC CGTGATGCAT
1351 GAGGCTCTGC ACAACCACTA CACGCAGAAG AGCCTCTCCC TGTCTCCGGG
1401 TAAA
```

Ab-5 Variable Domains:

Ab-5 light chain variable domain amino acid sequence (without signal sequence):

```
                                          (SEQ ID NO: 376)
  1 DIQMTQSPSS LSASVGDRVT ITCRASQDIS NYLNWYQQKP GKAPKLLIYY
 51 TSRLLSGVPS RFSGSGSGTD FTLTISSLQP EDFATYYCQQ GDTLPYTFGG
101 GTKVEIK
```

Ab-5 light chain variable domain DNA sequence (without signal sequence):

```
                                          (SEQ ID NO: 377)
  1 GACATCCAGA TGACCCAGTC TCCATCCTCC CTCTCCGCAT CCGTAGGCGA
 51 CCGCGTAACC ATAACATGTA GAGCATCTCA AGATATTTCC AACTATTTGA
101 ATTGGTACCA ACAAAAACCC GGCAAAGCAC CTAAACTCCT CATTTACTAT
151 ACATCAAGAC TCCTCTCCGG CGTTCCATCA CGATTCTCAG GCTCCGGCTC
201 CGGCACAGAT TTCACACTCA CTATTTCCTC CCTCCAACCA GAAGATTTTG
```

-continued

```
251 CAACCTATTA CTGTCAACAA GGCGATACAC TCCCATACAC ATTCGGCGGC

301 GGCACAAAAG TTGAAATTAA A
```

Ab-5 heavy chain variable domain amino acid sequence (without signal sequence):

(SEQ ID NO: 378)

```
  1 EVQLVQSGAE VKKPGASVKV SCKASGYTFT DYNMHWVRQA PGQGLEWMGE

 51 INPNSGGAGY NQKFKGRVTM TTDTSTSTAY MELRSLRSDD TAVYYCARLG

101 YDDIYDDWYF DVWGQGTTVT VSS
```

Ab-5 heavy chain variable domain DNA sequence (without signal sequence):

(SEQ ID NO: 379)

```
  1 GAGGTGCAGC TGGTGCAGAG CGGCGCCGAG GTAAAAAAAC CAGGAGCAAG

 51 CGTTAAAGTT TCTTGTAAAG CAAGCGGATA TACATTTACA GATTACAACA

101 TGCATTGGGT AAGACAAGCG CCAGGACAAG GATTGGAATG GATGGGCGAA

151 ATTAACCCTA ATAGTGGAGG AGCAGGCTAC AATCAAAAAT TCAAAGGGAG

201 AGTTACAATG ACAACAGACA CAAGCACTTC AACAGCATAT ATGGAACTGC

251 GATCACTTAG AAGCGACGAT ACAGCTGTAT ACTATTGCGC ACGACTTGGG

301 TATGATGATA TATATGATGA CTGGTATTTC GATGTTTGGG GCCAGGGAAC

351 AACAGTTACC GTCTCTAGT
```

The CDR (complementarity determining region) sequences in the variable region of the heavy chain of Ab-5 are as follows:

(SEQ ID NO: 245)
CDR-H1: DYNMH (SEQ ID NO: 246)
CDR-H2: EINPNSGGAGYNQKFKG (SEQ ID NO: 247)
CDR-H3: LGYDDIYDDWYFDV

The light chain variable region CDR sequences of Ab-5 are:

(SEQ ID NO: 78)
CDR-L1: RASQDISNYLN (SEQ ID NO: 79)
CDR-L2: YTSRLLS (SEQ ID NO: 80)
CDR-L3: QQGDTLPYT

Ab-6

The sequences of the Antibody 6 (also referred to herein as Ab-6) LC and HC are as follows:

Ab-6 Light Chain:

Amino acid sequence of the mature form (signal peptide removed) of the Ab-6 LC:

(SEQ ID NO: 149)

```
  1 DIQMTQTTSS LSASLGDRVT ISCRASQDIS NYLNWFQQKP DGTLKLLIFY

 51 TSRLHSGVPS RFSGSGSGTD YSLTISNLEQ EDIATYFCQQ GDTLPYTFGG

101 GTKLEIRRAD AAPTVSIFPP SSEQLTSGGA SVVCFLNNFY PKDINVKWKI

151 DGSERQNGVL NSWTDQDSKD STYSMSSTLT LTKDEYERHN SYTCEATHKT

201 STSPIVKSFN RNEC
```

Nucleic acid sequence encoding the mature form (signal peptide removed) of the Ab-6 LC:

(SEQ ID NO: 150)

```
 1  GATATCCAGA TGACACAGAC TACATCCTCC CTGTCTGCCT CTCTGGGAGA

51  CAGAGTCACC ATCAGTTGCA GGGCAAGTCA GGACATTAGC AATTATTTAA
```

-continued

101 ACTGGTTTCA GCAGAAACCA GATGGAACTC TTAAACTCCT GATCTTCTAC

151 ACATCAAGAT TACACTCAGG AGTTCCATCA AGGTTCAGTG GCAGTGGGTC

201 TGGAACAGAT TATTCTCTCA CCATTAGCAA CCTGGAGCAA GAAGATATTG

251 CCACTTACTT TTGCCAACAG GGTGATACGC TTCCGTACAC GTTCGGGGGG

301 GGGACCAAGC TGGAAATAAG ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG

Amino acid sequence of the Ab-6 LC including signal peptide:

(SEQ ID NO: 151)

1 MMSSAQFLGL LLLCFQGTRC DIQMTQTTSS LSASLGDRVT ISCRASQDIS

51 NYLNWFQQKP DGTLKLLIFY TSRLHSGVPS RFSGSGSGTD YSLTISNLEQ

101 EDIATYFCQQ GDTLPYTFGG GTKLEIRRAD AAPTVSIFPP SSEQLTSGGA

151 SVVCFLNNFY PKDINVKWKI DGSERQNGVL NSWTDQDSKD STYSMSSTLT

201 LTKDEYERHN SYTCEATHKT STSPIVKSFN RNEC

Nucleic acid sequence of the Ab-6 LC including signal peptide encoding sequence:

(SEQ ID NO: 152)

1 ATGATGTCCT CTGCTCAGTT CCTTGGTCTC CTGTTGCTCT GTTTTCAAGG

51 TACCAGATGT GATATCCAGA TGACACAGAC TACATCCTCC CTGTCTGCCT

101 CTCTGGGAGA CAGAGTCACC ATCAGTTGCA GGGCAAGTCA GGACATTAGC

151 AATTATTTAA ACTGGTTTCA GCAGAAACCA GATGGAACTC TTAAACTCCT

201 GATCTTCTAC ACATCAAGAT TACACTCAGG AGTTCCATCA AGGTTCAGTG

251 GCAGTGGGTC TGGAACAGAT TATTCTCTCA CCATTAGCAA CCTGGAGCAA

301 GAAGATATTG CCACTTACTT TTGCCAACAG GGTGATACGC TTCCGTACAC

351 GTTCGGGGGG GGGACCAAGC TGGAAATAAG ACGGGCTGAT GCTGCACCAA

401 CTGTATCCAT CTTCCCACCA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC

651 TCACAAGACA TCAACTTCAC CCATTGTCAA GAGCTTCAAC AGGAATGAGT

701 GTTAG

Ab-6 Heavy Chain:

Amino acid sequence of the mature form (signal peptide removed) of the Ab-6 HC:

```
                                                   (SEQ ID NO: 153)
  1 EVQLQQSGPE LMKPGASVKM SCKASGYTFT DYNMHWVKQN QGKSLEWIGE

 51 INPNSGGSGY NQKFKGKATL TVDKSSSTAY MELRSLTSED SAVYYCARLV

101 YDGSYEDWYF DVWGAGTTVT VSSAKTTPPS VYPLAPGSAA QTNSMVTLGC

151 LVKGYFPEPV TVTWNSGSLS SGVHTFPAVL QSDLYTLSSS VTVPSSTWPS

201 ETVTCNVAHP ASSTKVDKKI VPRDCGCKPC ICTVPEVSSV FIFPPKPKDV

251 LTITLTPKVT CVVVDISKDD PEVQFSWFVD DVEVHTAQTQ PREEQFNSTF

301 RSVSELPIMH QDWLNGKEFK CRVNSAAFPA PIEKTISKTK GRPKAPQVYT

351 IPPPKEQMAK DKVSLTCMIT DFFPEDITVE WQWNGQPAEN YKNTQPIMDT

401 DGSYFIYSKL NVQKSNWEAG NTFTCSVLHE GLHNHHTEKS LSHSPGK
```

Nucleic acid sequence encoding the mature form (signal peptide removed) of the Ab-6 HC:

```
                                                      (SEQ ID NO: 154)
   1 GAGGTCCAGC TGCAACAGTC TGGACCTGAA CTAATGAAGC CTGGGGCTTC

  51 AGTGAAGATG TCCTGCAAGG CTTCTGGATA CACATTCACT GACTACAACA

 101 TGCACTGGGT GAAACAGAAC CAAGGAAAGA GCCTAGAGTG GATAGGAGAA

 151 ATTAATCCTA ACAGTGGTGG TAGTGGCTAC AACCAAAAGT TCAAAGGCAA

 201 GGCCACATTG ACTGTAGACA AGTCTTCCAG CACAGCCTAC ATGGAGCTCC

 251 GCAGCCTGAC ATCTGAGGAC TCTGCAGTCT ATTACTGTGC AAGATTGGTC

 301 TACGATGGCA GCTACGAGGA CTGGTACTTC GATGTCTGGG GCGCAGGGAC

 351 CACGGTCACC GTCTCCTCAG CCAAAACGAC ACCCCCATCT GTCTATCCAC

 401 TGGCCCCTGG ATCTGCTGCC CAAACTAACT CCATGGTGAC CCTGGGATGC

 451 CTGGTCAAGG GCTATTTCCC TGAGCCAGTG ACAGTGACCT GGAACTCTGG

 501 ATCCCTGTCC AGCGGTGTGC ACACCTTCCC AGCTGTCCTG CAGTCTGACC

 551 TCTACACTCT GAGCAGCTCA GTGACTGTCC CCTCCAGCAC CTGGCCCAGC

 601 GAGACCGTCA CCTGCAACGT TGCCCACCCG GCCAGCAGCA CCAAGGTGGA

 651 CAAGAAAATT GTGCCCAGGG ATTGTGGTTG TAAGCCTTGC ATATGTACAG

 701 TCCCAGAAGT ATCATCTGTC TTCATCTTCC CCCCAAAGCC CAAGGATGTG

 751 CTCACCATTA CTCTGACTCC TAAGGTCACG TGTGTTGTGG TAGACATCAG

 801 CAAGGATGAT CCCGAGGTCC AGTTCAGCTG GTTTGTAGAT GATGTGGAGG

 851 TGCACACAGC TCAGACGCAA CCCCGGGAGG AGCAGTTCAA CAGCACTTTC

 901 CGCTCAGTCA GTGAACTTCC CATCATGCAC CAGGACTGGC TCAATGGCAA

 951 GGAGTTCAAA TGCAGGGTCA ACAGTGCAGC TTTCCCTGCC CCCATCGAGA

1001 AAACCATCTC CAAAACCAAA GGCAGACCGA AGGCTCCACA GGTGTACACC

1051 ATTCCACCTC CCAAGGAGCA GATGGCCAAG GATAAAGTCA GTCTGACCTG

1101 CATGATAACA GACTTCTTCC CTGAAGACAT TACTGTGGAG TGGCAGTGGA

1151 ATGGGCAGCC AGCGGAGAAC TACAAGAACA CTCAGCCCAT CATGGACACA

1201 GATGGCTCTT ACTTCATCTA CAGCAAGCTC AATGTGCAGA AGAGCAACTG
```

-continued

```
1251 GGAGGCAGGA AATACTTTCA CCTGCTCTGT GTTACATGAG GGCCTGCACA

1301 ACCACCATAC TGAGAAGAGC CTCTCCCACT CTCCTGGTAA ATGA
```

Amino acid sequence of the Ab-6 HC including signal peptide:

```
                                         (SEQ ID NO: 155)
  1 MGWSWTFLFL LSGTAGVLSE VQLQQSGPEL MKPGASVKMS CKASGYTFTD

 51 YNMHWVKQNQ GKSLEWIGEI NPNSGGSGYN QKFKGKATLT VDKSSSTAYM

101 ELRSLTSEDS AVYYCARLVY DGSYEDWYFD VWGAGTTVTV SSAKTTPPSV

151 YPLAPGSAAQ TNSMVTLGCL VKGYFPEPVT VTWNSGSLSS GVHTFPAVLQ

201 SDLYTLSSSV TVPSSTWPSE TVTCNVAHPA SSTKVDKKIV PRDCGCKPCI

251 CTVPEVSSVF IFPPKPKDVL TITLTPKVTC VVVDISKDDP EVQFSWFVDD

301 VEVHTAQTQP REEQFNSTFR SVSELPIMHQ DWLNGKEFKC RVNSAAFPAP

351 IEKTISKTKG RPKAPQVYTI PPPKEQMAKD KVSLTCMITD FFPEDITVEW

401 QWNGQPAENY KNTQPIMDTD GSYFIYSKLN VQKSNWEAGN TFTCSVLHEG

451 LHNHHTEKSL SHSPGK
```

Nucleic acid sequence of the Ab-6 HC including signal peptide encoding sequence:

```
                                         (SEQ ID NO: 156)
   1 ATGGGATGGA GCTGGACCTT TCTCTTCCTC CTGTCAGGAA CTGCAGGTGT

  51 CCTCTCTGAG GTCCAGCTGC AACAGTCTGG ACCTGAACTA ATGAAGCCTG

 101 GGGCTTCAGT GAAGATGTCC TGCAAGGCTT CTGGATACAC ATTCACTGAC

 151 TACAACATGC ACTGGGTGAA ACAGAACCAA GGAAAGAGCC TAGAGTGGAT

 201 AGGAGAAATT AATCCTAACA GTGGTGGTAG TGGCTACAAC CAAAAGTTCA

 251 AAGGCAAGGC CACATTGACT GTAGACAAGT CTTCCAGCAC AGCCTACATG

 301 GAGCTCCGCA GCCTGACATC TGAGGACTCT GCAGTCTATT ACTGTGCAAG

 351 ATTGGTCTAC GATGGCAGCT ACGAGGACTG GTACTTCGAT GTCTGGGGCG

 401 CAGGGACCAC GGTCACCGTC TCCTCAGCCA AAACGACACC CCCATCTGTC

 451 TATCCACTGG CCCCTGGATC TGCTGCCCAA ACTAACTCCA TGGTGACCCT

 501 GGGATGCCTG GTCAAGGGCT ATTTCCCTGA GCCAGTGACA GTGACCTGGA

 551 ACTCTGGATC CCTGTCCAGC GGTGTGCACA CCTTCCCAGC TGTCCTGCAG

 601 TCTGACCTCT ACACTCTGAG CAGCTCAGTG ACTGTCCCCT CCAGCACCTG

 651 GCCCAGCGAG ACCGTCACCT GCAACGTTGC CCACCCGGCC AGCAGCACCA

 701 AGGTGGACAA GAAAATTGTG CCCAGGGATT GTGGTTGTAA GCCTTGCATA

 751 TGTACAGTCC CAGAAGTATC ATCTGTCTTC ATCTTCCCCC CAAAGCCCAA

 801 GGATGTGCTC ACCATTACTC TGACTCCTAA GGTCACGTGT GTTGTGGTAG

 851 ACATCAGCAA GGATGATCCC GAGGTCCAGT TCAGCTGGTT TGTAGATGAT

 901 GTGGAGGTGC ACACAGCTCA GACGCAACCC CGGGAGGAGC AGTTCAACAG

 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT
```

-continued

```
1101 GTACACCATT CCACCTCCCA AGGAGCAGAT GGCCAAGGAT AAAGTCAGTC
1151 TGACCTGCAT GATAACAGAC TTCTTCCCTG AAGACATTAC TGTGGAGTGG
1201 CAGTGGAATG GGCAGCCAGC GGAGAACTAC AAGAACACTC AGCCCATCAT
1251 GGACACAGAT GGCTCTTACT TCATCTACAG CAAGCTCAAT GTGCAGAAGA
1301 GCAACTGGGA GGCAGGAAAT ACTTTCACCT GCTCTGTGTT ACATGAGGGC
1351 CTGCACAACC ACCATACTGA GAAGAGCCTC TCCCACTCTC CTGGTAAATG
1401 A
```

Ab-7

The sequences of the Antibody 7 (also referred to herein as Ab-7) LC and HC are as follows:

Ab-7 Light Chain:

Amino acid sequence of the mature form (signal peptide removed) of the Ab-7 LC:

(SEQ ID NO: 157)

1 DIQMTQTTSS LSASLGDRVT ICCRASQVIT NYLYWYQQKP DGTFKLLIYY

51 TSRLHSGVPS RFSGSGSGTD YSLTISNLEQ EDIATYFCQQ GDTLPYTFGG

101 GTKLEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-7 LC:

(SEQ ID NO: 158)

```
  1 GATATCCAGA TGACACAGAC TACATCCTCC CTGTCTGCCT CTCTGGGAGA
 51 CAGAGTCACC ATCTGTTGCA GGGCAAGTCA GGTCATTACC AATTATTTAT
101 ACTGGTATCA GCAGAAACCA GATGGAACTT TTAAACTCCT GATCTACTAC
151 ACATCAAGAT TACACTCAGG AGTCCCATCA AGGTTCAGTG GCAGTGGGTC
201 TGGAACAGAT TATTCTCTCA CCATTAGCAA CCTGGAACAG GAAGATATTG
251 CCACTTACTT TTGCCAACAG GGTGATACGC TTCCGTACAC GTTCGGAGGG
301 GGGACCAAGC TGGAAATAAA ACGGGCTGAT GCTGCACCAA CTGTATCCAT
351 CTTCCCACCA TCCAGTGAGC AGTTAACATC TGGAGGTGCC TCAGTCGTGT
401 GCTTCTTGAA CAACTTCTAC CCCAAAGACA TCAATGTCAA GTGGAAGATT
451 GATGGCAGTG AACGACAAAA TGGCGTCCTG AACAGTTGGA CTGATCAGGA
501 CAGCAAAGAC AGCACCTACA GCATGAGCAG CACCCTCACG TTGACCAAGG
551 ACGAGTATGA ACGACATAAC AGCTATACCT GTGAGGCCAC TCACAAGACA
601 TCAACTTCAC CCATTGTCAA GAGCTTCAAC AGGAATGAGT GT
```

Amino acid sequence of the Ab-7 LC including signal peptide:

(SEQ ID NO: 159)

```
  1 MMSSAQFLGL LLLCFQGTRC DIQMTQTTSS LSASLGDRVT ICCRASQVIT
 51 NYLYWYQQKP DGTFKLLIYY TSRLHSGVPS RFSGSGSGTD YSLTISNLEQ
101 EDIATYFCQQ GDTLPYTFGG GTKLEIKRAD AAPTVSIFPP SSEQLTSGGA
```

-continued

```
151 SVVCFLNNFY PKDINVKWKI DGSERQNGVL NSWTDQDSKD STYSMSSTLT

201 LTKDEYERHN SYTCEATHKT STSPIVKSFN RNEC
```

Nucleic acid sequence of the Ab-7 LC including signal peptide encoding sequence:

```
                                      (SEQ ID NO: 160)
  1 ATGATGTCCT CTGCTCAGTT CCTTGGTCTC CTGTTGCTCT GTTTTCAAGG

 51 TACCAGATGT GATATCCAGA TGACACAGAC TACATCCTCC CTGTCTGCCT

101 CTCTGGGAGA CAGAGTCACC ATCTGTTGCA GGGCAAGTCA GGTCATTACC

151 AATTATTTAT ACTGGTATCA GCAGAAACCA GATGGAACTT TTAAACTCCT

201 GATCTACTAC ACATCAAGAT TACACTCAGG AGTCCCATCA AGGTTCAGTG

251 GCAGTGGGTC TGGAACAGAT TATTCTCTCA CCATTAGCAA CCTGGAACAG

301 GAAGATATTG CCACTTACTT TTGCCAACAG GGTGATACGC TTCCGTACAC

351 GTTCGGAGGG GGGACCAAGC TGGAAATAAA ACGGGCTGAT GCTGCACCAA

401 CTGTATCCAT CTTCCCACCA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC

651 TCACAAGACA TCAACTTCAC CCATTGTCAA GAGCTTCAAC AGGAATGAGT

701 GT
```

Ab-7 Heavy Chain:

Amino acid sequence of the mature form (signal peptide removed) of the Ab-7 HC:

(SEQ ID NO: 161)

1 EVQLQQSGPE LMKPGASVKM SCKASGYTFT DYNMHWMKQN QGKSLEWIGE

51 INPNSGGAGY NQQFKGKATL TVDKSSRTAY MELRSLTSED SAVYYCARLG

101 YVGNYEDWYF DVWGAGTTVT VSS*AKTTPPS VYPLAPGSAA QTNSMVTLGC*

*151 LVKGYFPEPV TVTWNSGSLS SGVHTFPAVL QSDLYTLSSS VTVPSSTWPS*

*201 ETVTCNVAHP ASSTKVDKKI VPRDCGCKPC ICTVPEVSSV FIFPPKPKDV*

*251 LTITLTPKVT CVVVDISKDD PEVQFSWFVD DVEVHTAQTQ PREEQFNSTF*

*301 RSVSELPIMH QDWLNGKEFK CRVNSAAFPA PIEKTISKTK GRPKAPQVYT*

*351 IPPPKEQMAK DKVSLTCMIT DFFPEDITVE WQWNGQPAEN YKNTQPIMDT*

*401 DGSYFIYSKL NVQKSNWEAG NTFTCSVLHE GLHNHHTEKS LSHSPGK*

Nucleic acid sequence encoding the mature form (signal peptide removed) of the Ab-7 HC:

```
                                      (SEQ ID NO: 162)
  1 GAGGTCCAGC TGCAACAGTC TGGACCTGAA CTAATGAAGC CTGGGGCTTC

 51 AGTGAAGATG TCCTGCAAGG CTTCTGGATA CACATTCACT GACTACAACA

101 TGCACTGGAT GAAGCAGAAC CAAGGAAAGA GCCTAGAATG GATAGGAGAA

151 ATTAATCCTA ACAGTGGTGG TGCTGGCTAC AACCAGCAGT TCAAAGGCAA
```

-continued

201 GGCCACATTG ACTGTAGACA AGTCCTCCAG GACAGCCTAC ATGGAGCTCC

251 GCAGCCTGAC ATCTGAGGAC TCTGCAGTCT ATTACTGTGC AAGATTGGGC

301 TACGTTGGTA ATTACGAGGA CTGGTACTTC GATGTCTGGG GCGCAGGGAC

351 CACGGTCACC GTCTCCTCAG CCAAAACGAC ACCCCCATCT GTCTATCCAC

401 TGGCCCCTGG ATCTGCTGCC CAAACTAACT CCATGGTGAC CCTGGGATGC

451 CTGGTCAAGG GCTATTTCCC TGAGCCAGTG ACAGTGACCT GGAACTCTGG

501 ATCCCTGTCC AGCGGTGTGC ACACCTTCCC AGCTGTCCTG CAGTCTGACC

551 TCTACACTCT GAGCAGCTCA GTGACTGTCC CCTCCAGCAC CTGGCCCAGC

601 GAGACCGTCA CCTGCAACGT TGCCCACCCG GCCAGCAGCA CCAAGGTGGA

651 CAAGAAAATT GTGCCCAGGG ATTGTGGTTG TAAGCCTTGC ATATGTACAG

701 TCCCAGAAGT ATCATCTGTC TTCATCTTCC CCCCAAAGCC CAAGGATGTG

751 CTCACCATTA CTCTGACTCC TAAGGTCACG TGTGTTGTGG TAGACATCAG

801 CAAGGATGAT CCCGAGGTCC AGTTCAGCTG GTTTGTAGAT GATGTGGAGG

851 TGCACACAGC TCAGACGCAA CCCCGGGAGG AGCAGTTCAA CAGCACTTTC

901 CGCTCAGTCA GTGAACTTCC CATCATGCAC CAGGACTGGC TCAATGGCAA

951 GGAGTTCAAA TGCAGGGTCA ACAGTGCAGC TTTCCCTGCC CCCATCGAGA

1001 AAACCATCTC CAAAACCAAA GGCAGACCGA AGGCTCCACA GGTGTACACC

1051 ATTCCACCTC CCAAGGAGCA GATGGCCAAG GATAAAGTCA GTCTGACCTG

1101 CATGATAACA GACTTCTTCC CTGAAGACAT TACTGTGGAG TGGCAGTGGA

1151 ATGGGCAGCC AGCGGAGAAC TACAAGAACA CTCAGCCCAT CATGGACACA

1201 GATGGCTCTT ACTTCATCTA CAGCAAGCTC AATGTGCAGA AGAGCAACTG

1251 GGAGGCAGGA AATACTTTCA CCTGCTCTGT GTTACATGAG GGCCTGCACA

1301 ACCACCATAC TGAGAAGAGC CTCTCCCACT CTCCTGGTAA A

Amino acid sequence of the Ab-7 HC including signal peptide:

(SEQ ID NO: 163)

1 MGWSWTFLFL LSGTAGVLSE VQLQQSGPEL MKPGASVKMS CKASGYTFTD

51 YNMHWMKQNQ GKSLEWIGEI NPNSGGAGYN QQFKGKATLT VDKSSRTAYM

101 ELRSLTSEDS AVYYCARLGY VGNYEDWYFD VWGAGTTVTV SSAKTTPPSV

151 YPLAPGSAAQ TNSMVTLGCL VKGYFPEPVT VTWNSGSLSS GVHTFPAVLQ

201 SDLYTLSSSV TVPSSTWPSE TVTCNVAHPA SSTKVDKKIV PRDCGCKPCI

251 CTVPEVSSVF IFPPKPKDVL TITLTPKVTC VVVDISKDDP EVQFSWFVDD

301 VEVHTAQTQP REEQFNSTFR SVSELPIMHQ DWLNGKEFKC RVNSAAFPAP

351 IEKTISKTKG RPKAPQVYTI PPPKEQMAKD KVSLTCMITD FFPEDITVEW

401 QWNGQPAENY KNTQPIMDTD GSYFIYSKLN VQKSNWEAGN TFTCSVLHEG

451 LHNHHTEKSL SHSPGK

Nucleic acid sequence of the Ab-7 HC including signal peptide encoding sequence:

(SEQ ID NO: 164)

1 ATGGGATGGA GCTGGACCTT TCTCTTCCTC CTGTCAGGAA CTGCAGGTGT

-continued

```
  51 CCTCTCTGAG GTCCAGCTGC AACAGTCTGG ACCTGAACTA ATGAAGCCTG

 101 GGGCTTCAGT GAAGATGTCC TGCAAGGCTT CTGGATACAC ATTCACTGAC

 151 TACAACATGC ACTGGATGAA GCAGAACCAA GGAAAGAGCC TAGAATGGAT

 201 AGGAGAAATT AATCCTAACA GTGGTGGTGC TGGCTACAAC CAGCAGTTCA

 251 AAGGCAAGGC CACATTGACT GTAGACAAGT CCTCCAGGAC AGCCTACATG

 301 GAGCTCCGCA GCCTGACATC TGAGGACTCT GCAGTCTATT ACTGTGCAAG

 351 ATTGGGCTAC GTTGGTAATT ACGAGGACTG GTACTTCGAT GTCTGGGGCG

 401 CAGGGACCAC GGTCACCGTC TCCTCAGCCA AAACGACACC CCCATCTGTC

 451 TATCCACTGG CCCCTGGATC TGCTGCCCAA ACTAACTCCA TGGTGACCCT

 501 GGGATGCCTG GTCAAGGGCT ATTTCCCTGA GCCAGTGACA GTGACCTGGA

 551 ACTCTGGATC CCTGTCCAGC GGTGTGCACA CCTTCCCAGC TGTCCTGCAG

 601 TCTGACCTCT ACACTCTGAG CAGCTCAGTG ACTGTCCCCT CCAGCACCTG

 651 GCCCAGCGAG ACCGTCACCT GCAACGTTGC CCACCCGGCC AGCAGCACCA

 701 AGGTGGACAA GAAAATTGTG CCCAGGGATT GTGGTTGTAA GCCTTGCATA

 751 TGTACAGTCC CAGAAGTATC ATCTGTCTTC ATCTTCCCCC CAAAGCCCAA

 801 GGATGTGCTC ACCATTACTC TGACTCCTAA GGTCACGTGT GTTGTGGTAG

 851 ACATCAGCAA GGATGATCCC GAGGTCCAGT TCAGCTGGTT TGTAGATGAT

 901 GTGGAGGTGC ACACAGCTCA GACGCAACCC CGGGAGGAGC AGTTCAACAG

 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT

1101 GTACACCATT CCACCTCCCA AGGAGCAGAT GGCCAAGGAT AAAGTCAGTC

1151 TGACCTGCAT GATAACAGAC TTCTTCCCTG AAGACATTAC TGTGGAGTGG

1201 CAGTGGAATG GGCAGCCAGC GGAGAACTAC AAGAACACTC AGCCCATCAT

1251 GGACACAGAT GGCTCTTACT TCATCTACAG CAAGCTCAAT GTGCAGAAGA

1301 GCAACTGGGA GGCAGGAAAT ACTTTCACCT GCTCTGTGTT ACATGAGGGC

1351 CTGCACAACC ACCATACTGA GAAGAGCCTC TCCCACTCTC CTGGTAAA
```

Ab-8

The sequences of the Antibody 8 (also referred to herein as Ab-8) LC and HC are as follows:

Ab-8 Light Chain:

Amino acid sequence of the mature form (signal peptide removed) of the Ab-8 LC:

(SEQ ID NO: 165)

1 DIQMTQTTSS LSASLGDRVS ISCRASQDIS NYLNWYQQKP DGTFKLLIFY

51 TSRLLSGVPS RFSGSGSGTD YSLTIYNLEQ EDFATYFCQQ GDTLPYTFGG

101 GTKLEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-8 LC:

```
                                              (SEQ ID NO: 166)
  1 GATATCCAGA TGACACAGAC TACATCCTCC CTGTCTGCCT CTCTGGGAGA

 51 CAGGGTCTCC ATCAGTTGCA GGGCAAGTCA AGACATTAGC AATTATTTAA

101 ACTGGTATCA GCAGAAACCA GATGGAACTT TTAAACTCCT TATCTTCTAC

151 ACATCAAGAT TACTCTCAGG AGTCCCATCA AGGTTCAGTG GCAGTGGGTC

201 TGGAACAGAT TATTCTCTCA CCATTTACAA CCTGGAGCAA GAAGATTTTG

251 CCACTTACTT TTGCCAACAG GGAGATACGC TTCCGTACAC TTTCGGAGGG

301 GGGACCAAAC TGGAAATAAA ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG
```

Amino acid sequence of the Ab-8 LC including signal peptide:

```
                                              (SEQ ID NO: 167)
  1 MMSSAQFLGL LLLCFQGTRC DIQMTQTTSS LSASLGDRVS ISCRASQDIS

 51 NYLNWYQQKP DGTFKLLIFY TSRLLSGVPS RFSGSGSGTD YSLTIYNLEQ

101 EDFATYFCQQ GDTLPYTFGG GTKLEIKRAD AAPTVSIFPP SSEQLTSGGA

151 SVVCFLNNFY PKDINVKWKI DGSERQNGVL NSWTDQDSKD STYSMSSTLT

201 LTKDEYERHN SYTCEATHKT STSPIVKSFN RNEC
```

Nucleic acid sequence of the Ab-8 LC including signal peptide encoding sequence:

```
                                              (SEQ ID NO: 168)
  1 ATGATGTCCT CTGCTCAGTT CCTTGGTCTC CTGTTGCTCT GTTTTCAAGG

 51 TACCAGATGT GATATCCAGA TGACACAGAC TACATCCTCC CTGTCTGCCT

101 CTCTGGGAGA CAGGGTCTCC ATCAGTTGCA GGGCAAGTCA AGACATTAGC

151 AATTATTTAA ACTGGTATCA GCAGAAACCA GATGGAACTT TTAAACTCCT

201 TATCTTCTAC ACATCAAGAT TACTCTCAGG AGTCCCATCA AGGTTCAGTG

251 GCAGTGGGTC TGGAACAGAT TATTCTCTCA CCATTTACAA CCTGGAGCAA

301 GAAGATTTTG CCACTTACTT TTGCCAACAG GGAGATACGC TTCCGTACAC

351 TTTCGGAGGG GGGACCAAAC TGGAAATAAA ACGGGCTGAT GCTGCACCAA

401 CTGTATCCAT CTTCCCACCA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC
```

-continued

```
651 TCACAAGACA TCAACTTCAC CCATTGTCAA GAGCTTCAAC AGGAATGAGT

701 GTTAG
```

Ab-8 Heavy Chain:

Amino acid sequence of the mature form (signal peptide removed) of the Ab-8 HC:

```
                                                (SEQ ID NO: 169)
  1 EVQLQQSGPE LMKPGASVKM SCKASGYTFT DYNMHWVKQN QGKTLDWIGE

 51 INPNSGGAGY NQKFKGKATL TVDKSSTTAY MELRSLTSED SAVYYCARLG

101 YDDIYDDWYF DVWGAGTTVT VSSAKTTPPS VYPLAPGSAA QTNSMVTLGC

151 LVKGYFPEPV TVTWNSGSLS SGVHTFPAVL QSDLYTLSSS VTVPSSTWPS

201 ETVTCNVAHP ASSTKVDKKI VPRDCGCKPC ICTVPEVSSV FIFPPKPKDV

251 LTITLTPKVT CVVVDISKDD PEVQFSWFVD DVEVHTAQTQ PREEQFNSTF

301 RSVSELPIMH QDWLNGKEFK CRVNSAAFPA PIEKTISKTK GRPKAPQVYT

351 IPPPKEQMAK DKVSLTCMIT DFFPEDITVE WQWNGQPAEN YKNTQPIMDT

401 DGSYFIYSKL NVQKSNWEAG NTFTCSVLHE GLHNHHTEKS LSHSPGK
```

Nucleic acid sequence encoding the mature form (signal peptide removed) of the Ab-8 HC:

```
                                                (SEQ ID NO: 170)
   1 GAGGTCCAAC TGCAACAGTC TGGACCTGAA CTAATGAAGC CTGGGGCTTC

  51 AGTGAAGATG TCCTGCAAGG CTTCTGGATA TACATTCACT GACTACAACA

 101 TGCACTGGGT GAAGCAGAAC CAAGGAAAGA CCCTAGACTG GATAGGAGAA

 151 ATTAATCCTA ACAGTGGTGG TGCTGGCTAC AACCAGAAGT TCAAGGGCAA

 201 GGCCACATTG ACTGTAGACA AGTCCTCCAC CACAGCCTAC ATGGAGCTCC

 251 GCAGCCTGAC ATCTGAGGAC TCTGCAGTCT ATTACTGTGC AAGATTGGGC

 301 TACGATGATA TCTACGACGA CTGGTACTTC GATGTCTGGG GCGCAGGGAC

 351 CACGGTCACC GTCTCCTCAG CCAAAACGAC ACCCCCATCT GTCTATCCAC

 401 TGGCCCCTGG ATCTGCTGCC CAAACTAACT CCATGGTGAC CCTGGGATGC

 451 CTGGTCAAGG GCTATTTCCC TGAGCCAGTG ACAGTGACCT GGAACTCTGG

 501 ATCCCTGTCC AGCGGTGTGC ACACCTTCCC AGCTGTCCTG CAGTCTGACC

 551 TCTACACTCT GAGCAGCTCA GTGACTGTCC CCTCCAGCAC CTGGCCCAGC

 601 GAGACCGTCA CCTGCAACGT TGCCCACCCG GCCAGCAGCA CCAAGGTGGA

 651 CAAGAAAATT GTGCCCAGGG ATTGTGGTTG TAAGCCTTGC ATATGTACAG

 701 TCCCAGAAGT ATCATCTGTC TTCATCTTCC CCCCAAAGCC CAAGGATGTG

 751 CTCACCATTA CTCTGACTCC TAAGGTCACG TGTGTTGTGG TAGACATCAG

 801 CAAGGATGAT CCCGAGGTCC AGTTCAGCTG GTTTGTAGAT GATGTGGAGG

 851 TGCACACAGC TCAGACGCAA CCCCGGGAGG AGCAGTTCAA CAGCACTTTC

 901 CGCTCAGTCA GTGAACTTCC CATCATGCAC CAGGACTGGC TCAATGGCAA

 951 GGAGTTCAAA TGCAGGGTCA ACAGTGCAGC TTTCCCTGCC CCCATCGAGA

1001 AAACCATCTC CAAAACCAAA GGCAGACCGA AGGCTCCACA GGTGTACACC

1051 ATTCCACCTC CCAAGGAGCA GATGGCCAAG GATAAAGTCA GTCTGACCTG
```

-continued

```
1101 CATGATAACA GACTTCTTCC CTGAAGACAT TACTGTGGAG TGGCAGTGGA

1151 ATGGGCAGCC AGCGGAGAAC TACAAGAACA CTCAGCCCAT CATGGACACA

1201 GATGGCTCTT ACTTCATCTA CAGCAAGCTC AATGTGCAGA AGAGCAACTG

1251 GGAGGCAGGA AATACTTTCA CCTGCTCTGT GTTACATGAG GGCCTGCACA

1301 ACCACCATAC TGAGAAGAGC CTCTCCCACT CTCCTGGTAA ATGA
```

Amino acid sequence of the Ab-8 HC including signal peptide:

```
                                                (SEQ ID NO: 171)
  1 MGWSWTFLFL LSGTAGVLSE VQLQQSGPEL MKPGASVKMS CKASGYTFTD

 51 YNMHWVKQNQ GKTLDWIGEI NPNSGGAGYN QKFKGKATLT VDKSSTTAYM

101 ELRSLTSEDS AVYYCARLGY DDIYDDWYFD VWGAGTTVTV SSAKTTPPSV

151 YPLAPGSAAQ TNSMVTLGCL VKGYFPEPVT VTWNSGSLSS GVHTFPAVLQ

201 SDLYTLSSSV TVPSSTWPSE TVTCNVAHPA SSTKVDKKIV PRDCGCKPCI

251 CTVPEVSSVF IFPPKPKDVL TITLTPKVTC VVVDISKDDP EVQFSWFVDD

301 VEVHTAQTQP REEQFNSTFR SVSELPIMHQ DWLNGKEFKC RVNSAAFPAP

351 IEKTISKTKG RPKAPQVYTI PPPKEQMAKD KVSLTCMITD FFPEDITVEW

401 QWNGQPAENY KNTQPIMDTD GSYFIYSKLN VQKSNWEAGN TFTCSVLHEG

451 LHNHHTEKSL SHSPGK
```

Nucleic acid sequence of the Ab-8 HC including signal peptide encoding sequence:

```
                                                (SEQ ID NO: 172)
  1  ATGGGATGGA GCTGGACCTT TCTCTTCCTC CTGTCAGGAA CTGCAGGTGT

 51  CCTCTCTGAG GTCCAACTGC AACAGTCTGG ACCTGAACTA ATGAAGCCTG

101  GGGCTTCAGT GAAGATGTCC TGCAAGGCTT CTGGATATAC ATTCACTGAC

151  TACAACATGC ACTGGGTGAA GCAGAACCAA GGAAAGACCC TAGACTGGAT

201  AGGAGAAATT AATCCTAACA GTGGTGGTGC TGGCTACAAC CAGAAGTTCA

251  AGGGCAAGGC CACATTGACT GTAGACAAGT CCTCCACCAC AGCCTACATG

301  GAGCTCCGCA GCCTGACATC TGAGGACTCT GCAGTCTATT ACTGTGCAAG

351  ATTGGGCTAC GATGATATCT ACGACGACTG GTACTTCGAT GTCTGGGGCG

401  CAGGGACCAC GGTCACCGTC TCCTCAGCCA AAACGACACC CCCATCTGTC

451  TATCCACTGG CCCCTGGATC TGCTGCCCAA ACTAACTCCA TGGTGACCCT

501  GGGATGCCTG GTCAAGGGCT ATTTCCCTGA GCCAGTGACA GTGACCTGGA

551  ACTCTGGATC CCTGTCCAGC GGTGTGCACA CCTTCCCAGC TGTCCTGCAG

601  TCTGACCTCT ACACTCTGAG CAGCTCAGTG ACTGTCCCCT CCAGCACCTG

651  GCCCAGCGAG ACCGTCACCT GCAACGTTGC CCACCCGGCC AGCAGCACCA

701  AGGTGGACAA GAAAATTGTG CCCAGGGATT GTGGTTGTAA GCCTTGCATA

751  TGTACAGTCC CAGAAGTATC ATCTGTCTTC ATCTTCCCCC CAAAGCCCAA

801  GGATGTGCTC ACCATTACTC TGACTCCTAA GGTCACGTGT GTTGTGGTAG

851  ACATCAGCAA GGATGATCCC GAGGTCCAGT TCAGCTGGTT TGTAGATGAT

901  GTGGAGGTGC ACACAGCTCA GACGCAACCC CGGGAGGAGC AGTTCAACAG
```

-continued

```
 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT

1101 GTACACCATT CCACCTCCCA AGGAGCAGAT GGCCAAGGAT AAAGTCAGTC

1151 TGACCTGCAT GATAACAGAC TTCTTCCCTG AAGACATTAC TGTGGAGTGG

1201 CAGTGGAATG GGCAGCCAGC GGAGAACTAC AAGAACACTC AGCCCATCAT

1251 GGACACAGAT GGCTCTTACT TCATCTACAG CAAGCTCAAT GTGCAGAAGA

1301 GCAACTGGGA GGCAGGAAAT ACTTTCACCT GCTCTGTGTT ACATGAGGGC

1351 CTGCACAACC ACCATACTGA GAAGAGCCTC TCCCACTCTC CTGGTAAATG

1401 A
```

Ab-9

The sequences of the Antibody 9 (also referred to herein as Ab-9) LC and HC are as follows:

Ab-9 Light Chain:

Amino acid sequence of the mature form (signal peptide removed) of the Ab-9 LC:

(SEQ ID NO: 173)

1 DIQMTQITSS LSASLGDRVS ISCRASQDIS NYLNWYQQKP DGTFKLLIFY

51 TSRLFSGVPS RFSGSGSGTD YSLTIYNLEQ EDFATYFCQQ GDTLPYTFGG

101 GTKVEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-9 LC:

(SEQ ID NO: 174)

```
  1 GATATCCAGA TGACACAGAT TACATCCTCC CTGTCTGCCT CTCTGGGAGA

 51 CAGGGTCTCC ATCAGTTGCA GGGCAAGTCA AGACATTAGC AATTATTTAA

101 ATTGGTATCA GCAGAAACCA GATGGAACTT TTAAACTCCT TATCTTCTAC

151 ACATCAAGAT TATTTTCAGG AGTCCCATCA AGGTTCAGTG GCAGTGGGTC

201 TGGAACAGAT TATTCTCTCA CCATTTACAA CCTGGAGCAA GAAGATTTTG

251 CCACTTACTT TTGCCAACAG GGAGATACGC TTCCGTACAC TTTCGGAGGG

301 GGGACCAAGG TGGAAATAAA ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GT
```

Amino acid sequence of the Ab-9 LC including signal peptide:

(SEQ ID NO: 175)

```
1 MMSSAQFLGL LLLCFQGTRC DIQMTQITSS LSASLGDRVS ISCRASQDIS
```

-continued

```
 51 NYLNWYQQKP DGTFKLLIFY TSRLFSGVPS RFSGSGSGTD YSLTIYNLEQ

101 EDFATYFCQQ GDTLPYTFGG GTKVEIKRAD AAPTVSIFPP SSEQLTSGGA

151 SVVCFLNNFY PKDINVKWKI DGSERQNGVL NSWTDQDSKD STYSMSSTLT

201 LTKDEYERHN SYTCEATHKT STSPIVKSFN RNEC
```

Nucleic acid sequence of the Ab-9 LC including signal peptide encoding sequence:

```
                                         (SEQ ID NO: 176)
  1 ATGATGTCCT CTGCTCAGTT CCTTGGTCTC CTGTTGCTCT GTTTTCAAGG

 51 TACCAGATGT GATATCCAGA TGACACAGAT TACATCCTCC CTGTCTGCCT

101 CTCTGGGAGA CAGGGTCTCC ATCAGTTGCA GGGCAAGTCA AGACATTAGC

151 AATTATTTAA ATTGGTATCA GCAGAAACCA GATGGAACTT TTAAACTCCT

201 TATCTTCTAC ACATCAAGAT TATTTTCAGG AGTCCCATCA AGGTTCAGTG

251 GCAGTGGGTC TGGAACAGAT TATTCTCTCA CCATTTACAA CCTGGAGCAA

301 GAAGATTTTG CCACTTACTT TTGCCAACAG GGAGATACGC TTCCGTACAC

351 TTTCGGAGGG GGGACCAAGG TGGAAATAAA ACGGGCTGAT GCTGCACCAA

401 CTGTATCCAT CTTCCCACCA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC

651 TCACAAGACA TCAACTTCAC CCATTGTCAA GAGCTTCAAC AGGAATGAGT

701 GT
```

Ab-9 Heavy Chain:

Amino acid sequence of the mature form (signal peptide removed) of the Ab-9 HC:

```
                                           (SEQ ID NO: 177)
  1 EVQLQQSGPE LMKPGTSVKM SCKASGYTFT DYNMHWVKQT QGKTLEWIGE

 51 INPNSGGAGY NQKFKGKATL TVDKSSTTAY MELRSLTSED SAVYYCAKLG

101 YDDIYDDWYF DVWGAGTTVT VSSAKTTAPS VYPLAPVCGD TTGSSVTLGC

151 LVKGYFPEPV TLTWNSGSLS SDVHTFPALL QSGLYTLSSS VTVTTWPSQT

201 ITCNVAHPAS STKVDKKIEP RGSPTHKPCP PCPAPNLLGG PSVFIFPPKI

251 KDVLMISLSP MVTCVVVDVS EDDPDVHVSW FVNNVEVHTA QTQTHREDYN

301 STIRVVSALP IQHQDWMSGK EFKCKVNNKA LPAPIERTIS KPKGPVRAPQ

351 VYVLPPPEEE MTKKQVTLTC MITDFMPEDI YVEWTNNGQT ELNYKNTEPV

401 LDSDGSYFMY SKLRVEKKNW VERNSYSCSV VHEGLHNHHT TKSFSRTPGK
```

Nucleic acid sequence encoding the mature form (signal peptide removed) of the Ab-9 HC:

```
                                         (SEQ ID NO: 178)
  1 GAGGTCCAAC TGCAACAGTC TGGACCTGAA CTAATGAAGC CTGGGACTTC

 51 AGTGAAGATG TCCTGCAAGG CTTCTGGATA TACATTCACT GACTACAACA
```

-continued

```
 101 TGCACTGGGT GAAGCAGACC CAAGGAAAGA CCCTAGAGTG GATAGGAGAA
 151 ATTAATCCTA ACAGTGGTGG TGCTGGCTAC AACCAGAAGT TCAAGGGCAA
 201 GGCCACATTG ACTGTAGACA AGTCCTCCAC CACAGCCTAC ATGGAGCTCC
 251 GCAGCCTGAC ATCTGAGGAC TCTGCAGTCT ATTACTGTGC AAAATTGGGC
 301 TACGATGATA TCTACGACGA CTGGTATTTC GATGTCTGGG GCGCAGGGAC
 351 CACGGTCACC GTCTCCTCAG CCAAAACAAC AGCCCCATCG GTCTATCCAC
 401 TGGCCCCTGT GTGTGGAGAT ACAACTGGCT CCTCGGTGAC TCTAGGATGC
 451 CTGGTCAAGG GTTATTTCCC TGAGCCAGTG ACCTTGACCT GGAACTCTGG
 501 ATCCCTGTCC AGTGATGTGC ACACCTTCCC AGCTCTCCTG CAGTCTGGCC
 551 TCTACACCCT CAGCAGCTCA GTGACTGTAA CCACCTGGCC CAGCCAGACC
 601 ATCACCTGCA ATGTGGCCCA CCCGGCAAGC AGCACCAAAG TGGACAAGAA
 651 AATTGAGCCC AGAGGGTCCC CAACACATAA ACCCTGTCCT CCATGCCCAG
 701 CTCCTAACCT CTTGGGTGGA CCATCCGTCT TCATCTTCCC TCCAAAGATC
 751 AAGGATGTAC TCATGATCTC CCTGAGCCCC ATGGTCACGT GTGTGGTGGT
 801 GGATGTGAGC GAGGATGACC CAGATGTCCA TGTCAGCTGG TTCGTGAACA
 851 ACGTGGAAGT ACACACAGCT CAGACACAAA CCCATAGAGA GGATTACAAC
 901 AGTACTATCC GGGTGGTCAG TGCCCTCCCC ATCCAGCACC AGGACTGGAT
 951 GAGTGGCAAG GAGTTCAAAT GCAAGGTCAA CAACAAAGCC CTCCCAGCGC
1001 CCATCGAGAG AACCATCTCA AAACCCAAAG GGCCAGTAAG AGCTCCACAG
1051 GTATATGTCT TGCCTCCACC AGAAGAAGAG ATGACTAAGA AACAGGTCAC
1101 TCTGACCTGC ATGATCACAG ACTTCATGCC TGAAGACATT TACGTGGAGT
1151 GGACCAACAA CGGGCAAACA GAGCTAAACT ACAAGAACAC TGAACCAGTC
1201 CTGGACTCTG ATGGTTCTTA CTTCATGTAC AGCAAGCTGA GAGTGGAAAA
1251 GAAGAACTGG GTGGAAAGAA ATAGCTACTC CTGTTCAGTG GTCCACGAGG
1301 GTCTGCACAA TCACCACACG ACTAAGAGCT TCTCCCGGAC TCCGGGTAAA
```

Amino acid sequence of the Ab-9 HC including signal peptide:

```
                                         (SEQ ID NO: 179)
  1 MGWSWTFLFL LSGTAGVLSE VQLQQSGPEL MKPGTSVKMS CKASGYTFTD
 51 YNMHWVKQTQ GKTLEWIGEI NPNSGGAGYN QKFKGKATLT VDKSSTTAYM
101 ELRSLTSEDS AVYYCAKLGY DDIYDDWYFD VWGAGTTVTV SSAKTTAPSV
151 YPLAPVCGDT TGSSVTLGCL VKGYFPEPVT LTWNSGSLSS DVHTFPALLQ
201 SGLYTLSSSV TVTTWPSQTI TCNVAHPASS TKVDKKIEPR GSPTHKPCPP
251 CPAPNLLGGP SVFIFPPKIK DVLMISLSPM VTCVVVDVSE DDPDVHVSWF
301 VNNVEVHTAQ TQTHREDYNS TIRVVSALPI QHQDWMSGKE FKCKVNNKAL
351 PAPIERTISK PKGPVRAPQV YVLPPPEEEM TKKQVTLTCM ITDFMPEDIY
401 VEWTNNGQTE LNYKNTEPVL DSDGSYFMYS KLRVEKKNWV ERNSYSCSVV
451 HEGLHNHHTT KSFSRTPGK
```

Nucleic acid sequence of the Ab-9 HC including signal peptide encoding sequence:

(SEQ ID NO: 180)

1 ATGGGATGGA GCTGGACCTT TCTCTTCCTC CTGTCAGGAA CTGCAGGTGT

51 CCTCTCTGAG GTCCAACTGC AACAGTCTGG ACCTGAACTA ATGAAGCCTG

101 GGACTTCAGT GAAGATGTCC TGCAAGGCTT CTGGATATAC ATTCACTGAC

151 TACAACATGC ACTGGGTGAA GCAGACCCAA GGAAAGACCC TAGAGTGGAT

201 AGGAGAAATT AATCCTAACA GTGGTGGTGC TGGCTACAAC CAGAAGTTCA

251 AGGGCAAGGC CACATTGACT GTAGACAAGT CCTCCACCAC AGCCTACATG

301 GAGCTCCGCA GCCTGACATC TGAGGACTCT GCAGTCTATT ACTGTGCAAA

351 ATTGGGCTAC GATGATATCT ACGACGACTG GTATTTCGAT GTCTGGGGCG

401 CAGGGACCAC GGTCACCGTC TCCTCAGCCA AAACAACAGC CCCATCGGTC

451 TATCCACTGG CCCCTGTGTG TGGAGATACA ACTGGCTCCT CGGTGACTCT

501 AGGATGCCTG GTCAAGGGTT ATTTCCCTGA GCCAGTGACC TTGACCTGGA

551 ACTCTGGATC CCTGTCCAGT GATGTGCACA CCTTCCCAGC TCTCCTGCAG

601 TCTGGCCTCT ACACCCTCAG CAGCTCAGTG ACTGTAACCA CCTGGCCCAG

651 CCAGACCATC ACCTGCAATG TGGCCCACCC GGCAAGCAGC ACCAAAGTGG

701 ACAAGAAAAT TGAGCCCAGA GGGTCCCCAA CACATAAACC CTGTCCTCCA

751 TGCCCAGCTC CTAACCTCTT GGGTGGACCA TCCGTCTTCA TCTTCCCTCC

801 AAAGATCAAG GATGTACTCA TGATCTCCCT GAGCCCCATG GTCACGTGTG

851 TGGTGGTGGA TGTGAGCGAG GATGACCCAG ATGTCCATGT CAGCTGGTTC

901 GTGAACAACG TGGAAGTACA CACAGCTCAG ACACAAACCC ATAGAGAGGA

951 TTACAACAGT ACTATCCGGG TGGTCAGTGC CCTCCCCATC CAGCACCAGG

1001 ACTGGATGAG TGGCAAGGAG TTCAAATGCA AGGTCAACAA CAAAGCCCTC

1051 CCAGCGCCCA TCGAGAGAAC CATCTCAAAA CCCAAAGGGC CAGTAAGAGC

1101 TCCACAGGTA TATGTCTTGC CTCCACCAGA AGAAGAGATG ACTAAGAAAC

1151 AGGTCACTCT GACCTGCATG ATCACAGACT TCATGCCTGA AGACATTTAC

1201 GTGGAGTGGA CCAACAACGG GCAAACAGAG CTAAACTACA AGAACACTGA

1251 ACCAGTCCTG GACTCTGATG GTTCTTACTT CATGTACAGC AAGCTGAGAG

1301 TGGAAAAGAA GAACTGGGTG GAAAGAAATA GCTACTCCTG TTCAGTGGTC

1351 CACGAGGGTC TGCACAATCA CCACACGACT AAGAGCTTCT CCCGGACTCC

1401 GGGTAAA

Ab-10

The sequences of the Antibody 10 (also referred to herein as Ab-10) LC and HC are as follows:

Ab-10 Light Chain:

Amino acid sequence of the mature form (signal peptide removed) of the Ab-10 LC:

(SEQ ID NO: 181)

1 DIQMTQTTSS LSASLGDRVS ISCRASQDIS NYLNWYQQKP DGTFKLLIFY

51 TSRLLSGVPS RFSGSGSGTD YSLTIYNLEQ EDFATYFCQQ GDTLPYTFGG

101 GTKLEIK*RAD AAPTVSIFPL SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-10 LC:

```
                                              (SEQ ID NO: 182)
  1 GATATCCAGA TGACACAGAC TACATCCTCC CTGTCTGCCT CTCTGGGAGA

 51 CAGGGTCTCC ATCAGTTGCA GGGCAAGTCA AGACATTAGC AATTATTTAA

101 ACTGGTATCA GCAGAAACCA GATGGAACTT TTAAACTCCT TATCTTCTAC

151 ACATCAAGAT TACTCTCAGG AGTCCCATCA AGGTTCAGTG GCAGTGGGTC

201 TGGAACAGAT TATTCTCTCA CCATTTACAA CCTGGAGCAA GAAGATTTTG

251 CCACTTACTT TTGCCAACAG GGAGATACGC TTCCGTACAC TTTCGGAGGG

301 GGGACCAAAC TGGAAATAAA ACGGGCTGAT GCTGCACCAA CTGTATCCAT

351 CTTCCCACTA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG
```

Amino acid sequence of the Ab-10 LC including signal peptide:

```
                                              (SEQ ID NO: 183)
  1 MMSSAQFLGL LLLCFQGTRC DIQMTQTTSS LSASLGDRVS ISCRASQDIS

 51 NYLNWYQQKP DGTFKLLIFY TSRLLSGVPS RFSGSGSGTD YSLTIYNLEQ

101 EDFATYFCQQ GDTLPYTFGG GTKLEIKRAD AAPTVSIFPL SSEQLTSGGA

151 SVVCFLNNFY PKDINVKWKI DGSERQNGVL NSWTDQDSKD STYSMSSTLT

201 LTKDEYERHN SYTCEATHKT STSPIVKSFN RNEC
```

Nucleic acid sequence of the Ab-10 LC including signal peptide encoding sequence:

```
                                              (SEQ ID NO: 184)
  1 ATGATGTCCT CTGCTCAGTT CCTTGGTCTC CTGTTGCTCT GTTTTCAAGG

 51 TACCAGATGT GATATCCAGA TGACACAGAC TACATCCTCC CTGTCTGCCT

101 CTCTGGGAGA CAGGGTCTCC ATCAGTTGCA GGGCAAGTCA AGACATTAGC

151 AATTATTTAA ACTGGTATCA GCAGAAACCA GATGGAACTT TTAAACTCCT

201 TATCTTCTAC ACATCAAGAT TACTCTCAGG AGTCCCATCA AGGTTCAGTG

251 GCAGTGGGTC TGGAACAGAT TATTCTCTCA CCATTTACAA CCTGGAGCAA

301 GAAGATTTTG CCACTTACTT TTGCCAACAG GGAGATACGC TTCCGTACAC

351 TTTCGGAGGG GGGACCAAAC TGGAAATAAA ACGGGCTGAT GCTGCACCAA

401 CTGTATCCAT CTTCCCACTA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC
```

-continued

```
651 TCACAAGACA TCAACTTCAC CCATTGTCAA GAGCTTCAAC AGGAATGAGT

701 GTTAG
```

Ab-10 Heavy Chain:

Amino acid sequence of the mature form (signal peptide removed) of the Ab-10 HC:

```
                                        (SEQ ID NO: 185)
  1 EVQLQQSGPE LMKPGASVKM SCKASGYTFT DYNMHWVKQN QGKTLEWIGE

 51 INPNSGGAGY NQKFKGKATL TVDKSSTTAY MELRSLTSED SAVYYCARLG

101 YDDIYDDWYF DVWGAGTTVT VSSAKTTPPS VYPLAPGSAA QTNSMVTLGC

151 LVKGYFPEPV TVTWNSGSLS SGVHTFPAVL QSDLYTLSSS VTVPSSTWPS

201 ETVTCNVAHP ASSTKVDKKI VPRDCGCKPC ICTVPEVSSV FIFPPKPKDV

251 LTITLTPKVT CVVVDISKDD PEVQFSWFVD DVEVHTAQTQ PREEQFNSTF

301 RSVSELPIMH QDWLNGKEFK CRVNSAAFPA PIEKTISKTK GRPKAPQVYT

351 IPPPKEQMAK DKVSLTCMIT DFFPEDITVE WQWNGQPAEN YKNTQPIMDT

401 DGSYFIYSKL NVQKSNWEAG NTFTCSVLHE GLHNHHTEKS LSHSPGK
```

Nucleic acid sequence encoding the mature form (signal peptide removed) of the Ab-10 HC:

```
                                        (SEQ ID NO: 186)
   1 GAGGTCCAAC TGCAACAGTC TGGACCTGAA CTAATGAAGC CTGGGGCTTC

  51 AGTGAAGATG TCCTGCAAGG CTTCTGGATA TACATTCACT GACTACAACA

 101 TGCACTGGGT GAAGCAGAAC CAAGGAAAGA CCCTAGAATG GATAGGAGAA

 151 ATTAATCCTA ACAGTGGTGG TGCTGGCTAC AACCAGAAGT TCAAGGGCAA

 201 GGCCACATTG ACTGTAGACA AGTCCTCCAC CACAGCCTAC ATGGAGCTCC

 251 GCAGCCTGAC ATCTGAGGAC TCTGCAGTCT ATTACTGTGC AAGATTGGGC

 301 TACGATGATA TCTACGACGA CTGGTACTTC GATGTCTGGG GCGCAGGGAC

 351 CACGGTCACC GTCTCCTCAG CCAAAACGAC ACCCCCATCT GTCTATCCAC

 401 TGGCCCCTGG ATCTGCTGCC CAAACTAACT CCATGGTGAC CCTGGGATGC

 451 CTGGTCAAGG GCTATTTCCC TGAGCCAGTG ACAGTGACCT GGAACTCTGG

 501 ATCCCTGTCC AGCGGTGTGC ACACCTTCCC AGCTGTCCTG CAGTCTGACC

 551 TCTACACTCT GAGCAGCTCA GTGACTGTCC CCTCCAGCAC CTGGCCCAGC

 601 GAGACCGTCA CCTGCAACGT TGCCCACCCG GCCAGCAGCA CCAAGGTGGA

 651 CAAGAAAATT GTGCCCAGGG ATTGTGGTTG TAAGCCTTGC ATATGTACAG

 701 TCCCAGAAGT ATCATCTGTC TTCATCTTCC CCCCAAAGCC CAAGGATGTG

 751 CTCACCATTA CTCTGACTCC TAAGGTCACG TGTGTTGTGG TAGACATCAG

 801 CAAGGATGAT CCCGAGGTCC AGTTCAGCTG GTTTGTAGAT GATGTGGAGG

 851 TGCACACAGC TCAGACGCAA CCCCGGGAGG AGCAGTTCAA CAGCACTTTC

 901 CGCTCAGTCA GTGAACTTCC CATCATGCAC CAGGACTGGC TCAATGGCAA

 951 GGAGTTCAAA TGCAGGGTCA ACAGTGCAGC TTTCCCTGCC CCCATCGAGA

1001 AAACCATCTC CAAAACCAAA GGCAGACCGA AGGCTCCACA GGTGTACACC

1051 ATTCCACCTC CCAAGGAGCA GATGGCCAAG GATAAAGTCA GTCTGACCTG
```

-continued

1101 CATGATAACA GACTTCTTCC CTGAAGACAT TACTGTGGAG TGGCAGTGGA

1151 ATGGGCAGCC AGCGGAGAAC TACAAGAACA CTCAGCCCAT CATGGACACA

1201 GATGGCTCTT ACTTCATCTA CAGCAAGCTC AATGTGCAGA AGAGCAACTG

1251 GGAGGCAGGA AATACTTTCA CCTGCTCTGT GTTACATGAG GGCCTGCACA

1301 ACCACCATAC TGAGAAGAGC CTCTCCCACT CTCCTGGTAA ATGA

Amino acid sequence of the Ab-10 HC including signal peptide:

(SEQ ID NO: 187)

1 MGWSWTFLFL LSGTAGVLSE VQLQQSGPEL MKPGASVKMS CKASGYTFTD

51 YNMHWVKQNQ GKTLEWIGEI NPNSGGAGYN QKFKGKATLT VDKSSTTAYM

101 ELRSLTSEDS AVYYCARLGY DDIYDDWYFD VWGAGTTVTV SSAKTTPPSV

151 YPLAPGSAAQ TNSMVTLGCL VKGYFPEPVT VTWNSGSLSS GVHTFPAVLQ

201 SDLYTLSSSV TVPSSTWPSE TVTCNVAHPA SSTKVDKKIV PRDCGCKPCI

251 CTVPEVSSVF IFPPKPKDVL TITLTPKVTC VVVDISKDDP EVQFSWFVDD

301 VEVHTAQTQP REEQFNSTFR SVSELPIMHQ DWLNGKEFKC RVNSAAFPAP

351 IEKTISKTKG RPKAPQVYTI PPPKEQMAKD KVSLTCMITD FFPEDITVEW

401 QWNGQPAENY KNTQPIMDTD GSYFIYSKLN VQKSNWEAGN TFTCSVLHEG

451 LHNHHTEKSL SHSPGK

Nucleic acid sequence of the Ab-10 HC including signal peptide encoding sequence:

(SEQ ID NO: 188)

1 ATGGGATGGA GCTGGACCTT TCTCTTCCTC CTGTCAGGAA CTGCAGGTGT

51 CCTCTCTGAG GTCCAACTGC AACAGTCTGG ACCTGAACTA ATGAAGCCTG

101 GGGCTTCAGT GAAGATGTCC TGCAAGGCTT CTGGATATAC ATTCACTGAC

151 TACAACATGC ACTGGGTGAA GCAGAACCAA GGAAAGACCC TAGAATGGAT

201 AGGAGAAATT AATCCTAACA GTGGTGGTGC TGGCTACAAC CAGAAGTTCA

251 AGGGCAAGGC CACATTGACT GTAGACAAGT CCTCCACCAC AGCCTACATG

301 GAGCTCCGCA GCCTGACATC TGAGGACTCT GCAGTCTATT ACTGTGCAAG

351 ATTGGGCTAC GATGATATCT ACGACGACTG GTACTTCGAT GTCTGGGGCG

401 CAGGGACCAC GGTCACCGTC TCCTCAGCCA AAACGACACC CCCATCTGTC

451 TATCCACTGG CCCCTGGATC TGCTGCCCAA ACTAACTCCA TGGTGACCCT

501 GGGATGCCTG GTCAAGGGCT ATTTCCCTGA GCCAGTGACA GTGACCTGGA

551 ACTCTGGATC CCTGTCCAGC GGTGTGCACA CCTTCCCAGC TGTCCTGCAG

601 TCTGACCTCT ACACTCTGAG CAGCTCAGTG ACTGTCCCCT CCAGCACCTG

651 GCCCAGCGAG ACCGTCACCT GCAACGTTGC CCACCCGGCC AGCAGCACCA

701 AGGTGGACAA GAAAATTGTG CCCAGGGATT GTGGTTGTAA GCCTTGCATA

751 TGTACAGTCC CAGAAGTATC ATCTGTCTTC ATCTTCCCCC CAAAGCCCAA

801 GGATGTGCTC ACCATTACTC TGACTCCTAA GGTCACGTGT GTTGTGGTAG

851 ACATCAGCAA GGATGATCCC GAGGTCCAGT TCAGCTGGTT TGTAGATGAT

901 GTGGAGGTGC ACACAGCTCA GACGCAACCC CGGGAGGAGC AGTTCAACAG

-continued

```
 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT

1101 GTACACCATT CCACCTCCCA AGGAGCAGAT GGCCAAGGAT AAAGTCAGTC

1151 TGACCTGCAT GATAACAGAC TTCTTCCCTG AAGACATTAC TGTGGAGTGG

1201 CAGTGGAATG GGCAGCCAGC GGAGAACTAC AAGAACACTC AGCCCATCAT

1251 GGACACAGAT GGCTCTTACT TCATCTACAG CAAGCTCAAT GTGCAGAAGA

1301 GCAACTGGGA GGCAGGAAAT ACTTTCACCT GCTCTGTGTT ACATGAGGGC

1351 CTGCACAACC ACCATACTGA GAAGAGCCTC TCCCACTCTC CTGGTAAATG

1401 A
```

Ab-11

The sequences of the Antibody 11 (also referred to herein as Ab-11) LC and HC are as follows:

Ab-11 Light Chain:

Amino acid sequence of the mature form (signal peptide removed) of the Ab-11 LC:

(SEQ ID NO: 189)

1 QIVLSQSPAF LSVSPGDKVT MTC<u>RASSSIS YIH</u>WFQQKPG SSPRSWIY<u>AT</u>

51 <u>SNLA</u>SGVPGR FSGSGSGTSY SLTISRVEAE DAATYYC<u>QQW SSDPLT</u>FGAG

101 TKLELK*RADA APTVSIFPPS SEQLTSGGAS VVCFLNNFYP KDINVKWKID*

*151 GSERQNGVLN SWTDQDSKDS TYSMSSTLTL TKDEYERHNS YTCEATHKTS*

*201 TSPIVKSFNT NEC*

Nucleic acid sequence encoding the mature form (signal peptide removed) of the Ab-11 LC:

(SEQ ID NO: 190)

```
  1 CAAATTGTTC TCTCCCAGTC TCCAGCATTC CTGTCTGTAT CTCCAGGGGA

 51 TAAGGTCACA ATGACTTGCA GGGCCAGCTC AAGTATAAGT TACATACACT

101 GGTTTCAGCA GAAGCCAGGA TCCTCCCCCA GATCCTGGAT TTATGCCACA

151 TCCAACCTGG CTTCTGGAGT CCCTGGTCGC TTCAGTGGCA GTGGGTCTGG

201 GACCTCTTAC TCTCTCACAA TCAGCAGAGT GGAGGCTGAG GATGCTGCCA

251 CTTATTACTG CCAGCAGTGG AGTAGTGACC CACTCACGTT CGGTGCTGGG

301 ACCAAGCTGG AGCTGAAACG GGCTGATGCT GCACCAACTG TATCCATCTT

351 CCCACCATCC AGTGAGCAGT TAACATCTGG AGGTGCCTCA GTCGTGTGCT

401 TCTTGAACAA CTTCTACCCC AAAGACATCA ATGTCAAGTG GAAGATTGAT

451 GGCAGTGAAC GACAAAATGG CGTCCTGAAC AGTTGGACTG ATCAGGACAG

501 CAAAGACAGC ACCTACAGCA TGAGCAGCAC CCTCACGTTG ACCAAGGACG

551 AGTATGAACG ACATAACAGC TATACCTGTG AGGCCACTCA CAAGACATCA

601 ACTTCACCCA TTGTCAAGAG CTTCAACAGG AATGAGTGTT AG
```

Amino acid sequence of the Ab-11 LC including signal peptide:

(SEQ ID NO: 191)

```
1  MDFQVQIFSF LLISASVIMS RGQIVLSQSP AFLSVSPGDK VTMTCRASSS
```

-continued

51 ISYIHWFQQK PGSSPRSWIY ATSNLASGVP GRFSGSGSGT SYSLTISRVE

101 AEDAATYYCQ QWSSDPLTFG AGTKLELKRA DAAPTVSIFP PSSEQLTSGG

151 ASVVCFLNNF YPKDINVKWK IDGSERQNGV LNSWTDQDSK DSTYSMSSTL

201 TLTKDEYERH NSYTCEATHK TSTSPIVKSF NRNEC

Nucleic acid sequence of the Ab-11 LC including signal peptide encoding sequence:

(SEQ ID NO: 192)

1 ATGGATTTTC AAGTGCAGAT TTTCAGCTTC CTGCTAATCA GTGCTTCAGT

51 CATAATGTCC AGAGGACAAA TTGTTCTCTC CCAGTCTCCA GCATTCCTGT

101 CTGTATCTCC AGGGGATAAG GTCACAATGA CTTGCAGGGC CAGCTCAAGT

151 ATAAGTTACA TACACTGGTT TCAGCAGAAG CCAGGATCCT CCCCCAGATC

201 CTGGATTTAT GCCACATCCA ACCTGGCTTC TGGAGTCCCT GGTCGCTTCA

251 GTGGCAGTGG GTCTGGGACC TCTTACTCTC TCACAATCAG CAGAGTGGAG

301 GCTGAGGATG CTGCCACTTA TTACTGCCAG CAGTGGAGTA GTGACCCACT

351 CACGTTCGGT GCTGGGACCA AGCTGGAGCT GAAACGGGCT GATGCTGCAC

401 CAACTGTATC CATCTTCCCA CCATCCAGTG AGCAGTTAAC ATCTGGAGGT

451 GCCTCAGTCG TGTGCTTCTT GAACAACTTC TACCCCAAAG ACATCAATGT

501 CAAGTGGAAG ATTGATGGCA GTGAACGACA AAATGGCGTC CTGAACAGTT

551 GGACTGATCA GGACAGCAAA GACAGCACCT ACAGCATGAG CAGCACCCTC

601 ACGTTGACCA AGGACGAGTA TGAACGACAT AACAGCTATA CCTGTGAGGC

651 CACTCACAAG ACATCAACTT CACCCATTGT CAAGAGCTTC AACAGGAATG

701 AGTGTTAG

Ab-11 Heavy Chain:

Amino acid sequence of the mature form (signal peptide removed) of the Ab-11 HC:

(SEQ ID NO: 193)

1 EVQLQQSGAD LVQPGASVKV SCTASGFDIK DYYIHWMKQR PDQGLEWIGR

51 VDPDNGETEF APKFPGKATF TTDTSSNTAY LQLRGLTSED TAIYYCGRED

101 YDGTYTWFPY WGQGTLVTVS A*AKTTPPSVY PLAPGSAAQT NSMVTLGCLV*

*151 KGYFPEPVTV TWNSGSLSSG VHTFPAVLQS DLYTLSSSVT VPSSTWPSET*

*201 VTCNVAHPAS STKVDKKIVP RDCGCKPCIC TVPEVSSVFI FPPKPKDVLT*

*251 ITLTPKVTCV VVDISKDDPE VQFSWFVDDV EVHTAQTQPR EEQFNSTFRS*

*301 VSELPIMHQD WLNGKEFKCR VNSAAFPAPI EKTISKTKGR PKAPQVYTIP*

*351 PPKEQMAKDK VSLTCMITDF FPEDITVEWQ WNGQPAENYK NTQPIMDTDG*

*401 SYFIYSKLNV QKSNWEAGNT FTCSVLHEGL HNHHTEKSLS HSPGK*

Nucleic acid sequence encoding the mature form (signal peptide removed) of the Ab-11 HC:

(SEQ ID NO: 194)

1 GAAGTTCAGC TGCAACAGTC TGGGGCAGAC CTTGTGCAGC CAGGGGCCTC

51 AGTCAAGGTG TCCTGCACAG CTTCTGGCTT CGACATTAAG GACTACTATA

-continued

```
 101 TACACTGGAT GAAACAGAGG CCTGACCAGG GCCTGGAGTG GATTGGAAGG
 151 GTTGATCCTG ACAATGGTGA GACTGAATTT GCCCCGAAGT TCCCGGGCAA
 201 GGCCACTTTT ACAACAGACA CATCCTCCAA CACAGCCTAC CTACAACTCA
 251 GAGGCCTGAC ATCTGAGGAC ACTGCCATCT ATTACTGTGG GAGAGAAGAC
 301 TACGATGGTA CCTACACCTG GTTTCCTTAT TGGGGCCAAG GGACTCTGGT
 351 CACTGTCTCT GCAGCCAAAA CGACACCCCC ATCTGTCTAT CCACTGGCCC
 401 CTGGATCTGC TGCCCAAACT AACTCCATGG TGACCCTGGG ATGCCTGGTC
 451 AAGGGCTATT TCCCTGAGCC AGTGACAGTG ACCTGGAACT CTGGATCCCT
 501 GTCCAGCGGT GTGCACACCT TCCCAGCTGT CCTGCAGTCT GACCTCTACA
 551 CTCTGAGCAG CTCAGTGACT GTCCCCTCCA GCACCTGGCC CAGCGAGACC
 601 GTCACCTGCA ACGTTGCCCA CCCGGCCAGC AGCACCAAGG TGGACAAGAA
 651 AATTGTGCCC AGGGATTGTG GTTGTAAGCC TTGCATATGT ACAGTCCCAG
 701 AAGTATCATC TGTCTTCATC TTCCCCCCAA AGCCCAAGGA TGTGCTCACC
 751 ATTACTCTGA CTCCTAAGGT CACGTGTGTT GTGGTAGACA TCAGCAAGGA
 801 TGATCCCGAG GTCCAGTTCA GCTGGTTTGT AGATGATGTG GAGGTGCACA
 851 CAGCTCAGAC GCAACCCCGG GAGGAGCAGT TCAACAGCAC TTTCCGCTCA
 901 GTCAGTGAAC TTCCCATCAT GCACCAGGAC TGGCTCAATG GCAAGGAGTT
 951 CAAATGCAGG GTCAACAGTG CAGCTTTCCC TGCCCCCATC GAGAAAACCA
1001 TCTCCAAAAC CAAAGGCAGA CCGAAGGCTC CACAGGTGTA CACCATTCCA
1051 CCTCCCAAGG AGCAGATGGC CAAGGATAAA GTCAGTCTGA CCTGCATGAT
1101 AACAGACTTC TTCCCTGAAG ACATTACTGT GGAGTGGCAG TGGAATGGGC
1151 AGCCAGCGGA GAACTACAAG AACACTCAGC CCATCATGGA CACAGATGGC
1201 TCTTACTTCA TCTACAGCAA GCTCAATGTG CAGAAGAGCA ACTGGGAGGC
1251 AGGAAATACT TTCACCTGCT CTGTGTTACA TGAGGGCCTG CACAACCACC
1301 ATACTGAGAA GAGCCTCTCC CACTCTCCTG GTAAATGA
```

Amino acid sequence of the Ab-11 HC including signal peptide:

```
                                                (SEQ ID NO: 195)
  1 MKCSWVIFFL MAVVTGVNSE VQLQQSGADL VQPGASVKVS CTASGFDIKD
 51 YYIHWMKQRP DQGLEWIGRV DPDNGETEFA PKFPGKATFT TDTSSNTAYL
101 QLRGLTSEDT AIYYCGREDY DGTYTWFPYW GQGTLVTVSA AKTTPPSVYP
151 LAPGSAAQTN SMVTLGCLVK GYFPEPVTVT WNSGSLSSGV HTFPAVLQSD
201 LYTLSSSVTV PSSTWPSETV TCNVAHPASS TKVDKKIVPR DCGCKPCICT
251 VPEVSSVFIF PPKPKDVLTI TLTPKVTCVV VDISKDDPEV QFSWFVDDVE
301 VHTAQTQPRE EQFNSTFRSV SELPIMHQDW LNGKEFKCRV NSAAFPAPIE
351 KTISKTKGRP KAPQVYTIPP PKEQMAKDKV SLTCMITDFF PEDITVEWQW
401 NGQPAENYKN TQPIMDTDGS YFIYSKLNVQ KSNWEAGNTF TCSVLHEGLH
451 NHHTEKSLSH SPGK
```

Nucleic acid sequence of the Ab-11 HC including signal peptide encoding sequence:

```
                                              (SEQ ID NO: 196)
   1 ATGAAATGCA GCTGGGTCAT CTTCTTCCTG ATGGCAGTGG TTACAGGGGT

  51 CAATTCAGAA GTTCAGCTGC AACAGTCTGG GGCAGACCTT GTGCAGCCAG

 101 GGGCCTCAGT CAAGGTGTCC TGCACAGCTT CTGGCTTCGA CATTAAGGAC

 151 TACTATATAC ACTGGATGAA ACAGAGGCCT GACCAGGGCC TGGAGTGGAT

 201 TGGAAGGGTT GATCCTGACA ATGGTGAGAC TGAATTTGCC CCGAAGTTCC

 251 CGGGCAAGGC CACTTTTACA ACAGACACAT CCTCCAACAC AGCCTACCTA

 301 CAACTCAGAG GCCTGACATC TGAGGACACT GCCATCTATT ACTGTGGGAG

 351 AGAAGACTAC GATGGTACCT ACACCTGGTT TCCTTATTGG GGCCAAGGGA

 401 CTCTGGTCAC TGTCTCTGCA GCCAAAACGA CACCCCCATC TGTCTATCCA

 451 CTGGCCCCTG GATCTGCTGC CCAAACTAAC TCCATGGTGA CCCTGGGATG

 501 CCTGGTCAAG GGCTATTTCC CTGAGCCAGT GACAGTGACC TGGAACTCTG

 551 GATCCCTGTC CAGCGGTGTG CACACCTTCC CAGCTGTCCT GCAGTCTGAC

 601 CTCTACACTC TGAGCAGCTC AGTGACTGTC CCCTCCAGCA CCTGGCCCAG

 651 CGAGACCGTC ACCTGCAACG TTGCCCACCC GGCCAGCAGC ACCAAGGTGG

 701 ACAAGAAAAT TGTGCCCAGG GATTGTGGTT GTAAGCCTTG CATATGTACA

 751 GTCCCAGAAG TATCATCTGT CTTCATCTTC CCCCCAAAGC CCAAGGATGT

 801 GCTCACCATT ACTCTGACTC CTAAGGTCAC GTGTGTTGTG GTAGACATCA

 851 GCAAGGATGA TCCCGAGGTC CAGTTCAGCT GGTTTGTAGA TGATGTGGAG

 901 GTGCACACAG CTCAGACGCA ACCCCGGGAG GAGCAGTTCA ACAGCACTTT

 951 CCGCTCAGTC AGTGAACTTC CCATCATGCA CCAGGACTGG CTCAATGGCA

1001 AGGAGTTCAA ATGCAGGGTC AACAGTGCAG CTTTCCCTGC CCCCATCGAG

1051 AAAACCATCT CCAAAACCAA AGGCAGACCG AAGGCTCCAC AGGTGTACAC

1101 CATTCCACCT CCCAAGGAGC AGATGGCCAA GGATAAAGTC AGTCTGACCT

1151 GCATGATAAC AGACTTCTTC CCTGAAGACA TTACTGTGGA GTGGCAGTGG

1201 AATGGGCAGC CAGCGGAGAA CTACAAGAAC ACTCAGCCCA TCATGGACAC

1251 AGATGGCTCT TACTTCATCT ACAGCAAGCT CAATGTGCAG AAGAGCAACT

1301 GGGAGGCAGG AAATACTTTC ACCTGCTCTG TGTTACATGA GGGCCTGCAC

1351 AACCACCATA CTGAGAAGAG CCTCTCCCAC TCTCCTGGTA AATGA
```

Ab-12

The sequences of the Antibody 12 (also referred to herein as Ab-12) LC and HC are as follows:

Ab-12 Light Chain:

Amino acid sequence of the mature form (signal peptide removed) of the Ab-12 LC:

(SEQ ID NO: 197)

1 DLQMTQTTSS LSASLGDRVT ISCRASQDIS NYLNWYQQKP DGTVKLLIFY

51 TSTLQSGVPS RFSGSGSGTN YSLTITNLEQ DDAATYFCQQ GDTLPYTFGG

101 GTKLEIK*RAD AAPTVSIFPP SSEQLTSGGA SVVCFLNNFY PKDINVKWKI*

*151 DGSERQNGVL NSWTDQDSKD STYSMSSTLT LTKDEYERHN SYTCEATHKT*

*201 STSPIVKSFN RNEC*

Nucleic acid sequence encoding the mature form (signal peptide removed) of the Ab-12 LC:

```
                                           (SEQ ID NO: 198)
  1 GATCTCCAGA TGACACAGAC TACTTCCTCC CTGTCTGCCT CTCTGGGAGA

 51 CAGAGTCACC ATCAGTTGCA GGGCAAGTCA GGACATTAGC AATTATTTAA

101 ACTGGTATCA GCAGAAACCA GATGGAACTG TTAAGCTCCT GATCTTCTAC

151 ACATCAACAT TACAGTCAGG AGTCCCATCG AGGTTCAGTG GCAGTGGGTC

201 TGGAACAAAT TATTCTCTCA CCATTACCAA CCTGGAGCAA GATGATGCTG

251 CCACTTACTT TTGCCAACAG GGTGATACGC TTCCGTACAC GTTCGGAGGG

301 GGGACCAAGC TGGAAATAAA ACGGGCTGAT GCTGCACCAA CTGTATCCAT

351 CTTCCCACCA TCCAGTGAGC AGTTAACATC TGGAGGTGCC TCAGTCGTGT

401 GCTTCTTGAA CAACTTCTAC CCCAAAGACA TCAATGTCAA GTGGAAGATT

451 GATGGCAGTG AACGACAAAA TGGCGTCCTG AACAGTTGGA CTGATCAGGA

501 CAGCAAAGAC AGCACCTACA GCATGAGCAG CACCCTCACG TTGACCAAGG

551 ACGAGTATGA ACGACATAAC AGCTATACCT GTGAGGCCAC TCACAAGACA

601 TCAACTTCAC CCATTGTCAA GAGCTTCAAC AGGAATGAGT GTTAG
```

Amino acid sequence of the Ab-12 LC including signal peptide:

```
                                           (SEQ ID NO: 199)
  1 MMSSAQFLGL LLLCFQGSRC DLQMTQTTSS LSASLGDRVT ISCRASQDIS

 51 NYLNWYQQKP DGTVKLLIFY TSTLQSGVPS RFSGSGSGTN YSLTITNLEQ

101 DDAATYFCQQ GDTLPYTFGG GTKLEIKRAD AAPTVSIFPP SSEQLTSGGA

151 SVVCFLNNFY PKDINVKWKI DGSERQNGVL NSWTDQDSKD STYSMSSTLT

201 LTKDEYERHN SYTCEATHKT STSPIVKSFN RNEC
```

Nucleic acid sequence of the Ab-12 LC including signal peptide encoding sequence:

```
                                           (SEQ ID NO: 200)
  1 ATGATGTCCT CTGCTCAGTT CCTTGGTCTC CTGTTGCTCT GTTTTCAAGG

 51 TTCCAGATGT GATCTCCAGA TGACACAGAC TACTTCCTCC CTGTCTGCCT

101 CTCTGGGAGA CAGAGTCACC ATCAGTTGCA GGGCAAGTCA GGACATTAGC

151 AATTATTTAA ACTGGTATCA GCAGAAACCA GATGGAACTG TTAAGCTCCT

201 GATCTTCTAC ACATCAACAT TACAGTCAGG AGTCCCATCG AGGTTCAGTG

251 GCAGTGGGTC TGGAACAAAT TATTCTCTCA CCATTACCAA CCTGGAGCAA

301 GATGATGCTG CCACTTACTT TTGCCAACAG GGTGATACGC TTCCGTACAC

351 GTTCGGAGGG GGGACCAAGC TGGAAATAAA ACGGGCTGAT GCTGCACCAA

401 CTGTATCCAT CTTCCCACCA TCCAGTGAGC AGTTAACATC TGGAGGTGCC

451 TCAGTCGTGT GCTTCTTGAA CAACTTCTAC CCCAAAGACA TCAATGTCAA

501 GTGGAAGATT GATGGCAGTG AACGACAAAA TGGCGTCCTG AACAGTTGGA

551 CTGATCAGGA CAGCAAAGAC AGCACCTACA GCATGAGCAG CACCCTCACG

601 TTGACCAAGG ACGAGTATGA ACGACATAAC AGCTATACCT GTGAGGCCAC
```

-continued

651 TCACAAGACA TCAACTTCAC CCATTGTCAA GAGCTTCAAC AGGAATGAGT

701 GTTAG

Ab-12 Heavy Chain:

Amino acid sequence of the mature form (signal peptide removed) of the Ab-12 HC:

(SEQ ID NO: 201)

1 EVQLQQSGPE LMKPGASVKM SCKASGYTFT DYNMHWMKQN QGKSLEWIGE

51 INPNSGGSGY NQKFKGKATL TVDKSSSTAY MELRSLTSED SAVYYCARLG

101 YYGNYEDWYF DVWGAGTTVT VSS*AKTTPPS VYPLAPGSAA QTNSMVTLGC*

*151 LVKGYFPEPV TVTWNSGSLS SGVHTFPAVL QSDLYTLSSS VTVPSSTWPS*

*201 ETVTCNVAHP ASSTKVDKKI VPRDCGCKPC ICTVPEVSSV FIFPPKPKDV*

*251 LTITLTPKVT CVVVDISKDD PEVQFSWFVD DVEVHTAQTQ PREEQFNSTF*

*301 RSVSELPIMH QDWLNGKEFK CRVNSAAFPA PIEKTISKTK GRPKAPQVYT*

*351 IPPPKEQMAK DKVSLTCMIT DFFPEDITVE WQWNGQPAEN YKNTQPIMDT*

*401 DGSYFIYSKL NVQKSNWEAG NTFTCSVLHE GLHNHHTEKS LSHSPGK*

Nucleic acid sequence encoding the mature form (signal peptide removed) of the Ab-12 HC:

(SEQ ID NO: 202)

1 GAGGTCCAGT TGCAACAGTC TGGACCTGAA CTAATGAAGC CTGGGGCTTC

51 AGTGAAGATG TCCTGCAAGG CTTCTGGATA CACATTCACT GACTACAACA

101 TGCACTGGAT GAAGCAGAAC CAAGGAAAGA GCCTAGAGTG GATAGGAGAG

151 ATTAATCCTA ACAGTGGTGG TTCTGGTTAC AACCAGAAGT TCAAAGGCAA

201 GGCCACATTG ACTGTAGACA AGTCCTCCAG CACAGCCTAC ATGGAGCTCC

251 GCAGCCTGAC ATCTGAGGAC TCTGCAGTCT ATTACTGTGC AAGATTGGGC

301 TACTATGGTA ACTACGAGGA CTGGTATTTC GATGTCTGGG GCGCAGGGAC

351 CACGGTCACC GTCTCCTCTG CCAAAACGAC ACCCCCATCT GTCTATCCAC

401 TGGCCCCTGG ATCTGCTGCC CAAACTAACT CCATGGTGAC CCTGGGATGC

451 CTGGTCAAGG GCTATTTCCC TGAGCCAGTG ACAGTGACCT GGAACTCTGG

501 ATCCCTGTCC AGCGGTGTGC ACACCTTCCC AGCTGTCCTG CAGTCTGACC

551 TCTACACTCT GAGCAGCTCA GTGACTGTCC CCTCCAGCAC CTGGCCCAGC

601 GAGACCGTCA CCTGCAACGT TGCCCACCCG GCCAGCAGCA CCAAGGTGGA

651 CAAGAAAATT GTGCCCAGGG ATTGTGGTTG TAAGCCTTGC ATATGTACAG

701 TCCCAGAAGT ATCATCTGTC TTCATCTTCC CCCCAAAGCC CAAGGATGTG

751 CTCACCATTA CTCTGACTCC TAAGGTCACG TGTGTTGTGG TAGACATCAG

801 CAAGGATGAT CCCGAGGTCC AGTTCAGCTG GTTTGTAGAT GATGTGGAGG

851 TGCACACAGC TCAGACGCAA CCCCGGGAGG AGCAGTTCAA CAGCACTTTC

901 CGCTCAGTCA GTGAACTTCC CATCATGCAC CAGGACTGGC TCAATGGCAA

951 GGAGTTCAAA TGCAGGGTCA ACAGTGCAGC TTTCCCTGCC CCCATCGAGA

1001 AAACCATCTC CAAAACCAAA GGCAGACCGA AGGCTCCACA GGTGTACACC

1051 ATTCCACCTC CCAAGGAGCA GATGGCCAAG GATAAAGTCA GTCTGACCTG

-continued

```
1101 CATGATAACA GACTTCTTCC CTGAAGACAT TACTGTGGAG TGGCAGTGGA

1151 ATGGGCAGCC AGCGGAGAAC TACAAGAACA CTCAGCCCAT CATGGACACA

1201 GATGGCTCTT ACTTCATCTA CAGCAAGCTC AATGTGCAGA AGAGCAACTG

1251 GGAGGCAGGA AATACTTTCA CCTGCTCTGT GTTACATGAG GGCCTGCACA

1301 ACCACCATAC TGAGAAGAGC CTCTCCCACT CTCCTGGTAA ATGA
```

Amino acid sequence of the Ab-12 HC including signal peptide:

```
                                         (SEQ ID NO: 203)
  1 MGWSWTFLFL LSGTSGVLSE VQLQQSGPEL MKPGASVKMS CKASGYTFTD

 51 YNMHWMKQNQ GKSLEWIGEI NPNSGGSGYN QKFKGKATLT VDKSSSTAYM

101 ELRSLTSEDS AVYYCARLGY YGNYEDWYFD VWGAGTTVTV SSAKTTPPSV

151 YPLAPGSAAQ TNSMVTLGCL VKGYFPEPVT VTWNSGSLSS GVHTFPAVLQ

201 SDLYTLSSSV TVPSSTWPSE TVTCNVAHPA SSTKVDKKIV PRDCGCKPCI

251 CTVPEVSSVF IFPPKPKDVL TITLTPKVTC VVVDISKDDP EVQFSWFVDD

301 VEVHTAQTQP REEQFNSTFR SVSELPIMHQ DWLNGKEFKC RVNSAAFPAP

351 IEKTISKTKG RPKAPQVYTI PPPKEQMAKD KVSLTCMITD FFPEDITVEW

401 QWNGQPAENY KNTQPIMDTD GSYFIYSKLN VQKSNWEAGN TFTCSVLHEG

451 LHNHHTEKSL SHSPGK
```

Nucleic acid sequence of the Ab-12 HC including signal peptide encoding sequence:

```
                                          (SEQ ID NO: 204)
  1  ATGGGATGGA GCTGGACCTT TCTCTTCCTC CTGTCAGGAA CTTCGGGTGT

 51  CCTCTCTGAG GTCCAGTTGC AACAGTCTGG ACCTGAACTA ATGAAGCCTG

101  GGGCTTCAGT GAAGATGTCC TGCAAGGCTT CTGGATACAC ATTCACTGAC

151  TACAACATGC ACTGGATGAA GCAGAACCAA GGAAAGAGCC TAGAGTGGAT

201  AGGAGAGATT AATCCTAACA GTGGTGGTTC TGGTTACAAC CAGAAGTTCA

251  AAGGCAAGGC CACATTGACT GTAGACAAGT CCTCCAGCAC AGCCTACATG

301  GAGCTCCGCA GCCTGACATC TGAGGACTCT GCAGTCTATT ACTGTGCAAG

351  ATTGGGCTAC TATGGTAACT ACGAGGACTG GTATTTCGAT GTCTGGGGCG

401  CAGGGACCAC GGTCACCGTC TCCTCTGCCA AAACGACACC CCCATCTGTC

451  TATCCACTGG CCCCTGGATC TGCTGCCCAA ACTAACTCCA TGGTGACCCT

501  GGGATGCCTG GTCAAGGGCT ATTTCCCTGA GCCAGTGACA GTGACCTGGA

551  ACTCTGGATC CCTGTCCAGC GGTGTGCACA CCTTCCCAGC TGTCCTGCAG

601  TCTGACCTCT ACACTCTGAG CAGCTCAGTG ACTGTCCCCT CCAGCACCTG

651  GCCCAGCGAG ACCGTCACCT GCAACGTTGC CCACCCGGCC AGCAGCACCA

701  AGGTGGACAA GAAAATTGTG CCCAGGGATT GTGGTTGTAA GCCTTGCATA

751  TGTACAGTCC CAGAAGTATC ATCTGTCTTC ATCTTCCCCC CAAAGCCCAA

801  GGATGTGCTC ACCATTACTC TGACTCCTAA GGTCACGTGT GTTGTGGTAG

851  ACATCAGCAA GGATGATCCC GAGGTCCAGT TCAGCTGGTT TGTAGATGAT

901  GTGGAGGTGC ACACAGCTCA GACGCAACCC CGGGAGGAGC AGTTCAACAG
```

-continued

```
 951 CACTTTCCGC TCAGTCAGTG AACTTCCCAT CATGCACCAG GACTGGCTCA

1001 ATGGCAAGGA GTTCAAATGC AGGGTCAACA GTGCAGCTTT CCCTGCCCCC

1051 ATCGAGAAAA CCATCTCCAA AACCAAAGGC AGACCGAAGG CTCCACAGGT

1101 GTACACCATT CCACCTCCCA AGGAGCAGAT GGCCAAGGAT AAAGTCAGTC

1151 TGACCTGCAT GATAACAGAC TTCTTCCCTG AAGACATTAC TGTGGAGTGG

1201 CAGTGGAATG GGCAGCCAGC GGAGAACTAC AAGAACACTC AGCCCATCAT

1251 GGACACAGAT GGCTCTTACT TCATCTACAG CAAGCTCAAT GTGCAGAAGA

1301 GCAACTGGGA GGCAGGAAAT ACTTTCACCT GCTCTGTGTT ACATGAGGGC

1351 CTGCACAACC ACCATACTGA GAAGAGCCTC TCCCACTCTC CTGGTAAATG

1401 A
```

Ab-13

The sequences of the Antibody 13 (also referred to herein as Ab-13) LC and HC are as follows:

Ab-13 Light Chain:

Amino acid sequence of the mature form (signal peptide removed) of the Ab-13 LC:

(SEQ ID NO: 205)

1 QIVLTQSPAI MSASPGEKVT MTCRASSSVT SSYLNWYQQK PGSSPKLWIY

51 STSNLASGVP ARFSGSGSGT SYSLTISSVE AEDAATYYCQ QYDFFPSTFG

101 GGTKLEIK*RA DAAPTVSIFP PSSEQLTSGG ASVVCFLNNF YPKDINVKWK*

*151 IDGSERQNGV LNSWTDQDSK DSTYSMSSTL TLTKDEYERH NSYTCEATHK*

*201 TSTSPIVKSF NRNEC*

Nucleic acid sequence encoding the mature form (signal peptide removed) of the Ab-13 LC:

(SEQ ID NO: 206)

```
  1 CAGATTGTTC TCACCCAGTC TCCAGCAATC ATGTCTGCAT CTCCAGGGGA

 51 GAAGGTCACC ATGACCTGCA GGGCCAGCTC AAGTGTAACT TCCAGTTACT

101 TGAACTGGTA CCAGCAGAAG CCAGGATCTT CCCCCAAACT CTGGATTTAT

151 AGCACATCCA ACCTGGCTTC AGGAGTCCCA GCTCGCTTCA GTGGCAGTGG

201 GTCTGGGACC TCTTACTCTC TCACAATCAG CAGTGTGGAG GCTGAGGATG

251 CTGCCACTTA TTACTGCCAG CAGTATGATT TTTTCCCATC GACGTTCGGT

301 GGAGGCACCA AGCTGGAAAT CAAGCGGGCT GATGCTGCAC CAACTGTATC

351 CATCTTCCCA CCATCCAGTG AGCAGTTAAC ATCTGGAGGT GCCTCAGTCG

401 TGTGCTTCTT GAACAACTTC TACCCCAAAG ACATCAATGT CAAGTGGAAG

451 ATTGATGGCA GTGAACGACA AAATGGCGTC CTGAACAGTT GGACTGATCA

501 GGACAGCAAA GACAGCACCT ACAGCATGAG CAGCACCCTC ACGTTGACCA

551 AGGACGAGTA TGAACGACAT AACAGCTATA CCTGTGAGGC CACTCACAAG

601 ACATCAACTT CACCCATCGT CAAGAGCTTC AACAGGAATG AGTGT
```

Amino acid sequence of the Ab-13 LC including signal peptide:

(SEQ ID NO: 207)

1 MDSQVQIFSF LLISALVKMS RGQIVLTQSP AIMSASPGEK VTMTCRASSS

-continued

```
 51 VTSSYLNWYQ QKPGSSPKLW IYSTSNLASG VPARFSGSGS GTSYSLTISS

101 VEAEDAATYY CQQYDFFPST FGGGTKLEIK RADAAPTVSI FPPSSEQLTS

151 GGASVVCFLN NFYPKDINVK WKIDGSERQN GVLNSWTDQD SKDSTYSMSS

201 TLTLTKDEYE RHNSYTCEAT HKTSTSPIVK SFNRNEC
```

Nucleic acid sequence of the Ab-13 LC including signal peptide encoding sequence:

```
                                                 (SEQ ID NO: 208)
  1 ATGGATTCTC AAGTGCAGAT TTTCAGCTTC CTTCTAATCA GTGCCTTAGT

 51 CAAAATGTCC AGAGGACAGA TTGTTCTCAC CCAGTCTCCA GCAATCATGT

101 CTGCATCTCC AGGGGAGAAG GTCACCATGA CCTGCAGGGC CAGCTCAAGT

151 GTAACTTCCA GTTACTTGAA CTGGTACCAG CAGAAGCCAG GATCTTCCCC

201 CAAACTCTGG ATTTATAGCA CATCCAACCT GGCTTCAGGA GTCCCAGCTC

251 GCTTCAGTGG CAGTGGGTCT GGGACCTCTT ACTCTCTCAC AATCAGCAGT

301 GTGGAGGCTG AGGATGCTGC CACTTATTAC TGCCAGCAGT ATGATTTTTT

351 CCCATCGACG TTCGGTGGAG GCACCAAGCT GGAAATCAAG CGGGCTGATG

401 CTGCACCAAC TGTATCCATC TTCCCACCAT CCAGTGAGCA GTTAACATCT

451 GGAGGTGCCT CAGTCGTGTG CTTCTTGAAC AACTTCTACC CCAAAGACAT

501 CAATGTCAAG TGGAAGATTG ATGGCAGTGA ACGACAAAAT GGCGTCCTGA

551 ACAGTTGGAC TGATCAGGAC AGCAAAGACA GCACCTACAG CATGAGCAGC

601 ACCCTCACGT TGACCAAGGA CGAGTATGAA CGACATAACA GCTATACCTG

651 TGAGGCCACT CACAAGACAT CAACTTCACC CATCGTCAAG AGCTTCAACA

701 GGAATGAGTG T
```

Ab-13 Heavy Chain:

Amino acid sequence of the mature form (signal peptide removed) of the Ab-13 HC:

(SEQ ID NO: 209)

1 EVQLQQSGPE LVKPGASVKM SCKASGYTFT DYYMNWVKQS HGESLEWOGD

51 INPYNDDTTY NHKFKGKATL TVDKSSNTAY MQLNSLTSED SAVYYCARET

101 AVITTNAMDY WGQGTSVTVS S*AKTTPPSVY PLAPGSAAQT NSMVTLGCLV*

*151 KGYFPEPVTV TWNSGSLSSG VHTFPAVLQS DLYTLSSSVT VPSSTWPSET*

*201 VTCNVAHPAS STKVDKKIVP RDCGCKPCIC TVPEVSSVFI FPPKPKDVLT*

*251 ITLTPKVTCV VVDISKDDPE VQFSWFVDDV EVHTAQTQPR EEQFNSTFRS*

*301 VSELPIMHQD WLNGKEFKCR VNSAAFPAPI EKTISKTKGR PKAPQVYTIP*

*351 PPKEQMAKDK VSLTCMITDF FPEDITVEWQ WNGQPAENYK NTQPIMDTDG*

*401 SYFIYSKLNV QKSNWEAGNT FTCSVLHEGL HNHHTEKSLS HSPGK*

Nucleic acid sequence encoding the mature form (signal peptide removed) of the Ab-13 HC:

```
                                                 (SEQ ID NO: 210)
 1 GAGGTCCAGC TGCAACAATC TGGACCTGAG CTGGTGAAGC CTGGGGCTTC

51 AGTGAAGATG TCCTGTAAGG CTTCTGGATA CACATTCACT GACTACTACA
```

-continued

```
 101  TGAACTGGGT GAAGCAGAGC CATGGAGAGA GCCTTGAGTG GATTGGAGAT
 151  ATTAATCCTT ACAACGATGA TACTACCTAC AACCACAAGT TCAAGGGCAA
 201  GGCCACATTG ACTGTAGACA AATCCTCCAA CACAGCCTAC ATGCAGCTCA
 251  ACAGCCTGAC ATCTGAGGAC TCTGCAGTCT ATTACTGTGC AAGAGAGACG
 301  GCCGTTATTA CTACGAATGC TATGGACTAC TGGGGTCAAG GAACCTCAGT
 351  CACCGTCTCC TCAGCCAAAA CGACACCCCC ATCTGTCTAT CCACTGGCCC
 401  CTGGATCTGC TGCCCAAACT AACTCCATGG TGACCCTGGG ATGCCTGGTC
 451  AAGGGCTATT TCCCTGAGCC AGTGACAGTG ACCTGGAACT CTGGATCCCT
 501  GTCCAGCGGT GTGCACACCT TCCCAGCTGT CCTGCAGTCT GACCTCTACA
 551  CTCTGAGCAG CTCAGTGACT GTCCCCTCCA GCACCTGGCC CAGCGAGACC
 601  GTCACCTGCA ACGTTGCCCA CCCGGCCAGC AGCACCAAGG TGGACAAGAA
 651  AATTGTGCCC AGGGATTGTG GTTGTAAGCC TTGCATATGT ACAGTCCCAG
 701  AAGTATCATC TGTCTTCATC TTCCCCCCAA AGCCCAAGGA TGTGCTCACC
 751  ATTACTCTGA CTCCTAAGGT CACGTGTGTT GTGGTAGACA TCAGCAAGGA
 801  TGATCCCGAG GTCCAGTTCA GCTGGTTTGT AGATGATGTG GAGGTGCACA
 851  CAGCTCAGAC GCAACCCCGG GAGGAGCAGT TCAACAGCAC TTTCCGCTCA
 901  GTCAGTGAAC TTCCCATCAT GCACCAGGAC TGGCTCAATG GCAAGGAGTT
 951  CAAATGCAGG GTCAACAGTG CAGCTTTCCC TGCCCCCATC GAGAAAACCA
1001  TCTCCAAAAC CAAAGGCAGA CCGAAGGCTC CACAGGTGTA CACCATTCCA
1051  CCTCCCAAGG AGCAGATGGC CAAGGATAAA GTCAGTCTGA CCTGCATGAT
1101  AACAGACTTC TTCCCTGAAG ACATTACTGT GGAGTGGCAG TGGAATGGGC
1151  AGCCAGCGGA GAACTACAAG AACACTCAGC CCATCATGGA CACAGATGGC
1201  TCTTACTTCA TCTACAGCAA GCTCAATGTG CAGAAGAGCA ACTGGGAGGC
1251  AGGAAATACT TTCACCTGCT CTGTGTTACA TGAGGGCCTG CACAACCACC
1301  ATACTGAGAA GAGCCTCTCC CACTCTCCTG GTAAA
```

Amino acid sequence of the Ab-13 HC including signal peptide:

```
                                              (SEQ ID NO: 211)
  1 MGWNWIFLFL LSGTAGVYSE VQLQQSGPEL VKPGASVKMS CKASGYTFTD
 51 YYMNWVKQSH GESLEWIGDI NPYNDDTTYN HKFKGKATLT VDKSSNTAYM
101 QLNSLTSEDS AVYYCARETA VITTNAMDYW GQGTSVTVSS AKTTPPSVYP
151 LAPGSAAQTN SMVTLGCLVK GYFPEPVTVT WNSGSLSSGV HTFPAVLQSD
201 LYTLSSSVTV PSSTWPSETV TCNVAHPASS TKVDKKIVPR DCGCKPCICT
251 VPEVSSVFIF PPKPKDVLTI TLTPKVTCVV VDISKDDPEV QFSWFVDDVE
301 VHTAQTQPRE EQFNSTFRSV SELPIMHQDW LNGKEFKCRV NSAAFPAPIE
351 KTISKTKGRP KAPQVYTIPP PKEQMAKDKV SLTCMITDFF PEDITVEWQW
401 NGQPAENYKN TQPIMDTDGS YFIYSKLNVQ KSNWEAGNTF TCSVLHEGLH
451 NHHTEKSLSH SPGK
```

Nucleic acid sequence of the Ab-13 HC including signal peptide encoding sequence:

(SEQ ID NO: 212)

1 ATGGGATGGA ACTGGATCTT TCTCTTCCTC TTGTCAGGAA CTGCAGGTGT

51 CTACTCTGAG GTCCAGCTGC AACAATCTGG ACCTGAGCTG GTGAAGCCTG

101 GGGCTTCAGT GAAGATGTCC TGTAAGGCTT CTGGATACAC ATTCACTGAC

151 TACTACATGA ACTGGGTGAA GCAGAGCCAT GGAGAGAGCC TTGAGTGGAT

201 TGGAGATATT AATCCTTACA ACGATGATAC TACCTACAAC CACAAGTTCA

251 AGGGCAAGGC CACATTGACT GTAGACAAAT CCTCCAACAC AGCCTACATG

301 CAGCTCAACA GCCTGACATC TGAGGACTCT GCAGTCTATT ACTGTGCAAG

351 AGAGACGGCC GTTATTACTA CGAATGCTAT GGACTACTGG GGTCAAGGAA

401 CCTCAGTCAC CGTCTCCTCA GCCAAAACGA CACCCCCATC TGTCTATCCA

451 CTGGCCCCTG GATCTGCTGC CCAAACTAAC TCCATGGTGA CCCTGGGATG

501 CCTGGTCAAG GGCTATTTCC CTGAGCCAGT GACAGTGACC TGGAACTCTG

551 GATCCCTGTC CAGCGGTGTG CACACCTTCC CAGCTGTCCT GCAGTCTGAC

601 CTCTACACTC TGAGCAGCTC AGTGACTGTC CCCTCCAGCA CCTGGCCCAG

651 CGAGACCGTC ACCTGCAACG TTGCCCACCC GGCCAGCAGC ACCAAGGTGG

701 ACAAGAAAAT TGTGCCCAGG GATTGTGGTT GTAAGCCTTG CATATGTACA

751 GTCCCAGAAG TATCATCTGT CTTCATCTTC CCCCCAAAGC CCAAGGATGT

801 GCTCACCATT ACTCTGACTC CTAAGGTCAC GTGTGTTGTG GTAGACATCA

851 GCAAGGATGA TCCCGAGGTC CAGTTCAGCT GGTTTGTAGA TGATGTGGAG

901 GTGCACACAG CTCAGACGCA ACCCCGGGAG GAGCAGTTCA ACAGCACTTT

951 CCGCTCAGTC AGTGAACTTC CCATCATGCA CCAGGACTGG CTCAATGGCA

1001 AGGAGTTCAA ATGCAGGGTC AACAGTGCAG CTTTCCCTGC CCCCATCGAG

1051 AAAACCATCT CCAAAACCAA AGGCAGACCG AAGGCTCCAC AGGTGTACAC

1101 CATTCCACCT CCCAAGGAGC AGATGGCCAA GGATAAAGTC AGTCTGACCT

1151 GCATGATAAC AGACTTCTTC CCTGAAGACA TTACTGTGGA GTGGCAGTGG

1201 AATGGGCAGC CAGCGGAGAA CTACAAGAAC ACTCAGCCCA TCATGGACAC

1251 AGATGGCTCT TACTTCATCT ACAGCAAGCT CAATGTGCAG AAGAGCAACT

1301 GGGAGGCAGG AAATACTTTC ACCTGCTCTG TGTTACATGA GGGCCTGCAC

1351 AACCACCATA CTGAGAAGAG CCTCTCCCAC TCTCCTGGTA AA

Ab-13 was humanized to generate Ab-14.

The sequences of the Antibody 14 (also referred to herein as Ab-14) LC and HC are as follows:

Ab-14 Light Chain:

Amino acid sequence of the mature form (signal peptide removed) of the Ab-14 LC:

(SEQ ID NO: 213)

1 DIQLTQSPSF LSASVGDRVT ITCRASSSVT SSYLNWYQQK PGKAPKLLIY

51 STSNLASGVP SRFSGSGSGT EFTLTISSLQ PEDFATYYCQ QYDFFPSTFG

101 GGTKVEIK*RT VAAPSVFIFP PSDEQLKSGT ASVVCLLNNF YPREAKVQWK*

*151 VDNALQSGNS QESVTEQDSK DSTYSLSSTL TLSKADYEKH KVYACEVTHQ*

*201 GLSSPVTKSF NRGEC*

Nucleic acid sequence encoding the mature form (signal peptide removed) of the Ab-14 LC:

```
                                          (SEQ ID NO: 214)
  1 GACATCCAGC TGACCCAGAG CCCCAGCTTC CTTTCCGCAT CCGTTGGTGA

 51 CCGAGTAACA ATCACATGCC GCGCCTCATC TTCAGTTACA TCTTCTTATC

101 TTAATTGGTA TCAACAAAAA CCAGGAAAAG CACCTAAACT TCTTATATAC

151 TCTACATCTA ATCTCGCATC AGGAGTTCCC TCTCGATTTT CAGGATCTGG

201 ATCAGGCACA GAATTTACAC TTACTATATC ATCACTCCAA CCAGAAGACT

251 TCGCCACTTA TTACTGCCAA CAATACGATT TTTTTCCAAG CACATTCGGA

301 GGAGGTACAA AAGTAGAAAT CAAGCGTACG GTGGCTGCAC CATCTGTCTT

351 CATCTTCCCG CCATCTGATG AGCAGTTGAA ATCTGGAACT GCCTCTGTTG

401 TGTGCCTGCT GAATAACTTC TATCCCAGAG AGGCCAAAGT ACAGTGGAAG

451 GTGGATAACG CCCTCCAATC GGGTAACTCC CAGGAGAGTG TCACAGAGCA

501 GGACAGCAAG GACAGCACCT ACAGCCTCAG CAGCACCCTG ACGCTGAGCA

551 AAGCAGACTA CGAGAAACAC AAAGTCTACG CCTGCGAAGT CACCCATCAG

601 GGCCTGAGCT CGCCCGTCAC AAAGAGCTTC AACAGGGGAG AGTGT
```

Amino acid sequence of the Ab-14 LC including signal peptide:

```
                                          (SEQ ID NO: 215)
  1 MDMRVPAQLL GLLLLWLPGA RCDIQLTQSP SFLSASVGDR VTITCRASSS

 51 VTSSYLNWYQ QKPGKAPKLL IYSTSNLASG VPSRFSGSGS GTEFTLTISS

101 LQPEDFATYY CQQYDFFPST FGGGTKVEIK RTVAAPSVFI FPPSDEQLKS

151 GTASVVCLLN NFYPREAKVQ WKVDNALQSG NSQESVTEQD SKDSTYSLSS

201 TLTLSKADYE KHKVYACEVT HQGLSSPVTK SFNRGEC
```

Nucleic acid sequence of the Ab-14 LC including signal peptide encoding sequence:

```
                                          (SEQ ID NO: 216)
  1 ATGGACATGA GGGTCCCCGC TCAGCTCCTG GGGCTCCTGC TACTCTGGCT

 51 CCCAGGTGCC AGATGTGACA TCCAGCTGAC CCAGAGCCCC AGCTTCCTTT

101 CCGCATCCGT TGGTGACCGA GTAACAATCA CATGCCGCGC CTCATCTTCA

151 GTTACATCTT CTTATCTTAA TTGGTATCAA CAAAAACCAG GAAAAGCACC

201 TAAACTTCTT ATATACTCTA CATCTAATCT CGCATCAGGA GTTCCCTCTC

251 GATTTTCAGG ATCTGGATCA GGCACAGAAT TTACACTTAC TATATCATCA

301 CTCCAACCAG AAGACTTCGC CACTTATTAC TGCCAACAAT ACGATTTTTT

351 TCCAAGCACA TTCGGAGGAG GTACAAAAGT AGAAATCAAG CGTACGGTGG

401 CTGCACCATC TGTCTTCATC TTCCCGCCAT CTGATGAGCA GTTGAAATCT

451 GGAACTGCCT CTGTTGTGTG CCTGCTGAAT AACTTCTATC CCAGAGAGGC

501 CAAAGTACAG TGGAAGGTGG ATAACGCCCT CCAATCGGGT AACTCCCAGG

551 AGAGTGTCAC AGAGCAGGAC AGCAAGGACA GCACCTACAG CCTCAGCAGC

601 ACCCTGACGC TGAGCAAAGC AGACTACGAG AAACACAAAG TCTACGCCTG
```

-continued

```
651 CGAAGTCACC CATCAGGGCC TGAGCTCGCC CGTCACAAAG AGCTTCAACA

701 GGGGAGAGTG T
```

Ab-14 Heavy Chain:

Amino acid sequence of the mature form (signal peptide removed) of the Ab-14 HC:

```
                                             (SEQ ID NO: 217)
  1 EVQLVQSGAE VKKPGASVKV SCKASGYTFT DYYMNWVRQA PGQRLEWMGD

 51 INPYNDDTTY NHKFKGRVTI TRDTSASTAY MELSSLRSED TAVYYCARET

101 AVITTNAMDY WGQGTTVTVS SASTKGPSVF PLAPCSRSTS ESTAALGCLV

151 KDYFPEPVTV SWNSGALTSG VHTFPAVLQS SGLYSLSSVV TVPSSNFGTQ

201 TYTCNVDHKP SNTKVDKTVE RKCCVECPPC PAPPVAGPSV FLFPPKPKDT

251 LMISRTPEVT CVVVDVSHED PEVQFNWYVD GVEVHNAKTK PREEQFNSTF

301 RVVSVLTVVH QDWLNGKEYK KCVSNKGLPA PIEKTISKTK GQPREPQVYT

351 LPPSREEMTK NQVSLTCLVK GFYPSDIAVE WESNGOPENN YKTTPPMLDS

401 DGSFFLYSKL TVDKSRWQQG NVFSCSVMHE ALHNHYTQKS LSLSPGK
```

Amino acid sequence of the mature form (signal peptide removed) of the Ab-14 HC without carboxy-terminal lysine:

```
                                             (SEQ ID NO: 393)
  1 EVQLVQSGAE VKKPGASVKV SCKASGYTFT DYYMNWVRQA PGQRLEWMGD

 51 INPYNDDTTY NHKFKGRVTI TRDTSASTAY MELSSLRSED TAVYYCARET

101 AVITTNAMDY WGQGTTVTVS SASTKGPSVF PLAPCSRSTS ESTAALGCLV

151 KDYFPEPVTV SWNSGALTSG VHTFPAVLQS SGLYSLSSVV TVPSSNFGTQ

201 TYTCNVDHKP SNTKVDKTVE RKCCVECPPC PAPPVAGPSV PAPPVAGPSV

251 LMISRTPEVT CVVVDVSHED PEVQFNWYVD GVEVHNAKTK PREEQFNSTF

301 RVVSVLTVVH QDWLNGKEYK CKVSNKGLPA PIEKTISKTK GQPREPQVYT

351 LPPSREEMTK NQVSLTCLVK GFYPSDIAVE WESNGQPENN YKTTPPMLDS

401 DGSFFLYSKL TVDKSRWQQG NVFSCSVMHE ALHNHYTQKS LSLSPG
```

Nucleic acid sequence encoding the mature form (signal peptide removed) of the Ab-14 HC:

```
                                             (SEQ ID NO: 218)
  1 GAGGTGCAGC TGGTGCAGAG CGGCGCCGAG GTCAAGAAAC CTGGAGCAAG

 51 CGTAAAGGTT AGTTGCAAAG CATCTGGATA CACATTTACC GACTACTACA

101 TGAATTGGGT ACGACAAGCC CCTGGACAAA GACTTGAATG GATGGGAGAC

151 ATTAACCCTT ATAACGACGA CACTACATAC AATCATAAAT TTAAAGGAAG

201 AGTTACAATT ACAAGAGATA CATCCGCATC AACCGCCTAT ATGGAACTTT

251 CCTCATTGAG ATCTGAAGAC ACTGCTGTTT ATTACTGTGC AAGAGAAACT

301 GCCGTTATTA CTACTAACGC TATGGATTAC TGGGGTCAAG GAACCACTGT

351 TACCGTCTCT AGTGCCTCCA CCAAGGGCCC ATCGGTCTTC CCCCTGGCGC

401 CCTGCTCCAG GAGCACCTCC GAGAGCACAG CGGCCCTGGG CTGCCTGGTC

451 AAGGACTACT TCCCCGAACC GGTGACGGTG TCGTGGAACT CAGGCGCTCT
```

-continued

```
 501 GACCAGCGGC GTGCACACCT TCCCAGCTGT CCTACAGTCC TCAGGACTCT

 551 ACTCCCTCAG CAGCGTGGTG ACCGTGCCCT CCAGCAACTT CGGCACCCAG

 601 ACCTACACCT GCAACGTAGA TCACAAGCCC AGCAACACCA AGGTGGACAA

 651 GACAGTTGAG CGCAAATGTT GTGTCGAGTG CCCACCGTGC CCAGCACCAC

 701 CTGTGGCAGG ACCGTCAGTC TTCCTCTTCC CCCCAAAACC CAAGGACACC

 751 CTCATGATCT CCCGGACCCC TGAGGTCACG TGCGTGGTGG TGGACGTGAG

 801 CCACGAAGAC CCCGAGGTCC AGTTCAACTG GTACGTGGAC GGCGTGGAGG

 851 TGCATAATGC CAAGACAAAG CCACGGGAGG AGCAGTTCAA CAGCACGTTC

 901 CGTGTGGTCA GCGTCCTCAC CGTTGTGCAC CAGGACTGGC TGAACGGCAA

 951 GGAGTACAAG TGCAAGGTCT CCAACAAAGG CCTCCCAGCC CCCATCGAGA

1001 AAACCATCTC CAAAACCAAA GGGCAGCCCC GAGAACCACA GGTGTACACC

1051 CTGCCCCCAT CCCGGGAGGA GATGACCAAG AACCAGGTCA GCCTGACCTG

1101 CCTGGTCAAA GGCTTCTACC CCAGCGACAT CGCCGTGGAG TGGGAGAGCA

1151 ATGGGCAGCC GGAGAACAAC TACAAGACCA CACCTCCCAT GCTGGACTCC

1201 GACGGCTCCT TCTTCCTCTA CAGCAAGCTC ACCGTGGACA AGAGCAGGTG

1251 GCAGCAGGGG AACGTCTTCT CATGCTCCGT GATGCATGAG GCTCTGCACA

1301 ACCACTACAC GCAGAAGAGC CTCTCCCTGT CTCCGGGTAA A
```

Amino acid sequence of the Ab-14 HC including signal peptide:

```
                                                (SEQ ID NO: 219)
  1 MDWTWRILFL VAAATGAHSE VQLVQSGAEV KKPGASVKVS CKASGYTFTD

 51 YYMNWVRQAP GQRLEWMGDI NPYNDDTTYN HKFKGRVTIT RDTSASTAYM

101 ELSSLRSEDT AVYYCARETA VITTNAMDYW GQGTTVTVSS ASTKGPSVFP

151 LAPCSRSTSE STAALGCLVK DYFPEPVTVS WNSGALTSGV HTFPAVLQSS

201 GLYSLSSVVT VPSSNFGTQT YTCNVDHKPS NTKVDKTVER KCCVECPPCP

251 APPVAGPSVF LFPPKPKDTL MISRTPEVTC VVVDVSHEDP EVQFNWYVDG

301 VEVHNAKTKP REEQFNSTFR VVSVLTVVHQ DWLNGKEYKC KVSNKGLPAP

351 IEKTISKTKG QPREPQVYTL PPSREEMTKN QVSLTCLVKG FYPSDIAVEW

401 ESNGQPENNY KTTPPMLDSD GSFFLYSKLT VDKSRWQQGN VFSCSVMHEA

451 LHNHYTQKSL SLSPGK
```

Nucleic acid sequence of the Ab-14 HC including signal peptide encoding sequence:

```
                                                (SEQ ID NO: 220)
  1 ATGGACTGGA CCTGGAGGAT CCTCTTCTTG GTGGCAGCAG CCACAGGAGC

 51 CCACTCCGAG GTGCAGCTGG TGCAGAGCGG CGCCGAGGTC AAGAAACCTG

101 GAGCAAGCGT AAAGGTTAGT TGCAAAGCAT CTGGATACAC ATTTACCGAC

151 TACTACATGA ATTGGGTACG ACAAGCCCCT GGACAAAGAC TTGAATGGAT

201 GGGAGACATT AACCCTTATA ACGACGACAC TACATACAAT CATAAATTTA

251 AAGGAAGAGT TACAATTACA AGAGATACAT CCGCATCAAC CGCCTATATG

301 GAACTTTCCT CATTGAGATC TGAAGACACT GCTGTTTATT ACTGTGCAAG
```

-continued

```
 351 AGAAACTGCC GTTATTACTA CTAACGCTAT GGATTACTGG GGTCAAGGAA
 401 CCACTGTTAC CGTCTCTAGT GCCTCCACCA AGGGCCCATC GGTCTTCCCC
 451 CTGGCGCCCT GCTCCAGGAG CACCTCCGAG AGCACAGCGG CCCTGGGCTG
 501 CCTGGTCAAG GACTACTTCC CCGAACCGGT GACGGTGTCG TGGAACTCAG
 551 GCGCTCTGAC CAGCGGCGTG CACACCTTCC CAGCTGTCCT ACAGTCCTCA
 601 GGACTCTACT CCCTCAGCAG CGTGGTGACC GTGCCCTCCA GCAACTTCGG
 651 CACCCAGACC TACACCTGCA ACGTAGATCA CAAGCCCAGC AACACCAAGG
 701 TGGACAAGAC AGTTGAGCGC AAATGTTGTG TCGAGTGCCC ACCGTGCCCA
 751 GCACCACCTG TGGCAGGACC GTCAGTCTTC CTCTTCCCCC CAAAACCCAA
 801 GGACACCCTC ATGATCTCCC GGACCCCTGA GGTCACGTGC GTGGTGGTGG
 851 ACGTGAGCCA CGAAGACCCC GAGGTCCAGT TCAACTGGTA CGTGGACGGC
 901 GTGGAGGTGC ATAATGCCAA GACAAAGCCA CGGGAGGAGC AGTTCAACAG
 951 CACGTTCCGT GTGGTCAGCG TCCTCACCGT TGTGCACCAG GACTGGCTGA
1001 ACGGCAAGGA GTACAAGTGC AAGGTCTCCA ACAAAGGCCT CCCAGCCCCC
1051 ATCGAGAAAA CCATCTCCAA AACCAAAGGG CAGCCCCGAG AACCACAGGT
1101 GTACACCCTG CCCCCATCCC GGGAGGAGAT GACCAAGAAC CAGGTCAGCC
1151 TGACCTGCCT GGTCAAAGGC TTCTACCCCA GCGACATCGC CGTGGAGTGG
1201 GAGAGCAATG GGCAGCCGGA GAACAACTAC AAGACCACAC CTCCCATGCT
1251 GGACTCCGAC GGCTCCTTCT TCCTCTACAG CAAGCTCACC GTGGACAAGA
1301 GCAGGTGGCA GCAGGGGAAC GTCTTCTCAT GCTCCGTGAT GCATGAGGCT
1351 CTGCACAACC ACTACACGCA GAAGAGCCTC TCCCTGTCTC CGGGTAAA
```

The CDR sequences in the variable region of the heavy chain of Ab-14 are:

```
                                (SEQ ID NO: 296)
CDR-H1: DYYMN

                                (SEQ ID NO: 297)
CDR-H2: DINPYNDDTTYNHKFKG

                                (SEQ ID NO: 298)
CDR-H3: ETAVITTNAMD
```

The light chain variable region CDR sequences of Ab-14 are:

```
                                (SEQ ID NO: 284)
CDR-L1: RASSSVTSSYLN

                                (SEQ ID NO: 285)
CDR-L2: STSNLAS

                                (SEQ ID NO: 286)
CDR-L3: QQYDFFPST
```

Ab-14 Variable Domains:

Ab-14 light chain variable domain amino acid sequence (without signal sequence):

```
                                                    (SEQ ID NO: 380)
  1 DIQLTQSPSF LSASVGDRVT ITCRASSSVT SSYLNWYQQK PGKAPKLLIY
 51 STSNLASGVP SRFSGSGSGT EFTLTISSLQ PEDFATYYCQ QYDFFPSTFG
101 GGTKVEIK
```

-

Ab-14 light chain variable domain DNA sequence (without signal sequence):

```
                                                    (SEQ ID NO: 381)
  1 GACATCCAGC TGACCCAGAG CCCCAGCTTC CTTTCCGCAT CCGTTGGTGA
 51 CCGAGTAACA ATCACATGCC GCGCCTCATC TTCAGTTACA TCTTCTTATC
101 TTAATTGGTA TCAACAAAAA CCAGGAAAAG CACCTAAACT TCTTATATAC
```

-continued

```
151 TCTACATCTA ATCTCGCATC AGGAGTTCCC TCTCGATTTT CAGGATCTGG

201 ATCAGGCACA GAATTTACAC TTACTATATC ATCACTCCAA CCAGAAGACT

251 TCGCCACTTA TTACTGCCAA CAATACGATT TTTTTCCAAG CACATTCGGA

301 GGAGGTACAA AAGTAGAAAT CAAG
```

Ab-14 heavy chain variable domain amino acid sequence (without signal sequence):

```
                                                (SEQ ID NO: 382)
  1 EVQLVQSGAE VKKPGASVKV SCKASGYTFT DYYMNWVRQA PGQRLEWMGD

 51 INPYNDDTTY NHKFKGRVTI TRDTSASTAY MELSSLRSED TAVYYCARET

101 AVITTNAMDY WGQGTTVTVS S
```

Ab-14 heavy chain variable domain DNA sequence (without signal sequence):

```
                                                (SEQ ID NO: 383)
  1 GAGGTGCAGC TGGTGCAGAG CGGCGCCGAG GTCAAGAAAC CTGGAGCAAG

 51 CGTAAAGGTT AGTTGCAAAG CATCTGGATA CACATTTACC GACTACTACA

101 TGAATTGGGT ACGACAAGCC CCTGGACAAA GACTTGAATG GATGGGAGAC

151 ATTAACCCTT ATAACGACGA CACTACATAC AATCATAAAT TTAAAGGAAG

201 AGTTACAATT ACAAGAGATA CATCCGCATC AACCGCCTAT ATGGAACTTT

251 CCTCATTGAG ATCTGAAGAC ACTGCTGTTT ATTACTGTGC AAGAGAAACT

301 GCCGTTATTA CTACTAACGC TATGGATTAC TGGGGTCAAG GAACCACTGT

351 TACCGTCTCT AGT
```

Ab-3 was humanized to generate Ab-15.

Ab-15

The sequences of the Antibody 15 (also referred to herein as Ab-15) LC and HC are as follows:

Ab-15 Light Chain:

Amino acid sequence of the mature form (signal peptide removed) of the Ab-15 LC:

```
                                                (SEQ ID NO: 221)
  1 DIQMTQSPSS LSASVGDRVT ITCSVSSTIS SNHLHWFQQK PGKAPKSLIY

 51 GTSNLASGVP SRFSGSGSGT DFTLTISSLQ PEDFATYYCQ QWSSYPLTFG

101 GGTKVEIKRT VAAPSVFIFP PSDEQLKSGT ASVVCLLNNF YPREAKVQWK

151 VDNALQSGNS QESVTEQDSK DSTYSLSSTL TLSKADYEKH KVYACEVTHQ

201 GLSSPVTKSF NRGEC
```

Nucleic acid sequence encoding the mature form (signal peptide removed) of the Ab-15 LC:

```
                                                (SEQ ID NO: 222)
  1 GACATCCAGA TGACCCAGTC TCCATCCTCC CTCTCAGCAT CCGTAGGCGA

 51 TAGAGTTACA ATAACATGCA GCGTATCATC AACTATATCA TCAAATCATC

101 TTCATTGGTT CCAACAGAAA CCCGGCAAAG CACCTAAATC ACTTATATAC

151 GGCACATCAA ATCTCGCATC AGGCGTTCCT TCAAGATTTT CAGGCTCTGG
```

-continued

```
201 CTCAGGCACC GACTTTACTC TTACAATATC CTCCCTCCAA CCCGAAGACT

251 TCGCAACCTA TTACTGTCAA CAATGGTCCT CATATCCACT CACATTTGGC

301 GGCGGCACAA AAGTAGAAAT TAAACGTACG GTGGCTGCAC CATCTGTCTT

351 CATCTTCCCG CCATCTGATG AGCAGTTGAA ATCTGGAACT GCCTCTGTTG

401 TGTGCCTGCT GAATAACTTC TATCCCAGAG AGGCCAAAGT ACAGTGGAAG

451 GTGGATAACG CCCTCCAATC GGGTAACTCC CAGGAGAGTG TCACAGAGCA

501 GGACAGCAAG GACAGCACCT ACAGCCTCAG CAGCACCCTG ACGCTGAGCA

551 AAGCAGACTA CGAGAAACAC AAAGTCTACG CCTGCGAAGT CACCCATCAG

601 GGCCTGAGCT CGCCCGTCAC AAAGAGCTTC AACAGGGGAG AGTGT
```

Amino acid sequence of the Ab-15 LC including signal peptide:

```
                                              (SEQ ID NO: 223)
  1 MDMRVPAQLL GLLLLWLRGA RCDIQMTQSP SSLSASVGDR VTITCSVSST

 51 ISSNHLHWFQ QKPGKAPKSL IYGTSNLASG VPSRFSGSGS GTDFTLTISS

101 LQPEDFATYY CQQWSSYPLT FGGGTKVEIK RTVAAPSVFI FPPSDEQLKS

151 GTASVVCLLN NFYPREAKVQ WKVDNALQSG NSQESVTEQD SKDSTYSLSS

201 TLTLSKADYE KHKVYACEVT HQGLSSPVTK SFNRGEC
```

Nucleic acid sequence of the Ab-15 LC including signal peptide encoding sequence:

```
                                              (SEQ ID NO: 224)
  1 ATGGACATGA GGGTCCCCGC TCAGCTCCTG GGGCTCCTGC TACTCTGGCT

 51 CCGAGGTGCC AGATGTGACA TCCAGATGAC CCAGTCTCCA TCCTCCCTCT

101 CAGCATCCGT AGGCGATAGA GTTACAATAA CATGCAGCGT ATCATCAACT

151 ATATCATCAA ATCATCTTCA TTGGTTCCAA CAGAAACCCG GCAAAGCACC

201 TAAATCACTT ATATACGGCA CATCAAATCT CGCATCAGGC GTTCCTTCAA

251 GATTTTCAGG CTCTGGCTCA GGCACCGACT TTACTCTTAC AATATCCTCC

301 CTCCAACCCG AAGACTTCGC AACCTATTAC TGTCAACAAT GGTCCTCATA

351 TCCACTCACA TTTGGCGGCG GCACAAAAGT AGAAATTAAA CGTACGGTGG

401 CTGCACCATC TGTCTTCATC TTCCCGCCAT CTGATGAGCA GTTGAAATCT

451 GGAACTGCCT CTGTTGTGTG CCTGCTGAAT AACTTCTATC CCAGAGAGGC

501 CAAAGTACAG TGGAAGGTGG ATAACGCCCT CCAATCGGGT AACTCCCAGG

551 AGAGTGTCAC AGAGCAGGAC AGCAAGGACA GCACCTACAG CCTCAGCAGC

601 ACCCTGACGC TGAGCAAAGC AGACTACGAG AAACACAAAG TCTACGCCTG

651 CGAAGTCACC CATCAGGGCC TGAGCTCGCC CGTCACAAAG AGCTTCAACA

701 GGGGAGAGTG T
```

Ab-15 Heavy Chain

Amino acid sequence of the mature form (signal peptide removed) of Ab-15 HC.

```
                                              (SEQ ID NO: 225)
1 EVQLVQSGAE VKKPGASVKV SCKASDFNIK DFYLHWVRQA PGQGLEWIGR
```

-continued

51 IDPENGDTLY DPKFQDKVTM TTDTSTSTAY MELRSLRSDD TAVYYCAREA

101 DYFHDGTSYW YFDVWGRGTL VTVSS*ASTKG PSVFPLAPCS RSTSESTAAL*

*151 GCLVKDYFPE PVTVSWNSGA LTSGVHTHPA VLQSSGLYSL SSVVTVPSSN*

*201 FGTQTYTCNV DHKPSNTKVD KTVERKCCVE CPPCPAPPVA GPSVFLFPPK*

*251 PKDTLMISRT PEVTCVVVDV SHEDPEVQFN WYVDGVEVHN AKTKPREEQF*

*301 NSTFRVVSVL TVVHQDWLNG KEYKCKVSNK GLPAPIEKTI SKTKGQPREP*

*351 QVYTLPPSRE EMTKNQVSLT CLVKGFYPSD IAVEWESNGQ PENNYKTTPP*

*401 MLDSDGSFFL YSKLTVDKSR WQQGNVFSCS VMHEALHNHY TQKSLSLSPG*

*451 K*

Amino acid sequence of the mature form (signal peptide removed) of Ab-15 HC without carboxy-terminal lysine:

(SEQ ID NO: 394)

1 EVQLVQSGAE VKKPGASVKV SCKASDFNIK DFYLHWVRQA PGQGLEWIGR

51 IDPENGDTLY DPKFQDKVTM TTDTSTSTAY MELRSLRSDD TAVYYCAREA

101 DYFHDGTSYW YFDVWGRGTL VTVSS*ASTKG PSVFPLAPCS RSTSESTAAL*

*151 GCLVKDYFPE PVTVSWNSGA LTSGVHTFPA VLQSSGLYSL SSVVTVPSSN*

*201 FGTQTYTCNV DHKPSNTKVD KTVERKCCVE CPPCPAPPVA GPSVFLFPPK*

*251 PKDTLMISRT PEVTCVVVDV SHEDPEVQFN WYVDGVEVHN AKTKPREEQF*

*301 NSTFRVVSVL TVVHQDWLNG KEYKCKVSNK GLPAPIEKTI SKTKGQPREP*

*351 QVYTLPPSRE EMTKNQVSLT CLVKGFYPSD IAVEWESNGQ PENNYKTTPP*

*401 MLDSDGSFFL YSKLTVDKSR WQQGNVFSCS VMHEALHNHY TQKSLSLSPG*

*451*

Nucleic acid sequence encoding the mature form (signal peptide removed) of the Ab-15 HC:

(SEQ ID NO: 226)

1 GAGGTGCAGC TGGTGCAGTC TGGGGCTGAG GTGAAGAAGC CTGGGGCCTC

51 AGTGAAGGTC TCCTGCAAGG CTTCTGACTT CAACATTAAA GACTTCTATC

101 TACACTGGGT GCGACAGGCC CCTGGACAAG GGCTTGAGTG GATTGGAAGG

151 ATTGATCCTG AGAATGGTGA TACTTTATAT GACCCGAAGT TCCAGGACAA

201 GGTCACCATG ACCACAGACA CGTCCACCAG CACAGCCTAC ATGGAGCTGA

251 GGAGCCTGAG ATCTGACGAC ACGGCCGTGT ATTACTGTGC GAGAGAGGCG

301 GATTATTTCC ACGATGGTAC CTCCTACTGG TACTTCGATG TCTGGGGCCG

351 TGGCACCCTG GTCACCGTCT CTAGTGCCTC CACCAAGGGC CCATCGGTCT

401 TCCCCCTGGC GCCCTGCTCC AGGAGCACCT CCGAGAGCAC AGCGGCCCTG

451 GGCTGCCTGG TCAAGGACTA CTTCCCCGAA CCGGTGACGG TGTCGTGGAA

501 CTCAGGCGCT CTGACCAGCG GCGTGCACAC CTTCCCAGCT GTCCTACAGT

551 CCTCAGGACT CTACTCCCTC AGCAGCGTGG TGACCGTGCC CTCCAGCAAC

601 TTCGGCACCC AGACCTACAC CTGCAACGTA GATCACAAGC CCAGCAACAC

651 CAAGGTGGAC AAGACAGTTG AGCGCAAATG TTGTGTCGAG TGCCCACCGT

701 GCCCAGCACC ACCTGTGGCA GGACCGTCAG TCTTCCTCTT CCCCCCAAAA

-continued

```
 751 CCCAAGGACA CCCTCATGAT CTCCCGGACC CCTGAGGTCA CGTGCGTGGT

 801 GGTGGACGTG AGCCACGAAG ACCCCGAGGT CCAGTTCAAC TGGTACGTGG

 851 ACGGCGTGGA GGTGCATAAT GCCAAGACAA AGCCACGGGA GGAGCAGTTC

 901 AACAGCACGT TCCGTGTGGT CAGCGTCCTC ACCGTTGTGC ACCAGGACTG

 951 GCTGAACGGC AAGGAGTACA AGTGCAAGGT CTCCAACAAA GGCCTCCCAG

1001 CCCCCATCGA GAAAACCATC TCCAAAACCA AAGGGCAGCC CCGAGAACCA

1051 CAGGTGTACA CCCTGCCCCC ATCCCGGGAG GAGATGACCA AGAACCAGGT

1101 CAGCCTGACC TGCCTGGTCA AAGGCTTCTA CCCCAGCGAC ATCGCCGTGG

1151 AGTGGGAGAG CAATGGGCAG CCGGAGAACA ACTACAAGAC CACACCTCCC

1201 ATGCTGGACT CCGACGGCTC CTTCTTCCTC TACAGCAAGC TCACCGTGGA

1251 CAAGAGCAGG TGGCAGCAGG GGAACGTCTT CTCATGCTCC GTGATGCATG

1301 AGGCTCTGCA CAACCACTAC ACGCAGAAGA GCCTCTCCCT GTCTCCGGGT

1351 AAA
```

Amino acid sequence of the Ab-15 HC including signal peptide:

```
                                           (SEQ ID NO: 227)
  1 MDWTWRILFL VAAATGAHSE VQLVQSGAEV KKPGASVKVS CKASDFNIKD

 51 FYLHWVRQAP GQGLEWIGRI DPENGDTLYD PKFQDKVTMT TDTSTSTAYM

101 ELRSLRSDDT AVYYCAREAD YFHDGTSYWY FDVWGRGTLV TVSSASTKGP

151 SVFPLAPCSR STSESTAALG CLVKDYFPEP VTVSWNSGAL TSGVHTFPAV

201 LQSSGLYSLS SVVTVPSSNF GTQTYTCNVD HKPSNTKVDK TVERKCCVEC

251 PPCPAPPVAG PSVFLFPPKP KDTLMISRTP EVTCVVVDVS HEDPEVQFNW

301 YVDGVEVHNA KTKPREEQFN STFRVVSVLT VVHQDWLNGK EYKCKVSNKG

351 LPAPIEKTIS KTKGQPREPQ VYTLPPSREE MTKNQVSLTC LVKGFYPSDI

401 AVEWESNGQP ENNYKTTPPM LDSDGSFFLY SKLTVDKSRW QQGNVFSCSV

451 MHEALHNHYT QKSLSLSPGK
```

Nucleic acid sequence of the Ab-15 HC including signal peptide encoding sequence:

```
                                           (SEQ ID NO: 228)
  1 ATGGACTGGA CCTGGAGGAT CCTCTTCTTG GTGGCAGCAG CCACAGGAGC

 51 CCACTCCGAG GTGCAGCTGG TGCAGTCTGG GGCTGAGGTG AAGAAGCCTG

101 GGGCCTCAGT GAAGGTCTCC TGCAAGGCTT CTGACTTCAA CATTAAAGAC

151 TTCTATCTAC ACTGGGTGCG ACAGGCCCCT GGACAAGGGC TTGAGTGGAT

201 TGGAAGGATT GATCCTGAGA ATGGTGATAC TTTATATGAC CCGAAGTTCC

251 AGGACAAGGT CACCATGACC ACAGACACGT CCACCAGCAC AGCCTACATG

301 GAGCTGAGGA GCCTGAGATC TGACGACACG GCCGTGTATT ACTGTGCGAG

351 AGAGGCGGAT TATTTCCACG ATGGTACCTC CTACTGGTAC TTCGATGTCT

401 GGGGCCGTGG CACCCTGGTC ACCGTCTCTA GTGCCTCCAC CAAGGGCCCA

451 TCGGTCTTCC CCCTGGCGCC CTGCTCCAGG AGCACCTCCG AGAGCACAGC

501 GGCCCTGGGC TGCCTGGTCA AGGACTACTT CCCCGAACCG GTGACGGTGT
```

-continued

```
551 CGTGGAACTC AGGCGCTCTG ACCAGCGGCG TGCACACCTT CCCAGCTGTC
601 CTACAGTCCT CAGGACTCTA CTCCCTCAGC AGCGTGGTGA CCGTGCCCTC
651 CAGCAACTTC GGCACCCAGA CCTACACCTG CAACGTAGAT CACAAGCCCA
701 GCAACACCAA GGTGGACAAG ACAGTTGAGC GCAAATGTTG TGTCGAGTGC
751 CCACCGTGCC CAGCACCACC TGTGGCAGGA CCGTCAGTCT TCCTCTTCCC
801 CCCAAAACCC AAGGACACCC TCATGATCTC CCGGACCCCT GAGGTCACGT
851 GCGTGGTGGT GGACGTGAGC CACGAAGACC CCGAGGTCCA GTTCAACTGG
901 TACGTGGACG GCGTGGAGGT GCATAATGCC AAGACAAAGC CACGGGAGGA
951 GCAGTTCAAC AGCACGTTCC GTGTGGTCAG CGTCCTCACC GTTGTGCACC
1001 AGGACTGGCT GAACGGCAAG GAGTACAAGT GCAAGGTCTC CAACAAAGGC
1051 CTCCCAGCCC CCATCGAGAA AACCATCTCC AAAACCAAAG GGCAGCCCCG
1101 AGAACCACAG GTGTACACCC TGCCCCCATC CCGGGAGGAG ATGACCAAGA
1151 ACCAGGTCAG CCTGACCTGC CTGGTCAAAG GCTTCTACCC CAGCGACATC
1201 GCCGTGGAGT GGGAGAGCAA TGGGCAGCCG GAGAACAACT ACAAGACCAC
1251 ACCTCCCATG CTGGACTCCG ACGGCTCCTT CTTCCTCTAC AGCAAGCTCA
1301 CCGTGGACAA GAGCAGGTGG CAGCAGGGGA ACGTCTTCTC ATGCTCCGTG
1351 ATGCATGAGG CTCTGCACAA CCACTACACG CAGAAGAGCC TCTCCCTGTC
1401 TCCGGGTAAA
```

The CDR sequences in the variable region of the heavy chain of Ab-15 are:

```
                                   (SEQ ID NO: 290)
CDR-H1: DFYLH

                                   (SEQ ID NO: 291)
CDR-H2: RIDPENGDTLYDPKFQD

                                   (SEQ ID NO: 292)
CDR-H3: EADYFHDGTSYWYFDV
```

The light chain variable region CDR sequences of Ab-15 are:

```
                                   (SEQ ID NO: 278)
CDR-L1: SVSSTISSNHLH

                                   (SEQ ID NO: 279)
CDR-L2: GTSNLAS

                                   (SEQ ID NO: 280)
CDR-L3: QQWSSYPLT
```

Ab-15 Variable Domains:

Ab-15 light chain variable domain amino acid sequence (without signal sequence):

```
                                                        (SEQ ID NO: 384)
  1 DIQMTQSPSS LSASVGDRVT ITCSVSSTIS SNHLHWFQQK PGKAPKSLIY
 51 GTSNLASGVP SRFSGSGSGT DFTLTISSLQ PEDFATYYCQ QWSSYPLTFG
101 GGTKVEIK
```

-

Ab-15 light chain variable domain DNA sequence (without signal sequence):

```
                                                        (SEQ ID NO: 385)
  1 GACATCCAGA TGACCCAGTC TCCATCCTCC CTCTCAGCAT CCGTAGGCGA
 51 TAGAGTTACA ATAACATGCA GCGTATCATC AACTATATCA TCAAATCATC
101 TTCATTGGTT CCAACAGAAA CCCGGCAAAG CACCTAAATC ACTTATATAC
151 GGCACATCAA ATCTCGCATC AGGCGTTCCT TCAAGATTTT CAGGCTCTGG
201 CTCAGGCACC GACTTTACTC TTACAATATC CTCCCTCCAA CCCGAAGACT
```

-continued

251 TCGCAACCTA TTACTGTCAA CAATGGTCCT CATATCCACT CACATTTGGC

301 GGCGGCACAA AAGTAGAAAT TAAA

Ab-15 heavy chain variable domain amino acid sequence (without signal sequence):

(SEQ ID NO: 386)
1 EVQLVQSGAE VKKPGASVKV SCKASDFNIK DFYLHWVRQA PGQGLEWIGR

51 IDPENGDTLY DPKFQDKVTM TTDTSTSTAY MELRSLRSDD TAVYYCAREA

101 DYFHDGTSYW YFDVWGRGTL VTVSS

Ab-15 heavy chain variable domain DNA sequence (without signal sequence):

(SEQ ID NO: 387)
1 GAGGTGCAGC TGGTGCAGTC TGGGGCTGAG GTGAAGAAGC CTGGGGCCTC

51 AGTGAAGGTC TCCTGCAAGG CTTCTGACTT CAACATTAAA GACTTCTATC

101 TACACTGGGT GCGACAGGCC CCTGGACAAG GGCTTGAGTG GATTGGAAGG

151 ATTGATCCTG AGAATGGTGA TACTTTATAT GACCCGAAGT TCCAGGACAA

201 GGTCACCATG ACCACAGACA CGTCCACCAG CACAGCCTAC ATGGAGCTGA

251 GGAGCCTGAG ATCTGACGAC ACGGCCGTGT ATTACTGTGC GAGAGAGGCG

301 GATTATTTCC ACGATGGTAC CTCCTACTGG TACTTCGATG TCTGGGGCCG

351 TGGCACCCTG GTCACCGTCT CTAGT

Ab-11 was humanized to generate Ab-16.

Ab-16

The sequences of the Antibody 16 (also referred to herein as Ab-16) LC and HC are as follows:

Ab-16 Light Chain:

Amino acid sequence of the mature form (signal peptide removed) of the Ab-16 LC:

(SEQ ID NO: 229)
1 DIQLTQSPSF LSASVGDRVT ITCRASSSIS YIHWYQQKPG KAPKLLIYAT

51 SNLASGVPSR FSGSGSGTEF TLTISSLQPE DFATYYCQQW SSDPLTFGGG

101 TKVEIK*RTVA APSVFIFPPS DEQLKSGTAS VVCLLNNFYP REAKVQWKVD*

*151 NALQSGNSQE SVTEQDSKDS TYSLSSTLTL SKADYEKHKV YACEVTHQGL*

*201 SSPVTKSFNR GEC*

Nucleic acid sequence encoding the mature form (signal peptide removed) of the Ab-16 LC:

(SEQ ID NO: 230)
1 GACATCCAGT TGACCCAGTC TCCATCCTTC CTGTCTGCAT CTGTAGGAGA

51 CAGAGTCACC ATCACTTGCA GGGCCAGCTC AAGTATAAGT TACATACACT

101 GGTATCAGCA AAAACCAGGG AAAGCCCCTA AGCTCCTGAT CTATGCCACA

151 TCCAACCTGG CTTCTGGGGT CCCATCAAGG TTCAGCGGCA GTGGATCTGG

201 GACAGAATTC ACTCTCACAA TCAGCAGCCT GCAGCCTGAA GATTTTGCAA

251 CTTATTACTG TCAGCAGTGG AGTAGTGACC CACTCACGTT CGGCGGAGGG

-continued

```
301 ACCAAGGTGG AGATCAAACG TACGGTGGCT GCACCATCTG TCTTCATCTT

351 CCCGCCATCT GATGAGCAGT TGAAATCTGG AACTGCCTCT GTTGTGTGCC

401 TGCTGAATAA CTTCTATCCC AGAGAGGCCA AAGTACAGTG GAAGGTGGAT

451 AACGCCCTCC AATCGGGTAA CTCCCAGGAG AGTGTCACAG AGCAGGACAG

501 CAAGGACAGC ACCTACAGCC TCAGCAGCAC CCTGACGCTG AGCAAAGCAG

551 ACTACGAGAA ACACAAAGTC TACGCCTGCG AAGTCACCCA TCAGGGCCTG

601 AGCTCGCCCG TCACAAAGAG CTTCAACAGG GGAGAGTGT
```

Amino acid sequence of the Ab-16 LC including signal peptide:

```
                                              (SEQ ID NO: 231)
  1 MDMRVPAQLL GLLLLWLPGA RCDIQLTQSP SFLSASVGDR VTITCRASSS

 51 ISYIHWYQQK PGKAPKLLIY ATSNLASGVP SRFSGSGSGT EFTLTISSLQ

101 PEDFATYYCQ QWSSDPLTFG GGTKVEIKRT VAAPSVFIFP PSDEQLKSGT

151 ASVVCLLNNF YPREAKVQWK VDNALQSGNS QESVTEQDSK DSTYSLSSTL

201 TLSKADYEKH KVYACEVTHQ GLSSPVTKSF NRGEC
```

Nucleic acid sequence of the Ab-16 LC including signal peptide encoding sequence:

```
                                              (SEQ ID NO: 232)
  1 ATGGACATGA GGGTCCCCGC TCAGCTCCTG GGGCTCCTGC TGCTCTGGCT

 51 CCCAGGTGCC AGATGTGACA TCCAGTTGAC CCAGTCTCCA TCCTTCCTGT

101 CTGCATCTGT AGGAGACAGA GTCACCATCA CTTGCAGGGC CAGCTCAAGT

151 ATAAGTTACA TACACTGGTA TCAGCAAAAA CCAGGGAAAG CCCCTAAGCT

201 CCTGATCTAT GCCACATCCA ACCTGGCTTC TGGGGTCCCA TCAAGGTTCA

251 GCGGCAGTGG ATCTGGGACA GAATTCACTC TCACAATCAG CAGCCTGCAG

301 CCTGAAGATT TTGCAACTTA TTACTGTCAG CAGTGGAGTA GTGACCCACT

351 CACGTTCGGC GGAGGGACCA AGGTGGAGAT CAAACGTACG GTGGCTGCAC

401 CATCTGTCTT CATCTTCCCG CCATCTGATG AGCAGTTGAA ATCTGGAACT

451 GCCTCTGTTG TGTGCCTGCT GAATAACTTC TATCCCAGAG AGGCCAAAGT

501 ACAGTGGAAG GTGGATAACG CCCTCCAATC GGGTAACTCC CAGGAGAGTG

551 TCACAGAGCA GGACAGCAAG GACAGCACCT ACAGCCTCAG CAGCACCCTG

601 ACGCTGAGCA AAGCAGACTA CGAGAAACAC AAAGTCTACG CCTGCGAAGT

651 CACCCATCAG GGCCTGAGCT CGCCCGTCAC AAAGAGCTTC AACAGGGGAG

701 AGTGT
```

Ab-16 Heavy Chain:

Amino acid sequence of the mature form (signal peptide removed) of the Ab-16 HC:

```
                                              (SEQ ID NO: 233)
  1 EVQLVQSGAE VKKPGASVKV SCKASGFDIKDYYIHWVRQA PGQGLEWIGR

 51 VDPDNGETEF APKFPGKVTM TTDTSISTAY MELSRLRSDD TAVYYCARED

101 YDGTYTWFPY WGQGTLVTVS SASTKGPSVF PLAPCSRSTS ESTAALGCLV
```

-continued

*151 KDYFPEPVTV SWNSGALTSG VHTFPAVLQS SGLYSLSSVV TVPSSNFGTQ*

*201 TYTCNVDHKP SNTKVDKTVE RKCCVECPPC PAPPVAGPSV FLFPPKPKDT*

*251 LMISRTPEVT CVVVDVSHED PEVQFNWYVD GVEVHNAKTK PREEQFNSTF*

*301 RVVSVLTVVH QDWLNGKEYK CKVSNKGLPA PIEKTISKTK GQPREPQVYT*

*351 LPPSREEMTK NQVSLTCLVK GFYPSDIAVE WESNGOPENN YKTTPPMLDS*

*401 DGSFFLYSKL TVDKSRWQQG NVFSCSVMHE ALHNHYTQKS LSLSPGK*

Amino acid sequence of the mature form (signal peptide removed) of the Ab-16 HC without carboxy-terminal lysine:

(SEQ ID NO: 395)

1 EVQLVQSGAE VKKPGASVKV SCKASGFDIKDYYIHWVRQA PGQGLEWIGR

51 VDPDNGETEF APKFPGKVTM TTDTSISTAY MELSRLRSDD TAVYYCARED

101 YDGTYTWFPY WGQGTLVTVS S*ASTKGPSVF PLAPCSRSTS ESTAALGCLV*

*151 KDYFPEPVTV SWNSGALTSG VHTFPAVLQS SGLYSLSSVV TVPSSNFGTQ*

*201 TYTCNVDHKP SNTKVDKTVE RKCCVECPPC PAPPVAGPSV FLFPPKPKDT*

*251 LMISRTPEVT CVVVDVSHED PEVQFNWYVD GVEVHNAKTK PREEQFNSTF*

*301 RVVSVLTVVH QDWLNGKEYK CKVSNKGLPA PIEKTISKTK GQPREPQVYT*

*351 LPPSREEMTK NOVSLTCLVK GFYPSDIAVE WESNGQPENN YKTTPPMLDS*

*401 DGSFFLYSKL TVDKSRWQQG NVFSCSVMHE ALHNHYTQKS LSLSPG*

Nucleic acid sequence encoding the mature form (signal peptide removed) of the Ab-16 HC:

(SEQ ID NO: 234)

1 GAGGTGCAGC TGGTGCAGTC TGGGGCTGAG GTGAAGAAGC CTGGGGCCTC

51 AGTGAAGGTC TCCTGCAAGG CTTCTGGATT CGACATTAAG GACTACTATA

101 TACACTGGGT GCGACAGGCC CCTGGACAAG GGCTTGAGTG GATCGGAAGG

151 GTTGATCCTG ACAATGGTGA GACTGAATTT GCCCCGAAGT TCCCGGGCAA

201 GGTCACCATG ACCACAGACA CGTCCATCAG CACAGCCTAC ATGGAGCTGA

251 GCAGGCTGAG ATCTGACGAC ACGGCCGTGT ATTACTGTGC GAGAGAAGAC

301 TACGATGGTA CCTACACCTG GTTTCCTTAT TGGGGCCAAG GGACTCTGGT

351 CACCGTCTCT AGTGCCTCCA CCAAGGGCCC ATCGGTCTTC CCCCTGGCGC

401 CCTGCTCCAG GAGCACCTCC GAGAGCACAG CGGCCCTGGG CTGCCTGGTC

451 AAGGACTACT TCCCCGAACC GGTGACGGTG TCGTGGAACT CAGGCGCTCT

501 GACCAGCGGC GTGCACACCT TCCCAGCTGT CCTACAGTCC TCAGGACTCT

551 ACTCCCTCAG CAGCGTGGTG ACCGTGCCCT CCAGCAACTT CGGCACCCAG

601 ACCTACACCT GCAACGTAGA TCACAAGCCC AGCAACACCA AGGTGGACAA

651 GACAGTTGAG CGCAAATGTT GTGTCGAGTG CCCACCGTGC CCAGCACCAC

701 CTGTGGCAGG ACCGTCAGTC TTCCTCTTCC CCCCAAAACC CAAGGACACC

751 CTCATGATCT CCCGGACCCC TGAGGTCACG TGCGTGGTGG TGGACGTGAG

801 CCACGAAGAC CCCGAGGTCC AGTTCAACTG GTACGTGGAC GGCGTGGAGG

851 TGCATAATGC CAAGACAAAG CCACGGGAGG AGCAGTTCAA CAGCACGTTC

901 CGTGTGGTCA GCGTCCTCAC CGTTGTGCAC CAGGACTGGC TGAACGGCAA

-continued

```
 951 GGAGTACAAG TGCAAGGTCT CCAACAAAGG CCTCCCAGCC CCCATCGAGA

1001 AAACCATCTC CAAAACCAAA GGGCAGCCCC GAGAACCACA GGTGTACACC

1051 CTGCCCCCAT CCCGGGAGGA GATGACCAAG AACCAGGTCA GCCTGACCTG

1101 CCTGGTCAAA GGCTTCTACC CCAGCGACAT CGCCGTGGAG TGGGAGAGCA

1151 ATGGGCAGCC GGAGAACAAC TACAAGACCA CACCTCCCAT GCTGGACTCC

1201 GACGGCTCCT TCTTCCTCTA CAGCAAGCTC ACCGTGGACA AGAGCAGGTG

1251 GCAGCAGGGG AACGTCTTCT CATGCTCCGT GATGCATGAG GCTCTGCACA

1301 ACCACTACAC GCAGAAGAGC CTCTCCCTGT CTCCGGGTAA A
```

Amino acid sequence of the Ab-16 HC including signal peptide:

```
                                                  (SEQ ID NO: 235)
  1 MDWTWRILFL VAAATGAHSE VQLVQSGAEV KKPGASVKVS CKASGFDIKD

 51 YYIHWVRQAP GQGLEWIGRV DPDNGETEFA PKFPGKVTMT TDTSISTAYM

101 ELSRLRSDDT AVYYCAREDY DGTYTWFPYW GQGTLVTVSS ASTKGPSVFP

151 LAPCSRSTSE STAALGCLVK DYFPEPVTVS WNSGALTSGV HTFPAVLQSS

201 GLYSLSSVVT VPSSNFGTQT YTCNVDHKPS NTKVDKTVER KCCVECPPCP

251 APPVAGPSVF LFPPKPKDTL MISRTPEVTC VVVDVSHEDP EVQFNWYVDG

301 VEVHNAKTKP REEQFNSTFR VVSVLTVVHQ DWLNGKEYKC KVSNKGLPAP

351 IEKTISKTKG QPREPQVYTL PPSREEMTKN QVSLTCLVKG FYPSDIAVEW

401 ESNGQPENNY KTTPPMLDSD GSFFLYSKLT VDKSRWQQGN VFSCSVMHEA

451 LHNHYTQKSL SLSPGK
```

Nucleic acid sequence of the Ab-16 HC including signal peptide encoding sequence:

```
                                                  (SEQ ID NO: 236)
  1 ATGGACTGGA CCTGGAGGAT CCTCTTCTTG GTGGCAGCAG CCACAGGAGC

 51 CCACTCCGAG GTGCAGCTGG TGCAGTCTGG GGCTGAGGTG AAGAAGCCTG

101 GGGCCTCAGT GAAGGTCTCC TGCAAGGCTT CTGGATTCGA CATTAAGGAC

151 TACTATATAC ACTGGGTGCG ACAGGCCCCT GGACAAGGGC TTGAGTGGAT

201 CGGAAGGGTT GATCCTGACA ATGGTGAGAC TGAATTTGCC CCGAAGTTCC

251 CGGGCAAGGT CACCATGACC ACAGACACGT CCATCAGCAC AGCCTACATG

301 GAGCTGAGCA GGCTGAGATC TGACGACACG GCCGTGTATT ACTGTGCGAG

351 AGAAGACTAC GATGGTACCT ACACCTGGTT TCCTTATTGG GGCCAAGGGA

401 CTCTGGTCAC CGTCTCTAGT GCCTCCACCA AGGGCCCATC GGTCTTCCCC

451 CTGGCGCCCT GCTCCAGGAG CACCTCCGAG AGCACAGCGG CCCTGGGCTG

501 CCTGGTCAAG GACTACTTCC CCGAACCGGT GACGGTGTCG TGGAACTCAG

551 GCGCTCTGAC CAGCGGCGTG CACACCTTCC CAGCTGTCCT ACAGTCCTCA

601 GGACTCTACT CCCTCAGCAG CGTGGTGACC GTGCCCTCCA GCAACTTCGG

651 CACCCAGACC TACACCTGCA ACGTAGATCA CAAGCCCAGC AACACCAAGG

701 TGGACAAGAC AGTTGAGCGC AAATGTTGTG TCGAGTGCCC ACCGTGCCCA

751 GCACCACCTG TGGCAGGACC GTCAGTCTTC CTCTTCCCCC CAAAACCCAA
```

-continued

```
801 GGACACCCTC ATGATCTCCC GGACCCCTGA GGTCACGTGC GTGGTGGTGG

851 ACGTGAGCCA CGAAGACCCC GAGGTCCAGT TCAACTGGTA CGTGGACGGC

901 GTGGAGGTGC ATAATGCCAA GACAAAGCCA CGGGAGGAGC AGTTCAACAG

951 CACGTTCCGT GTGGTCAGCG TCCTCACCGT TGTGCACCAG GACTGGCTGA

1001 ACGGCAAGGA GTACAAGTGC AAGGTCTCCA ACAAAGGCCT CCCAGCCCCC

1051 ATCGAGAAAA CCATCTCCAA AACCAAAGGG CAGCCCCGAG AACCACAGGT

1101 GTACACCCTG CCCCCATCCC GGGAGGAGAT GACCAAGAAC CAGGTCAGCC

1151 TGACCTGCCT GGTCAAAGGC TTCTACCCCA GCGACATCGC CGTGGAGTGG

1201 GAGAGCAATG GGCAGCCGGA GAACAACTAC AAGACCACAC CTCCCATGCT

1251 GGACTCCGAC GGCTCCTTCT TCCTCTACAG CAAGCTCACC GTGGACAAGA

1301 GCAGGTGGCA GCAGGGGAAC GTCTTCTCAT GCTCCGTGAT GCATGAGGCT

1351 CTGCACAACC ACTACACGCA GAAGAGCCTC TCCCTGTCTC CGGGTAAA
```

The CDR sequences in the variable region of the heavy chain of Ab-16 are:

(SEQ ID NO: 293)
CDR-H1: DYYIH (SEQ ID NO: 294)
CDR-H2: RVDPDNGETEFAPKFPG (SEQ ID NO: 295)
CDR-H3: EDYDGTYTWFPY

The light chain variable region CDR sequences of Ab-16 are:

(SEQ ID NO: 281)
CDR-L1: RASSSISYIH (SEQ ID NO: 282)
CDR-L2: ATSNLAS (SEQ ID NO: 283)
CDR-L3: QQWSSDPLT

Ab-16 Variable Domains:

Ab-16 light chain variable domain amino acid sequence (without signal sequence):

(SEQ ID NO: 388)

```
1 DIQLTQSPSF LSASVGDRVT ITCRASSSIS YIHWYQQKPG KAPKLLIYAT

51 SNLASGVPSR FSGSGSGTEF TLTISSLQPE DFATYYCQQW SSDPLTFGGG

101 TKVEIK
```

-

Ab-16 light chain variable domain DNA sequence (without signal sequence):

(SEQ ID NO: 389)

```
1 GACATCCAGT TGACCCAGTC TCCATCCTTC CTGTCTGCAT CTGTAGGAGA

51 CAGAGTCACC ATCACTTGCA GGGCCAGCTC AAGTATAAGT TACATACACT

101 GGTATCAGCA AAAACCAGGG AAAGCCCCTA AGCTCCTGAT CTATGCCACA

151 TCCAACCTGG CTTCTGGGGT CCCATCAAGG TTCAGCGGCA GTGGATCTGG

201 GACAGAATTC ACTCTCACAA TCAGCAGCCT GCAGCCTGAA GATTTTGCAA

251 CTTATTACTG TCAGCAGTGG AGTAGTGACC CACTCACGTT CGGCGGAGGG

301 ACCAAGGTGG AGATCAAA
```

Ab-16 heavy chain variable domain amino acid sequence (without signal sequence):

(SEQ ID NO: 390)

```
1 EVQLVQSGAE VKKPGASVKV SCKASGFDIKDYYIHWVRQA PGQGLEWIGR
```

-continued

```
 51 VDPDNGETEF APKFPGKVTM TTDTSISTAY MELSRLRSDD TAVYYCARED

101 YDGTYTWFPY WGQGTLVTVS S
```

Ab-16 heavy chain variable domain DNA sequence (without signal sequence):

```
                                            (SEQ ID NO: 391)
  1 GAGGTGCAGC TGGTGCAGTC TGGGGCTGAG GTGAAGAAGC CTGGGGCCTC

 51 AGTGAAGGTC TCCTGCAAGG CTTCTGGATT CGACATTAAG GACTACTATA

101 TACACTGGGT GCGACAGGCC CCTGGACAAG GGCTTGAGTG GATCGGAAGG

151 GTTGATCCTG ACAATGGTGA GACTGAATTT GCCCCGAAGT TCCCGGGCAA

201 GGTCACCATG ACCACAGACA CGTCCATCAG CACAGCCTAC ATGGAGCTGA

251 GCAGGCTGAG ATCTGACGAC ACGGCCGTGT ATTACTGTGC GAGAGAAGAC

301 TACGATGGTA CCTACACCTG GTTTCCTTAT TGGGGCCAAG GGACTCTGGT

351 CACCGTCTCT AGT
```

Additional antibodies are referred to herein as Antibodies 17-22 (also referred to herein as Ab-17, Ab-18, Ab-19, Ab-20, Ab-21, and Ab-22). The Kappa Constant region for all VK regions of Ab-17, Ab-19, and Ab-21 is as follows:

```
                                            (SEQ ID NO: 323)
TDAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVK

SFNRNEC
```

The Heavy Constant Region for all $V_H$ regions of antibodies 17, 19 and 21 is as follows:

```
                                            (SEQ ID NO: 324)
AKTTPPSVYPLAPGSAAQTNSMVTLGCLVKGYFPEPVTVTWNSGSLSSG

VHTFPAVLQSDLYTLSSSVTVPSSTWPSETVTCNVAHPASSTKVDKKIV

PRDCGCKPCICTVPEVSSVFIFPPKPKDVLTITLTPKVTCVVVDISKDD

PEVQFSWFVDDVEVHTAQTQPREEQFNSTFRSVSELPIMHQDWLNGKEF

KCRVNSAAFPAPIEKTISKTKGRPKAPQVYTIPPPKEQMAKDKVSLTCM

ITDFFPEDITVEWQWNGQPAENYKNTQPIMDTDGSYFVYSKLNVQKSNW

EAGNTFTCSVLHEGLHNHHTEKSLSHSPGK
```

In the following antibody amino acid sequences, the boxed-shaded amino acids represent complement-determining regions (CDRs) and the underlined and italicized amino acids represent signal peptide.

Ab-17

Amino acid sequence of the Ab-17 LC including signal peptide:

```
                                            (SEQ ID NO: 299)
MDFQVQIFSFMLISVTVILSSGEIVLTQSPALMAASPGEK

VTITCSVSSSISSSNLHWSQQKSGTSPKLWIYGTSNLASGVP

VRFSGSGSGTSYSLTISSMEAEDAATYYCQQWTTTYTFGSGTKLELKR
```

Nucleic acid sequence of the Ab-17 LC including signal peptide:

```
                                            (SEQ ID NO: 300)
ATGGATTTTCAGGTGCAGATTTTCAGCTTCATGCTAATCAGTGTCACAG

TCATATTGTCCAGTGGAGAAATTGTGCTCACCCAGTCTCCAGCACTCAT

GGCTGCATCTCCAGGGGAGAAGGTCACCATCACCTGCAGTGTCAGCTCG

AGTATAAGTTCCAGCAACTTACACTGGTCCCAGCAGAAGTCAGGAACCT

CCCCCAAACTCTGGATTTATGGCACATCCAACCTTGCTTCTGGAGTCCC

TGTTCGCTTCAGTGGCAGTGGATCTGGGACCTCTTATTCTCTCACAATC

AGCAGCATGGAGGCTGAAGATGCTGCCACTTATTACTGTCAACAGTGGA

CTACTACGTATACGTTCGGATCGGGGACCAAGCTGGAGCTGAAACGT
```

Amino acid sequence of the Ab-17 HC including signal peptide:

```
                                            (SEQ ID NO: 301)
MGWNWIIFFLMAVVTGVNSEVQLRQSGADLVKPGASVKLSCTASGFNI

KDYYIHWVKQRPEQGLEWIGRIDPDNGESTYVPKF

QGKATITADTSSNTAYLQLRSLTSEDTAIYYCGREGLDYGD

YYAVDYWGQGTSVTVSS
```

Nucleic acid sequence of the Ab-17 HC including signal peptide:

```
                                            (SEQ ID NO: 302)
ATGGGATGGAACTGGATCATCTTCTTCCTGATGGCAGTGGTTACAGGGG

TCAATTCAGAGGTGCAGTTGCGGCAGTCTGGGGCAGACCTTGTGAAGCC

AGGGGCCTCAGTCAAGTTGTCCTGCACAGCTTCTGGCTTCAACATTAAA

GACTACTATATACACTGGGTGAAGCAGAGGCCTGAACAGGGCCTGGAGT

GGATTGGAAGGATTGATCCTGATAATGGTGAAAGTACATATGTCCCGAA

GTTCCAGGGCAAGGCCACTATAACAGCAGACACATCATCCAACACAGCC

TACCTACAACTCAGAAGCCTGACATCTGAGGACACTGCCATCTATTATT
```

-continued

GTGGGAGAGAGGGGCTCGACTATGGTGACTACTATGCTGTGGACTACTG

GGGTCAAGGAACCTCGGTCACAGTCTCGAGC

Ab-17 was humanized to generate Ab-18.

Ab-18

Amino acid sequence of the Ab-18 LC including signal peptide:

(SEQ ID NO: 303)

MDMRVPAOLLGLLLLWLPGARCDIQLTQSPSFLSASVGDRVTITCSV

SSSISSSNLHWYQQKPGKAPKLLIYGTSNLASGVPSRFSGSGSGTEFTLT

ISSLQPEDFATYYCQQWTTTYTFGQGTKLEIKR

Nucleic acid sequence of the Ab-18 LC including signal peptide:

(SEQ ID NO: 304)

ATGGATATGCGCGTGCCGGCGCAGCTGCTGGGCCTGCTGCTGCTGTGGC

TGCCGGGCGCGCGCTGCGATATTCAGCTGACCCAGAGCCCGAGCTTTCT

GAGCGCGAGCGTGGGCGATCGCGTGACCATTACCTGCAGCGTGAGCAGC

AGCATTAGCAGCAGCAACCTGCATTGGTATCAGCAGAAACCGGGCAAAG

CGCCGAAACTGCTGATTTATGGCACCAGCAACCTGGCGAGCGGCGTGCC

GAGCCGCTTTAGCGGCAGCGGCAGCGGCACCGAATTTACCCTGACCATT

AGCAGCCTGCAGCCGGAAGATTTTGCGACCTATTATTGCCAGCAGTGGA

CCACCACCTATACCTTTGGCCAGGGCACCAAACTGGAAATTAAACGT

Amino acid sequence of the Ab-18 HC including signal peptide:

(SEQ ID NO: 305)

MDWTWSILFLVAAPTGAHSEVQLVQSGAEVKKPGAS

VKVSCKASGFNIKDYYIHWVRQAPGQGLEWMGRIDPDNGESTYVPKFQG

RVTMTTDTSTSTAYMELRSLRSDDTAVYYCAREGLDYGDYYAVDYWGQGT

LVTVSS

Nucleic acid sequence of the Ab-18 HC including signal peptide:

(SEQ ID NO: 306)

ATGGATTGGACCTGGAGCATTCTGTTTCTGGTGGCGGCGCCGACCGGCG

CGCATAGCGAAGTGCAGCTGGTGCAGAGCGGCGCGGAAGTGAAAAAACC

GGGCGCGAGCGTGAAAGTGAGCTGCAAAGCGAGCGGCTTTAACATTAAA

GATTATTATATTCATTGGGTGCGCCAGGCGCCGGGCCAGGGCCTGGAAT

GGATGGGCCGCATTGATCCGGATAACGGCGAAAGCACCTATGTGCCGAA

ATTTCAGGGCCGCGTGACCATGACCACCGATACCAGCACCAGCACCGCG

TATATGGAACTGCGCAGCCTGCGCAGCGATGATACCGCGGTGTATTATT

GCGCGCGCGAAGGCCTGGATTATGGCGATTATTATGCGGTGGATTATTG

GGGCCAGGGCACCCTGGTGACCGTCTCGAGC

Ab-18 light chain variable domain amino acid sequence (without signal sequence):

(SEQ ID NO: 368)

DIQLTQSPSFLSASVGDRVTITCSVSSSISSSNLHWYQQKP

GKAPKWYGTSNLASGVPSRFSGSGSGTEFTLTISSLQPEDFATYYCQ

QWTTTYTFGQGTKLEIKR

Ab-18 light chain variable domain DNA sequence (without signal sequence):

(SEQ ID NO: 369)

GATATTCAGCTGACCCAGAGCCCGAGCTTTCTGAGCGCGAGCGTGGGCG

ATCGCGTGACCATTACCTGCAGCGTGAGCAGCAGCATTAGCAGCAGCAA

CCTGCATTGGTATCAGCAGAAACCGGGCAAAGCGCCGAAACTGCTGATT

TATGGCACCAGCAACCTGGCGAGCGGCGTGCCGAGCCGCTTTAGCGGCA

GCGGCAGCGGCACCGAATTTACCCTGACCATTAGCAGCCTGCAGCCGGA

AGATTTTGCGACCTATTATTGCCAGCAGTGGACCACCACCTATACCTTT

GGCCAGGGCACCAAACTGGAAATTAAACGT

Ab-18 heavy chain variable domain amino acid sequence (without signal sequence):

(SEQ ID NO: 370)

EVQLVQSGAEVKKPGASVKVSCKASGFNIKDYYIHWVRQAP

GQGLEWMGRIDPDNGESTYVPKFQGRVTMTTDTSTSTAYMELRSLRS

DDTAVYYCAREGLDYGDYYAVDYWGQGTLVTVSS

Ab-18 heavy chain variable domain DNA sequence (without signal sequence):

(SEQ ID NO: 371)

GAAGTGCAGCTGGTGCAGAGCGGCGCGGAAGTGAAAAAACCGGGCGCGA

GCGTGAAAGTGAGCTGCAAAGCGAGCGGCTTTAACATTAAAGATTATTA

TATTCATTGGGTGCGCCAGGCGCCGGGCCAGGGCCTGGAATGGATGGGC

CGCATTGATCCGGATAACGGCGAAAGCACCTATGTGCCGAAATTTCAGG

GCCGCGTGACCATGACCACCGATACCAGCACCAGCACCGCGTATATGGA

ACTGCGCAGCCTGCGCAGCGATGATACCGCGGTGTATTATTGCGCGCGC

GAAGGCCTGGATTATGGCGATTATTATGCGGTGGATTATTGGGGCCAGG

GCACCCTGGTGACCGTCTCGAGC

Ab-19

Amino acid sequence of the Ab-19 LC including signal peptide:

(SEQ ID NO: 307)

MMSSAQFLGLLLLCFQGTRCDIQMTQTTSSLSAS

LGDRVNISCRASQDISSYLNWYQQKPDGTVKLLIYSTSRLNSGVP

SRFSGSGSGTDYSLTISNLAQEDIATYFCQQDIKHPTFGGGTKLELKR

Nucleic acid sequence of the Ab-19 LC including signal peptide:

(SEQ ID NO: 308)

ATGATGTCCTCTGCTCAGTTCCTTGGTCTCCTGTTGCTCTGTTTTCAAG

-continued

GTACCAGATGTGATATCCAGATGACACAGACTACATCCTCCCTGTCTGC

CTCTCTGGGAGACAGAGTCAACATCAGCTGCAGGGCAAGTCAGGACATT

AGCAGTTATTTAAACTGGTATCAGCAGAAACCAGATGGAACTGTTAAAC

TCCTGATCTACTCCACATCAAGATTAAACTCAGGAGTCCCATCAAGGTT

CAGTGGCAGTGGGTCTGGGACAGATTATTCTCTCACTATTAGCAACCTG

GCACAAGAAGATATTGCCACTTACTTTTGCCAACAGGATATTAAGCATC

CGACGTTCGGTGGAGGCACCAAGTTGGAGCTGAAACGT

Amino acid sequence of the Ab-19 HC including signal peptide:

(SEQ ID NO: 309)

*MEWIWIFLFLLSGTAGVHS*EVQLQQSGPELVKPGASVKMSCKASGFTFT

DYIMHWVKQKPGQGLEWIGYINPYNDDTEYNEKFKGKATLTSDKSSSTA

YMDLSSLTSEGSAVYYCARSIYYYDAPFAYWGQGTLVTVSS

Nucleic acid sequence of the Ab-19 HC including signal peptide:

(SEQ ID NO: 310)

ATGGAATGGATCTGGATATTTCTCTTCCCTCCTGTCAGGAACTGCAGGT

GTCCACTCTGAGGTCCAGCTGCAGCAGTCTGGACCTGAGCTGGTAAAGC

CTGGGGCTTCAGTGAAGATGTCCTGCAAGGCTTCTGGGTTCACATTCAC

TGACTACATTATGCACTGGGTGAAGCAGAAGCCTGGGCAGGGCCTTGAG

TGGATTGGATATATTAATCCTTACAATGATGATACTGAATACAATGAGA

AGTTCAAAGGCAAGGCCACACTGACTTCAGACAAATCCTCCAGCACAGC

CTACATGGATCTCAGCAGTCTGACCTCTGAGGGCTCTGCGGTCTATTAC

TGTGCAAGATCGATTTATTACTACGATGCCCCGTTTGCTTACTGGGGCC

AAGGGACTCTGGTCACAGTCTCGAGC

Ab-19 was humanized to generate Antibody 20 (also referred to herein as Ab-20) and Antibody 23 (also referred to herein as Ab-23).

Ab-20

IgG4 version

Amino acid sequence of the Ab-20 LC including signal peptide:

(SEQ ID NO: 311)

*MMSSAQFLGLLLLCFQGTRC*DIQMTQSPSSLSASVGDRVTITCRASQDI

SSYLNWYQQKPGKAPKLLIYSTSRLNSGVPSRFSGSGSGTDFTLTISSL

QPEDFATYYCQQDIKHPTFGQGTKVEIKR

Nucleic acid sequence of the Ab-20 LC including signal peptide:

(SEQ ID NO: 312)

ATGATGTCCTCTGCTCAGTTCCTTGGTCTCCTGTTGCTCTGTTTTCAAG

GTACCAGATGTGATATCCAGATGACCCAGTCTCCATCCTCCCTGTCTGC

ATCTGTAGGTGACCGTGTCACCATCACTTGCCGCGCAAGTCAGGATATT

AGCAGCTATTTAAATTGGTATCAGCAGAAACCAGGGAAAGCCCCTAAGC

TCCTGATCTATTCTACTTCCCGTTTGAATAGTGGGGTCCCATCACGCTT

CAGTGGCAGTGGCTCTGGGACAGATTTCACTCTCACCATCAGCAGTCTG

CAACCTGAAGATTTTGCAACTTACTACTGTCAACAGGATATTAAACACC

CTACGTTCGGTCAAGGCACCAAGGTGGAGATCAAACGT

Amino acid sequence of the Ab-20 HC including signal peptide:

(SEQ ID NO: 313)

*MEWIWIFLFLLSGTAGVHS*EVQLVQSGAEVKKPGSSVKVSCKASGFTFT

DYIMHWVRQAPGQGLEWMGYINPYNDDTEYNEKFKGRVTITADKSTSTA

YMELSSLRSEDTAVYYCARSIYYYDAPFAYWGQGTLVTVSS

Nucleic acid sequence of the Ab-20 HC including signal peptide:

(SEQ ID NO: 349)

ATGGAATGGATCTGGATATTTCTCTTCCTCCTGTCAGGAACTGCAGGTG

TCCACTCTGAGGTGCAGCTGGTGCAGTCTGGGGCTGAGGTGAAGAAGCC

TGGGTCCTCGGTGAAGGTCTCCTGCAAGGCTTCTGGTTTTACCTTCACC

GACTATATTATGCACTGGGTGCGTCAGGCCCCTGGTCAAGGGCTTGAGT

GGATGGGCTATATCAACCCTTATAATGATGACACCGAATACAACGAGAA

GTTCAAGGGCCGTGTCACGATTACCGCGGACAAATCCACGAGCACAGCC

TACATGGAGCTGAGCAGCCTGCGCTCTGAGGACACGGCCGTGTATTACT

GTGCGCGTTCGATTTATTACTACGATGCCCCGTTTGCTTACTGGGGCCA

AGGGACTCTGGTCACAGTCTCGAGC

Ab-23

IgG2 version

Light Chain:

Amino acid sequence of the mature form (signal peptide removed) of the Ab-23 LC:

(SEQ ID NO: 341)

1 DIQMTQSPSS LSASVGDRVT ITCRASQDIS SYLNWYQQKP GKAPKLLIYS

51 TSRLNSGVPS RFSGSGSGTD FTLTISSLQP EDFATYYCQQ DIKHPTFGQG

101 TKVEIK *RTVA APSVFIFPPS DEQLKSGTAS VVCLLNNFYP REAKVQWKVD*

*151 NALQSGNSQE SVTEQDSKDS TYSLSSTLTL SKADYEKHKV YACEVTHQGL*

*201 SSPVTKSFNR GEC*

Nucleic acid sequence encoding the mature form (signal peptide removed) of the Ab-23 LC:

(SEQ ID NO: 342)

```
  1 GACATCCAGA TGACCCAGTC TCCATCCTCC CTGTCTGCAT CTGTAGGTGA
 51 CCGTGTCACC ATCAGTTGCC GCGCAAGTCA GGATATTAGC AGCTATTTAA
101 ATTGGTATCA GCAGAAACCA GGGAAAGCCC CTAAGCTCCT GATCTATTCT
151 ACTTCCCGTT TGAATAGTGG GGTCCCATCA CGCTTCAGTG GCAGTGGCTC
201 TGGGACAGAT TTCACTCTCA CCATCAGCAG TCTGCAACCT GAAGATTTTG
251 CAACTTACTA CTGTCAACAG GATATTAAAC ACCCTACGTT CGGTCAAGGC
301 ACCAAGGTGG AGATCAAACG TACGGTGGCT GCACCATCTG TCTTCATCTT
351 CCCGCCATCT GATGAGCAGT TGAAATCTGG AACTGCCTCT GTTGTGTGCC
401 TGCTGAATAA CTTCTATCCC AGAGAGGCCA AAGTACAGTG GAAGGTGGAT
451 AACGCCCTCC AATCGGGTAA CTCCCAGGAG AGTGTCACAG AGGAGGACAG
501 CAAGGACAGC ACCTACAGCC TCAGCAGCAC CCTGACGCTG AGCAAAGCAG
551 ACTACGAGAA ACACAAAGTC TACGCCTGCG AAGTCACCCA TCAGGGCCTG
601 AGCTCGCCCG TCACAAAGAG CTTCAACAGG GGAGAGTGT
```

Amino acid sequence of the Ab-23 LC including signal peptide:

(SEQ ID NO: 343)

```
  1 MDMRVPAQLL GLLLLWLRGA RCDIQMTQSP SSLSASVGDR VTITCRASQD
 51 ISSYLNWYQQ KPGKAPKLLI YSTSRLNSGV PSRFSGSGSG TDFTLTISSL
101 QPEDFATYYC QQDIKHPTFG QGTKVEIKRT VAAPSVFIFP PSDEQLKSGT
151 ASVVCLLNNF YPREAKVQWK VDNALQSGNS QESVTEQDSK DSTYSLSSTL
201 TLSKADYEKH KVYACEVTHQ GLSSPVTKSF NRGEC
```

Nucleic acid sequence of the Ab-23 LC including signal peptide encoding sequence:

(SEQ ID NO: 344)

```
  1 ATGGACATGA GGGTGCCCGC TCAGCTCCTG GGGCTCCTGC TGCTGTGGCT
 51 GAGAGGTGCC AGATGTGACA TCCAGATGAC CCAGTCTCCA TCCTCCCTGT
101 CTGCATCTGT AGGTGACCGT GTCACCATCA CTTGCCGCGC AAGTCAGGAT
151 ATTAGCAGCT ATTTAAATTG GTATCAGCAG AAACCAGGGA AAGCCCCTAA
201 GCTCCTGATC TATTCTACTT CCCGTTTGAA TAGTGGGGTC CCATCACGCT
251 TCAGTGGCAG TGGCTCTGGG ACAGATTTCA CTCTCACCAT CAGCAGTCTG
301 CAACCTGAAG ATTTTGCAAC TTACTACTGT CAACAGGATA TTAAACACCC
351 TACGTTCGGT CAAGGCACCA AGGTGGAGAT CAAACGTACG GTGGCTGCAC
401 CATCTGTCTT CATCTTCCCG CCATCTGATG AGCAGTTGAA ATCTGGAACT
451 GCCTCTGTTG TGTGCCTGCT GAATAACTTC TATCCCAGAG AGGCCAAAGT
501 ACAGTGGAAG GTGGATAACG CCCTCCAATC GGGTAACTCC CAGGAGAGTG
551 TCACAGAGCA GGACAGCAAG GACAGCACCT ACAGCCTCAG CAGCACCCTG
601 ACGCTGAGCA AAGCAGACTA CGAGAAACAC AAAGTCTACG CCTGCGAAGT
```

-continued

651 CACCCATCAG GGCCTGAGCT CGCCCGTCAC AAAGAGCTTC AACAGGGGAG

701 AGTGT

Heavy Chain:

Amino acid sequence of the mature form (signal peptide removed) of the Ab-23 HC:

(SEQ ID NO: 345)

1 EVQLVQSGAE VKKPGSSVKV SCKASGFTFT DYIMHWVRQA PGQGLEWMGY

51 INPYNDDTEY NEKFKGRVTI TADKSTSTAY MELSSLRSED TAVYYCARSI

101 YYYDAPFAYW GQGTLVTVSS *ASTKGPSVFP LAPCSRSTSE STAALGCLVK*

*151 DYFPEPVTVS WNSGALTSGV HTFPAVLQSS GLYSLSSVVT VPSSNFGTQT*

*201 YTCNVDHKPS NTKVDKTVER KCCVECPPCP APPVAGPSVF LFPPKPKDTL*

*251 MISRTPEVTC VVVDVSHEDP EVQFNWYVDG VEVHNAKTKP REEQFNSTFR*

*301 VVSVLTVVHQ DWLNGKEYKC KVSNKGLPAP IEKTISKTKG QPREPQVYTL*

*351 PPSREEMTKN QVSLTCLVKG FYPSDIAVEW ESNGQPENNY KTTPPMLDSD*

*401 GSFFLYSKLT VDKSRWQQGN VFSCSVMHEA LHNHYTQKSL SLSPG*

Amino acid sequence of the mature form (signal peptide removed) of the Ab-23 HC without carboxy-terminal lysine:

(SEQ ID NO: 196)

1 EVQLVQSGAE VKKPGSSVKV SCKASGFTFT DYIMHWVRQA PGQGLEWMGY

51 INPYNDDTEY NEKFKGRVTI TADKSTSTAY MELSSLRSED TAVYYCARSI

101 YYYDAPFAYW GQGTLVTVSS *ASTKGPSVFP LAPCSRSTSE STAALGCLVK*

*151 DYFPEPVTVS WNSGALTSGV HTFPAVLQSS GLYSLSSVVT VPSSNFGTQT*

*201 YTCNVDHKPS NTKVDKTVER KCCVECPPCP APPVAGPSVF LFPPKPKDTL*

*251 MISRTPEVTC VVVDVSHEDP EVQFNWYVDG VEVHNAKTKP REEQFNSTFR*

*301 VVSVLTVVHQ DWLNGKEYKC KVSNKGLPAP IEKTISKTKG QPREPQVYTL*

*351 PPSREEMTKN QVSLTCLVKG FYPSDIAVEW ESNGQPENNY KTTPPMLDSD*

*401 GSFFLYSKLT VDKSRWQQGN VFSCSVMHEA LHNHYTQKSL SLSPG*

Nucleic acid sequence encoding the mature form (signal peptide removed) of the Ab-23 HC:

(SEQ ID NO: 346)

1 GAGGTGCAGC TGGTGCAGTC TGGGGCTGAG GTGAAGAAGC CTGGGTCCTC

51 GGTGAAGGTC TCCTGCAAGG CTTCTGGTTT TACCTTCACC GACTATATTA

101 TGCACTGGGT GCGTCAGGCC CCTGGTCAAG GGCTTGAGTG GATGGGCTAT

151 ATCAACCCTT ATAATGATGA CACCGAATAC AACGAGAAGT TCAAGGGCCG

201 TGTCACGATT ACCGCGGACA AATCCACGAG CACAGCCTAC ATGGAGCTGA

251 GCAGCCTGCG CTCTGAGGAC ACGGCCGTGT ATTACTGTGC GCGTTCGATT

301 TATTACTACG ATGCCCCGTT TGCTTACTGG GGCCAAGGGA CTCTGGTCAC

351 CGTCTCTAGT GCCTCCACCA AGGGCCCATC GGTCTTCCCC CTGGCGCCCT

401 GCTCCAGGAG CACCTCCGAG AGCACAGCGG CCCTGGGCTG CCTGGTCAAG

451 GACTACTTCC CCGAACCGGT GACGGTGTCG TGGAACTCAG GCGCTCTGAC

-continued

```
501   CAGCGGCGTG CACACCTTCC CAGCTGTCCT ACAGTCCTCA GGACTCTACT
551   CCCTCAGCAG CGTGGTGACC GTGCCCTCCA GCAACTTCGG CACCCAGACC
601   TACACCTGCA ACGTAGATCA CAAGCCCAGC AACACCAAGG TGGACAAGAC
651   AGTTGAGCGC AAATGTTGTG TCGAGTGCCC ACCGTGCCCA GCACCACCTG
701   TGGCAGGACC GTCAGTCTTC CTCTTCCCCC CAAAACCCAA GGACACCCTC
751   ATGATCTCCC GGACCCCTGA GGTCACGTGC GTGGTGGTGG ACGTGAGCCA
801   CGAAGACCCC GAGGTCCAGT TCAACTGGTA CGTGGACGGC GTGGAGGTGC
851   ATAATGCCAA GACAAAGCCA CGGGAGGAGC AGTTCAACAG CACGTTCCGT
901   GTGGTCAGCG TCCTCACCGT TGTGCACCAG GACTGGCTGA ACGGCAAGGA
951   GTACAAGTGC AAGGTCTCCA ACAAAGGCCT CCCAGCCCCC ATCGAGAAAA
1001  CCATCTCCAA AACCAAAGGG CAGCCCCGAG AACCACAGGT GTACACCCTG
1051  CCCCCATCCC GGGAGGAGAT GACCAAGAAC CAGGTCAGCC TGACCTGCCT
1101  GGTCAAAGGC TTCTACCCCA GCGACATCGC CGTGGAGTGG GAGAGCAATG
1151  GGCAGCCGGA GAACAACTAC AAGACCACAC CTCCCATGCT GGACTCCGAC
1201  GGCTCCTTCT TCCTCTACAG CAAGCTCACC GTGGACAAGA GCAGGTGGCA
1251  GCAGGGGAAC GTCTTCTCAT GCTCCGTGAT GCATGAGGCT CTGCACAACC
1301  ACTACACGCA GAAGAGCCTC TCCCTGTCTC CGGGTAAA
```

Amino acid sequence of the Ab-23 HC including signal peptide:

```
                                            (SEQ ID NO: 347)
1     MDWTWRILFL VAAATGAHSE VQLVQSGAEV KKPGSSVKVS CKASGFTFTD
51    YIMHWVRQAP GQGLEWMGYI NPYNDDTEYN EKFKGRVTIT ADKSTSTAYM
101   ELSSLRSEDT AVYYCARSIY YYDAPFAYWG QGTLVTVSSA STKGPSVFPL
151   APCSRSTSES TAALGCLVKD YFPEPVTVSW NSGALTSGVH TFPAVLQSSG
201   LYSLSSVVTV PSSNFGTQTY TCNVDHKPSN TKVDKTVERK CCVECPPCPA
251   PPVAGPSVFL FPPKPKDTLM ISRTPEVTCV VVDVSHEDPE VQFNWYVDGV
301   EVHNAKTKPR EEQFNSTFRV VSVLTVVHQD WLNGKEYKCK VSNKGLPAPI
351   EKTISKTKGQ PREPQVYTLP PSREEMTKNQ VSLTCLVKGF YPSDIAVEWE
401   SNGQPENNYK TTPPMLDSDG SFFLYSKLTV DKSRWQQGNV FSCSVMHEAL
451   HNHYTQKSLS LSPGK
```

Nucleic acid sequence of the Ab-23 HC including signal peptide encoding sequence:

```
                                            (SEQ ID NO: 348)
1     ATGGACTGGA CCTGGAGGAT CCTCTTCTTG GTGGCAGCAG CCACAGGAGC
51    CCACTCCGAG GTGCAGCTGG TGCAGTCTGG GGCTGAGGTG AAGAAGCCTG
101   GGTCCTCGGT GAAGGTCTCC TGCAAGGCTT CTGGTTTTAC CTTCACCGAC
151   TATATTATGC ACTGGGTGCG TCAGGCCCCT GGTCAAGGGC TTGAGTGGAT
201   GGGCTATATC AACCCTTATA ATGATGACAC CGAATACAAC GAGAAGTTCA
251   AGGGCCGTGT CACGATTACC GCGGACAAAT CCACGAGCAC AGCCTACATG
301   GAGCTGAGCA GCCTGCGCTC TGAGGACACG GCCGTGTATT ACTGTGCGCG
```

-continued

```
 351  TTCGATTTAT TACTACGATG CCCCGTTTGC TTACTGGGGC CAAGGGACTC
 401  TGGTCACCGT CTCTAGTGCC TCCACCAAGG GCCCATCGGT CTTCCCCCTG
 451  GCGCCCTGCT CCAGGAGCAC CTCCGAGAGC ACAGCGGCCC TGGGCTGCCT
 501  GGTCAAGGAC TACTTCCCCG AACCGGTGAC GGTGTCGTGG AACTCAGGCG
 551  CTCTGACCAG CGGCGTGCAC ACCTTCCCAG CTGTCCTACA GTCCTCAGGA
 601  CTCTACTCCC TCAGCAGCGT GGTGACCGTG CCCTCCAGCA ACTTCGGCAC
 651  CCAGACCTAC ACCTGCAACG TAGATCACAA GCCCAGCAAC ACCAAGGTGG
 701  ACAAGACAGT TGAGCGCAAA TGTTGTGTCG AGTGCCCACC GTGCCCAGCA
 751  CCACCTGTGG CAGGACCGTC AGTCTTCCTC TTCCCCCCAA AACCCAAGGA
 801  CACCCTCATG ATCTCCCGGA CCCCTGAGGT CACGTGCGTG GTGGTGGACG
 851  TGAGCCACGA AGACCCCGAG GTCCAGTTCA ACTGGTACGT GGACGGCGTG
 901  GAGGTGCATA ATGCCAAGAC AAAGCCACGG GAGGAGCAGT TCAACAGCAC
 951  GTTCCGTGTG GTCAGCGTCC TCACCGTTGT GCACCAGGAC TGGCTGAACG
1001  GCAAGGAGTA CAAGTGCAAG GTCTCCAACA AAGGCCTCCC AGCCCCCATC
1051  GAGAAAACCA TCTCCAAAAC CAAAGGGCAG CCCCGAGAAC CACAGGTGTA
1101  CACCCTGCCC CCATCCCGGG AGGAGATGAC CAAGAACCAG GTCAGCCTGA
1151  CCTGCCTGGT CAAAGGCTTC TACCCCAGCG ACATCGCCGT GGAGTGGGAG
1201  AGCAATGGGC AGCCGGAGAA CAACTACAAG ACCACACCTC CCATGCTGGA
1251  CTCCGACGGC TCCTTCTTCC TCTACAGCAA GCTCACCGTG GACAAGAGCA
1301  GGTGGCAGCA GGGGAACGTC TTCTCATGCT CCGTGATGCA TGAGGCTCTG
1351  CACAACCACT ACACGCAGAA GAGCCTCTCC CTGTCTCCGG GTAAA
```

The CDR (complementarity determining region) sequences in the variable region of the heavy chain of Ab-23 are as follows:

CDR-H1: (SEQ ID NO: 269)
DYIMH

CDR-H2: (SEQ ID NO: 270)
YINPYNDDTEYNEKFKG

CDR-H3: (SEQ ID NO: 271)
SIYYYDAPFAY

The light chain variable region CDR sequences of Ab-23 are:

CDR-L1: (SEQ ID NO: 239)
RASQDISSYLN

CDR-L2: (SEQ ID NO: 240)
STSRLNS

CDR-L3: (SEQ ID NO: 241)
QQDIKHPT

Ab-23 Variable Domains:

Ab-23 light chain variable domain amino acid sequence (without signal sequence):

```
                                            (SEQ ID NO: 364)
DIQMTQSPSS LSASVGDRVT ITCRASQDIS SYLNWYQQKP
GKAPKLLIYS TSRLNSGVPS RFSGSGSGTD FTLTISSLQP
EDFATYYCQQ DIKHPTFGQG TKVEIK
```

Ab-23 light chain variable domain DNA sequence (without signal sequence):

```
                                            (SEQ ID NO: 365)
GACATCCAGATGACCCAGTCTCCATCCTCCCT
GTCTGCATCTGTAGGTGACCGTGTCACC
ATCACTTGCC GCGCAAGTCA GGATATTAGC
AGCTATTTAAATTGGTATCA
GCAGAAACCA GGGAAAGCCC CTAAGCTCCT
GATCTATTCTACTTCCCGTT
TGAATAGTGG GGTCCCATCA CGCTTCAGTG
GCAGTGGCTCTGGGACAGAT
TTCACTCTCA CCATCAGCAG TCTGCAACCT
GAAGATTTTGCAACTTACTA
CTGTCAACAG GATATTAAAC ACCCTACGTT
CGGTCAAGGCACCAAGGTGG
AGATCAAA
```

Ab-23 heavy chain variable domain amino acid sequence (without signal sequence):

(SEQ ID NO: 366)
EVQLVQSGAE VICKPOSSVKV SCKASGFTFT DYIMHWVRQA

PGQGLEWMGYINPYNDDTEY NEKFKGRVTI TADKSTSTAY

MELSSLRSED TAVYYCARSIYYYDAPFAYW GQGTLVTVSS

Ab-23 heavy chain variable domain DNA sequence (without signal sequence):

(SEQ ID NO: 367)
GAGGTGCAGCTGGTGCAGTCTGGGGCTGAGGT

GAAGAAGCCTGGGTCCTCGGTGAAGGTC

TCCTGCAAGG CTTCTGGTTT TACCTTCACC

GACTATATTATGCACTGGGT

GCGTCAGGCC CCTGGTCAAG GGCTTGAGTG

GATGGGCTATATCAACCCTT

ATAATGATGA CACCGAATAC AACGAGAAGT

TCAAGGGCCGTGTCACGATT

ACCGCGGACA AATCCACGAG CACAGCCTAC

ATGGAGCTGAGCAGCCTGCG

CTCTGAGGAC ACGGCCGTGT ATTACTGTGC

GCGTTCGATTTATTACTACG

ATGCCCCGTT TGCTTACTGG GGCCAAGGGA

CTCTGGTCACCGTCTCTAGT

Ab-21

Amino acid sequence of the Ab-21 LC including signal peptide:

(SEQ ID NO: 315)
MKSQTQVFVYMLLWLSGVEGDIVMTQSHKFMSTSVGDRVTITCKASQDVF

TAVAWYQQKPGQSPKLLIYWASTRHTGVPDRFTGSGSGTDFTLTISNVQS

EDLADYFCQQYSSYPLTFGAGTKLELKR

Nucleic acid sequence of the Ab-21 LC including signal peptide:

(SEQ ID NO: 316)
ATGAAGTCACAGACCCAGGTCTTTGTATACATGTTGCTGTGGTTG

TCTGGTGTTGAAGGAGACATTGTGATGACCCAGTCTCACAAATTC

ATGTCCACGTCAGTAGGAGACAGGGTCACCATCACCTGCAAGGCC

AGTCAGGATGTCTTTACTGCTGTAGCCTGGTATCAACAGAAACCA

GGACAATCTCCTAAACTACTGATTTACTGGGCATCCACCCGGCAC

ACTGGAGTCCCTGATCGCTTCACAGGCAGTGGATCTGGGACAGAT

TTCACTCTCACCATTAGCAATGTGCAGTCTGAAGACTTGGCAGAT

TATTTCTGTCAACAATATAGCAGCTATCCTCTCACGTTCGGTGCT

GGGACCAAGTTGGAGCTGAAACGT

Amino acid sequence of the Ab-21 HC including signal peptide:

(SEQ ID NO: 317)
MGWNWIIFFLMAVVTGVNSEVQLQQSGAELVRPGALVKLSCKASGFNIKD

YYMHWVKQRPEQGLEWIGRIDPENGDIIYDPKFQGKASITTDTSSNTAYL

QLSSLTSEDTAVYYCAYDAGDPAWFTYWGQGTLVTVSS

Nucleic acid sequence of the Ab-21 HC including signal peptide:

(SEQ ID NO: 318)
ATGGGATGGAACTGGATCATCTTCTTCCTGATGGCAGTGGTTACA

GGGGTCAATTCAGAGGTTCAGCTGCAGCAGTCTGGGGCTGAGCTT

GTGAGGCCAGGGGCCTTAGTCAAGTTGTCCTGCAAAGCTTCTGGC

TTCAATATTAAAGACTACTATATGCACTGGGTGAAGCAGAGGCCT

GAACAGGGCCTGGAGTGGATTGGAAGGATTGATCCTGAGAATGGT

GATATTATATATGACCCGAAGTTCCAGGGCAAGGCCAGTATAACA

ACAGACACATCCTCCAACACAGCCTACCTGCAGCTCAGCAGCCTG

ACGTCTGAGGACACTGCCGTCTATTACTGTGCTTACGATGCTGGT

GACCCCGCCTGGTTTACTTACTGGGGCCAAGGGACTCTGGTCACC

GTCTCGAGC

Ab-21 was humanized to yield Ab-22.

Ab-22

Amino acid sequence of the Ab-22 LC including signal peptide:

(SEQ ID NO: 319)
MDMRVPAQLLGLLLLWLRGARCDIQMTQSPSSLSASVGDRVTITCKASQD

VFTAVAWYQQKPGKAPKLLIYWASTRHTGVPSRFSGSGSGTDFTLTISSL

QPEDFATYYCQQYSSYPLTFGGGTKVEIKR

Nucleic acid sequence of the Ab-22 LC including signal peptide:

(SEQ ID NO: 320)
ATGGATATGCGCGTGCCGGCGCAGCTGCTGGGCCTGCTGCTGCTG

TGGCTGCGCGGCGCGCGCTGCGATATCCAGATGACCCAGAGCCCG

AGCAGCCTGAGCGCGAGCGTGGGCGATCGCGTGACCATTACCTGC

AAAGCGAGCCAGGATGTGTTTACCGCGGTGGCGTGGTATCAGCAG

AAACCGGCTCAAAGCGCCGAAACTGCTGATTTATTGGGCGAGCAC

CCGCCATACCGGCGTGCCGAGTCGCTTTAGCGGCAGCGGCAGCGG

CACCGATTTTACCCTGACCATTAGCAGCCTGCAGCCGGAAGATTT

TGCGACCTATTATTGCCAGCAGTATAGCAGCTATCCGCTGACCTT

TGGCGGCGGCACCAAAGTGGAAATTAAACGT

Amino acid sequence of the Ab-22 HC including signal peptide:

(SEQ ID NO: 321)
MDWTWSILFLVAAPTGAHSEVQLVQSGAEVKKPGASVKVSCKASGFNIK

-continued

DYYMHWVRQAPGQGLEWIGRIDPENGDIIYDPKFQGRVTMTTDTSTSTA

YMELRSLRSDDTAVYYCAYDAGDPAWFTYWGQGTLVTVSS

Nucleic acid sequence of the Ab-22 HC including signal peptide:

(SEQ ID NO: 322)

ATGGATTGGACCTGGAGCATTCTGTTTCTGGTGGCGGCGCCGACC

GGCGCGCATAGCGAAGTGCAGCTGGTGCAGAGCGGCGCGGAAGTG

AAAAAACCGGGCGCGAGCGTGAAAGTGAGCTGCAAAGCGAGCGGC

TTTAACATTAAAGATTATTATATGCATTGGGTGCGCCAGGCGCCG

GGCCAGGGCCTGGAATGGATCGGCCGCATTGATCCGGAAAACGGC

GATATTATTTATGATCCGAAATTTCAGGGCCGCGTGACCATGACC

ACCGATACCAGCACCAGCACCGCGTATATGGAACTGCGCAGCCTG

CGCAGCGATGATACCGCGGTGTATTATTGCGCGTATGATGCGGGC

GATCCGGCGTGGTTTACCTATTGGGGCCAGGGCACCCTGGTGACC

GTCTCGAGC

Ab-22 light chain variable domain amino acid sequence (without signal sequence):

(SEQ ID NO: 336)

DIQMTQSPSS LSASVGDRVT ITCKASQDVF TAVAWYQQKP

GKAPKLLIYW ASTRHTGVPS RFSGSGSGTD FTLTISSLQP

EDFATYYCQQ YSSYPLTFGG GTKVEIKR

Ab-22 light chain variable domain DNA sequence (without signal sequence):

(SEQ ID NO: 337)

GATATCCAGATGACCCAGAGCCCGAGCAGCCTGAGCGCGAGCGTGGGCGA

TCGCGTGACCATTACCTGCAAAGCGAGCCAGGATGTGTTTACCGCGGTGG

CGTGGTATCAGCAGAAACCGGGCAAAGCGCCGAAACTGCTGATTTATTGG

GCGAGCACCCGCCATACCGGCGTGCCGAGTCGCTTTAGCGGCAGCGGCAG

CGGCACCGATTTTACCCTGACCATTAGCAGCCTGCAGCCGGAAGATTTTG

CGACCTATTATTGCCAGCAGTATAGCAGCTATCCGCTGACCTTTGGCGGC

GGCACCAAAGTGGAAATTAAACGT

Ab-22 heavy chain variable domain amino acid sequence (without signal sequence):

(SEQ ID NO: 338)

EVQLVQSGAE VKKPGASVKV SCKASGFNIK DYYMHWVRQA

-continued

PGQGLEWIGRIDPENGDIIY DPKFQGRVTM TTDTSTSTAY

MELRSLRSDD TAVYYCAYDAGDPAWFTYWG QGTLVTVSS

Ab-22 heavy chain variable domain DNA sequence (without signal sequence):

(SEQ ID NO: 339)

GAAGTGCAGCTGGTGCAGAGCGGCGCGGAAGTGAAAAAACCGGGCGCGAG

CGTGAAAGTGAGCTGCAAAGCGAGCGGCTTTAACATTAAAGATTATTATA

TGCATTGGGTGCGCCAGGCGCCGGGCCAGGGCCTGGAATGGATCGGCCGC

ATTGATCCGGAAAACGGCGATATTATTTATGATCCGAAATTTCAGGGCCG

CGTGACCATGACCACCGATACCAGCACCAGCACCGCGTATATGGAACTGC

GCAGCCTGCGCAGCGATGATACCGCGGTGTATTATTGCGCGTATGATGCG

GGCGATCCGGCGTGGTTTACCTATTGGGGCCAGGGCACCCTGGTGACCGT

CTCGAGC.

For Ab-18, Ab-20, and Ab-22, the light chain human kappa constant region is as follows:

(SEQ ID NO: 325)

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC* and the heavy chain human gamma-4 constant region is as follows:

(SEQ ID NO: 326)

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK*

The hinge region contains the Ser-241-Pro mutation to improve hinge stability (Angal S et al, (1993), Mol Immunol, 30(1), 105-108).

Ab-24

The sequences of Antibody 24 (also referred to herein as Ab-24) LC and HC are as follows:

Light Chain:

Amino acid sequence of the mature form (signal peptide removed) of the Ab-24 LC:

(SEQ ID NO: 350)

1 DIVLTQSPAS LAVSLGQRAT IACKASOSVD YDGTSYMNWY QQKPGQPPKL

51 LIYAASNLES EIPARFSGTG SGTDFTLNIH PVEEEDITTY YCQQSNEDPF

101 TFGGGTKLEI K*RADAAPTVS IFPPSSEQLT SGGASVVCFL NNFYPKDINV*

-continued

*151 KWKIDGSERQ NGVLNSWTDQ DSKDSTYSMS STLTLTKDEY ERHNSYTCEA*

*201 THKTSTSPIV KSFNRNEC*

Nucleic acid sequence encoding the mature form (signal peptide removed) of the Ab-24 LC:

(SEQ ID NO: 354)
```
  1 GACATTGTGT TGACCCAGTC TCCAGCTTCT TTGGCTGTGT CTCTAGGGCA

 51 GAGGGCCACC ATCGCCTGCA AGGCCAGCCA AAGTGTTGAT TATGATGGTA

101 CTAGTTATAT GAATTGGTAC CAACAGAAAC CAGGACAGCC ACCCAAACTC

151 CTCATCTATG CTGCATCCAA TCTAGAATCT GAGATCCCAG CCAGGTTTAG

201 TGGCACTGGG TCTGGGACAG ACTTCACCCT CAACATCCAT CCTGTGGAGG

251 AGGAGGATAT CACAACCTAT TACTGTCAGC AAAGTAATGA GGATCCGTTC

301 ACGTTCGGAG GGGGGACCAA GTTGGAAATA AAACGGGCTG ATGCTGCACC

351 AACTGTATCC ATCTTCCCAC CATCCAGTGA GCAGTTAACA TCTGGAGGTG

401 CCTCAGTCGT GTGCTTCTTG AACAACTTCT ACCCCAAAGA CATCAATGTC

451 AAGTGGAAGA TTGATGGCAG TGAACGACAA AATGGCGTCC TGAACAGTTG

501 GACTGATCAG GACAGCAAAG ACAGCACCTA CAGCATGAGC AGCACCCTCA

551 CGTTGACCAA GGACGAGTAT GAACGACATA ACAGCTATAC CTGTGAGGCC

601 ACTCACAAGA CATCAACTTC ACCCATTGTC AAGAGCTTCA ACAGGAATGA

651 GTGTTAG
```

Amino acid sequence of the Ab-24 LC including signal peptide:

(SEQ ID NO: 355)
```
  1 METDTILLWV LLLWVPGSTG DIVLTQSPAS LAVSLGQRAT IACKASQSVD

 51 YDGTSYMNWY QQKPGQPPKL LIYAASNLES EIPARFSGTG SGTDFTLNIH

101 PVEEEDITTY YCQQSNEDPF TFGGGTKLEI KRADAAPTVS IFPPSSEQLT

151 SGGASVVCFL NNFYPKDINV KWKIDGSERQ NGVLNSWTDQ DSKDSTYSMS

201 STLTLTKDEY ERHNSYTCEA THKTSTSPIV KSFNRNEC
```

Nucleic acid sequence of the Ab-24 LC including signal peptide encoding sequence:

(SEQ ID NO: 356)
```
  1 ATGGAGACAG ACACAATCCT GCTATGGGTG CTGCTGCTCT GGGTTCCAGG

 51 CTCCACTGGT GACATTGTGT TGACCCAGTC TCCAGCTTCT TTGGCTGTGT

101 CTCTAGGGCA GAGGGCCACC ATCGCCTGCA AGGCCAGCCA AAGTGTTGAT

151 TATGATGGTA CTAGTTATAT GAATTGGTAC CAACAGAAAC CAGGACAGCC

201 ACCCAAACTC CTCATCTATG CTGCATCCAA TCTAGAATCT GAGATCCCAG

251 CCAGGTTTAG TGGCACTGGG TCTGGGACAG ACTTCACCCT CAACATCCAT

301 CCTGTGGAGG AGGAGGATAT CACAACCTAT TACTGTCAGC AAAGTAATGA

351 GGATCCGTTC ACGTTCGGAG GGGGGACCAA GTTGGAAATA AAACGGGCTG

401 ATGCTGCACC AACTGTATCC ATCTTCCCAC CATCCAGTGA GCAGTTAACA

451 TCTGGAGGTG CCTCAGTCGT GTGCTTCTTG AACAACTTCT ACCCCAAAGA
```

-continued

```
501 CATCAATGTC AAGTGGAAGA TTGATGGCAG TGAACGACAA AATGGCGTCC

551 TGAACAGTTG GACTGATCAG GACAGCAAAG ACAGCACCTA CAGCATGAGC

601 AGCACCCTCA CGTTGACCAA GGACGAGTAT GAACGACATA ACAGCTATAC

651 CTGTGAGGCC ACTCACAAGA CATCAACTTC ACCCATTGTC AAGAGCTTCA

701 ACAGGAATGA GTGTTAG
```

Ab-24 Heavy Chain:

Amino acid sequence of the mature form (signal peptide removed) of the Ab-24 HC:

```
                                                     (SEQ ID NO: 357)
  1 QVQLQQPGTE LVRPGTSVKL SCKASGYIFT TYWMNWVKQR PGQGLEWIGM

 51 IHPSASEIRL DQKFKDKATL TLDKSSSTAY MHLSGPTSVD SAVYYCARSG

101 EWGSMDYWGQ GTSVTVSSAK TTPPSVYPLA PGSAAQTNSM VTLGCLVKGY

151 FPEPVTVTWN SGSLSSGVHT FPAVLQSDLY TLSSSVTVPS STWPSETVTC

201 NVAHPASSTK VDKKIVPRDC GCKPCICTVP EVSSVFIFPP KPKDVLTITL

251 TPKVTCVVVD ISKDDPEVQF SWFVDDVEVH TAQTQPREEQ FNSTFRSVSE

301 LPIMHQDWLN GKEFKCRVNS AAFPAPIEKT ISKTKGRPKA PQVYTIPPPK

351 EQMAKDKVSL TCMITDFFPE DITVEWQWNG QPAENYKNTQ PIMDTDGSYF

401 IYSKLNVQKS NWEAGNTFTC SVLHEGLHNH HTEKSLSHSP GK
```

Nucleic acid sequence encoding the mature form (signal peptide removed) of the Ab-24 HC:

```
                                                     (SEQ ID NO: 361)
  1  CAGGTCCAAC TACAGCAGCC TGGGACTGAG CTGGTGAGGC CTGGAACTTC

 51  AGTGAAGTTG TCCTGTAAGG CTTCTGGCTA CATCTTCACC ACCTACTGGA

101  TGAACTGGGT GAAACAGAGG CCTGGACAAG GCCTTGAGTG GATTGGCATG

151  ATTCATCCTT CCGCAAGTGA AATTAGGTTG GATCAGAAAT TCAAGGACAA

201  GGCCACATTG ACTCTTGACA AATCCTCCAG CACAGCCTAT ATGCACCTCA

251  GCGGCCCGAC ATCTGTGGAT TCTGCGGTCT ATTACTGTGC AAGATCAGGG

301  GAATGGGGGT CTATGGACTA CTGGGGTCAA GGAACCTCAG TCACCGTCTC

351  CTCAGCCAAA ACGACACCCC CATCTGTCTA TCCACTGGCC CCTGGATCTG

401  CTGCCCAAAC TAACTCCATG GTGACCCTGG GATGCCTGGT CAAGGGCTAT

451  TTCCCTGAGC CAGTGACAGT GACCTGGAAC TCTGGATCCC TGTCCAGCGG

501  TGTGCACACC TTCCCAGCTG TCCTGCAGTC TGACCTCTAC ACTCTGAGCA

551  GCTCAGTGAC TGTCCCCTCC AGCACCTGGC CCAGCGAGAC CGTCACCTGC

601  AACGTTGCCC ACCCGGCCAG CAGCACCAAG GTGGACAAGA AAATTGTGCC

651  CAGGGATTGT GGTTGTAAGC CTTGCATATG TACAGTCCCA GAAGTATCAT

701  CTGTCTTCAT CTTCCCCCCA AAGCCCAAGG ATGTGCTCAC CATTACTCTG

751  ACTCCTAAGG TCACGTGTGT TGTGGTAGAC ATCAGCAAGG ATGATCCCGA

801  GGTCCAGTTC AGCTGGTTTG TAGATGATGT GGAGGTGCAC ACAGCTCAGA

851  CGCAACCCCG GGAGGAGCAG TTCAACAGCA CTTTCCGCTC AGTCAGTGAA

901  CTTCCCATCA TGCACCAGGA CTGGCTCAAT GGCAAGGAGT TCAAATGCAG
```

-continued

```
 951 GGTCAACAGT GCAGCTTTCC CTGCCCCCAT CGAGAAAACC ATCTCCAAAA

1001 CCAAAGGCAG ACCGAAGGCT CCACAGGTGT ACACCATTCC ACCTCCCAAG

1051 GAGCAGATGG CCAAGGATAA AGTCAGTCTG ACCTGCATGA TAACAGACTT

1101 CTTCCCTGAA GACATTACTG TGGAGTGGCA GTGGAATGGG CAGCCAGCGG

1151 AGAACTACAA GAACACTCAG CCCATCATGG ACACAGATGG CTCTTACTTC

1201 ATCTACAGCA AGCTCAATGT GCAGAAGAGC AACTGGGAGG CAGGAAATAC

1251 TTTCACCTGC TCTGTGTTAC ATGAGGGCCT GCACAACCAC CATACTGAGA

1301 AGAGCCTCTC CCACTCTCCT GGTAAATGA
```

Amino acid sequence of the Ab-24 HC including signal peptide:

```
                                              (SEQ ID NO: 362)
  1 MGWSSIILFL VATATGVHSQ VQLQQPGTEL VRPGTSVKLS CKASGYIFTT

 51 YWMNWVKQRP GQGLEWIGMI HPSASEIRLD QKFKDKATLT LDKSSSTAYM

101 HLSGPTSVDS AVYYCARSGE WGSMDYWGQG TSVTVSSAKT TPPSVYPLAP

151 GSAAQTNSMV TLGCLVKGYF PEPVTVTWNS GSLSSGVHTF PAVLQSDLYT

201 LSSSVTVPSS TWPSETVTCN VAHPASSTKV DKKIVPRDCG CKPCICTVPE

251 VSSVFIFPPK PKDVLTITLT PKVTCVVVDI SKDDPEVQFS WFVDDVEVHT

301 AQTQPREEQF NSTFRSVSEL PIMHQDWLNG KEFKCRVNSA AFPAPIEKTI

351 SKTKGRPKAP QVYTIPPPKE QMAKDKVSLT CMITDFFPED ITVEWQWNGQ

401 PAENYKNTQP IMDTDGSYFI YSKLNVQKSN WEAGNTFTCS VLHEGLHNHH

451 TEKSLSHSPG K
```

Nucleic acid sequence of the Ab-24 HC including signal peptide encoding sequence:

```
                                              (SEQ ID NO: 363)
  1 ATGGGATGGA GCTCTATCAT CCTCTTCTTG GTAGCAACAG CTACAGGTGT

 51 CCACTCCCAG GTCCAACTAC AGCAGCCTGG GACTGAGCTG GTGAGGCCTG

101 GAACTTCAGT GAAGTTGTCC TGTAAGGCTT CTGGCTACAT CTTCACCACC

151 TACTGGATGA ACTGGGTGAA ACAGAGGCCT GGACAAGGCC TTGAGTGGAT

201 TGGCATGATT CATCCTTCCG CAAGTGAAAT TAGGTTGGAT CAGAAATTCA

251 AGGACAAGGC CACATTGACT CTTGACAAAT CCTCCAGCAC AGCCTATATG

301 CACCTCAGCG GCCCGACATC TGTGGATTCT GCGGTCTATT ACTGTGCAAG

351 ATCAGGGGAA TGGGGGTCTA TGGACTACTG GGGTCAAGGA ACCTCAGTCA

401 CCGTCTCCTC AGCCAAAACG ACACCCCCAT CTGTCTATCC ACTGGCCCCT

451 GGATCTGCTG CCCAAACTAA CTCCATGGTG ACCCTGGGAT GCCTGGTCAA

501 GGGCTATTTC CCTGAGCCAG TGACAGTGAC CTGGAACTCT GGATCCCTGT

551 CCAGCGGTGT GCACACCTTC CCAGCTGTCC TGCAGTCTGA CCTCTACACT

601 CTGAGCAGCT CAGTGACTGT CCCCTCCAGC ACCTGGCCCA GCGAGACCGT

651 CACCTGCAAC GTTGCCCACC CGGCCAGCAG CACCAAGGTG GACAAGAAAA

701 TTGTGCCCAG GGATTGTGGT TGTAAGCCTT GCATATGTAC AGTCCCAGAA

751 GTATCATCTG TCTTCATCTT CCCCCCAAAG CCCAAGGATG TGCTCACCAT
```

-continued

```
801  TACTCTGACT CCTAAGGTCA CGTGTGTTGT GGTAGACATC AGCAAGGATG

851  ATCCCGAGGT CCAGTTCAGC TGGTTTGTAG ATGATGTGGA GGTGCACACA

901  GCTCAGACGC AACCCCGGGA GGAGCAGTTC AACAGCACTT TCCGCTCAGT

951  CAGTGAACTT CCCATCATGC ACCAGGACTG GCTCAATGGC AAGGAGTTCA

1001 AATGCAGGGT CAACAGTGCA GCTTTCCCTG CCCCCATCGA GAAAACCATC

1051 TCCAAAACCA AAGGCAGACC GAAGGCTCCA CAGGTGTACA CCATTCCACC

1101 TCCCAAGGAG CAGATGGCCA AGGATAAAGT CAGTCTGACC TGCATGATAA

1151 CAGACTTCTT CCCTGAAGAC ATTACTGTGG AGTGGCAGTG GAATGGGCAG

1201 CCAGCGGAGA ACTACAAGAA CACTCAGCCC ATCATGGACA CAGATGGCTC

1251 TTACTTCATC TACAGCAAGC TCAATGTGCA GAAGAGCAAC TGGGAGGCAG

1301 GAAATACTTT CACCTGCTCT GTGTTACATG AGGGCCTGCA CAACCACCAT

1351 ACTGAGAAGA GCCTCTCCCA CTCTCCTGGT AAATGA
```

The CDR sequences in the variable region of the light chain of Ab-24 are as follows:

CDR-L1: (SEQ ID NO: 351)
KASQSVDYDGTSYMN

CDR-L2: (SEQ ID NO: 352)
AASNLES

CDR-L3: (SEQ ID NO: 353)
QQSNEDPFT

The CDR sequences in the variable region of the heavy chain of Ab-24 are as follows:

CDR-H1: (SEQ ID NO: 358)
TYWMN

-continued

CDR-H2: (SEQ ID NO: 359)
MIHPSASEIRLDQKFKD

CDR-H3: (SEQ ID NO: 360)
SGEWGSMDY

Table 1 below provides the SEQ ID NOs and amino acid sequences of the CDR's of Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24. L1, L2, and L3 refer to light chain CDR's 1, 2, and 3, and H1, H2, and H3 refer to heavy chain CDR's 1, 2, and 3 according to the Kabat numbering system (Kabat et al., 1987 in *Sequences of Proteins of Immunological Interest*, U.S. Department of Health and Human Services, NIH, USA).

TABLE 1

| SEQ ID NO | DESCRIPTION | AMINO ACID SEQUENCE |
|---|---|---|
| 54 | Ab-A and Ab-1 CDR-L1 | QSSQSVYDNNWLA |
| 55 | Ab-A and Ab-1 CDR-L2 | DASDLAS |
| 56 | Ab-A and Ab-1 CDR-L3 | QGAYNDVIYA |
| 51 | Ab-A and Ab-1 CDR-H1 | SYWMN |
| 52 | Ab-A and Ab-1 CDR-H2 | TIDSGGRTDYASWAKG |
| 53 | Ab-A and Ab-1 CDR-H3 | NWNL |
| 60 | Ab-B CDR-L1 | SASSSVSFVD |
| 61 | Ab-B CDR-L2 | RTSNLGF |
| 62 | Ab-B CDR-L3 | QQRSTYPPT |
| 57 | Ab-B CDR-H1 | TSGMGVG |
| 58 | Ab-B CDR-H2 | HIWWDDVKRYNPVLKS |
| 59 | Ab-B CDR-H3 | EDFDYDEEYYAMDY |
| 48 | Ab-C CDR-L1 | KASQSVDYDGDSYMN |

TABLE 1-continued

| SEQ ID NO | DESCRIPTION | AMINO ACID SEQUENCE |
|---|---|---|
| 49 | Ab-C CDR-L2 | AASNLES |
| 50 | Ab-C CDR-L3 | QQSNEDPWT |
| 45 | Ab-C CDR-H1 | DCYMN |
| 46 | Ab-C CDR-H2 | DINPPNGGTTYNQKFKG |
| 47 | Ab-C CDR-H3 | SHYYFDGRVPWDAMDY |
| 42 | Ab-D CDR-L1 | QASQGTSINLN |
| 43 | Ab-D CDR-L2 | GSSNLED |
| 44 | Ab-D CDR-L3 | LQHSYLPYT |
| 39 | Ab-D CDR-H1 | DHYMS |
| 40 | Ab-D CDR-H2 | DINPYSGETTYNQKFKG |
| 41 | Ab-D CDR-H3 | DDYDASPFAY |
| 275 | Ab-2 CDR-L1 | RASSSVYYYMH |
| 276 | Ab-2 CDR-L2 | ATSNLAS |
| 277 | Ab-2 CDR-L3 | QQWSSDPLT |
| 287 | Ab-2 CDR-H1 | DYFIH |
| 288 | Ab-2 CDR-H2 | RLDPEDGESDYAPKFQD |
| 289 | Ab-2 CDR-H3 | EDYDGTYTFFPY |
| 278 | Ab-3 and Ab-15 CDR-L1 | SVSSTISSNHLH |
| 279 | Ab-3 and Ab-15 CDR-L2 | GTSNLAS |
| 280 | Ab-3 and Ab-15 CDR-L3 | QQWSSYPLT |
| 290 | Ab-3 and Ab-15 CDR-H1 | DFYLH |
| 291 | Ab-3 and Ab-15 CDR-H2 | RIDPENGDTLYDPKFQD |
| 292 | Ab-3 and Ab-15 CDR-H3 | EADYFHDGTSYWYFDV |
| 78 | Ab-4 and Ab-5 CDR-L1 | RASQDISNYLN |
| 79 | Ab-4 and Ab-5 CDR-L2 | YTSRLLS |
| 80 | Ab-4 and Ab-5 CDR-L3 | QQGDTLPYT |
| 245 | Ab-4 and Ab-5 CDR-H1 | DYNMH |
| 246 | Ab-4 and Ab-5 CDR-H2 | EINPNSGGAGYNQKFKG |
| 247 | Ab-4 and Ab-5 CDR-H3 | LGYDDIYDDWYFDV |
| 81 | Ab-6 CDR-L1 | RASQDISNYLN |
| 99 | Ab-6 CDR-L2 | YTSRLHS |
| 100 | Ab-6 CDR-L3 | QQGDTLPYT |
| 248 | Ab-6 CDR-H1 | DYNMH |
| 249 | Ab-6 CDR-H2 | EINPNSGGSGYNQKFKG |
| 250 | Ab-6 CDR-H3 | LVYDGSYEDWYFDV |
| 101 | Ab-7 CDR-L1 | RASQVITNYLY |
| 102 | Ab-7 CDR-L2 | YTSRLHS |
| 103 | Ab-7 CDR-L3 | QQGDTLPYT |
| 251 | Ab-7 CDR-H1 | DYNMH |

TABLE 1-continued

| SEQ ID NO | DESCRIPTION | AMINO ACID SEQUENCE |
|---|---|---|
| 252 | Ab-7 CDR-H2 | EINPNSGGAGYNQQFKG |
| 253 | Ab-7 CDR-H3 | LGYVGNYEDWYFDV |
| 104 | Ab-8 CDR-L1 | RASQDISNYLN |
| 105 | Ab-8 CDR-L2 | YTSRLLS |
| 106 | Ab-8 CDR-L3 | QQGDTLPYT |
| 254 | Ab-8 CDR-H1 | DYNMH |
| 255 | Ab-8 CDR-H2 | EINPNSGGAGYNQKFKG |
| 256 | Ab-8 CDR-H3 | LGYDDIYDDWYFDV |
| 107 | Ab-9 CDR-L1 | RASQDISNYLN |
| 108 | Ab-9 CDR-L2 | YTSRLFS |
| 109 | Ab-9 CDR-L3 | QQGDTLPYT |
| 257 | Ab-9 CDR-H1 | DYNMH |
| 258 | Ab-9 CDR-H2 | EINPNSGGAGYNQKFKG |
| 259 | Ab-9 CDR-H3 | LGYDDIYDDWYFDV |
| 110 | Ab-10 CDR-L1 | RASQDISNYLN |
| 111 | Ab-10 CDR-L2 | YTSRLLS |
| 112 | Ab-10 CDR-L3 | QQGDTLPYT |
| 260 | Ab-10 CDR-H1 | DYNMH |
| 261 | Ab-10 CDR-H2 | EINPNSGGAGYNQKFKG |
| 262 | Ab-10 CDR-H3 | LGYDDIYDDWYFDV |
| 281 | Ab-11 and Ab-16 CDR-L1 | RASSSISYIH |
| 282 | Ab-11 and Ab-16 CDR-L2 | ATSNLAS |
| 283 | Ab-11 and Ab-16 CDR-L3 | QQWSSDPLT |
| 293 | Ab-11 and Ab-16 CDR-H1 | DYYIH |
| 294 | Ab-11 and Ab-16 CDR-H2 | RVDPDNGETEFAPKFPG |
| 295 | Ab-11 and Ab-16 CDR-H3 | EDYDGTYTWFPY |
| 113 | Ab-12 CDR-L1 | RASQDISNYLN |
| 114 | Ab-12 CDR-L2 | YTSTLQS |
| 115 | Ab-12 CDR-L3 | QQGDTLPYT |
| 263 | Ab-12 CDR-H1 | DYNMH |
| 264 | Ab-12 CDR-H2 | EINPNSGGSGYNQKFKG |
| 265 | Ab-12 CDR-H3 | LGYYGNYEDWYFDV |
| 284 | Ab-13 and Ab-14 CDR-L1 | RASSSVTSSYLN |
| 285 | Ab-13 and Ab-14 CDR-L2 | STSNLAS |
| 286 | Ab-13 and Ab-14 CDR-L3 | QQYDFFPST |
| 296 | Ab-13 and Ab-14 CDR-H1 | DYYMN |
| 297 | Ab-13 and Ab-14 CDR-H2 | DINPYNDDTTYNHKFKG |
| 298 | Ab-13 and Ab-14 CDR-H3 | ETAVITTNAMD |
| 116 | Ab-17 and Ab-18 CDR-L1 | SVSSSISSSNLH |

TABLE 1-continued

| SEQ ID NO | DESCRIPTION | AMINO ACID SEQUENCE |
|---|---|---|
| 237 | Ab-17 and Ab-18 CDR-L2 | GTSNLAS |
| 238 | Ab-17 and Ab-18 CDR-L3 | QQWTTTYT |
| 266 | Ab-17 and Ab-18 CDR-H1 | DYYIH |
| 267 | Ab-17 and Ab-18 CDR-H2 | RIDPDNGESTYVPKFQG |
| 268 | Ab-17 and Ab-18 CDR-H3 | EGLDYGDYYAVDY |
| 239 | Ab-19, Ab-20 and Ab-23 CDR-L1 | RASQDISSYLN |
| 240 | Ab-19, Ab-20 and Ab-23 CDR-L2 | STSRLNS |
| 241 | Ab-19, Ab-20 and Ab-23 CDR-L3 | QQDIKHPT |
| 269 | Ab-19, Ab-20 and Ab-23 CDR-H1 | DYIMH |
| 270 | Ab-19, Ab-20 and Ab-23 CDR-H2 | YINPYNDDTEYNEKFKG |
| 271 | Ab-19, Ab-20 and Ab-23 CDR-H3 | SIYYYDAPFAY |
| 242 | Ab-21 and Ab-22 CDR-L1 | KASQDVFTAVA |
| 243 | Ab-21 and Ab-22 CDR-L2 | WASTRHT |
| 244 | Ab-21 and Ab-22 CDR-L3 | QQYSSYPLT |
| 272 | Ab-21 and Ab-22 CDR-H1 | DYYMH |
| 273 | Ab-21 and Ab-22 CDR-H2 | RIDPENGDIIYDPKFQG |
| 274 | Ab-21 and Ab-22 CDR-H3 | DAGDPAWFTY |
| 351 | Ab-24 CDR-L1 | KASQSVDYDGTSYMN |
| 352 | Ab-24 CDR-L2 | AASNLES |
| 353 | Ab-24 CDR-L3 | QQSNEDPFT |
| 358 | Ab-24 CDR-H1 | TYWMN |
| 359 | Ab-24 CDR-H2 | MIHPSASEIRLDQKFKD |
| 360 | Ab-24 CDR-H3 | SGEWGSMDY |

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDR's of Table 1 above; and/or to a CDR of a sclerostin binding agent that cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or to a CDR of a sclerostin binding agent wherein the binding agent can block the inhibitory effect of sclerostin in a cell based mineralization assay (i.e. a sclerostin neutralizing binding agent); and/or to a CDR of a sclerostin binding agent that binds to a Loop 2 epitope; and/or to a CDR of a sclerostin binding agent that binds to a T20.6 epitope; and/or to a CDR of a sclerostin binding agent that binds to a "T20.6 derivative (cystine-knot+4 arms)" epitope.

Sclerostin binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cystine-knot+4 arms)" epitope.

Polynucleotides encoding sclerostin binding agents are within the scope of the invention if they have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and wherein the encoded sclerostin binding agents cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cystine-knot+4 arms)" epitope.

Antibodies according to the invention may have a binding affinity for human sclerostin of less than or equal to $1\times10^{-7}$M, less than or equal to $1\times10^{-8}$M, less than or equal to $1\times10^{-9}$M, less than or equal to $1\times10^{-10}$ M, less than or equal to $1\times10^{-11}$M, or less than or equal to $1\times10^{-12}$M.

The affinity of a binding agent such as an antibody or binding partner, as well as the extent to which a binding agent (such as an antibody) inhibits binding, can be determined by one of ordinary skill in the art using conventional techniques, for example those described by Scatchard et al. (*Ann. N.Y. Acad. Sci.* 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. Patent Publication No. 2004/0146888 A1.

Characterization Assays

In the methods described above to generate antibodies according to the invention, including the manipulation of the specific Ab-A, Ab-B, Ab-C, Ab-D, and Antibody 1-24 (Ab-1 to Ab-24) CDRs into new frameworks and/or constant regions, appropriate assays are available to select the desired antibodies or binding agents (i.e. assays for determining binding affinity to sclerostin; cross-blocking assays; Biacore-based "human sclerostin peptide epitope competition binding assay;" MC3T3-E1 cell based assay; in vivo assays).

Epitope Binding Assays

Figure 9:
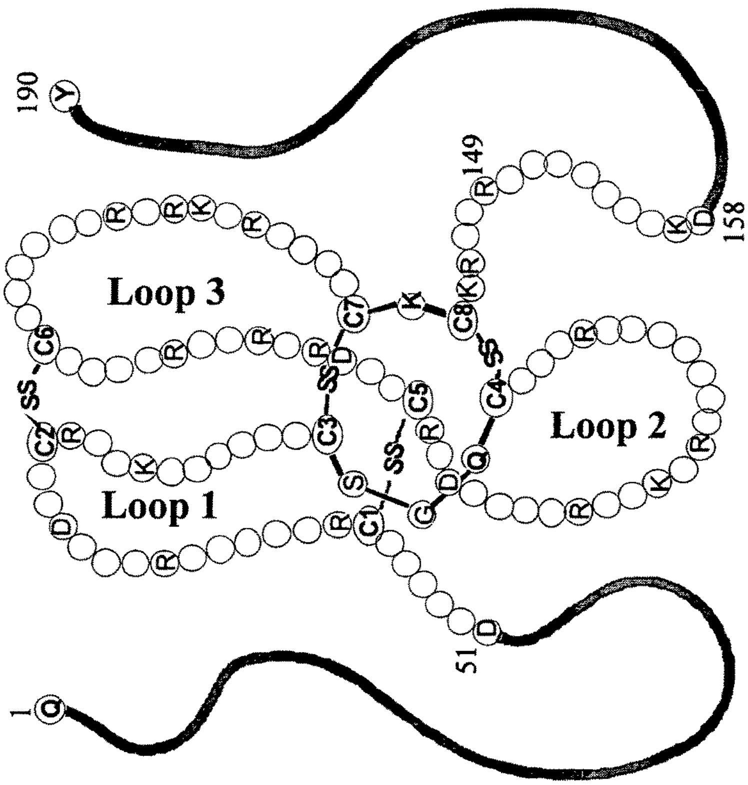
FIG. 9 depicts a schematic of the basic structure of human sclerostin. There is an N-terminal arm (from the first Q to C1) and a C-terminal arm (from C8 to the terminal Y). In between these arms there is the cystine-knot structure (formed by three disulfides: C1-05; C3-C7; C4-C8) and three loops which are designated Loop1, Loop 2 and Loop 3. The distal regions of Loop 1 and Loop 3 are linked by the C2-C6 disulfide. Potential trypsin cleavage sites are indicated (arginine=R and lysine=K). Some of the potential AspN cleavage sites are indicated (only aspartic acid (D) residues are shown).

Mature form human sclerostin is a 190 amino acid glycoprotein with a cystine-knot structure (FIGS. 8 and 9). In addition to the cystine-knot structure, the protein is characterized as having three loops designated as Loop 1, Loop 2 and Loop 3. Human sclerostin was subjected to proteolytic digestion to produce fragments. Briefly, using different proteases, including trypsin, aspN, and lysC, fragments with various cleavage sites and sizes were generated. The sequences and mass for various human sclerostin peptides were determined. Antibody protection was evaluated to determine the effect on accessibility for proteolysis, including clipped site masking and peptide shifting. Finally, a BIAcore-based "human sclerostin peptide epitope competition assay" was performed.

Figure 13:
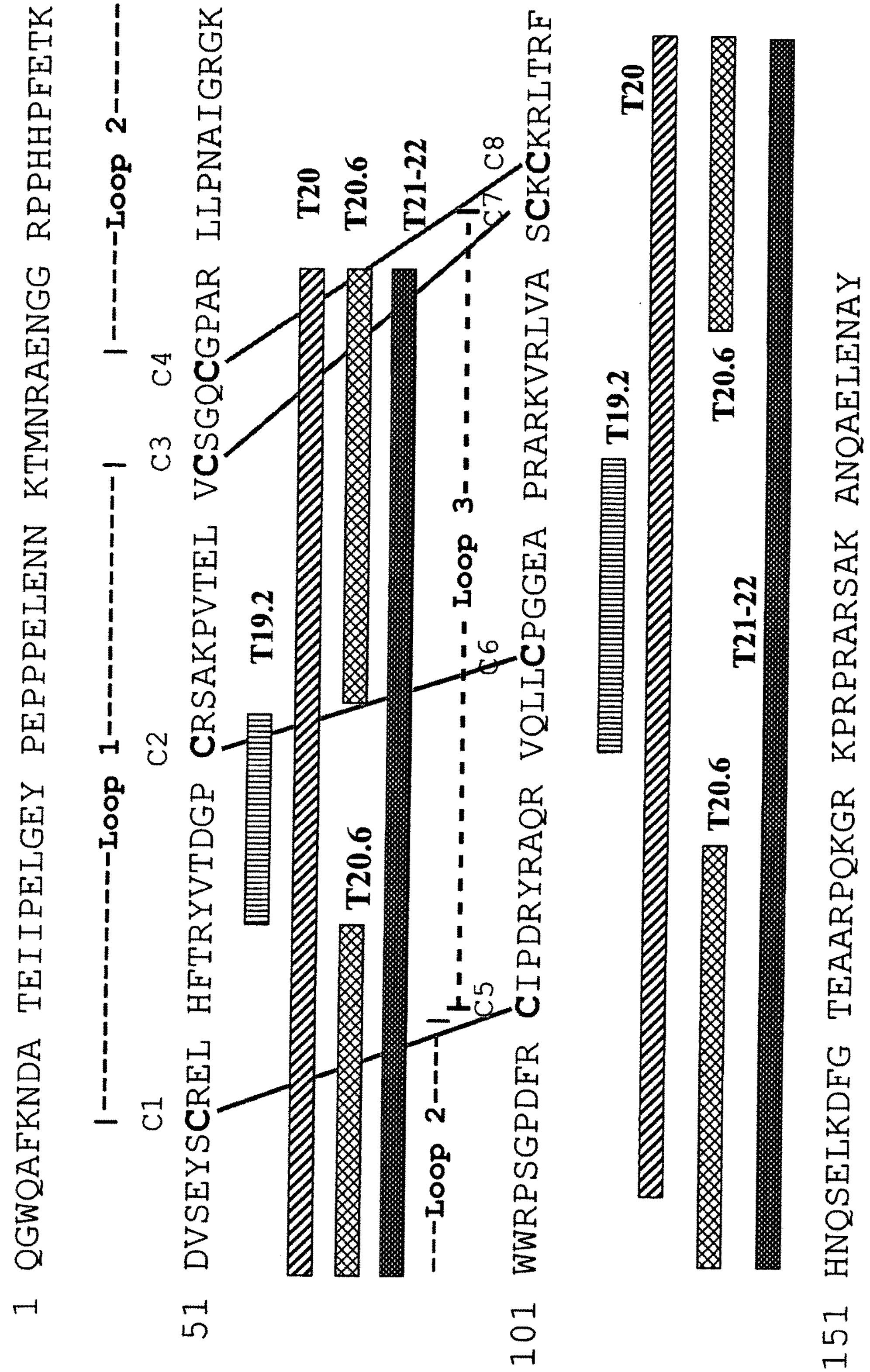
FIG. 13 shows a linear schematic of four human sclerostin peptides (T19.2, T20, T20.6 and T21-22) generated by trypsin digestion.

Exposure of sclerostin to trypsin cleavage resulted in a pattern of peptide fragments as summarized in FIG. 13. The fragments are referred to as T19.2, T20, T20.6, and T21-22. As shown schematically in FIG. 19B, the T20.6 epitope is a complex of four separate peptide sequences which are joined by the three disulfide bonds of the cystine-knot region. Two of the peptides are joined by two disulfide bonds. The other two peptides are linked by one disulfide bond that, schematically, bisects the first two polypeptides.

The T20.6 epitope that was generated by trypsin digestion retains the cystine-knot structure of the native polypeptide and is recognized by antibodies Ab-C and Ab-D. A derivative of epitope T20.6 consists of the cystine-knot region and amino acids 58-64, 73-81, 112-117 and 138-141 in sequence position with reference to SEQ ID NO:1. This derivative epitope is shown in FIG. 21. An epitope comprising the cystine-knot region may have one or more amino acids that is present in the T20.6 epitope (FIG. 19B) but not present in the T20.6 derivative epitope (FIG. 21).

Another epitope-containing region was identified in the Loop 2 region of human sclerostin (FIG. 19A) and is recognized by antibodies Ab-A and Ab-B. A Loop 2 epitope comprises amino acids 86-111 of SEQ ID NO:1 (C4GPARLLPNAIGRGKWWRPSGPDFRC5, SEQ ID NO:6). Sterically, with reference to full-length sclerostin of SEQ ID NO:1, the Loop 2-containing structure is defined at one end by a disulfide bond between cysteine at position 86 (C4) and cysteine at position 144 (C8), and at the other end by a disulfide bond between cysteine at position 111 (C5) and cysteine at position 57 (C1).

The peptides generated by aspN cleavage of human sclerostin are shown in FIG. 12. In the Figure, these peptides are designated as AspN14.6, AspN18.6, and AspN22.7-23.5, and are also referred to herein as N14.6, N18.6, and N22.7-23.5, respectively.

One group of antibodies exhibits a specific pattern of binding to certain epitopes as evidenced by a Biacore-based "human sclerostin peptide epitope competition binding assay." Briefly, the antibody is preincubated with the epitope to be tested, at concentrations that will saturate the epitope-binding sites on the antibody. The antibody is then exposed to sclerostin bound to a chip surface. After the appropriate incubation and washing procedures, a pattern of competitive binding is established. As shown in FIG. 18, exemplary antibody Ab-D bound to sclerostin molecules attached to the surface of the chip. Preincubation of antibody Ab-D with sclerostin decreased the binding of the antibody to the sclerostin on the chip to close to zero. Preincubation with a peptide consisting of epitope T19.2 showed that T19.2 did not compete with sclerostin for antibody binding. However, preincubation with any one of the epitopes designated T20, T20.6, T21-22, or N22.7-23.5 abolished a large proportion of the binding of antibody to sclerostin on the chip. In contrast, preincubation of the antibody with any one of the epitopes designated T19.2, N14.6 or N18.6 did not abolish the ability of the antibody to bind to sclerostin. A second exemplary antibody with this binding profile (FIG. 17) is Ab-C.

Antibody Ab-D therefore is exemplary and representative of a group of antibodies that bind to the epitopes T20, T20.6, T21-22, and N22.7-23.5, and have minimal detectable binding to epitopes T19.2, N14.6 and N18.6, as measured by the ability to block antibody binding to sclerostin. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-D are included in the invention. By "similar to" is meant, for example, the antibody will exhibit binding to each of the polypeptides T20, T20.6, T21-22 and N22.7-23.5 whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 18 suggests that the epitope space to which antibody Ab-D and other antibodies having the epitope binding pattern of Ab-D bind consists of a polypeptide comprising the cystine-knot region of sclerostin.

Figure 19:
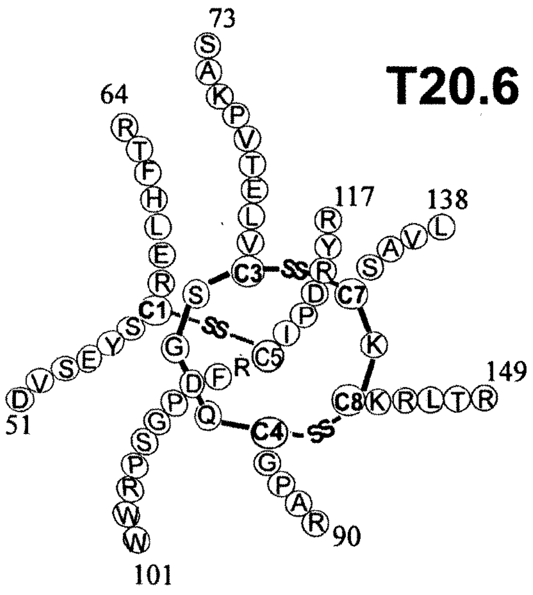
FIG. 19 shows two Mab binding epitopes of human sclerostin.

Thus, as disclosed herein and with reference to FIG. 19B, an exemplary T20.6 epitope comprises four peptide chains attached via three separate disulfide bonds. Peptide chain SAKPVTELVC3SGQC4GPAR (SEQ ID NO:3) is attached to peptide chain LVASC7KC8KRLTR (SEQ ID NO:5) by disulfide bonds from C3 to C7, and from C4 to C8. Peptide chain DVSEYSC1RELHFTR (SEQ ID NO:2) is attached to peptide chain WWRPSGPDFRC5IPDRYR (SEQ ID NO:4) by a disulfide bond from C1 to C5. The polypeptides of SEQ ID NOs:3 and 5 remain associated with the polypeptides of SEQ ID NOs:2 and 4 through a steric construct whereby the C1-05 bond crosses the plane of the C4-C8 and C3-C7 bonds and is located between them, as illustrated in FIG. 19B.

As disclosed herein and with reference to FIG. 21, an exemplary derivative epitope of T20.6 comprises four peptide chains attached via three separate disulfide bonds. Peptide chain SAKPVTELVC3SGQC4 (SEQ ID NO:70) is attached to peptide chain LVASC7KC8 (SEQ ID NO:71) by disulfide bonds from C3 to C7, and from C4 to C8. Peptide chain C1RELHFTR (SEQ ID NO:72) is attached to peptide chain C5IPDRYR (SEQ ID NO:73) by a disulfide bond from C1 to C5. The polypeptides of SEQ ID NOs:70 and 71 remain associated with the polypeptides of SEQ ID NOs:72 and 73 through a steric construct whereby the C1-05 bond crosses the plane of the C4-C8 and C3-C7 bonds and is located between them, as illustrated in FIG. 21.

Antibody Ab-A is exemplary and representative of a second group of antibodies that have a characteristic binding pattern to human sclerostin peptides that is distinct from that obtained for antibodies Ab-C and Ab-D. Ab-A and the group of antibodies it represents bind to the N22.7-23.5 epitope and have minimal detectable binding to epitopes T19.2, T20, T20.6, T21-22, N14.6 or N18.6, as measured by the ability to block antibody binding to sclerostin (FIG. 15). A second exemplary antibody with this binding profile (FIG. 16) is Ab-B. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-A are included in the invention. By "similar to" is meant, for example, the antibody will exhibit binding to the N22.7-23.5 polypeptide whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, T20, T20.6, T21-22, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 15 suggests that the epitope space to which antibody Ab-A and other antibodies having the epitope binding pattern of Ab-A bind consists of a polypeptide comprising the Loop 2 region of sclerostin. Thus, as disclosed herein and with reference to FIG. 19A, the Loop 2 region can be described as a linear peptide, but it acquires a tertiary structure when it is present in native sclerostin or a cystine-knot-containing portion of sclerostin in which the native disulfide bond structure is maintained. The linear or tertiary structure of the Loop 2 epitope can affect antibody binding thereto, as discussed in the Examples. A Loop 2 region can comprise the following amino acid sequence: C4GPARLLPNAIGRGKWWRPSGPDFRC5 (SEQ ID NO:6). "C4" refers to a cysteine residue located at position 86 with reference to SEQ ID NO:1. "C5" refers to a cysteine residue located at position 111 with reference to SEQ ID NO:1. In native sclerostin protein, C4 is linked to a cysteine at position 144 (C8) by a disulfide bond, and C5 is linked to a cysteine at position 57 (C1) by a disulfide bond. Epitopes derived from the Loop 2 region include CGPARLLPNAIGRGKWWRPS (SEQ ID NO:63); GPARLLPNAIGRGKWWRPSG (SEQ ID NO:64); PARLLPNAIGRGKWWRPSGP (SEQ ID NO:65); ARLLPNAIGRGKWWRPSGPD (SEQ ID NO:66); RLLPNAIGRGKWWRPSGPDF (SEQ ID NO:67); LLPNAIGRGKWWRPSGPDFR (SEQ ID NO:68); and LPNAIGRGKWWRPSGPDFRC (SEQ ID NO:69)

Cross-Blocking Assays

The terms "cross-block", "cross-blocked" and "cross-blocking" are used interchangeably herein to mean the ability of an antibody or other binding agent to interfere with the binding of other antibodies or binding agents to sclerostin.

The extent to which an antibody or other binding agent is able to interfere with the binding of another to sclerostin, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between antibodies or other binding agents in terms of their binding to sclerostin.

Biacore Cross-Blocking Assay

The following generally describes a suitable Biacore assay for determining whether an antibody or other binding agent cross-blocks or is capable of cross-blocking according to the invention. For convenience reference is made to two antibodies, but it will be appreciated that the assay can be used with any of the sclerostin binding agents described herein. The Biacore machine (for example the Biacore 3000) is operated in line with the manufacturer's recommendations.

Thus in one cross-blocking assay, sclerostin is coupled to a CM5 Biacore chip using standard amine coupling chemistry to generate a sclerostin-coated surface. Typically 200-800 resonance units of sclerostin would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of sclerostin binding sites on that antibody.

The concentration of each antibody in the test mix should be high enough to readily saturate the binding sites for that antibody on the sclerostin molecules captured on the Biacore chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the sclerostin-coated Biacore chip and the total amount of binding recorded. The chip is then treated in such a way as to remove the bound antibodies without damaging the chip-bound sclerostin. Typically this is done by treating the chip with 30 mM HCl for 60 seconds.

The solution of antibody A* alone is then passed over the sclerostin-coated surface and the amount of binding recorded. The chip is again treated to remove all of the bound antibody without damaging the chip-bound sclerostin.

The solution of antibody B* alone is then passed over the sclerostin-coated surface and the amount of binding recorded.

The maximum theoretical binding of the mixture of antibody A* and antibody B* is next calculated, and is the sum of the binding of each antibody when passed over the sclerostin surface alone. If the actual recorded binding of the mixture is less than this theoretical maximum then the two antibodies are cross-blocking each other.

Thus, in general, a cross-blocking antibody or other binding agent according to the invention is one which will bind to sclerostin in the above Biacore cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The Biacore assay described above is a primary assay used to determine if antibodies or other binding agents cross-block each other according to the invention. On rare occasions particular antibodies or other binding agents may not bind to sclerostin coupled via amine chemistry to a CM5 Biacore chip (this usually occurs when the relevant binding site on sclerostin is masked or destroyed by the coupling to the chip). In such cases cross-blocking can be determined using a tagged version of Sclerostin, for example N-terminal His-tagged Sclerostin (R & D Systems, Minneapolis, Minn., USA; 2005 cat#1406-ST-025). In this particular format, an anti-His antibody would be coupled to the Biacore chip and then the His-tagged Sclerostin would be passed over the surface of the chip and captured by the anti-His antibody. The cross blocking analysis would be carried out essentially as described above, except that after each chip regeneration cycle, new His-tagged sclerostin would be loaded back onto the anti-His antibody coated surface. In addition to the example given using N-terminal His-tagged Sclerostin, C-terminal His-tagged sclerostin could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

ELISA-Based Cross-Blocking Assay

The following generally describes an ELISA assay for determining whether an anti-sclerostin antibody or other sclerostin binding agent cross-blocks or is capable of cross-blocking according to the invention. For convenience, reference is made to two antibodies (Ab-X and Ab-Y), but it will be appreciated that the assay can be used with any of the sclerostin binding agents described herein.

The general principal of the assay is to have an anti-sclerostin antibody coated onto the wells of an ELISA plate. An excess amount of a second, potentially cross-blocking, anti-sclerostin antibody is added in solution (i.e. not bound to the ELISA plate). A limited amount of sclerostin is then added to the wells. The coated antibody and the antibody in solution compete for binding of the limited number of sclerostin molecules. The plate is washed to remove sclerostin that has not been bound by the coated antibody and to also remove the second, solution phase antibody as well as any complexes formed between the second, solution phase antibody and sclerostin. The amount of bound sclerostin is then measured using an appropriate sclerostin detection reagent. An antibody in solution that is able to cross-block the coated antibody will be able to cause a decrease in the number of sclerostin molecules that the coated antibody can bind relative to the number of sclerostin molecules that the coated antibody can bind in the absence of the second, solution phase, antibody.

This assay is described in more detail further below for Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y sclerostin binding sites per well are at least 10 fold higher than the moles of Ab-X sclerostin binding sites that were used, per well, during the coating of the ELISA plate. Sclerostin is then added such that the moles of sclerostin added per well are at least 25-fold lower than the moles of Ab-X sclerostin binding sites that were used for coating each well. Following a suitable incubation period the ELISA plate is washed and a sclerostin detection reagent is added to measure the amount of sclerostin specifically bound by the coated anti-sclerostin antibody (in this case Ab-X). The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and
2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

An example of such an ELISA-based cross blocking assay can be found in Example 7 ("ELISA-based cross-blocking assay").

Cell Based Neutralization Assay

Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J. Cell Biol. 96:191-198) and subclones of the original cell line can form mineral in culture upon growth in the presence of differentiating agents. Such subclones include MC3T3-E1-BF (Smith E, Redman R, Logg C, Coetzee G, Kasahara N, Frenkel B. 2000. *Glucocorticoids inhibit developmental stage-specific osteoblast cell cycle*. J. Biol. Chem. 275:19992-20001). For both the MC3T3-E1-BF subclone as well as the original MC3T3-E1 cells, sclerostin can inhibit one or more of the sequence of events leading up to and including mineral deposition (i.e. sclerostin inhibits mineralization). Anti-sclerostin antibodies that are able to neutralize sclerostin's inhibitory activity allow for mineralization of the culture in the presence of sclerostin such that there is a statistically significant increase in deposition of calcium phosphate (measured as calcium) as compared to the amount of calcium measured in the sclerostin-only (i.e. no antibody) treatment group. The antibodies used in the cell based mineralization assay experiments shown in FIGS. 22, 23 and 24 have molecular weights of about 145 Kd and have 2 sclerostin binding sites per antibody molecule.

When running the assay with the goal of determining whether a particular anti-sclerostin antibody or anti-sclerostin binding agent can neutralize sclerostin (i.e., is a sclerostin neutralizing antibody or derivative thereof, or is a sclerostin neutralizing binding agent), the amount of sclerostin used in the assay needs to be the minimum amount of sclerostin that causes at least a 70%, statistically significant, reduction in deposition of calcium phosphate (measured as calcium) in the sclerostin-only group, as compared to the amount of calcium measured in the no sclerostin group. An anti-sclerostin neutralizing antibody or an anti-sclerostin neutralizing binding agent is defined as one that causes a statistically significant increase in deposition of calcium phosphate (measured as calcium) as compared to the amount of calcium measured in the sclerostin-only (i.e. no antibody, no binding agent) treatment group. To determine whether an anti-sclerostin antibody or an anti-sclerostin binding agent is neutralizing or not, the amount of anti-sclerostin antibody or anti-sclerostin binding agent used in the assay needs to be such that there is an excess of moles of sclerostin binding sites per well as compared to the number of moles of sclerostin per well. Depending on the potency of the antibody, the fold excess that may be required can be 24, 18, 12, 6, 3, or 1.5, and one of skill is familiar with the routine practice of testing more than one concentration of binding agent. For example, a very potent anti-sclerostin neutralizing antibody or anti-sclerostin neutralizing binding agent will be able to neutralize sclerostin even when there is less than a 6-fold excess of moles of sclerostin binding sites per well as compared to the number of moles of sclerostin per well. A less potent anti-sclerostin neutralizing antibody or anti-sclerostin neutralizing binding agent will be able to neutralize sclerostin only at a 12, 18 or 24 fold excess. Sclerostin binding agents within this full range of potencies are suitable as neutralizing sclerostin binding agents. Exemplary cell based mineralization assays are described in detail in Example 8.

Anti-sclerostin antibodies and derivatives thereof that can neutralize human sclerostin, and sclerostin binding agents that can neutralize human sclerostin may be of use in the treatment of human conditions/disorders that are caused by, associated with, or result in at least one of low bone formation, low bone mineral density, low bone mineral content, low bone mass, low bone quality and low bone strength.

In Vivo Neutralization Assay

Increases in various parameters associated with, or that result from, the stimulation of new bone formation can be measured as an output from in vivo testing of sclerostin binding agents in order to identify those binding agents that are able to neutralize sclerostin and thus able to cause stimulation of new bone formation. Such parameters include various serum anabolic markers [e.g. osteocalcin, P1NP (n-terminal propeptide of type 1 procollagen)], histomorphometric markers of bone formation (e.g. osteoblast surface/bone surface; bone formation rate/bone surface; trabecular thickness), bone mineral density, bone mineral content, bone mass, bone quality and bone strength. A sclerostin neutralizing binding agent is defined as one capable of causing a statistically significant increase, as compared to vehicle treated animals, in any parameter associated with, or that results from, the stimulation of new bone formation. Such in vivo testing can be performed in any suitable mammal (e.g. mouse, rat, monkey). An example of such in vivo testing can be found in Example 5 ("In vivo testing of anti-sclerostin monoclonal antibodies").

Although the amino acid sequence of sclerostin is not 100% identical across mammalian species (e.g. mouse sclerostin is not 100% identical to human sclerostin), it will be appreciated by one skilled in the art that a sclerostin binding agent that can neutralize, in vivo, the sclerostin of a certain species (e.g. mouse) and that also can bind human sclerostin in vitro is very likely to be able to neutralize human sclerostin in vivo. Thus, such a human sclerostin binding agent (e.g. anti-human sclerostin antibody) may be of use in the treatment of human conditions/disorders that are caused by, associated with, or result in at least one of low bone formation, low bone mineral density, low bone mineral content, low bone mass, low bone quality and low bone strength. Mice in which homologous recombination had been used to delete the mouse sclerostin gene and insert the human sclerostin gene in its place (i.e. human sclerostin gene knock-in mice or human SOST knock-in mice) would be an example of an additional in vivo system.

Pharmaceutical compositions are provided, comprising one of the above-described binding agents such as at least one of antibody Ab-A, Ab-B, Ab-C, Ab-D and Ab-1 to Ab-24 to human sclerostin, along with a pharmaceutically or physiologically acceptable carrier, excipient, or diluent. Pharmaceutical compositions and methods of treatment are disclosed in copending application Ser. No. 10/868,497, filed Jun. 16, 2004, which claims priority to Ser. No. 60/478,977, both of which are incorporated by reference herein.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences,* 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3):691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. Nos. 5,567,434; 5,552,157; 5,565,213; 5,738,868 and 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 μm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 100 mg/kg of body weight. As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Increases in bone mineral content and/or bone mineral density may be determined directly through the use of X-rays (e.g., Dual Energy X-ray Absorptometry or "DEXA"), or by inference through the measurement of 1) markers of bone formation and/or osteoblast activity, such as, but not limited to, osteoblast specific alkaline phosphatase, osteocalcin, type 1 procollagen C' propeptide (PICP), total alkaline phosphatase (see Cornier, *Curr. Opin. in Rheu.* 7:243(1995)) and serum procollagen 1 N-terminal propeptide (P1NP) and/or 2) markers of bone resorption and/or osteoclast activity including, but not limited to, pyridinoline, deoxypryridinoline, N-telopeptide, urinary hydroxyproline, plasma tartrate-resistant acid phosphatases, and galactosyl hydroxylysine; (see Cornier, id), serum TRAP 5b (tartrate-resistant acid phosphatase isoform 5b) and serum cross-linked C-telopeptide (sCTXI). The amount of bone mass may also be calculated from body weights or by using other methods (see Guinness-Hey, *Metab. Bone Dis. Relat. Res.* 5:177-181, 1984). Animals and particular animal models are used in the art for testing the effect of the compositions and methods of the invention on, for example, parameters of bone loss, bone resorption, bone formation, bone strength or bone mineralization that mimic conditions of human disease such as osteoporosis and osteopenias. Examples of such models include the ovariectomized rat model (Kalu, D. N., *The ovariectomized rat model of postmenopausal bone loss. Bone and Mineral* 15:175-192 (1991); Frost, H. M. and Jee, W. S. S. *On the rat model of human osteopenias and osteoporosis. Bone and Mineral* 18:227-236 (1992); and Jee, W. S. S. and Yao, W., *Overview: animal models of osteopenia and osteoporosis. J. Musculoskel. Neuron. Interact.* 1:193-207 (2001)).

Particular conditions which may be treated by the compositions of the present invention include dysplasias, wherein growth or development of bone is abnormal and a wide variety of causes of osteopenia, osteoporosis and bone loss. Representative examples of such conditions include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, and pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, fabry disease, turner syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, idiopathic osteopenia or osteoporosis, congenital osteopenia or osteoporosis, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, fibrous dysplasia, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, and bone loss associated with space travel. Further conditions relate to bone loss associated with aging, including facial bone loss associated with aging, cranial bone loss associated with aging, jaw bone loss associated with aging, and skull bone loss associated with aging.

Compositions of the present invention may also be useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

The invention also provides a diagnostic kit comprising at least one anti-sclerostin binding agent according to the present invention. The binding agent may be an antibody. In addition, such a kit may optionally comprise one or more of the following:

(1) instructions for using the one or more binding agent(s) for screening, diagnosis, prognosis, therapeutic monitoring or any combination of these applications;
(2) a labeled binding partner to the anti-sclerostin binding agent(s);
(3) a solid phase (such as a reagent strip) upon which the anti-sclerostin binding agent(s) is immobilized; and
(4) a label or insert indicating regulatory approval for screening, diagnostic, prognostic or therapeutic use or any combination thereof.

If no labeled binding partner to the binding agent(s) is provided, the binding agent(s) itself can be labeled with one or more of a detectable marker(s), e.g. a chemiluminescent, enzymatic, fluorescent, or radioactive moiety.

The following examples are offered by way of illustration, and not by way of limitation.

EXAMPLES

Example 1

Recombinant Expression of Sclerostin

Recombinant human sclerostin/SOST is commercially available from R&D Systems (Minneapolis, Minn., USA; 2006 cat#1406-ST-025). Additionally, recombinant mouse sclerostin/SOST is commercially available from R&D Systems (Minneapolis, Minn., USA; 2006 cat#1589-ST-025).

Alternatively, the different species of sclerostin can be expressed transiently in serum-free suspension adapted 293T or 293EBNA cells. Transfections can be performed as 500 mL or 1 L cultures. The following reagents and materials are available from Gibco BRL (now Invitrogen, Carlsbad, Calif.). Catalog numbers are listed in parentheses: serum-free DMEM (21068-028); DMEM/F12 (3:1) (21068/11765); 1× Insulin-Transferrin-Selenium Supplement (51500-056); 1× Pen Strep Glut (10378-016); 2 mM 1-Glutamine (25030-081); 20 mM HEPES (15630-080); 0.01% Pluronic F68 (24040-032). Briefly, the cell inoculum (5.0-$10.0\times10^5$ cells/mL×culture volume) is centrifuged at 2,500 RPM for 10 minutes at 4° C. to remove the conditioned medium.

The cells are resuspended in serum-free DMEM and centrifuged again at 2,500 RPM for 10 minutes at 4° C. After aspirating the wash solution, the cells are resuspended in growth medium [DMEM/F12 (3:1)+1× Insulin-Transferrin-Selenium Supplement+1× Pen Strep Glut+2 mM L-Glutamine+20 mM HEPES+0.01% Pluronic F68] in a 1 L or 3 L spinner flask culture. The spinner flask culture is maintained on magnetic stir plate at 125 RPM which is placed in a humidified incubator maintained at 37° C. and 5% $CO_2$. The mammalian expression plasmid DNA (e.g. pcDNA3.1, pCEP4, Invitrogen Life Technologies, Carlsbad, Calif.), containing the complete coding region (and stop codon) of sclerostin with a Kozak consensus sequence (e.g., CCACC) directly 5' of the start site ATG, is complexed to the transfection reagent in a 50 mL conical tube.

The DNA-transfection reagent complex can be prepared in 5-10% of the final culture volume in serum-free DMEM or OPTI-MEM. The transfection reagents that can be used for this purpose include X-tremeGene RO-1539 (Roche Applied Science, Indianapolis, Ind.), FuGene6 (Roche Applied Science, Indianapolis, Ind.), Lipofectamine 2000 (Invitrogen, Carlsbad, Calif.) and 293fectin (Invitrogen, Carlsbad, Calif.). 1-5 μg plasmid DNA/mL culture is first added to serum-free DMEM, followed by 1-5 μl transfection reagent/mL culture. The complexes can be incubated at room temperature for approximately 10-30 minutes and then added to the cells in the spinner flask. The transfection/expression can be performed for 4-7 days, after which the conditioned medium (CM) is harvested by centrifugation at 4,000 RPM for 60 minutes at 4° C.

Example 2

Purification of Recombinant Sclerostin

Recombinant sclerostin was purified from mammalian host cells as follows. All purification processes were carried out at room temperature. One purification scheme was used to purify various species of sclerostin, including murine and human sclerostin. The purification scheme used affinity chromatography followed by cation exchange chromatography.

Heparin Chromatography

The mammalian host cell conditioned medium (CM) was centrifuged in a Beckman J6-M1 centrifuge at 4000 rpm for 1 hour at 4° C. to remove cell debris. The CM supernatant was then filtered through a sterile 0.2 μm filter. (At this point the sterile filtered CM may be optionally stored frozen until purification.) If the CM was frozen, it was thawed at the following temperatures, or combination thereof: 4° C., room temperature or warm water. Following thawing the CM was filtered through a sterile 0.2 μm filter and optionally concentrated by tangential flow ultrafiltration (TFF) using a 10 kD molecular weight cut-off membrane. The CM concentrate was filtered through a sterile 0.2 μm filter and then loaded onto a Heparin High Performance (Heparin HP) column (GE Healthcare, formerly Amersham Biosciences) equilibrated in PBS. Alternatively, the filtered CM supernatant may be loaded directly onto the Heparin HP column equilibrated in PBS.

After loading, the Heparin HP column was washed with PBS until the absorbance at 280 nm of the flow-through returned to baseline (i.e., absorbance measured before loading CM supernatant). The sclerostin was then eluted from the column using a linear gradient from 150 mM to 2M sodium chloride in PBS. The absorbance at 280 nm of the eluate was monitored and fractions containing protein were collected. The fractions were then assayed by Coomassie-stained SDS-PAGE to identify fractions containing a polypeptide that migrates at the size of glycosylated sclerostin. The appropriate fractions from the column were combined to make the Heparin HP pool.

Cation Exchange Chromatography

The sclerostin eluted from the Heparin HP column was further purified by cation exchange chromatography using SP High Performance (SPHP) chromatography media (GE Healthcare, formerly Amersham Biosciences). The Heparin HP pool was buffer exchanged into PBS by dialysis using 10,000 MWCO membranes (Pierce Slide-A-Lyzer). The dialyzed Heparin HP pool was then loaded onto an SPHP column equilibrated in PBS. After loading, the column was washed with PBS until the absorbance at 280 nm of the flow-through returned to baseline. The sclerostin was then eluted from the SPHP column using a linear gradient from 150 mM to 1 M sodium chloride in PBS. The absorbance at 280 nm of the eluate was monitored and the eluted sclerostin was collected in fractions. The fractions were then assayed by Coomassie-stained SDS-PAGE to identify fractions containing a polypeptide that migrates at the size of glycosylated sclerostin. The appropriate fractions from the column were combined to make the SPHP pool.

Formulation

Following purification, the SPHP pool was formulated in PBS by dialysis using 10,000 MWCO membranes (Pierce Slide-A-Lyzer). If concentration of sclerostin was necessary, a centrifugal device (Amicon Centricon or Centriprep) with a 10,000 MWCO membrane was used. Following formulation the sclerostin was filtered through a sterile 0.2 μm filter and stored at 4° C. or frozen.

Example 3

Peptide Binding ELISA

A series of overlapping peptides (each peptide being approximately 20-25 amino acids long) were synthesized based on the known amino acid sequence of rat sclerostin (SEQ ID NO:98). The peptides were designed such that they all contained a reduced cysteine residue; an additional cysteine was included at the C-terminus of each peptide which did not already contain one in its sequence. This enabled the peptides to be bound to the assay plates by covalent coupling, using commercially available sulfhydryl binding plates (Costar), at a concentration of 1 μg/ml, in phosphate buffered saline (PBS: pH 6.5) containing 1 mM EDTA. Following incubation for 1 hour at room temperature, the plates were washed three times with PBS containing 0.5% Tween 20. The plates were blocked by incubation with a PBS solution containing 0.5% fish skin gelatin (Sigma) for 30 minutes at room temperature and then washed three times in PBS containing 0.5% Tween 20.

Antibodies to be tested were diluted to 1 μg/ml in PBS containing 0.5% fish skin gelatin and incubated with the peptide-coated plates for 1 hour at room temperature. Excess antibody was removed by three washes with PBS, 0.5% Tween 20. The plates were then incubated with an appropriate secondary antibody conjugated to horseradish peroxidase (diluted appropriately in PBS containing 0.5% Tween 20) and capable of binding to the antibody of interest. The plates were then washed three times: once with PBS containing 0.5% Tween 20, and twice with PBS. Finally the plates were incubated with a horseradish peroxidase chromogenic substrate (TMB-Stable Stop, RDI) for 5 minutes at room temperature, the color development was stopped with acid, and the plates' optical density measured at 450 nm.

Materials

Costar's Sulfhydryl Binding Plates (VWR #29442-278)

Coating Buffer: 1×PBS PH 6.5+1 mM EDTA

Blocking Buffer: 1×PBS+0.5% Fish Skin Gelatin (PBS from CS; FSG from Sigma# G 7765)

Wash Buffer: 1×PBS+0.5% Tween 20

Rat Sclerostin peptides

Antibody Samples: Transient Ab, Purified recombinant Ab, rabbit Serum, etc.

Appropriate secondary Ab: Goat-anti-Rabbit/Mouse-HRP (Jackson Immuno Research, 115-036-072)

TMB-Stable Stop (RDI# RDI-TMBSX-1L)

0.5M HCl

Methods were as follows:

1. Coat plates with 100 μl/well of rat sclerostin peptide diluted in 1×PBS PH 6.5+1 mM EDTA at 1 μg/ml. Incubate plates 1 hour at room temperature. (Plates should be used within 30 minutes of opening).
2. Wash plates 3× with wash buffer.
3. Block plates with 200 ul/well blocking buffer. Incubate plates 30 minutes at room temp.
4. Repeat washing as described in (2).
5. Incubate plates with 50 ul/well of samples diluted in blocking buffer—Serum titers starting at 1:100; Transient Recombinant Ab use neat; Purified recombinant Ab use at 1 μg/ml (all samples run in duplicates). Incubate plates 1 h at room temp.
6. Wash plates as described in (2).
7. Incubate plates with 50 μl/well of appropriate Secondary Antibody (HRP labeled) diluted 1:1600 in Blocking Buffer. Incubate plates 1 hour at room temperature.
8. Wash plates 1× wash buffer, 2×PBS
9. Incubate plates with 50 μl/well of TMB, 5 minutes at room temp.
10. Stop reaction with 50 μl/well 0.5M HCl.
11. Read plates at 450 nm wavelength.

The following peptides sequences were screened as described above:

```
                                    (SEQ ID NO: 82)
QGWQAFKNDATEIIPGLREYPEPP

                                    (SEQ ID NO: 83)
TEIIPGLREYPEPPQELENN

                                    (SEQ ID NO: 84)
PEPPQELENNQTMNRAENGG

                                    (SEQ ID NO: 85)
ENGGRPPHHPYDTKDVSEYS

                                    (SEQ ID NO: 86)
CRELHYTRFVTDGP

                                    (SEQ ID NO: 87)
CRELHYTRFVTDGPSRSAKPVTELV

                                    (SEQ ID NO: 88)
CRSAKPVTELVSSGQSGPRARLL

                                    (SEQ ID NO: 89)
CGPARLLPNAIGRVKWWRPNGPDFR

                                    (SEQ ID NO: 90)
RAQRVQLLCPGGAAPRSRKV

                                    (SEQ ID NO: 91)
PGGAAPRSRKVRLVAS

                                    (SEQ ID NO: 92)
KRLTRFHNQSELKDFGPETARPQ

                                    (SEQ ID NO: 93)
IPDRYAQRVQLLSPGG

                                    (SEQ ID NO: 94)
SELKDFGPETARPQKGRKPRPRAR

                                    (SEQ ID NO: 95)
KGRKPRPRARGAKANQAELENAY
```

-continued

PNAIGRVKWWRPNGPDFR (SEQ ID NO: 96)

KWWRPNGPDFRCIPDRYRAQRV. (SEQ ID NO: 97)

A high-affinity neutralizing antibody (Ab-19) bound to two overlapping peptide sequences: PNAIGRVKWWRPNGPDFR (SEQ ID NO:96) and KWWRPNGPDFRCIPDRYRAQRV (SEQ ID NO:97).

This procedure allows the recognition of epitopes for antibodies that react with apparent linear epitopes. Peptides that contain all or part of the antibody binding site will bind antibody and thus be detected.

Example 4

Identification of Human Sclerostin Epitopes

Sclerostin Structure

Mature form (signal peptide removed) human sclerostin is a 190 amino acid protein (FIG. 8). FIG. 9 shows a schematic of the general structure of sclerostin with an N-terminal arm (from the N-terminal Q to Cysteine1) and a C-terminal arm (from Cysteine8 to the terminal Y). Sandwiched in between these two arms there is the cystine-knot structure and three loops which are designated Loop1, Loop2 and Loop 3. The four disulfide bonds in sclerostin are Cys1 at sequence position 57 linked to Cys5 at sequence position 111 (referred to as C1-05), Cyst at sequence position 71 linked to Cys6 at sequence position 125 (referred to as C2-C6), Cys3 at sequence position 82 linked to Cys7 at sequence position 142 (referred to as C3-C7), Cys4 at sequence position 86 linked to Cys8 at sequence position 144 (referred to as C4-C8). The eight-membered ring structure is formed via C3-C7 and C4-C8 disulfide bonding. This ring structure, together with the C1-05 disulfide bond penetrating through the ring, forms a typical cystine-knot. C2-C6, which is not part of the cystine-knot, brings two large loop structures, loop 1 (residues 57 to 82) and loop 3 (residues 111 to 142) close together. Loop 2 goes from C4 (residue 86) to C5 (residue 111).

Experimental

The general approach for characterizing the epitopes bound by anti-sclerostin monoclonal antibodies involved fragmenting human Sclerostin into peptides with different proteases, determining the sequence of the various human sclerostin peptides, isolating these peptides and testing each of them for their ability to bind to a particular monoclonal antibody using a Biacore-based "human sclerostin peptide epitope competition binding assay.". The resulting data permitted the location of the binding epitope to be determined.

The peptide digests were subjected to HPLC peptide mapping; the individual peaks were collected, and the peptides identified and mapped by matrix assisted laser desorption mass spectrometry (MALDI-MS) and electrospray ionization LC-MS (ESI-LC-MS) analyses and/or by N-terminal sequencing. All HPLC analyses for these studies were performed using a reverse-phase C8 column (2.1 mm i.d.×15 cm length). HPLC peptide mapping was performed with a linear gradient from 0.05% trifloroacetic acid (mobile phase A) to 90% acetonitrile in 0.05% trifluoroacetic acid. Columns were developed over 50 minutes at a flow rate of 0.2 ml/min.

Trypsin and AspN Endoproteinase Digestions

Mature form human sclerostin was digested with trypsin, which cleaves after arginine and lysine, or with AspN. About 200 µg of sclerostin at 0.5-1.0 mg/ml was incubated in PBS (pH 7.2) for 20 hrs at 37° C. with 8 µg of either trypsin or AspN.

Trypsin Digestion

Figure 10:
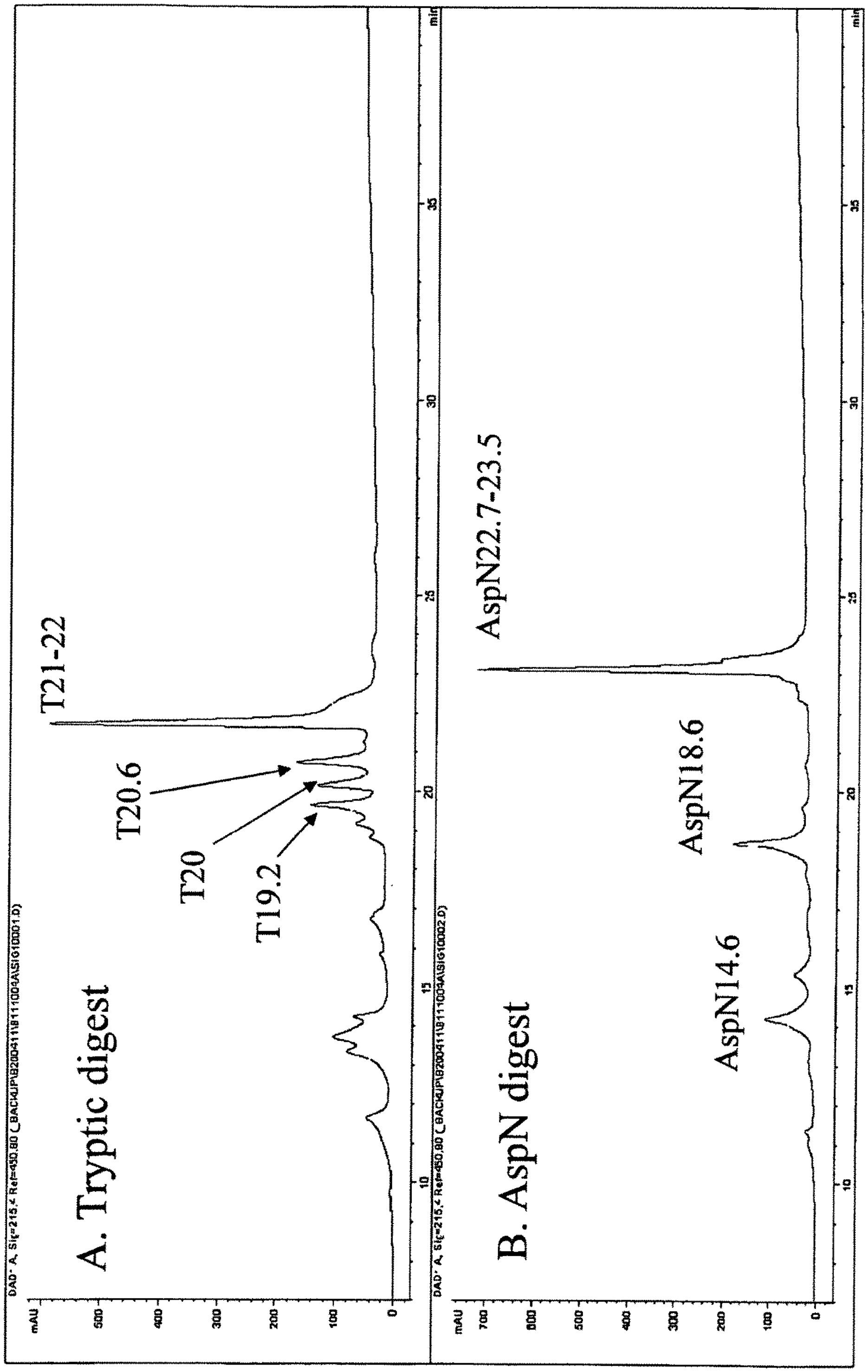
FIG. 10 depicts the HPLC peptide maps of human sclerostin after digestion with either trypsin or AspN. The human sclerostin peptides generated by trypsin digestion are indicated (T19.2, T20, T20.6 and T21-22) as are the human sclerostin peptides generated by AspN digestion (AspN14.6, AspN18.6 and AspN22.7-23.5).

HPLC chromatography of the trypsin digests yielded several major peaks (FIG. 10A). Sequence analysis was conducted on the peptide peaks recovered from HPLC after trypsin digestion. On-line ESI LC-MS analysis of the peptide digest was also performed to determine the precise mass of the peptides that were separated by HPLC. The identity of the peptides present in the peptide peaks was thus determined (FIG. 11). FIG. 13 shows the alignment of various peptide sequences (T19.2, T20, T20.6, T21-22) along the sclerostin sequence. The number following each T (e.g., T19.2) reflects the retention time. T19.2 contains two peptides (one from loop 1 and one from loop 3) linked by the C2-C6 disulfide bond. T20 contains two peptides held together by the cystine-knot structure, with intact loops 1 and 3 held together by the C2-C6 disulfide and with most of loop 2 absent. T20.6 contains four sequences held together by the cystine-knot structure, but is missing part of loop 1 and 3 (the T19.2 part) and is missing most of loop 2. T21-22 is almost identical to T20 but has 3 additional amino acids in the loop 2 region.

AspN Digestion

Figure 14:
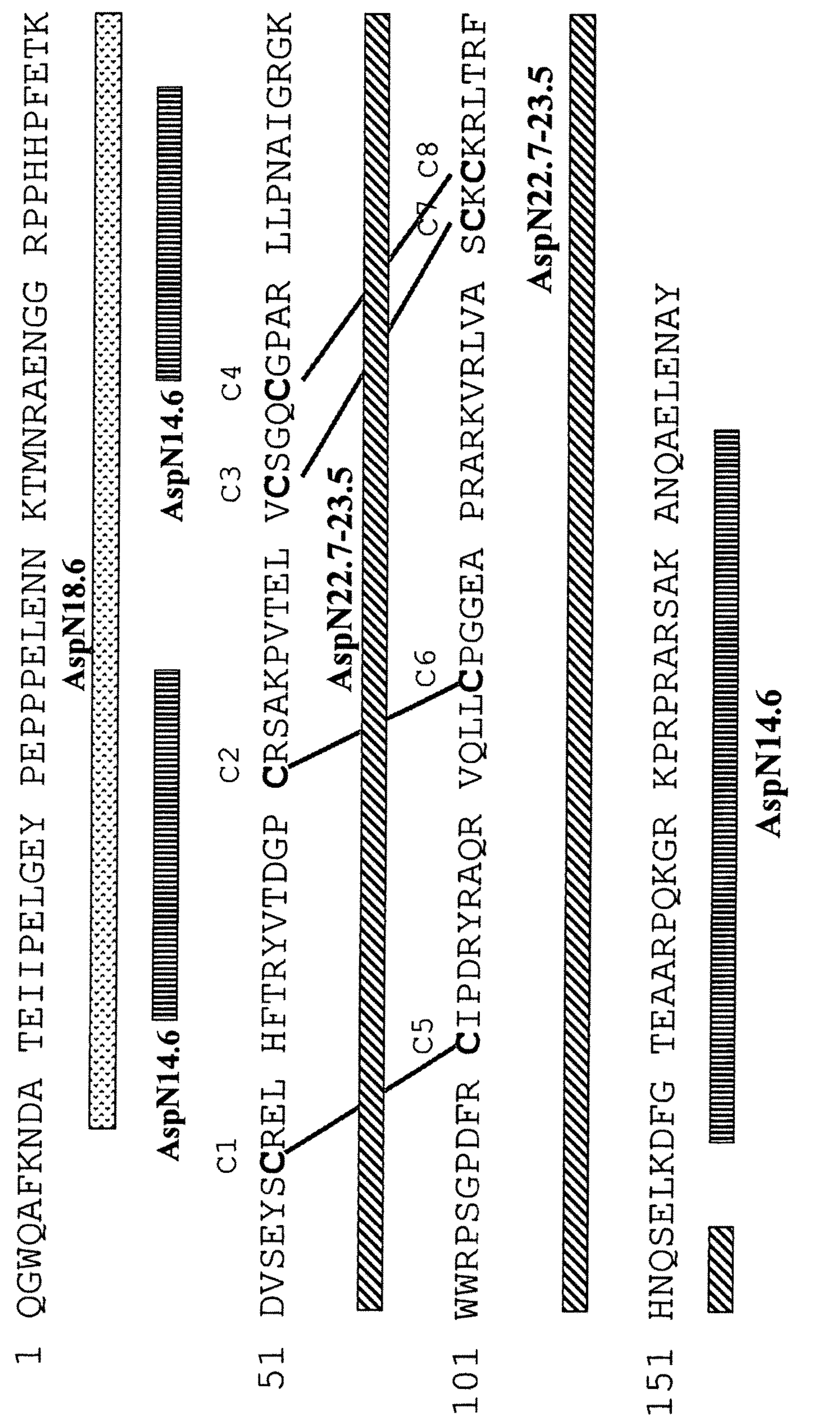
FIG. 14 shows a linear schematic of five human sclerostin peptides (AspN14.6, AspN18.6 and AspN22.7-23.5) generated by AspN digestion. The AspN14.6 HPLC peak is composed of three peptides not linked by any disulfide bonds.

HPLC chromatography of the AspN digests yielded several major peaks (FIG. 10B). Sequence analysis was conducted on the peptide peaks recovered from HPLC. On-line ESI LC-MS analysis of the peptide digest was also performed to determine the precise mass of the peptides that were separated by HPLC. The identity of the peptides present in the peptide peaks from the AspN digestion was thus determined (FIG. 12). FIG. 14 shows the alignment of various peptide sequences (AspN14.6, AspN18.6, AspN22.7-23.5) along the sclerostin sequence. The number following each AspN (e.g. AspN18.6) reflects the retention time. AspN14.6 contains three short peptides from both the N- and C-terminal arms of sclerostin, while AspN18.6 is a larger peptide from the N-terminal arm of sclerostin. AspN22.7-23.5 contains a single peptide fragment of 104 amino acids the encompasses all eight cysteines (the four disulfide bonds), the cystine-knot and all of loops 1, 2 and 3.

The strategy for characterizing the epitopes was to use these various trypsin and AspN generated human sclerostin peptides and determine which peptides could still be bound by the various Antibodies (Ab-A, Ab-B, Ab-C and Ab-D). Specifically this was tested in a Biacore-based "human sclerostin peptide epitope competition binding assay" where the binding of a particular monoclonal antibody to human sclerostin immobilized on the Biacore chip was determine in the presence or absence of each of the various isolated trypsin and AspN HPLC peptide fractions. In the absence of any competing peptides, the particular monoclonal antibody was able to bind the human sclerostin on the chip and produce a resonance unit, RU, response. Preincubation of the particular monoclonal antibody with intact human sclerostin in solution, followed by testing of binding to the chip, demonstrated that the binding of the Mab to human sclerostin in solution prevented the binding of the Mab to the human sclerostin on the chip, thus validating the general principal of this competition assay.

This general procedure was repeated individually for each peptide. A robust RU response was taken to indicate that the particular peptide being tested could not bind the Mab in solution (hence the Mab was free to bind the human sclerostin that had been immobilized on the chip). Conversely, the absence of a robust RU response indicated that the Mab was able to bind the sclerostin peptide in solution. These binding patterns, couple with the known identity of the various sclerostin peptides, were used to determine the epitopes of sclerostin that were bound by anti-sclerostin antibodies Ab-A, Ab-B, Ab-C and Ab-D.

Biacore-Based Human Sclerostin Peptide Epitope Competition Binding Assay

Preparation of Human Sclerostin Surface:

Immobilization of mature form human sclerostin to a BIAcore sensor chip (CM5) surface was performed according to manufacturer's instructions. Briefly, carboxyl groups on the sensor chip surfaces were activated by injecting 60 μL of a mixture containing 0.2 M N-ethyl-N'-(dimethylaminopropyl) carbodiimide (EDC) and 0.05 M N-hydroxysuccinimide (NHS). Human sclerostin was diluted in 10 mM sodium acetate, pH 4.0 at a concentration of 20 μg/mL followed by injecting over the activated CM5 surface. Excess reactive groups on the surfaces were deactivated by injecting 60 μL of 1 M ethanolamine. Final immobilized levels were ~5000 resonance units (RU) for the human sclerostin surface. A blank, mock-coupled reference surface was also prepared on the sensor chips.

Binding Specificity Analysis:

1× Phosphate-buffered saline without calcium chloride or magnesium chloride was from Gibco/Invitrogen, Carlsbad, Calif. Bovine serum albumin, fraction V, IgG-free was from Sigma-Aldrich, St. Louis, Mo. Each Mab (2 nM) was separately incubated with 20 nM human sclerostin or a particular human sclerostin peptide (note: there are 3 unlinked peptides in AspN14.6) in sample buffer (1×PBS+0.005% P-20+0.1 mg/mL BSA) before injection over the immobilized human sclerostin surface. The flow rate for sample injection was 5 μL/min followed by surface regeneration using 1 M NaCl in 8 mM Glycine, pH 2.0 at 30 μL/min for 30 seconds. The data was analyzed using BIAevaluation 3.2, and is presented in FIG. 15 (Ab-A), FIG. 16 (Ab-B), FIG. 17 (Ab-C) and FIG. 18 (Ab-D).

Loop 2 and T20.6 Epitopes:

The sclerostin peptide binding pattern for two representative antibodies (Ab-A and Ab-B) were virtually identical (FIG. 15 and FIG. 16) and showed that both of these Antibodies could only bind the AspN22.7-23.5 peptide. The unique difference between AspN22.7-23.5 and all the other sclerostin peptides is that AspN22.7-23.5 contains an intact loop 2. This shows that Ab-A and Ab-B bind the loop 2 region of sclerostin thus defining the loop 2 epitope (FIG. 19A). The sclerostin peptide binding pattern for Ab-C and Ab-D were virtually identical to each other (FIG. 17 and FIG. 18) but completely distinct from that found for Ab-A and Ab-B. Of the peptides tested in this Example, the most diminutive peptide that Ab-C and Ab-D could bind to was the T20.6 peptide. This result defines the T20.6 epitope (FIG. 19B).

Protease Protection Assay:

The general principle of this assay is that binding of a Mab to sclerostin can result in protection of certain specific protease cleavage sites and this information can be used to determine the region of sclerostin to where the Mab binds.

Figure 20:
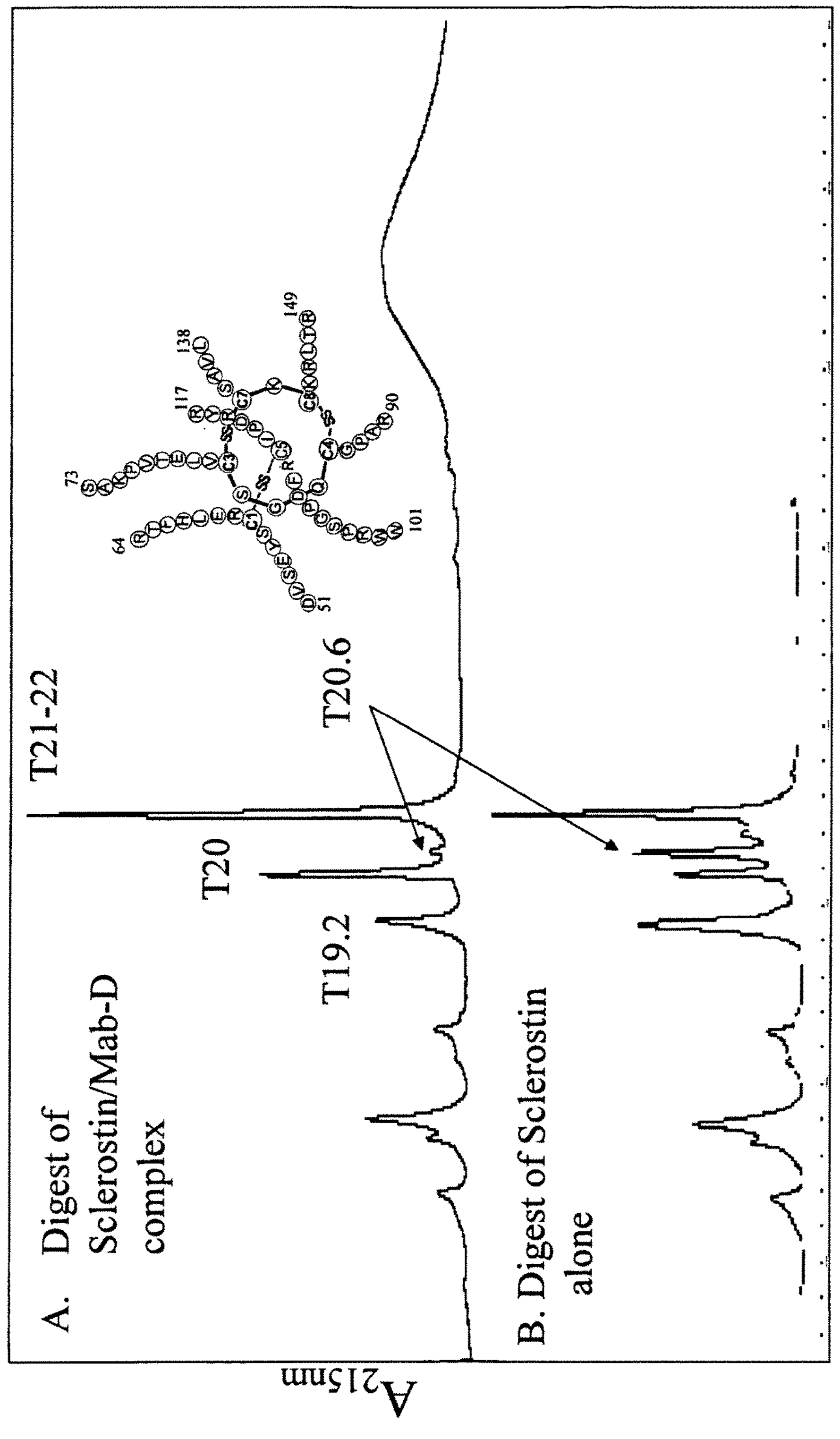
FIG. 20 depicts the HPLC peptide maps of human sclerostin after digestion with trypsin.

"T20.6 Derivative 1 (Cystine-Knot+4 Arms)" Epitope:

FIG. 20 shows the HPLC peptide maps for a human sclerostin Ab-D complex (FIG. 20A: human sclerostin was preincubated at a 1:1 molar ratio with Ab-D prior to digestion with trypsin as described above) and human sclerostin alone (FIG. 20B: human sclerostin was digested with trypsin as described above). The peptide peaks of T19.2 and T20.6 in FIG. 20A showed a clear reduction in their respective peak height, as compared to FIG. 20B. This reduction in peak heights was accompanied by an increase in peak height for peptides T20 and T21-22. These data indicate that basic amino acid residues in loop 1 and loop 3, which in the absence of Ab-D were cleaved by trypsin to generate peptides T19.2 and T20.6, were resistant to cleavage by trypsin when Ab-D was prebound to sclerostin. The presence of T20, T20.6 and T21-22 indicates that loop 2 was still cleaved efficiently when Ab-D was prebound to sclerostin. These data indicate that Ab-D bound on the loop 1 and loop 3 side of the T20.6 epitope thus defining the smaller "T20.6 derivative 1 (cystine-knot+4 arms)" epitope shown in FIG. 21.

Example 5

In Vivo Testing of Anti-Sclerostin Monoclonal Antibodies in Mice

Four week-old BDF1 male mice were obtained from Charles River Laboratories (Raleigh, N.C.) and housed in clean caging, five animals per cage. Room temperature was maintained between 68 and 72° F., and relative humidity was maintained between 34 and 73%. The laboratory housing the cages had a 12-hour light/dark cycle and met all AAALAC specifications. Clinical observations of all mice on study occurred once daily.

Figure 6:
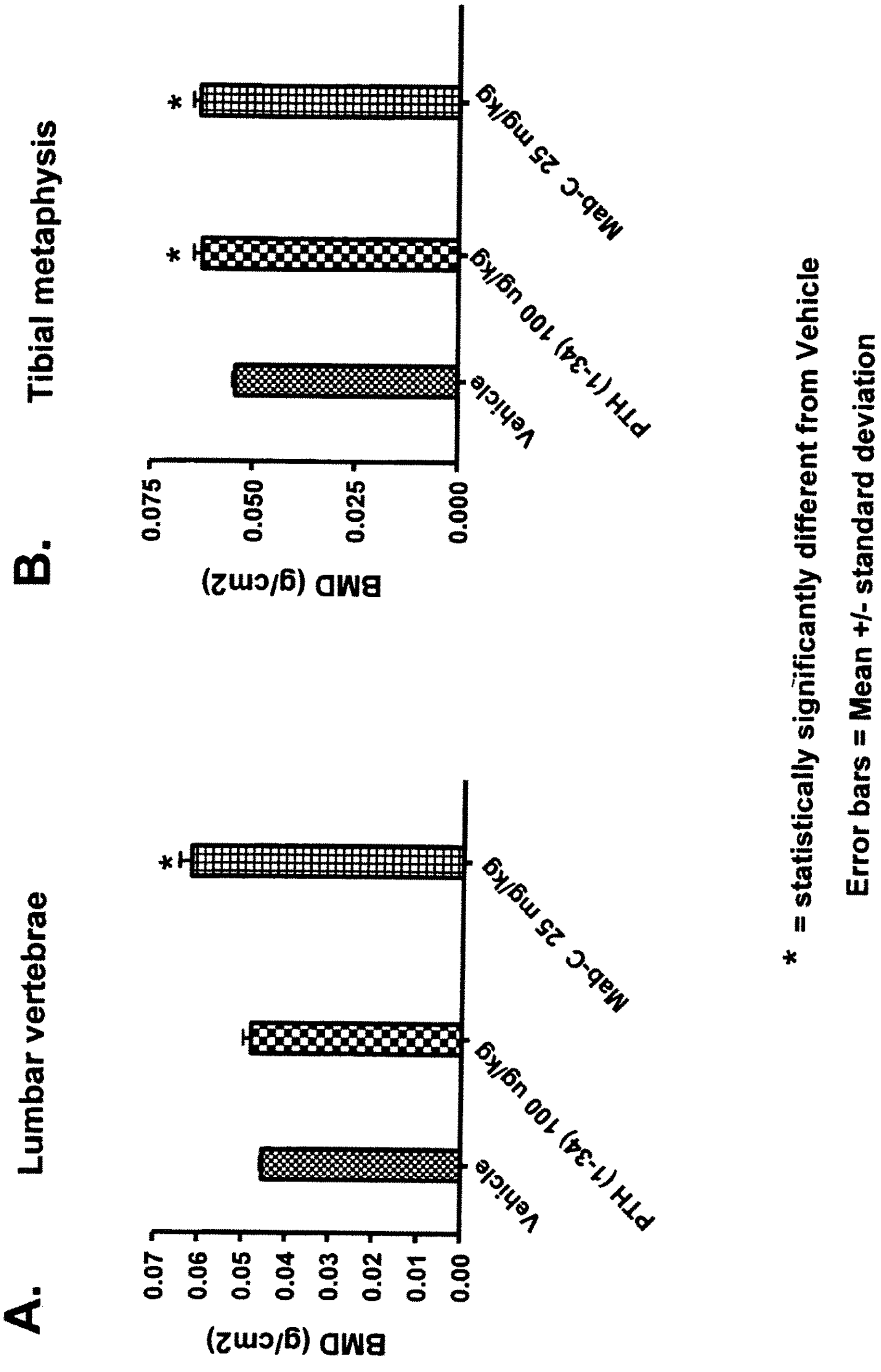
FIG. 6 shows bone mineral density in mice measured at two skeletal sites (lumbar vertebrae and tibial metaphysis) after 2 weeks of treatment with vehicle, PTH (1-34) or Ab-C.
Figure 7:
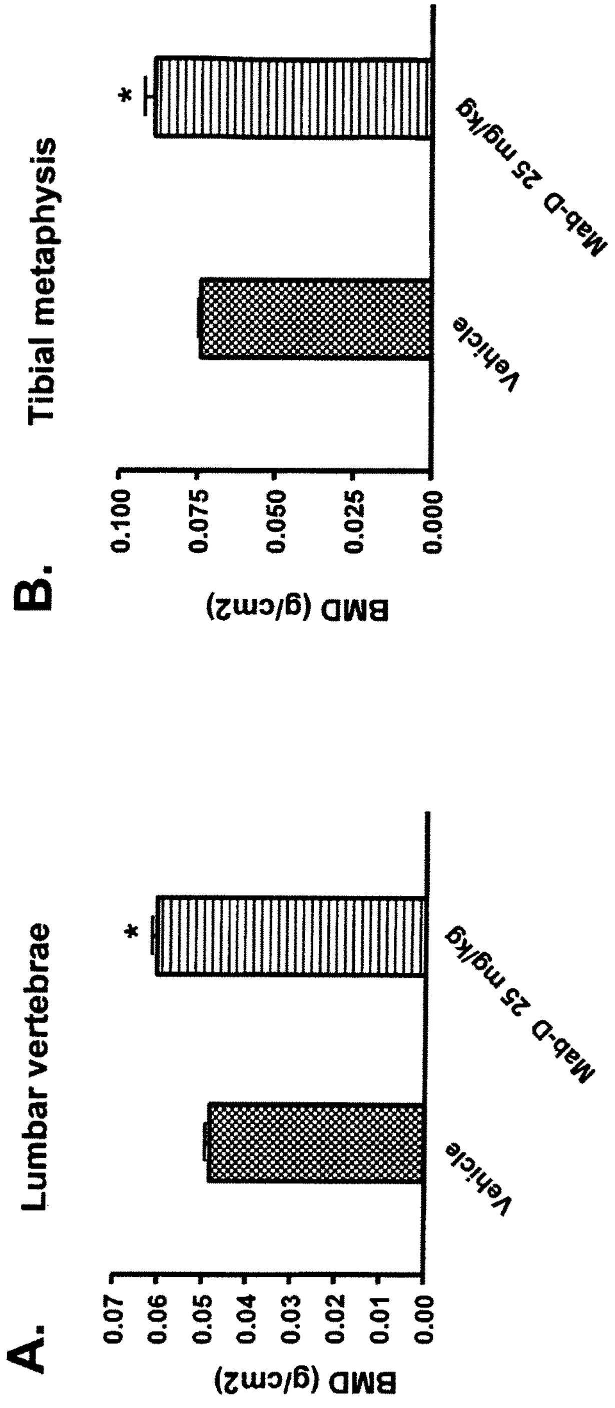
FIG. 7 depicts bone mineral density in mice measured at two skeletal sites (lumbar vertebrae and tibial metaphysis) after 3 weeks of treatment with vehicle or Ab-D.

Purified anti-sclerostin monoclonal antibodies (Ab-A FIG. 1; Ab-B FIG. 2; Ab-C FIG. 3; Ab-D FIG. 4) were diluted in sterile Dulbecco's phosphate buffered saline. Mice were injected with anti-sclerostin Antibodies or PBS vehicle subcutaneously at 21 μl per gram body weight, two times per week (Monday and Thursday) at 25 mg/kg. Human PTH (1-34) was diluted in PTH buffer (0.001 N HCl, 0.15 M NaCl, 2% BSA), and dosed subcutaneously at 21 μl per gram body weight five times per week (Monday, Tuesday, Wednesday, Thursday, Friday) at 100 μg/kg as a positive control (FIGS. 5 and 6). Number of mice per group was N=5 in FIGS. 5 and 6, and N=6 in FIG. 7.

PIXImus In Vivo Bone Densitometry

Bone mineral density (BMD) was determined weekly at the proximal tibial metaphysis and lumbar vertebrae by peripheral Dual Energy X-ray Absorptometry (pDEXA) with the PIXImus2 system from GE/Lunar Medical Systems, Madison, Wis. A 25 $mm^2$ region of interest (ROI) was placed to include the proximal articular surface, the epiphysis, and the proximal end on the metaphysis of the tibia. A region of interest (ROI) was placed to include the lumbar vertebrae (L1-L5). The proximal tibia and lumbar regions were analyzed to determine total bone mineral density. Group means were reported±Standard Deviation and compared to the vehicle treatment group for statistical analysis.

Statistical Analysis

Statistical analysis was performed with a Dunnett's and Tukey-Kramer (using MS Excel and JMP v. 5.0. for the BMD data). Group means for each data set were considered significantly different when the P value was less than 0.05 ($P<0.05$).

Sclerostin Neutralizing Activity of Antibodies

The statistically significant increases in BMD as compared to vehicle seen for each of Ab-A (FIG. 5), Ab-B (FIG. 5), Ab-C (FIG. 6) and Ab-D (FIG. 7) demonstrates that these four antibodies are sclerostin neutralizing antibodies. Furthermore this data shows that, for anti-sclerostin antibodies that bind mouse sclerostin, treatment and analysis of mice as described above can be used to identify sclerostin neutralizing antibodies.

Example 6

Screening Assay for Antibodies that Block Binding of an Antibody to Human Sclerostin Human sclerostin was coupled to a CM5 Biacore chip using standard amine coupling chemistry to generate a sclerostin coated surface. 300 resonance units of sclerostin were coupled to the surface.

The antibodies to be tested were diluted to a concentration of 200 ug/ml in HBS-EP buffer (being 10 mM HEPES pH 7.4, 150 mM NaCl, 3 mM EDTA, 0.005% (v/v) Surfactant P20) and then mixed in a one to one molar ratio (on a binding site basis) to generate the test mixture. This test mixture thus contained each antibody at a concentration of 100 ug/ml (1.3 um on a binding site basis). Separate solutions containing each of the antibodies in the test mix alone were also prepared. These solutions contained the individual antibodies in HBS-EP buffer at a concentration of 100 ug/ml (1.3 um on a binding site basis).

20 μL of the test mixture was passed over the sclerostin-coated chip at a flow rate of 10 μL/min and the amount of binding recorded. The chip was then treated with two 60 second pulses of 30 mM HCl to remove all of the bound antibody. A solution containing only one of the antibodies of the test mixture (at 1.3 μM in the same buffer as the test mixture on a binding site basis) was then passed over the chip in the same manner as the test mixture and the amount of binding recorded. The chip was again treated to remove all of the bound antibody and finally a solution containing the other antibody from the test mixture alone (at 1.3 μM in the same buffer as the test mixture on a binding site basis) was passed over the chip and the amount of binding recorded.

The table below show the results from cross-blocking assays on a range of different antibodies. The values in each square of the table represent the amount of binding (in RU) seen when the antibodies (at 1.3 μM on a binding site basis) or buffer indicated in the top row of the table were mixed with the antibodies (at 1.3 uM on a binding site basis) or buffer indicated in the first column of the table.

| | Buffer | Ab-4 | Ab-13 | Ab-A | Ab-3 | Ab-19 |
|---|---|---|---|---|---|---|
| Buffer | −0.5 | 693 | 428.5 | 707.3 | 316.1 | 649.9 |
| Ab-4 | 687.7 | 795.1 | 1018.2 | 860.5 | 869.3 | 822.5 |
| Ab-13 | 425.6 | 1011.3 | 442.7 | 1108.4 | 431.9 | 1042.4 |
| Ab-A | 692.4 | 833.1 | 1080.4 | 738.5 | 946.2 | 868.1 |
| Ab-3 | 305.5 | 845.1 | 428.2 | 952.2 | 344.4 | 895.7 |
| Ab-19 | 618.1 | 788.6 | 1022.5 | 863.3 | 891.5 | 658.7 |

Using the mean binding value (in RU) for each combination of antibodies in the above table (since each combination appears twice) it is possible to calculate the percentage of the theoretical binding shown by each combination of antibodies. The theoretical binding being calculated as the sum of the average values for the components of each test mixture when assayed alone (i.e., antibody and buffer).

| | Buffer | Ab-4 | Ab-13 | Ab-A | Ab-3 | Ab-19 |
|---|---|---|---|---|---|---|
| Buffer | | | | | | |
| Ab-4 | | | 90.75 | 60.45 | 85.4 | 60.75 |
| Ab-13 | | | | 96.9 | 58.0 | 97.0 |
| Ab-A | | | | | 93.5 | 65.0 |
| Ab-3 | | | | | | 94.4 |
| Ab-19 | | | | | | |

From the above data it is clear that Ab-4, Ab-A and Ab-19 cross-block each other. Similarly Ab-13 and Ab-3 cross block each other.

Example 7

ELISA-Based Cross-Blocking Assay

Liquid volumes used in this example would be those typically used in 96-well plate ELISAs (e.g. 50-200 μl/well). Ab-X and Ab-Y, in this example are assumed to have molecular weights of about 145 Kd and to have 2 sclerostin binding sites per antibody molecule. An anti-sclerostin antibody (Ab-X) is coated (e.g. 50μ of 1 μg/ml) onto a 96-well ELISA plate [e.g. Corning 96 Well EIA/RIA Flat Bottom Microplate (Product #3590), Corning Inc., Acton, Mass.] for at least one hour. After this coating step the antibody solution is removed, the plate is washed once or twice with wash solution (e.g., PBS and 0.05% Tween 20) and is then blocked using an appropriate blocking solution (e.g., PBS, 1% BSA, 1% goat serum and 0.5% Tween 20) and procedures known in the art. Blocking solution is then removed from the ELISA plate and a second anti-sclerostin antibody (Ab-Y), which is being tested for it's ability to cross-block the coated antibody, is added in excess (e.g. 50 μl of 10 μg/ml) in blocking solution to the appropriate wells of the ELISA plate. Following this, a limited amount (e.g. 50 μl of 10 ng/ml) of sclerostin in blocking solution is then added to the appropriate wells and the plate is incubated for at least one hour at room temperature while shaking. The plate is then washed 2-4 times with wash solution. An appropriate amount of a sclerostin detection reagent [e.g., biotinylated anti-sclerostin polyclonal antibody that has been pre-complexed with an appropriate amount of a streptavidin-horseradish peroxidase (HRP) conjugate] in blocking solution is added to the ELISA plate and incubated for at least one hour at room temperature. The plate is then washed at least 4 times with wash solution and is developed with an appropriate reagent [e.g. HRP substrates such as TMB (colorimetric) or various HRP luminescent substrates]. The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

In the event that a tagged version of sclerostin is used in the ELISA, such as a N-terminal His-tagged Sclerostin (R&D Systems, Minneapolis, Minn., USA; 2005 cat#1406-ST-025) then an appropriate type of sclerostin detection reagent would include an HRP labeled anti-His antibody. In addition to using N-terminal His-tagged Sclerostin, one could also use C-terminal His-tagged Sclerostin. Furthermore, various other tags and tag binding protein combinations that are known in the art could be used in this ELISA-based cross-blocking assay (e.g., HA tag with anti-HA antibodies; FLAG tag with anti-FLAG antibodies; biotin tag with streptavidin).

Example 8

Cell Based Mineralization Assay for Identifying Agents Able to Antagonize Sclerostin Activity Introduction Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

Deposition of mineral has a strong biophysical characteristic, in that once mineral "seeds" begin to form, the total amount of mineral that will be deposited in the entire culture can sometimes be deposited quite rapidly, such as within a few days thereafter. The timing and extent of mineral deposition in culture is influenced, in part, by the particular osteoblast-lineage cells/cell-line being used, the growth conditions, the choice of differentiation agents and the particular lot number of serum used in the cell culture media. For osteoblast-lineage cell/cell-line mineralization cultures, at least eight to fifteen serum lots from more than one supplier should be tested in order to identify a particular serum lot that allows for mineralization to take place.

MC3T3-E1 cells (Sudo H et al., *In vitro differentiation and calcification in a new clonal osteogenic cell line derived from newborn mouse calvaria*. J. Cell Biol. 96:191-198) and subclones of the original cell line can form mineral in culture upon growth in the presence of differentiating agents. Such subclones include MC3T3-E1-BF (Smith E, Redman R, Logg C, Coetzee G, Kasahara N, Frenkel B. 2000. *Glucocorticoids inhibit developmental stage-specific osteoblast cell cycle*. J Biol Chem 275:19992-20001).

Identification of Sclerostin Neutralizing Antibodies

MC3T3-E1-BF cells were used for the mineralization assay. Ascorbic acid and B-glycerophosphate were used to induce MC3T3-E1-BF cell differentiation leading to mineral deposition. The specific screening protocol, in 96-well format, involved plating cells on a Wednesday, followed by seven media changes (as described further below) over a 12-day period with most of the mineral deposition taking place in the final approximately eighteen hours (e.g. Sunday night through Monday). For any given treatment, 3 wells were used (N=3). The specific timing, and extent, of mineral deposition may vary depending, in part, on the particular serum lot number being used. Control experiments will allow such variables to be accounted for, as is well know in the art of cell culture experimentation generally.

Figure 22:
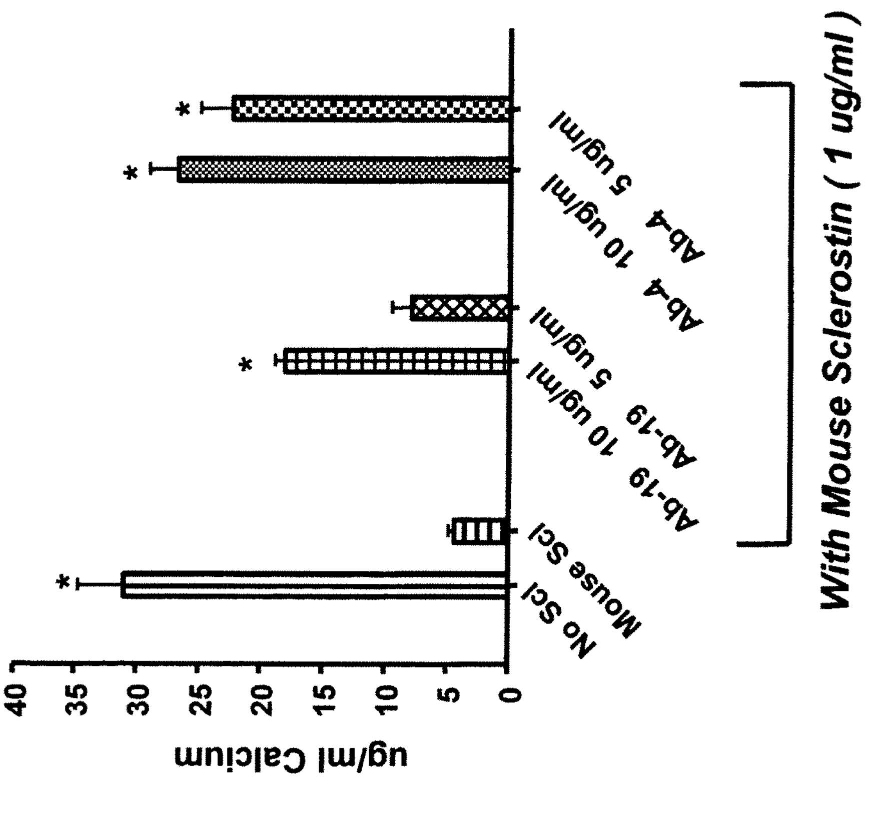
FIG. 22 shows results from the MC3T3-E1-BF osteoblast cell line mineralization assay used for identifying anti-sclerostin neutralizing Mabs. Mouse sclerostin (Scl) was used at 1 μg/ml. Monoclonal antibodies were used at 10 and 5 μg/ml. Extent of mineralization (various types of insoluble calcium phosphate) was quantitated by measuring calcium.

In this assay system sclerostin inhibited one or more of the sequence of events leading up to and including mineral deposition (i.e., sclerostin inhibited mineralization). Anti-sclerostin antibodies that were able to neutralize sclerostin's inhibitory activity allowed for mineralization of the culture in the presence of sclerostin such that there was a statistically significant increase in deposition of calcium phosphate (measured as calcium) as compared to the amount of calcium measured in the sclerostin-only (i.e., no antibody) treatment group. For statistical analysis (using MS Excel and JMP) a 1-way-ANOVA followed by Dunnett's comparison was used to determine differences between groups. Group means for each data set were considered significantly different when the P value was less than 0.05 ($P<0.05$). A representative result from running this assay is shown in FIG. 22. In the absence of recombinant mouse sclerostin, the sequence of events leading up to and including mineral deposition proceeded normally. Calcium levels in each treatment group are shown as means±Standard Error of the Mean (SEM). In this exemplary experiment calcium levels from the calcium assay were ~31 μg/ml. However, addition of recombinant mouse sclerostin caused inhibition of mineralization, and calcium was reduced by ~85%. Addition of anti-sclerostin monoclonal antibody Ab-19 or Ab-4 along with the recombinant sclerostin resulted in a statistically significant increase in mineral deposition, as compared to the sclerostin-only group, because the inhibitory activity of sclerostin was neutralized by either antibody. The results from this experiment indicate that Ab-19 and Ab-4 are sclerostin neutralizing monoclonal antibodies (Mabs).

Figure 23:
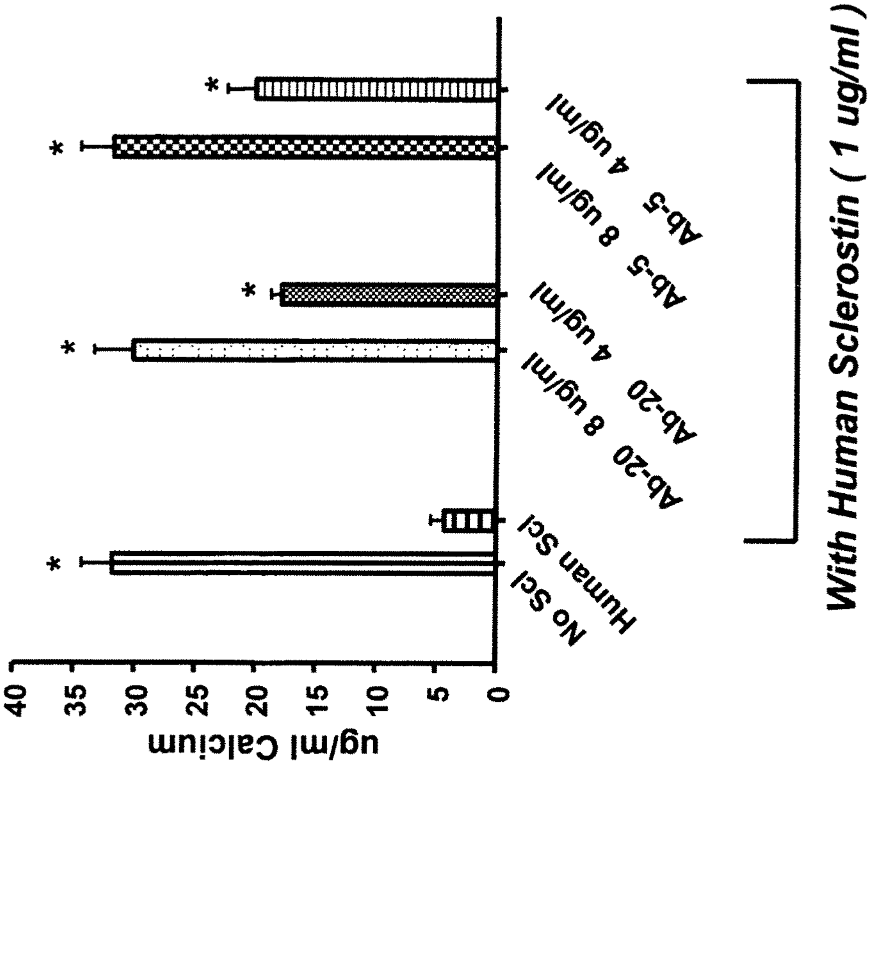
FIG. 23 depicts results from the MC3T3-E1-BF osteoblast cell line mineralization assay used for identifying anti-sclerostin neutralizing Mabs. Human sclerostin (Scl) was used at 1 μg/ml. Monoclonal antibodies were used at 8 and 4 μg/ml. Extent of mineralization (various types of insoluble calcium phosphate) was quantitated by measuring calcium.
Figure 24:
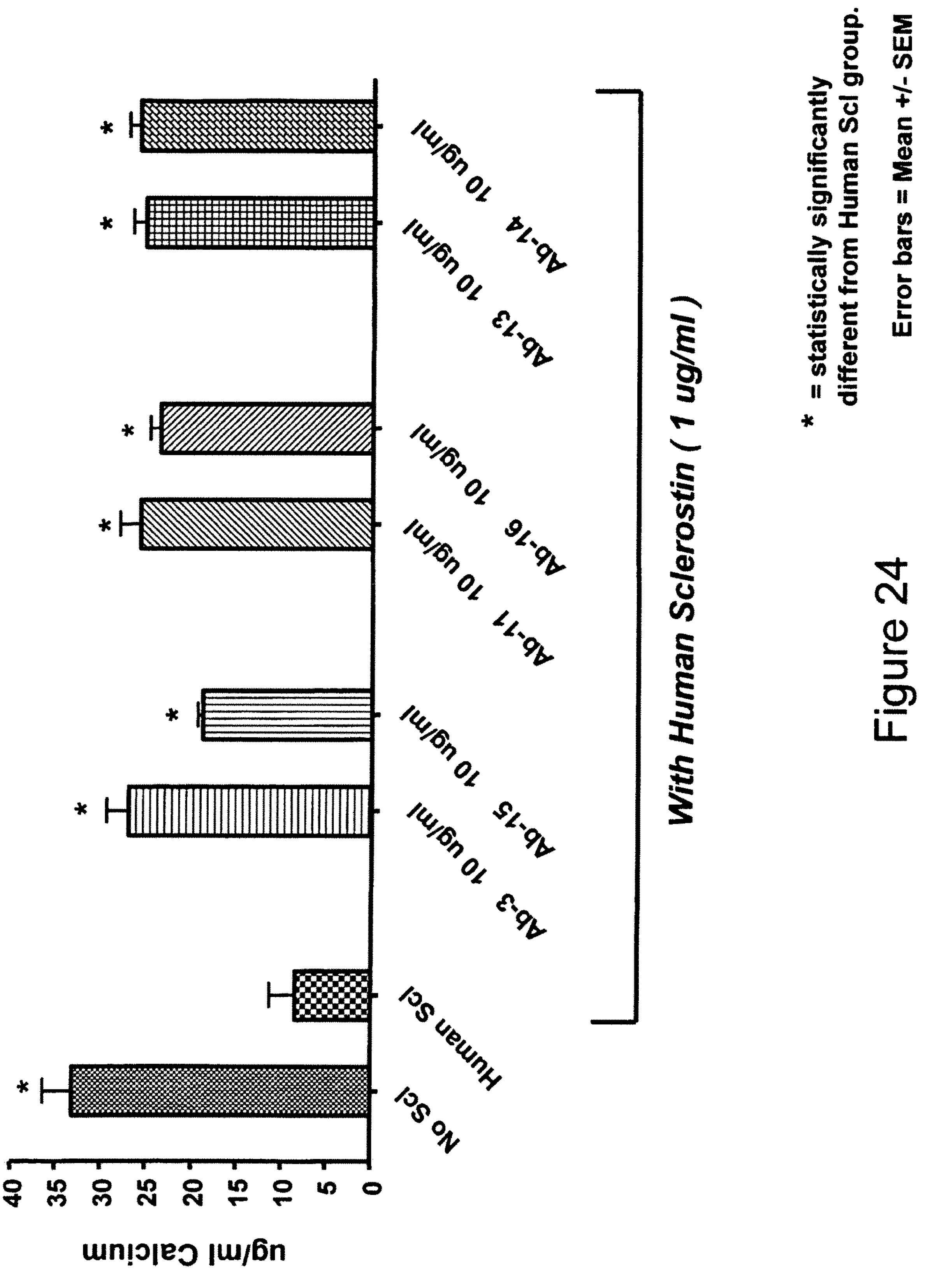
FIG. 24 shows results from the MC3T3-E1-BF osteoblast cell line mineralization assay used for identifying anti-sclerostin neutralizing Mabs. Human sclerostin (Scl) was used at 1 μg/ml. Monoclonal antibodies were used at 10 μg/ml. Extent of mineralization (various types of insoluble calcium phosphate) was quantitated by measuring calcium.

FIG. 23 shows a very similar result using recombinant human sclerostin and two humanized anti-sclerostin Mabs. FIG. 24 also shows a very similar result using recombinant human sclerostin and mouse and humanized anti-sclerostin Mabs as indicated.

The antibodies used for the experiments shown in FIGS. 22, 23 and 24 have molecular weights of about 145 Kd and have 2 sclerostin binding sites per antibody molecule.

A detailed MC3T3-E1-BF cell culture protocol is described below.

Reagents and Medias

| Reagents | Company | Catalog # |
|---|---|---|
| Alpha-MEM | Gibco-Invitrogen | 12571-048 |
| Ascorbic acid | Sigma | A4544 |
| Beta-glycerophosphate | Sigma | G6376 |
| 100X PenStrepGlutamine | Gibco-Invitrogen | 10378-016 |
| Dimethylsulphoxide (DMSO) | Sigma | D5879 or D2650 |
| Fetal bovine serum (FBS) | Cansera | CS-C08-500 (lot # SF50310) |
| or Fetal bovine serum (FBS) | TerraCell Int. | CS-C08-1000A (lot # SF-20308) |

Alpha-MEM is usually manufactured with a 1 year expiration date. Alpha-MEM that was not older than 6-months post-manufacture date was used for the cell culture.

Expansion Medium (Alpha-MEM/10% FBS/PenStrepGlu) was prepared as follows:

A 500 ml bottle of FBS was thawed and filter sterilized through a 0.22 micron filter. 100 mls of this FBS was added to 1 liter of Alpha-MEM followed by the addition of 10 mls of 100× PenStrepGlutamine. Unused FBS was aliquoted and refrozen for later use.

Differentiation Medium (Alpha-MEM/10% FBS/PenStrepGlu, +50 μg/ml ascorbic acid, +10 mM beta-glycerophosphate) was prepared as follows:

100 mls of Differentiation Medium was prepared by supplementing 100 mls of Expansion Medium with ascorbic acid and beta-glycerophosphate as follows:

| | Stock conc (see below) | Volume | Final Conc. |
|---|---|---|---|
| Ascorbic acid | 10 mg/ml | 0.5 mls | 100 μg/ml (50 ug/ml + 50 μg/ml) |
| β-glycerophosphate | 1M | 1.0 mls | 10 mM |

Differentiation Medium was made by supplementing Expansion Medium only on the day that the Differentiation media was going to be used for cell culture. The final concentration of ascorbic acid in Differentiation medium is 100 μg/ml because Alpha-MEM already contains 50 μg/ml ascorbic acid. Ascorbic acid stock solution (10 mg/ml) was made and aliquoted for freezing at −80° C. Each aliquot was only used once (i.e. not refrozen). Beta-glycerophosphate stock solution (1 M) was made and aliquoted for freezing at −20° C. Each aliquot was frozen and thawed a maximum of 5 times before being discarded.

Cell Culture for expansion of MC3T3-E1-BF cells.

Cell culture was performed at 37° C. and 5% $CO_2$. A cell bank was generated for the purposes of screening for sclerostin neutralizing antibodies. The cell bank was created as follows:

One vial of frozen MC3T3-E1-BF cells was thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrepGlu. After determining the number of cells using trypan blue and hemacytometer, $1\times10^6$ cells were plated in 50 mis Alpha-MEM/10% FBS/PenStrepGlu media in one T175 flask.

When this passage was confluent (at approximately 7 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mis Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at 1-$2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at 1-$2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1\times10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at 1-$2\times10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, the cells were frozen down at 1-$2\times10^6$ live cells/ml in 90% FBS/10% DMSO. This “final passage” of frozen cells was the passage that was used for the screening assay.

Cell Culture for Mineralizing MC3T3-E1-BF Cells.

Cell culture was performed at 37° C. and 5% $CO_2$. It is desirable to minimize temperature and % $CO_2$ fluctuations during the mineralization cell culture procedure. This can be achieved by minimizing the time that plates spend out of the incubator during feeding and also by minimizing the number of times the incubator door is opened and closed during the mineralization cell culture procedure. In this regard having a tissue culture incubator that is dedicated exclusively for the mineralization cell culture (and thus not opened and closed more than is necessary) can be helpful.

An appropriate number of “final passage” vials prepared as described above were thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrepGlu. After determining the number of cells by trypan blue and hemacytometer, 2500 cells were plated in 200 microliters of Expansion media per well on collagen I coated 96-well plates (Becton Dickinson Labware, cat #354407).

To avoid a mineralization plate-edge effect, cells were not plated in the outermost row/column all the way around the plate. Instead 200 microliters of PBS was added to these wells.

Exemplary Cell Culture Procedure

In the following procedure, the starting day for plating the cells is indicated to be a Wednesday. If a different day of the week is used as the starting day for plating the cells, that day will trigger the daily schedule for removing and adding media during the entire process as indicated below. For example, if the cells are plated on a Tuesday, media should not be removed and added on the first Friday and Saturday, nor on the second Friday and Saturday. With a Tuesday start, the plates would be prepared for the calcium assay on the final Sunday.

Cells were plated on a Wednesday at 2500 cells in 200 μl of Expansion media.

On Thursday all of the Expansion media was removed and 200 μl of Differentiation Media was added.

On Friday 100 μl of media was removed and 100 μl of fresh Differentiation Media was added.

On Monday 100 μl of media was removed and 100 μl of fresh Differentiation Media was added.

On Tuesday 100 μl of media was removed and 100 μl of fresh Differentiation Media was added.

On Wednesday 100 μl of media was removed and 100 μl of fresh Differentiation Media was added.

On Thursday 100 μl of media was removed and 100 μl of fresh Differentiation Media was added.

On Friday 100 μl of media was removed and 100 μl of fresh Differentiation Media was added.

On the following Monday plates were prepared for the calcium assay as follows:

Plates were washed once with 10 mM Tris, HCl pH 7-8.

Working under a fume hood, 200 μl of 0.5 N HCl was added per well. Plates were then frozen at −80° C.

Just prior to measuring calcium, the plates were freeze-thawed twice, and then trituration with a multichannel pipette was used to disperse the contents of the plate. The contents of the plate was then allowed to settle at 4° C. for 30 minutes at which point an appropriate amount of supernatant was removed for measuring calcium using a commercially available calcium kit. An exemplary and not-limiting kit is Calcium (CPC) Liquicolor, Cat. No. 0150-250, Stanbio Laboratory, Boerne, Tex.

In this cell based assay, sclerostin inhibits one or more of the sequence of events leading up to and including mineral deposition (i.e. sclerostin inhibits mineralization). Thus, in experiments where sclerostin was included in the particular cell culture experiment, the recombinant sclerostin was added to the media starting on the first Thursday and every feeding day thereafter. In cases where an anti-sclerostin monoclonal antibody (Mab) was being tested for the ability to neutralize sclerostin, i.e. allow for mineralization by neutralizing sclerostin's ability to inhibit mineralization, the Mab was added to the media starting on the first Thursday and every feeding day thereafter. According to the protocol, this was accomplished as follows: the Mab was preincubated with the recombinant sclerostin in Differentiation media for 45-60 minutes at 37° C. and then this media was used for feeding the cells.

Described above is a 12-day mineralization protocol for MC3T3-E1-BF cells. Using the same reagents and feeding protocol, the original MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J Cell Biol 96:191-198) which we obtained from the RIKEN Cell Bank (RCB 1126, RIKEN BioResource Center 3-1-1 Koyadai, Tsukuba-shi, Ibaraki 305-0074 Japan) took longer to mineralize (20 days total for mineralization) than the MC3T3-E1-BF cells. Mineralization of the original MC3T3-E1 cells was inhibited by recombinant sclerostin and this inhibition was blocked using a sclerostin neutralizing antibody.

Example 9

Anti-Sclerostin Antibody Protects from Inflammation-Induced Bone Loss in the CD4

CD45RB$^{Hi}$ Transfer Model of Colitis in Scid Mice

Summary of Model

Injection of the CD45RB$^{high}$ subset of CD4+ T cells into C.B-17 scid mice results in chronic intestinal inflammation with characteristics similar to those of human inflammatory bowel disease (IBD). Diarrhoea and wasting disease is noted 3-5 weeks after cell transfer with severe leukocyte infiltration into the colon accompanied by epithelial cell hyperplasia and granuloma formation. C.B-17 scid mice which receive the reciprocal subset of CD4+ cells, those which express CD45RB$^{low}$, do not exhibit colitis and have a weight gain indistinguishable from uninjected scid mice. In addition to colitis symptoms, the CD4+CD45RB$^{high}$ T cell transfer model of colitis is accompanied by a reduction in bone mineral density (BMD), thought to be primarily through inflammatory mechanisms rather than dietary malabsorption (Byrne, F. R. et al., *Gut* 54:78-86, 2005).

Induction of Colitis and Inflammation-Induced Bone Loss

Spleens were taken from female balb/c mice and disrupted through a 70 μm cell strainer. The CD4+ population was then enriched by negative selection with Dynabeads using antibodies against B220, MAC-1, CD8 and I-A$^{d}$. The enriched population was then stained with FITC conjugated anti-CD4 and PE conjugated anti-CD45RB and fractionated into CD4+CD45RB$^{high}$ and CD4+CD45RB$^{low}$ populations by two-color sorting on a Moflo (Dakocytomation). The CD45RB$^{high}$ and CD45RB$^{low}$ populations were defined as the brightest staining 40% and the dullest staining 20% of CD4+ cells respectively. $5\times10^5$ cells were then injected i.p. into C.B-17 scid mice on day 0 and the development of colitis was monitored through the appearance of soft stools or diarrhoea and weight loss. Bone mineral density measurements were taken at the termination of the study (day 88).

Effect of Anti-Sclerostin Treatment on Colitis Symptoms and BMD

Ab-A IgG was dosed at 10 mg/kg s.c. from the day prior to CD4+CD45RB$^{high}$ cell transfer and compared with mice which received the negative control antibody 101.4 also dosed at 10 mg/kg s.c. The antibodies were dosed weekly thereafter. A group of mice which received non-pathogenic CD4+CD45RB$^{low}$ cells and were dosed with 10 mg/kg 101.4 was studied as a control. At the termination of the study (day 88) the bone mineral density was measured and sections of the colon taken for analysis of cell infiltration and assessment of histological damage.

a) No Effect on Colitis Symptoms

Typical colitis symptoms such as weight loss and infiltration of inflammatory cells into the colon were unaffected by treatment with Ab-A. Similarly there was no improvement of histological damage to the colon after treatment with Ab-A.

b) Inhibition of Inflammation-Induced Loss of Bone Mineral Density.

Figure 25:
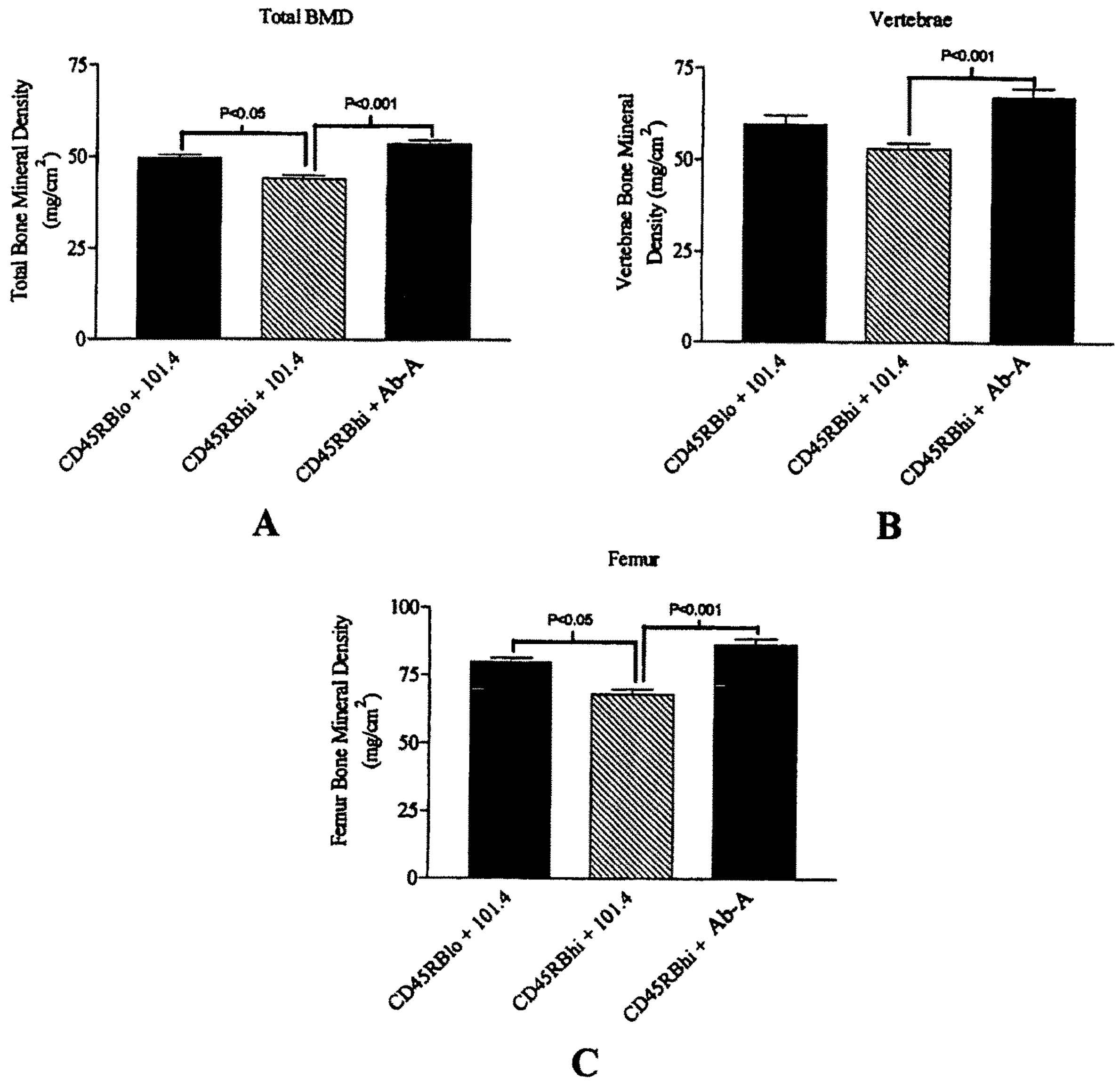
FIG. 25 depicts results from an inflammation-induced bone loss SCID mouse model. Ab-A treatment protected mice from inflammation-related bone loss associated with colitis when measured as total bone mineral density (FIG. 25A), vertebral bone density (FIG. 25B), and femur bone density (FIG. 25C).

On day 88 after transfer of cells into C.B-17 scid mice, the bone mineral density was measured (total BMD, vertebrae BMD and femur BMD). In comparison to control mice which received CD4+CD45RB$^{low}$ non-pathogenic cells, mice which received CD4+CD45RB$^{high}$ T cells and the negative control antibody 101.4 had reduced bone mineral density, as shown in FIG. 25. In contrast, no reduction in BMD was noted after treatment with Ab-A. Total, vertebrae and femur measurements of BMD were significantly higher in mice receiving CD4+CD45RB$^{high}$ T cells and treated with Ab-A than mice receiving CD4+CD45RB$^{high}$ T cells and treated with 101.4 (P<0.001 by Bonferroni multiple comparison test).

Example 10

KinExA-Based Determination of Affinity ($K_D$) of Anti-Sclerostin Antibodies for Human Sclerostin The affinity of several anti-sclerostin antibodies to human sclerostin was assessed by a solution equilibrium binding analysis using KinExA® 3000 (Sapidyne Instruments Inc., Boise, Id.). For these measurements, Reacti-Gel 6× beads (Pierce, Rockford, Ill.) were pre-coated with 40 μg/ml human sclerostin in 50 mM Na2CO3, pH 9.6 at 4° C. overnight. The beads were then blocked with 1 mg/ml BSA in 1 M Tris-HCl, pH 7.5 at 4° C. for two hours. 10 pM, 30 pM, or 100 pM of the antibody was mixed with various concentrations of human sclerostin, ranging in concentration from 0.1 pM to 1 nM, and equilibrated at room temperature for over 8 hours in PBS with 0.1 mg/ml BSA and 0.005% P20. The mixtures were then passed over the human sclerostin coated beads. The amount of bead-bound anti-sclerostin antibody was quantified using fluorescent Cy5-labeled goat anti-mouse-IgG or fluorescent Cy5-labeled goat anti-human-IgG antibodies (Jackson Immuno Research, West Grove, Pa.) for the mouse or human antibody samples, respectively. The amount of fluorescent signal measured was proportional to the concentration of free anti-sclerostin antibody in each reaction mixture at equilibrium. The dissociation equilibrium constant ($K_D$) was obtained from nonlinear regression of the competition curves using a n-curve one-site homogeneous binding model provided in the KinExA Pro software. Results of the KinExA assays for the selected antibodies are summarized in the table below.

| Antibodies | Antigen | $K_D$ (pM) | 95% confidence interval |
|---|---|---|---|
| Ab-13 | Human Sclerostin | 0.6 | 0.4~0.8 pM |
| Ab-4 | Human Sclerostin | 3 | 1.8~4 pM |
| Ab-19 | Human Sclerostin | 3 | 1.7~4 pM |
| Ab-14 | Human Sclerostin | 1 | 0.5~2 pM |
| Ab-5 | Human Sclerostin | 6 | 4.3~8 pM |
| Ab-23 | Human Sclerostin | 4 | 2.1~8 pM |

Example 11

Biacore Method for Determining the Affinity of Humanised Anti-Sclerostin Antibodies for Human Sclerostin The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation process is monitored when the analyte is replaced by buffer. In the affinity BIAcore assay, the ligand is the anti-sclerostin antibody and the analyte is sclerostin.

Instrument

Biacore® 3000, Biacore AB, Uppsala, Sweden

Sensor Chip

CM5 (research grade) Catalogue Number: BR-1001-14, Biacore AB, Uppsala, Sweden. Chips were stored at 4° C.

BIAnormalising Solution

70% (w/w) Glycerol. Part of BIAmaintenance Kit Catalogue Number: BR-1002-51, Biacore AB, Uppsala, Sweden. The BIAmaintenance kit was stored at 4° C.

Amine Coupling Kit

Catalogue Number: BR-1000-50, Biacore AB, Uppsala, Sweden.

Ethyl-3-(3-dimethylaminopropyl) carbodiimide hydrochloride (EDC). Made up to 75 mg/mL in distilled water and stored in 200 μL aliquots at −70° C.

N-Hydroxysuccinimide (NHS). Made up to 11.5 mg/mL in distilled water and stored in 200 μL aliquots at −70° C.

1 M Ethanolamine hydrochloride-NaOH pH 8.5. Stored in 200 μL aliquots at −70° C.

Buffers

Running buffer for immobilising capture antibody: HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.

Immobilisation buffer: Acetate 5.0 (being 10 mM sodium acetate pH 5.0). Catalogue number: BR-1003-51, Biacore AB, Uppsala, Sweden. Buffer stored at 4° C.

Running buffer for binding assay: HBS-EP (being 0.01 M HEPES pH 7.4, 0.15 M NaCl, 3 mM EDTA, 0.005% Surfactant P20, Catalogue Number: BR-1001-88, Biacore AB, Uppsala, Sweden) with CM-Dextran added at 1 mg/mL (Catalogue Number 27560, Fluka BioChemika, Buchs, Switzerland). Buffer stored at 4° C.

Ligand Capture

Affinipure F(ab')2 fragment goat anti-human IgG, Fc fragment specific. Jackson ImmunoResearch Inc (Pennsylvania, USA) Catalogue number: 109-006-098. Reagent stored at 4° C.

Ligand

Humanised anti-human sclerostin antibodies Ab5, Ab14 and Ab20.

Analyte

Recombinant human sclerostin. Aliquots stored at −70° C. and thawed once for each assay.

Regeneration Solution 40 mM HCl prepared by dilution with distilled water from an 11.6 M stock solution (BDH, Poole, England. Catalogue number: 101254H).

5 mM NaOH prepared by dilution with distilled water from a 50 mM stock solution. Catalogue number: BR-1003-58, Biacore AB, Uppsala, Sweden.

Assay Method

The assay format was capture of the anti-sclerostin antibody by immobilised anti-human IgG-Fc then titration of the sclerostin over the captured surface.

An example of the procedure is given below:

BIA (Biamolecular Interaction Analysis) was performed using a BIAcore 3000 (BIAcore AB). Affinipure $F(ab')_2$ Fragment goat anti-human IgG, Fc fragment specific (Jackson ImmunoResearch) was immobilised on a CM5 Sensor Chip via amine coupling chemistry to a capture level of ≈4000 response units (RUs). HBS-EP buffer (10 mM HEPES pH 7.4, 0.15 M NaCl, 3 mM EDTA, 0.005% Surfactant P20, BIAcore AB) containing 1 mg/mL CM-Dextran was used as the running buffer with a flow rate of 10 μl/min. A 10 μl injection of the anti-sclerostin antibody at ~5 μg/mL was used for capture by the immobilised anti-human IgG-Fc. Antibody capture levels were typically 100-200 RU. Sclerostin was titrated over the captured anti-sclerostin antibody at various concentrations at a flow rate of 30 μL/min. The surface was regenerated by two 10 μL injections of 40 mM HCl, followed by a 5 μL injection of 5 mM NaOH at a flowrate of 10 μL/min.

Background subtraction binding curves were analysed using the BIAevaluation software (version 3.2) following standard procedures. Kinetic parameters were determined from the fitting algorithm.

The kinetic data and calculated dissociation constants are given in Table 2.

TABLE 2

Affinity of anti-sclerostin antibodies for sclerostin

| Antibody | ka (1/Ms) | kd (1/s) | Kd (pM) |
|---|---|---|---|
| Ab-5 | 1.78E+06 | 1.74E−04 | 97.8 |
| Ab-14 | 3.30E+06 | 4.87E−06 | 1.48 |
| Ab-20 | 2.62E+06 | 4.16E−05 | 15.8 |

Example 12

In Vivo Testing of Anti-Sclerostin Monoclonal Antibodies in Cynomolgous Monkeys Thirty-three, approximately 3-5 year old, female cynomolgus monkeys (*Macaca fascicularis*) were used in this 2-month study. The study contained 11 groups:

Group 1: vehicle (N=4)
Group 2: Ab-23 (N=2, dose 3 mg/kg)
Group 3: Ab-23 (N=3, dose 10 mg/kg)
Group 4: Ab-23 (N=3, dose 30 mg/kg)
Group 5: Ab-5 (N=3, dose 3 mg/kg)
Group 6: Ab-5 (N=3, dose 10 mg/kg)
Group 7: Ab-5 (N=3, dose 30 mg/kg)
Group 8: Ab-14 (N=3, dose 3 mg/kg)
Group 9: Ab-14 (N=3, dose 10 mg/kg)
Group 10: Ab-14 (N=3, dose 30 mg/kg)
Group 11: Parathyroid Hormone (1-34) [PTH (1-34)] (N=3, dose 10 ug/kg)

All dosing was subcutaneous. PTH (1-34) was dosed everyday, monoclonal antibodies (Mabs) were dosed twice (first dose at the beginning of the study and second dose at the one month time point). For assessment of bone parameters (e.g. bone mineral density) pQCT (peripheral quantitative computed tomography) and DXA (dual energy X-ray absorptiometry) scans were performed prior to the beginning of the study (to obtain baseline values) and after a month (prior to the second dose of Mab) and finally at the end of the study (2-month time point) at which point the monkeys were necropsied for further analysis (e.g. histomorphometric analysis). Animals were fluorochrome labeled (days 14, 24, 47, and 57) for dynamic histomorphometry. Serum was collected at various time points during the study [day 1 pre-dose (the day of the first Mab dose), day 1 twelve hours post-dose, day 2, day 3, day 5, day 7, day 14, day 21, day 28, day 29 twelve hours post-dose (day 29 was the day of the second and final Mab dose), day 30, day 31, day 33, day 35, day 42, day 49 and day 56].

Three bone-related serum biomarkers were measured using commercially available kits:

Osteocalcin (OC) (DSL Osteocalcin Radioimmunoassay Kit; Diagnostic Systems Laboratories, Inc., Webster, Tex., USA)

N-terminal Propeptide of Type I Procollagen (P1NP) (P1NP Radioimmunoassay Kit; Orion Diagnostica, Espoo, Finland)

C-telopeptide fragments of collagen type I al chains (sCTXI) (Serum CrossLaps® ELISA; Nordic Bioscience Diagnostics A/S, Herlev, Denmark).

pQCT and DXA scans yielded data on various bone parameters (including bone mineral density (BMD) and bone mineral content) across numerous skeletal sites (including tibial metaphysis and diaphysis, radial metaphysis and diaphysis, femur neck, lumbar vertebrae). Analysis of this bone data (percent change from baseline for each animal) and the anabolic (OC, P1NP) serum biomarker data (percent change from baseline for each animal) revealed statistically significant increases, versus the vehicle group, in some parameters at some of the time points and doses for each Mab. This bone parameter data, serum biomarker data, as well as the histomorphometric data, indicated that each of the 3 Mabs (Ab-23, Ab-5 and Ab-14) was able to neutralize sclerostin in cynomolgous monkeys. This activity was most robust for Ab-23 and Ab-5, particularly at the highest dose (30 mg/kg), with a clear increase in bone formation (anabolic effect) as well as net gains in bone (e.g. BMD). Statistically significant increases in bone parameters and anabolic histomorphometric parameters were also found for the positive control group (PTH (1-34)).

Serum bone formation markers (P1NP, osteocalcin) were increased ($p<0.05$ vs vehicle (VEH)) at various time points and doses, but particularly in the 30 mg/kg groups for Ab-23 and Ab-5. Histomorphometric analysis revealed dramatic increases ($p<0.05$ vs VEH) in bone formation rates in cancellous bone at lumbar vertebra and proximal tibia (up to 5-fold increase), as well as at the endocortical surface of the femur midshaft (up to 10-fold increase) at the higher doses of Ab-23 and Ab-5. Trabecular thickness was increased with high dose Ab-23 and Ab-5 in lumbar vertebrae (>60%, $p<0.05$ vs VEH). By study end (2 months), areal BMD, as percent change from baseline, was increased ($p<0.05$ vs VEH) at the femur neck, ultra-distal radius (Ab-23, 30 mg/kg), and lumbar vertebrae (Ab-5, 30 mg/kg). The increases in areal BMD at the lumbar vertebrae were accompanied by increases in vertebral strength (97% increase in vertebral maximal load for Ab-23, 30 mg/kg; $p<0.05$ vs VEH); baseline values for lumbar areal BMD prior to Mab dosing were statistically similar across all groups. In summary, short-term administration of sclerostin-neutralizing Mabs in cynomolgous monkeys resulted, in part, in increases in bone formation, BMD and vertebral bone strength.

From the foregoing, although specific embodiments of the invention have been described herein for purposes of illustration, various modifications may be made without deviating from the spirit and scope of the invention. Accordingly, the invention is not limited except as by the appended claims. All publications, published patent applications, and patent documents disclosed herein are hereby incorporated by reference.

What is claimed is:

1. A method of isolating an antibody that binds sclerostin of SEQ ID NO: 1, the method comprising (a) performing a cross-blocking assay with (i) a first antibody and (ii) a second antibody comprising CDR sequences of SEQ ID NOs: 245-247 and 78-80 in the presence of sclerostin of SEQ ID NO: 1, and (b) isolating a first antibody that competes with the second antibody for binding to sclerostin.

2. The method of claim 1, wherein the cross-blocking assay is an ELISA assay and a reduction of between 60% and 100% of sclerostin detection signal in the presence of (i) and (ii) as compared to the sclerostin detection signal obtained in the presence of (i) or (ii) alone indicates that the first antibody competes with the second antibody for binding to sclerostin.

3. The method of claim 2, wherein the reduction in the amount of sclerostin detection signal is between 80% and 100%.

4. The method of claim 1, wherein the cross-blocking assay is a surface plasmon resonance assay and a recorded binding of between 80% and 4% of the maximum theoretical binding between (i) and sclerostin in the presence of (ii) indicates that the first antibody competes with the second antibody for binding to sclerostin.

5. The method of claim 4, wherein the recorded binding is between 70% and 4% of the maximum theoretical binding.

6. The method of claim 1, wherein the second antibody comprises light chain variable regions comprising the amino acid sequence of SEQ ID NO: 376 and heavy chain variable regions comprising the amino acid sequence of SEQ ID NO: 378.

7. The method of claim 1, wherein the second antibody comprises light chains of SEQ ID NO: 141 and heavy chains of SEQ ID NO: 145 or SEQ ID NO: 392.

8. The method of claim 1, wherein the second antibody demonstrates a binding affinity for sclerostin of SEQ ID NO: 1 of less than or equal to $1\times10^{7}$ M.

9. The method of claim 8, wherein the second antibody demonstrates a binding affinity for sclerostin of SEQ ID NO: 1 of less than or equal to $1\times10^{9}$ M.

10. The method of claim 1, further comprising screening the first antibody in a sclerostin neutralization assay.

11. The method of claim 10, wherein the sclerostin neutralization assay comprises (i) contacting osteoblast-lineage cells with the first antibody in the presence of sclerostin and (ii) measuring mineralization, wherein an increase in mineralization indicates that the first antibody neutralizes sclerostin activity.

12. The method of claim 10, wherein the sclerostin neutralization assay comprises (i) administering the first antibody to a non-human mammal, and (ii) measuring a serum anabolic marker, a histomorphometric marker of bone formation, bone mineral density, bone mineral content, bone mass, bone quality, or bone strength.

* * * * *